(12) United States Patent
Mjalli et al.

(10) Patent No.: US 7,544,699 B2
(45) Date of Patent: Jun. 9, 2009

(54) ARYL AND HETEROARYL COMPOUNDS, COMPOSITIONS, AND METHODS OF USE

(75) Inventors: Adnan M. M. Mjalli, Jamestown, NC (US); Robert C. Andrews, Jamestown, NC (US); Xiao-Chuan Guo, High Point, NC (US); Daniel Peter Christen, Jamestown, NC (US); Devi Reddy Gohimmukkula, Jamestown, NC (US); Guoxiang Huang, Greensboro, NC (US); Robert Rothlein, Summerfield, NC (US); Sameer Tyagi, High Point, NC (US); Tripura Yaramasu, Greensboro, NC (US); Christopher Behme, Jamestown, NC (US)

(73) Assignee: Transtech Pharma, Inc., High Point, NC (US)

( * ) Notice: Subject to any disclaimer, the term of this patent is extended or adjusted under 35 U.S.C. 154(b) by 528 days.

(21) Appl. No.: 10/913,168

(22) Filed: Aug. 6, 2004

(65) Prior Publication Data

US 2005/0059705 A1 Mar. 17, 2005

Related U.S. Application Data

(60) Provisional application No. 60/493,879, filed on Aug. 8, 2003, provisional application No. 60/493,878, filed on Aug. 8, 2003, provisional application No. 60/493,903, filed on Aug. 8, 2003.

(51) Int. Cl.
C07D 217/00 (2006.01)
A61K 31/47 (2006.01)
(52) U.S. Cl. ...................... 514/309; 546/146
(58) Field of Classification Search ................. 546/146; 514/307, 309
See application file for complete search history.

(56) References Cited

U.S. PATENT DOCUMENTS

| | | | |
|---|---|---|---|
| 4,717,736 A | 1/1988 | Rokach et al. | |
| 5,518,735 A | 5/1996 | Sturzebecher et al. | |
| 5,679,671 A | 10/1997 | Oinuma et al. | |
| 5,750,520 A | 5/1998 | Danilewicz et al. | |
| 5,780,498 A | 7/1998 | Saika et al. | |
| 5,977,075 A | 11/1999 | Ksander et al. | |
| 6,001,820 A | 12/1999 | Hirsh et al. | |
| 6,087,380 A | 7/2000 | Hauel et al. | |
| 6,093,731 A * | 7/2000 | Dickinson et al. | ........... 514/310 |
| 6,194,448 B1 | 2/2001 | Bredrget et al. | |
| 6,194,458 B1 | 2/2001 | Baker et al. | |
| 6,262,084 B1 | 7/2001 | Biediger et al. | |
| 6,284,871 B1 | 9/2001 | Mertens et al. | |
| 6,291,511 B1 | 9/2001 | Durette et al. | |
| 6,342,504 B1 | 1/2002 | Brunck et al. | |
| 6,358,978 B1 | 3/2002 | Ritzeler et al. | |
| 6,528,655 B1 | 3/2003 | N'Zemba et al. | |
| 6,559,174 B2 | 5/2003 | Lin et al. | |
| 6,743,790 B2 | 6/2004 | Klingler et al. | |
| 6,855,843 B2 | 2/2005 | Sircar et al. | |
| 6,908,939 B2 | 6/2005 | Bernadon et al. | |
| 7,208,601 B2 | 4/2007 | Mjalli et al. | |
| 2002/0016461 A1 | 2/2002 | Albers et al. | |
| 2002/0095041 A1 | 7/2002 | Chan et al. | |
| 2002/0103192 A1 | 8/2002 | Curtin et al. | |
| 2002/0151595 A1 | 10/2002 | Ries et al. | |
| 2002/0173656 A1 | 11/2002 | Peyman et al. | |
| 2002/0198195 A1 | 12/2002 | Nazare et al. | |
| 2003/0149083 A1 | 8/2003 | Tanaka et al. | |
| 2004/0106626 A1 | 6/2004 | South et al. | |
| 2004/0126856 A1 | 7/2004 | Bajaj et al. | |
| 2004/0254215 A1 * | 12/2004 | Arend et al. | ................ 514/310 |
| 2005/0065346 A1 | 3/2005 | Ries et al. | |
| 2005/0256116 A1 | 11/2005 | Clary et al. | |

FOREIGN PATENT DOCUMENTS

| | | |
|---|---|---|
| DE | 199 28 424 | 12/2000 |
| EP | 0150118 | 9/1987 |
| EP | 1213288 | 12/2002 |
| FR | 2 847 251 | 5/2004 |
| GB | 1 501 541 | 2/1978 |
| GB | 2354440 | 7/2000 |
| JP | 2001-089368 | 4/2001 |
| WO | WO 98/37075 | 8/1998 |

(Continued)

OTHER PUBLICATIONS

Burdick et al, "N-Benzoyl Amino Acids as LFA-1/ICAM Inhibitors 1: Amino Acid Structure-Activity Relationship" Bioorganic Medicinal Chemistry Letters, vol. 13, pp. 1015-1018 (2003).

(Continued)

*Primary Examiner*—Zinna N Davis
(74) *Attorney, Agent, or Firm*—Kilpatrick Stockton LLP

(57) ABSTRACT

This invention provides aryl and heteroaryl compounds, methods of their preparation, pharmaceutical compositions comprising the compounds, and their use in treating human or animal disorders. The compounds of the invention may be antagonists, or partial antagonist of factor IX and/or factor XI and thus, may be useful for inhibiting the intrinsic pathway of blood coagulation. The compounds may be useful in a variety of applications including the management, treatment and/or control of diseases caused in part by the intrinsic clotting pathway.

66 Claims, 2 Drawing Sheets

FOREIGN PATENT DOCUMENTS

| WO | WO 95/12611 | 11/1998 |
|---|---|---|
| WO | WO 98/53817 | 12/1998 |
| WO | WO 99/26923 | 6/1999 |
| WO | WO 99/36393 | 7/1999 |
| WO | WO 00-35864 | 6/2000 |
| WO | WO 00/37429 | 6/2000 |
| WO | WO 00/67746 | 11/2000 |
| WO | WO 00/68188 | 11/2000 |
| WO | WO 00/76971 | 12/2000 |
| WO | WO 01/10823 | 2/2001 |
| WO | WO 01/21584 | 3/2001 |
| WO | WO 01/38309 | 5/2001 |
| WO | WO 01/68586 | 9/2001 |
| WO | WO 02/18320 | 3/2002 |
| WO | WO 02/26717 | 4/2002 |
| WO | WO 02/062748 | 8/2002 |
| WO | WO 02/085841 | 10/2002 |
| WO | WO 03/007945 | 1/2003 |
| WO | WO 03/033496 | 4/2003 |
| WO | WO 2004/014844 | 2/2004 |
| WO | WO 2004/046091 | 6/2004 |
| WO | WO 2004/080970 | 9/2004 |
| WO | WO 2004/084842 | 10/2004 |

OTHER PUBLICATIONS

Castanedo et al, "Solid-Phase synthesis of dual alpha4beta1/alpha4beta7 integrin antagonists: Two Scaffolds with Overlapping Pharmacophores", Bioorganic & Medicinal Chemistry Letters, Oxford, GB vol. 12, pp. 2913-2917 (2002).

Database CAPLUS Chemical Abstracts Service, Columbus, Ohio, US, XP002319820, retrieved from STN Database accession No. 1973: 504834 abstract; RN 42787-97-3 abstract & I. Hahnemann et al, Journal Fuer Praktische Chemie, vol. 315, No. 4, 1973, pp. 796-800.

Greenspan P.D. et al., "N-aryl Cinnamides: A Novel Class of Rigid and Highly Potent Leukotriene B4 Receptor Antagonists", Bioorganic and Medicinal Chemistry Letters, vol. 7, pp. 949-954 (1997).

International Search Report for related PCT application PCT/US2004/025463 mailed Jan. 26, 2005.

International Search Report for related PCT application PCT/US2004/025478 mailed Jan. 26, 2005.

International Search Report for related PCT application No. PCT/US2004/025429 mailed Jan. 26, 2005.

International Search Report for PCT application PCT/US03/25045 mailed Mar. 14, 2005.

Knowles, H.S. et al., "A photochemical approach to phenylalanines and related compounds by alkylation of glycine", Tetrahedron, vol. 57, pp. 98115-98124 (2001).

O'Donnell M.J. et al., "Enantioselective Solid-Phase Synthesis of α-Amino Acid Derivatives", Tetrahedron, vol. 55, pp. 6347-6362 (1999).

Sircar et al, "Synthesis and SAR of N-benzoyl-L-Biphenylalanine derivatives: Discovery of TR-14035, A Dual Alpha4Beta7/Alpha4Beta1 Intergrin Antagonist", Bioorganic & Medicinal Chemistry, vol. 10, pp. 2051-2066 (2002).

Bebernitz et al., "Anilides of R-Trifluoro-2-hydroxy-2-methylpropionic Acid as inhibitors of Pyruvate Dehydrogenase Kinase", Journal of Medicinal Chemistry, vol. 43, pp. 7121-7124, (2000).

Shrader et al., "Neutral inhibitors of the Serine Protease Factor Xa", Bioorganic & Medicinal Chemistry Letters, vol. 11. pp. 1801-1804, (2001).

Knowles et al., "Photochemical alkylation of glycine leading to phenylalanines", Tetrahedron Letters, vol. 41, pp. 7121-7124, (2000).

Office Action mailed Jul. 9, 2007 for U.S. Appl. No. 10/913,168.

Office Action mailed Mar. 20, 2007 for U.S. Appl. No. 10/913,168.

Amendment mailed to USPTO on Apr. 16, 2007 for U.S. Appl. No. 10/913,168.

Office Action mailed Jun. 22, 2007 for U.S. Appl. No. 10/913,216.

Office Action mailed Feb. 1, 2007 for U.S. Appl. No. 10/913,216.

Office Action mailed Sep. 28, 2006 for U.S. Appl. No. 10/913,216.

Response Under 37 C F R § 1 111 mailed to USPTO on Apr. 1, 2007 for U.S. Appl. No. 10/913,216.

Amendment and Response mailed to USPTO on Nov. 27, 2006 for U.S. Appl. No. 10/913,216.

Preliminary Amendment mailed to USPTO on Nov. 12, 2004 for U.S. Appl. No. 10/913,216.

Interview Summary mailed Feb. 1, 2007 for U.S. Appl. No. 10/913,216.

Office Action mailed Apr. 5, 2007 for U.S. Appl. No. 10/913,682.

Office Action mailed Dec. 7, 2006 for U.S. Appl. No. 10/913,862.

Response mailed to USPTO on Jan. 8, 2007 for U.S. Appl. No. 10/913,882.

Patent Cooperation Treaty Notification Concerning Transmittal of International Preliminary Report on Patentability and Written Opinion of the International Searching Authority for Application Serial No. PCT/US2004/025463 dated Jan. 24, 2005.

Patent Cooperation Treaty Notification Concerning Transmittal of International Preliminary Report on Patentability and Written Opinion of the International Searching Authority for Application Serial No. PCT/US2004/025429 dated Jan. 24, 2005.

Patent Cooperation Treaty Notification Concerning Transmittal of International Preliminary Report on Patentability and Written Opinion of the International Searching Authority for Application Serial No. PCT/US2004/025478 dated Jan. 24, 2005.

Patent Cooperation Treaty Notification Concerning Transmittal of International Preliminary Report on Patentability and Written Opinion of the International Searching Authority for Application Serial No. PCT/US2006/006571 dated Sep. 11, 2007.

Bernardon et al CAS 139 101121.

Srivastava et al. 1981. CAS. 95: 125911.

St Hilaire et al CAS 141 150947.

* cited by examiner

ARYL AND HETEROARYL COMPOUNDS, COMPOSITIONS, AND METHODS OF USE

STATEMENT OF RELATED APPLICATIONS

The present application claims priority under 35 USC 119 from the following U.S. Provisional Patent Applications: Ser. No. 60/493,879, filed Aug. 8, 2003, entitled "Aryl and Heteroaryl Compounds as Antviral agents"; Ser. No. 60/493,878, filed Aug. 8, 2003, entitled "Aryl and Heteroaryl Componds and Methods to Modulate Red Blood Cell Production"; Ser. No. 60/493,903, filed Aug. 8, 2003, entitled "Aryl and Heteroaryl Compounds and Methods to Modulate Coagulation", the entirety of which are herein incorporated by reference.

FIELD OF THE INVENTION

This invention relates to aryl and heteroaryl compounds and compositions that may antagonize of the intrinsic clotting pathway by binding to, and inhibiting the function of, factor XI or factors XI and IX, and methods of use for such compounds and compositions.

BACKGROUND OF THE INVENTION

Hemostasis, the arrest of bleeding from an injured blood vessel, requires the coordinated regulation of vascular, platelet, and plasma factors to eventually form a hemostatic seal or a blood clot. In normal hemostasis, collective activity activity of these factors is counterbalanced by regulatory mechanisms that limit the accumulation of platelets and fibrin in the area of injury.

In normal hemostasis, the process of clot formation (blood coagulation) and clot dissolution (fibrinolysis) is delicately balanced. A slight imbalance between the processes of clot formation and dissolution can lead to excessive bleeding or thrombosis, and there are several disease states related to abnormal hemostasis. For example, abnormal thrombus formation in the coronary arterial vasculature due to the rupture of an established atherosclerotic plaque is a major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. Also, a high percentage of patients undergoing major surgery in the lower extremities or the abdominal area suffer from thrombus formation in the venous vasculature, which can result in reduced blood flow to the affected extremity and a predisposition to pulmonary embolism. Additionally, disseminated intravascular coagulopathy is characterized by the rapid consumption of coagulation factors and systemic coagulation which results in the formation of life-threatening thrombi occurring throughout the vasculature leading to widespread organ failure. Disseminated intravascular coagulopathy commonly occur within both vascular systems during septic shock, certain viral infections and cancer.

Thus, pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively [Ross, A. M., Thrombosis in Cardiovascular Disorder, p. 327, W.B. Saunders Co., Fuster, V. and Verstraete, M. eds. 1991); Califf, R. M. and Willerson, J. T., Id. at p 389]. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered intravenously, has not been shown to be universally effective in the treatment or prevention of acute arterial thrombosis or rethrombosis [Prins, M. H. and Hirsh, J., J. Am. Coll. Cardiol., 67: 3A (1991)].

Besides the unpredictable, recurrent thrombotic reocclusion which commonly occurs following PTCA, a profound restenosis of the recanalized vessel occurs in 30 to 40% of patients 1 to 6 months following this procedure [Califf, R. M. et al., J. Am. Coll. Cardiol., 17: 2B (1991)]. These patients require further treatment with either a repeat PTCA, or coronary artery bypass surgery, to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

Thus, there is a need for specific anti-thrombotic agents. Also, there is a need for anti-thrombotic agents that selectively inhibit factors in either the extrinsic pathway or the intrinisic pathway, while leaving the other pathway unaffected.

SUMMARY OF THE INVENTION

Embodiments of the present invention provide aryl and heteroaryl compounds, compositions, and methods of use of such compounds and compositions. The present invention may be embodied in a variety of ways.

In one embodiment, the present invention comprises compounds of Formula (I) as described herein. In another embodiment, the present invention also provides methods for the preparation of compounds of Formula (I).

The present invention also comprises pharmaceutical compositions comprising compounds of Formula (I). In another embodiment, the present invention provides methods for the preparation of compositions comprising the compounds of Formula (I). The pharmaceutical compositions may comprise pharmaceutically acceptable carriers, excipients, and/or diluents.

In another embodiment, the present invention provides methods for the use of compounds of Formula (I) and pharmaceutical compositions comprising compounds of Formula (I). In one embodiment, the compounds and pharmaceutical compositions of the present invention may be used for treating human or animal disorders. Compounds of Formula (I) may be useful as modulators of the intrinsic clotting pathway by inhibiting the biological activity of factor XI and/or both factor IX and factor XI. For example, compounds of Formula (I) may be used in the management, treatment, and/or control, and/or as an adjunct therapy for treatment, of diseases in humans caused in part by the intrinsic clotting pathway utilizing factor XI/IX. Such diseases or disease states include cardiopulmonary bypass, stroke, myocardial infarction, deep vein thrombosis associated with surgical procedures or long periods of confinement, acute and chronic inflammation and clotting associated with hemodialysis.

BRIEF DESCRIPTION OF THE FIGURES

The present invention will be described with reference to the accompanying drawings, wherein.

DETAILED DESCRIPTION

Upon injury to a blood vessel, vascular factors may reduce blood flow from the blood vessel by local vasoconstriction and compression of injured vessels. At the same time, platelets can adhere to the site of vessel wall injury and form aggregates called hemostatic plugs, which form the first key element of the hemostatic seal. Platelets can also release factors that provide surface membrane sites and components for the formation of enzyme/cofactor complexes in blood coagulation reactions. Through a series of interacting and propagating zymogen activations, the activated form of one plasma factor may catalyze the activation of the next plasma factor. This cascade of blood coagulation reactions eventually forms a fibrin clot. The fibrin clot, an insoluble fibrin matrix that radiates from and anchors the hemostatic plug, is the second key element of the hemostatic seal.

The cascade of blood coagulation reactions involves two interdependent pathways, an intrinsic pathway and an extrinsic pathway. Both pathways, however, ultimately catalyzes the proteolytic activation of factor X to factor Xa.

Figure 1:
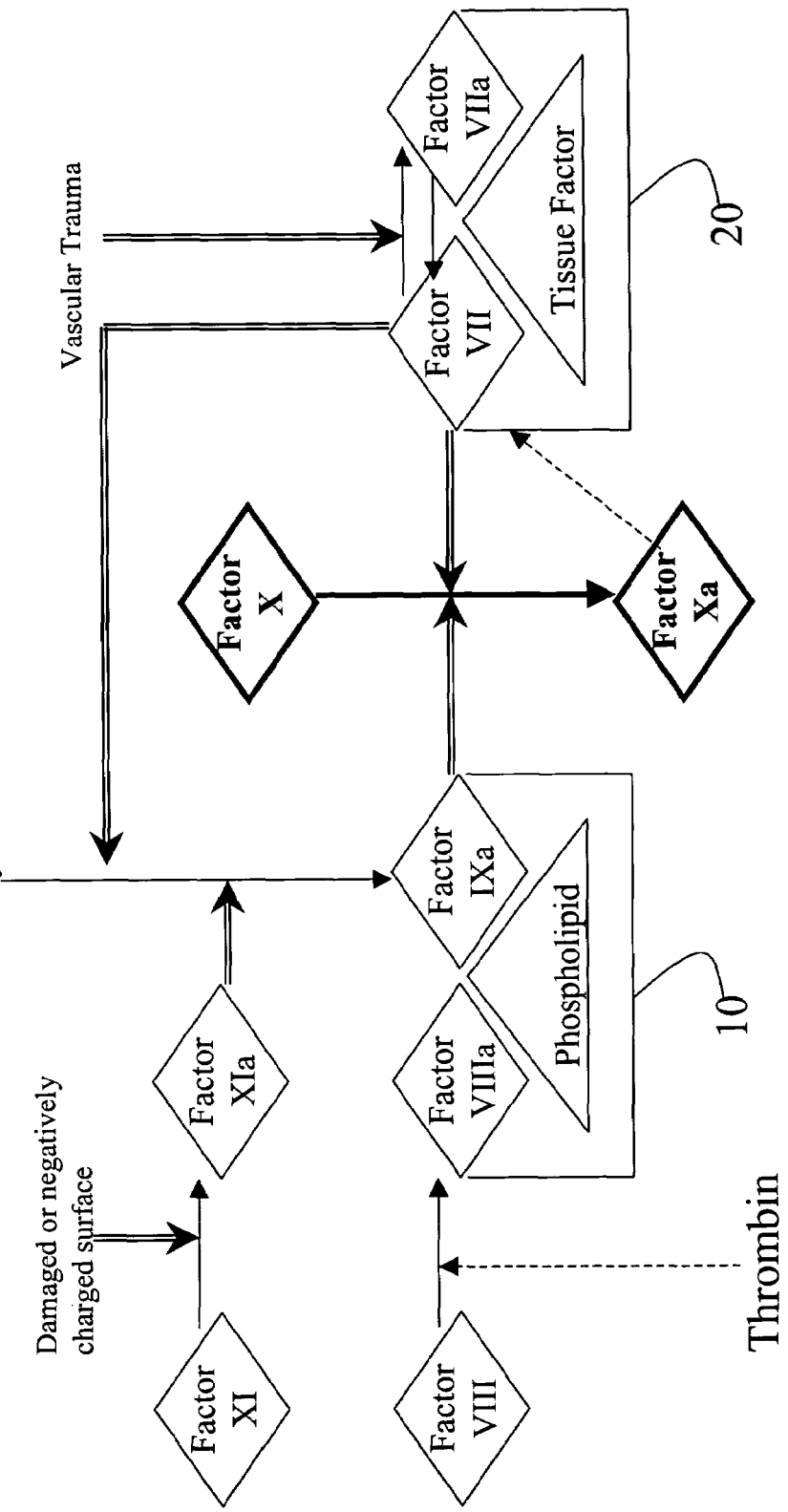
FIG. 1 is a diagram depicting the steps involved in the intrinsic and extrinsic blood clotting cascades, from time of trauma to the activation of factor X.

As shown in FIG. 1, damage to the blood vessel or a negatively charged surface may initiate blood clotting by the intrinsic pathway. Tthe major components of the intrinsic pathway include factor VIII, a non-enzymatic co-factor, and factors IX and XI, zymogen serine proteases. The initiation of the intrinsic pathway results in the activation of factor XI to XIa. Factor XIa, in the presence of the factor VIIa/tissue factor complex involved in the extrinsic pathway, can then catalyzes the activation of factor IX to factor IXa. The presence of factor IXa, in combination with the activated form of factor VIII (VIIIa) on an appropriate phospholipid surface, results in the formation of a tenase complex (10). The tenase complex then catalyzes the formation of factor Xa from its zymogen, factor X.

In contrast to the intrinsic pathway, the extrinsic pathway of blood clotting may be initiated by exposure of blood to injured tissue. As is shown in FIG. 1, the major components of the extrinsic pathway are factor VII (a zymogen serine protease), and tissue factor (a membrane bound protein). Tissue factor serves as the requisite non-enzymatic co-factor for factor VII. The initiation of the extrinsic pathway is thought to be an autocatalytic event resulting from the activation of factor VII by trace levels of activated factor VII (factor VIIa), both of which are bound to newly exposed tissue factor on membrane surfaces at sites of vascular damage (20). The factor VIIa/tissue factor complex directly catalyzes the formation of factor Xa from factor X.

Figure 2:
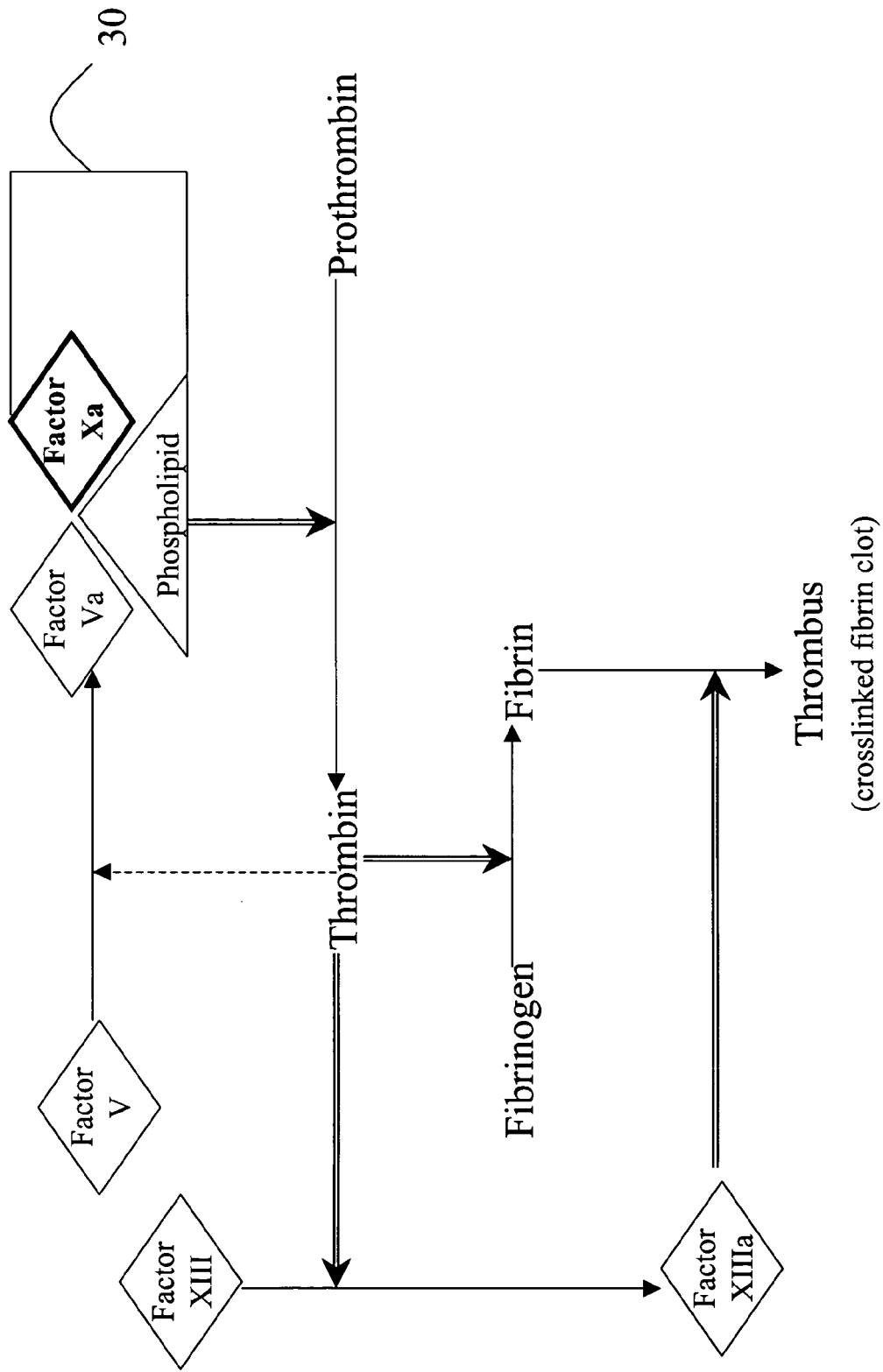
FIG. 2 is a diagram depicting the steps following initial intrinsic and extrinsic blood clotting cascades, beginning with the formation of Xa and culminating in the formation of a thrombus.

Once the initial intrinsic or extrinsic cascade results in the activation of factor X to Xa, factor Xa catalyzes the penultimate step in the blood coagulation cascade, the formation of serine protease thrombin. As seen in FIG. 2, thrombin formation occurs when a prothrombinase complex (30), comprising of factor Xa, the non-enzymatic co-factor Va, and the substrate prothrombin, is assembled on an appropriate phospholipid surface. Once formed, thrombin functions as part of a feedback loop, controlling the activation of factors V and VIII. Additionally, thrombin may catalyze both the activation of factor VIII and the conversion of fibrinogen to fibrin. Factor VIIIa then interacts with fibrin to catalyze the formation of a thrombus, or crosslinked fibrin clot.

Numerous strategies have been developed for the treatment of thrombotic disorders. Many antithrombotic therapies are based on interference in the hemostatic system. This approach carries the inherent risk of bleeding, since the hemostatic system is no longer fully responsive to potential injury. Therefore, antithrombotic benefits are normally associated with antihemostatic risks. In attempts to improve the benefit-to-risk ratio, antithrombotic agents are continuously being developed. Various antithrombotic strategies include administering general inhibitors of thrombin formation such as heparin or vitamin K antagonists; administering specific thrombin inhibitors; administering specific factor Xa inhibitors; and administering inhibitors of platelet activation and adhesion.

Evaluation of current antithrombotic strategies in terms of antithrombotic benefits versus antihemostatic risks reveals that the benefit-to-risk ratio tends to be more favorable for strategies that interfere with one specific step rather than in a more general phase of the hemostatic system [L. A. Harker, Biomedical Progress vol 8, 1995, 17-26]. For example, the development of inhibitors specific for factor Xa is an improvement from general and specific thrombin inhibitors. But, this approach blocks the common (intrinsic and extrinsic) pathway of thrombin generation (see FIG. 1), and thereby thrombin-dependent platelet activation. Thus, a need exists for more specific anti-thrombotic agents that selectively inhibit one single hemostatic pathway, while leaving other pathways unaffected.

The are two blood coagulation pathways associated with normal hemostasis, intrinsic and extrinsic are interdependent. Thus, complete elimination of the intrinsic pathway may lead to uncontrolled bleeding. For example, Type B hemophiliacs completely lack factor IX or factor IX function and have a phenotype characterized by a severe bleeding disorder. Also, activation of factor X directly by VIIa/tissue factor, which bypasses the need for factor VIII and factor IX, is insufficient for normal hemostasis. Also, formation of the factor VIIIa/IXa phospholipid factor X activator (tenase complex) (20) may be essential for normal hemostasis.

Selective inhibition of the intrinsic pathway of coagulation with a factor XI antagonist or a dual factor XI/IX antagonist can provide a method to inhibit the clotting cascade associated with some types of surgery, stroke, myocardial infarction and hemodialysis, while leaving the clotting pathway associated with external lesions such as trauma or abscess intact. As factors XI and IX are primarily associated with the intrinsic clotting pathway, antagonists that have activity to factor XI or dual activity to factor XI/IX may have a therapeutic benefit in diseases associated with intrinsic pathway clotting by inhibiting intravascular thrombosis. Additionally, antagonists of factor XI or dual antagonists of factor XI/IX may not have the side effect of unwanted or uncontrollable bleeding by impairing extravascular hemostasis associated with wound healing.

For example, certain point mutations in factor IX may partially inhibit its function and result in a mild or moderate phenotype manifested as a non-life threatening bleeding disorder [Bowen, D. J., J. Clin. Pathol: Mol. Pathol. 55:1-18 (2002)]. These point mutations cause factor IX to behave as if it were subject to a partial antagonist. In the presence of a partial antagonist, factor IX may maintain some activity, even at saturation levels of the partial antagonist. As a result of the point mutations in factor IX, its activity can be reduced along with clotting associated with the intrinsic pathway, while still maintaining some residual activity remains that leaves the extrinsic pathway intact. Additionally, an antibody directed against the gamma-carboxyglutamic acid domain of Factor XI demonstrated efficacy in animal models of throbosis without an increase in bleeding times [Refino, C. J., etal. Thromb Haemost. 82(3)1188-1195 (1999)]. Thus, embodiments of the present invention, provide compounds of Formula (I), pharmaceutical compositions, and methods to inhibit the clotting activities of factor XI and/or both factor IX and factor XI. Inhibition of hemostasis with agents that may selectively inhibit the intrinsic pathway of factor X activation may leave the extrinsic pathway intact and allow the formation of small, but hemostatically important amounts of factor Xa and thrombin.

In one embodiment, the present invention provides compounds of Formula (I) as depicted below. Embodiments of the present invention also provide methods of the preparation of compounds of Formula (I).

In addition, embodiments of the present invention may comprise pharmaceutical compositions comprising compounds of Formula (I), and well as methods of making such compositions.

In another embodiment, the present invention provides methods for the use of compounds of Formula (I) and pharmaceutical compositions comprising compounds of Formula (I) in treating human or animal disorders. Compounds of the Formula (I) and pharmaceutical compositions comprising compounds of Forumula (I) may be useful as modulators of the intrinsic clotting pathway by inhibiting the biological activities of factor XI and/or both factor IX and factor XI. Thus, the compounds and compositions of the present inveniton may be useful in a variety of applications including management, treatment, and/or control of diseases in humans caused in part by the intrinsic clotting pathway utilizing factors XI/IX. Also, the compounds and compositions of the present inveniton may be useful as adjunct therapeutics in the management, treatment, and/or control of diseases in humans caused in part by the intrinsic clotting pathway utilizing factors XI/IX. Such diseases or disease states include cardiopulmonary bypass, stroke, myocardial infarction, deep vein thrombosis associated with surgical procedures or long periods of confinement, acute and chronic inflammation and clotting associated with hemodialysis.

In one aspect, the present invention provides compounds which are represented by Formula (I):

$$Ar_2—K \qquad (I)$$

wherein $Ar_2$ comprises an aryl, heteroaryl, fused cycloalkylaryl, fused cycloalkylheteroaryl, fused heterocyclylaryl, or fused heterocyclylheteroaryl group optionally substituted 1 to 7 times. In an embodiment, $Ar_2$ comprises an aryl, heteroaryl, or fused arylheterocyclyl group optionally substituted 1 to 7 times. In another embodiment, $Ar_2$ comprises a phenyl, naphthyl, pyridyl, indolyl, isoquinolyl, pyrimidyl, tetrahydroisoquinolyl, quinoxazoyl, or quinazolyl group optionally substituted 1 to 7 times. In another embodiment, $Ar_2$ comprises a substituted phenyl, 2-naphthyl, 2-pyridyl, 3-isoquinolyl, 2-pyrimidyl, 2-quinazolyl, or 3-tetrahydroisoquinolyl group having 1 to 5 substituents. Substituents of $Ar_2$ throughout the various embodiments may independently comprise:

a) -fluoro;
b) -chloro;
c) -bromo;
d) -iodo;
e) -cyano;
f) -nitro;
g) -perfluoroalkyl;
h) -$T_1$-$R_{20}$;
i) -alkyl;
j) -aryl;
k) -heteroaryl;
l) -heterocyclyl;
m) -cycloalkyl;
n) -alkylene-aryl;
o) -alkylene-arylene-aryl;
p) -alkylene-arylene-alkyl;
q) -arylene-alkyl;
r) -arylene-aryl;
s) -arylene-heteroaryl;
t) -heteroarylene-aryl;
u) -heteroarylene-heteroaryl;
v) -heteroarylene-heterocyclyl;
w) -arylene-heterocyclyl;
x) -arylene-arylene-alkyl;
y) -$T_1$-alkyl;
z) -$T_1$-aryl;
aa) -$T_1$-alkylene-aryl;
bb) -$T_1$-alkenylene-aryl;
cc) -$T_1$-alkylene-heteroaryl;
dd) -$T_1$-alkenylene-heteroaryl;
ee) -$T_1$-cycloalkylene-aryl;
ff) -$T_1$-cycloalkylene-heteroaryl;
gg) -$T_1$-heterocyclylene-aryl;
hh) -$T_1$-heterocyclylene-heteroaryl;
ii) -$T_1$-arylene-alkyl;
jj) -$T_1$-arylene-alkenyl;
kk) -$T_1$-alkylene-arylene-aryl;
kk) -$T_1$-arylene-$T_2$-aryl;
mm) -$T_1$-arylene-arylene-aryl;
nn) -$T_1$-alkylene-arylene-alkyl;
oo) -alkylene-$T_1$-alkylene-aryl;
pp) -arylene-$T_1$-alkyl;
qq) -arylene-$T_1$-alkylene-aryl;
rr) -$T_1$-alkylene-$T_2$-aryl;
ss) -$T_1$-alkylene-aryl;
tt) -alkylene-$T_1$-heteroaryl;
uu) -alkylene-$T_1$-cycloalkyl;
vv) -alkylene-$T_1$-heterocyclyl;
ww) -alkylene-T-arylene-alkyl;
xx) -alkylene-$T_1$-alkylene-arylene-alkyl;
yy) -alkylene-$T_1$-alkyl;
zz) -alkylene-$T_1$-$R_{20}$;
aaa) -arylene-$T_1$-$R_{20}$;
bbb) -alkylene-cycloalkyl;
ccc) -$T_1$-arylene-$T_2$-alkylene-aryl;
ddd) -$T_1$-arylene-aryl;
eee) -$T_1$-alkylene-cycloalkyl;
fff) -$T_1$-cycloalkyl;
ggg) -$T_1$-heterocyclyl-$T_2$-aryl;
hhh) -$T_1$-alkynyl;
iii) -$T_1$-alkylene-$T_2$-alkyl;or
jjj) -hydrogen;

wherein $R_{20}$ comprises: -hydrogen, -alkyl, -alkenyl, -alkylene-cycloalkyl, -alkynene-heterocyclyl, -aryl, -heteroaryl, -arylenealkyl, -alkylene-aryl, -alkylene-arylene-alkyl, -alkylene-arylene-aryl, -alkylene-arylene-alkyl-aryl, -alkylene-arylene-O-arylene, or alkylene-arylene-O-alkylene-aryl;

$T_1$ comprises —$CH_2$—, —O—, —$N(R_{21})$—, —C(O)—, —$CON(R_{21})$—, —$N(R_{21})C(O)$—, —$N(R_{21})CON(R_{22})$—, —$N(R_{21})C(O)O$—, —$OC(O)N(R_{21})$—, —$N(R_{21})SO_2$—, —$SO_2N(R_{21})$—, —C(O)—O—, —O—C(O)—, —S—, —S(O)—, —$S(O_2)$—, —$N(R_{21})SO_2N(R_{22})$—,

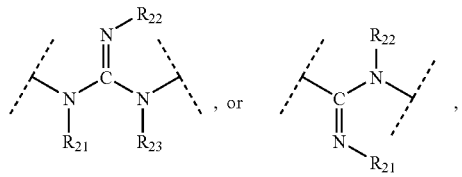
, or wherein $R_{21}$, $R_{22}$ and $R_{23}$, independently comprise: -hydrogen, -alkyl, -alkenyl, -alkylene-cycloalkyl, -alkynene-heterocyclyl, -aryl, -heteroaryl, -arylene-alkyl, -alkylene-aryl, -alkylene-arylene-alkyl, -alkylene-arylene-aryl, -alkylene-arylene-alkylene-aryl, -alkylene-arylene-O-arylene, or alkylene-arylene-O-alkylene-aryl; and $T_2$ comprises a direct bond, —$CH_2$—, —O—, —$N(R_{24})$—, —C(O)—, —$CON(R_{24})$—, —$N(R_{24})C(O)$—, —$N(R_{24})CON(R_{25})$—, —$N(R_{24})C(O)O$—, —$OC(O)N(R_{24})$—, —$N(R_{24})SO_2$—, —$SO_2N(R_{24})$—, —C(O)—O—, —O—C(O)—, —S—, —S(O)—, —$S(O_2)$—, —$N(R_{24})SO_2N(R_{25})$—, wherein $R_{24}$ and $R_{25}$ independently comprise; -hydrogen, -alkyl, -alkenyl, -alkylene-cycloalkyl, alkynene-heterocyclyl, -aryl, -heteroaryl, -arylene-alkyl, -alkylene-aryl, or -alkylene-arylene-alkyl.

In another embodiment, $Ar_2$ comprises a substituted phenyl, 2-naphthyl, 3-isoquinolyl, 2-quinazolyl, or 3-tetrahydroisoquinolyl group having 1 to 5 substituents independently comprising:

a) -fluoro;
b) -chloro;
c) -bromo;
d) -iodo;
e) -cyano;
f) -nitro;
g) -perfluoroalkyl;
h) -$T_1$-$R_{20}$;
i) -alkyl;
j) -aryl;
k) -arylene-alkyl;
l) -$T_1$-alkyl;
m) -$T_1$-alkylene-aryl;
n) -$T_1$-alkylene-arylene-aryl;
o) -$T_1$-alkylene-arylene-alkyl;
p) -arylene-$T_1$-alkyl;
q) -alkylene-cycloalkyl; or
r) -$T_1$-arylene-alkyl wherein $T_1$ comprises —$CH_2$—, —O—, —$N(R_{21})$—, —$CON(R_{21})$—, —$C(O)O$—$R_{21}$ or —$N(R_{21})C(O)$—; wherein $R_{20}$ and $R_{21}$ independently comprise: -hydrogen, -alkyl, or -aryl.

In another embodiment, $Ar_2$ comprises (1-alkylene-cycloalkyl)-(alkyl-phenoxy)-2-isoquinolyl group.

In another embodiment $Ar_2$ comprises: 5-bromo-2-heptyloxy-benzyl, 5-bromo-2-(3-trifluoromethyl-phenoxy)-benzyl, 4'-trifluoromethyl-biphenyl, 4'-trifluoromethoxy-biphenyl, 5-bromo-2-(4-tert-butyl-benzenesulfonylamino)-benzyl, 5-chloro-2-diethylamino-benzyl, 5-chloro-2-(4-trifluoromethyl-phenylamino)-benzyl, 2-(cyclopentyl-acetyl)-7-(4-trifluoromethyl-benzyloxy)-1,2,3,4-tetrahydro-isoquinoline, (4-trifluoromethyl-phenoxy)-3,4-dihydro-1H-isoquinoline-2-carboxylic acid tert-butyl ester, (4-trifluoromethyl-benzyloxy)-3,4-dihydro-1H-isoquinoline-2-carboxylic acid tert-butyl ester, 2-(2-Cyclopentyl-acetyl)-7-(4-trifluoromethyl-phenoxy)-1,2,3,4-tetrahydro-isoquinoline, 7-(4-tert-butyl-phenoxy)-2-(2-cyclopentyl-acetyl)-1,2,3,4-tetrahydro-isoquinoline, 6-(4-tert-butyl-phenoxy)-2-(2-cyclopentyl-acetyl)-1,2,3,4-tetrahydro-isoquinoline, 7-(4-tert-butyl-phenoxy)-3,4-dihydro-1H-isoquinoline-2-carboxylic acid isobutyl ester, 4-Hydroxy-4'-trifluoromethyl-biphenyl, 4-methoxy-4'-trifluoromethyl-biphenyl, 4-hydroxy-4'-trifluoromethyl-biphenyl, 6-(4-tert-butyl-phenoxy)-isoquinoline, 7-(4-tert-butyl-phenoxy)-isoquinoline, 6-(4-tert-butyl-phenoxy)-isoquinoline, 6-(4-trifluoromethoxy-phenoxy)-isoquinoline, 5-(4-tert-butyl-phenoxy)-indole-1-carboxylic acid tert-butyl ester, 6-(4-tert-butyl-phenoxy)-3-ethylsulfanyl-quinoxaline, 7-(4-tert-butyl-phenoxy)-1-cyclopentylmethyl-isoquinoline, 7-(4-tert-butyl-phenoxy)-1-cyclohexyl-isoquinoline, 7-(4-tert-Butyl-phenoxy)-1-cycloheptyl-isoquinoline, 7-(4-tert-Butyl-phenoxy)-1-phenethyl-isoquinoline, or 6-(4-tert-butyl-phenoxy)-1-cyclopentylmethyl-isoquinoline.

K comprises: —$CO_2H$, an acid isotere, or a group of the formula

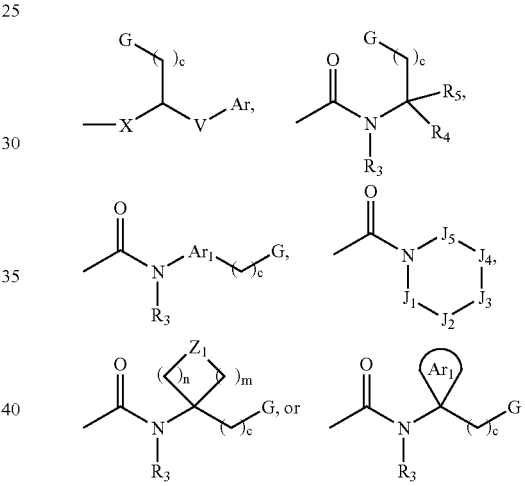

wherein c is equal to 0, 1, or 2; wherein the values of 0, 1, and 2 comprise a direct bond, —$CH_2$—, and —$CH_2$—$CH_2$—, optionally substituted 1 to 4 times with a substituent comprising: -alkyl, -aryl, -alkylene-aryl, -arylene-alkyl, -alkylene-arylene-alkyl, —O-alkyl, —O-aryl, or -hydroxyl. In an embodiment, c is equal to 0 or 1. In another embodiment, c is equal to 0.

G comprises: -hydrogen, —$CO_2R_1$, —$CH_2OR_1$, —C(O)—$R_1$, —$C(R_1)$=N—O—$R_2$, —C(O)N ($R_1$)($R_2$), —C(O)—NH—$NH_2$, an acid isotere, or an ester isotere, wherein $R_1$ and $R_2$ independently comprise: -hydrogen, -alkyl, alkoxy, alkylhydroxy, alkyl-N,N'-dialkyl-amino, alkyl-amino-acyl, -aryl, -arylene-alkyl, -alkylene-aryl, -alkylene-arylene-alkyl, or when $R_1$ and $R_2$ are bonded to a nitrogen group in G, $R_1$ and $R_2$ may be taken together to form a ring having the formula —$(CH_2)_m$-$Z_2$—$(CH_2)_n$—, wherein m and n are, independently, 1, 2, 3, or 4; $Z_2$ comprises —$CH_2$—, —C(O)—, —O—, —N(H)—, —S—, —S(O)—, —$S(O_2)$—, —CON(H)—, —NHC(O)—, —$NHC(O)N(H)$—, —NH($SO_2$)—, —$S(O_2)N(H)$—, —(O)CO—, —$NHS(O_2)NH$—, —OC(O)—, —$N(R_{24})$—, —$N(C(O)R_{24})$—, —N(C(O)

$NHR_{12}$)—, —N(S(O$_2$)NHR$_{24}$)—, —N(SO$_2$R$_{24}$)—, or —N(C(O)OR$_{24}$)—; wherein R$_{24}$ comprises hydrogen, aryl, alkyl, or alkylene-aryl. In an embodiment, G comprises: -hydrogen, —CO$_2$R$_1$, —CH$_2$OR$_1$, —C(O)—R$_1$, —C(R$_1$)=N—O—R$_2$, an acid isostere, or an ester isostere; wherein R$_1$ and R$_2$ independently comprise: -hydrogen, -alkyl, -aryl, -arylene-alkyl, -alkylene-aryl, or -alkylene-arylene-alkyl. In another embodiment, G comprises: -hydrogen or —CO$_2$R$_1$; wherein R$_1$ comprises: -hydrogen, -alkyl, or -aryl. In another embodiment, G comprises: -hydrogen or —CO$_2$H. In another embodiment, G comprises: —CO$_2$R$_1$ or an ester isostere, wherein R$_1$ comprises -alkyl, -alkylene-aryl, or -aryl. In another embodiment, G comprises an ester isostere comprising a 3-alkyl-[1,2,4]oxadiazol-5-yl group.

R$_3$ comprises: hydrogen, -alkyl, alkylene-aryl, -aryl, or -alkylene-cycloalkyl. In an embodiment, R$_3$ comprises: hydrogen. In another embodiment, R$_3$ comprises: -alkyl, alkylene-aryl, or -alkylene-cycloalkyl.

R$_4$ comprises: hydrogen, -alkyl, -alkylene-cycloalkyl, or -alkylene-heterocyclyl, -alkylene. R$_5$ comprises: hydrogen, -alkyl, -alkylene-cycloalkyl, -alkylene-heterocyclyl, -alkoxy, alkylhydroxy, alkyl-N,N'-dialkyl-amino, or -alkyl-aminoacyl. In an embodiment, R$_4$ comprises: hydrogen, and R$_5$ comprises: alkyl, -alkoxy, alkylhydroxy, or -alkylene-cycloalkyl.

J$_1$, J$_2$, J$_3$, J$_4$, J$_5$ independently comprise —C(R$_{25}$)(R$_{26}$)— or a direct bond, wherein R$_{25}$ and R$_{26}$ independently comprise hydrogen, -alkyl, -aryl, -alkylene-aryl, alkoxy, alkylhydroxy, alkylene-O-alkyl, alkylene-O-alkylene-aryl, —CO$_2$H, -alkylene-CO$_2$H, , —CO$_2$-alkyl, -alkylene-CO$_2$-alkyl, -acid isostere, or -ester isostere, and wherein the ring comprising nitrogen and J$_1$ through J$_5$ contains at least four carbon atoms and at least one of J$_1$ through J$_5$ is substituted with —CO$_2$H, -alkylene-CO$_2$H, —CO$_2$-alkyl, -alkylene-CO$_2$-alkyl, -acid isostere, or -ester isostere.

Z$_1$ comprises —CH$_2$—, —C(O)—, —O—, —N(H)—, —S—, —S(O)—, —S(O)$_2$—, —CON(H)—, —NHC(O)—, —NHC(O)N(H)—, —NH(SO$_2$)—, —S(O)$_2$N(H)—, —(O)CO—, —NHS(O)$_2$NH—, —OC(O)—, —N(R$_6$)—, —N(C(O)R$_6$)—, —N(C(O)NHR$_6$)—, —N(S(O)$_2$)NHR$_6$)—, —N(SO$_2$R$_6$)—, or —N(C(O)OR$_6$)—; wherein R$_6$ comprises: -hydrogen, alkyl, aryl, or alkylene-aryl. In an embodiment, Z$_1$ comprises —CH$_2$—, —O—, —N(H)—, —S—, —S(O$_2$)—, —N(R$_6$)—, or —N(C(O)OR$_6$)—, wherein R$_6$ comprises alkyl or alkylene-aryl.

V comprises: —(CH$_2$)$_b$—S—(CH$_2$)$_a$—, —(CH$_2$)$_b$—S—, —S—(CH$_2$)$_a$—, —(CH$_2$)$_b$—S(O$_2$)—(CH$_2$)$_a$—, —(CH$_2$)$_b$—S(O$_2$)—, S(O$_2$)—(CH$_2$)$_a$—, —(CH$_2$)$_b$—O—(CH$_2$)$_a$—, (CH$_2$)$_b$—N(R$_7$)—(CH$_2$)$_a$—, —(CH$_2$)$_b$—O—, —(CH$_2$)$_b$—N(R$_7$), —(CH$_2$)$_a$—, or a direct bond; in which a is equal to 0, 1, or 2, b is equal to 1 or 2, and R$_7$ comprises: -hydrogen, -alkyl, -aryl, -arylene-alkyl, -alkylene-aryl, or -alkylene-arylene-alkyl; wherein the values of 0, 1, and 2 comprise a direct bond, —CH$_2$—, and —CH$_2$—CH$_2$—, optionally substituted 1 to 4 times with a substituent group comprising: -alkyl, -aryl, -alkylene-aryl, -arylene-alkyl, -alkylene-arylene-alkyl, —O-alkyl, —O-aryl, or -hydroxyl. In an embodiment, V comprises: —(CH$_2$)$_b$—O—(CH$_2$)$_a$—, —(CH$_2$)b—N(R$_7$)—(CH$_2$)$_a$—, —(CH$_2$)$_b$—O—, —(CH$_2$)$_b$—N(R$_7$), —(CH$_2$)$_a$—, or a direct bond; in which a is equal to 0, 1, or 2, b is equal to 1 or 2, and R$_7$ comprises: -hydrogen, -alkyl, -aryl, -arylene-alkyl, -alkylene-aryl, or -alkylene-arylene-alkyl; wherein the values of 0, 1, and 2 comprise a direct bond, —CH$_2$—, and —CH$_2$—CH$_2$—, optionally substituted 1 to 4 times with a substituent comprising: -alkyl, -aryl, -alkylene-aryl, -arylene-alkyl, -alkylene-arylene-alkyl, —O-alkyl, —O-aryl, or -hydroxyl. In another embodiment, V comprises: —(CH$_2$)$_a$—, —(CH$_2$)$_b$—O—(CH$_2$)$_a$—, or a direct bond, wherein a is equal to 1 or 2, and b is equal to 1. In another embodiment, V comprises: —(CH$_2$)$_a$— or a direct bond, wherein a is equal to 1.

X comprises: —N(R$_8$)—, —CON(R$_8$)—, —N(R$_8$)CO—, —N(R$_8$)CON(R$_9$)—, —OC(O)N(R$_8$)—, —SO$_2$N(R$_8$)—, or —N(R$_8$)SO$_2$N(R$_9$)—; wherein R$_8$ and R$_9$ independently comprise: -hydrogen, -alkyl, -aryl, -arylene-alkyl, -alkylene-aryl, -alkylene-arylene-alkyl, -alkylene-cycloalkylene-C(O)-alkylene-aryl, -alkylene-heterocyclylene-C(O)-alkylene-aryl, -alkylene-C(H)(R$_{10}$)(R$_{11}$), -alkylene-N—(R$_{10}$)(R$_{11}$), or -alkylene-cycloalkyl, wherein R$_{10}$ comprises H, alkyl, alkylene-aryl, alkylene-heteroaryl, aryl, or heteroaryl, and R$_{11}$ comprises H, -alkyl, -alkylene-aryl, -alkylene-heteroaryl, -aryl, -heteroaryl, —C(O)—O-alkyl, —C(O)—O-alkylene-aryl, —C(O)—O-alkylene-heteroaryl, —C(O)-alkyl, —C(O)-alkylene-aryl, —C(O)-alkylene-heteroaryl, —S(O)$_2$-alkyl, —S(O)$_2$-aryl, —S(O)$_2$-heteroaryl, —S(O)$_2$-alkylene-aryl, —S(O)$_2$-alkylene-heteroaryl, —S(O)$_2$—NH-alkyl, —S(O)$_2$—NH-alkylene-aryl, —S(O)$_2$—NH-alkylene-heteroaryl, —S(O)$_2$—NH-aryl, or —S(O)$_2$-NH-heteroaryl;

R$_{10}$ and R$_{11}$ may be taken together to form a ring having the formula —(CH$_2$)$_m$-Z$_2$—(CH$_2$)$_n$— bonded to the nitrogen or carbon atom to which R$_{10}$ and R$_{11}$ are attached, wherein m and n are, independently, 1, 2, 3, or 4; Z$_2$ comprises —CH$_2$—, —C(O)—, —O—, —N(H)—, —S—, —S(O)—, —S(O)$_2$—, —CON(H)—, —NHC(O)—, —NHC(O)N(H)—, —NH(SO$_2$)—, —S(O)$_2$N(H)—, —(O)CO—, —NHS(O)$_2$NH—, —OC(O)—, —N(R$_{12}$)—, —N(C(O)R$_{12}$)—, —N(C(O)NHR$_{12}$)—, —N(S(O)$_2$)NHR$_{12}$)—, —N(SO$_2$Rl$_2$)—, or —N(C(O)OR$_{12}$)—; wherein R$_{12}$ comprises hydrogen, aryl, alkyl, or alkylene-aryl; or R$_{10}$ and R$_{11}$ may be taken together, with the nitrogen or carbon atom to which they are attached, to form a heteroaryl ring; and;

In an embodiment, X comprises: —N(R$_8$)—, —CON(R$_8$)—, —N(R$_8$)CO—, or —N(R$_8$)CON(R$_9$)—, wherein R$_8$ and R$_9$ independently comprise: -hydrogen, -alkyl, -aryl, -arylene-alkyl, -alkylene-aryl, or -alkylene-arylene-alkyl. In another embodiment, X comprises: —N(R$_8$)—, —CON(R$_8$)—, or —N(R$_8$)CO—, wherein R$_8$ comprises: -hydrogen, -alkyl, -aryl, -arylene-alkyl, -alkylene-aryl, or -alkylene-arylene-alkyl. In another embodiment, X comprises —CON(R$_8$)—, wherein R$_8$ comprises -hydrogen, -alkyl, -aryl, -arylene-alkyl, -alkylene-aryl, -alkylene-arylene-alkyl, or -alkylene-cycloalkyl. In another embodiment, X comprises —CON(R$_8$)—, wherein R$_8$ comprises -alkylene-C(H)(R$_{10}$)(R$_{11}$), wherein R$_{10}$ and R$_{11}$ form a ring having the formula —(CH$_2$)$_m$-Z$_2$—(CH$_2$)$_n$— bonded to the carbon atom to which R$_{10}$ and R$_{11}$ are attached, wherein m and n are, independently, 2 or 3, and Z$_2$ comprises —N(R$_{12}$)—, —N(C(O)R$_{12}$)—, or —N(C(O)OR$_{12}$)—, wherein R$_{12}$ comprises R$_{12}$ comprises hydrogen, aryl, alkyl, or alkylene-aryl.

Ar$_1$ comprises an aryl, heteroaryl, fused cycloalkylaryl, fused cycloalkylheteroaryl, fused heterocyclylaryl, or fused heterocyclylheteroaryl group optionally substituted 1 to 7 times. In an embodiment, Ar$_1$ comprises a mono- or bicyclic aryl or heteroaryl group optionally substituted 1 to 7 times. In another embodiment, Ar$_1$ comprises a phenyl, pyridyl, indolyl, naphthyl, thiophenyl, thiazole, or benzothiazole group optionally substituted 1 to 5 times. In various embodiments, the substituents of Ar$_1$ may independently comprise:

a) -fluoro;
b) -chloro;
c) -bromo;
d) -iodo;
e) -cyano;

f) -nitro;
g) -perfluoroalkyl;
h) -$D_1$-$R_{14}$;
i) -alkyl;
j) -aryl;
k) -heteroaryl;
l) -heterocyclyl;
m) -cycloalkyl;
n) -alkylene-aryl;
o) -alkylene-heteroaryl;
p) -alkylene-arylene-$D_1$-$R_{14}$;
q) -alkylene-heteroarylene-$D_1$-$R_{14}$;
r) -alkylene-arylene-aryl;
s) -alkylene-heteroarylene-aryl;
t) -alkylene-arylene-heteroaryl;
u) -alkylene-arylene-arylene-$D_1$-$R_{14}$;
v) -alkylene-arylene-alkyl;
w) -alkylene-heteroarylene-alkyl;
x) -$D_1$-cycloalkyl;
y) -arylene-cycloalkyl;
z) -heteroarylene-alkyl;
aa) -arylene-arylene-alkyl;
bb) -$D_1$-alkyl;
cc) -$D_1$-aryl;
dd) -$D_1$-heteroaryl;
ee) -$D_1$-arylene-$D_2$-$R_{14}$;
ff) -$D_1$-heteroarylene-$D_2$-$R_{14}$;
gg) -$D_1$-alkylene-heteroaryl;
hh) -$D_1$-alkylene-aryl;
ii) -$D_1$-alkylene-arylene-$D_2$-$R_{14}$
jj) -$D_1$-alkylene-heteroarylene-$D_2$-$R_{14}$
kk) -$D_1$-arylene-alkyl;
ll) -$D_1$-heteroarylene-alkyl;
mm) -$D_1$-alkylene-arylene-aryl;
nn) -$D_1$-alkylene-heteroarylene-aryl;
oo) -$D_1$-arylene-arylene-aryl;
pp) -$D_1$-alkylene-arylene-alkyl;
qq) -$D_1$-alkylene-heteroarylene-alky
ss) -alkylene-$D_1$-alkylene-aryl;
tt) -alkylene-$D_1$-alkylene-arylene-$D_2$-$R_{14}$
uu) -arylene-$D_1$-alkyl;
vv) -arylene-$D_1$-cycloalkyl;
ww) -arylene-$D_1$-heterocyclyl;
xx) -alkylene-$D_1$-aryl;
yy) -alkylene-$D_1$-heteroaryl;
zz) -alkylene-$D_1$-arylene-$D_2$-$R_{14}$
aaa) -alkylene-$D_1$-heteroarylene-$D_2$-$R_{14}$
bbb) -alkylene-$D_1$-heteroaryl;
ccc) -alkylene-$D_1$-cycloalkyl;
ddd) -alkylene-$D_1$-heterocyclyl;
eee) -alkylene-$D_1$-arylene-alkyl;
fff) -alkylene-$D_1$-heteroarylene-alkyl;
ggg) -alkylene-$D_1$-alkylene-arylene-alkyl;
hh) -alkylene-$D_1$-alkylene-heteroarylene-alkyl;
iii) -alkylene-$D_1$-alkyl;
jjj) -alkylene-$D_1$-$R_{14}$;
kkk) -arylene-$D_1$-$R_{14}$;
lll) -heteroarylene-$D_1$-$R_{14}$;
mmm) -$D_1$-alkynyl;
nnn) -$D_1$-alkylene-cycloalkyl;
ooo) -arylene-$D_1$-arylene-$D_2$-$R_{14}$ or
ppp) -hydrogen;

wherein
$R_{14}$, comprises: -hydrogen, -alkyl, -aryl, -heteroaryl, -arylene-alkyl, -heteroarylene-alkyl, -alkylene-aryl, -alkylene-heteroaryl, -alkylene-arylene-alkyl, or -alkylene-heteroarylene-alkyl;
$D_1$ comprises —$CH_2$—, -alkylene-, -alkenylene-, -alkylene-S—, —S-alkylene-, -alkylene-O—, —O-alkylene-, -alkylene-S(O)$_2$—, —S(O)$_2$-alkylene, —O—, —N($R_{15}$)—, —C(O)—, —CON($R_{15}$)—, —N($R_{15}$)C(O)—, —N($R_{15}$)CON($R_{16}$)—, —N($R_{15}$)C(O)O—, —OC(O)N($R_{15}$)—, —N($R_{15}$)SO$_2$—, —SO$_2$N($R_{15}$)—, —C(O)—O—, —O—C(O)—, —S—, —S(O)—, —S(O$_2$)—, —N($R_{15}$)SO$_2$N($R_{16}$)—,

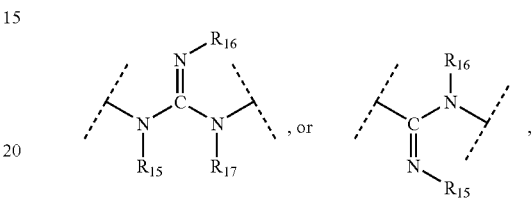

wherein $R_{15}$, $R_{16}$, and $R_{17}$ independently comprise: -hydrogen, -alkyl, -aryl, -heteroaryl, -arylene-alkyl, -heteroarylene-alkyl, -alkylene-aryl, -alkylene-heteroaryl, -alkylene-arylene-alkyl, or -alkylene-heteroarylene-alkyl; and
$D_2$ comprises —$CH_2$—, -alkylene-, -alkenylene-, -alkylene-S—, —S-alkylene-, -alkylene-O—, —O-alkylene-, -alkylene-S(O)$_2$—, —S(O)$_2$-alkylene, —O—, —N($R_{18}$)—, —C(O)—, —CON($R_{18}$)—, —N($R_{18}$)C(O)—, —N($R_{18}$)CON($R_{19}$)—, —N($R_{18}$)C(O)O—, —OC(O)N($R_{18}$)—, —N($R_{18}$)SO$_2$—, —SO$_2$N($R_{18}$)—, —C(O)—O—, —O—C(O)—, —S—, —S(O)—, —S(O$_2$)—, —N($R_{18}$)SO$_2$N($R_{19}$)—,
wherein $R_{18}$ and $R_{19}$ independently comprise: -hydrogen, -alkyl, -aryl, -arylene-alkyl, -alkylene-aryl, or -alkylene-arylene-alkyl.

In another embodiment, $Ar_1$ comprises a mono-substituted phenyl group wherein the substituent comprises: -aryl, -arylene-alkyl, -$D_1$-aryl, -$D_1$-alkylene-arylene-alkyl, or -arylene-$D_1$-alkyl; wherein $D_1$ comprises —O—, —N($R_{15}$)—, —CON($R_{15}$)—, or —N($R_{15}$)C(O)—, and wherein $R_{15}$ comprises: -hydrogen; -alkyl; or -aryl.

In another embodiment, $Ar_1$ comprises a phenyl group substituted with at least one of the following sustituents:
a) -$D_1$-$R_{14}$;
b) -alkyl;
c) -aryl;
d) -heteroaryl;
e) -heterocyclyl;
f) -arylene-alkyl;
g) -$D_1$-alkyl;
h) -$D_1$-aryl;
i) -$D_1$-heteroaryl;
j) -$D_1$-arylene-$D_2$-$R_{14}$;
k) -$D_1$-alkylene-heteroaryl;
l) -$D_1$-alkylene-aryl;
m) -$D_1$-alkylene-arylene-$D_2$-$R_{14}$;
n) -arylene-$D_1$-alkyl;
o) -alkylene-$D_1$-alkyl;
p) -alkylene-$D_1$-$R_{14}$;
q) -arylene-$D_1$-$R_{14}$;
r) -$D_1$-alkynyl;
s) -$D_1$-alkylene-cycloalkyl; or
t) -arylene-$D_1$-arylene-$D_2$-$R_{14}$;

wherein

D₁ and D₂ independently comprise: —O— or —S(O₂)—, and R₁₄ comprises hydrogen, -alkyl, -aryl, -arylene-aryl, -alkylene-aryl.

In another embodiment, wherein K comprises the group of the formula

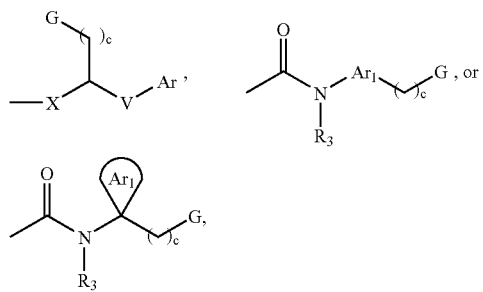

Ar₁ comprises phenyl, 2'-phenoxy-biphenyl-4-yl, 2'-(4-trifluoromethyl-phenoxy)-biphenyl-4-yl, 3-biphenyl-4-yl, 4'-phenoxy-biphenyl-4-yl, 2'-trifluoromethyl-biphenyl-4-yl, 3'-(4-trifluoromethyl-phenoxy)-biphenyl-4-yl, 2-(4-benzyloxy-phenyl), 4-(4-trifluoromethyl-phenoxy)-phenyl, 3'-chloro-4'-fluoro-biphenyl-4-yl, 4-(4-trifluoromethyl-phenoxy)-phenyl, 4-phenoxy-phenyl, 4-(3-trifluoromethyl-phenoxy)-phenyl, 2-biphenyl-4-yl, 4'-trifluoromethyl-biphenyl-4-yl, 3'-chloro-4'-fluoro-biphenyl-4-yl, 4'-methanesulfonyl-biphenyl-4-yl, 4-cyclopentylmethoxy-phenyl, 4'-trifluoromethoxy-biphenyl-4-yl, 2-cyclopentyl-ethoxy)-phenyl, 4-(4-trifluoromethoxy-phenoxy)-phenyl, 3-thiophen-3-yl, benzoic acid methyl ester, or 3-trifluoromethyl-phenyl.

The alkyl, aryl, heteroaryl, alkylene, and arylene groups in Ar₁, Ar₂, R₁ through R₂₆ may be optionally substituted 1 to 4 times with a substituent comprising:
a) -hydrogen;
b) -fluoro;
c) -chloro;
d) -bromo;
e) -iodo;
f) -cyano;
g) -nitro;
h) -perfluoroalkyl;
i) -Q-perfluoroalkyl
j) -Q-R₂₇;
k) -Q-alkyl;
l) -Q-aryl;
m) -Q-alkylene-aryl;
n) -Q-alkylene-NR₂₇R₂₈; or
o) -Q-alkyl-W—R₂₈;

wherein Q and W independently comprise: —CH₂—, —O—, —N(R₂₉)—, —C(O)—, —CON(R₂₉)—, —N(R₂₉)C(O)—, —N(R₂₉)CON(R₃₀)—, —N(R₂₉)C(O)O—, —OC(O)N(R₂₉)—, —N(R₂₉)SO₂—, —SO₂N(R₂₉)—, —C(O)—O—, —O—C(O)—, or —N(R₂₉)SO₂N(R₃₀)—, wherein R₂₇, R₂₈, R₂₉, and R₃₀ independently comprise: -hydrogen, -alkyl, -aryl, -arylene-alkyl, -alkylene-aryl, or -alkylene-arylene-alkyl.

Example compounds of the present invention are listed below in Table 1.

TABLE 1

| Example | Structure | Name |
|---|---|---|
| 1 | 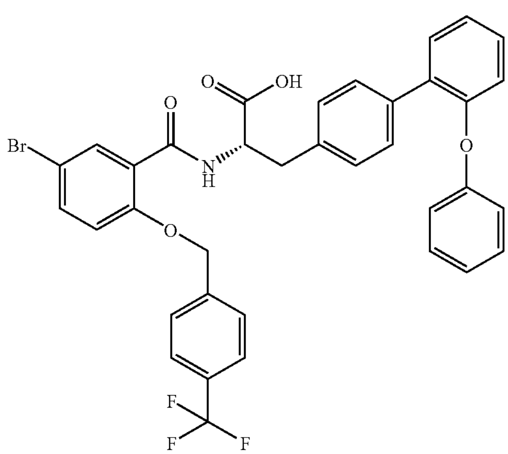 | (2S)-[5-Bromo-2-(4-trifluoromethyl-benzyloxy)-benzoylamino]-3-(2'-phenoxy-biphenyl-4-yl)-propionic acid |

TABLE 1-continued

| Example | Structure | Name |
|---|---|---|
| 2 | 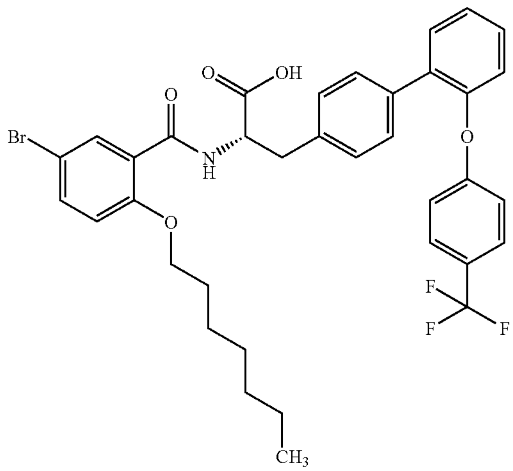 | (2S)-(5-Bromo-2-heptyloxy-benzoylamino)-3-[2'-(4-trifluoromethyl-phenoxy)-biphenyl-4-yl]-propionic acid |
| 3 | 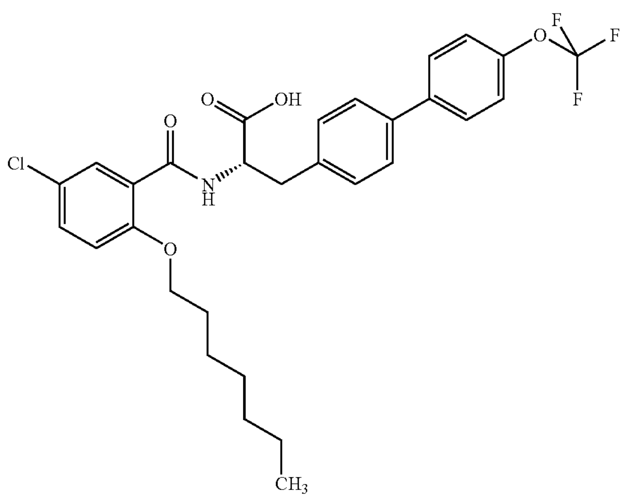 | (2S)-(5-Chloro-2-heptyloxy-benzoylamino)-3-(4'-trifluoromethoxy-biphenyl-4-yl)-propionic acid |
| 4 | 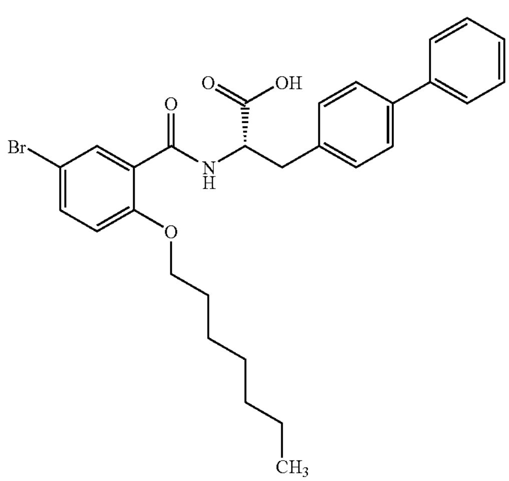 | 3-Biphenyl-4-yl-(2S)-(5-bromo-2-heptyloxy-benzoylamino)-propionic acid |

TABLE 1-continued

| Example | Structure | Name |
|---|---|---|
| 5 | 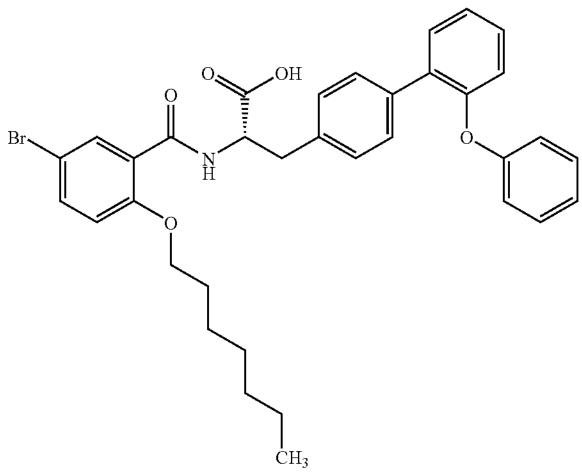 | (2S)-(5-Bromo-2-heptyloxy-benzoylamino)-3-(2'-phenoxy-biphenyl-4-yl)-propionic acid |
| 6 | 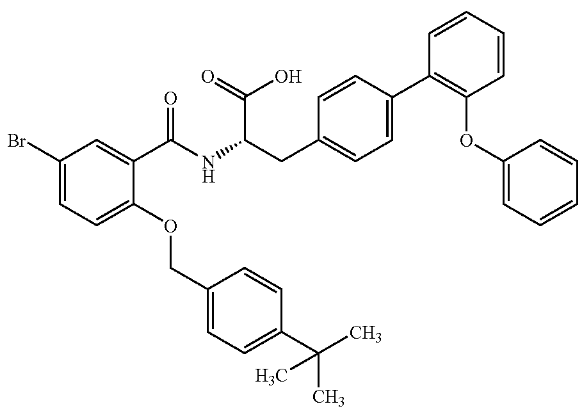 | (2S)-[5-Bromo-2-(4-tert-butyl-benzyloxy)-benzoyl-amino]-3-(2'-phenoxy-biphenyl-4-yl)-propionic acid |
| 7 | 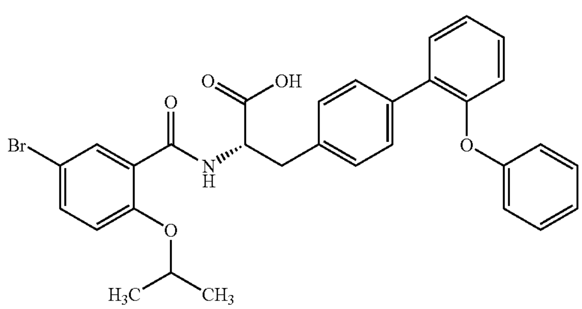 | (2S)-(5-Bromo-2-isopropoxy-benzoylamino)-3-(2'-phenoxy-biphenyl-4-yl)-propionic acid |
| 8 | 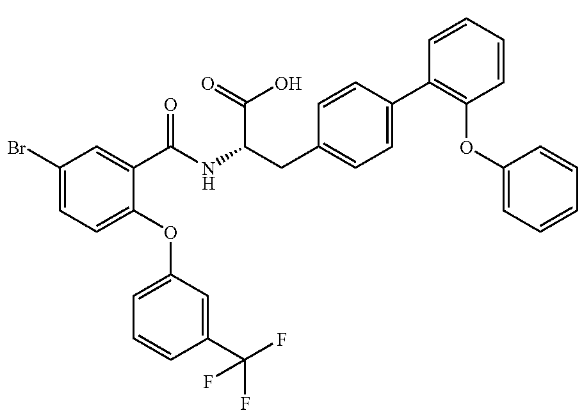 | (2S)-[5-Bromo-2-(3-trifluoromethyl-phenoxy)-benzoyl-amino]-3-(2'-phenoxy-biphenyl-4-yl)-propionic acid |

TABLE 1-continued

| Example | Structure | Name |
| --- | --- | --- |
| 9 | 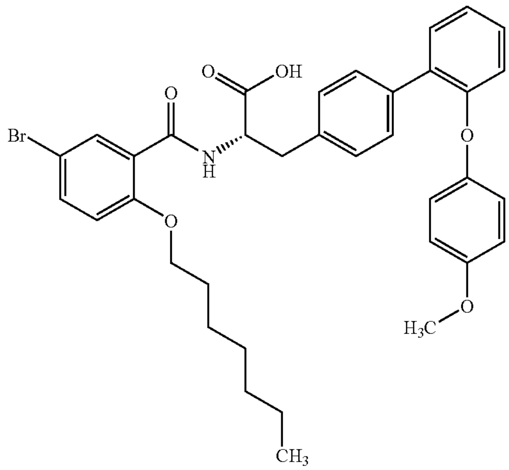 | (2S)-(5-Bromo-2-heptyloxy-benzoylamino)-3-[2'-(4-methoxy-phenoxy)-biphenyl-4-yl]-propionic acid |
| 10 | 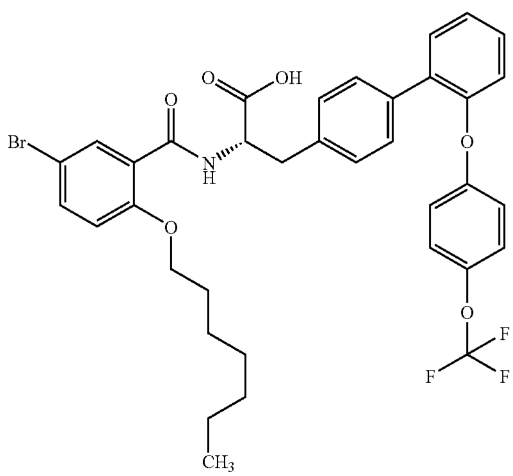 | (2S)-(5-Bromo-2-heptyloxy-benzoylamino)-3-[2'-(4-trifluoromethoxy-phenoxy)-biphenyl-4-yl]-propionic acid |
| 11 | 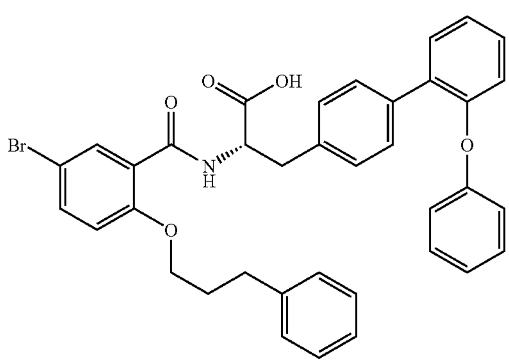 | (2S)-[5-Bromo-2-(3-phenyl-propoxy)-benzoylamino]-3-(2'-phenoxy-biphenyl-4-yl)-propionic acid |

TABLE 1-continued

| Example | Structure | Name |
|---|---|---|
| 12 | 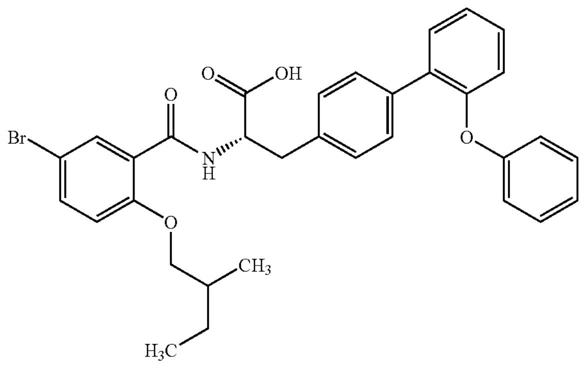 | (2S)-[5-Bromo-2-(2-methyl-butoxy)-benzoylamino]-3-(2'-phenoxy-biphenyl-4-yl)-propionic acid |
| 13 | 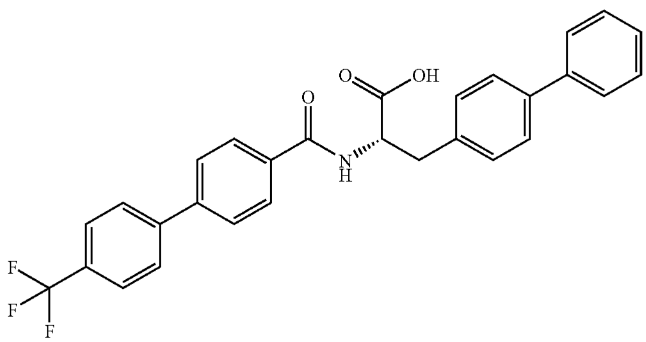 | 3-Biphenyl-4-yl-(2S)-[(4'-trifluoromethyl-biphenyl-4-carbonyl)-amino]-propionic acid |
| 14 | 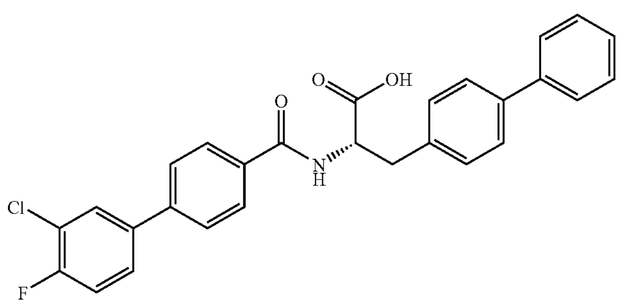 | 3-Biphenyl-4-yl-(2S)-[(3'-chloro-4'-fluoro-biphenyl-4-carbonyl)-amino]-propionic acid |
| 15 | 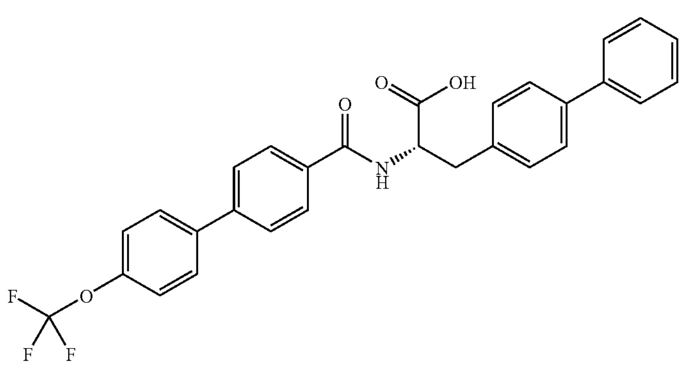 | 3-Biphenyl-4-yl-(2S)-[(4'-trifluoromethoxy-biphenyl-4-carbonyl)-amino]-propionic acid |

TABLE 1-continued

| Example | Structure | Name |
|---|---|---|
| 16 | 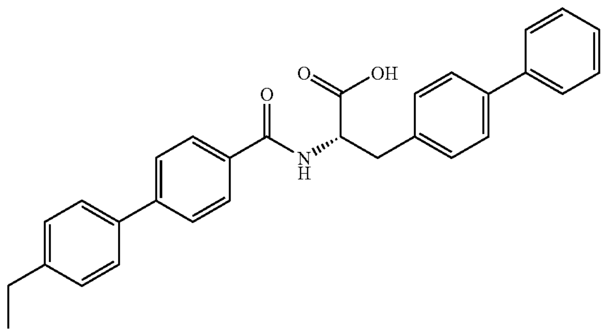 | 3-Biphenyl-4-yl-(2S)-[(4'-ethyl-biphenyl-4-carbonyl)-amino]-propionic acid |
| 17 | 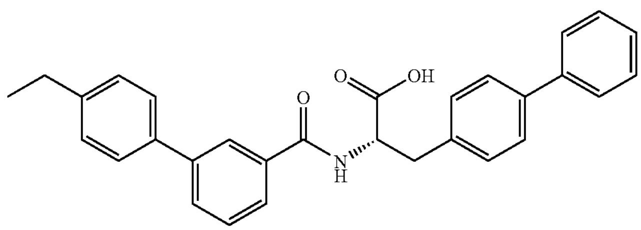 | 3-Biphenyl-4-yl-(2S)-[(3'-ethyl-biphenyl-3-carbonyl)-amino]-propionic acid |
| 18 | 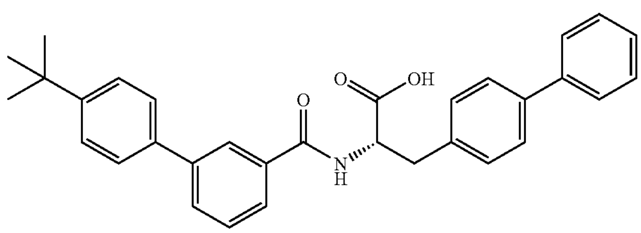 | 3-Biphenyl-4-yl-(2S)-[(4'-tert-butylbiphenyl-3-carbonyl)-amino]-propionic acid |
| 19 | 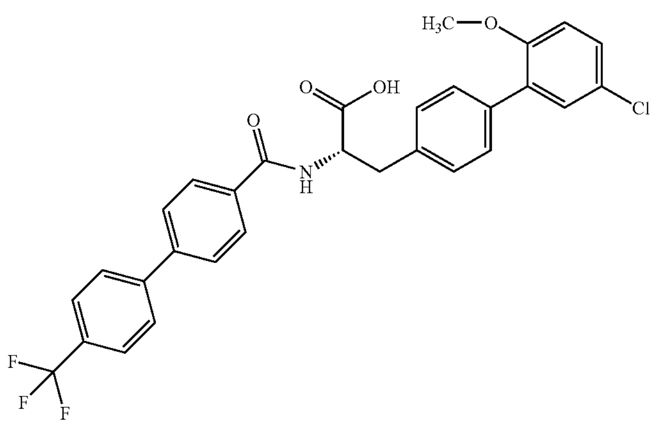 | 3-(5'-Chloro-2'-methoxy-biphenyl-4-yl)-(2S)-[(4'-trifluoromethyl-biphenyl-4-carbonyl)-amino]-propionic acid |
| 20 | 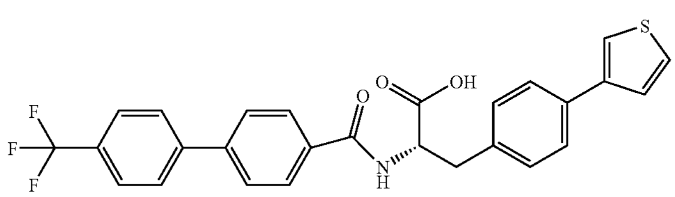 | 3-(4-Thiophen-3-yl-phenyl)-(2S)-[(4'-trifluoromethyl-biphenyl-4-carbonyl)-amino]-propionic acid |

TABLE 1-continued

| Example | Structure | Name |
|---|---|---|
| 21 | 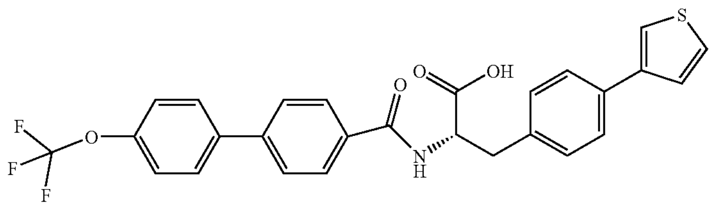 | 3-(4-Thiophen-3-yl-phenyl)-(2S)-[(4'-trifluoromethoxy-biphenyl-4-carbonyl)-amino]-propionic acid |
| 22 | 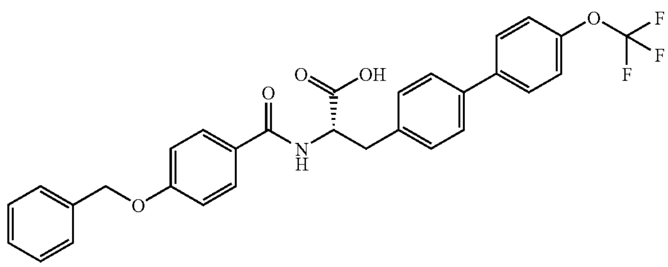 | (2S)-(4-Benzyloxy-benzoylamino)-3-(4'-trifluoromethoxy-biphenyl-4-yl)-propionic acid |
| 23 | 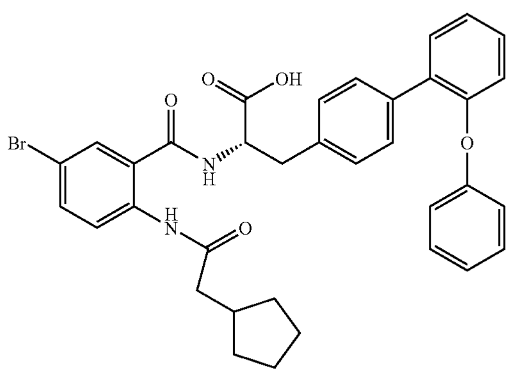 | (2S)-[5-bromo-2-(2-cyclopentyl-acetylamino)-benzoyl-amino]-3-(2'-phenoxy-biphenyl-4-yl)-propionic acid |
| 24 | 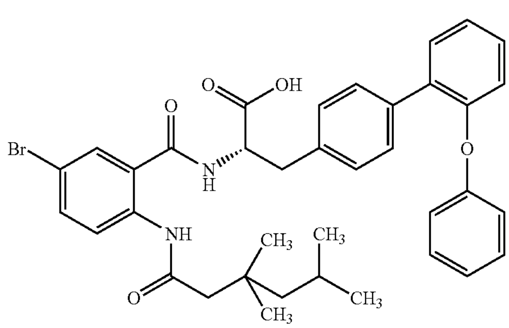 | (2S)-[5-Bromo-2-(3,3,5-trimethyl-hexanoyl-amino)-benzoylamino]-3-(2'-phenoxy-biphenyl-4-yl)-propionic acid |

TABLE 1-continued

| Example | Structure | Name |
|---|---|---|
| 25 | 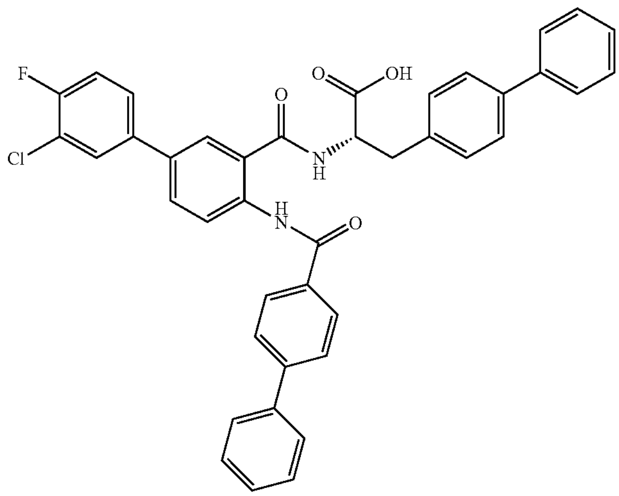 | (2S)-({4-[(Biphenyl-4-carbonyl)-amino]-3'-chloro-4'-fluoro-biphenyl-3-carbonyl}-amino)-3-biphenyl-4-yl-propionic acid |
| 26 | 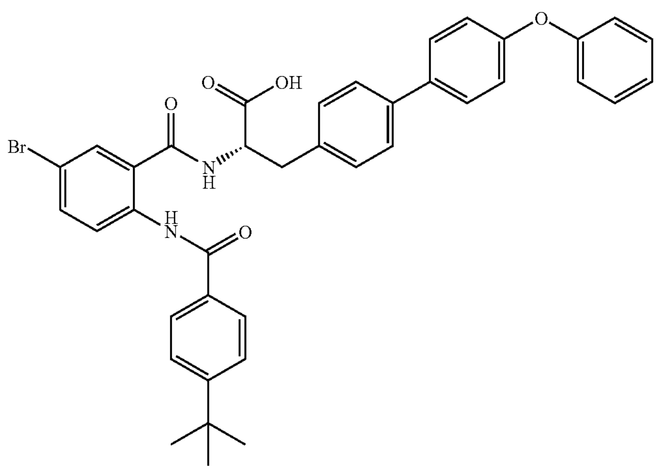 | 2-[5-Bromo-(2S)-(4-tert-butyl-benzoylamino)-benzoylamino]-3-(4'-phenoxy-biphenyl-4-yl)-propionic acid |
| 27 | 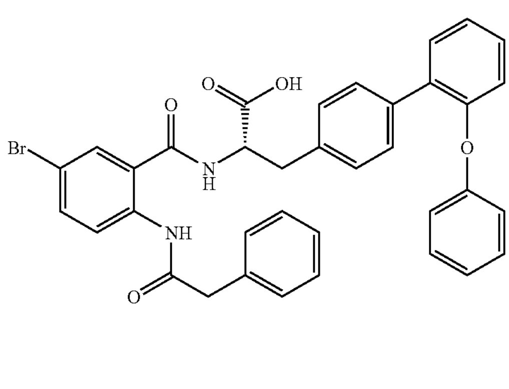 | (2S)-(5-Bromo-2-phenylacetylamino-benzoylamino)-3-(2'-phenoxy-biphenyl-4-yl)-propionic acid |

TABLE 1-continued

| Example | Structure | Name |
|---|---|---|
| 28 | 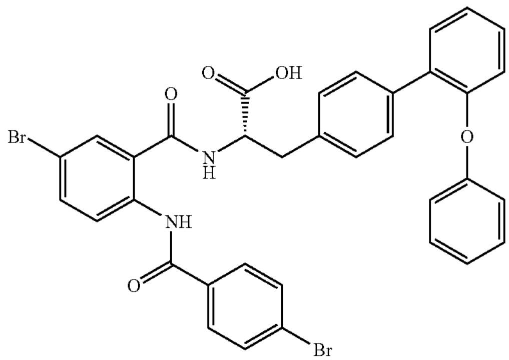 | (2S)-[5-Bromo-2-(4-bromo-benzoylamino)-benzoylamino]-3-(2'-phenoxy-biphenyl-4-yl)-propionic acid |
| 29 | 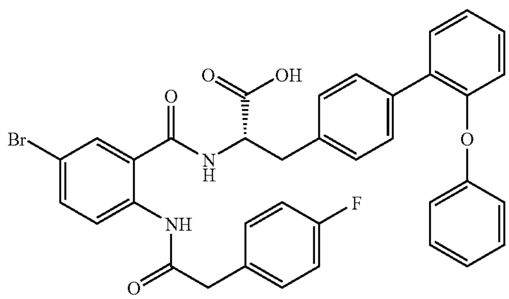 | (2S)-{5-Bromo-2-[2-(4-fluoro-phenyl)-acetylamino]-benzoyl-amino}-3-(2'-phenoxy-biphenyl-4-yl)-propionic acid |
| 30 | 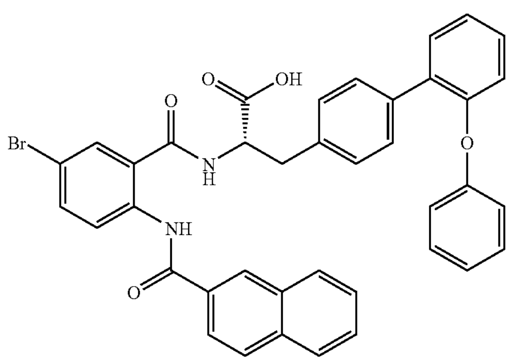 | 2-{5-Bromo-(2S)-[(naphthalene-2-carbonyl)-amino]-benzoylamino}-3-(2'-phenoxy-biphenyl-4-yl)-propionic acid |
| 31 | 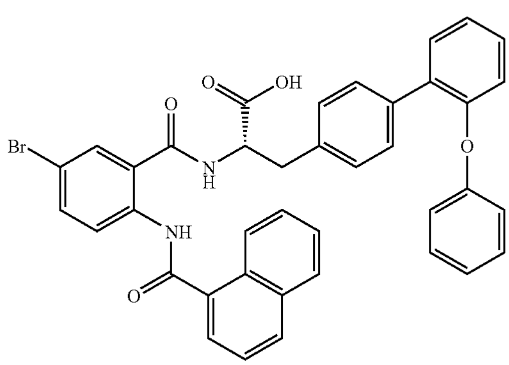 | (2S)-{5-Bromo-2-[(naphthalene-1-carbonyl)-amino]-benzoylamino}-3-(2'-phenoxy-biphenyl-4-yl)-propionic acid |

TABLE 1-continued

| Example | Structure | Name |
|---|---|---|
| 32 | 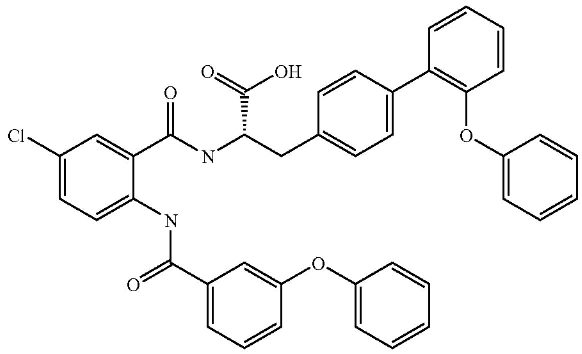 | (2S)-[5-Chloro-2-(3-phenoxy-benzoylamino)-benzoylamino]-3-(2'-phenoxy-biphenyl-4-yl)-propionic acid |
| 33 | 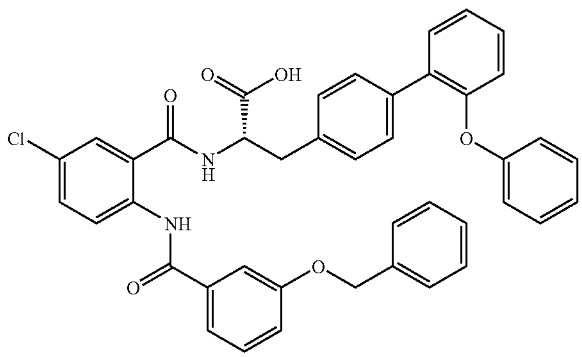 | (2S)-[2-(3-Benzyloxy-benzoylamino)-5-chloro-benzoylamino]-3-(2'-phenoxy-biphenyl-4-yl)-propionic acid |
| 34 | 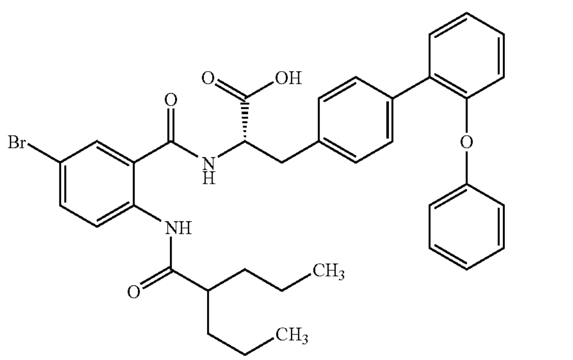 | (2S)-[5-Bromo-2-(2-propyl-pentanoylamino)-benzoylamino]-3-(2'-phenoxy-biphenyl-4-yl)-propionic acid |
| 35 | 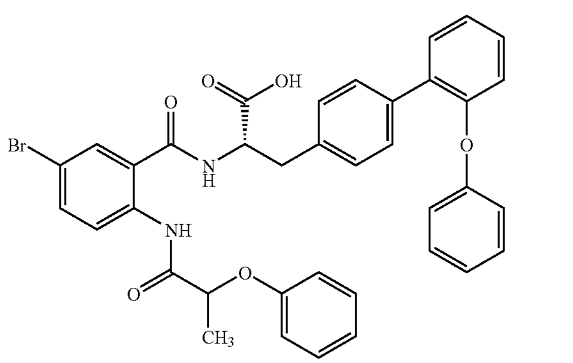 | (2S)-[5-Bromo-2-(2-phenoxy-propionyl-amino)-benzoylamino]-3-(2'-phenoxy-biphenyl-4-yl)-propionic acid |

TABLE 1-continued

| Example | Structure | Name |
|---|---|---|
| 36 | 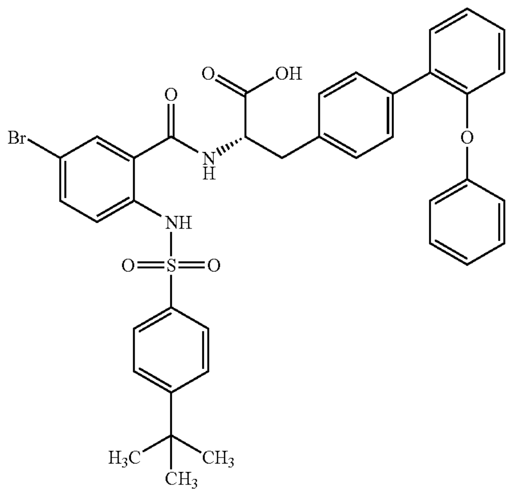 | (2S)-[5-Bromo-2-(4-tert-butyl-benzenesulfonylamino)-benzoylamino]-3-(2'-phenoxy-biphenyl-4-yl)-propionic acid |
| 37 | 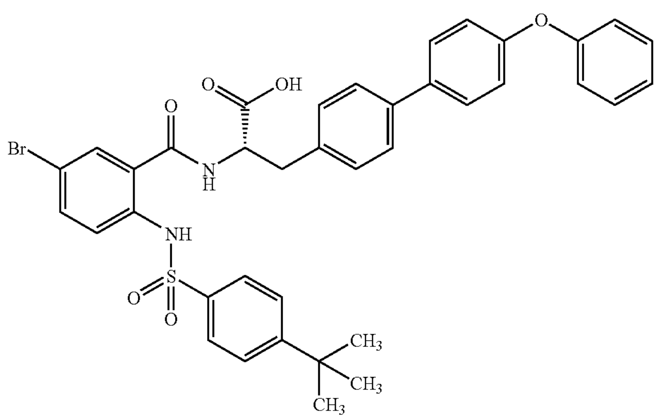 | (2S)-[5-Bromo-2-(4-tert-butyl-benzenesulfonylamino)-benzoylamino]-3-(4'-phenoxy-biphenyl-4-yl)-propionic acid |
| 38 | 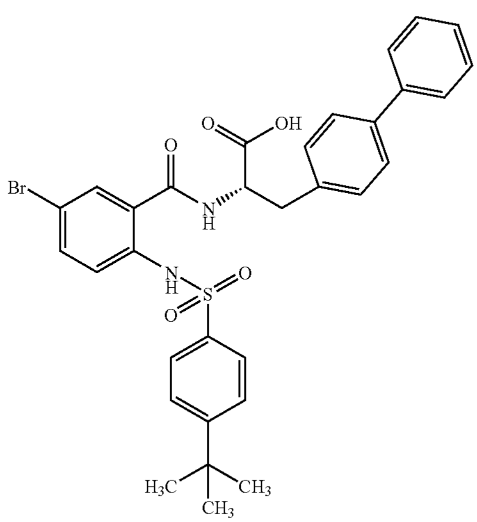 | 3-Biphenyl-4-yl-(2S)-[5-bromo-2-(4-tert-butyl-benzenesulfonylamino)-benzoylamino]-propionic acid |

TABLE 1-continued

| Example | Structure | Name |
|---|---|---|
| 39 | 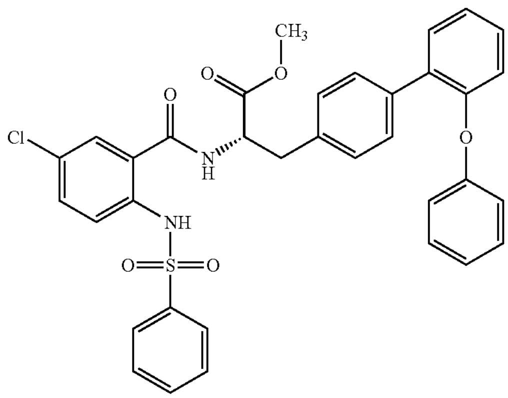 | (2S)-(2-Benzenesulfonylamino-5-chloro-benzoylamino)-3-(2'-phenoxy-biphenyl-4-yl)-propionic acid methyl ester |
| 40 | 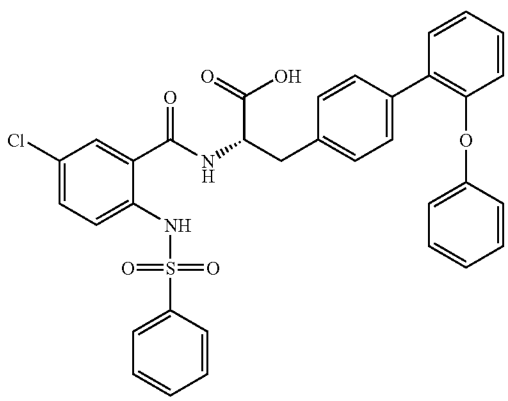 | (2S)-(2-Benzenesulfonylamino-5-chloro-benzoylamino)-3-(2'-phenoxy-biphenyl-4-yl)-propionic acid |
| 41 | 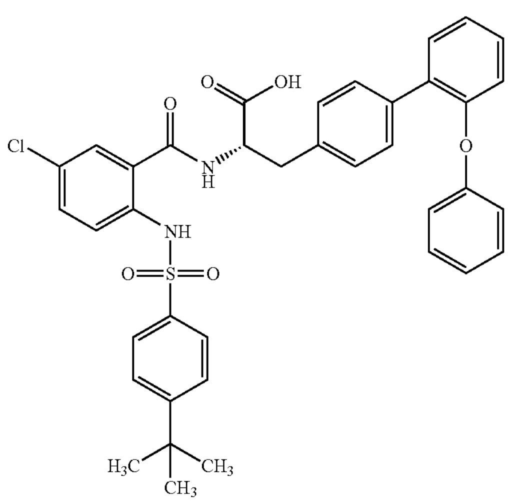 | (2S)-[2-(4-tert-Butyl-benzenesulfonylamino)-5-chloro-benzoylamino]-3-(2'-phenoxy-biphenyl-4-yl)-propionic acid |

TABLE 1-continued

| Example | Structure | Name |
|---|---|---|
| 42 | 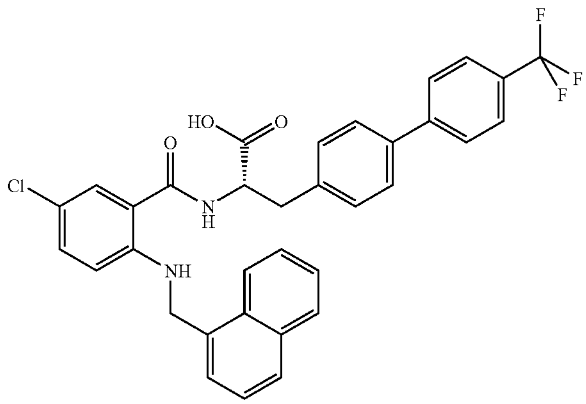 | 2-{5-Chloro-2-[(naphthalen-1-ylmethyl)-amino]-benzoylamino}-3-(4'-trifluoromethyl-biphenyl-4-yl)-propionic acid |
| 43 | 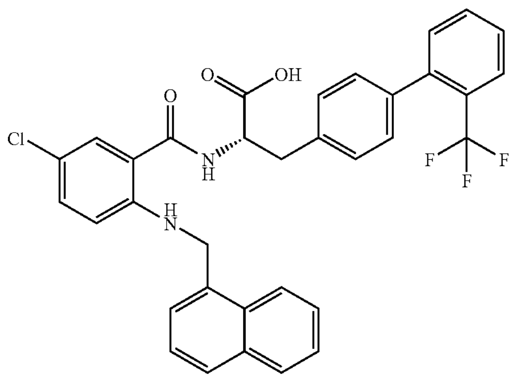 | (2S)-{5-Chloro-2-[(naphthalen-1-ylmethyl)-amino]-benzoylamino}-3-(2'-trifluoromethyl-biphenyl-4-yl)-propionic acid |
| 44 | 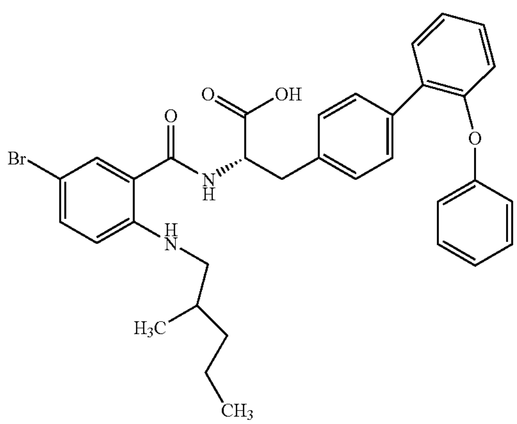 | (2S)-[5-Bromo-2-(2-methyl-pentylamino)-benzoylamino]-3-(2'-phenoxy-biphenyl-4-yl)-propionic acid |
| 45 | 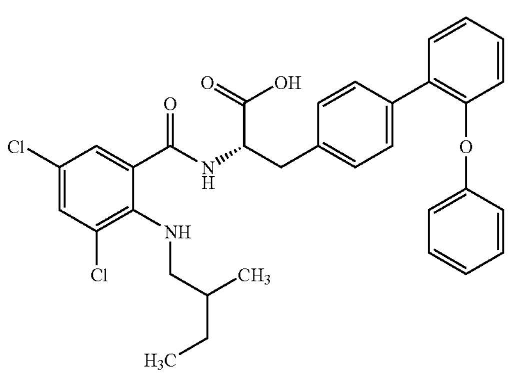 | (2S)-[3,5-Dichloro-2-(2-methyl-butylamino)-benzoylamino]-3-(2'-phenoxy-biphenyl-4-yl)-propionic acid |

TABLE 1-continued

| Example | Structure | Name |
|---|---|---|
| 46 | 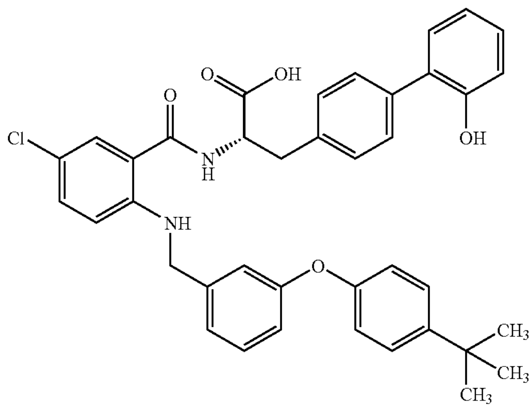 | (2S)-{2-[3-(4-tert-Butyl-phenoxy)-benzylamino]-5-chloro-benzoylamino}-3-(2'-hydroxy-biphenyl-4-yl)-propionic acid |
| 47 | 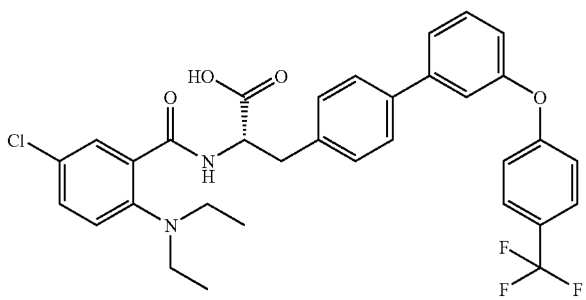 | (2S)-(5-Chloro-2-diethylamino-benzoyl-amino)-3-[3'-(4-trifluoromethyl-phenoxy)-biphenyl-4-yl]-propionic acid |
| 48 | 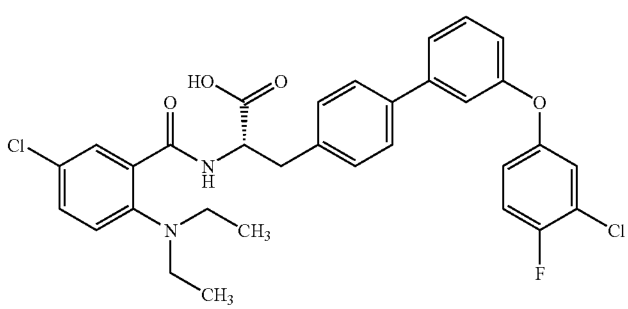 | (2S)-(5-Chloro-2-diethylamino-benzoyl-amino)-3-(3'-(3-chloro-4-fluorophenoxy)-biphenyl-4-yl]-propionic acid |
| 49 | 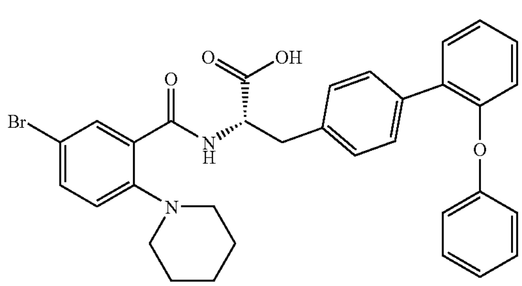 | (2S)-(5-Bromo-2-piperidin-1-yl-benzoylamino)-3-(2'-phenoxy-biphenyl-4-yl)-propionic acid |

TABLE 1-continued

| Example | Structure | Name |
|---|---|---|
| 50 | 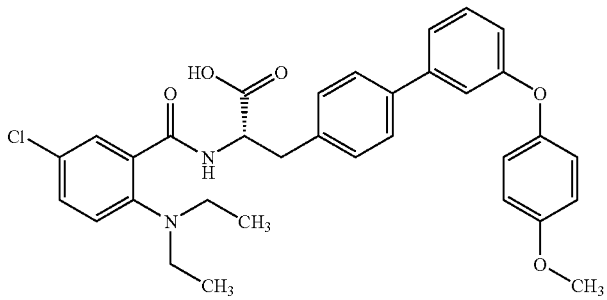 | (2S)-(5-Chloro-2-diethylamino-benzoylamino)-3-[3'-(4-methoxy-phenoxy)-biphenyl-4-yl]-propionic acid |
| 51 | 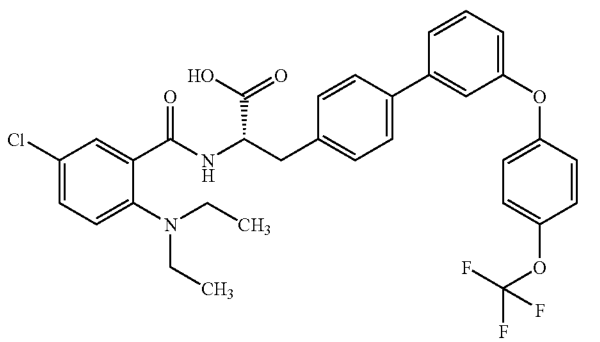 | (2S)-(5-Chloro-2-diethylamino-benzoylamino)-3-[3'-(4-trifluoromethoxy-phenoxy)-biphenyl-4-yl]-propionic acid |
| 52 | 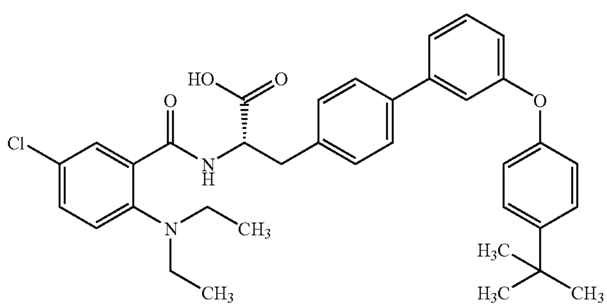 | 3-[3'-(4-tert-Butyl-phenoxy)-biphenyl-4-yl]-(2S)-(5-chloro-2-diethylamino-benzoyl-amino)-propionic acid |
| 53 | 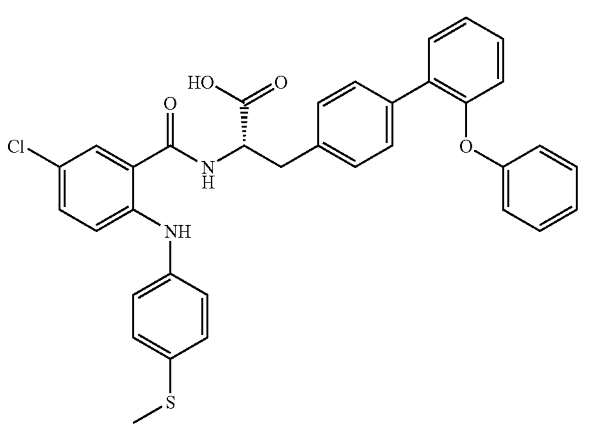 | (2S)-[5-Chloro-2-(4-methylsulfanyl-phenylamino)-benzoyl-amino]-3-(2'-phenoxy-biphenyl-4-yl)-propionic acid |

TABLE 1-continued

| Example | Structure | Name |
|---|---|---|
| 54 | 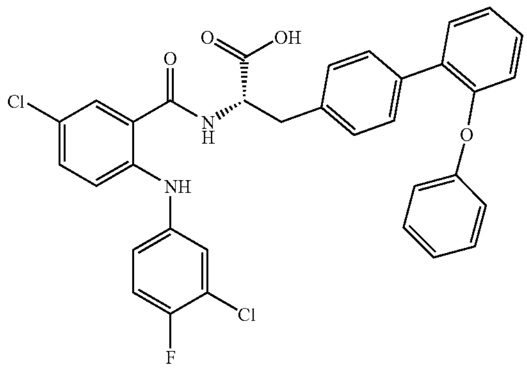 | (2S)-[5-Chloro-2-(3-chloro-4-fluoro-phenylamino)-benzoyl-amino]-3-(2'-phenoxy-biphenyl-4-yl)-propionic acid |
| 55 | 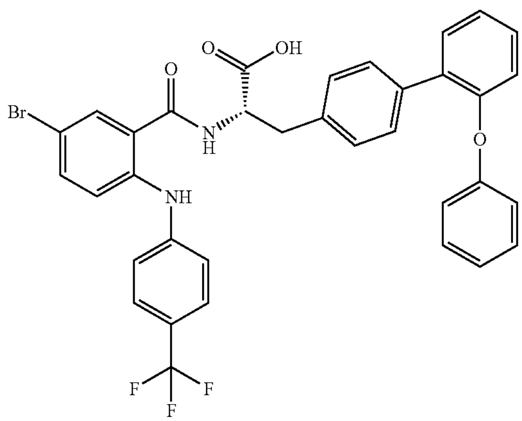 | (2S)-[5-Bromo-2-(4-trifluoromethyl-phenylamino)-benzoyl-amino]-3-(2'-phenoxy-biphenyl-4-yl)-propionic acid |
| 56 | 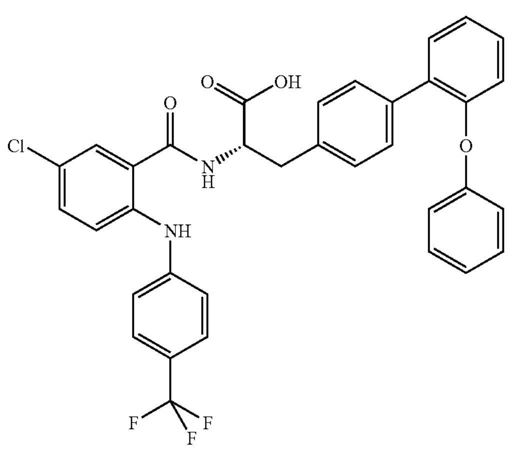 | (2S)-[5-Chloro-2-(4-trifluoromethyl-phenylamino)-benzoyl-amino]-3-(2'-phenoxy-biphenyl-4-yl)-propionic acid |

TABLE 1-continued

| Example | Structure | Name |
|---|---|---|
| 57 | 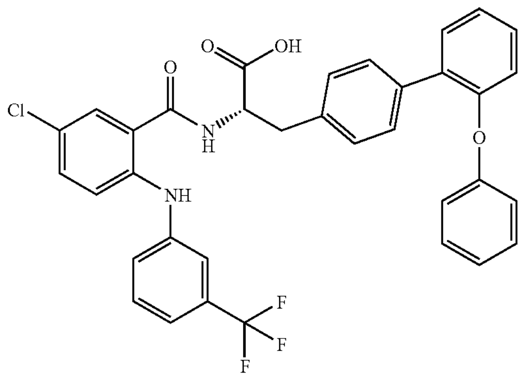 | (2S)-[5-Chloro-2-(3-trifluoromethyl-phenylamino)-benzoyl-amino]-3-(2'-phenoxy-biphenyl-4-yl)-propionic acid |
| 58 | 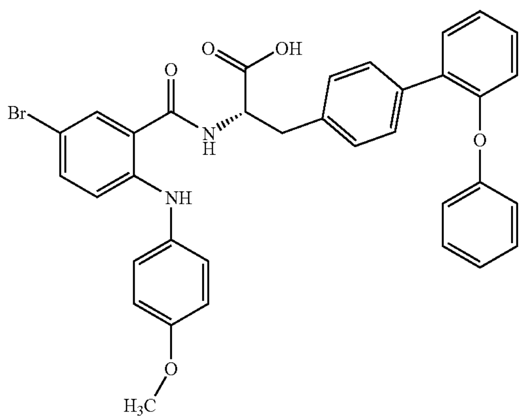 | (2S)-[5-Chloro-2-(4-methoxy-phenylamino)-benzoylamino]-3-(2'-phenoxy-biphenyl-4-yl)-propionic acid |
| 59 | 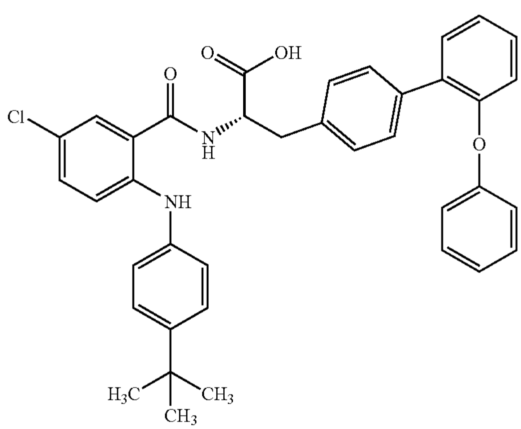 | (2S)-[2-(4-tert-Butyl-phenylamino)-5-chloro-benzoylamino]-3-(2'-phenoxy-biphenyl-4-yl)-propionic acid |
| 60 | 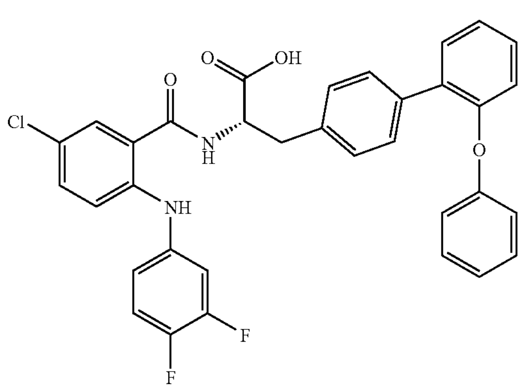 | (2S)-[5-Chloro-2-(3,4-difluoro-phenylamino)-benzoylamino]-3-(2'-phenoxy-biphenyl-4-yl)-propionic acid |

TABLE 1-continued

| Example | Structure | Name |
|---|---|---|
| 61 | 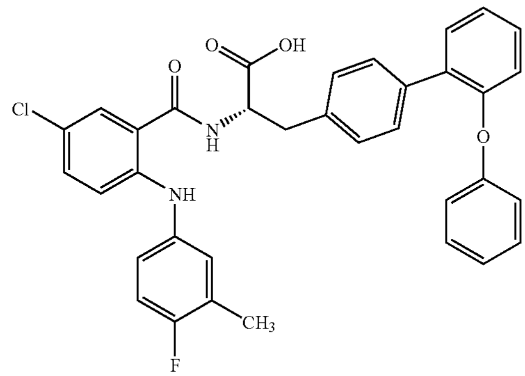 | (2S)-[5-Chloro-2-(4-fluoro-3-methyl-phenylamino)-benzoyl-amino]-3-(2'-phenoxy-biphenyl-4-yl)-propionic acid |
| 62 | 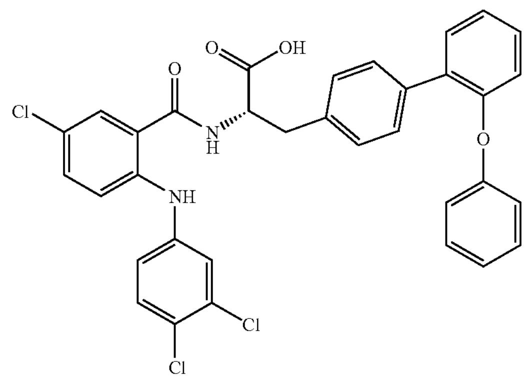 | (2S)-[5-Chloro-2-(3,4-dichloro-phenylamino)-benzoylamino]-3-(2'-phenoxy-biphenyl-4-yl)-propionic acid |
| 63 | 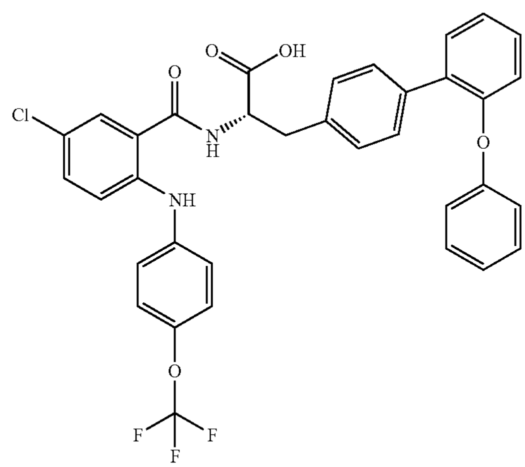 | (2S)-[5-Chloro-2-(4-trifluoromethoxy-phenylamino)-benzoyl-amino]-3-(2'-phenoxy-biphenyl-4-yl)-propionic acid |
| 64 | 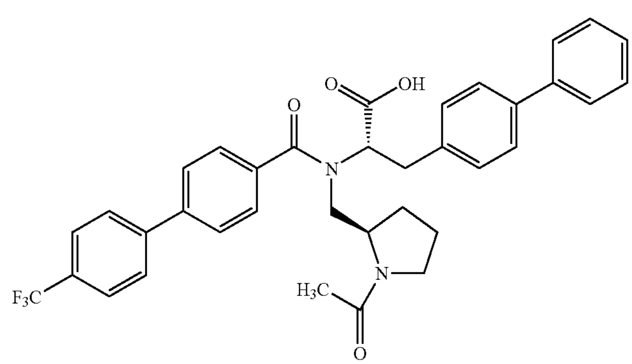 | (2S)-[(1-Acetyl-(2R)-pyrrolidin-2-ylmethyl)-(4-trifluoromethyl-biphenyl-4-carbonyl)-amino]-3-biphenyl-4-yl-propionic acid |

TABLE 1-continued

| Example | Structure | Name |
|---|---|---|
| 65 | 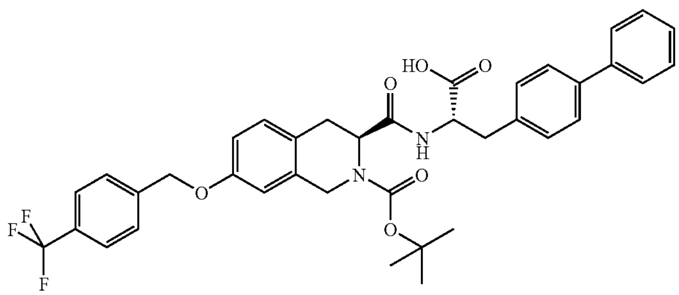 | (3S)-(2-Biphenyl-4yl-(1S)-carboxy-ethylcarbamoyl)-7-(4-trifluoromethyl-benzyloxy)-3,4-dihydro-1H-isoquinoline-2-carboxylic acid tert-butyl ester |
| 66 | 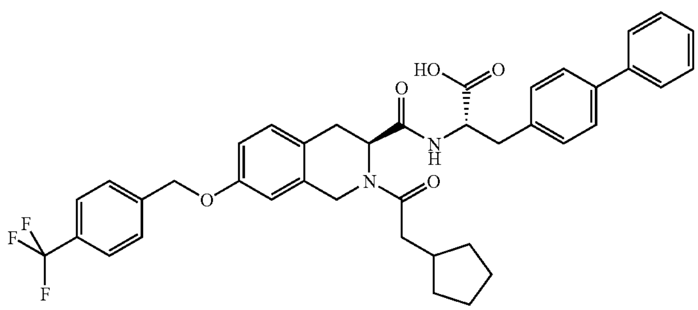 | 3-Biphenyl-4-yl-(2S)-{[2-(cyclopentyl-acetyl)-7-(4-trifluoromethyl-benzyloxy)-1,2,3,4-tetrahydro-isoquinoline-(3S)-carbonyl]-amino}-propionic acid: |
| 67 | 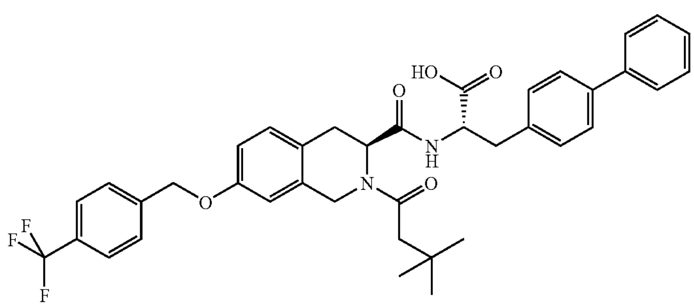 | 3-Biphenyl-4-yl-(2S)-{(2-(3,3-dimethyl-butyryl)-7-(4-trifluoromethyl-benzyloxy)-1,2,3,4-tetrahydro-isoquinoline-(3S)-carbonyl]-amino}-propionic acid |
| 68 | 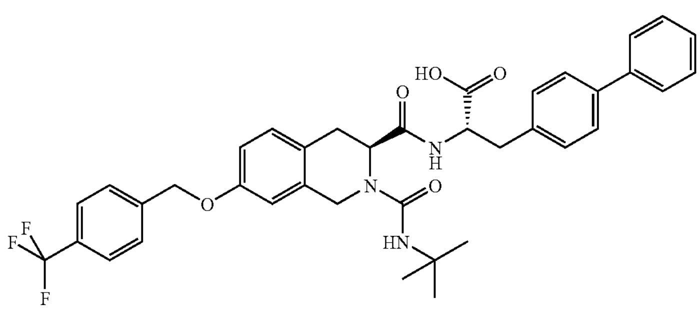 | 3-Biphenyl-4-yl-(2S)-{[2-tert-butylcarbamoyl-7-(4-trifluoromethyl-benzyloxy)-1,2,3,4-tetrahydro-isoquinoline-(3S)-carbonyl]-amino}-propionic acid |
| 69 | 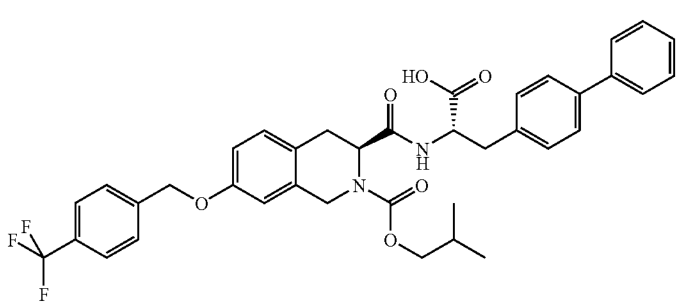 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid isobutyl ester |

TABLE 1-continued

| Example | Structure | Name |
|---|---|---|
| 70 | 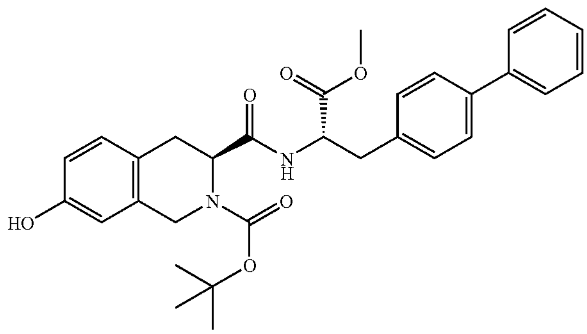 | (3S)-(2-Biphenyl-4-yl-(1S)-methoxycarbonyl-ethylcarbamoyl)-7-hydroxy-3,4-dihydro-1H-isoquinoline-2-carboxylic acid tert-butyl ester |
| 71 | 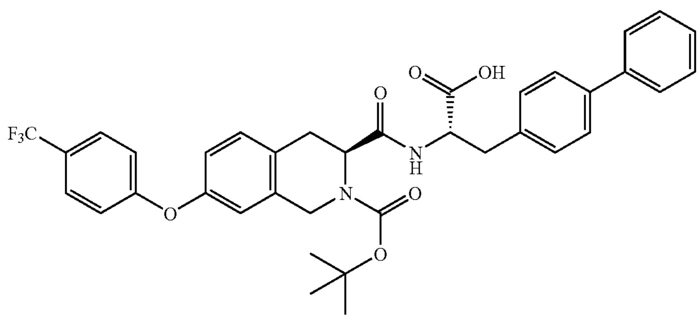 | (3S)-(2-Biphenyl-4-yl-(1S)-methoxycarbonyl-ethylcarbamoyl)-7-(4-trifluoromethyl-phenoxy)-3,4-dihydro-1H-isoquinoline-2-carboxylic acid |
| 72 | 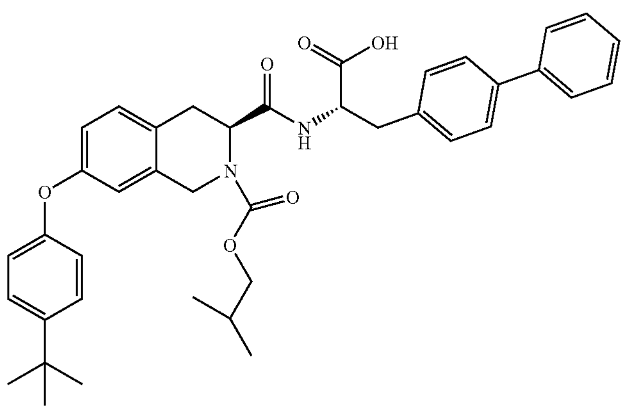 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid isobutyl ester |
| 73 | 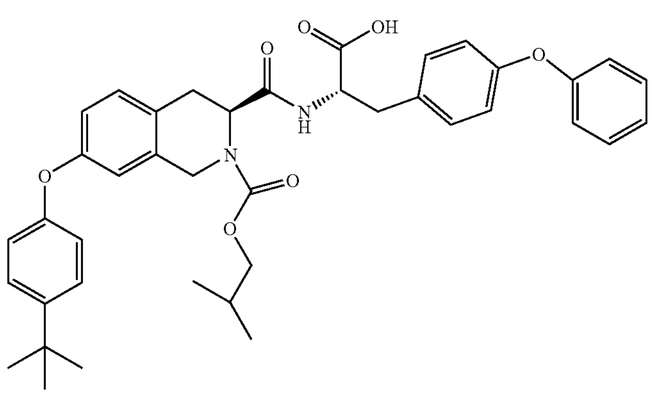 | 7-(4-tert-Butyl-phenoxy)-(3S)-[(1S)-carboxy-2-(4-phenoxy-phenyl)-ethylcarbamoyl]-3,4-dihydro-1H-isoquinoline-2-carboxylic acid isobutyl ester |

TABLE 1-continued

| Example | Structure | Name |
|---|---|---|
| 74 | 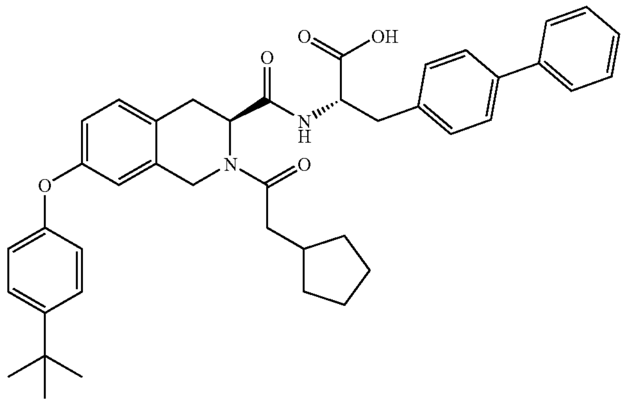 | 3-Biphenyl-4-yl-(2S)-{[7-(4-tert-butyl-phenoxy)-2-(2-cyclopentyl-acetyl)-1,2,3,4-tetrahydro-isoquinoline-(3S)-carbonyl]-amino}-propionic acid |
| 75 | 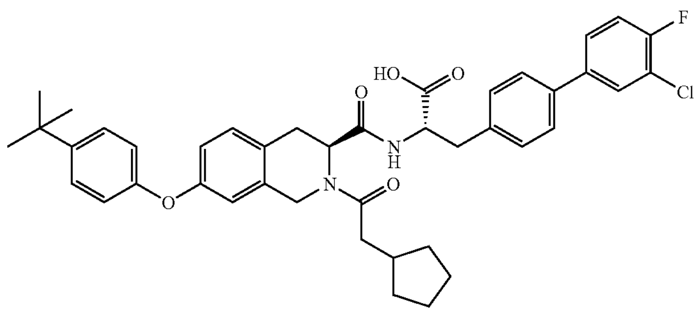 | (3S)-(2-Biphenyl-4-yl-(1S)-carboxy-ethylcarbamoyl)-7-hydroxy-3,4-dihydro-1H-isoquinoline-2-carboxylic acid tert-butyl ester |
| 76 | 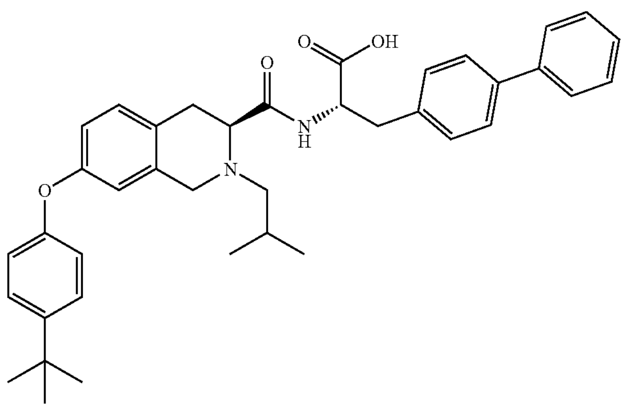 | 3-Biphenyl-4-yl-(2S)-{[2-(2,2-dimethyl-propionyl)-7-(4-trifluoromethyl-benzyloxy)-1,2,3,4-tetrahydro-isoquinoline-(3S)-carbonyl]-amino}-propionic acid |
| 77 | 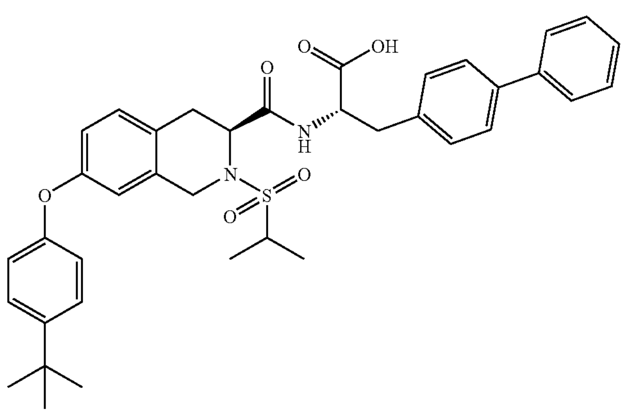 | 3-Biphenyl-4-yl-(2S)-{[7-(4-tert-butyl-phenoxy)-2-(propane-2-sulfonyl)-1,2,3,4-tetrahydro-isoquinoline-(3S)-carbonyl]-amino}-propionic acid |

TABLE 1-continued

| Example | Structure | Name |
|---|---|---|
| 78 | 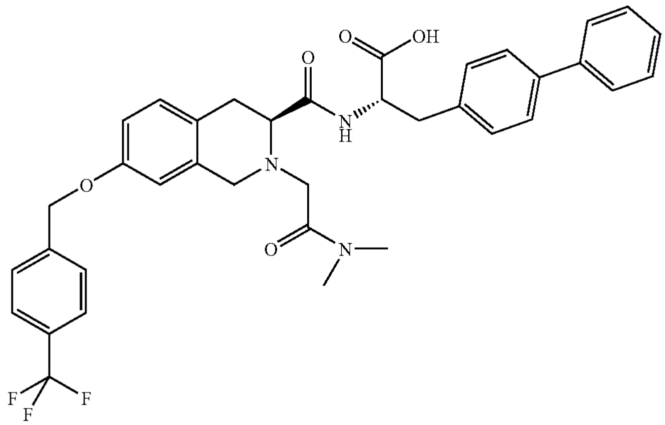 | 3-Biphenyl-4-yl-(2S)-{[2-dimethylcarbamoylmethyl-7-(4-trifluoromethyl-benzyloxy)-,2,3,4-tetrahydro-isoquinoline-(3S)-carbonyl]-amino}-propionic acid |
| 79 | 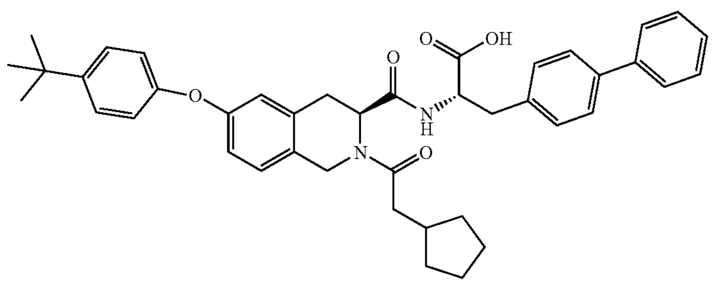 | 3-Biphenyl-4-yl-(2S)-{[6-(4-tert-butyl-phenoxy)-2-(2-cyclopentyl-acetyl)-1,2,3,4-tetrahydro-isoquino-line-(3S)-carbonyl]-amino}-propionic acid |
| 80 | 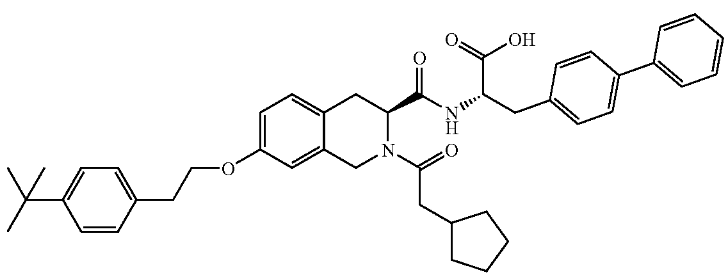 | 3-Biphenyl-4-yl-2-{[7-[2-(4-tert-butyl-phenyl)-ethoxy]-2-(2-cyclo-pentyl-acetyl)-1,2,3,4-tetrahydro-isoquinoline-(3S)-carbonyl]-amino}-propionic acid |
| 81 | 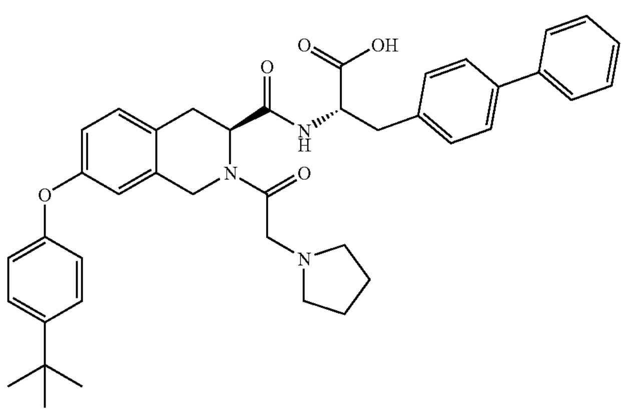 | 3-Biphenyt-4-yl-(2S)-{[7-(4-tert-butyl-phenoxy)-2-(2-pyrrolidin-1-yl-acetyl-(3S)-carbonyl]-amino}-propionic acid |

TABLE 1-continued

| Example | Structure | Name |
|---|---|---|
| 82 | 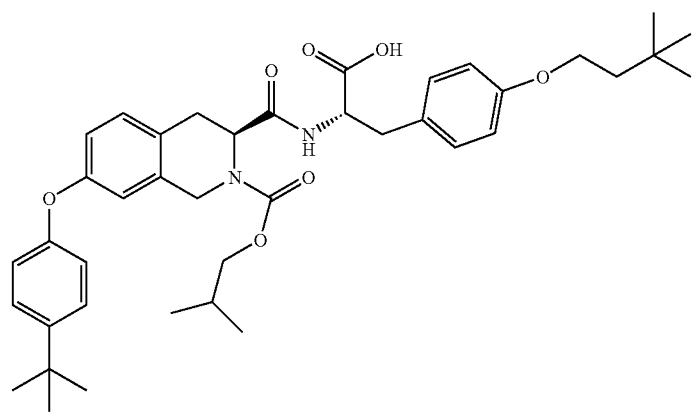 | 7-(4-tert-Butyl-phenoxy)-(3S)-{(1S)-carboxy-2-[4-(3,3-dimethyl-butoxy)-phenyl]-ethylcarbamoyl}-3,4-dihydro-1H-isoquinoline-2-carboxylic acid isobutyl ester |
| 83 | 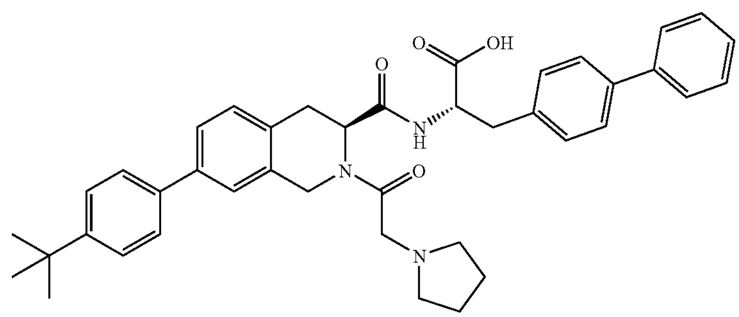 | 3-Biphenyl-4-yl-(2S)-{[7-(4-tert-butyl-phenyl)-2-(2-cyclopentyl-acetyl)-1,2,3,4-tetrahydro-isoquinoline-(3S)-carbonyl]-amino}-propionic acid |
| 84 | 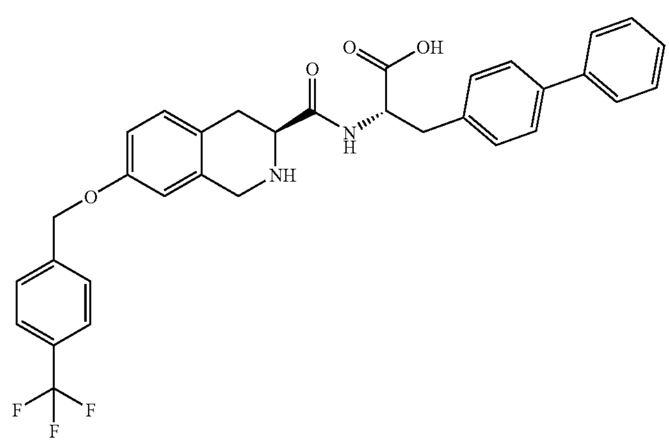 | 3-Biphenyl-4-yl-(2S)-{[7-(4-trifluoromethyl-benzyloxy)-1,2,3,4-tetrahydro-isoquinoline-(3S)-carbonyl]-amino}-propionic acid |

TABLE 1-continued

| Example | Structure | Name |
|---------|-----------|------|
| 85 | 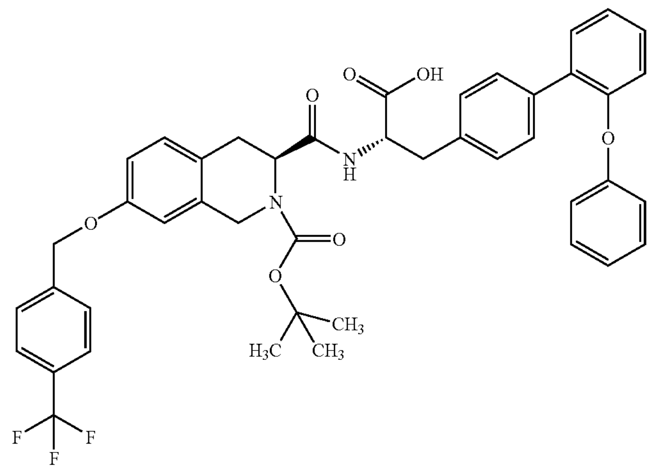 | (3S)-[1-Carboxy-(2S)-(2'-phenoxy-biphenyl-4-yl)-ethylcarbamoyl]-7-(4-trifluoromethyl-benzyloxy)-3,4-dihydro-1H-isoquinoline-2-carboxylic acid tert-butyl ester |
| 86 | 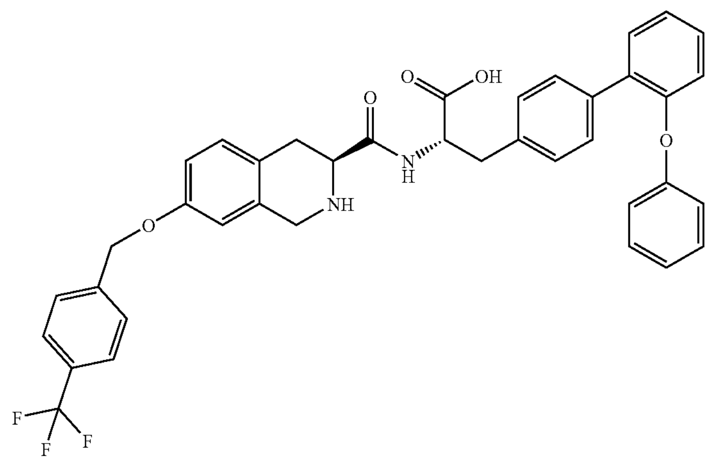 | 3-(2'-Phenoxy-biphenyl-4-yl)-(2S)-{[7-(4-trifluoromethyl-benzyloxy)-1,2,3,4-tetrahydro-isoquinoline-(3S)-carbonyl]-amino}-propionic acid |
| 87 | 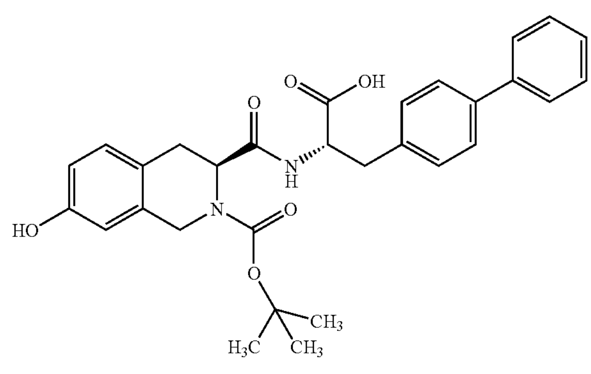 | (3S)-(2-Biphenyl-4-yl-(1S)-carboxy-ethylcarbamoyl)-7-hydroxy-3,4-dihydro-1H-isoquinoline-2-carboxylic acid tert-butyl ester |
| 88 | 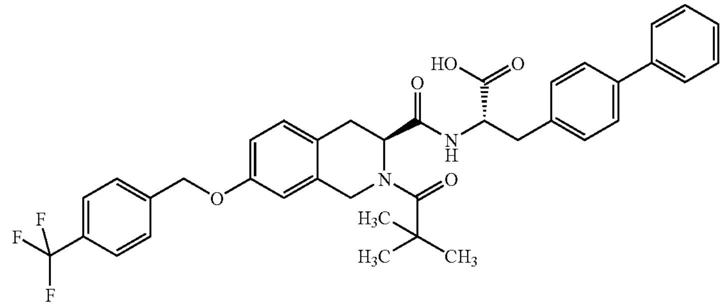 | 3-Biphenyl-4-yl-(2S)-{[2-(2,2-dimethyl-propionyl)-7-(4-trifluoromethyl-benzyloxy)-1,2,3,4-tetrahydro-isoquinoline-(3S)-carbonyl]-amino}-propionic acid |

TABLE 1-continued

| Example | Structure | Name |
|---|---|---|
| 89 | 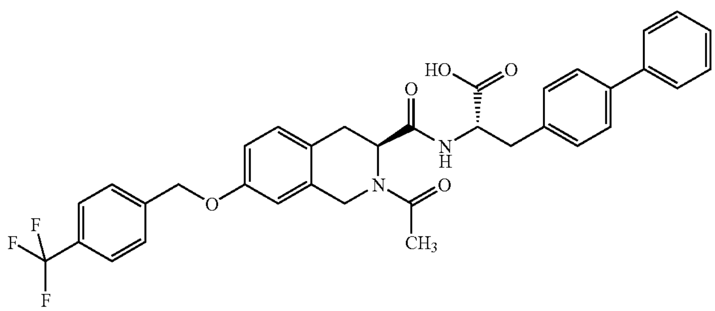 | (2S)-{[2-Acetyl-7-(4-trifluoromethyl-benzyloxy)-1,2,3,4-tetrahydro-isoquinoline-(3S)-carbonyl]-amino}-3-biphenyl-4-yl-propionic acid |
| 90 | 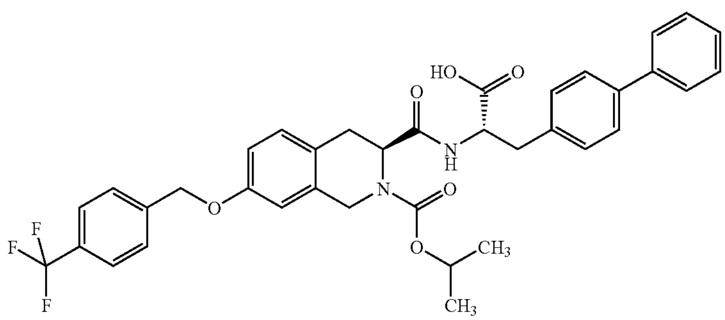 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid isopropyl ester |
| 91 | 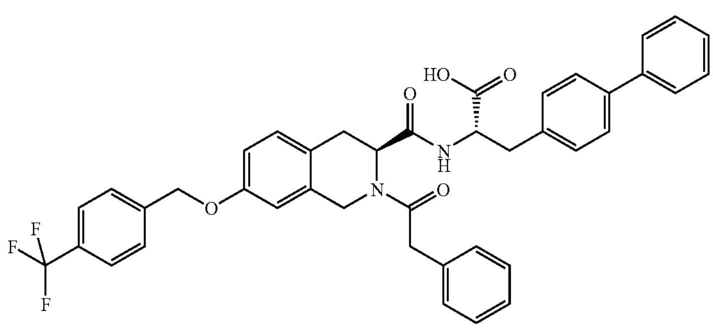 | 3-Biphenyl-4-yl-(2S)-{[2-phenylacetyl-7-(4-trifluoromethyl-benzyloxy)-1,2,3,4-tetrahydro-isoquinoline-(3S)-carbonyl]-amino}-propionic acid |
| 92 | 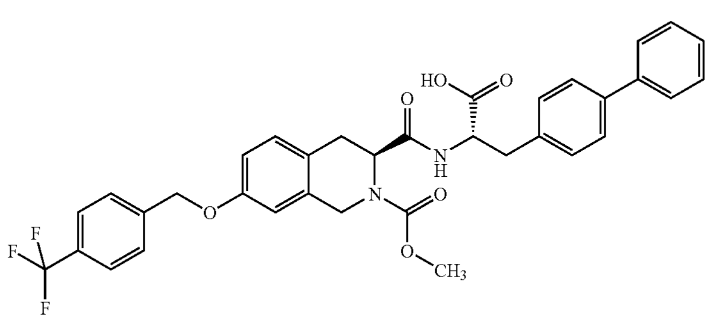 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid methyl ester |

TABLE 1-continued

| Example | Structure | Name |
|---|---|---|
| 93 | 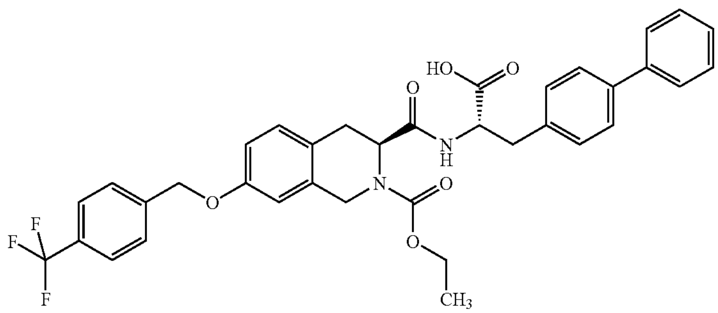 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid ethyl ester |
| 94 | 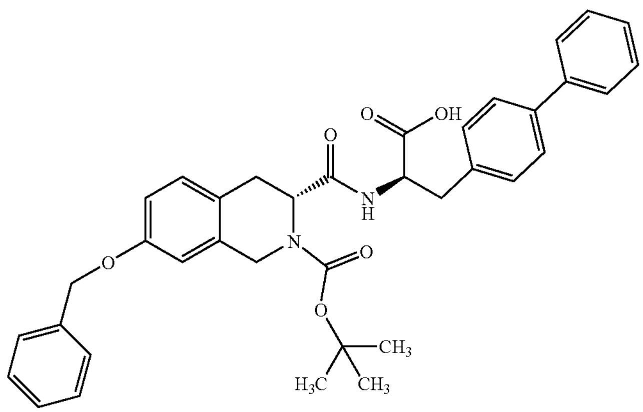 | 7-Benzyloxy-(3R)-(2-biphenyl-4-yl-(1R)-carboxy-ethylcarbamoyl)-3,4-dihydro-1H-isoquinoline-2-carboxylic acid tert-butyl ester |
| 95 | 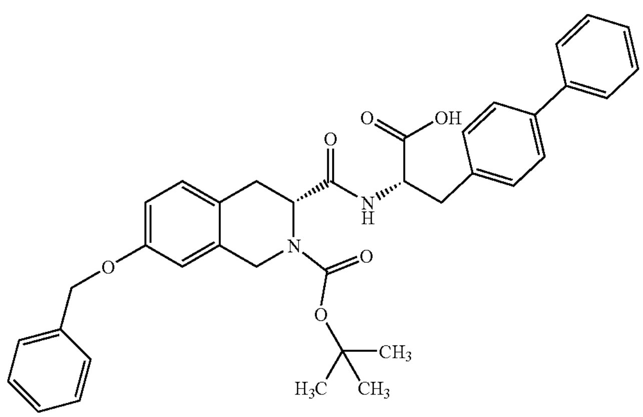 | 7-Benzyloxy-(3R)-(2-biphenyl-4-yl-(1S)-carboxy-ethylcarbamoyl)-3,4-dihydro-1H-isoquinoline-2-carboxylic acid tert-butyl ester |
| 96 | 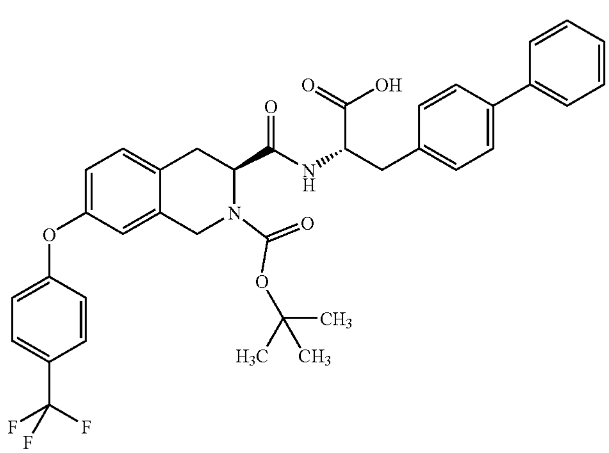 | (3S)-(2-Biphenyl-4-yl-(1S)-carboxy-ethylcarbamoyl)-7-(4-trifluoromethyl-phenoxy)-3,4-dihydro-1H-isoquinoline-2-carboxylic acid tert-butyl ester |

TABLE 1-continued

| Example | Structure | Name |
|---|---|---|
| 97 | 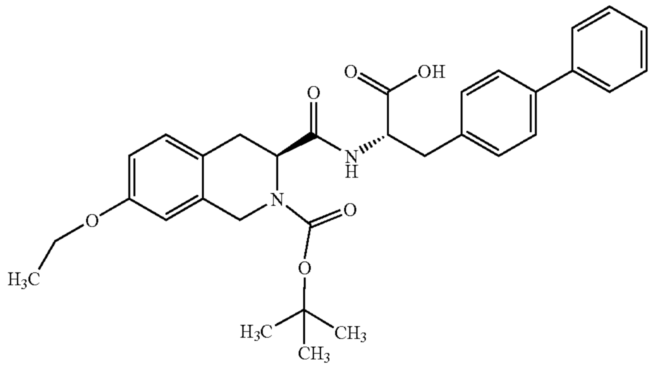 | (3S)-(2-Biphenyl-4-yl-(1S)-carboxy-ethylcarbamoyl)-7-ethoxy-3,4-dihydro-1H-isoquinoline-2-carboxylic acid tert-butyl ester |
| 98 | 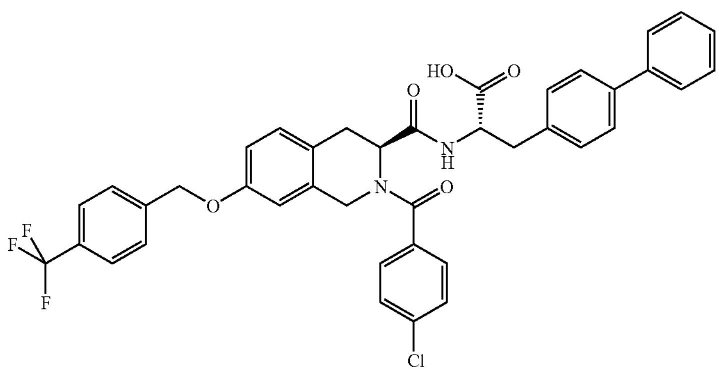 | 3-Biphenyl-4-yl-(2S)-{[2-(4-chloro-benzoyl)-7-(4-trifluorom-ethyl-benzyloxy)-1,2,3,4-tetrahydro-isoquinoline-(3S)-carbonyl]-amino}-propionic acid |
| 99 | 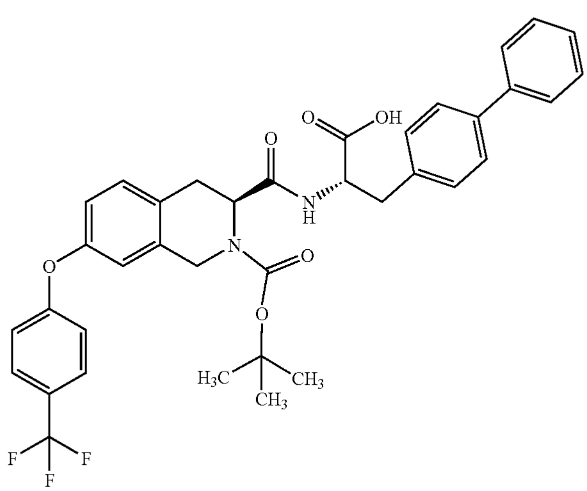 | (3S)-(2-Biphenyl-4-yl-(1S)-carboxy-ethylcarbamoyl)-7-(4-trifluoromethoxy-phenoxy)-3,4-dihydro-1H-isoquinoline-2-carboxylic acid tert-butyl ester |

TABLE 1-continued

| Example | Structure | Name |
|---|---|---|
| 100 | 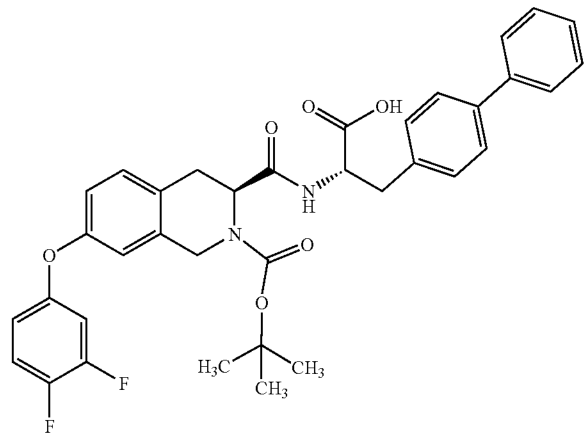 | (3S)-(2-Biphenyl-4-yl-(1S)-carboxy-ethylcarbamoyl)-7-(3-chloro-4-fluoro-phenoxy)-3,4-dihydro-1H-isoquinoline-2-carboxylic acid tert-butyl ester |
| 101 | 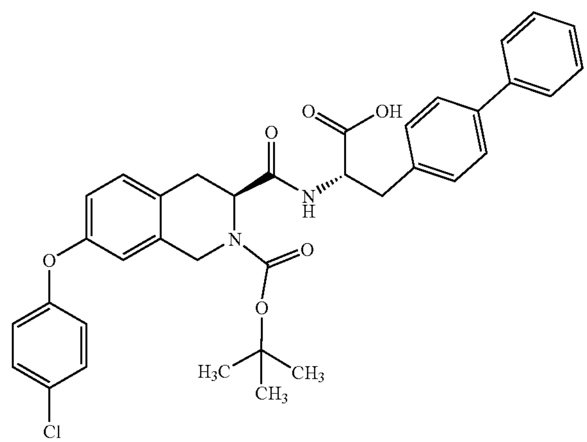 | (3S)-(2-Biphenyl-4-yl-(1S)-carboxy-ethylcarbamoyl)-7-(4-chlorophenoxy)-3,4-dihydro-1H-isoquinoline-2-carboxylic acid tert-butyl ester |
| 102 | 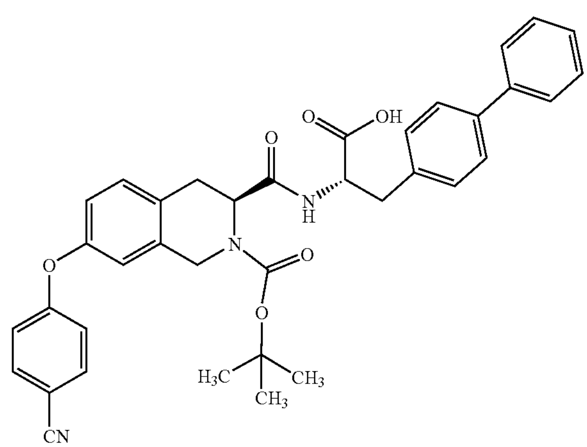 | (3S)-(2-Biphenyl-4-yl-(1S)-carboxy-ethylcarbamoyl)-7-(4-cyanophenoxy)-3,4-dihydro-1H-isoquinoline-2-carboxylic acid tert-butyl ester |

TABLE 1-continued

| Example | Structure | Name |
|---|---|---|
| 103 | 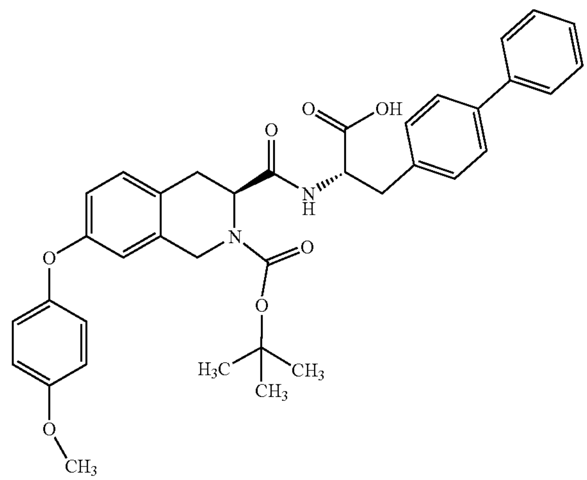 | (3S)-(2-Biphenyl-4-yl-(1S)-carboxy-ethylcarbamoyl)-7-(4-methoxy-phenoxy)-3,4-dihydro-1H-isoquinoline-2-carboxylic acid tert-butyl ester |
| 104 | 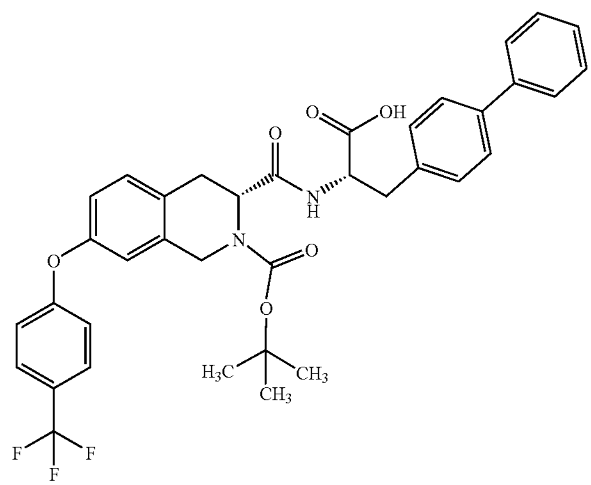 | (3R)-(2-Biphenyl-4-yl-(1S)-carboxy-ethylcarbamoyl)-7-(4-trifluoromethyl-phenoxy)-3,4-dihydro-1H-isoquinoline-2-carboxylic acid tert-butyl ester |
| 105 | 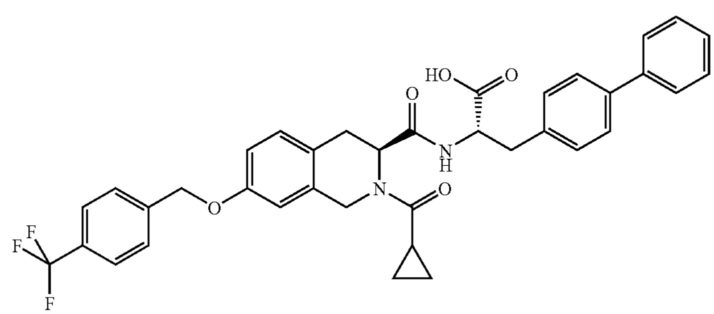 | 3-Biphenyl-4-yl-(2S)-{[2-cyclopropanecarbonyl-7-(4-trifluoromethyl-benzyloxy)-1,2,3,4-tetrahydro-isoquinoline-(3S)-carbonyl]-amino}-propionic acid |
| 106 | 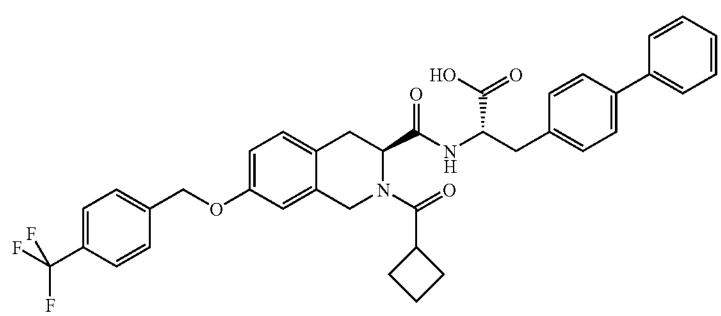 | 3-Biphenyl-4-yl-(2S)-{[2-cyclobutanecarbonyl-7-(4-trifluoromethyl-benzyloxy)-1,2,3,4-tetrahydro-isoquinoline-(3S)-carbonyl]-amino}-propionic acid |

TABLE 1-continued

| Example | Structure | Name |
|---|---|---|
| 107 | 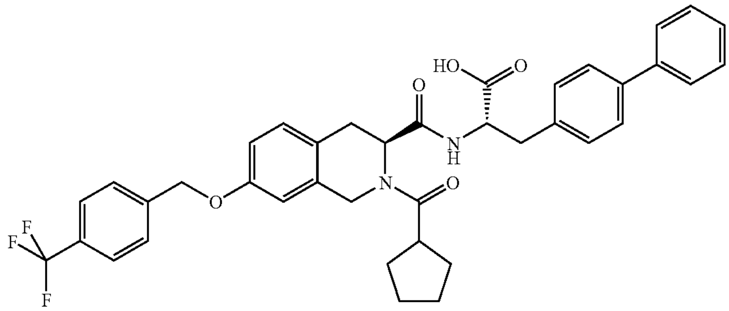 | 3-Biphenyl-4-yl-(2S)-{[2-cyclopentanecarbonyl-7-(4-trifluoromethyl-benzyloxy)-1,2,3,4-tetrahydro-isoquinoline-(3S)-carbonyl]-amino}-propionic acid |
| 108 | 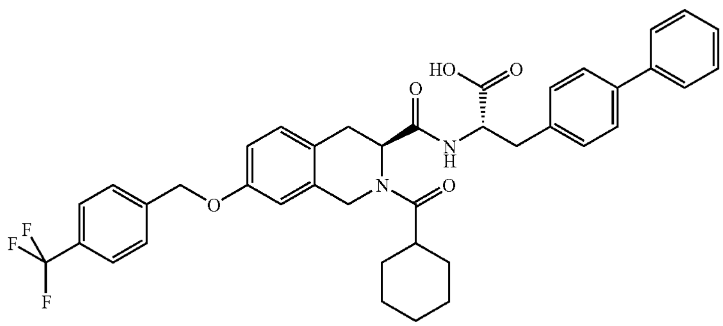 | 3-Biphenyl-4-yl-(2S)-{[2-cyclohexanecarbonyl-7-(4-trifluoromethyl-benzyloxy)-1,2,3,4-tetrahydro-isoquinoline-(3S)-carbonyl]-amino}-propionic acid |
| 109 | 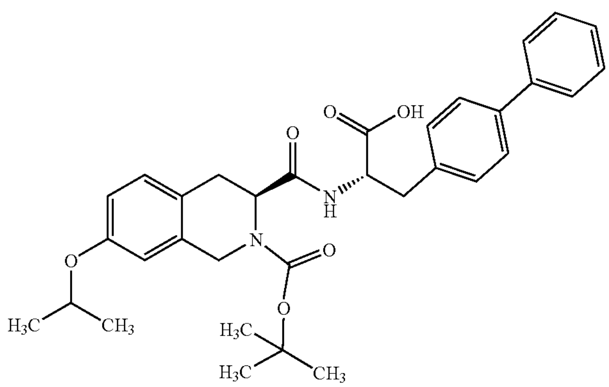 | (3S)-(2-Biphenyl-4-yl-(1S)-carboxy-ethylcarbamoyl)-7-isopropoxy-3,4-dihydro-1H-isoquinoline-2-carboxylic acid tert-butyl ester |
| 110 | 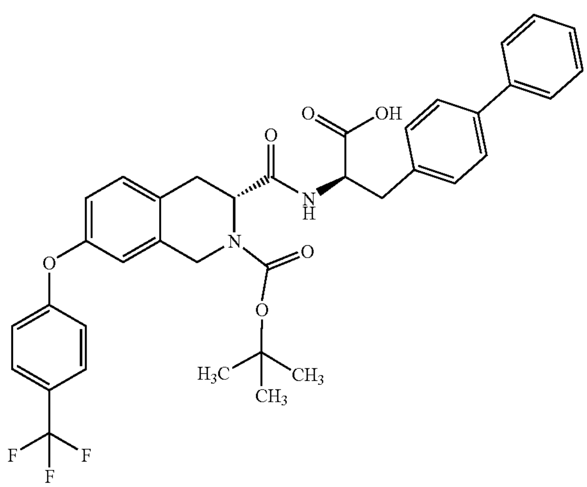 | (3R)-(2-Biphenyl-4-yl-(1R)-carboxy-ethylcarbamoyl)-7-(4-trifluoromethyl-phenoxy)-3,4-dihydro-1H-isoquinoline-2-carboxylic acid tert-butyl ester |

TABLE 1-continued

| Example | Structure | Name |
|---|---|---|
| 111 | 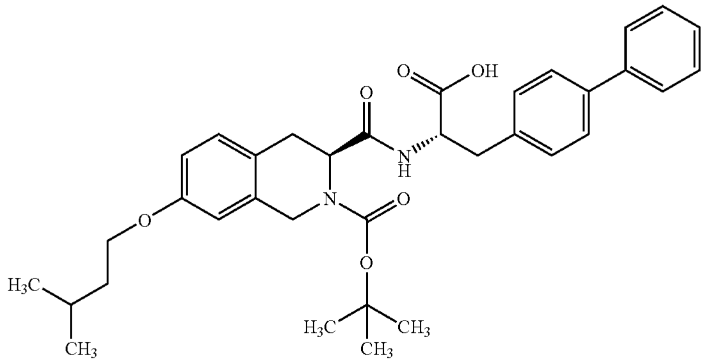 | (3S)-(2-Biphenyl-4-yl-(1S)-carboxy-ethylcarbamoyl)-7-(3-methyl-butoxy)-3,4-dihydro-1H-isoquinoline-2-carboxylic acid tert-butyl ester |
| 112 | 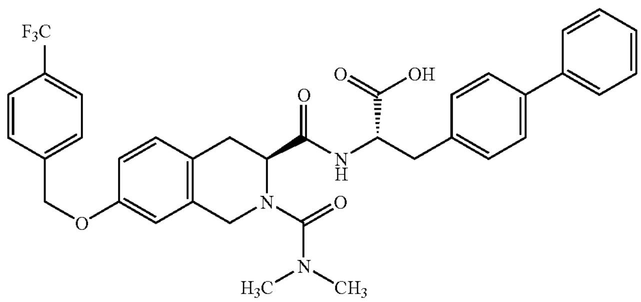 | 3-Biphenyl-4-yl-(2S)-{(2-dimethylcarbamoyl-7-(4-trifluoromethyl-benzyloxy)-1,2,3,4-tetrahydro-isoquinoline-(3S)-carbonyl]-amino}-propionic acid |
| 113 | 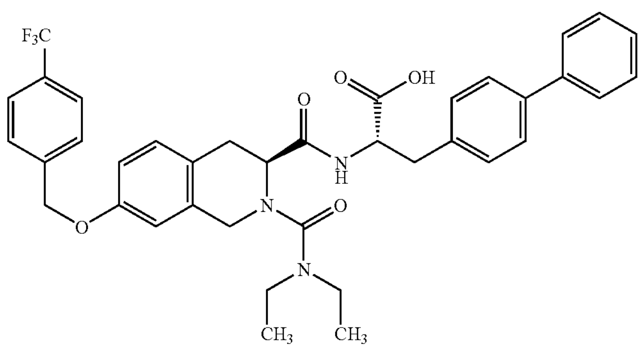 | 3-Biphenyl-4-yl-(2S)-{[2-diethylcarbamoyl-7-(4-trifluoromethyl-benzyloxy)-1,2,3,4-tetrahydro-isoquinoline-(3S)-carbonyl]-amino}-propionic acid |
| 114 | 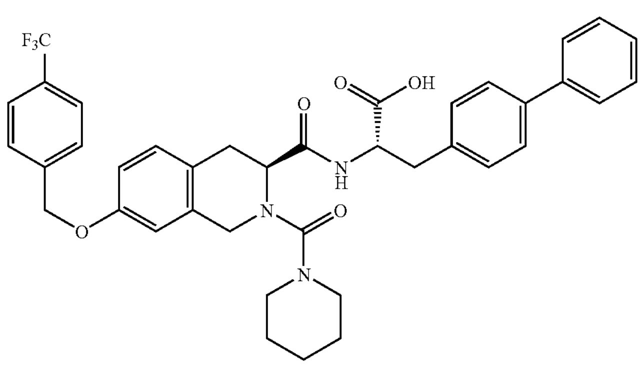 | 3-Biphenyl-4-yl-(2S)-{[2-(piperidine-1-carbonyl)-7-(4-trifluoromethyl-benzyloxy)-1,2,3,4-tetrahydro-isoquinoline-(3S)-carbonyl]-amino)-propionic acid |

TABLE 1-continued

| Example | Structure | Name |
|---|---|---|
| 115 | 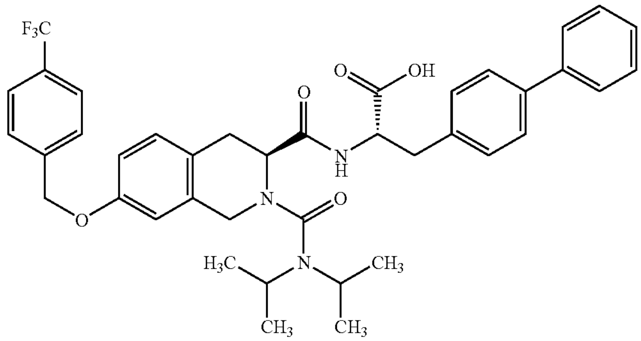 | 3-Biphenyl-4-yl-(2S)-{[2-diisopropylcarbamoyl-7-(4-trifluoromethyl-benzyloxy)-1,2,3,4-tetrahydro-isoquinoline-(3S)-carbonyl]-amino}-propionic acid |
| 116 | 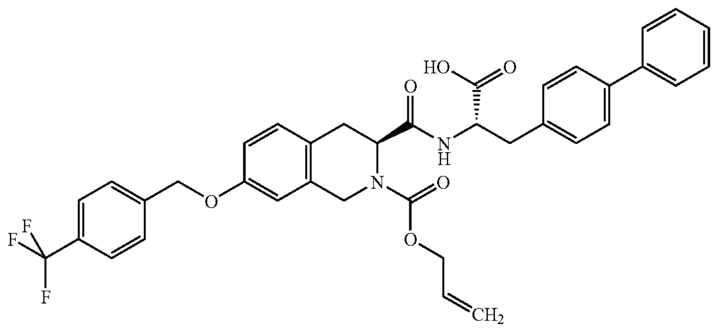 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid allyl ester |
| 117 | 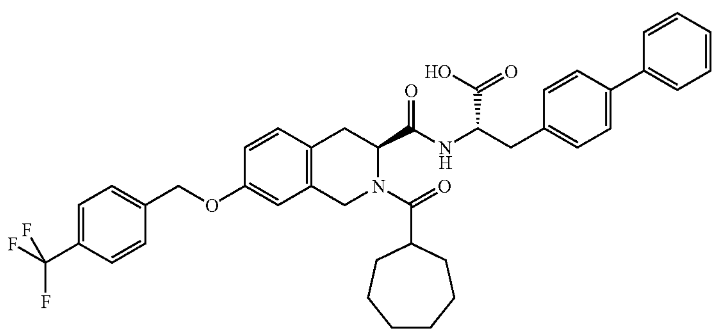 | 3-Biphenyl-4-yl-(2S)-{[2-cycloheptanecarbonyl-7-(4-trifluoromethyl-benzyloxy)-1,2,3,4-tetrahydro-isoquinoline-(3S)-carbonyl]-amino}-propionic acid |
| 118 | 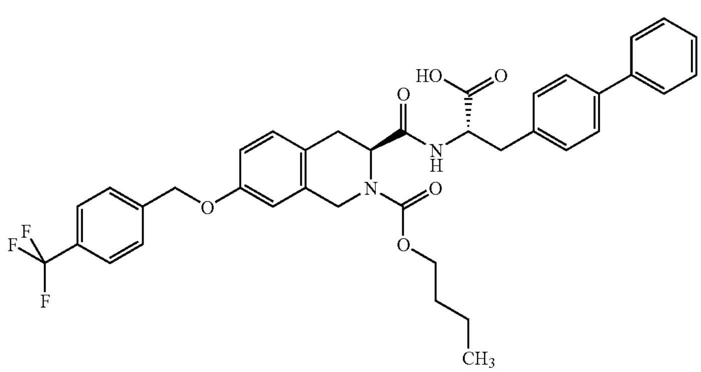 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid butyl ester |

TABLE 1-continued

| Example | Structure | Name |
|---|---|---|
| 119 | 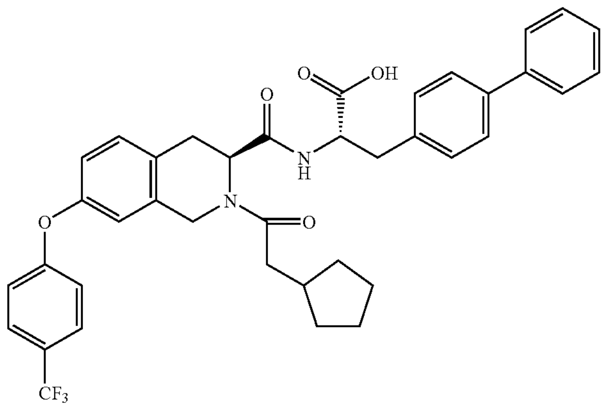 | 3-Biphenyl-4-yl-(2S)-{[2-(2-cyclopentyl-acetyl)-7-(4-trifluoromethyl-phenoxy)-1,2,3,4-tetrahydro-isoquinoline-(3S)-carbonyl]-amino}-propionic acid |
| 120 | 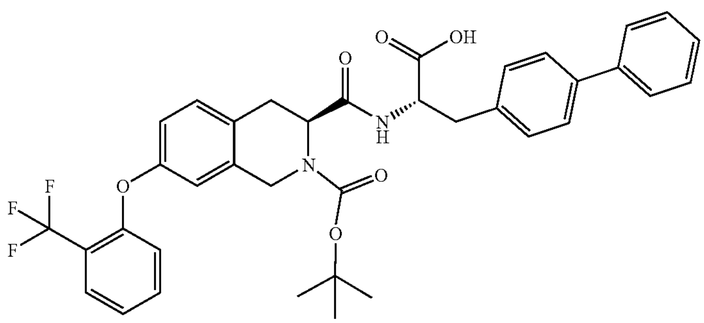 | (3S)-(2-Biphenyl-4-yl-(1S)-carboxy-ethylcarbamoyl)-7-(2-trifluoromethyl-phenoxy)-3,4-dihydro-1H-isoquinoline-2-carboxylic acid tert-butyl ester |
| 121 | 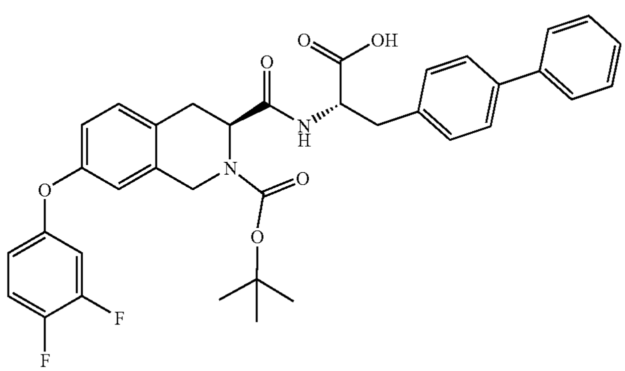 | (3S)-(2-Biphenyl-4-yl-(1S)-carboxy-ethylcarbamoyl)-7-(3,4-difluoro-phenoxy)-3,4-dihydro-1H-isoquinoline-2-carboxylic acid tert-butyl ester |
| 122 | 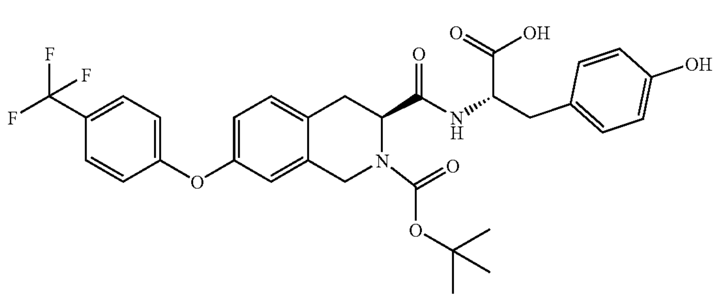 | (3S)-[1-Carboxy-(2S)-(4-hydroxy-phenyl)-ethylcarbamoyl]-7-(4-trifluoromethyl-phenoxy)-3,4-dihydro-1H-isoquinoline-2-carboxylic acid tert-butyl ester |

TABLE 1-continued

| Example | Structure | Name |
|---|---|---|
| 123 | 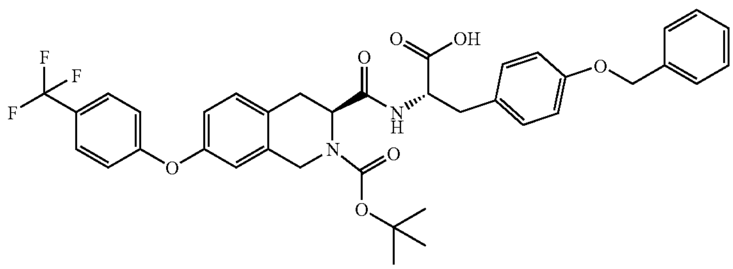 | (3S)-[2-(4-Benzyloxy-phenyl)-(1S)-carboxy-ethylcarbamoyl]-7-(4-trifluoromethyl-phenoxy)-3,4-dihydro-1H-isoquinoline-2-carboxylic acid tert-butyl ester |
| 124 | 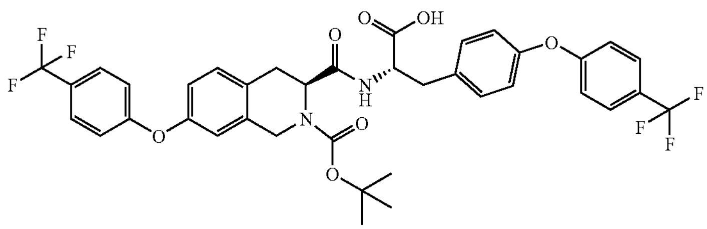 | (3S)-{(1S)-Carboxy-2-[4-(4-trifluoromethyl-phenoxy)-phenyl]-ethylcarbamoyl}-7-(4-trifluoromethyl-henoxy)-3,4-dihydro-1H-isoquinoline-2-carboxylic acid tert-butyl ester |
| 125 | 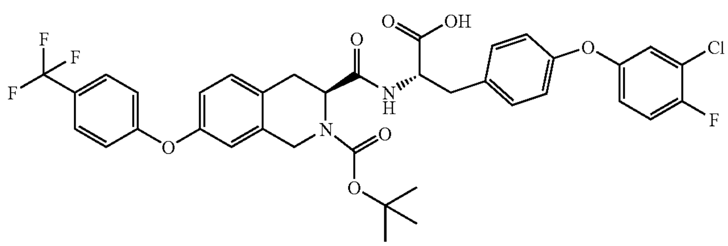 | (3S)-{(1S)-Carboxy-2-[4-(3-chloro-4-fluoro-phenoxy)-phenyl]-ethylcarbamoyl}-7-(4-trifluoromethyl-henoxy)-3,4-dihydro-1H-isoquinoline-2-carboxylic acid tert-butyl ester |
| 126 | 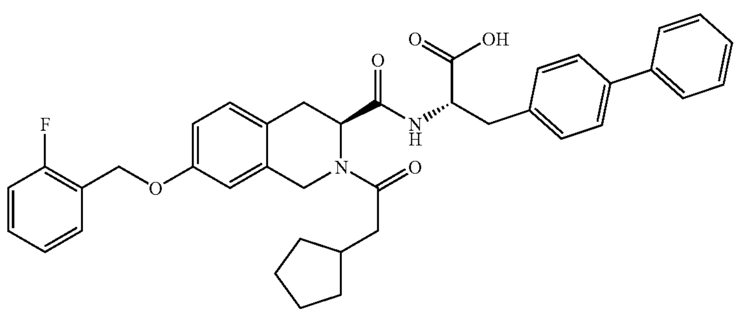 | 3-Biphenyl-4-yl-(2S)-{(2-(2-cyclopentyl-acetyl)-7-(2-fluoro-benzyloxy)-1,2,3,4-tetrahydro-isoquinoline-(3S)-carbonyl]-amino}-propionic acid |
| 127 | 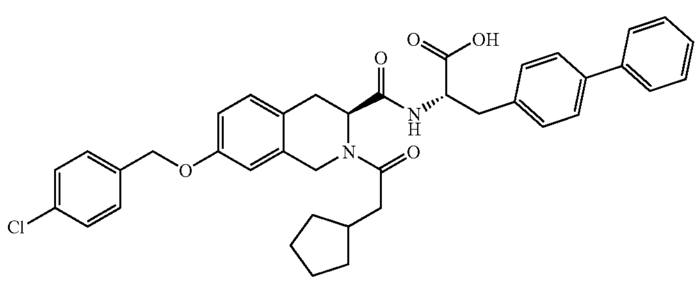 | 3-Biphenyl-4-yl-(2S)-{[7-(4-chloro-benzyloxy)-2-(2-cyclopentyl-acetyl)-1,2,3,4-tetrahydro-isoquinoline-(3S)-carbonyl]-amino}-propionic acid |

TABLE 1-continued

| Example | Structure | Name |
|---|---|---|
| 128 | 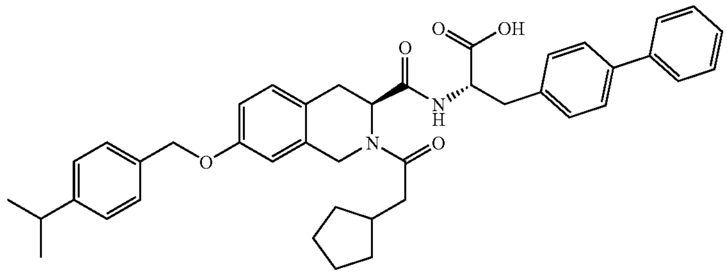 | 3-Biphenyl-4-yl-(2S)-{[2-(2-cyclopentyl-acetyl)-7-(4-isopropyl-benzyloxy)-1,2,3,4-tetrahydro-isoquinoline-(3S)-carbonyl]-amino}-propionic acid |
| 129 | 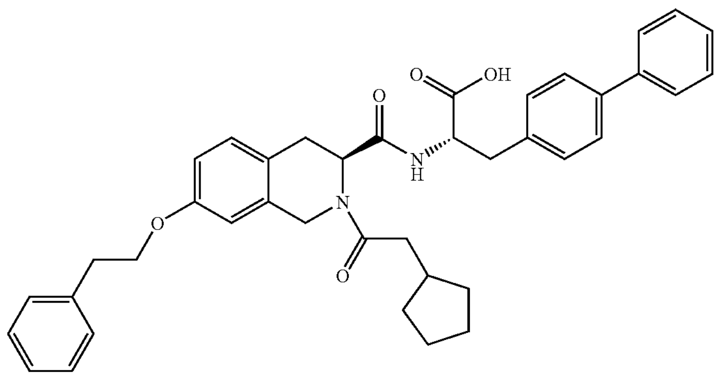 | 3-Biphenyl-4-yl-(2S)-{[2-(2-cyclopentyl-acetyl)-7-phenethyloxy-1,2,3,4-tetrahydro-isoquinoline-(3S)-carbonyl]-amino}-propionic acid |
| 130 | 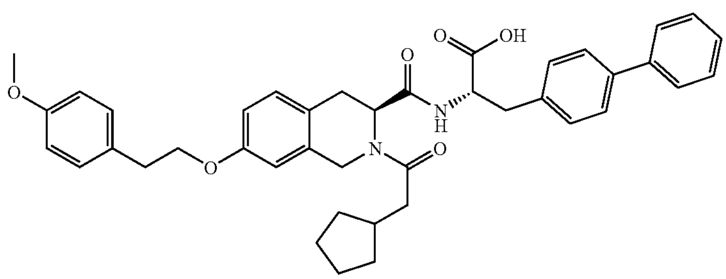 | 3-Biphenyl-4-yl-(2S)-({2-(2-cyclopentyl-acetyl)-7-[2-(4-methoxy-phenyl)-ethoxy]-1,2,3,4-tetrahydro-isoquinoline-(3S)-carbonyl}-amino)-propionic acid |
| 131 | 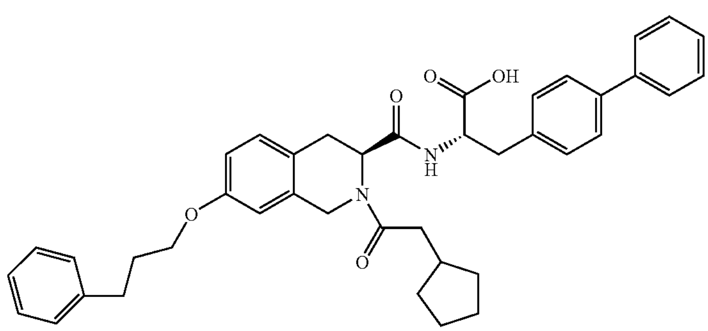 | 3-Biphenyl-4-yl-(2S)-{[2-(2-cyclopentyl-acetyl)-7-(3-phenyl-propoxy)-1,2,3,4-tetrahydro-isoquinoline-(3S)-carbonyl]-amino}-propionic acid |

TABLE 1-continued

| Example | Structure | Name |
|---|---|---|
| 132 | 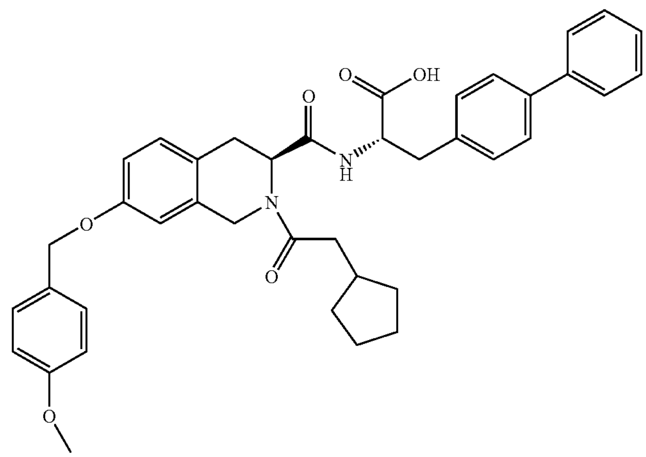 | 3-Biphenyl-4-yl-(2S)-{[2-(2-cyclopentyl-acetyl)-7-(4-methoxy-benzyloxy)-1,2,3,4-tetrahydro-isoquinoline-(3S)-carbonyl]-amino}-propionic acid |
| 133 | 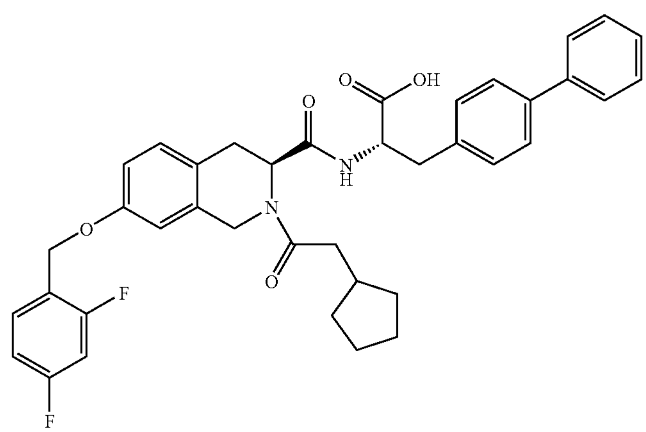 | 3-Biphenyl-4-yl-(2S)-{[2-(2-cyclopentyl-acetyl)-7-(2,4-difluoro-benzyloxy)-1,2,3,4-tetrahydro-isoquinoiine-(3S)-carbonyl]-amino}-propionic acid |
| 134 | 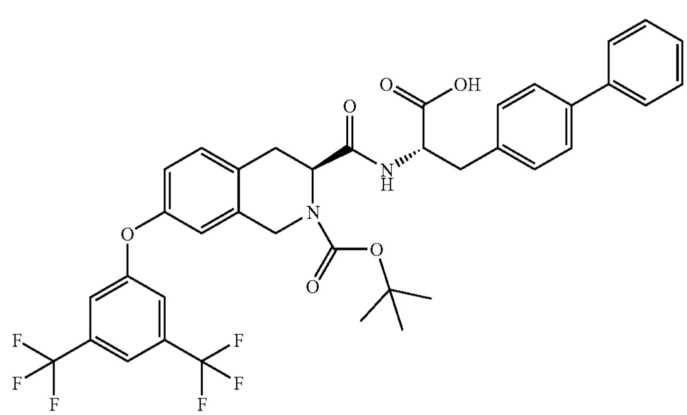 | (3S)-(2-Biphenyl-4-yl-(1S)-carboxy-ethylcarbamoyl)-7-(3,5-bis-trifluoromethyl-phenoxy)-3,4-dihydro-1H-isoquinoline-2-carboxylic acid tert-butyl ester |

TABLE 1-continued

| Example | Structure | Name |
|---|---|---|
| 135 | 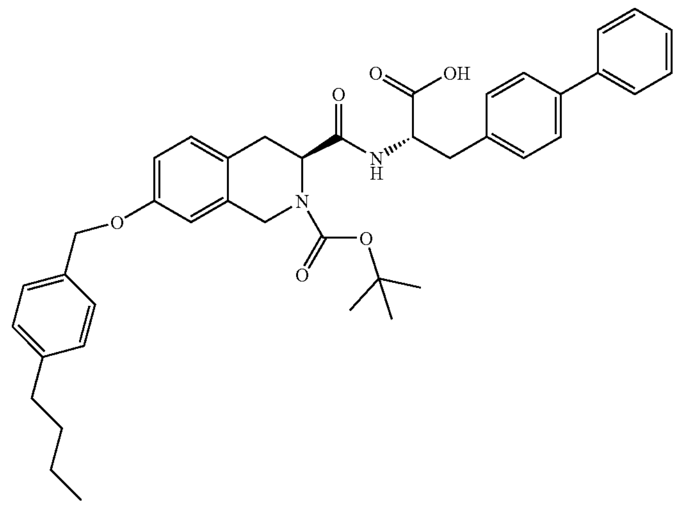 | (3S)-(2-Biphenyl-4-yl-(1S)-carboxy-ethylcarbamoyl)-7-(4-butyl-benzyloxy)-3,4-dihydro-1H-isoquinoline-2-carboxylic acid tert-butyl ester |
| 136 | 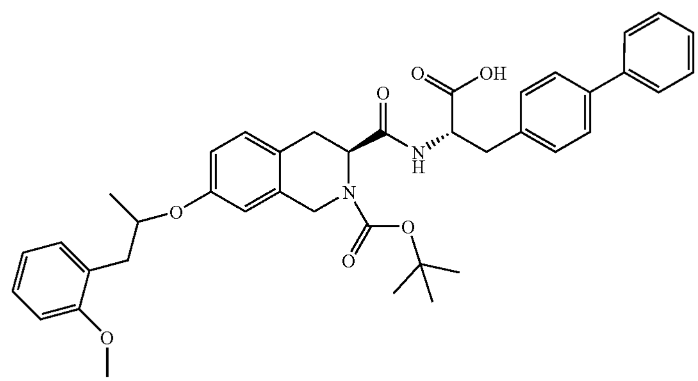 | (3S)-(2-Biphenyl-4-yl-(1S)-carboxy-ethylcarbamoyl)-7-[2-(2-methoxy-phenyl)-1-methyl-ethoxy]-3,4-dihydro-1H-isoquinoline-2-carboxylic acid tert-butyl ester |
| 137 | 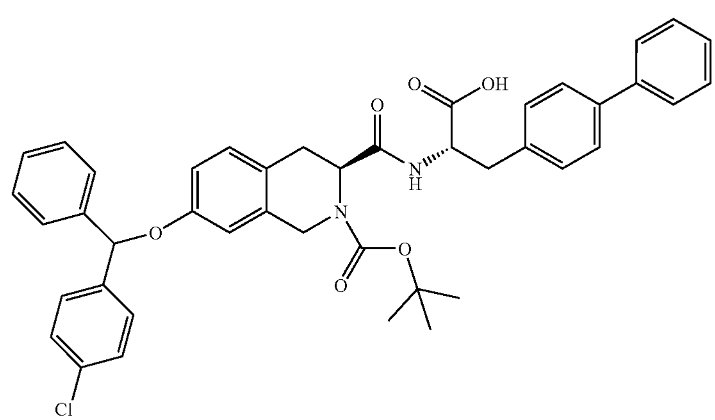 | (3S)-(2-Biphenyl-4-yl-(1S)-carboxy-ethylcarbamoyl)-7-[(4-chloro-phenyl)-phenyl-methoxy]-3,4-dihydro-1H-isoquinoline-2-carboxylic acid tert-butyl ester |

TABLE 1-continued

| Example | Structure | Name |
|---|---|---|
| 138 | 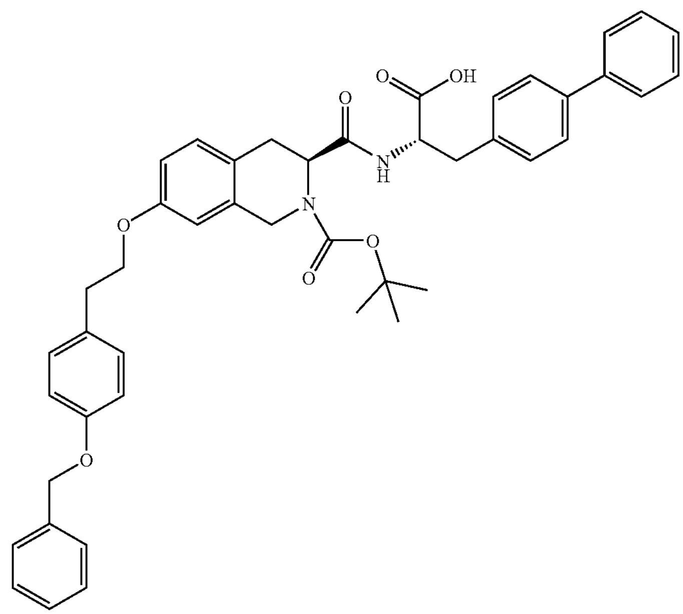 | 7-[2-(4-Benzyloxy-phenyl)-ethoxy]-(3S)-(2-biphenyl-4-yl-(1S)-carboxy-ethylcarbamoyl)-3,4-dihydro-1H-isoquinoline-2-carboxylic acid tert-butyl ester |
| 139 | 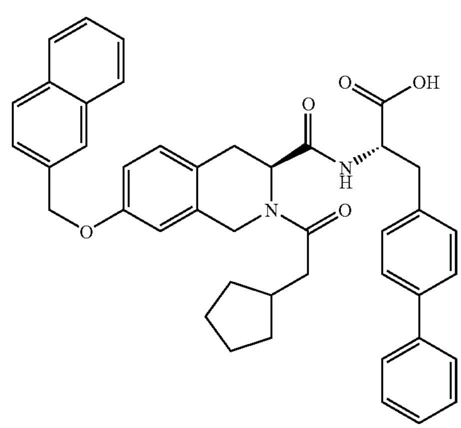 | 3-Biphenyl-4-yl-(2S)-{[2-(2-cyclopentyl-acetyl)-7-(naphthalen-2-ylmethoxy)-1,2,3,4-tetrahydro-isoquinoline-(3S)-carbonyl]-amino}-propionic acid |
| 140 | 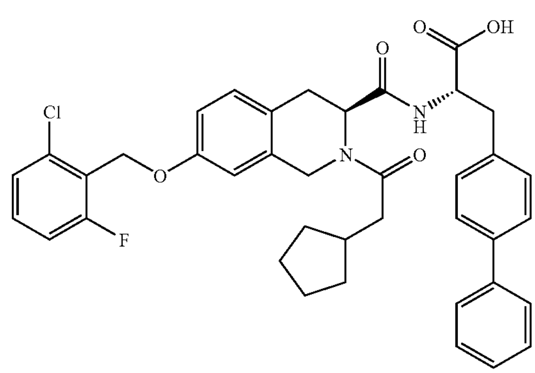 | 3-Biphenyl-4-yl-(2S)-{[7-(2-chloro-6-fluoro-benzyloxy)-2-(2-cyclopentyl-acetyl)-1,2,3,4-tetrahydro-isoquinoline-(3S)-carbonyl]-amino}-propionic acid |

TABLE 1-continued

| Example | Structure | Name |
|---|---|---|
| 141 | 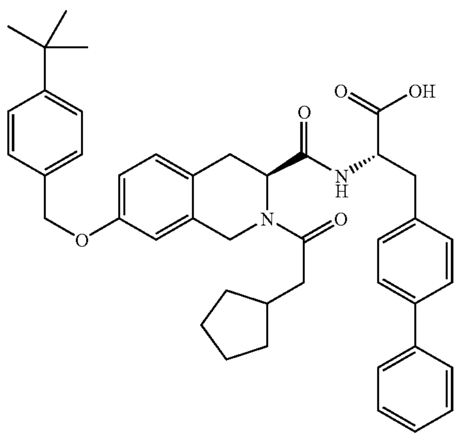 | 3-Biphenyl-4-yl-(2S)-{[7-(4-tert-butyl-benzyloxy)-2-(2-cyclopentyl-acetyl)-1,2,3,4-tetrahydro-isoquinoline-(3S)-carbonyl]-amino}-propionic acid |
| 142 | 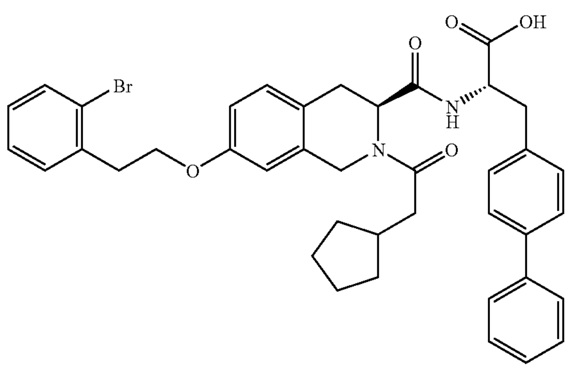 | 3-Biphenyl-4-yl-(2S)-{[7-[2-(2-bromo-phenyl)-ethoxy]-2-(2-cyclopentyl-acetyl)-1,2,3,4-tetrahydro-isoquinoline-(3S)-carbonyl]-amino}-propionic acid |
| 143 | 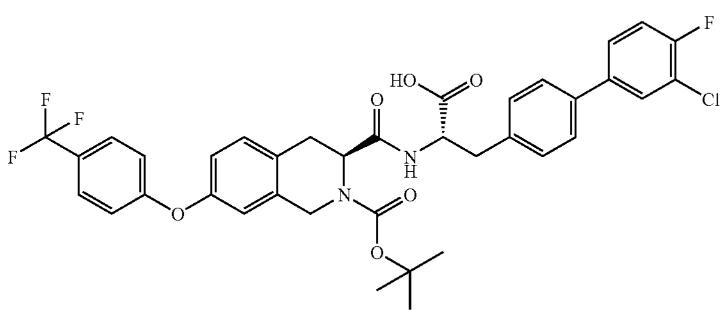 | (3S)-[(1S)-Carboxy-2-(3'-chloro-4'-fluoro-biphenyl-4-yl)-ethyl-carbamoyl]-7-(4-trifluoromethyl-phenoxy)-3,4-dihydro-1H-isoquinoline-2-carboxylic acid tert-butyl ester |
| 144 | 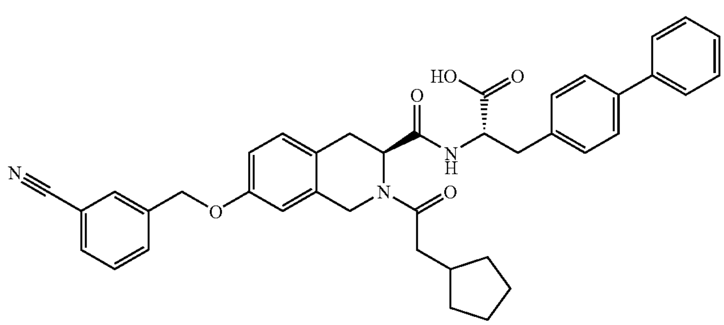 | 3-Biphenyl-4-yl-(2S)-{[7-(3-cyano-benzyloxy)-2-(2-cyclopentyl-acetyl)-1,2,3,4-tetrahydro-isoquinoline-(3S)-carbonyl]-amino}-propionic acid |

TABLE 1-continued

| Example | Structure | Name |
|---|---|---|
| 145 | 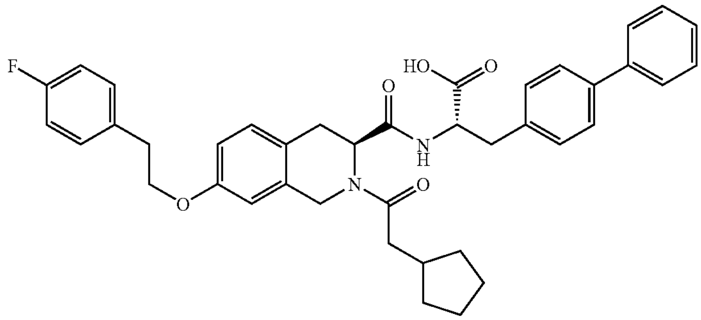 | 3-Biphenyl-4-yl-(2S)-({2-(2-cyclopentyl-acetyl)-7-[2-(4-fluoro-phenyl)-ethoxy]-1,2,3,4-tetrahydro-isoquinoline-(3S)-carbonyl}-amino)-propionic acid |
| 146 | 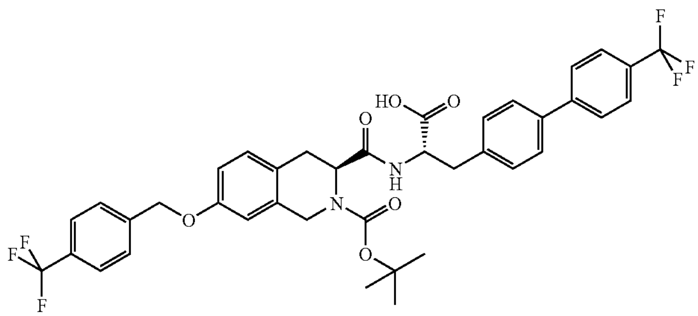 | (3S)-[(1S)-Carboxy-2-(4'-trifluoromethyl-biphenyl-4-yl)-ethylcarbamoyl]-7-(4-trifluoromethyl-benzyloxy)-3,4-dihydro-1H-isoquinoline-2-carboxylic acid tert-butyl ester |
| 147 | 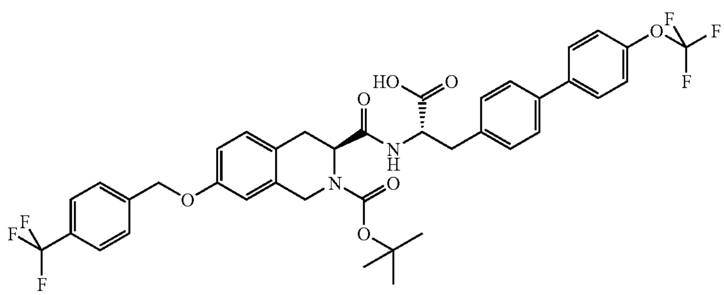 | (3S)-[(1S)-Carboxy-2-(4'-trifluoromethoxy-biphenyl-4-yl)-ethylcarbamoyl]-7-(4-trifluoromethyl-benzyloxy)-3,4-dihydro-1H-isoquinoline-2-carboxylic acid tert-butyl ester |
| 148 | 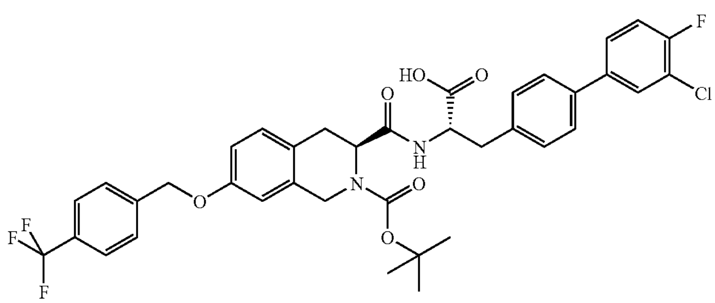 | (3S)-[(1S)-Carboxy-2-(3'-chloro-4'-fluoro-biphenyl-4-yl)-ethylcarbamoyl]-7-(4-trifluoromethyl-benzyloxy)-3,4-dihydro-1H-isoquinoline-2-carboxylic acid tert-butyl ester |
| 149 | 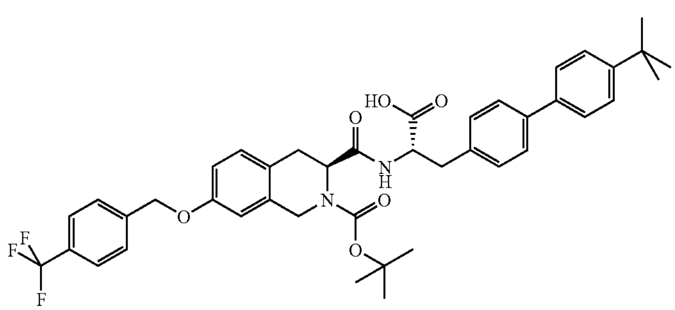 | (3S)-[2-(4'-tert-Butyl-biphenyl-4-yl)-(1S)-carboxy-ethylcarbamoyl]-7-(4-trifluoromethyl-benzyloxy)-3,4-dihydro-1H-isoquinoline-2-carboxylic acid tert-butyl ester |

TABLE 1-continued

| Example | Structure | Name |
|---|---|---|
| 150 | 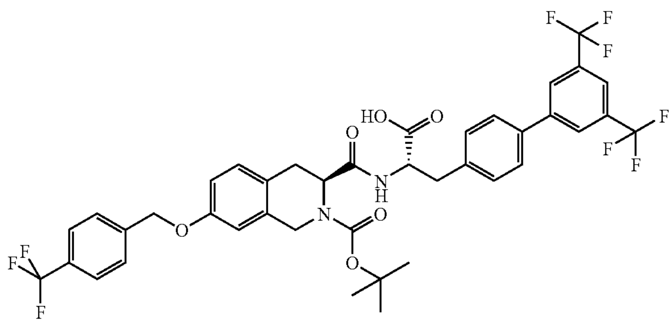 | (3S)-[2-(3,5'-Bis-trifluorom-ethyl-biphenyl-4-yl)-(1S)-carboxy-ethylcarbamoyl]-7-(4-trifluoromethyl-benzyloxy)-3,4-dihydro-1H-isoquinoline-2-carboxylic acid tert-butyl ester |
| 151 | 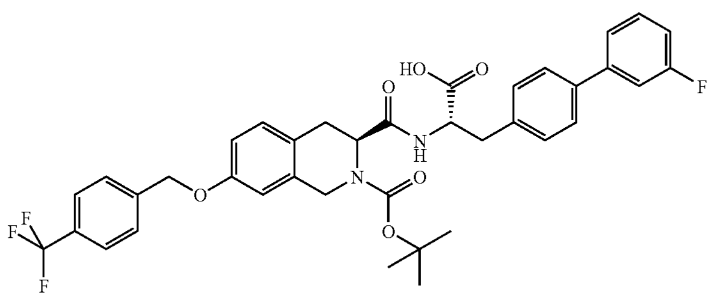 | (3S)-[(1S)-Carboxy-2-(3'-fluoro-biphenyl-4-yl)-ethylcarbamoyl]-7-(4-trifluoromethyl-benzyloxy)-3,4-dihydro-1H-isoquinoline-2-carboxylic acid tert-butyl ester |
| 152 | 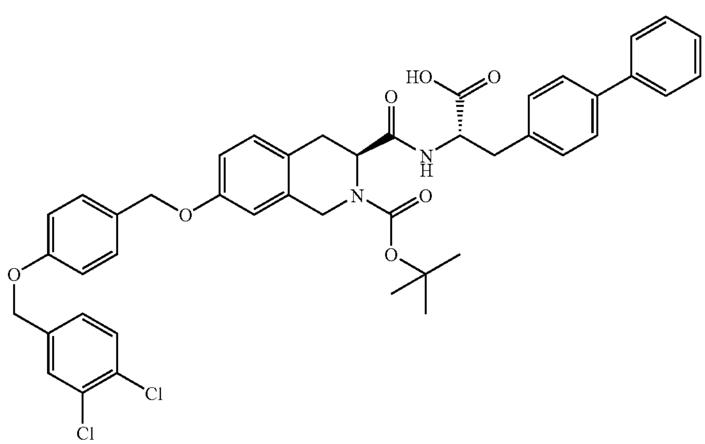 | (3S)-(2-Biphenyl-4-yl-(1S)-carboxy-ethylcarbamoyl)-7-[4-(3,4-dichloro-benzyloxy)-benzyloxy]-3,4-dihydro-1H-isoquinoline-2-carboxylic acid tert-butyl ester |
| 153 | 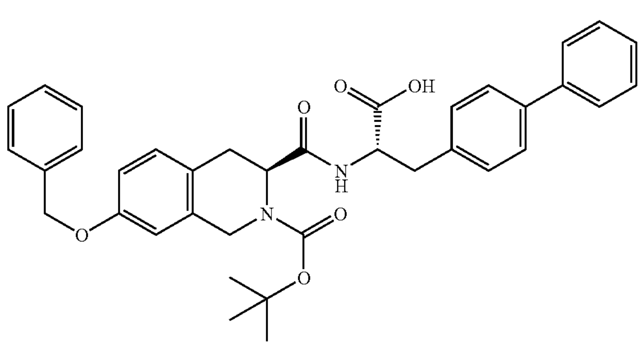 | 7-Benzyloxy-(3S)-(2-biphenyl-4-yl-(1S)-carboxy-ethylcarbamoyl)-3,4-dihydro-1H-isoquinoline-2-carboxylic acid tert-butyl ester |

TABLE 1-continued

| Example | Structure | Name |
|---|---|---|
| 154 | 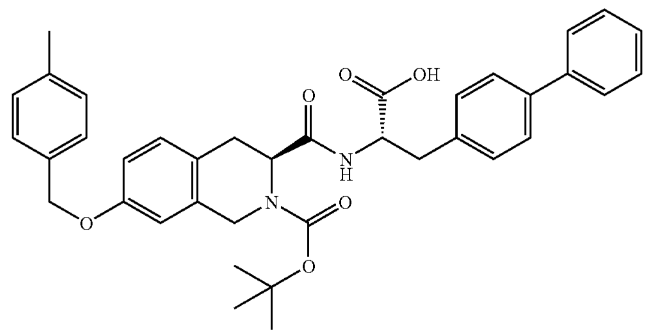 | (3S)-(2-Biphenyl-4-yl-(1S)-carboxy-ethylcarbamoyl)-7-(4-methyl-benzyloxy)-3,4-dihydro-1H-isoquinoline-2-carboxylic acid tert-butyl ester |
| 155 | 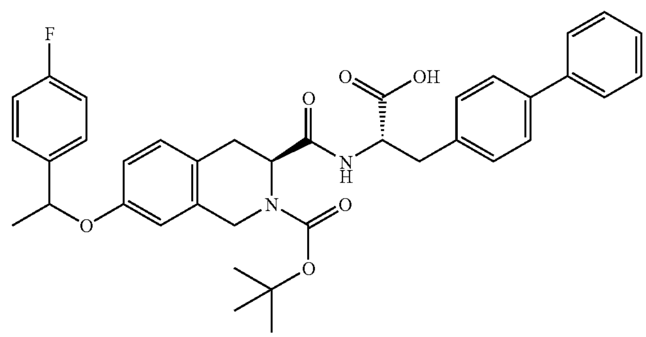 | (3S)-(2-Biphenyl-4-yl-(1S)-carboxy-ethylcarbamoyl)-7-[1-(4-fluoro-phenyl)-ethoxy]-3,4-dihydro-1H-isoquinoline-2-carboxylic acid tert-butyl ester |
| 156 | 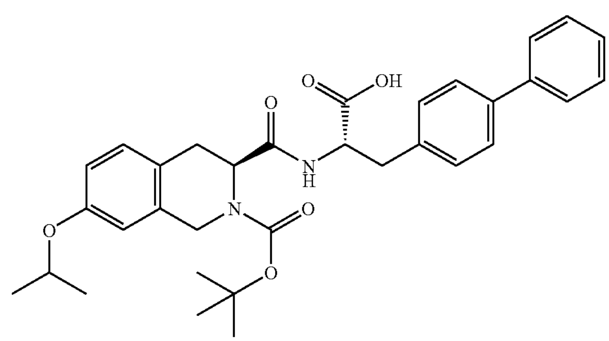 | (3S)-(2-Biphenyl-4-yl-(1S)-carboxy-ethylcarbamoyl)-7-isopropoxy-3,4-dihydro-1H-isoquinoline-2-carboxylic acid tert-butyl ester |
| 157 | 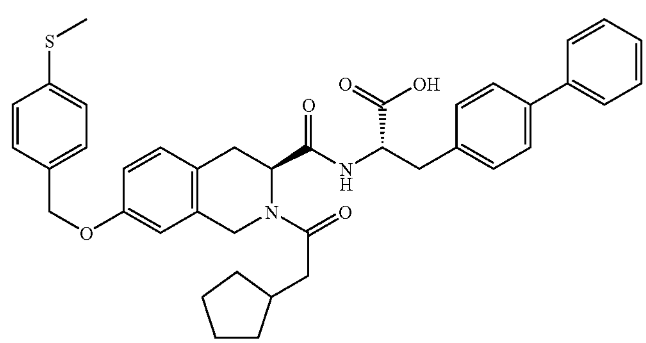 | 3-Biphenyl-4-yl-(2S)-{[2-(2-cyclopentyl-acetyl)-7-(4-methylsulfanyl-benzyloxy)-1,2,3,4-tetrahydro-isoquinoline-(3S)-carbonyl]-amino}-propionic acid |

TABLE 1-continued

| Example | Structure | Name |
|---|---|---|
| 158 | 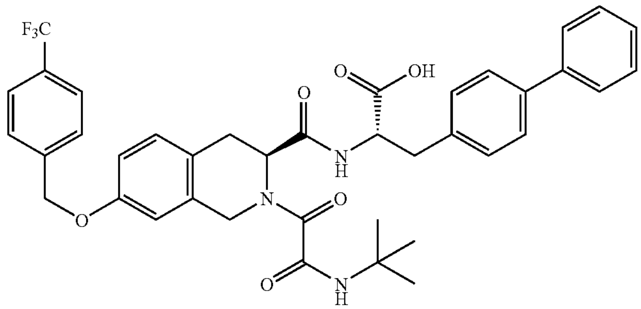 | 3-Biphenyl-4-yl-(2S)-{[2-(tert-butylcarbamoyl-methyl)-7-(4-trifluoromethyl-benzyloxy)-1,2,3,4-tetrahydro-isoquinoline-(3S)-carbonyl]-amino}-propionic acid |
| 159 | 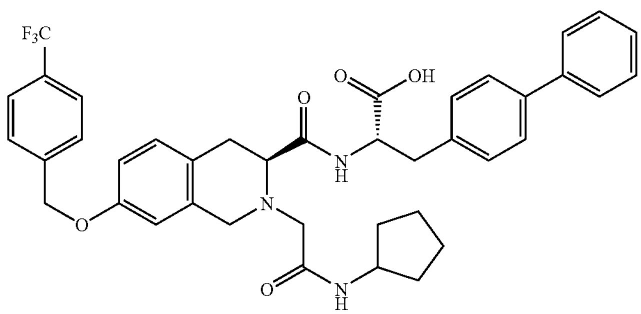 | 3-Biphenyl-4-yl-(2S)-{[2-cyclopentylcarbamoylmethyl-7-(4-trifluoromethyl-benzyloxy)-1,2,3,4-tetrahydro-isoquinoline-(3S)-carbonyl]-amino}-propionic acid |
| 160 | 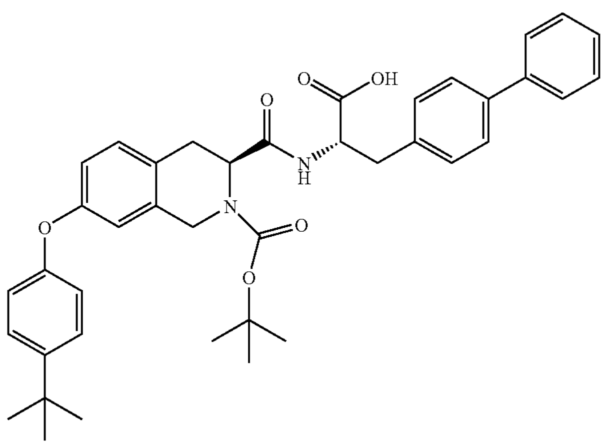 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid tert-butyl ester |
| 161 | 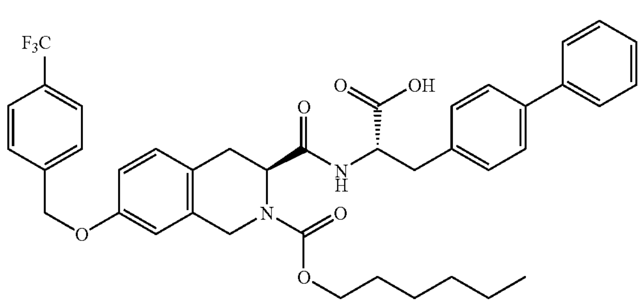 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid hexyl ester |

TABLE 1-continued

| Example | Structure | Name |
|---|---|---|
| 162 | 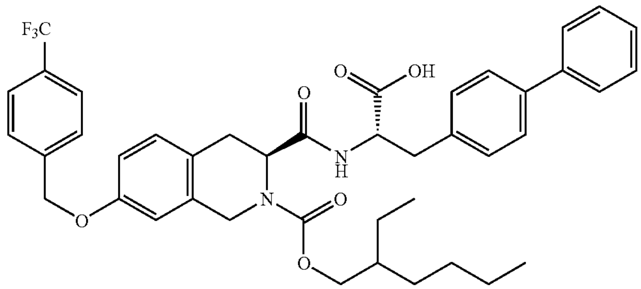 | (3S)-(2-Biphenyl-4-yl-(1S)-carboxy-ethylcarbamoyl)-7-(4-rifluoromethyl-benzyloxy)-3,4-dihydro-1H-isoquinoline-2-carboxylic acid 2-ethyl-hexyl ester |
| 163 | 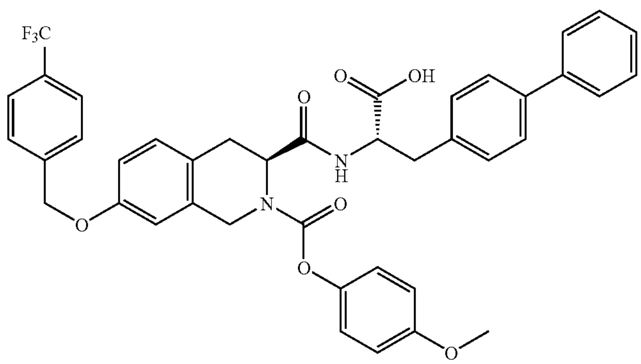 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid 4-methoxy-phenyl ester |
| 164 | 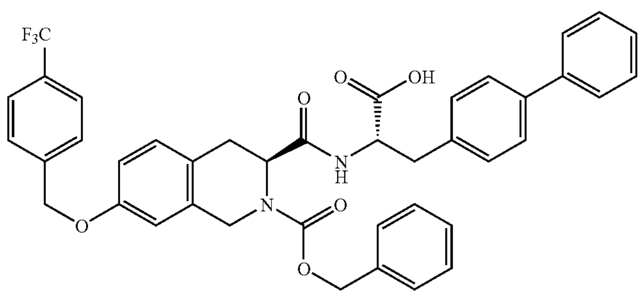 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid benzyl ester |
| 165 | 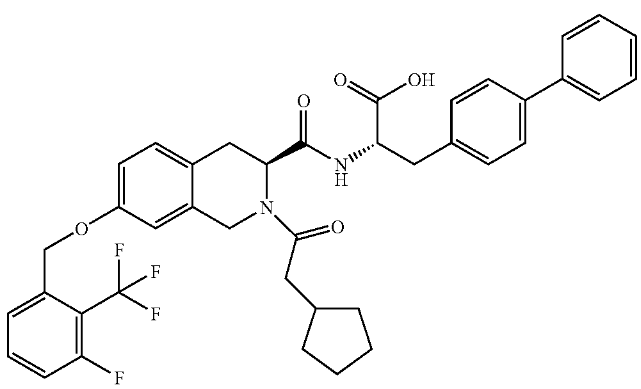 | 3-Biphenyl-4-yl-(2S)-{[2-(2-cyclopentyl-acetyl)-7-(3-fluoro-2-trifluoromethyl-benzyloxy)-1,2,3,4-tetrahydro-isoquinoline-(3S)-carbonyl]-amino}-propionic acid |

TABLE 1-continued

| Example | Structure | Name |
|---|---|---|
| 166 | 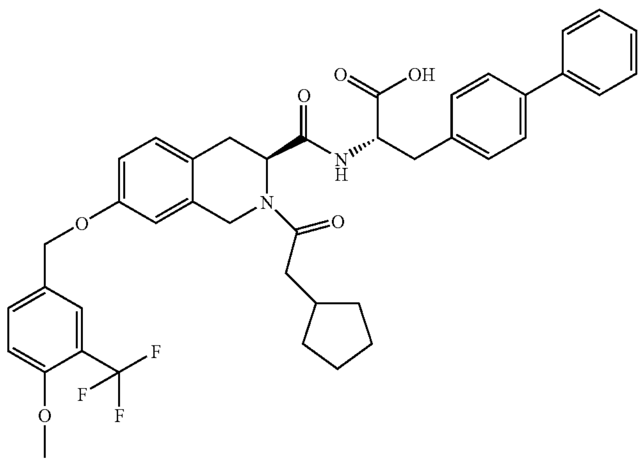 | 3-Biphenyl-4-yl-(2S)-{[2-(2-cyclopentyl-acetyl)-7-(4-methoxy-3-trifluoromethyl-benzyloxy)-1,2,3,4-tetrahydro-isoquinoline-(3S)-carbonyl]-amino}-propionic acid |
| 167 | 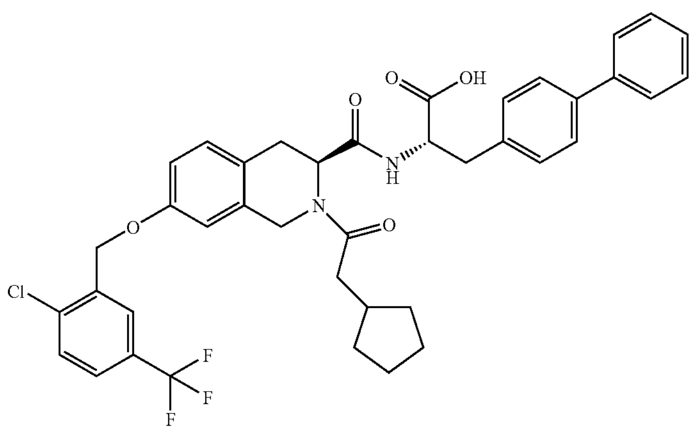 | 3-Biphenyl-4-yl-(2S)-{[7-(2-chloro-5-trifluoromethyl-benzyloxy)-2-(2-cyclopentyl-acetyl)-1,2,3,4-tetrahydro-isoquinoline-(3S)-carbonyl]-amino}-propionic acid |
| 168 | 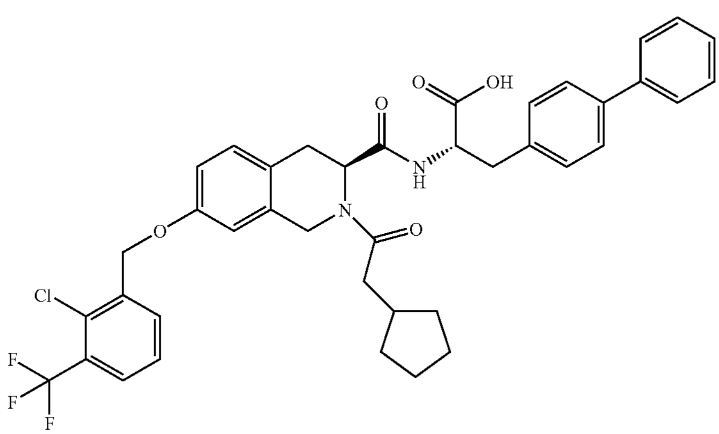 | 3-Biphenyl-4-yl-(2S)-{[7-(2-chloro-3-trifluoromethyl-benzyloxy)-2-(2-cyclopentyl-acetyl)-1,2,3,4-tetrahydro-isoquinoline-(3S)-carbonyl]-amino}-propionic acid |

TABLE 1-continued

| Example | Structure | Name |
|---|---|---|
| 169 | 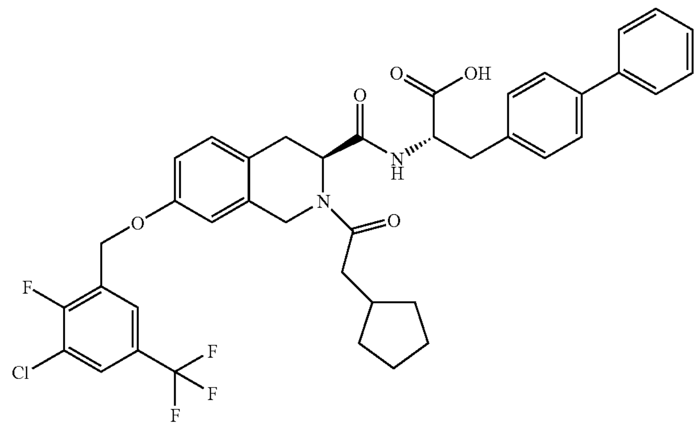 | 3-Biphenyl-4-yl-(2S)-{[7-(3-chloro-2-fluoro-5-trifluoromethyl-benzyloxy)-2-(2-cyclopentyl-acetyl)-1,2,3,4-tetrahydro-isoquinoline-(3S)-carbonyl]-amino}-propionic acid |
| 170 | 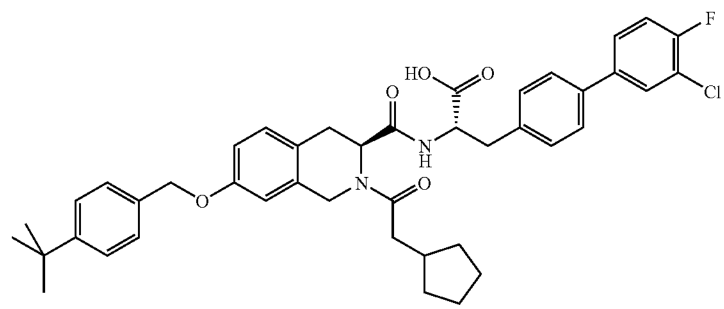 | (2S)-{[7-(4-tert-Butyl-benzyloxy)-2-(2-cyclopentyl-acetyl)-1,2,3,4-tetrahydro-isoquinoline-(3S)-carbonyl]-amino}-3-(3'-chloro-4'-fluoro-biphenyl-4-yl)-propionic acid |
| 171 | 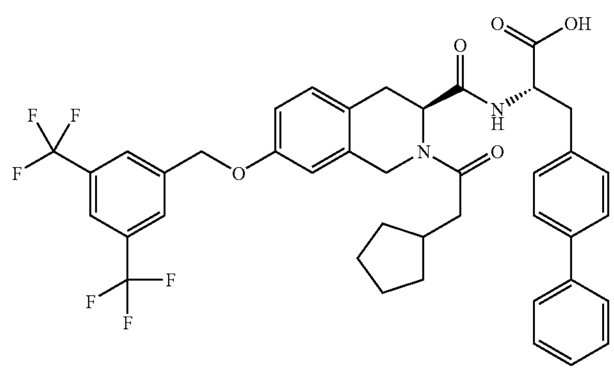 | 3-Biphenyl-4-yl-(2S)-{[7-(3,5-bis-trifluoromethyl-benzyloxy)-2-(2-cyclopentyl-acetyl)-1,2,3,4-tetrahydro-isoquinoline-(3S)-carbonyl]-amino}-propionic acid |
| 172 | 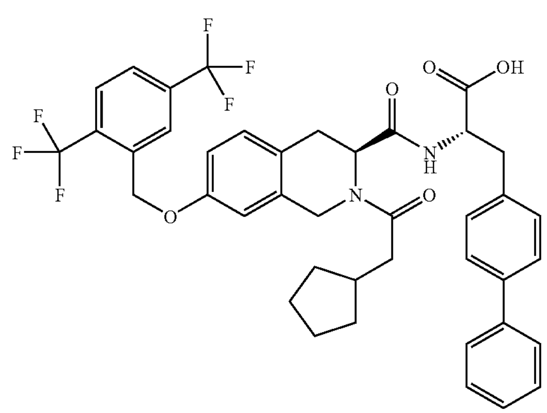 | 3-Biphenyl-4-yl-(2S)-{[7-(2,5-bis-trifluoromethyl-benzyloxy)-2-(2-cyclopentyl-acetyl)-1,2,3,4-tetrahydro-isoquinoline-(3S)-carbonyl]-amino}-propionic acid |

TABLE 1-continued

| Example | Structure | Name |
|---|---|---|
| 173 | 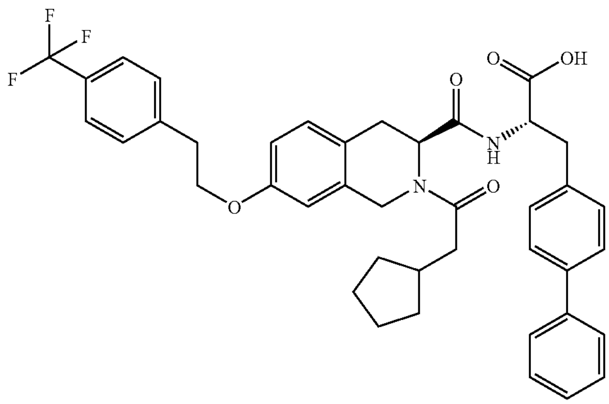 | 3-Biphenyl-4-yl-(2S)-({2-(2-cyclopentyl-acetyl)-7-[2-(4-trifluoromethyl-phenyl)-ethoxy]-1,2,3,4-tetrahydro-isoquinoline-(3S)-carbonyl}-amino)-propionic acid |
| 174 | 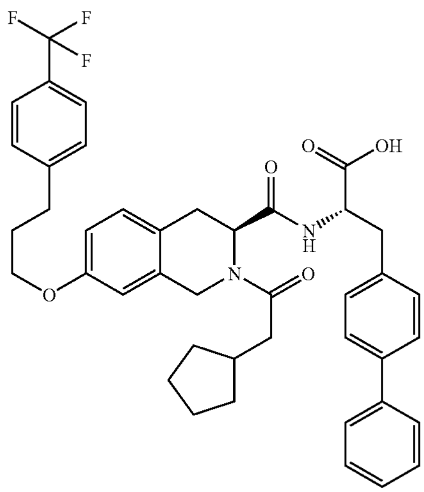 | 3-Biphenyl-4-yl-(2S)-({2-(2-cyclopentyl-acetyl)-7-[3-(4-trifluoromethyl-phenyl)-propoxy]-1,2,3,4-tetrahydro-isoquinoline-(3S)-carbonyl}-amino)-propionic acid |
| 175 | 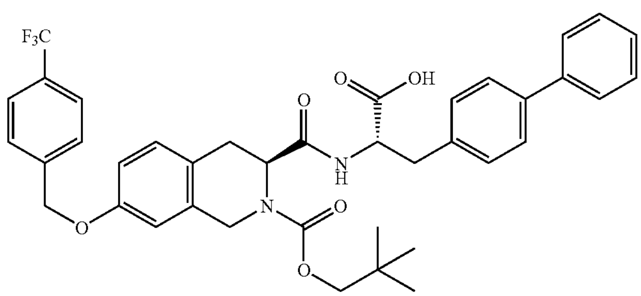 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid 2,2-dimethyl-propyl ester |
| 176 | 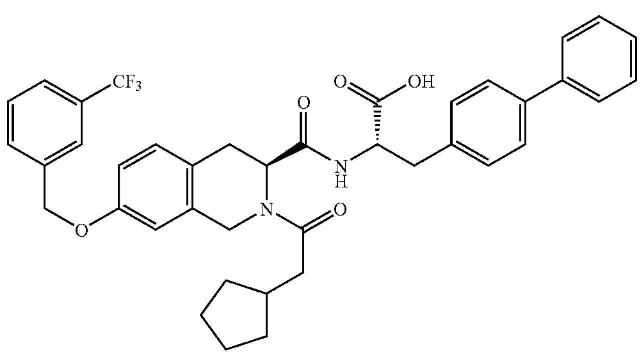 | 3-Biphenyl-4-yl-(2S)-{[2-(2-cyclopentyl-acetyl)-7-(3-trifluoromethyl-benzyloxy)-1,2,3,4-tetrahydro-isoquinoline-(3S)-carbonyl]-amino}-propionic acid |

TABLE 1-continued

| Example | Structure | Name |
|---|---|---|
| 177 | 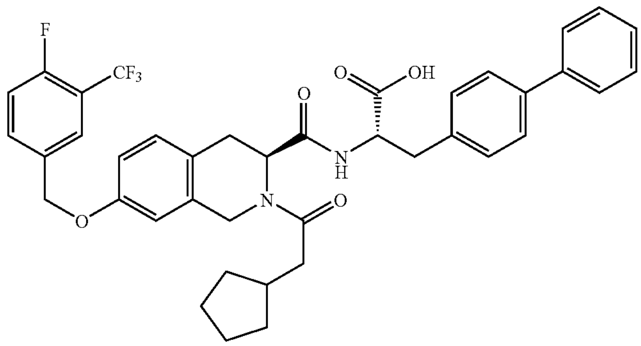 | 3-Biphenyl-4-yl-(2S)-{[2-(2-cyclopentyl-acetyl)-7-(4-fluoro-3-trifluoromethyl-benzyloxy)-1,2,3,4-tetrahydro-isoquinoline-(3S)-carbonyl]-amino}-propionic acid |
| 178 | 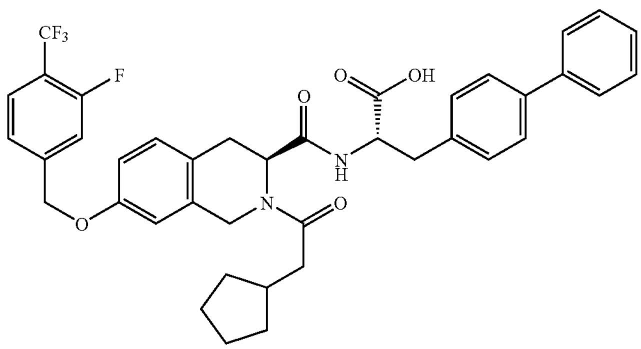 | 3-Biphenyl-4-yl-(2S)-{[2-(2-cyclopentyl-acetyl)-7-(3-fluoro-4-trifluoromethyl-benzyloxy)-1,2,3,4-tetrahydro-isoquinoline-(3S)-carbonyl]-amino}-propionic acid |
| 179 | 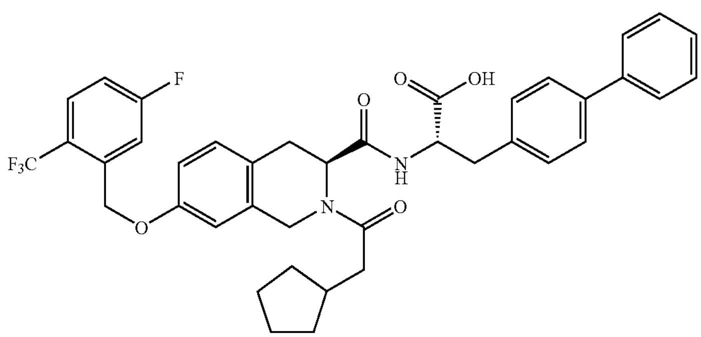 | 3-Biphenyl-4-yl-(2S)-{[2-(2-cyclopentyl-acetyl)-7-(5-fluoro-2-trifluoromethyl-benzyloxy)-1,2,3,4-tetrahydro-isoquinoline-(3S)-carbonyl]-amino}-propionic acid |
| 180 | 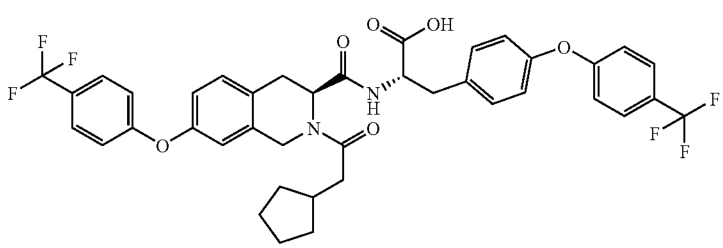 | (2S)-{[2-(2-Cyclopentyl-acetyl)-7-(4-trifluoromethyl-phenoxy)-1,2,3,4-tetrahydro-isoquinoline-(3S)-carbonyl]-amino}-3-[4-(4-trifluoromethyl-phenoxy)-phenyl]-propionic acid |
| 181 | 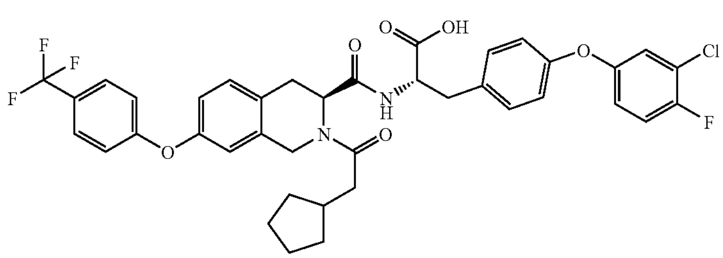 | 3-[4-(3-Chloro-4-fluoro-phenoxy)-phenyl]-(2S)-{[2-(2-cyclopentyl-acetyl)-7-(4-trifluoromethyl-phenoxy)-1,2,3,4-tetrahydro-isoquinoline-(3S)-carbonyl]-amino}-propionic acid |

TABLE 1-continued

| Example | Structure | Name |
|---|---|---|
| 182 | 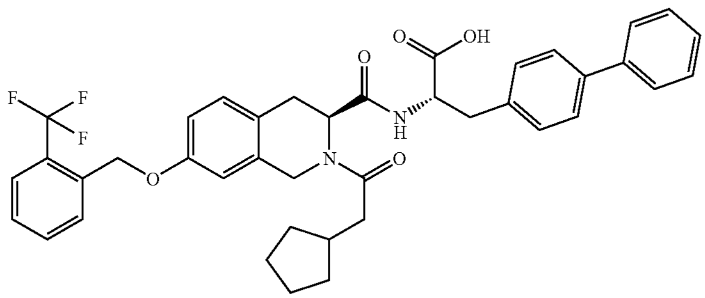 | 3-Biphenyl-4-yl-(2S)-{[2-(2-cyclopentyl-acetyl)-7-(2-trifluoromethyl-benzyloxy)-1,2,3,4-tetrahydro-isoquinoline-(3S)-carbonyl]-amino}-propionic acid |
| 183 | 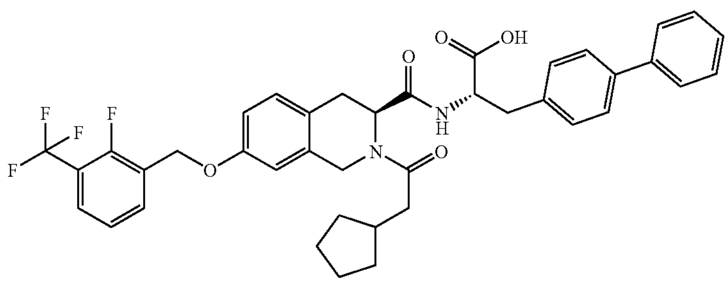 | 3-Biphenyl-4-yl-(2S)-{[2-(2-cyclopentyl-acetyl)-7-(2-fluoro-3-trifluoromethyl-benzyloxy)-1,2,3,4-tetrahydro-isoquinoline-(3S)-carbonyl]-amino}-propionic acid |
| 184 | 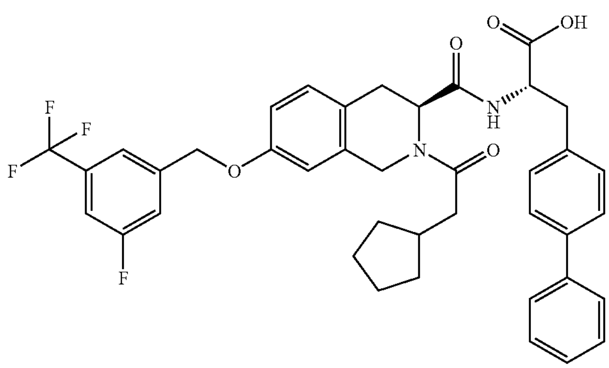 | 3-Biphenyl-4-yl-(2S)-{[2-(2-cyclopentyl-acetyl)-7-(3-fluoro-5-trifluoromethyl-benzyloxy)-1,2,3,4-tetrahydro-isoquinoline-(3S)-carbonyl]-amino}-propionic acid |
| 185 | 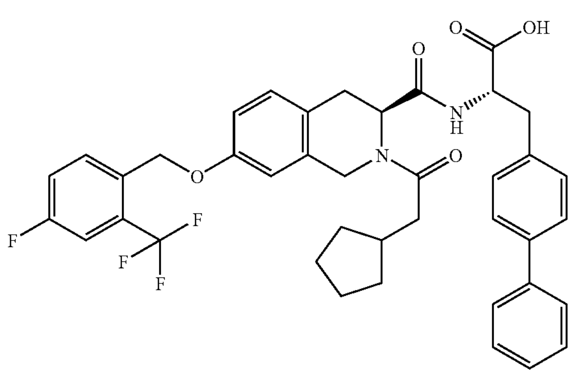 | 3-Biphenyl-4-yl-(2S)-{[2-(2-cyclopentyl-acetyl)-7-(4-fluoro-2-trifluoromethyl-benzyloxy)-1,2,3,4-tetrahydro-isoquinoline-(3S)-carbonyl]-amino}-propionic acid |

TABLE 1-continued

| Example | Structure | Name |
|---|---|---|
| 186 | 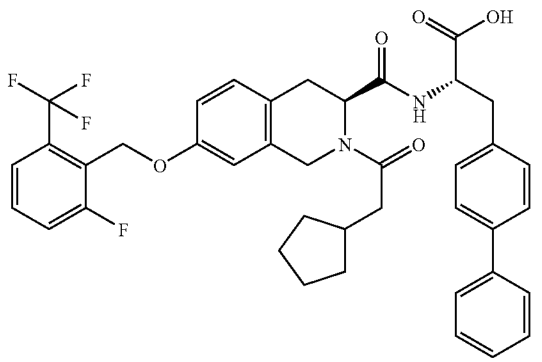 | 3-Biphenyl-4-yl-(2S)-{[2-(2-cyclopentyl-acetyl)-7-(2-fluoro-6-trifluoromethyl-benzyloxy)-1,2,3,4-tetrahydro-isoquinoline-(3S)-carbonyl]-amino}-propionic acid |
| 187 | 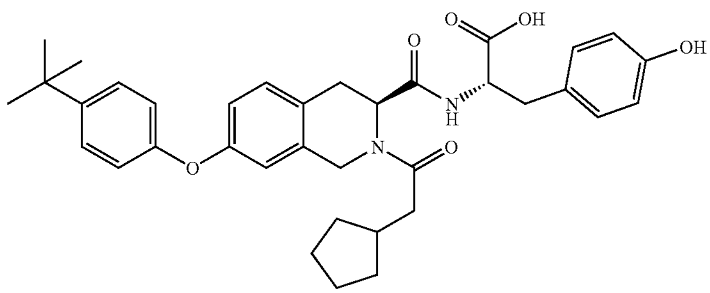 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4-hydroxy-henyl)-propionic acid |
| 188 | 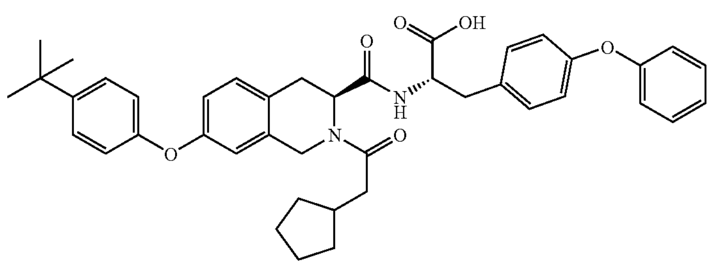 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4-phenoxy-phenyl)-propionic acid |
| 189 | 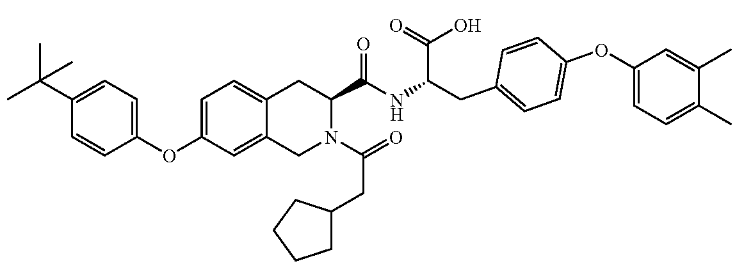 | (2S)-{[7-(4-tert-Butyl-phenoxy)-2-(2-cyclopentyl-acetyl)-1,2,3,4-tetrahydro-isoquinoline-(3S)-carbonyl]-amino}-3-[4-(3-chloro-4-fluoro-phenoxy)-phenyl]-propionic acid |
| 190 | 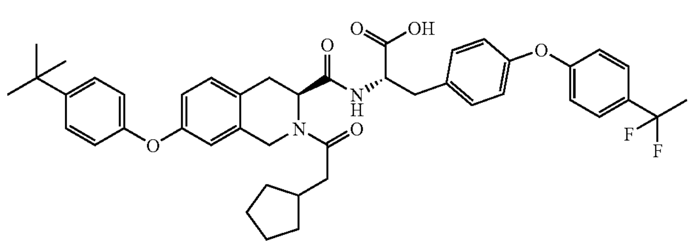 | (2S)-{[7-(4-tert-Butyl-phenoxy)-2-(2-cyclopentyl-acetyl)-1,2,3,4-tetrahydro-isoquinoline-(3S)-carbonyl]-amino}-3-[4-(4-trifluoromethyl-phenoxy)-phenyl]-propionic acid |

TABLE 1-continued

| Example | Structure | Name |
|---|---|---|
| 191 | 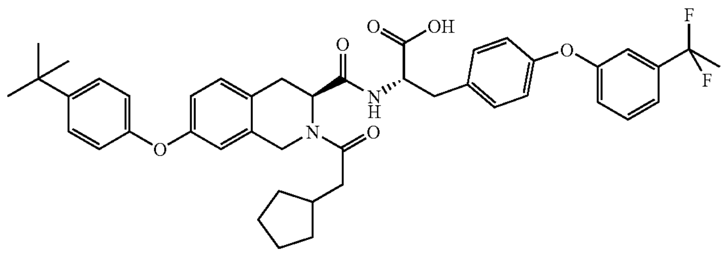 | (2S)-{[7-(4-tert-Butyl-phenoxy)-2-(2-cyclopentyl-acetyl)-1,2,3,4-tetrahydro-isoquinoline-(3S)-carbonyl]-amino}-3-[4-(3-trifluoromethyl-phenoxy)-phenyl]-propionic acid |
| 192 | 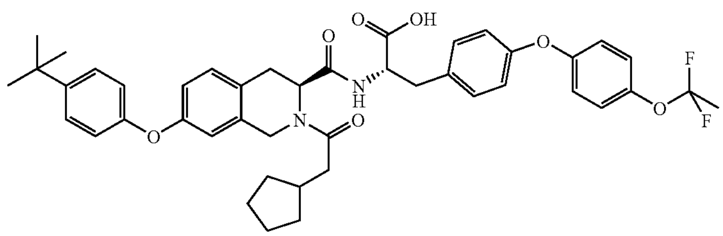 | (2S)-{[7-(4-tert-Butyl-phenoxy)-2-(2-cyclopentyl-acetyl)-1,2,3,4-tetrahydro-isoquinoline-(3S)-carbonyl]-amino}-3-[4-(4-trifluoromethoxy-phenoxy)-phenyl]-propionic acid |
| 193 | 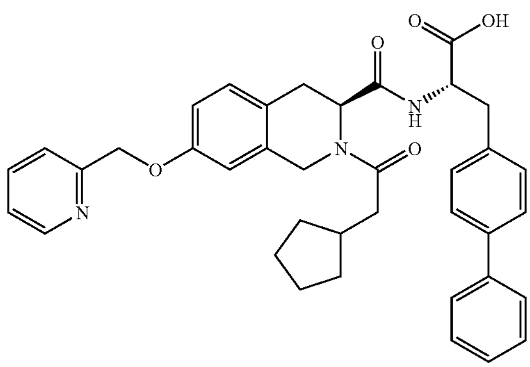 | 3-Biphenyl-4-yl-(2S)-{[2-(2-cyclopentyl-acetyl)-7-(pyridin-2-ylmethoxy)-1,2,3,4-tetrahydro-isoquinoline-(3S)-carbonyl]-amino}-propionic acid |
| 194 | 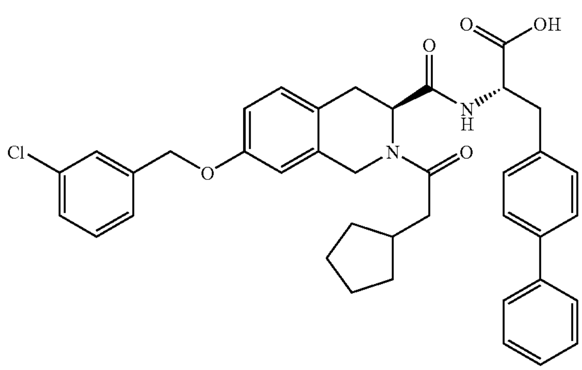 | 3-Biphenyl-4-yl-(2S)-{[7-(3-chloro-benzyloxy)-2-(2-cyclopentyl-acetyl)-1,2,3,4-tetrahydro-isoquinoline-(3S)-carbonyl]-amino}-propionic acid |
| 195 | 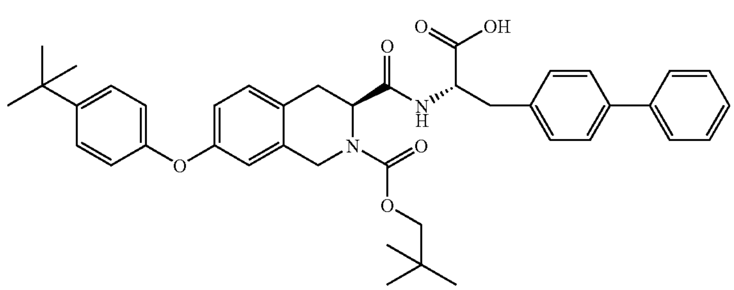 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid 2,2-dimethyl-propyl ester |

TABLE 1-continued

| Example | Structure | Name |
|---|---|---|
| 196 | 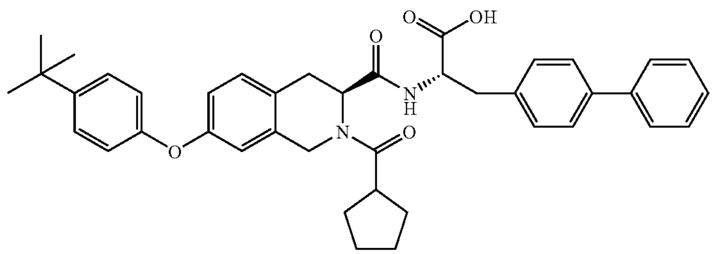 | 3-Biphenyl-4-yl-(2S)-{[7-(4-tert-butyl-phenoxy)-2-cyclopentanecarbonyl-1,2,3,4-tetrahydro-isoquinoline-(3S)-carbonyl]-amino}-propionic acid |
| 197 | 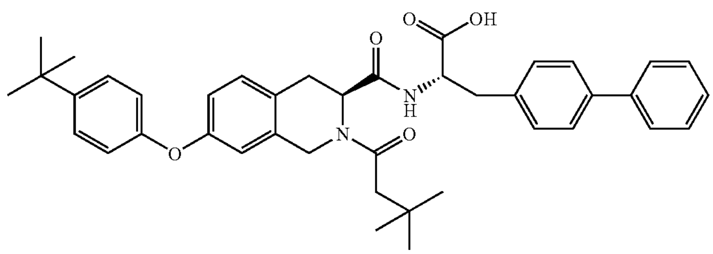 | 3-Biphenyl-4-yl-(2S)-{[7-(4-tert-butyl-phenoxy)-2-(3,3-dimethyl-butyryl)-1,2,3,4-tetrahydro-isoquinoline-(3S)-carbonyl]-amino}-propionic acid |
| 198 | 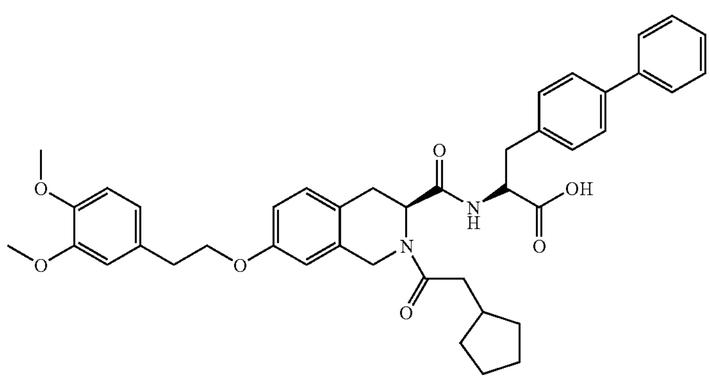 | 3-Biphenyl-4-yl-(2S)-({2-(2-cyclopentyl-acetyl)-7-[2-(3,4-dimethoxy-phenyl)-ethoxy]-1,2,3,4-tetrahydro-isoquinoline-(3S)-carbonyl}-amino)-propionic acid |
| 199 | 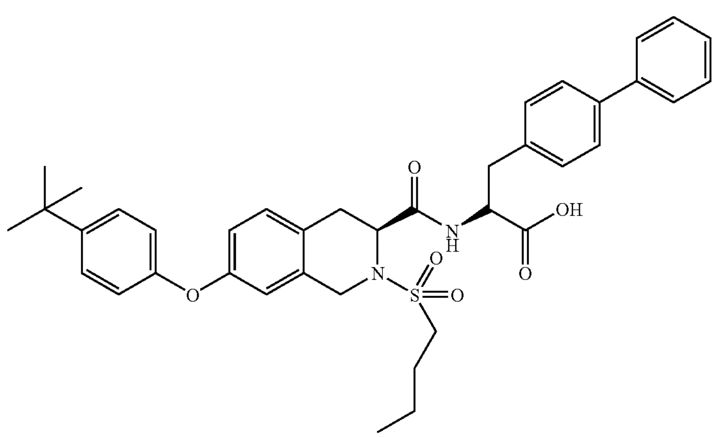 | 3-Biphenyl-4-yl-(2S)-{[2-(butane-1-sulfonyl)-7-(4-tert-butyl-phenoxy)-1,2,3,4-tetrahydro-isoquinoline-(3S)-carbonyl]-amino}-propionic acid |

TABLE 1-continued

| Example | Structure | Name |
|---|---|---|
| 200 | 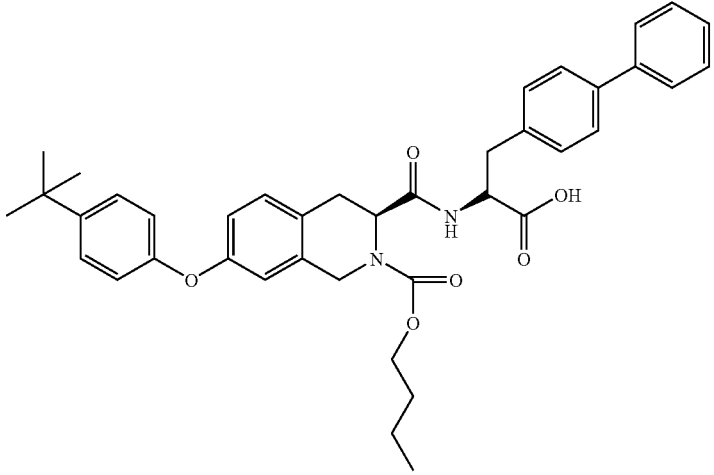 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid butyl ester |
| 201 | 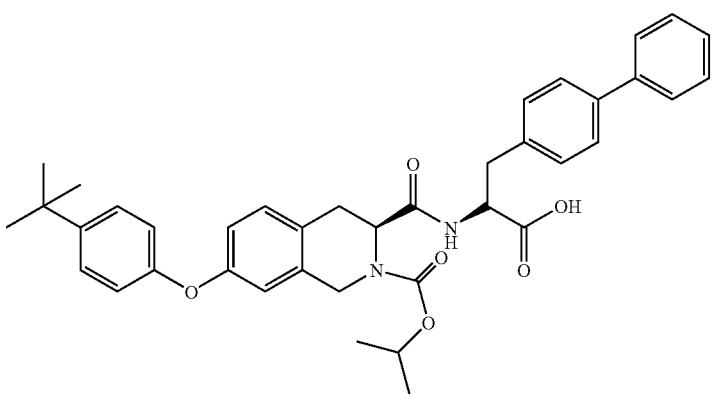 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid isopropyl ester |
| 202 | 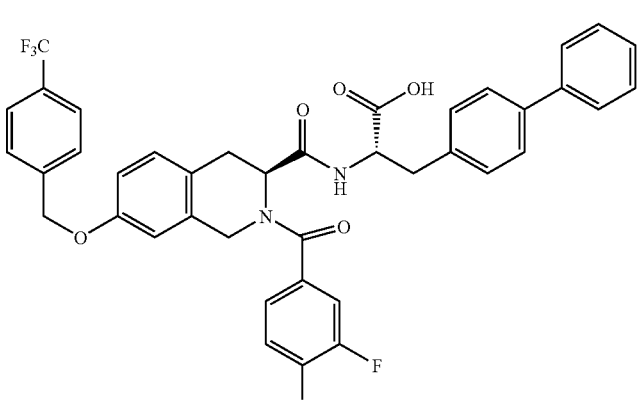 | 3-Biphenyl-4-yl-(2S)-{(2-(3,4-difluoro-benzoyl)-7-(4-trifluoromethyl-benzyloxy)-1,2,3,4-tetrahydro-isoquinoline-(3S)-carbonyl]-amino}-propionic acid |

TABLE 1-continued

| Example | Structure | Name |
|---|---|---|
| 203 | 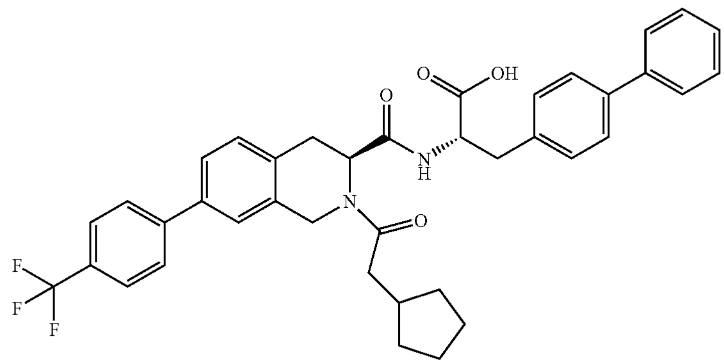 | 3-Biphenyl-4-yl-(2S)-{[2-(2-cyclopentyl-acetyl)-7-(4-trifluoromethyl-phenyl)-1,2,3,4-tetrahydro-isoquinoline-3-carbonyl]-amino}-propionic acid |
| 204 | 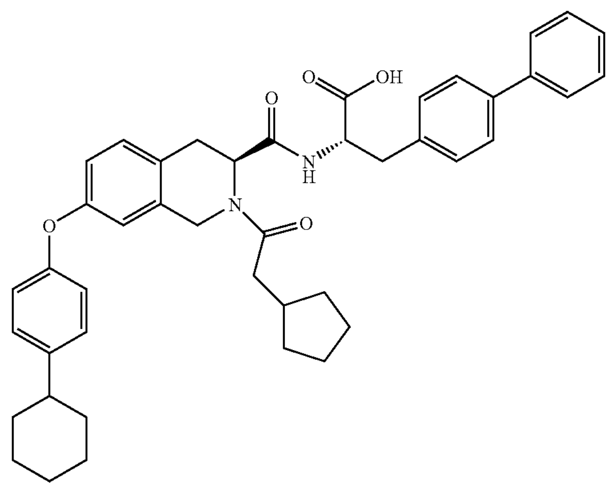 | 3-Biphenyl-4-yl-(2S)-{[7-(4-cyclohexyl-phenoxy)-2-(2-cyclopentyl-acetyl)-1,2,3,4-tetrahydro-isoquinoline-(3S)-carbonyl]-amino}-propionic acid |
| 205 | 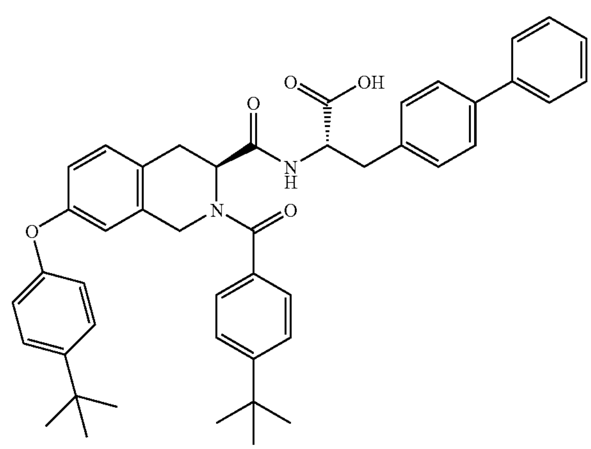 | 3-Biphenyl-4-yl-(2S)-{[2-(4-tert-butyl-benzoyl)-7-(4-tert-butyl-phenoxy)-1,2,3,4-tetrahydro-isoquinoline-(3S)-carbonyl]amino]-propionic acid |

TABLE 1-continued

| Example | Structure | Name |
|---|---|---|
| 206 | 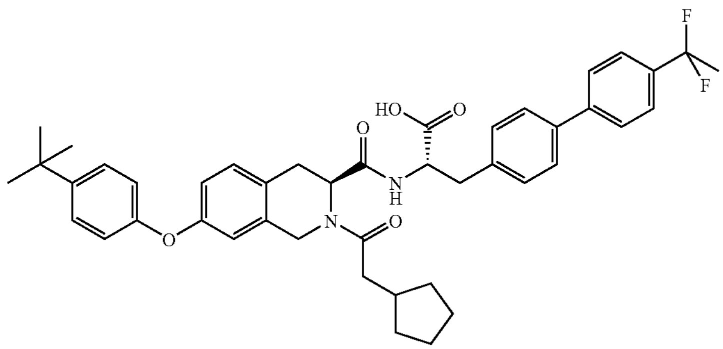 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4'-trifluoromethyl-biphenyl-4-yl)-propionic acid |
| 207 | 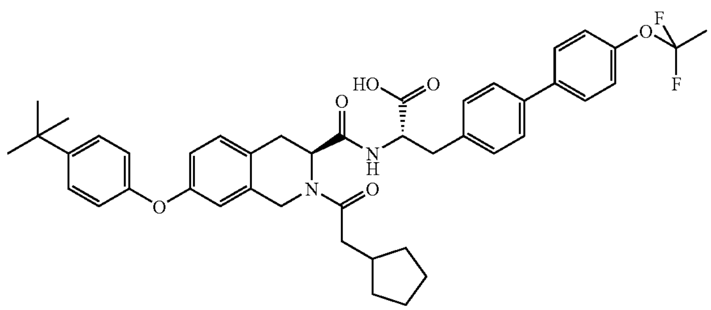 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4'-trifluoromethoxy-biphenyl-4-yl)-propionic acid |
| 208 | 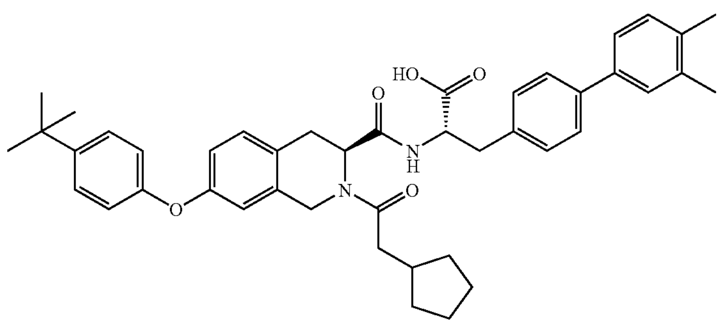 | (2S)-{[7-(4-tert-Butyl-phenoxy)-2-(2-cyclopentyl-acetyl)-1,2,3,4-tetrahydro-isoquinoline-(3S)-carbonyl]-amino}-3-(3'-chloro-4'-fluoro-biphenyl-4-yl)-propionic acid |
| 209 | 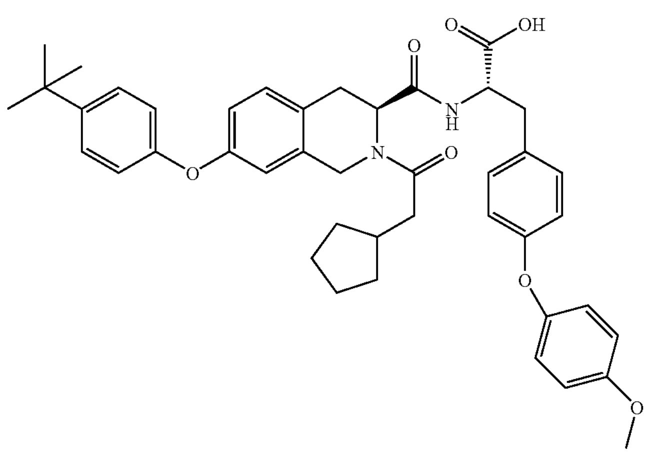 | (2S)-{[7-(4-tert-Butyl-phenoxy)-2-(2-cyclopentyl-acetyl)-1,2,3,4-tetrahydro-isoquinoline-(3S)-carbonyl]-amino}-3-[4-(4-methoxy-phenoxy)-phenyl]-propionic acid |

TABLE 1-continued

| Example | Structure | Name |
|---|---|---|
| 210 | 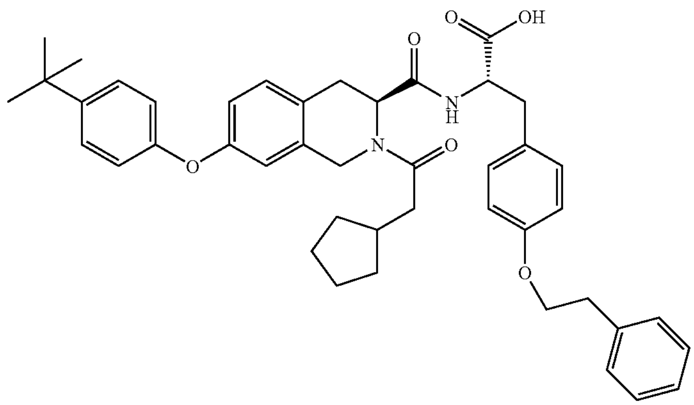 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4-phenethyloxy-phenyl)-propionic acid |
| 211 | 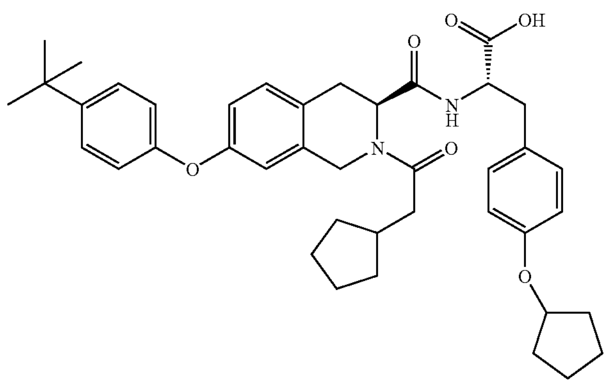 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4-cyclopentyloxy-phenyl)-propionic acid |
| 212 | 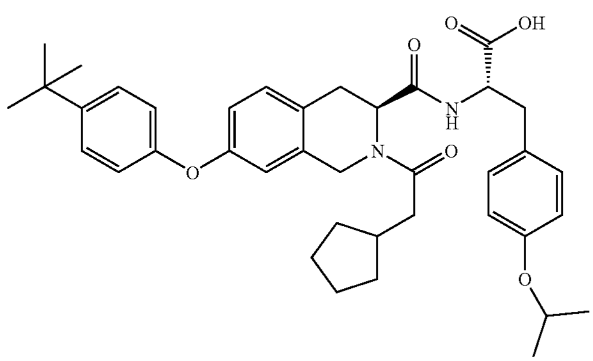 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4-isopropoxy-phenyl)-propionic acid |
| 213 | 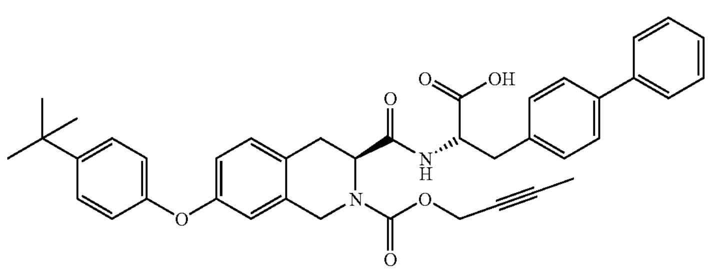 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid but-2-ynyl ester |

TABLE 1-continued

| Example | Structure | Name |
|---|---|---|
| 214 | 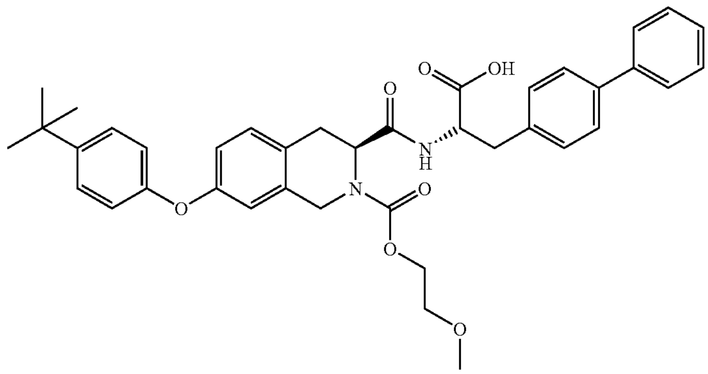 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid 2-methoxy-ethyl ester |
| 215 | 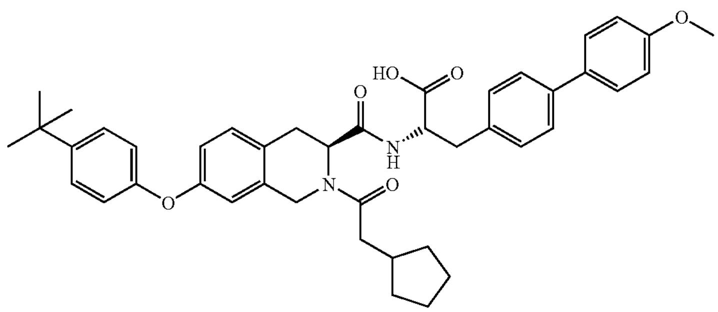 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4'-methoxy-biphenyl-4-yl)-propionic acid |
| 216 | 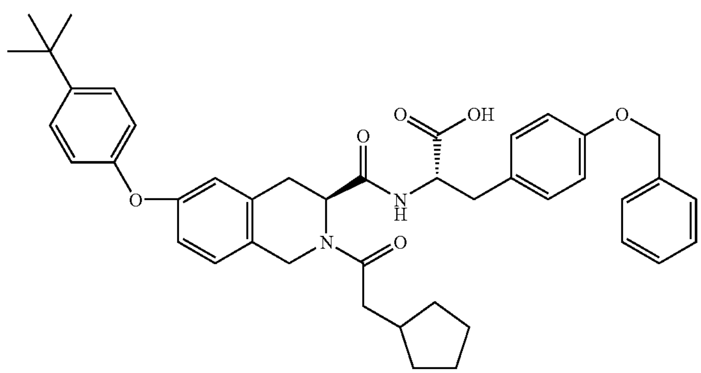 | 3-(4-Benzyloxy-phenyl)-(2S)-{[6-(4-tert-butyl-phenoxy)-2-(2-cyclopentyl-acetyl)-1,2,3,4-tetrahydro-isoquinoline-(3S)-carbonyl]-amino}-propionic acid |
| 217 | 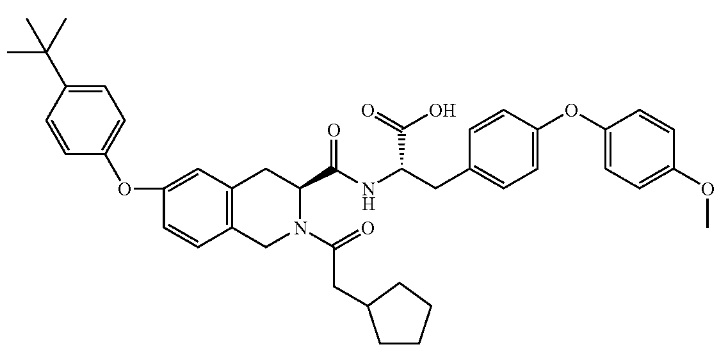 | (2S)-{[6-(4-tert-Butyl-phenoxy)-2-(2-cyclopentyl-acetyl)-1,2,3,4-tetrahydro-isoquinoline-(3S)-carbonyl]-amino}-3-[4-(4-methoxy-phenoxy)-phenyl]-propionic acid |

TABLE 1-continued

| Example | Structure | Name |
|---|---|---|
| 218 | 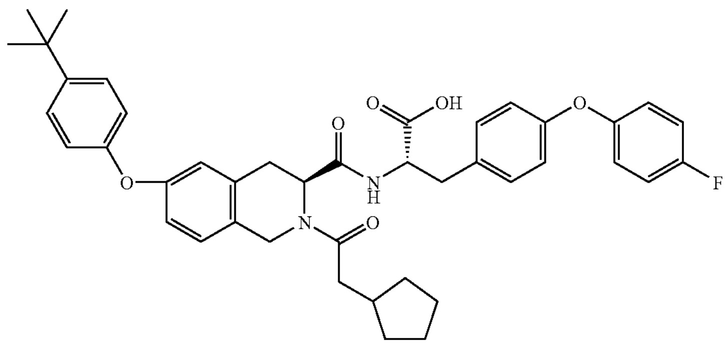 | (2S)-{[6-(4-tert-Butyl-phenoxy)-2-(2-cyclopentyl-acetyl)-1,2,3,4-tetrahydro-isoquinoline-(3S)-carbonyl]-amino}-3-[4-(4-fluoro-phenoxy)-phenyl]-propionic acid |
| 219 | 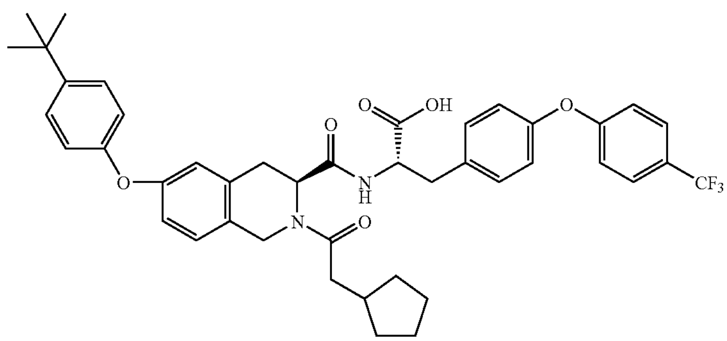 | (2S)-{[6-(4-tert-Butyl-phenoxy)-2-(2-cyclopentyl-acetyl)-1,2,3,4-tetrahydro-isoquinoline-(3S)-carbonyl]-amino}-3-[4-(4-trifluoromethyl-phenoxy)-phenyl]-propionic acid |
| 220 | 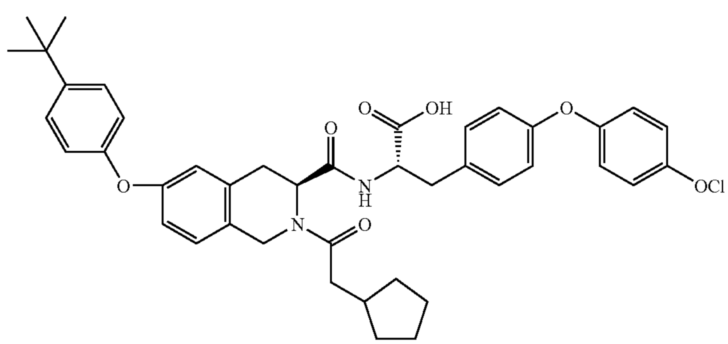 | (2S)-{[6-(4-tert-Butyl-phenoxy)-2-(2-cyclopentyl-acetyl)-1,2,3,4-tetrahydro-isoquinoline-(3S)-carbonyl]-amino}-3-[4-(4-trifluoromethoxy-phenoxy)-phenyl]propionic acid |
| 221 | 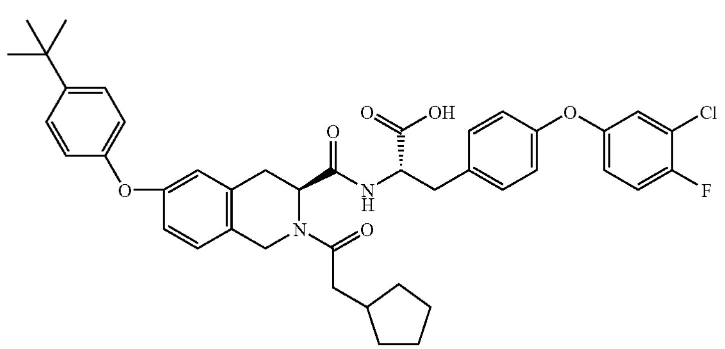 | (2S)-{[6-(4-tert-Butyl-phenoxy)-2-(2-cyclopentyl-acetyl)-1,2,3,4-tetrahydro-isoquinoline-(3S)-carbonyl]-amino}-3-[4-(3-chloro-4-fluoro-phenoxy)-phenyl]-propionic acid |

TABLE 1-continued

| Example | Structure | Name |
|---|---|---|
| 222 | 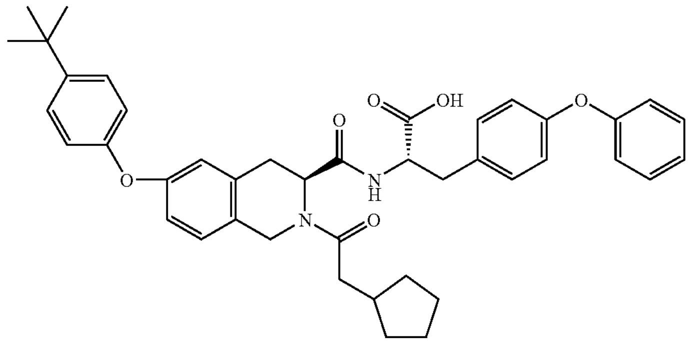 | (2S)-{[6-(4-tert-Butyl-phenoxy)-2-(2-cyclopentyl-acetyl)-1,2,3,4-tetrahydro-isoquinoline-(3S)-carbonyl]-amino}-3-(4-phenoxy-phenyl)-propionic acid |
| 223 | 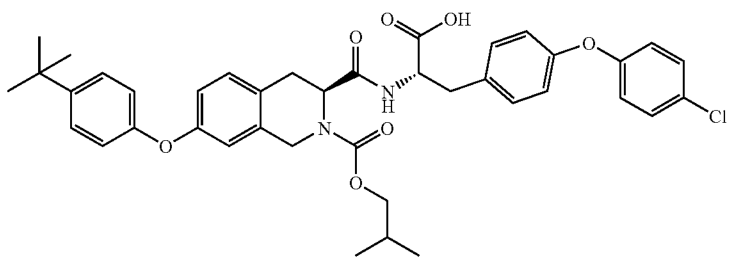 | 7-(4-tert-Butyl-phenoxy)-(3S)-{(1S)-carboxy-2-[4-(4-chloro-phenoxy)-phenyl]-ethylcarbamoyl}-3,4-dihydro-1H-isoquinoline-2-carboxylic acid isobutyl ester |
| 224 | 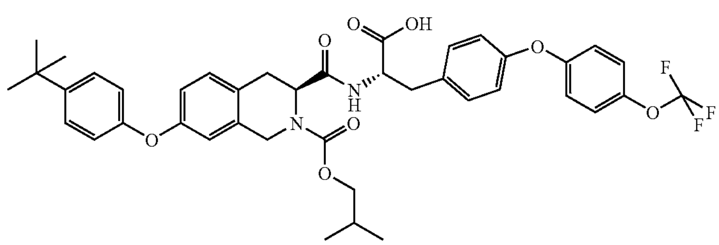 | 7-(4-tert-Butyl-phenoxy)-(3S)-{(1S)-carboxy-2-[4-(4-trifluoromethoxy-phenoxy)-phenyl]-ethylcarbamoyl}-3,4-dihydro-1H-isoquinoline-2-carboxylic acid isobutyl ester |
| 225 | 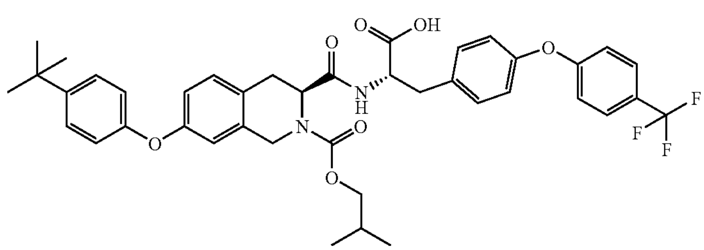 | 7-(4-tert-Butyl-phenoxy)-(3S)-{(1S)-carboxy-2-[4-(4-trifluoromethyl-phenoxy)-phenyl]-ethylcarbamoyl}-3,4-dihydro-1H-isoquinoline-2-carboxylic acid isobutyl ester |
| 226 | 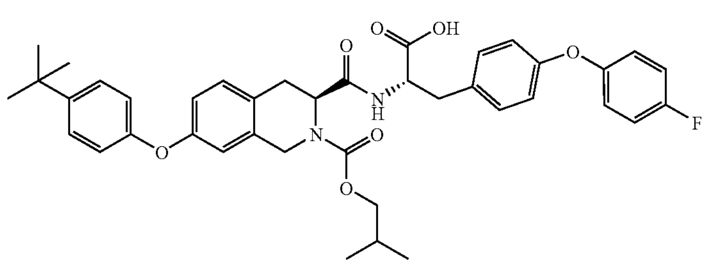 | 7-(4-tert-Butyl-phenoxy)-(3S)-{(1S)-carboxy-2-[4-(4-fluoro-phenoxy)-phenyl]-ethylcarbamoyl}-3,4-dihydro-1H-isoquinoline-2-carboxylic acid isobutyl ester |

TABLE 1-continued

| Example | Structure | Name |
|---|---|---|
| 227 | 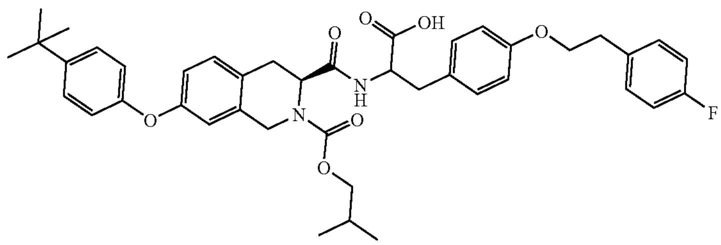 | -(4-tert-Butyl-phenoxy)-(3S)-((1S)-carboxy-2-{4-[2-(4-fluoro-phenyl)-ethoxy]-phenyl}-ethylcarbamoyl)-3,4-dihydro-1H-isoquinoiine-2-carboxylic acid isobutyl ester |
| 228 | 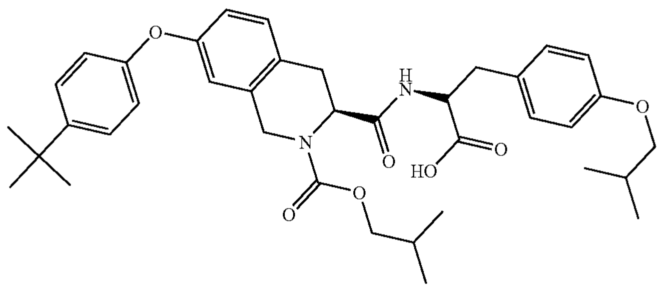 | 7-(4-tert-Butyl-phenoxy)-(3S)-[(1S)-carboxy-2-(4-isobutoxy-phenyl)-ethylcarbamoyl]-3,4-dihydro-1H-isoquinoline-2-carboxylic acid isobutyl ester |
| 229 | 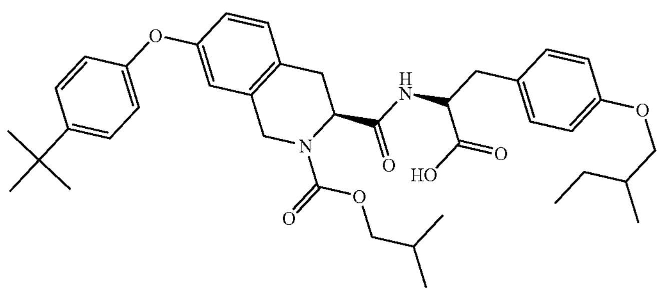 | 7-(4-tert-Butyl-phenoxy)-(3S)-{(1S)-carboxy-2-[4-(2-methyl-butoxy)-phenyl]-ethylcarbamoyl}-3,4-dihydro-1H-isoquinoline-2-carboxylic acid isobutyl ester |
| 230 | 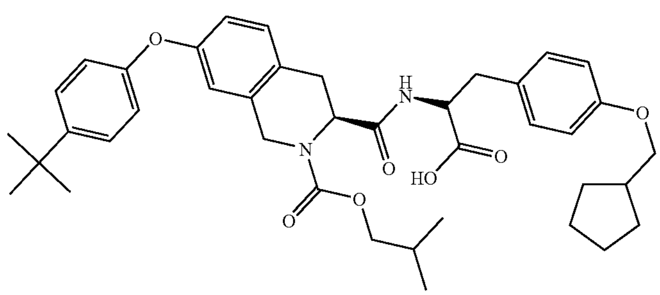 | 7-(4-tert-Butyl-phenoxy)-(3S)-[(1S)-carboxy-2-(4-cyclopentyl-methoxy-phenyl)-ethylcarbamoyl]-3,4-dihydro-1H-isoquinoline-2-carboxylic acid isobutyl ester |
| 231 | 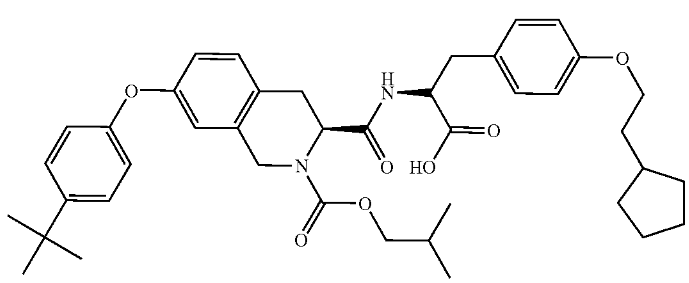 | 7-(4-tert-Butyl-phenoxy)-(3S)-{(1S)-carboxy-2-[4-(2-cyclopentyl-ethoxy)-phenyl]-ethylcarbamoyl}-3,4-dihydro-1H-isoquinoline-2-carboxylic acid isobutyl ester |

TABLE 1-continued

| Example | Structure | Name |
|---|---|---|
| 232 | 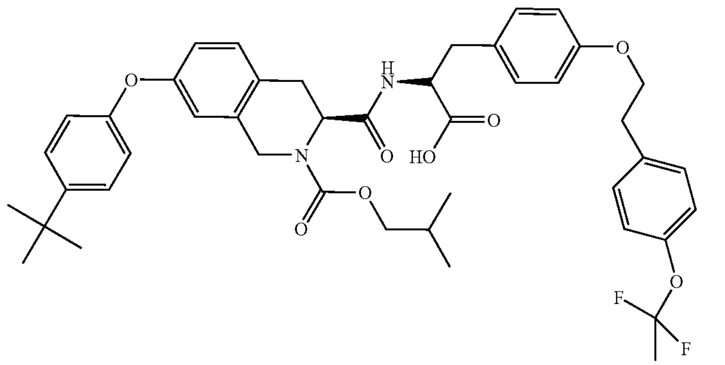 | 7-(4-tert-Butyl-phenoxy)-(3S)-((1S)-carboxy-2-{4-[2-(4-trifluoromethoxy-phenyl)-ethoxy]-phenyl}-ethylcarbamoyl)-3,4-dihydro-1H-isoquinoline-2-carboxylic acid isobutyl ester |
| 233 | 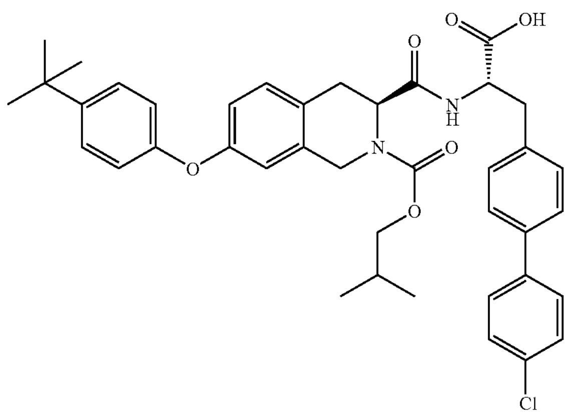 | 7-(4-tert-Butyl-phenoxy)-(3S)-[(1S)-carboxy-2-(4'-chloro-biphenyl-4-yl)-ethylcarbamoyl]-3,4-dihydro-1H-isoquinoline-2-carboxylic acid isobutyl ester |
| 234 | 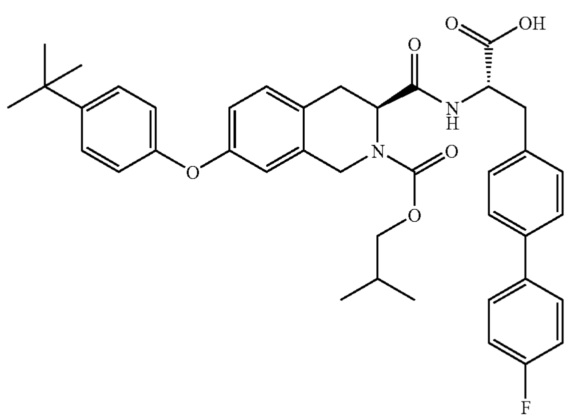 | 7-(4-tert-Butyl-phenoxy)-(3S)-[(1S)-carboxy-2-(4'-fluoro-biphenyl-4-yl)-ethylcarbamoyl]-3,4-dihydro-1H-isoquinoline-2-carboxylic acid isobutyl ester |
| 235 | 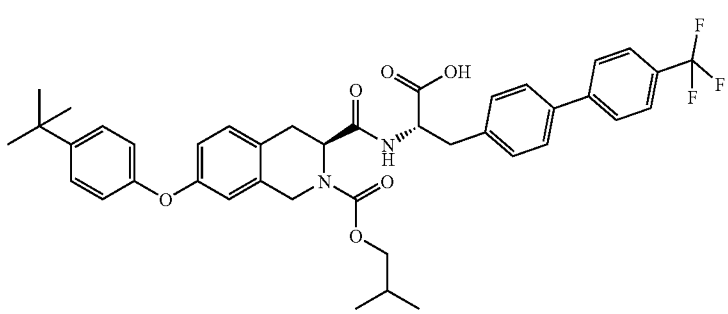 | 7-(4-tert-Butyl-phenoxy)-(3S)-[(1S)-carboxy-2-(4'-trifluoromethyl-biphenyl-4-yl)-ethylcarbamoyl]-3,4-dihydro-1H-isoquinoline-2-carboxylic acid isobutyl ester |

TABLE 1-continued

| Example | Structure | Name |
|---|---|---|
| 236 | 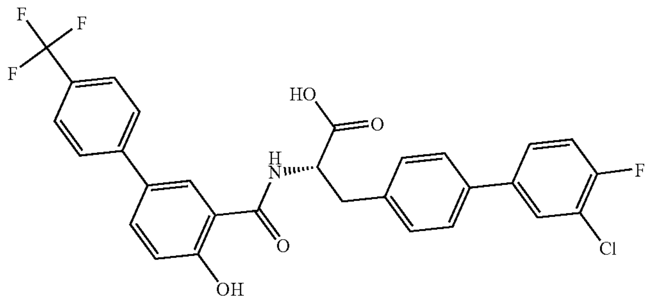 | 3-(3'-Chloro-4'-fluoro-biphenyl-4-yl)-(2S)-[(4-hydroxy-4'-trifluoromethyl-biphenyl-3-carbonyl)-amino]-propionic acid |
| 237 | 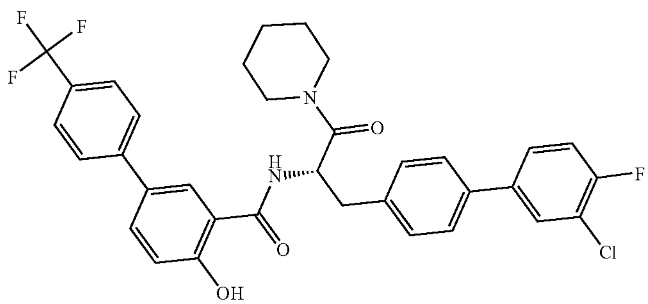 | 4-Hydroxy-4'-trifluoromethyl-biphenyl-3-carboxylic acid [1-(3'-chloro-4'-fluoro-biphenyl-4-ylmethyl)-(2S)-oxo-2-piperidin-1-yl-ethyl]-amide |
| 238 | 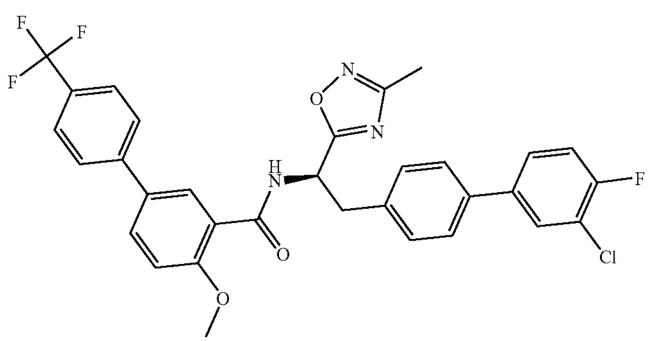 | 4-Methoxy-4'-trifluoromethyl-biphenyl-3-carboxylic acid [2-(3'-chloro-4'-fluoro-biphenyl-4-yl)-(1R)-(3-methyl-[1,2,4]oxadiazo]-5-yl)-ethyl]-amide |
| 239 | 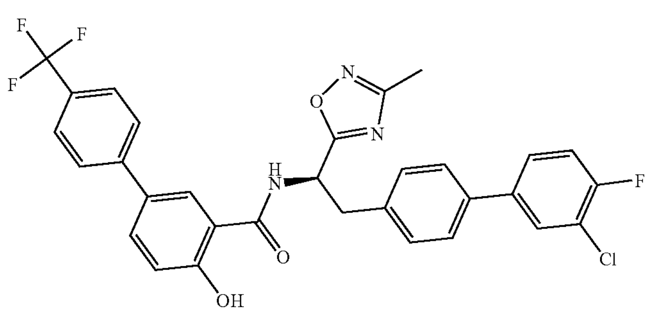 | 4-Hydroxy-4'-trifluoromethyl-biphenyl-3-carboxylic acid [2-(3'-chloro-4'-fluoro-biphenyl-4-yl)-(1R)-(3-methyl-[1,2,4]oxadiazo]-5-yl)-ethyl]-amide |
| 240 | 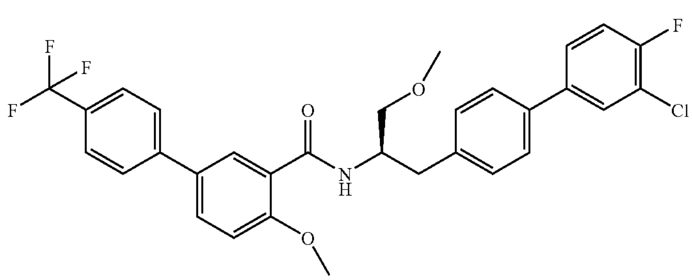 | 4-Methoxy-4'-trifluoromethyl-biphenyl-3-carboxylic acid [2-(3'-chloro-4'-fluoro-biphenyl-4-yl)-(1R)-methoxymethyl-ethyl]-amide |

TABLE 1-continued

| Example | Structure | Name |
|---------|-----------|------|
| 241 | 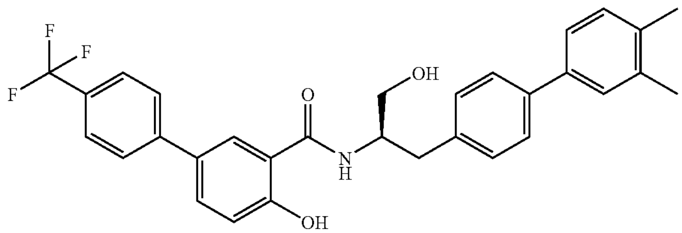 | 4-Hydroxy-4'-trifluoromethyl-biphenyl-3-carboxylic acid [2-(3'-chloro-4'-fluoro-biphenyl-4-yl)-(1R)-hydroxymethyl-ethyl]-amide |
| 242 | 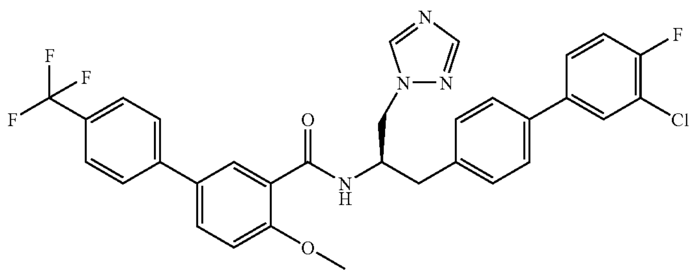 | 4-Methoxy-4'-trifluoromethyl-biphenyl-3-carboxylic acid [2-(3'-chloro-4'-fluoro-biphenyl-4-yl)-(1R)-[1,2,4]triazol-1-ylmethyl-ethyl]-amide |
| 243 | 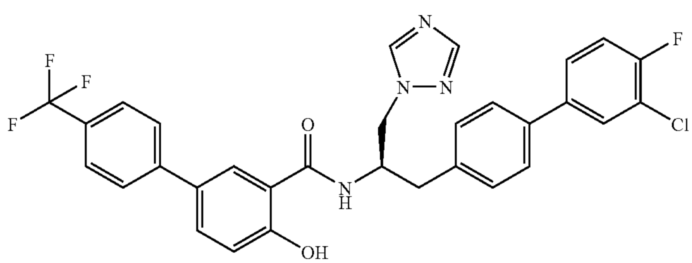 | 4-Hydroxy-4'-trifluoromethyl-biphenyl-3-carboxylic acid [2-(3'-chloro-4'-fluoro-biphenyl-4-yl)-(1R)-[1,2,4]triazol-1-ylmethyl-ethyl]-amide |
| 244 | 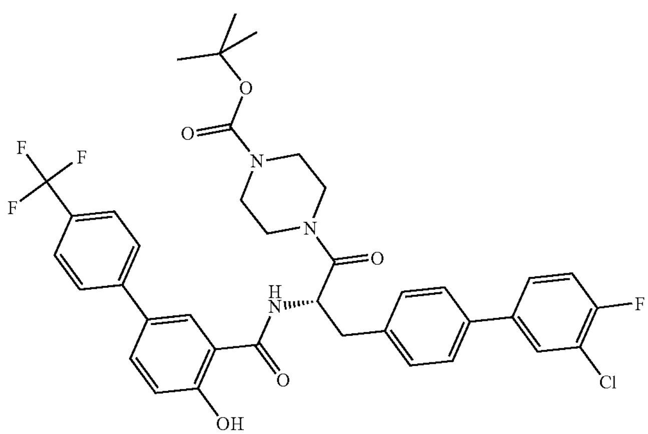 | 4-{3-(3'-Chloro-4'-fluoro-biphenyl-4-yl)-(2S)-[(4-hydroxy-4'-trifluoromethyl-biphenyl-3-carbonyl)-amino]-propionyl}-piperazine-1-carboxylic acid tert-butyl ester |
| 245 | 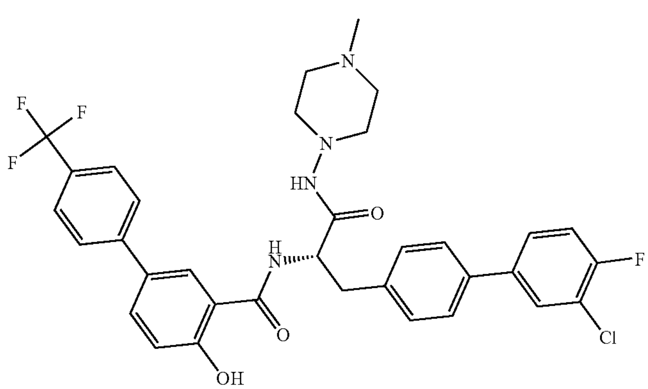 | 4-Hydroxy-4'-trifluoromethyl-biphenyl-3-carboxylic acid [2-(3'-chloro-4'-fluoro-biphenyl-4-yl)-(1S)-(4-methyl-piperazin-1-ylcarbamoyl)-ethyl]-amide |

TABLE 1-continued

| Example | Structure | Name |
|---|---|---|
| 246 | 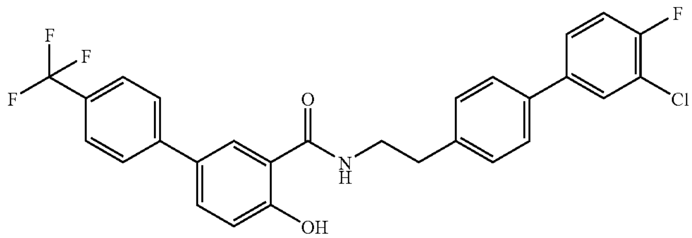 | 4-Hydroxy-4'-trifluoromethyl-biphenyl-3-carboxylic acid [2-(3'-chloro-4'-fluoro-biphenyl-4-yl)-ethyl]-amide |
| 247 | 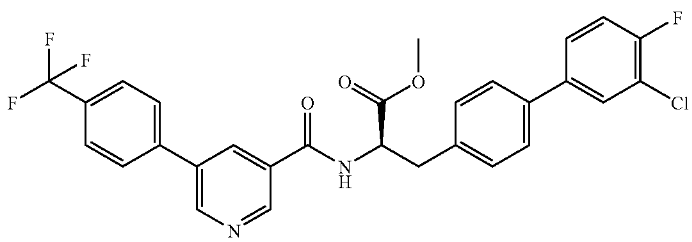 | 3-(3'-Chloro-4'-fluoro-biphenyl-yl)-(2R)-{[5-(4-trifluoromethyl-phenyl)-pyridine-3-carbonyl]-amino}-propionic acid methyl ester |
| 248 | 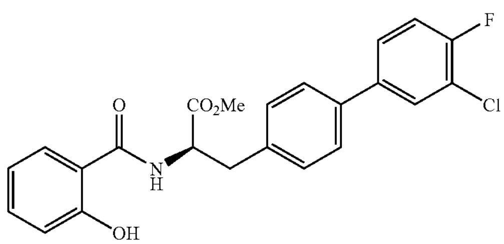 | 3-(3'-Chloro-4'-fluoro-biphenyl-4-yl)-(2R)-(2-hydroxy-benzoylamino)-propionic acid methyl ester |
| 249 | 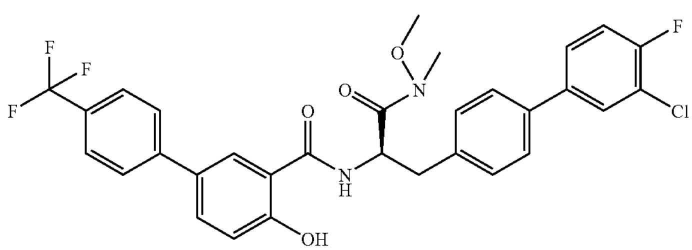 | 4-Hydroxy-4'-trifluoromethyl-biphenyl-3-carboxylic acid [2-(3'-chloro-4'-fluoro-biphenyl-4-yl)-(1R)-(methoxy-methyl-carbamoyl)-ethyl]-amide |
| 250 | 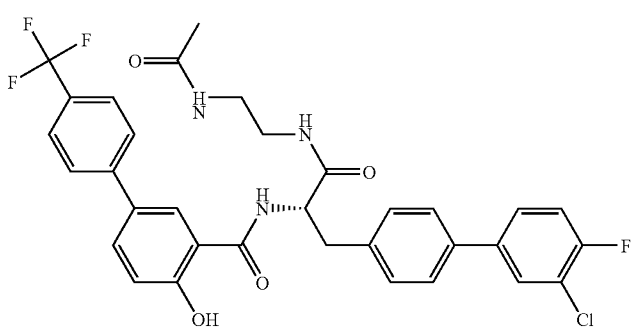 | 4-Hydroxy-4'-trifluoromethyl-biphenyl-3-carboxylic acid [(1S)-(2-acetylamino-ethylcarbamoyl)-2-(3'-chloro-4'-fluoro-biphenyl-4-yl)-ethyl]-amide |

TABLE 1-continued

| Example | Structure | Name |
|---|---|---|
| 251 | 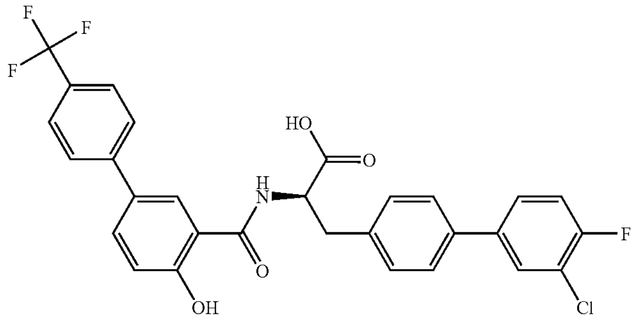 | 3-(3'-Chloro-4'-fluoro-biphenyl-4-yl)-(2R)-[(4-hydroxy-4'-trifluoromethyl-biphenyl-3-carbonyl)-amino]-propionic acid |
| 252 | 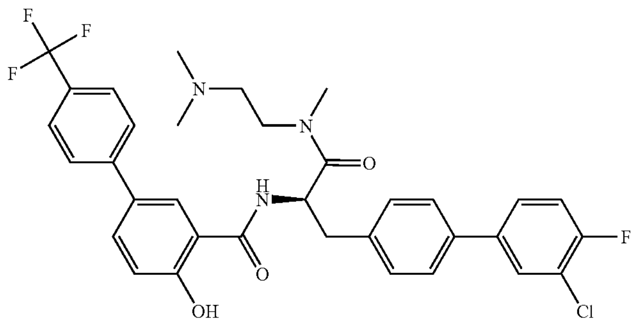 | 4-Hydroxy-4'-trifluoromethyl-biphenyl-3-carboxylic acid {2-(3'-chloro-4'-fluoro-biphenyl-4-yl)-(1R)-[(2-dimethylamino-ethyl)-methyl-carbamoyl]-ethyl}-amide |
| 253 | 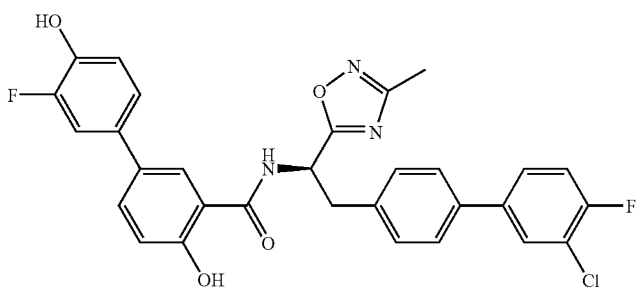 | 3'-Fluoro-4,4'-dihydroxy-biphenyl-3-carboxylic acid [2-(3'-chloro-4'-fluoro-biphenyl-4-yl)-(1R)-(3-methyl-[1,2,4]oxadiazo]-5-yl)-ethyl]-amide |
| 254 | 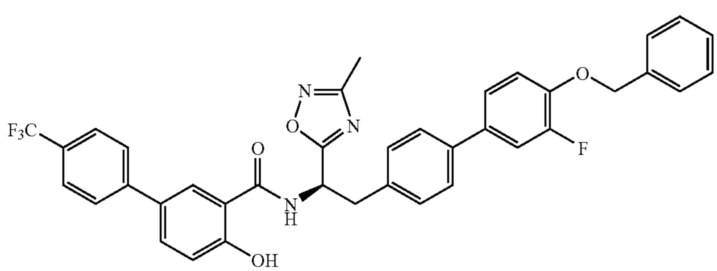 | 4-Hydroxy-4'-trifluoromethyl-biphenyl-3-carboxylic acid [2-(4'-benzyloxy-3'-fluoro-biphenyl-4-yl)-(1R)-(3-methyl-[1,2,4]oxadiazo]-5-yl)-ethyl]-amide |
| 255 | 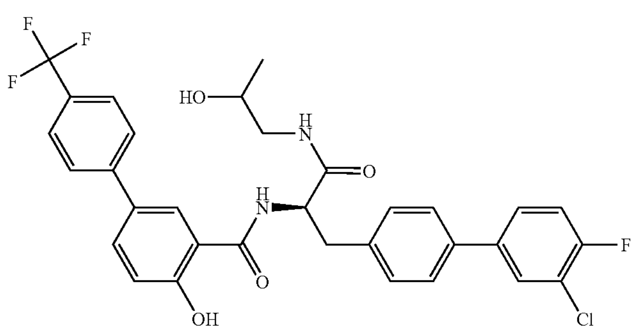 | 4-Hydroxy-4'-trifluoromethyl-biphenyl-3-carboxylic acid [2-(3'-chloro-4'-fluoro-biphenyl-4-yl)-(1R)-(2-hydroxy-propylcarbamoyl)-ethyl]-amide |

TABLE 1-continued

| Example | Structure | Name |
|---|---|---|
| 256 | 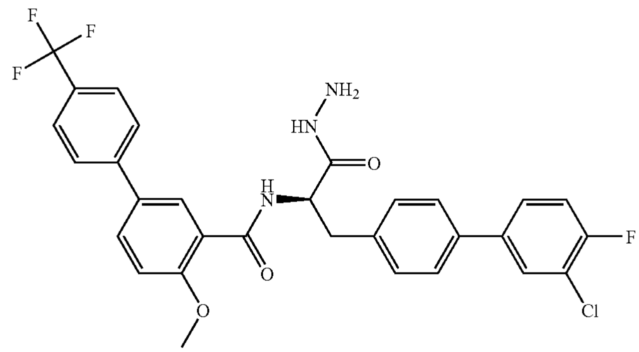 | 4-Methoxy-4'-trifluoromethyl-biphenyl-3-carboxylic acid [2-(3'-chloro-4'-fluoro-biphenyl-4-yl)-(1R)-hydrazinocarbonyl-ethyl]-amide |
| 257 | 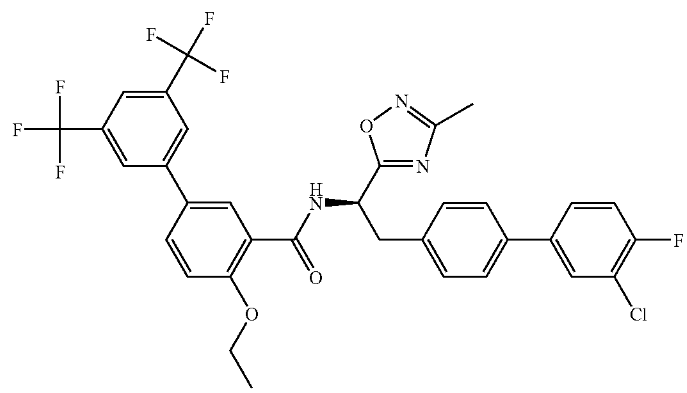 | 4-Ethoxy-3',5'-bis-trifluoromethyl-biphenyl-3-carboxylic acid [2-(3'-chloro-4'-fluoro-biphenyl-4-yl)-(1R)-(3-methyl-[1,2,4]oxadiazo]-5-yl)-ethyl]-amide |
| 258 | 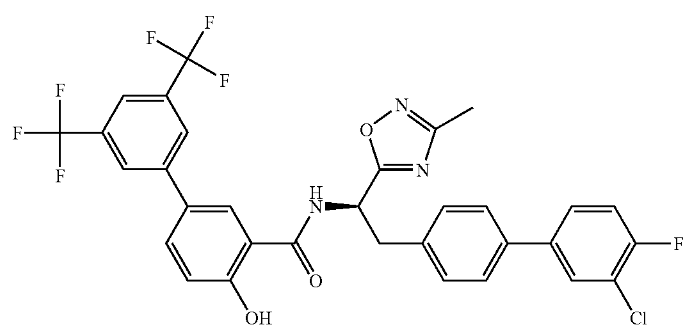 | 4-Hydroxy-3',5-bis-trifluoromethyl-biphenyl-3-carboxylic acid [2-(3'-chloro-4'-fluoro-biphenyl-4-yl)-(1R)-(3-methyl-[1,2,4]oxadiazo]-5-yl)-ethyl]-amide |
| 259 | 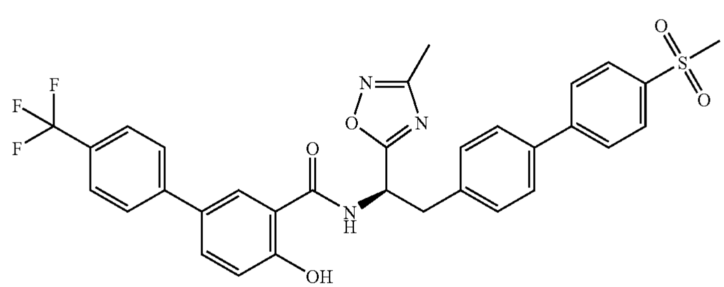 | 4-Hydroxy-4'-trifluoromethyl-biphenyl-3-carboxylic acid [2-(4'-methanesulfonyl-biphenyl-4-yl)-(1R)-(3-methyl-[1,2,4]oxadiazo]-5-yl)-ethyl]-amide |

TABLE 1-continued

| Example | Structure | Name |
|---|---|---|
| 260 | 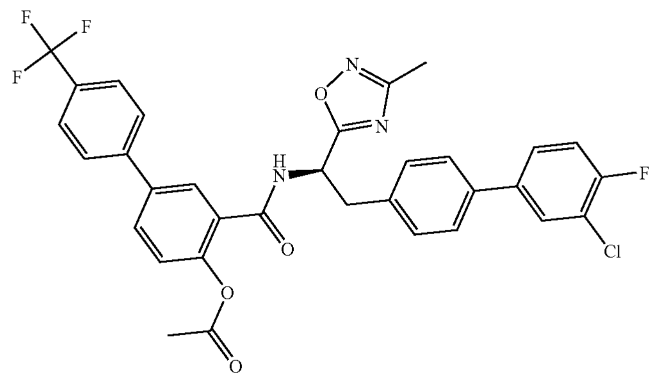 | Acetic acid 3-[2-(3'-chloro-4'-fluoro-biphenyl-4-yl)-(1R)-(3-methyl-[1,2,4]oxadiazo]-5-yl)-ethyl-carbamoyl]-4'-trifluoromethyl-biphenyl-4-yl ester |
| 261 | 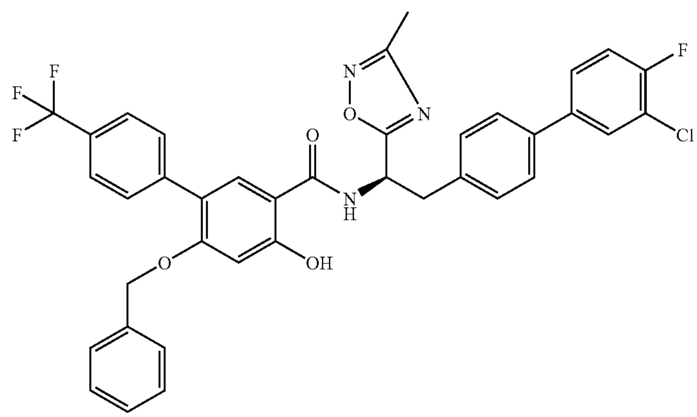 | 6-Benzyloxy-4-hydroxy-4'-trifluoromethyl-biphenyl-3-carboxylic acid [2-(3-chloro-4'-fluoro-biphenyl-4-yl)-(1R)-(3-methyl-[1,2,4]oxadiazo]-5-yl)-ethyl]-amide |
| 262 | 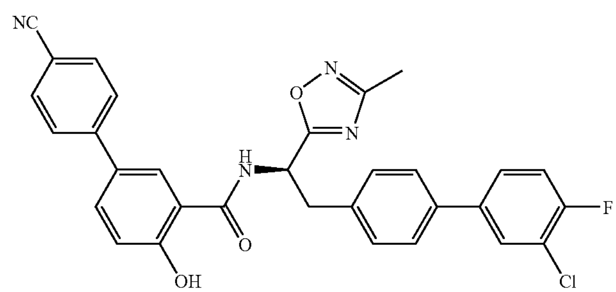 | 4'-Cyano-4-hydroxy-biphenyl-3-carboxylic acid [2-(3'-chloro-4'-fluoro-biphenyl-4-yl)-(1R)-(3-methyl-[1,2,4]oxadiazo]-5-yl)-ethyl]-amide |
| 263 | 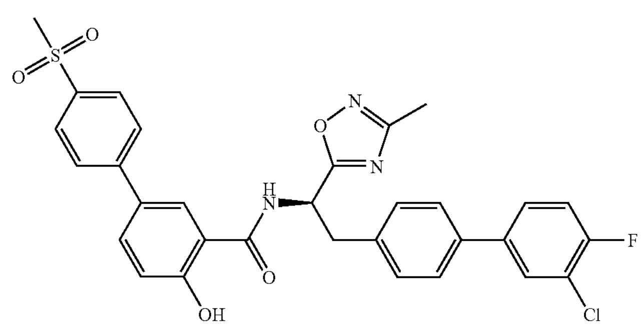 | 4-Hydroxy-4'-methanesulfonyl-biphenyl-3-carboxylic acid [2-(3'-chloro-4'-fluoro-biphenyl-4-yl)-(1R)-(3-methyl-[1,2,4]oxadiazo]-5-yl)-ethyl]-amide |

TABLE 1-continued

| Example | Structure | Name |
|---|---|---|
| 264 | 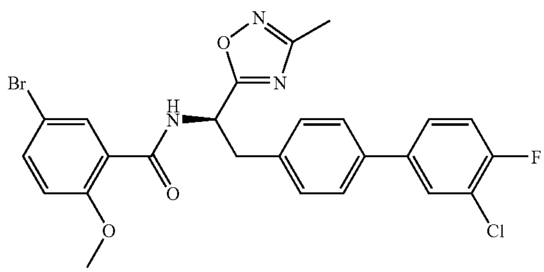 | 5-Bromo-N-[2-(3'-chloro-4'-fluoro-biphenyl-4-yl)-(1R)-(3-methyl-[1,2,4]oxadiazo]-5-yl)-ethyl]-2-methoxy-benzamide |
| 265 | 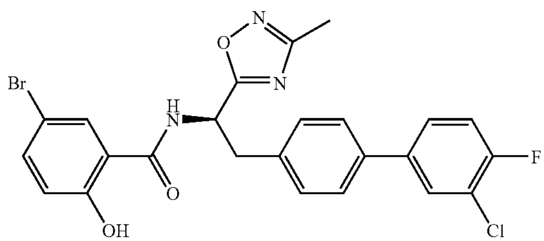 | 5-Bromo-N-[2-(3'-chloro-4'-fluoro-biphenyl-4-yl)-(1R)-(3-methyl-[1,2,4]oxadiazo]-5-yl)-ethyl]-2-hydroxy-benzamide |
| 266 | 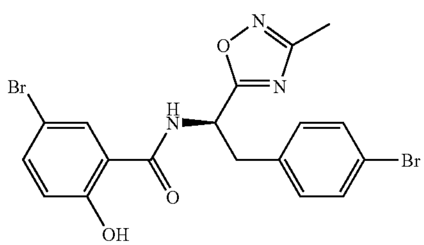 | 5-Bromo-N-[2-(4-bromo-phenyl)-(1R)-(3-methyl-[1,2,4]oxadiazo]-5-yl)-ethyl]-2-hydroxy-benzamide |
| 267 | 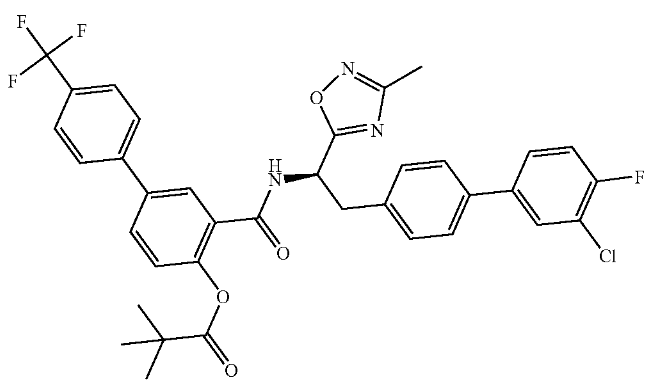 | 2,2-Dimethyl-propionic acid 3-[2-(3'-chloro-4'-fluoro-biphenyl-4-yl)-(1R)-(3-methyl-[1,2,4]oxadiazo]-5-yl)-ethylcarbamoyl]-4'-trifluoromethyl-biphenyl-4-yl ester |
| 268 | 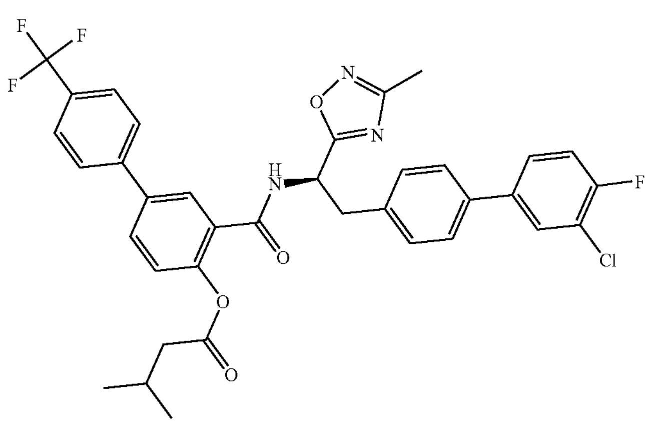 | 3-Methyl-butyric acid 3-[2-(3'-chloro-4'-fluoro-biphenyl-4-yl)-(1R)-(3-methyl-[1,2,4]oxadiazo]-5-yl)-ethylcarbamoyl]-4'-trifluoromethyl-biphenyl-4-yl ester |

TABLE 1-continued

| Example | Structure | Name |
|---|---|---|
| 269 | 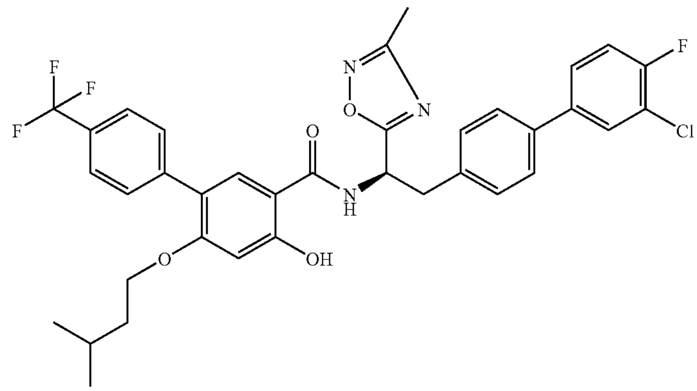 | 4-Hydroxy-6-(3-methyl-butoxy)-4'-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]amide |
| 270 | 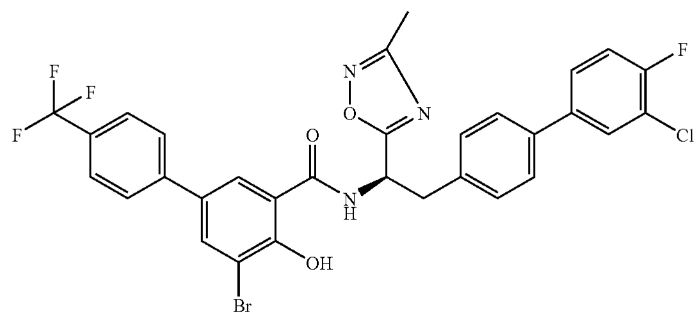 | 5-Bromo-4-hydroxy-4'-trifluoromethyl-biphenyl-3-carboxylic acid [2-(3'-chloro-4'-fluoro-biphenyl-4-yl)-(1R)-(3-methyl-[1,2,4]oxadiazo]-5-yl)-ethyl]-amide |
| 271 | 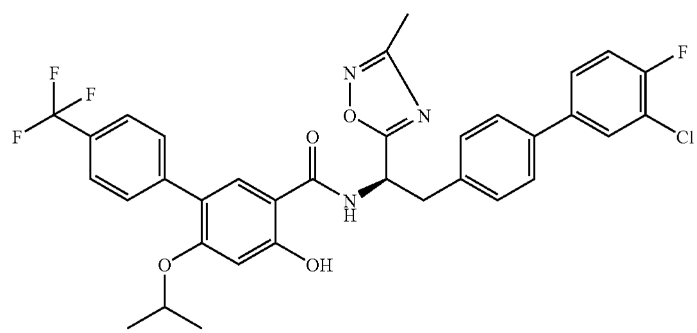 | 4-Hydroxy-6-isopropoxy-4'-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide |
| 272 | 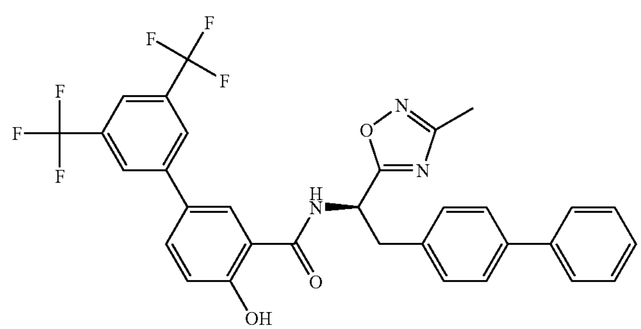 | 4-Hydroxy-3',5'-bis-trifluoromethyl-biphenyl-3-carboxylic acid [2-biphenyl-4-yl-(1R)-(3-methyl-[1,2,4]oxadiazo]-5-yl)-ethyl]-amide |

TABLE 1-continued

| Example | Structure | Name |
|---|---|---|
| 273 | 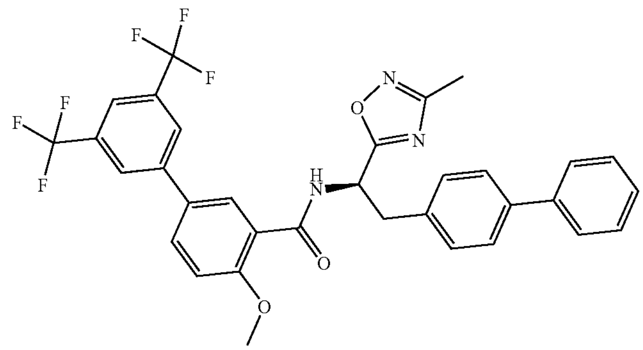 | 4-Methoxy-3',5'-bis-trifluoromethyl-biphenyl-3-carboxylic acid [2-biphenyl-4-yl-(1R)-(3-methyl-1,2,4]oxadiazo]-5-yl)-ethyl]-amide |
| 274 | 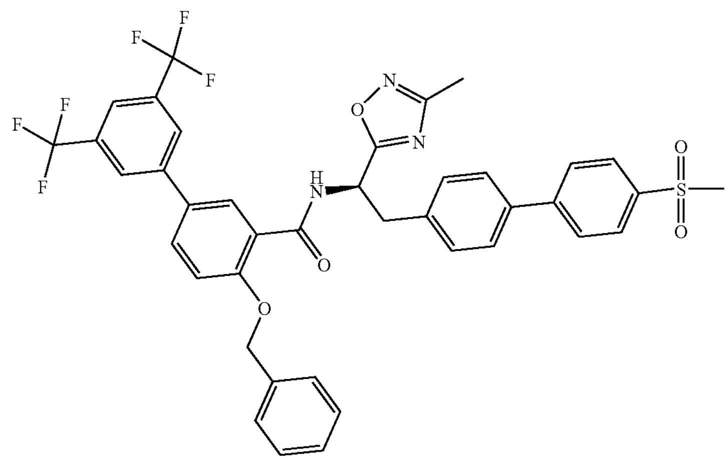 | 4-Benzyloxy-3',5'-bis-trifluoromethyl-biphenyl-3-carboxylic acid [2-(4'-methanesulfonyl-biphenyl-4-yl)-(1R)-(3-methyl-[1,2,4]oxadiazo]-5-yl)-ethyl]-amide |
| 275 | 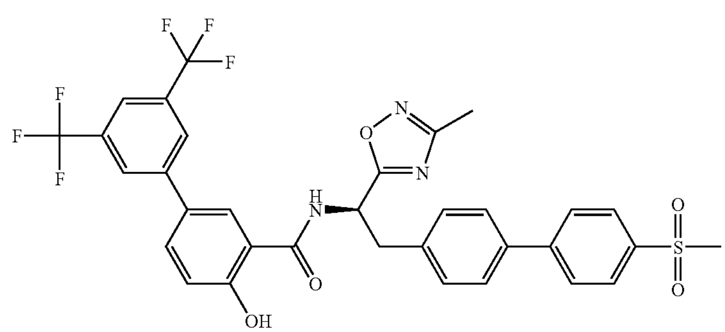 | 4-Hydroxy-3',5'-bis-trifluoromethyl-biphenyl-3-carboxylic acid [2-(4'-methanesulfonyl-biphenyl-4-yl)-(1R)-(3-methyl-[1,2,4]oxadiazo]-5-yl)-ethyl]-amide |
| 276 | 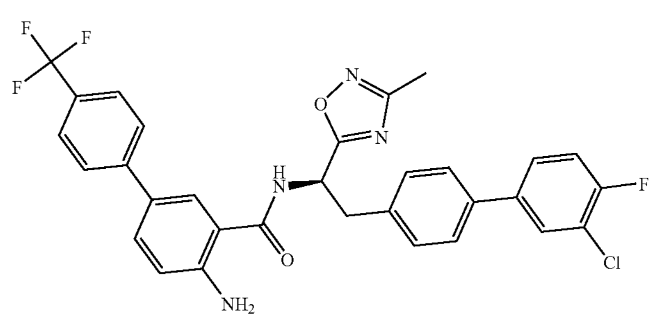 | 4-Amino-4'-trifluoromethyl-biphenyl-3-carboxyl [2-(3'-chloro-4'-fluoro-biphenyl-4-yl)-(1R)-(3-methyl-[1,2,4]oxadiazo]-5-yl)-ethyl]-amide |

TABLE 1-continued

| Example | Structure | Name |
|---|---|---|
| 277 | 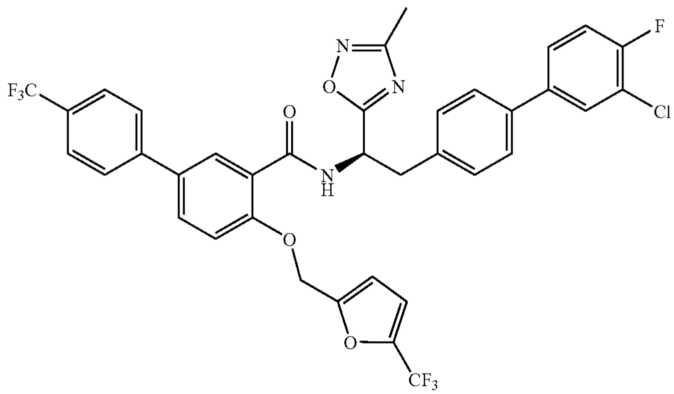 | 4'-Trifluoromethyl-4-(5-trifluoromethyl-furan-2-ylmethoxy)-biphenyl-3-carboxylic acid [2-(3'-chloro-4'-fluoro-biphenyl-4-yl)-(1R)-(3-methyl-[1,2,4]oxadiazo]-5-yl)-ethyl] amide |
| 278 | 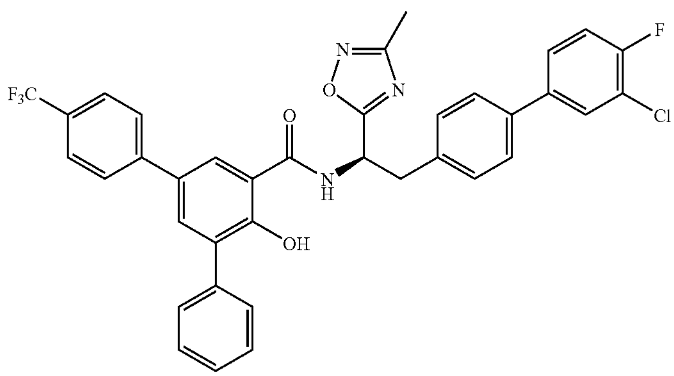 | 4'-Hydroxy-4-trifluoromethyl-[1,1';3',1'']terphenyl-5'-carboxylic acid [2-(3'-chloro-4'-fluoro-biphenyl-4-yl)-(1R)-(3-methyl-[1,2,4]oxadiazol-5-yl)-ethyl]-amide |
| 279 | 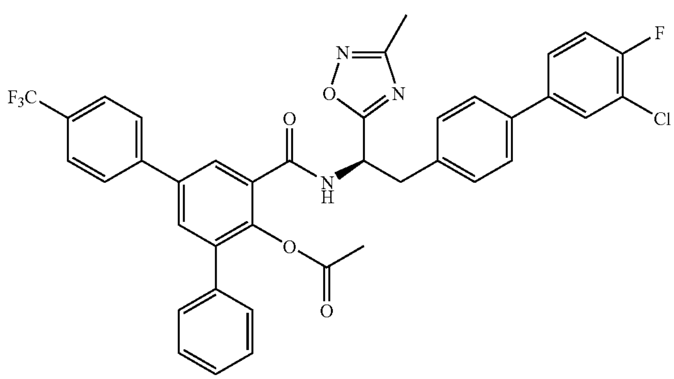 | Acetic acid 5'-[2-(3'-chloro-4'-fluoro-biphenyl-4-yl)-(1R)-(3-methyl-[1,2,4]oxadiazo]-5-yl)-ethyl-carbamoyl]-4-trifluoromethyl-[1,1';3',1''] terphenyl-4'-yl ester |
| 280 | 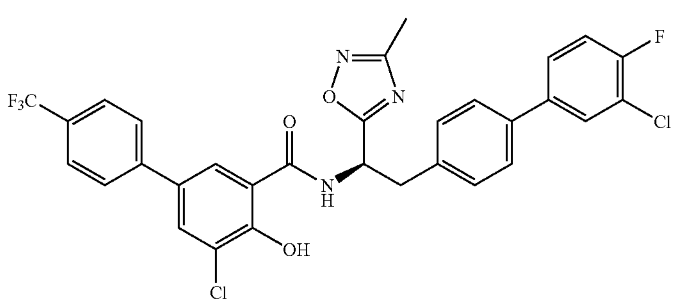 | 5-Chloro-4-hydroxy-4'-trifluoromethyl-biphenyl-3-carboxylicacid [2-(3'-chloro-4'-fluoro-biphenyl-4-yl)-(1R)-(3-methyl-[1,2,4]oxadiazo]-5-yl)-ethyl]-amide |

TABLE 1-continued

| Example | Structure | Name |
|---|---|---|
| 281 | 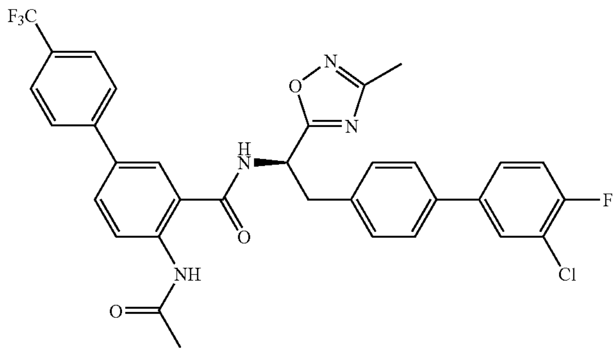 | 4-Acetylamino-4'-trifluoromethyl-biphenyl-3-carboxylic acid [2-(3'-chloro-4'-fluoro-biphenyl-4-yl)-(1R)-(3-methyl-[1,2,4]oxadiazo]-5-yl)-ethyl]-amide |
| 282 | 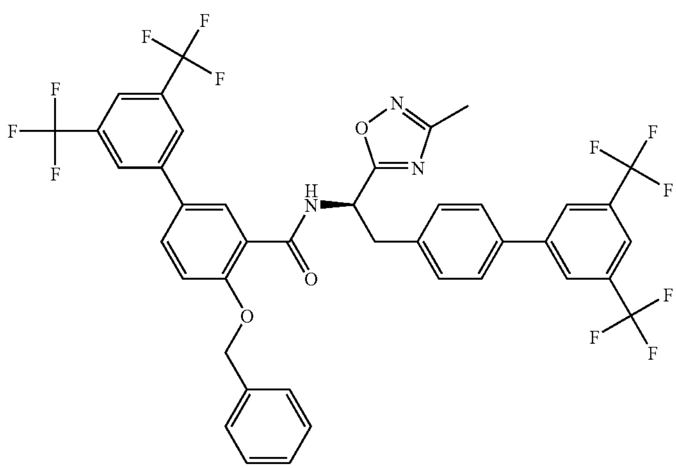 | 4-Benzyloxy-3',5'-bis-trifluoromethyl-biphenyl-3-carboxylicacid [2-(3',5'-bis-trifluoromethyl-biphenyl-4-yl)-(1R)-(3-methyl-[1,2,4]oxadiazo]-5-yl)-ethyl]-amide |
| 283 | 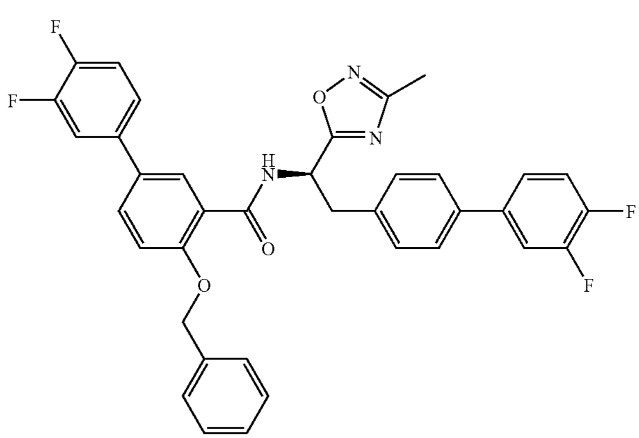 | 4-Benzyloxy-3',4'-difluoro-biphenyl-3-carboxylic acid [2-(3',4'-difluoro-biphenyl-4-yl)-(1R)-(3-methyl-[1,2,4]oxadiazo]-5-yl)-ethyl]-amide |

TABLE 1-continued

| Example | Structure | Name |
|---|---|---|
| 284 | 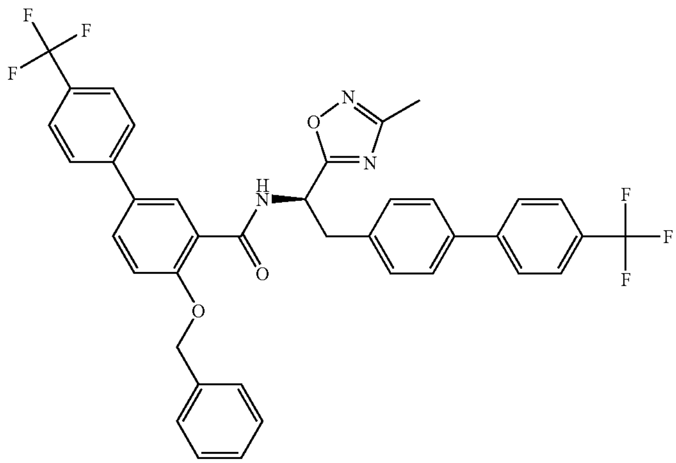 | 4-Benzyloxy-4'-trifluoromethyl-biphenyl-3-carboxylic acid [(1R)-(3-methyl-[1,2,4]oxadiazo]-5-yl)-2-(4'-trifluoromethyl-biphenyl-4-yl)-ethyl]-amide |
| 285 | 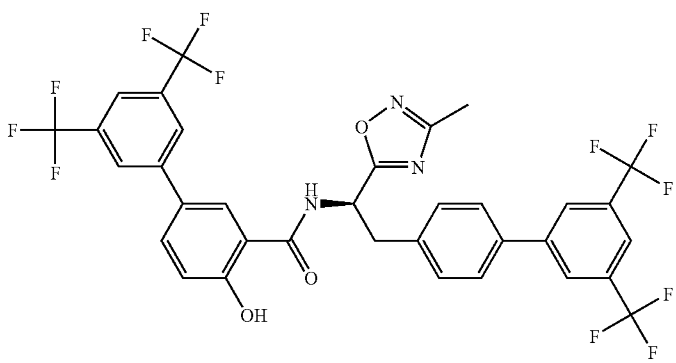 | 4-Hydroxy-3',5'-bis-trifluoromethyl-biphenyl-3-carboxylic acid [2-(3',5'-bis-trifluoromethyl-biphenyl-4-yl)-(1R)-(3-methyl-[1,2,4]oxadiazo]-5-yl)-ethyl]-amide |
| 286 | 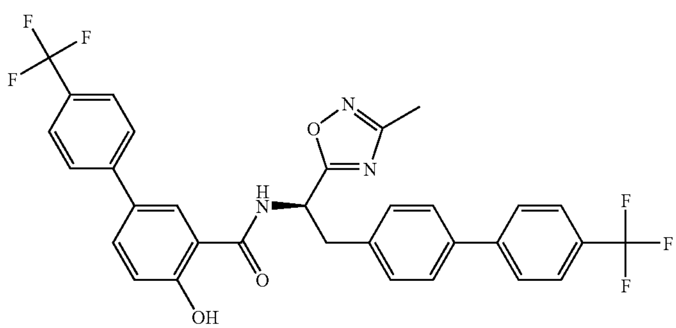 | 4-Hydroxy-4'-trifluoromethyl-biphenyl-3-carboxylic acid [(1R)-(3-methyl-[1,2,4]oxadiazo]-5-yl)-2-(4'-trifluoromethyl-biphenyl-4-yl)-ethyl]-amide |
| 287 | 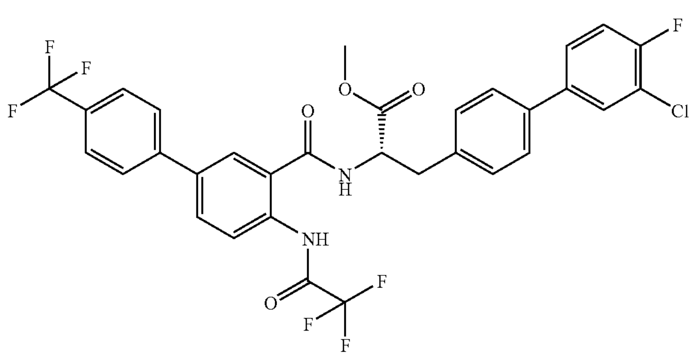 | 3-(3'-Chloro-4'-fluoro-biphenyl-4-yl)-(2S)-{[4-(2,2,2-trifluoro-acetylamino)-4'-trifluoromethyl-biphenyl-3-carbonyl]-amino}-propionic acid methyl ester |

TABLE 1-continued

| Example | Structure | Name |
|---|---|---|
| 288 | 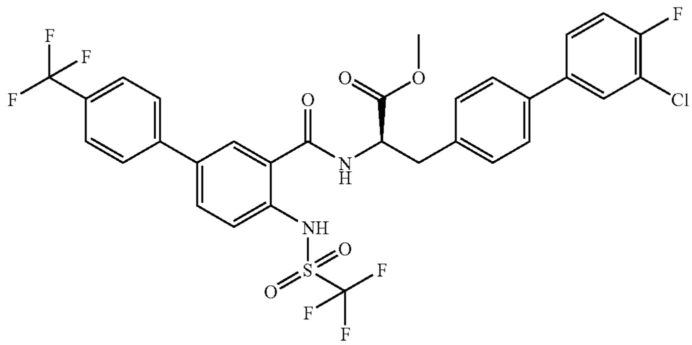 | 3-(3'-Chloro-4'-fluoro-biphenyl-4-yl)-(2R)-[(4-trifluoromethanesulfonylamino-4'-trifluoromethyl-biphenyl-3-carbonyl)-amino]-propionic acid methyl ester |
| 289 | 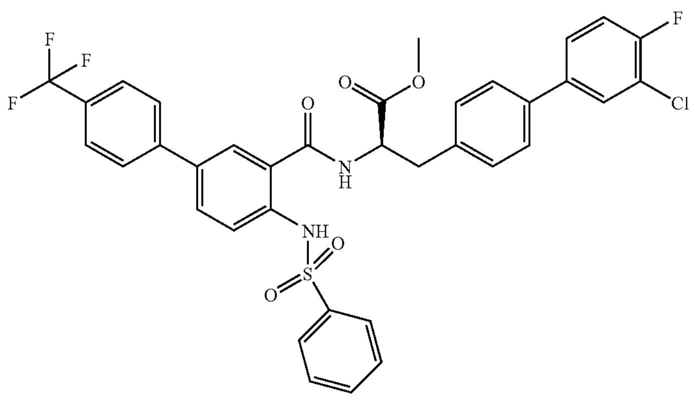 | (2R)-[(4-Benzenesulfonylamino-4'-trifluoromethyl-biphenyl-3-carbonyl)-amino]-(3R)-(3'-chloro-4'-fluoro-biphenyl-4-yl)-propionic acid methyl ester |
| 290 | 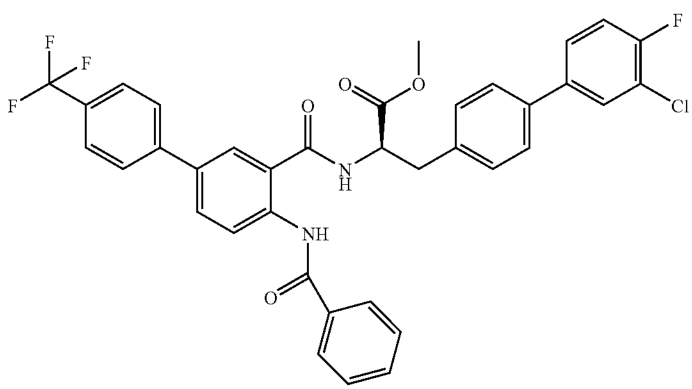 | (2R)-[(4-Benzoylamino-4'-trifluoromethyl-biphenyl-3-carbonyl)-amino]-(3R)-(3'-chloro-4'-fluoro-biphenyl-4-yl)-propionic acid methyl ester |
| 291 | 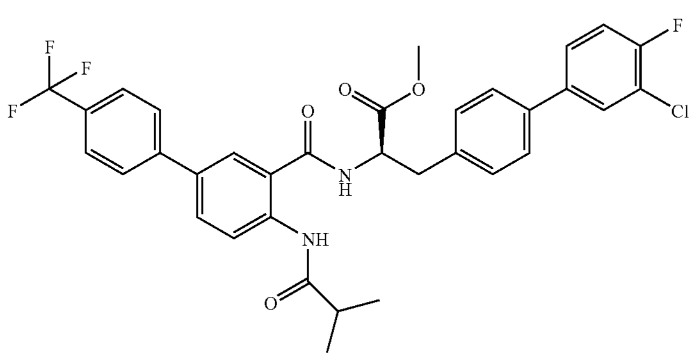 | 3-(3'-Chloro-4'-fluoro-biphenyl-4-yl)-(2R)-[(4-isobutyrylamino-4'-trifluoromethyl-biphenyl-3-carbonyl)-amino]-propionic acid methyl ester |

TABLE 1-continued

| Example | Name |
|---|---|
| 292 | 2-(3'-Chloro-4'-fluoro-biphenyl-4-yl)-ethyl [(4-Hydroxymethyl-4'-trifluoromethyl-biphenyl-3-carboxamide |
| 293 | 3-(3'-Chloro-4'-fluoro-biphenyl-4-yl)-(2R)-[4-oxo-2-trifluoromethyl-6-(4-trifluoromethyl-phenyl)-4H-quinazolin-3-yl]-propionic acid methyl ester |
| 294 | 3-(3'-Chloro-4'-fluoro-biphenyl-4-yl)-(2R)-[4-oxo-2-trifluoromethyl-6-(4-trifluoromethyl-phenyl)-4H-quinazolin-3-yl]-propionic acid methyl ester |
| 295 | 6-(4-tert-Butyl-phenoxy)-isoquinoline-3-carboxylic acid |
| 296 | 3-Biphenyl-4-yl-(2S)-{[6-(4-tert-butyl-phenoxy)-isoquinoline-3-carbonyl]-amino]-propionic acid methyl ester |
| 297 | 3-Biphenyl-4-yl-(2S)-{[6-(4-tert-butyl-phenoxy)-isoquinoline-3-carbonyl]-amino}-propionic acid |

TABLE 1-continued

| Example | Structure | Name |
|---|---|---|
| 298 | 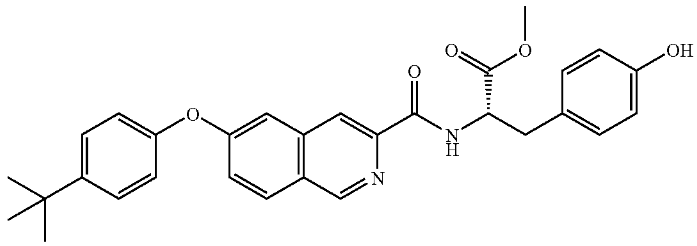 | (2S)-{[6-(4-tert-Butyl-phenoxy)-isoquinoline-3-carbonyl]-amino}-3-(4-hydroxy-phenyl)-propionic acid methyl ester |
| 299 | 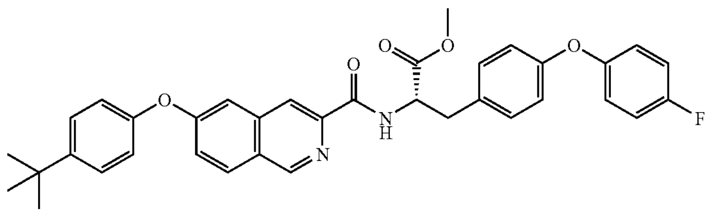 | (2S)-{[6-(4-tert-Butyl-phenoxy)-isoquinoline-3-carbonyl]-amino}-3-[4-(4-fluoro-phenoxy)-phenyl]-propionic acid methyl ester |
| 300 | 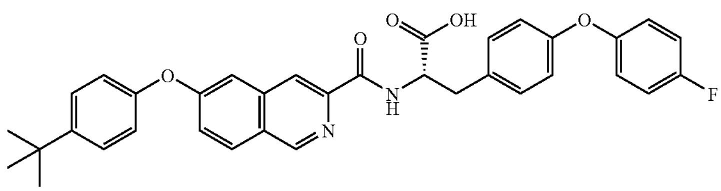 | (2S)-{[6-(4-tert-Butyl-phenoxy)-isoquinoiine-3-carbonyl]-amino}-3-[4-(4-trifluoromethyl-phenoxy)-phenyl]-propionic acid |
| 301 | 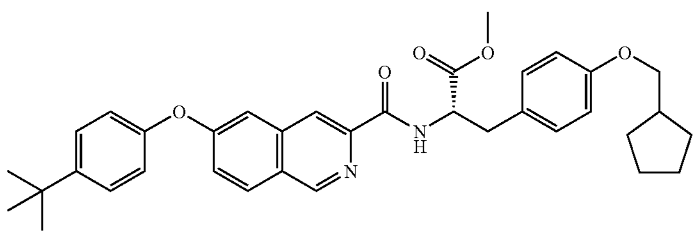 | (2S)-{[6-(4-tert-Butyl-phenoxy)-isoquinoline-3-carbonyl]-amino}-3-(4-cyclopentylmethoxy-phenyl)-propionic acid methyl ester |
| 302 | 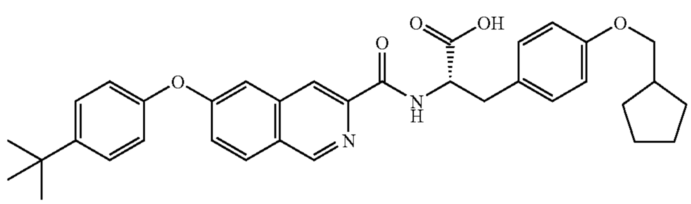 | (2S)-{[6-(4-tert-Butyl-phenoxy)-isoquinoline-3-carbonyl]-amino}-3-(4-cyclopentylmethoxy-phenyl)-propionic acid |
| 303 | 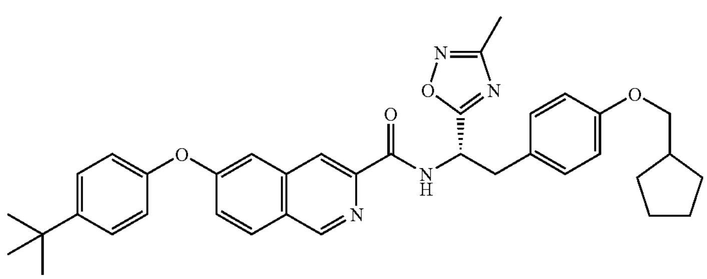 | 6-(4-tert-Butyl-phenoxy)-isoquinoline-3-carboxylic acid [2-(4-cyclopentylmethoxy-phenyl)-(1S)-(3-methyl-[1,2,4]oxadiazo]-5-yl)-ethyl]-amide |

TABLE 1-continued

| Example | Structure | Name |
|---|---|---|
| 304 | 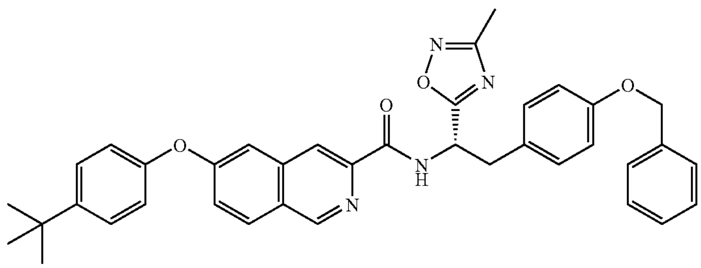 | 6-(4-tert-Butyl-phenoxy)-isoquinoline-3-carboxylic acid [(2S)-(4-benzyloxy-penyl)-1-(3-methyl-[1,2,4]oxadiazo]-5-yl)-ethyl]-amide |
| 305 | 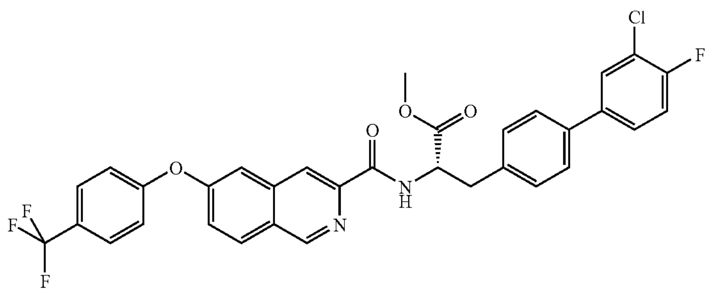 | 3-(3'-Chloro-4'-fluoro-biphenyl-4-yl)-(2S)-{[6-(4-trifluoromethyl-phenoxy)-isoquinoline-3-carbonyl]-amino}-propionic acid methyl ester |
| 306 | 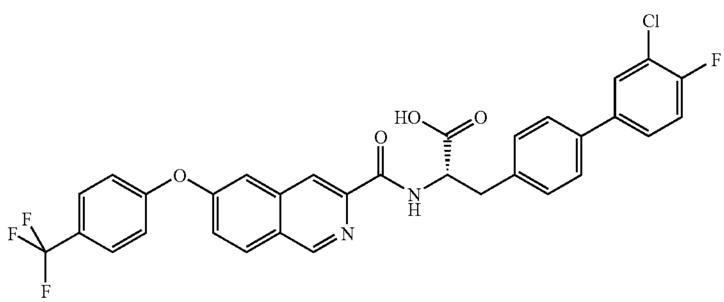 | 3-(3'-Chloro-4'-fluoro-biphenyl-4-yl)-(2S)-{[6-(4-trifluoromethyl-phenoxy)-isoquinoline-3-carbonyl]-amino}-propionic acid |
| 307 | 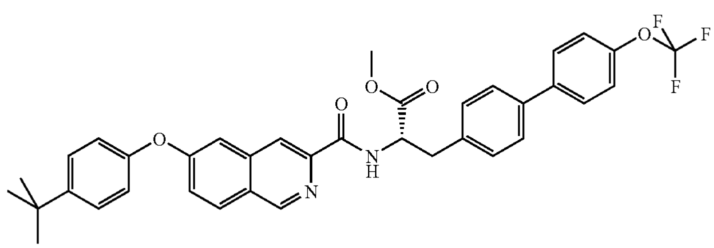 | (2S)-{[6-(4-tert-Butyl-phenoxy)-isoquinoline-3-carbonyl]-amino}-3-(4'-trifluoromethoxy-biphenyl-4-yl)-propionic acid methyl ester |
| 308 | 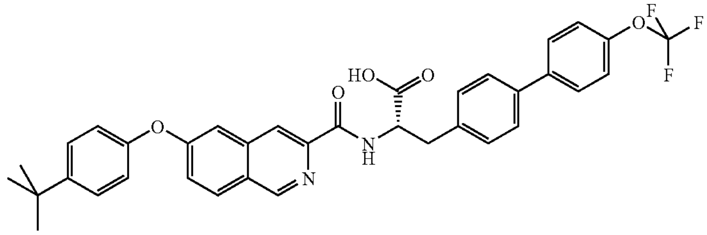 | (2S)-{[6-(4-tert-Butyl-phenoxy)-isoquinoline-3-carbonyl]-amino}-3-(4'-trifluoromethoxy-biphenyl-4-yl)-propionic acid |

TABLE 1-continued

| Example | Structure | Name |
|---|---|---|
| 309 | 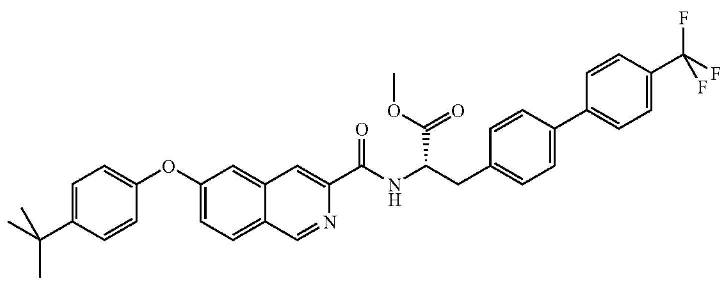 | (2S)-{[6-(4-tert-Butyl-phenoxy)-isoquinoline-3-carbonyl]-amino}-3-(4'-trifluoromethyl-biphenyl-4-yl)-propionic acid methyl ester |
| 310 | 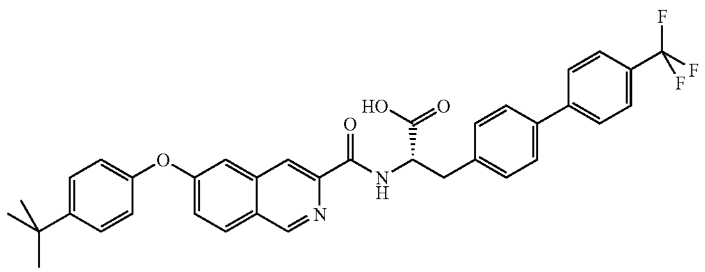 | (2S)-{[6-(4-tert-Butyl-phenoxy)-isoquinoline-3-carbonyl]-amino}-3-(4'-trifluoromethyl-biphenyl-4-yl)-propionic acid |
| 311 | 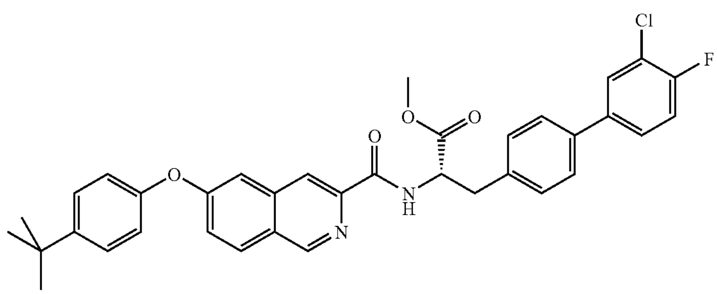 | (2S)-{[6-(4-tert-Butyl-phenoxy)-isoquinoline-3-carbonyl]-amino}-3-(3'-chloro-4'-fluoro-biphenyl-4-yl)-propionic acid methyl ester |
| 312 | 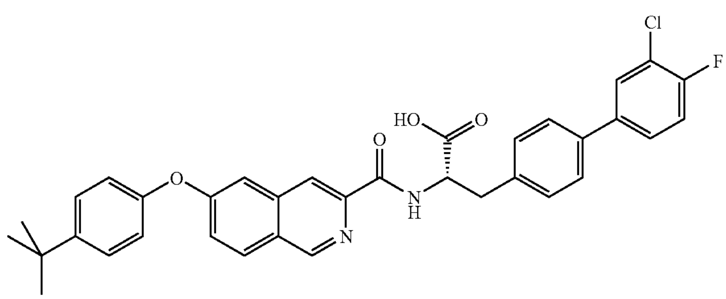 | (2S)-{[6-(4-tert-Butyl-phenoxy)-isoquinoline-3-carbonyl]-amino}-3-(3'-chloro-4'-fluoro-biphenyl-4-yl)-propionic acid |
| 313 | 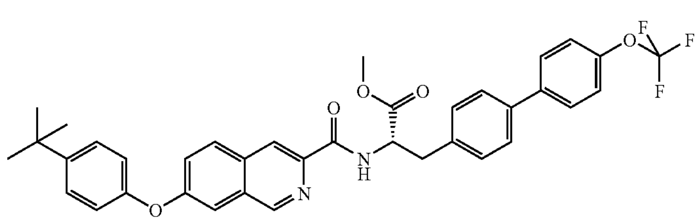 | (2S)-{[7-(4-tert-Butyl-phenoxy)-isoquinoline-3-carbonyl]-amino}-3-(4'-trifluoromethoxy-biphenyl-4-yl)-propionic acid methyl ester |
| 314 | 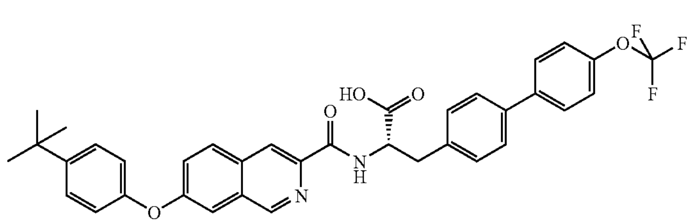 | (2S)-{[7-(4-tert-Butyl-phenoxy)-isoquinoline-3-carbonyl]-amino}-3-(4'-trifluoromethoxy-biphenyl-4-yl)-propionic acid |

TABLE 1-continued

| Example | Structure | Name |
|---|---|---|
| 315 | 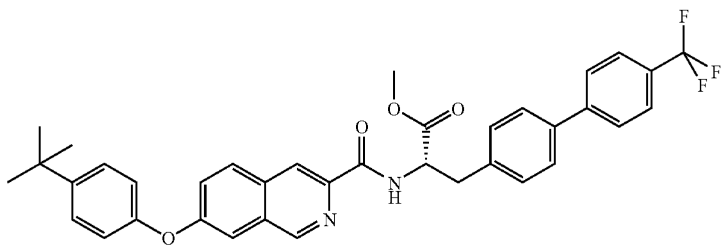 | (2S)-{[7-(4-tert-Butyl-phenoxy)-isoquinoiine-3-carbonyl]-amino}-3-(4'-trifluoromethyl-biphenyl-4-yl)-propionic acid methyl ester |
| 316 | 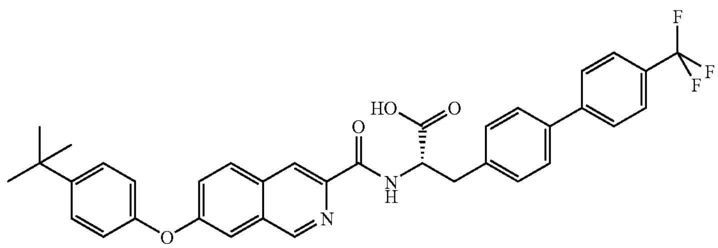 | (2S)-{[7-(4-tert-Butyl-phenoxy)-isoquinoline-3-carbonyl]-amino}-3-(4'-trifluoromethyl-biphenyl-4-yl)-propionic acid |
| 317 | 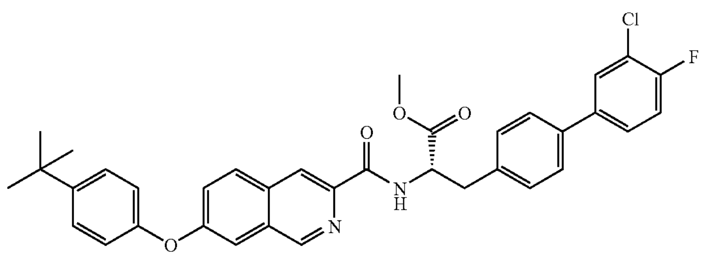 | (2S)-{[7-(4-tert-Butyl-phenoxy)-isoquinoline-3-carbonyl]-amino}-3-(3'-chloro-4'-fluoro-biphenyl-4-yl)-propionic acid methyl ester |
| 318 | 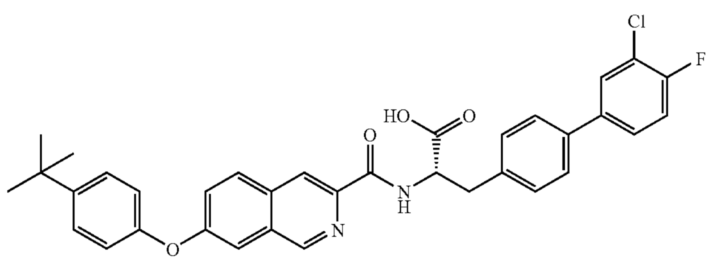 | (2S)-{[7-(4-tert-Butyl-phenoxy)-isoquinoline-3-carbonyl]-amino}-3-(3'-chloro-4'-fluoro-biphenyl-4-yl)-propionic acid |
| 319 | 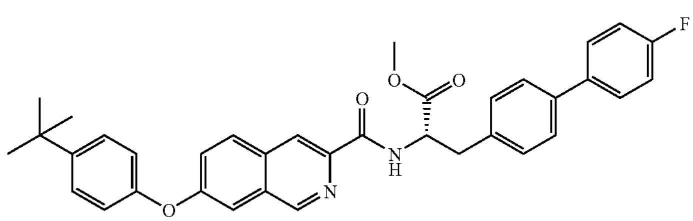 | (2S)-{[7-(4-tert-Butyl-phenoxy)-isoquinoline-3-carbonyl]-amino}-3-(4'-fluoro-biphenyl-4-yl)-propionic acid methyl ester |
| 320 | 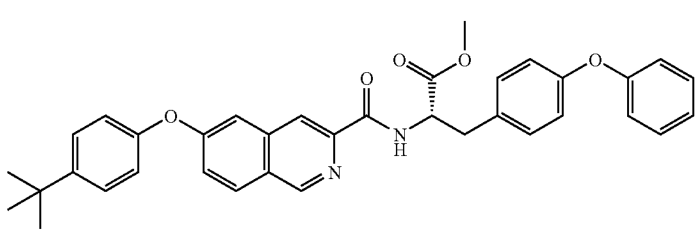 | (2S)-{[6-(4-tert-Butyl-phenoxy)-isoquinoline-3-carbonyl]-amino}-3-(4-phenoxy-phenyl)-propionic acid methyl ester |

TABLE 1-continued

| Example | Structure | Name |
|---|---|---|
| 321 | 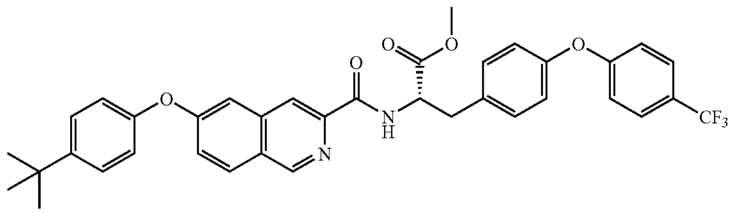 | (2S)-{[6-(4-tert-Butyl-phenoxy)-isoquinoiine-3-carbonyl]-amino}-3-[4-(4-trifluoromethyl-phenoxy)-phenyl]-propionic acid methyl ester |
| 322 | 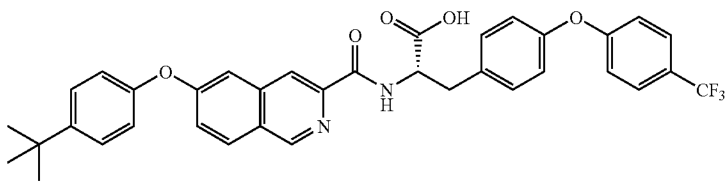 | (2S)-{[6-(4-tert-Butyl-phenoxy)-isoquinoline-3-carbonyl]-amino}-3-[4-(4-trifluoromethyl-phenoxy)-phenyl]-propionic acid |
| 323 | 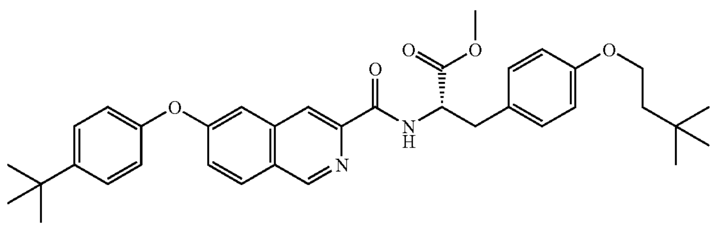 | (2S)-{[6-(4-tert-Butyl-phenoxy)-isoquinoiine-3-carbonyl]-amino}-3-[4-(3,3-dimethyl-butoxy)-phenyl]-propionic acid methyl ester |
| 324 | 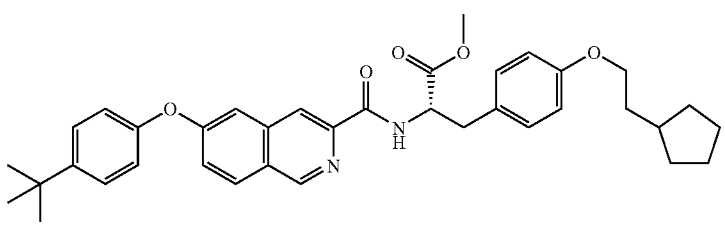 | (2S)-{[6-(4-tert-Butyl-phenoxy)-isoquinoline-3-carbonyl]-amino}-3-[4-(2-cyclopentyl-ethoxy)-phenyl]-propionic acid methyl ester |
| 325 | 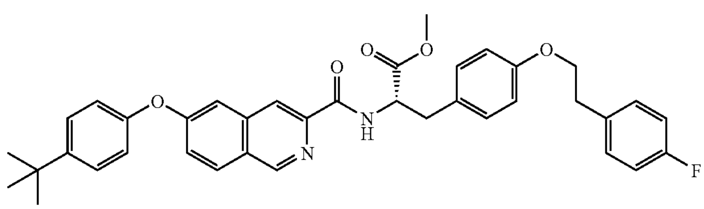 | (2S)-{[6-(4-tert-Butyl-phenoxy)-isoquinoline-3-carbonyl]-amino}-3-{4-[2-(4-fluoro-phenyl)-ethoxy]-phenyl}-propionic acid methyl ester |
| 326 | 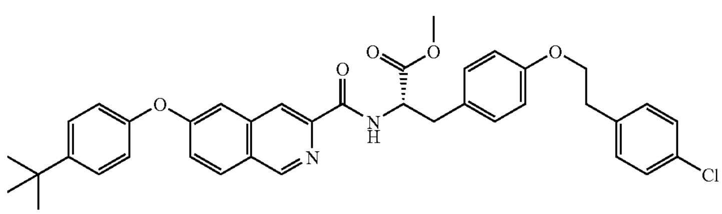 | (2S)-{[6-(4-tert-Butyl-phenoxy)-isoquinoline-3-carbonyl]-amino}-3-{4-[2-(4-chloro-phenyl)-ethoxy]-phenyl}-propionic acid methyl ester |
| 327 | 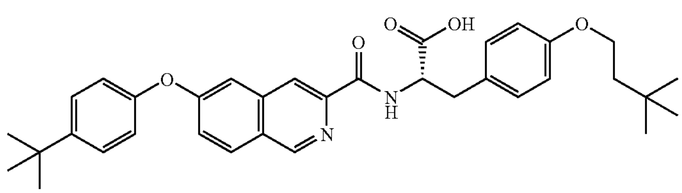 | (2S)-{[6-(4-tert-Butyl-phenoxy)-isoquinoline-3-carbonyl]-amino}-3-[4-(3,3-dimethyl-butoxy)-phenyl]-propionic acid |

TABLE 1-continued

| Example | Structure | Name |
|---|---|---|
| 328 | 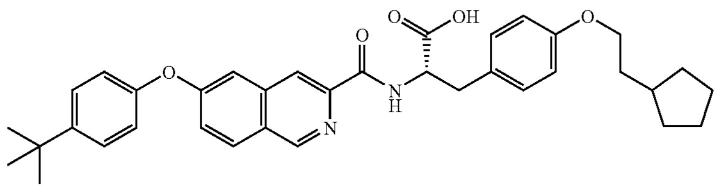 | (2S)-{[6-(4-tert-Butyl-phenoxy)-isoquinoline-3-carbonyl]-amino}-3-[4-(2-cyclopentyl-ethoxy)-phenyl]-propionic acid |
| 329 | 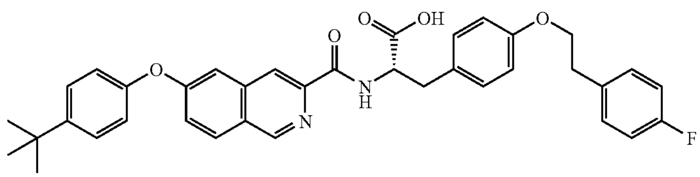 | (2S)-{[6-(4-tert-Butyl-phenoxy)-isoquinoline-3-carbonyl]-amino}-3-{4-[2-(4-fluoro-phenyl)-ethoxy]-phenyl}-propionic acid |
| 330 | 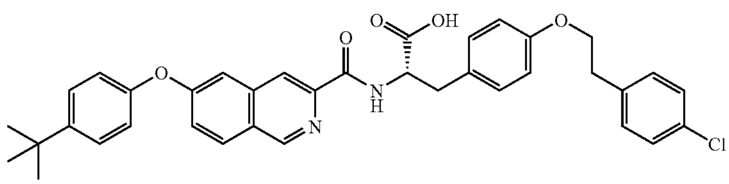 | (2S)-{[6-(4-tert-Butyl-phenoxy)-isoquinoline-3-carbonyl]-amino}-3-{4-[2-(4-chloro-phenyl)-ethoxy]-phenyl}-propionic acid |
| 331 | 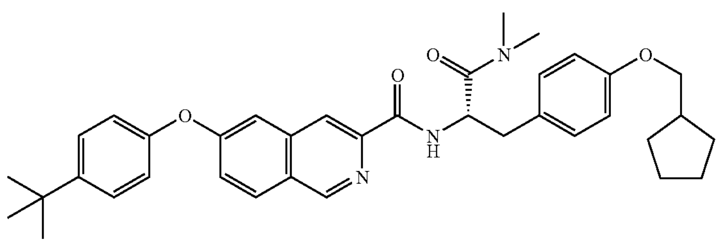 | 6-(4-tert-Butyl-phenoxy)-isoquinoline-3-carboxylic acid [2-(4-cyclopentylmethoxy-phenyl)-(1S)-dimethylcarbamoyl-ethyl]-amide |
| 332 | 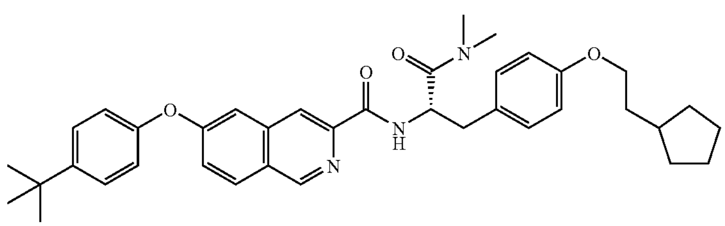 | 6-(4-tert-Butyl-phenoxy)-isoquinoline-3-carboxylic acid {2-[4-(2-cyclopentyl-ethoxy)-phenyl]-(1S)-dimethylcarbamoyl-ethyl}-amide |
| 333 | 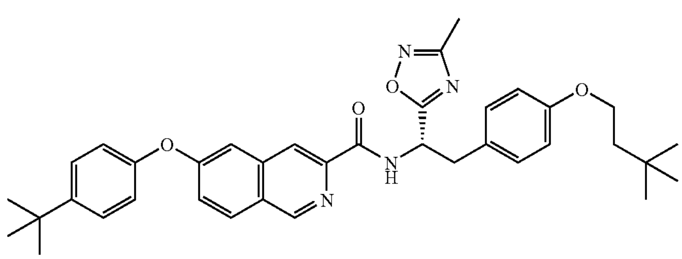 | 6-(4-tert-Butyl-phenoxy)-isoquinoline-3-carboxylic acid [2-[4-(3,3-dimethyl-butoxy)-phenyl]-(1S)-(3-methyl-[1,2,4]oxadiazol-5-yl)-ethyl]-amide |
| 334 | 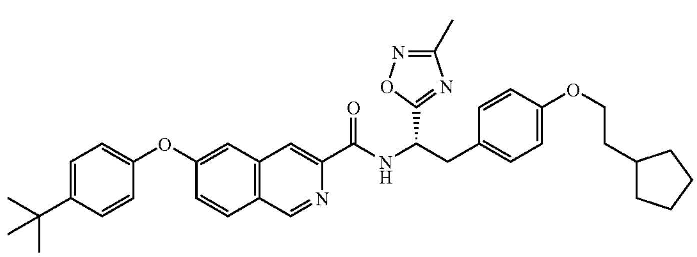 | 6-(4-tert-Butyl-phenoxy)-isoquinoline-3-carboxylic acid [2-[4-(2-cyclopentyl-ethoxy)-phenyl]-(1S)-(3-methyl-[1,2,4]oxadiazol-5-yl)-ethyl]-amide |

TABLE 1-continued

| Example | Structure | Name |
|---|---|---|
| 335 | 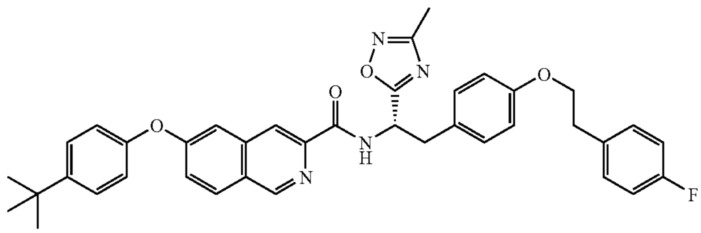 | 6-(4-tert-Butyl-phenoxy)-isoquinoline-3-carboxylic acid [2-{4-[2-(4-fluoro-phenyl)-ethoxy]-phenyl}-(1S)-(3-methyl-[1,2,4]oxadiazol-5-yl)-ethyl]-amide |
| 336 | 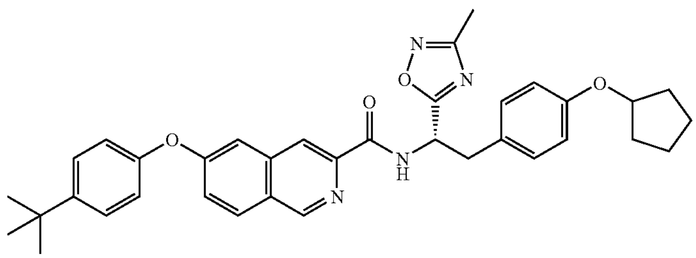 | 6-(4-tert-Butyl-phenoxy)-isoquinoline-3-carboxylic acid [2-(4-cyclopentyloxy-phenyl)-(1S)-(3-methyl-[1,2,4]oxadiazol-5-yl)-ethyl]-amide |
| 337 | 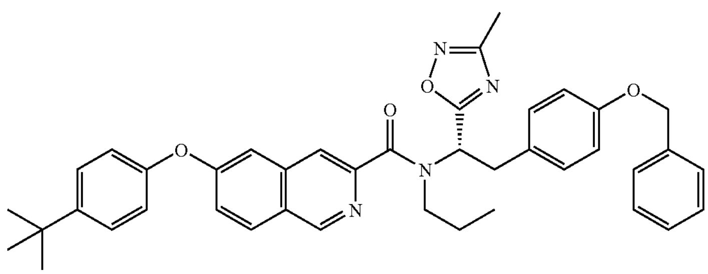 | 6-(4-tert-Butyl-phenoxy)-isoquinoline-3-carboxylic acid [2-(4-benzyloxy-phenyl)-(1S)-(3-methyl-[1,2,4]oxadiazo]-5-yl)-ethyl]-propyl-amide |
| 338 | 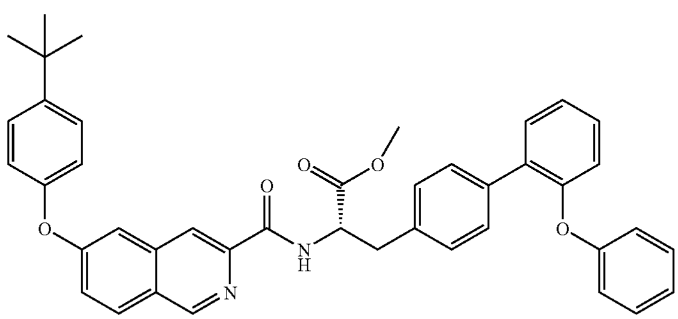 | (2S)-{[6-(4-tert-Butyl-phenoxy)-isoqunoline-3-carbonyl]-amino}-3-(2'-phenoxy-biphenyl-4-yl)-propionic acid methyl ester |
| 339 | 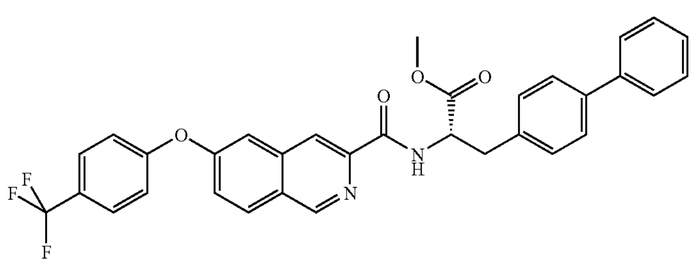 | 3-Biphenyl-4-yl-(2S)-{[6-(4-trifluoromethyl-phenoxy)-isoquinoline-3-carbonyl]-amino}-propionic acid methyl ester |

TABLE 1-continued

| Example | Structure | Name |
|---|---|---|
| 340 | 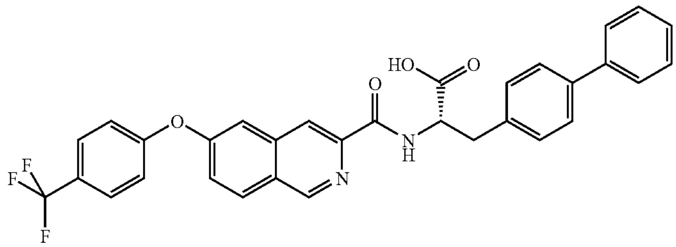 | 3-Biphenyl-4-yl-(2S)-{[6-(4-trifluoromethyl-phenoxy)-isoquinoline-3-carbonyl]-amino}-propionic acid |
| 341 | 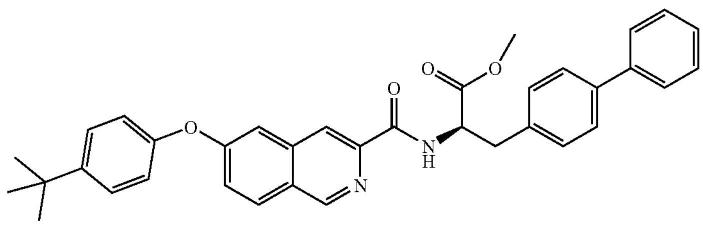 | 3-Biphenyl-4-yl-(2R)-{[6-(4-tert-butyl-phenoxy)-isoquinoline-3-carbonyl]-amino}-propionic acid methyl ester |
| 342 | 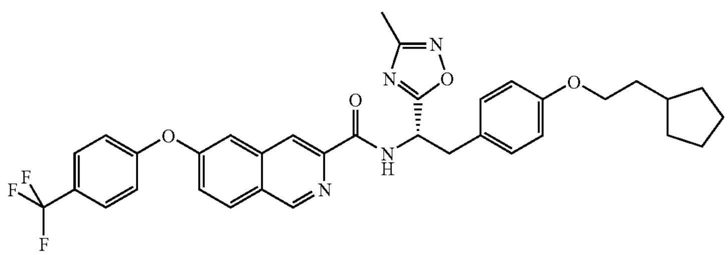 | 6-(4-Trifluoromethyl-phenoxy)-isoquinoline-3-carboxylic acid [2-[4-(2-cyclopentyl-ethoxy)-phenyl]-(1S)-(3-methyl-[1,2,4]oxadiazol-5-yl)-ethyl]-amide |
| 343 | 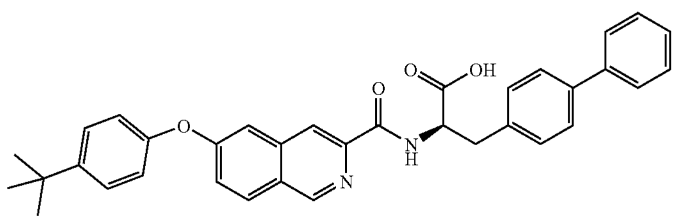 | 3-Biphenyl-4-yl-(2R)-{[6-(4-tert-butyl-phenoxy)-isoquinoline-3-carbonyl]-amino]-propionic acid |
| 344 | 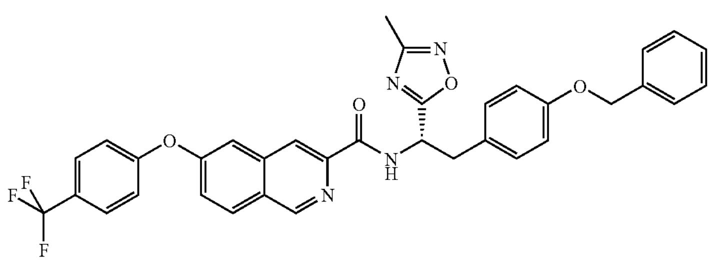 | 6-(4-Trifluoromethyl-phenoxy)-isoquinoline-3-carboxylic acid [2-(4-benzyloxy-phenyl)-(1S)-(3-methyl-[1,2,4]oxadiazol-5-yl)-ethyl]-amide |
| 345 | 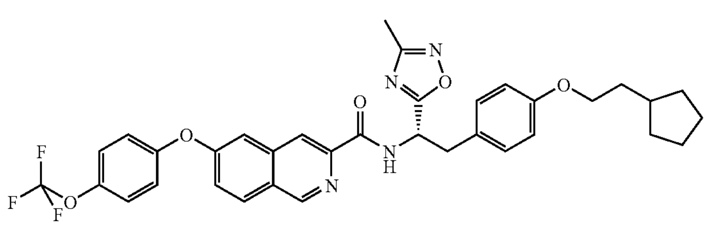 | 6-(4-Trifluoromethoxy-phenoxy)-isoquinoline-3-carboxylic acid [2-[4-(2-cyclopentyl-ethoxy)-phenyl]-(1S)-(3-methyl-[1,2,4]oxadiazol-5-yl)-ethyl]-amide |

| Example | Structure | Name |
|---|---|---|
| 346 | 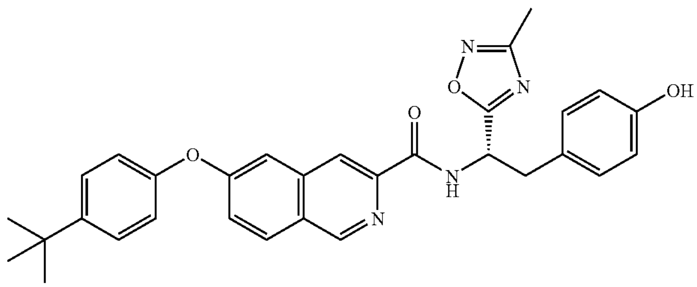 | 6-(4-tert-Butyl-phenoxy)-isoquinoline-3-carboxylic acid[2-(4-hydroxy-phenyl)-(1S)-(3-methyl-[1,2,4]oxadiazol-5-yl)-ethyl]-amide |
| 347 | 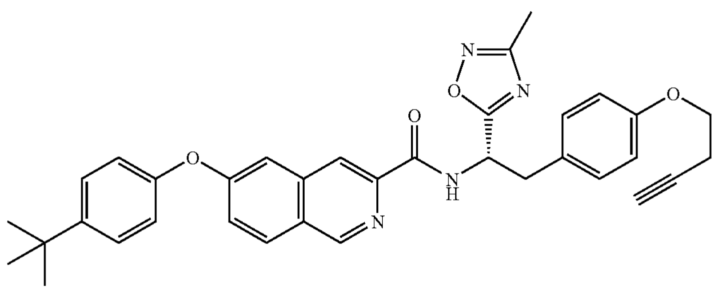 | 6-(4-tert-Butyl-phenoxy)-isoquinoline-3-carboxylic acid[2-(4-but-3-ynyloxy-phenyl)-(1S)-(3-methyl-[1,2,4]oxadiazol-5-yl)-ethyl]-amide |
| 348 | 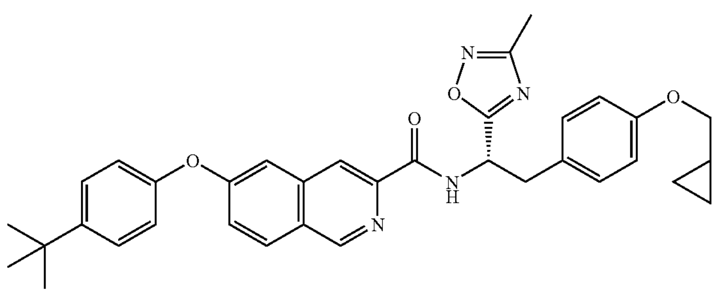 | 6-(4-tert-Butyl-phenoxy)-isoquinoline-3-carboxylic acid[2-(4-cyclopropylmethoxy-phenyl)-(1S)-(3-methyl-[1,2,4]oxadiazol-5-yl)-ethyl]-amide |
| 349 | 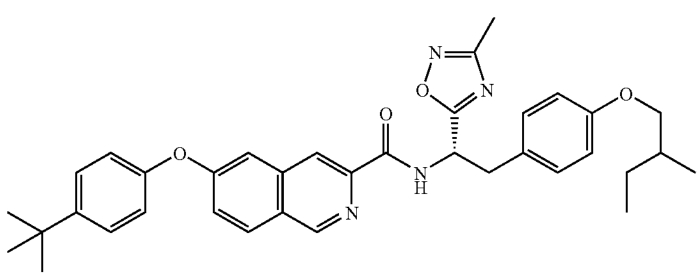 | 6-(4-tert-Butyl-phenoxy)-isoquinoline-3-carboxylic acid[2-[4-(2-methyl-butoxy)-phenyl]-(1S)-(3-methyl-[1,2,4]oxadiazo]-5-yl)-ethyl]-amide |
| 350 | 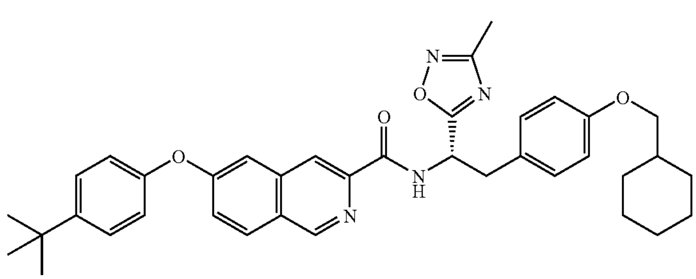 | 6-(4-tert-Butyl-phenoxy)-isoquinoline-3-carboxylic acid[2-(4-cyclohexylmethoxy-phenyl)-(1S)-(3-methyl-[1,2,4]oxadiazol-5-yl)-ethyl]-amide |

TABLE 1-continued

| Example | Structure | Name |
|---------|-----------|------|
| 351 | 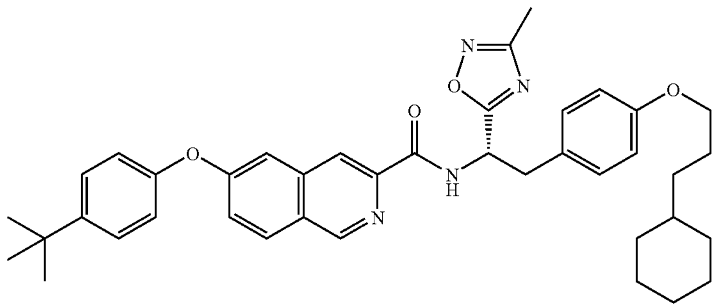 | 6-(4-tert-Butyl-phenoxy)-isoquinoline-3-carboxylic acid[2-[4-(3-cyclohexyl-propoxy)-phenyl]-(1S)-(3-methyl-[1,2,4]oxadiazol-5-yl)-ethyl]-amide |
| 352 | 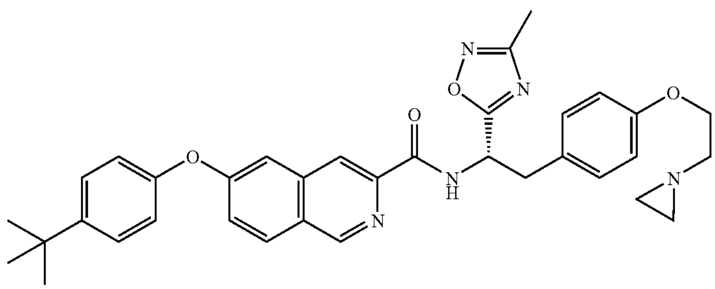 | 6-(4-tert-Butyl-phenoxy)-isoquinoline-3-carboxylic acid[2-[4-(2-aziridin-1-yl-ethoxy)-phenyl]-(1S)-(3-methyl-[1,2,4]oxadiazol-5-yl)-ethyl]-amide |
| 353 | 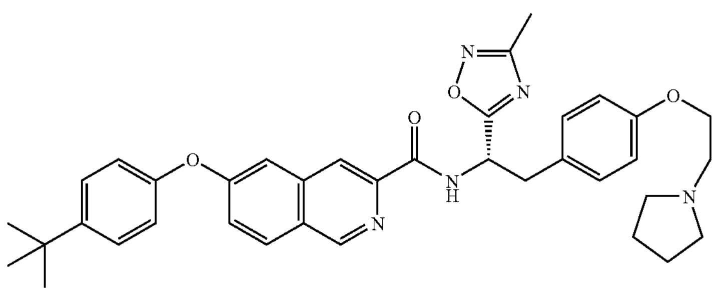 | 6-(4-tert-Butyl-phenoxy)-isoquinoline-3-carboxylic acid{(1S)-(3-methyl-[1,2,4]oxadiazol-5-yl)-2-[4-(2-pyrrolidin-1-yl-ethoxy)-phenyl]-ethyl}-amide |
| 354 | 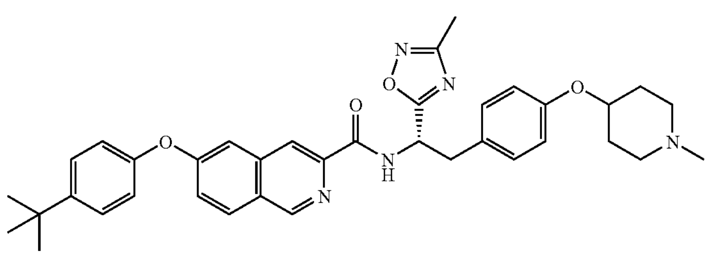 | 6-(4-tert-Butyl-phenoxy)-isoquinoline-3-carboxylic acid{(1S)-(3-methyl-[1,2,4]oxadiazol-5-yl)-2-[4-(1-methyl-piperidin-4-yloxy)-phenyl]-ethyl}-amide |
| 355 | 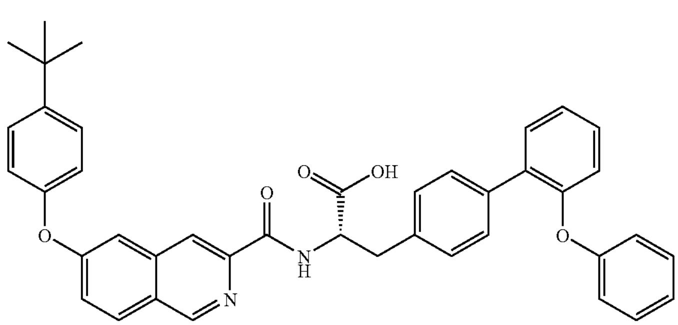 | (2S)-{[6-(4-tert-Butyl-phenoxy)-isoquinoline-3-carbonyl]-amino}-3-(2'-phenoxy-biphenyl-4-yl)-propionic acid |

TABLE 1-continued

| Example | Structure | Name |
|---|---|---|
| 356 | 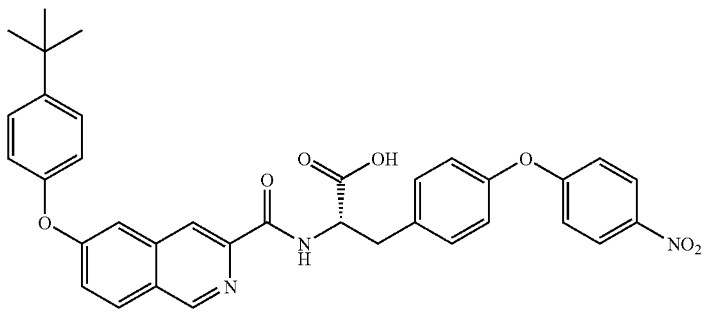 | (2S)-{[6-(4-tert-Butyl-phenoxy)-isoquinoline-3-carbonyl]-amino}-3-[4-(4-nitro-phenoxy)-phenyl]-propionic acid |
| 357 | 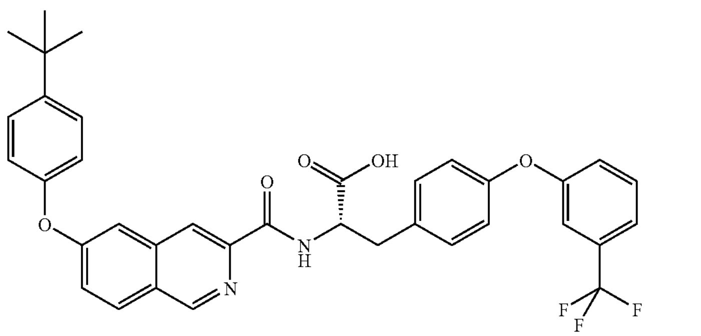 | (2S)-{[6-(4-tert-Butyl-phenoxy)-isoquinoline-3-carbonyl]-amino}-3-[4-(3-trifluoromethyl-phenoxy)-phenyl]-propionic acid |
| 358 | 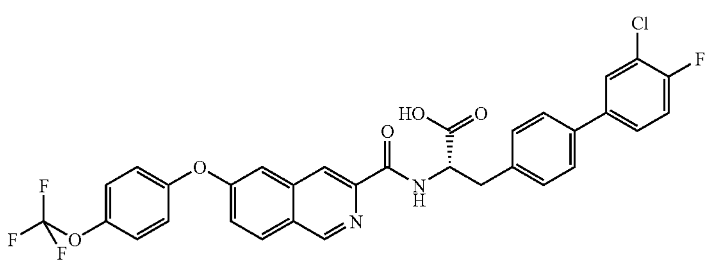 | 3-(3'-Chloro-4'-fluoro-biphenyl-4-yl)-(2S)-{[6-(4-trifluoromethoxy-phenoxy)-isoquinoline-3-carbonyl]-amino}-propionic acid |
| 359 | 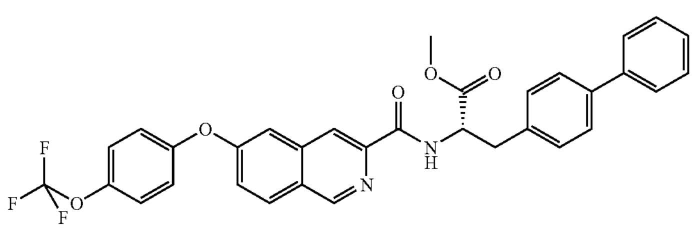 | 3-Biphenyl-4-yl-(2S)-{[6-(4-trifluoromethoxy-phenoxy)-isoquinoline-3-carbonyl]-amino}-propionic acid methyl ester |
| 360 | 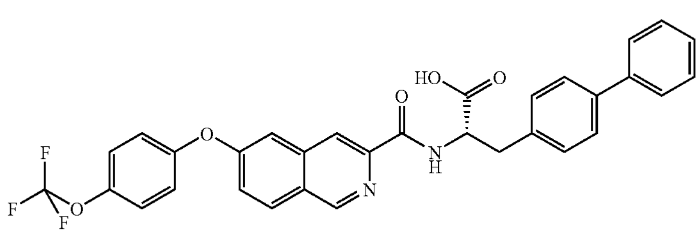 | 3-Biphenyl-4-yl-(2S)-{[6-(4-trifluoromethoxy-phenoxy)-isoquinoline-3-carbonyl]-amino}-propionic acid |

TABLE 1-continued

| Example | Structure | Name |
|---|---|---|
| 361 | 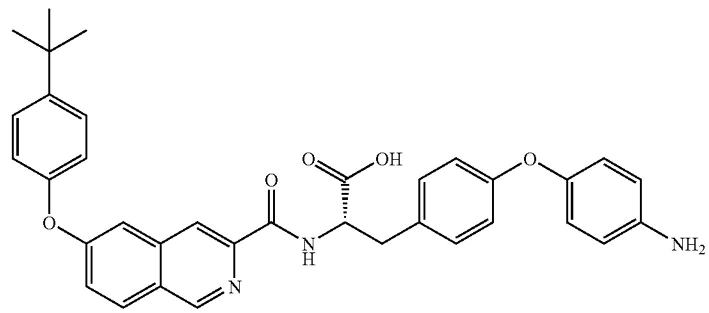 | 3-[4-(4-Amino-phenoxy)-phenyl]-(2S)-{[6-(4-tert-butyl-phenoxy)-isoquinoline-3-carbonyl]-amino}-propionic acid |
| 362 | 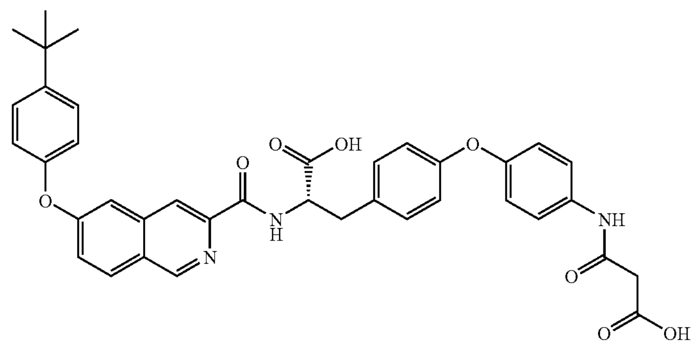 | (2S)-{[6-(4-tert-Butyl-phenoxy)-isoquinoline-3-carbonyl]-amino}-3-{4-[4-(2-carboxy-acetylamino)-phenoxy]-phenyl}-propionic acid |
| 363 | 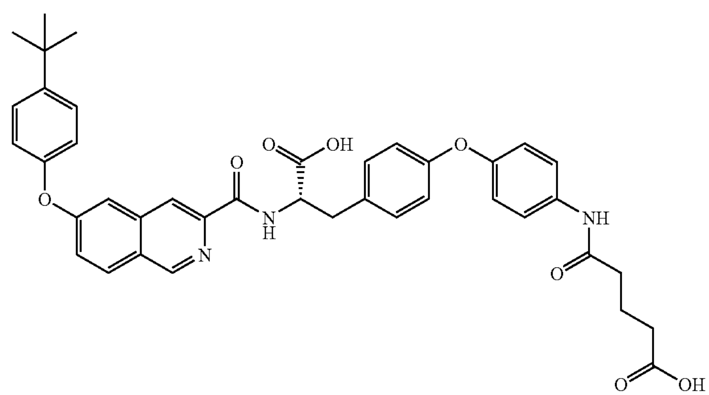 | 4-{4-[4-((2S)-{[6-(4-tert-Butyl-phenoxy)-isoquinoline-3-carbonyl]-amino}-2-carboxy-ethyl)-phenoxy]-phenylcarbamoyl}-butyric acid |
| 364 | 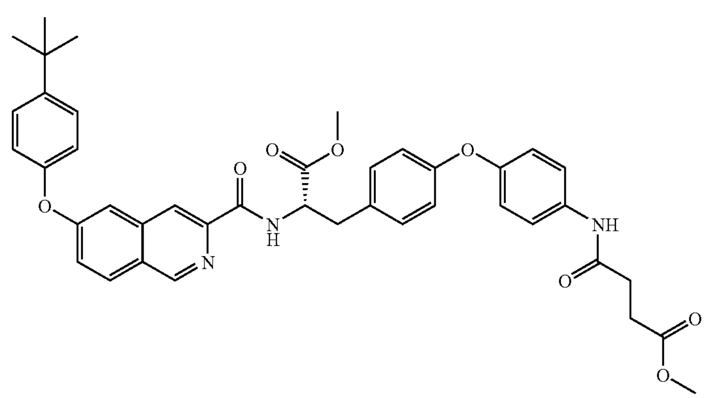 | N-{4-[4-((2S)-{[6-(4-tert-Butyl-phenoxy)-isoquinoline-3-carbonyl]-amino}-2-methoxycarbonyl-ethyl)-phenoxy]-phenyl}-succinamic acid methyl ester |

TABLE 1-continued

| Example | Structure | Name |
|---|---|---|
| 365 | 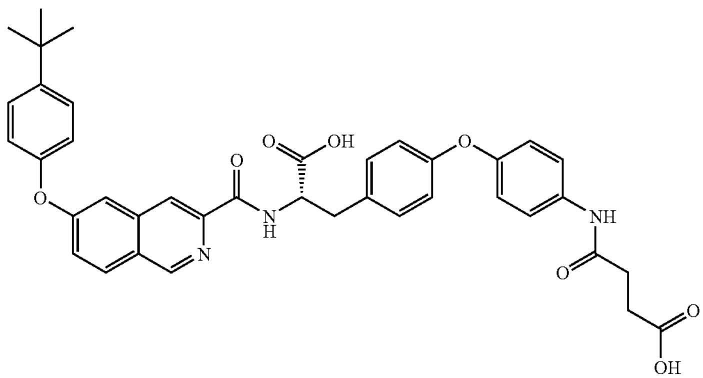 | N-{4-[4-((2S)-{[6-(4-tert-Butyl-phenoxy)-isoquinoline-3-carbonyl]-amino}-2-carboxy-ethyl)-phenoxy]-phenyl]succinamic acid |
| 366 | 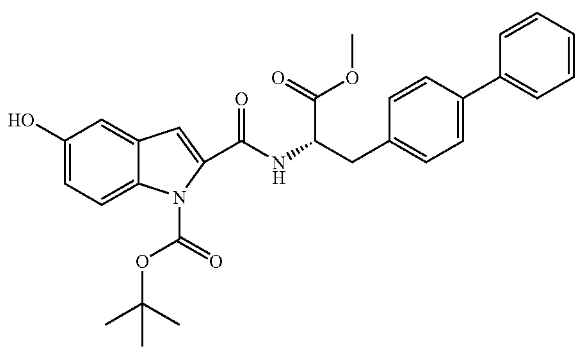 | 2-(2-Biphenyl-4-yl-(1S)-methoxycarbonyl-ethylcarbamoyl)-5-hydroxy-indole-1-carboxylic acid tert-butyl ester |
| 367 | 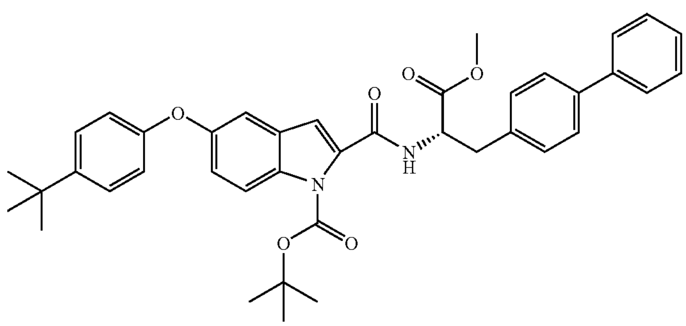 | 2-(2-Biphenyl-4-yl-(1S)-methoxycarbonyl-ethylcarbamoyl)-5-(4-tert-butyl-phenoxy)-indole-1-carboxylic acid tert-butyl ester |
| 368 | 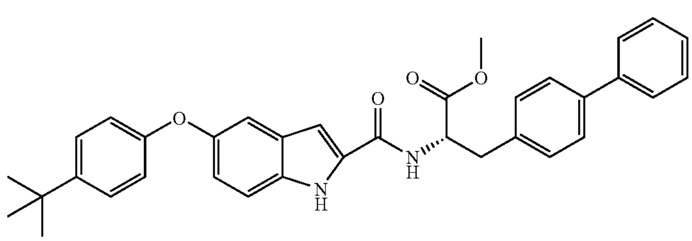 | 3-Biphenyl-4-yl-(2S)-{[5-(4-tert-butyl-phenoxy)-1H-indole-2-carbonyl]-amino}-propionic acid methyl ester |

TABLE 1-continued

| Example | Structure | Name |
|---|---|---|
| 369 | 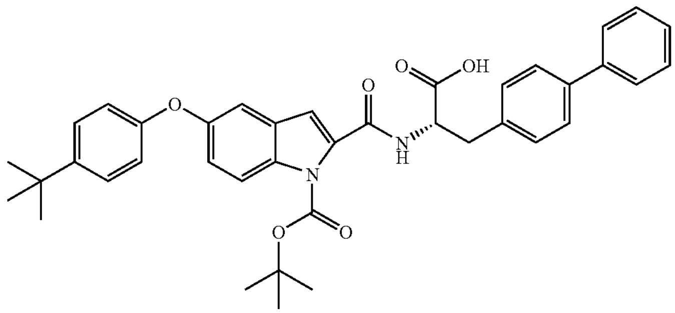 | 2-(2-Biphenyl-4-yl-(1S)-carboxyethylcarbamoyl)-5-(4-tert-butylphenoxy)-indole-1-carboxylic acid tert-butyl ester |
| 370 | 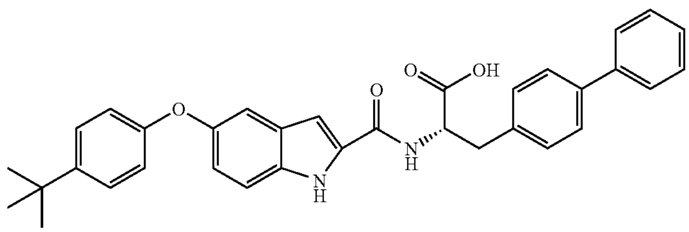 | (2S)-(2-Biphenyl-4-yl-1-carboxyethylcarbamoyl)-5-(4-tert-butylphenoxy)-indole-1-carboxylic acid tert-butyl ester |
| 371 | 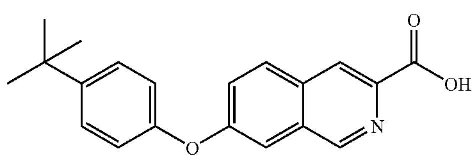 | 7-(4-tert-Butylphenoxy)-isoquinoiine-3-carboxylic acid |
| 372 | 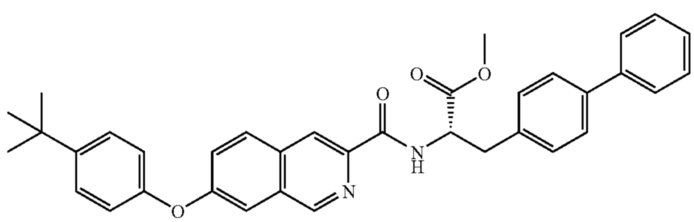 | 3-Biphenyl-4-yl-2S-{[7-(4-tert-butylphenoxy)-isoquinoline-3-carbonyl]amino}-propionic acid methyl ester |
| 373 | 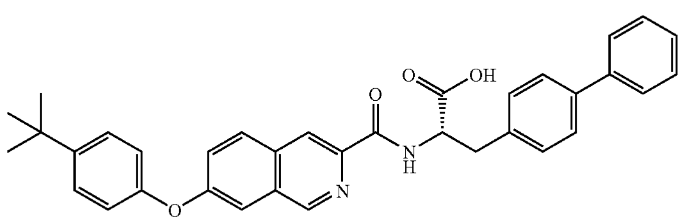 | 3-Biphenyl-4-yl-2S-{[7-(4-tert-butylphenoxy)-isoquinoline-3-carbonyl]amino}-propionic acid |
| 374 | 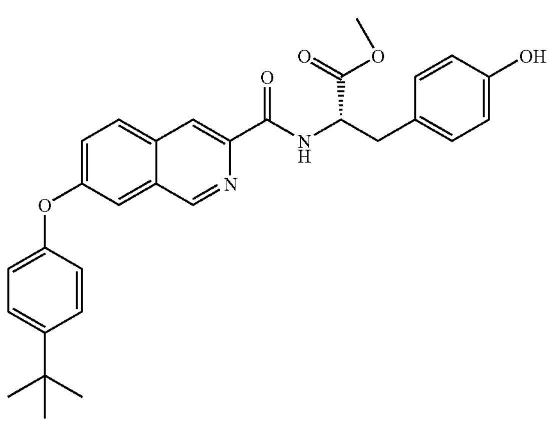 | 2S-{[7-(4-tert-Butyl-phenoxy)-isoquinoline-3-carbonyl]-amino}-3-(4-hydroxy-phenyl)-propionic acid methyl ester |

TABLE 1-continued

| Example | Structure | Name |
|---|---|---|
| 375 | 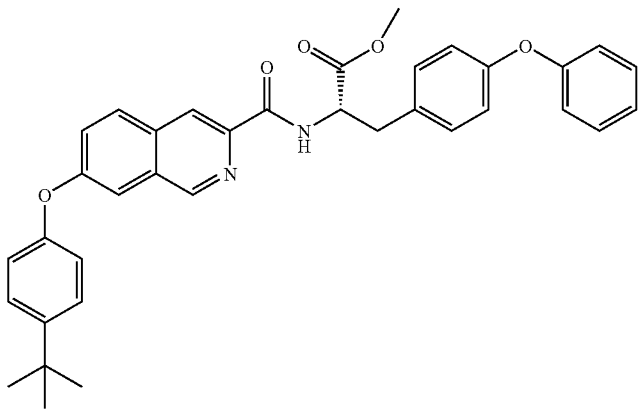 | (2S)-{[7-(4-tert-Butyl-phenoxy)-isoquinoline-3-carbonyl]-amino}-3-(4-phenoxy-phenyl)-propionic acid methyl ester |
| 376 | 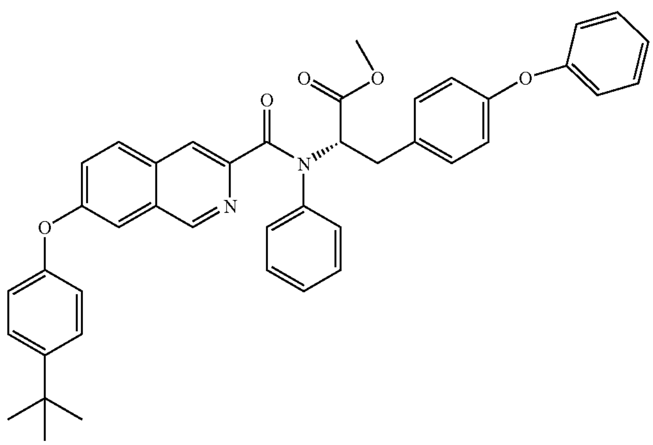 | (2S)-{[7-(4-tert-Butyl-phenoxy)-isoquinoline-3-carbonyl]-aminophenyl}-3-(4-phenoxy-phenyl)-propionic acid methyl ester |
| 377 | 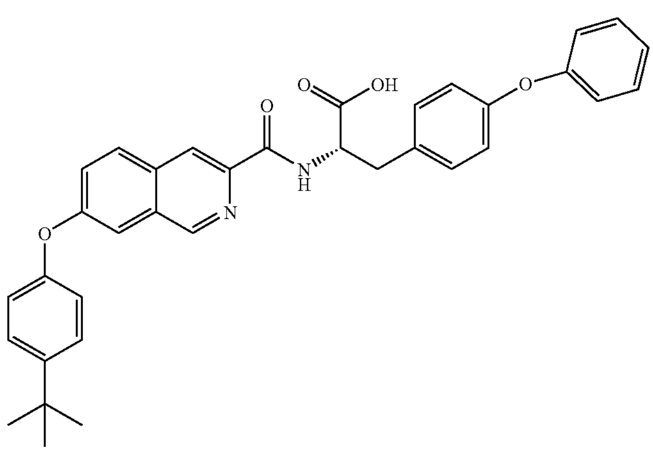 | (2S)-{[7-(4-tert-Butyl-phenoxy)-isoquinoline-3-carbonyl]-amino}-3-(4-phenoxy-phenyl)-propionic acid |

TABLE 1-continued

| Example | Structure | Name |
|---|---|---|
| 378 | 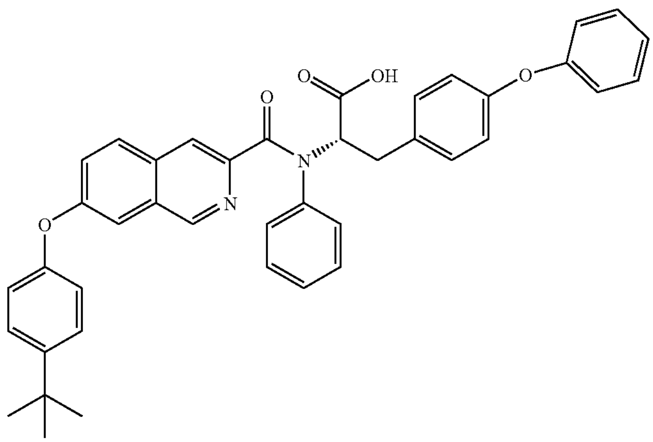 | (2S)-{[7-(4-tert-Butyl-phenoxy)-isoquinoline-3-carbonyl]-phenyl-amino}-3-(4-phenoxy-phenyl)-propionic acid |
| 379 | 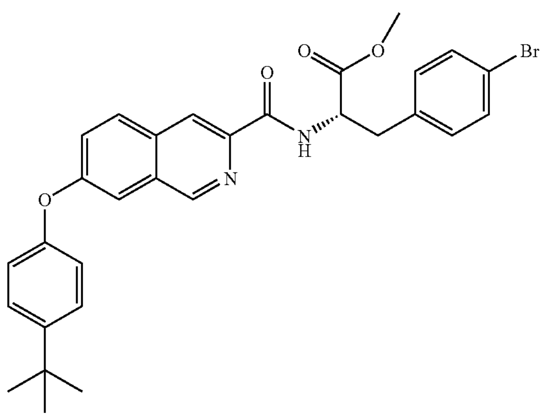 | 3-(4-Bromo-phenyl)-(2S)-{[7-(4-tert-butyl-phenoxy)-isoquinoline-3-carbonyl]-amino}-propionic acid methyl ester |
| 380 | 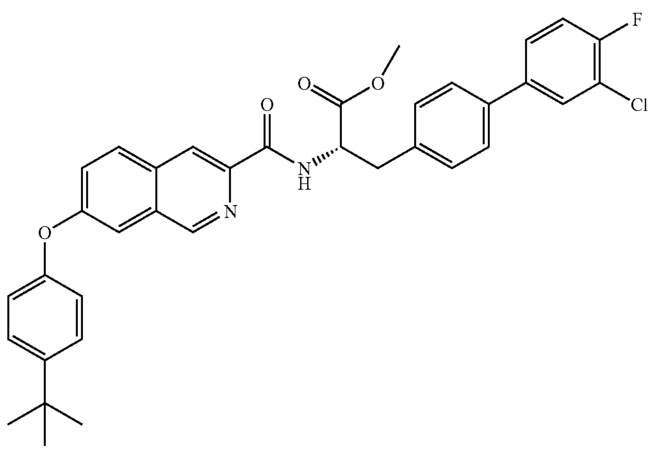 | (2S)-{[7-(4-tert-Butyl-phenoxy)-isoquinoline-3-carbonyl]-amino}-3-(3'-chloro-4'-fluoro-biphenyl-4-yl)-propionic acid methyl ester |

TABLE 1-continued

| Example | Name |
|---|---|
| 381 | (2S)-{[7-(4-tert-Butyl-phenoxy)-isoquinoline-3-carbonyl]-amino}-3-(3'-chloro-4'-fluoro-biphenyl-4-yl)-propionic acid |
| 382 | (2S)-[(7-Benzyloxy-isoquinoline-3-carbonyl)-amino]-3-biphenyl-4-yl-propionic acid methyl ester |
| 383 | (2S)-[(7-Benzyloxy-isoquinoline-3-carbonyl)-amino]-3-biphenyl-4-yl-propionic acid |
| 384 | 3-Biphenyl-4-yl-(2S)-[(7-hydroxy-isoquinoline-3-carbonyl)-amino]-propionic acid methyl ester |

TABLE 1-continued

| Example | Structure | Name |
|---------|-----------|------|
| 385 | 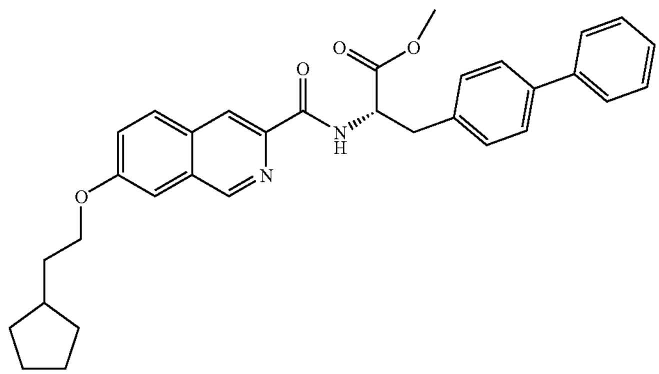 | 3-Biphenyl-4-yl-(2S)-[(7-cyclopentyloxy-isoquinoline-3-carbonyl)-amino]-propionic acid methyl ester |
| 386 | 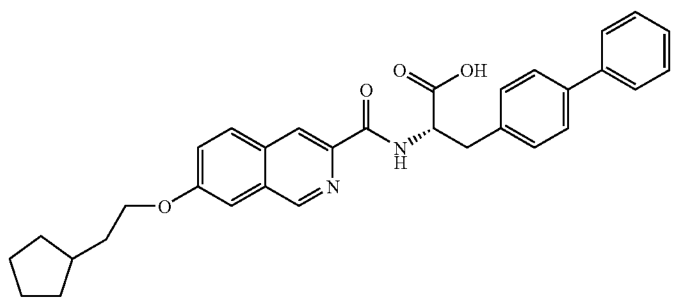 | 3-Biphenyl-4-yl-(2S)-{[7-(2-cyclopentyl-ethoxy)-iso-quinoline-3-carbonyl]-amino}-propionic acid |
| 387 | 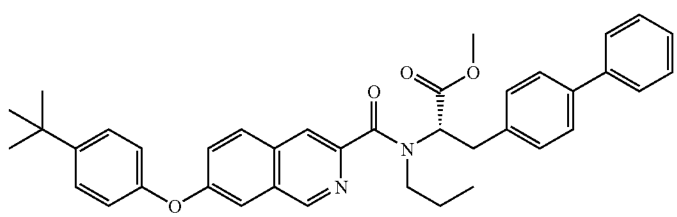 | 3-Biphenyl-4-yl-(2S)-{[7-(4-tert-butyl-phenoxy)-isoquinoline-3-carbonyl]-propyl-amino}-propionic acid methyl ester |
| 388 | 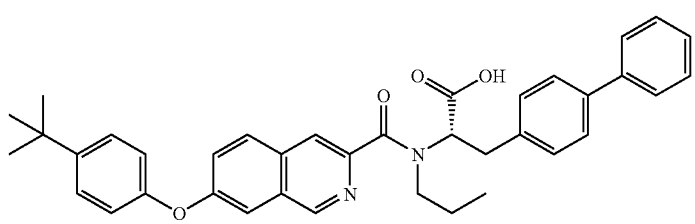 | 3-Biphenyl-4-yl-(2S)-{[7-(4-tert-butyl-phenoxy)-isoquinoline-3-carbonyl]-propyl-amino}-propionic acid |
| 389 | 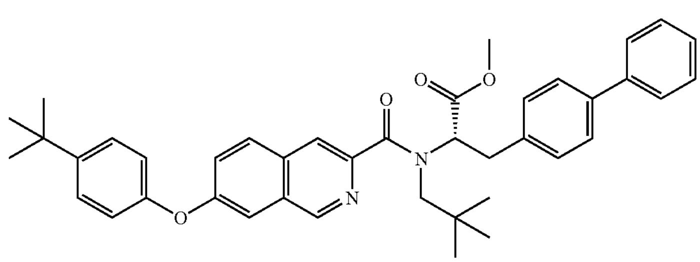 | 3-Biphenyl-4-yl-(2S)-[[7-(4-tert-butyl-phenoxy)-isoquinoline-3-carbonyl]-(2,2-dimethyl-propyl)-amino]-propionic acid methyl ester |

TABLE 1-continued

| Example | Structure | Name |
| --- | --- | --- |
| 390 | 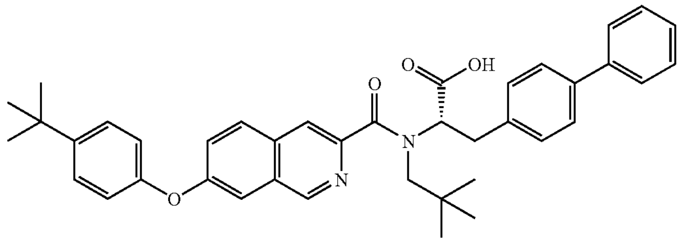 | 3-Biphenyl-4-yl-(2S)-{[7-(4-tert-butylphenoxy)-isoquinoline-3-carbonyl]-(2,2-dimethylpropyl)-amino}-propionic acid |
| 391 | 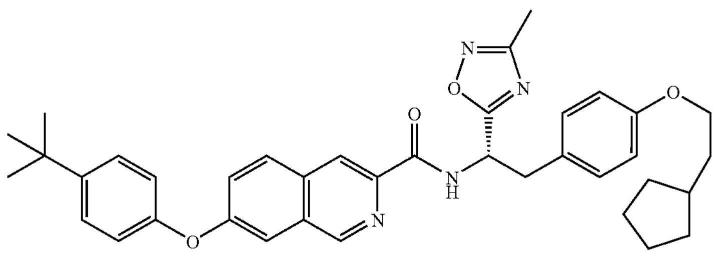 | 7-(4-tert-Butyl-phenoxy)-isoquinoline-3-carboxylic acid [2-[4-(2-cyclopentyl-ethoxy)-phenyl]-(1S)-(3-methyl-[1,2,4]oxadiazol-5-yl)-ethyl]-amide |
| 392 | 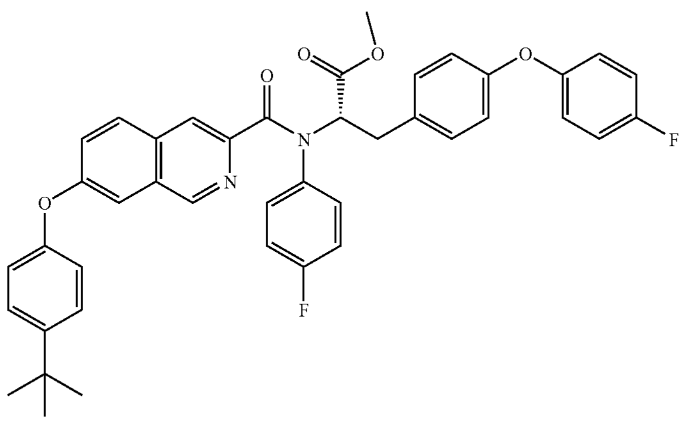 | (2S)-[[7-(4-tert-Butyl-phenoxy)-isoquinoline-3-carbonyl]-(4-fluoro-phenyl)-amino]-3-[4-(4-fluoro-phenoxy)-phenyl]-propionic acid methyl ester |
| 393 | 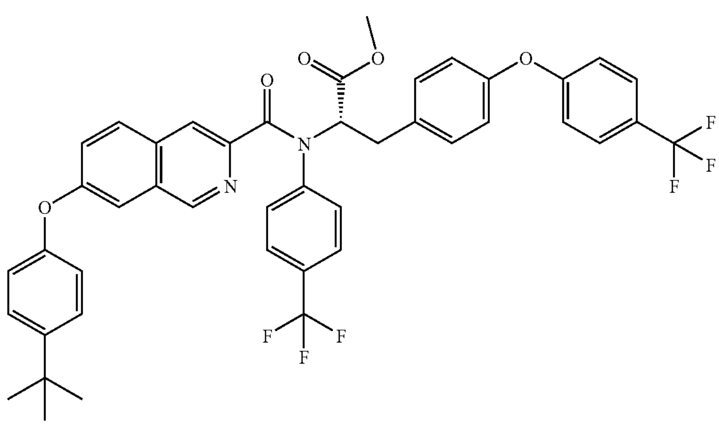 | (2S)-[[7-(4-tert-Butyl-phenoxy)-isoquinoline-3-carbonyl]-(4-trifluoromethyl-phenyl)-amino]-3-[4-(4-trifluoromethyl-phenoxy)-phenyl]-propionic acid methyl ester |

TABLE 1-continued

| Example | Structure | Name |
|---|---|---|
| 394 | 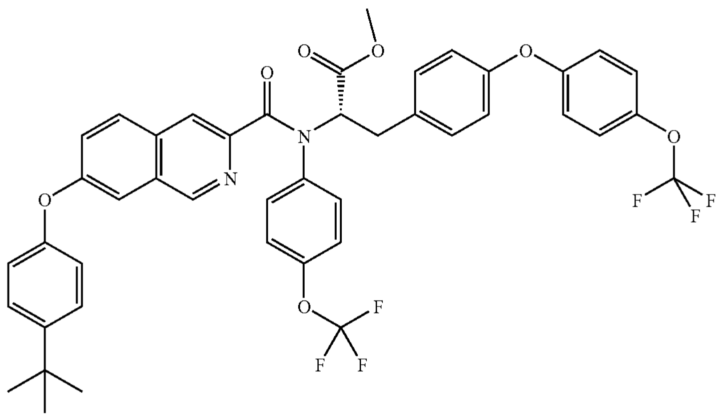 | (2S)-[[7-(4-tert-Butyl-phenoxy)-isoquinoline-3-carbonyl]-(4-trifluoromethoxy-phenyl)-amino]-3-[4-(4-trifluoromethoxy-phenoxy)-phenyl]-propionic acid methyl ester |
| 395 | 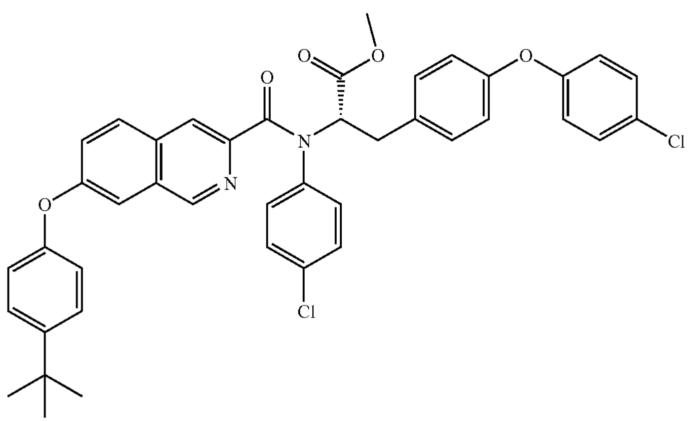 | (2S)-[[7-(4-tert-Butyl-phenoxy)-isoquinoline-3-carbonyl]-(4-chloro-phenyl)-amino]-3-[4-(4-chloro-phenoxy)-phenyl]-propionic acid methyl ester |
| 396 | 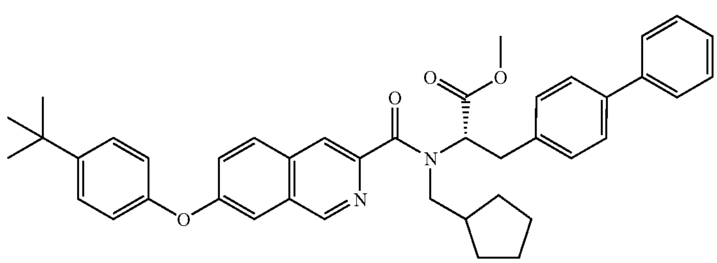 | 3-Biphenyl-4-yl-(2S)-{[7-(4-tert-butyl-phenoxy)-isoquinoline-3-carbonyl]-cyclopentylmethyl-amino}-propionic acid methyl ester |
| 397 | 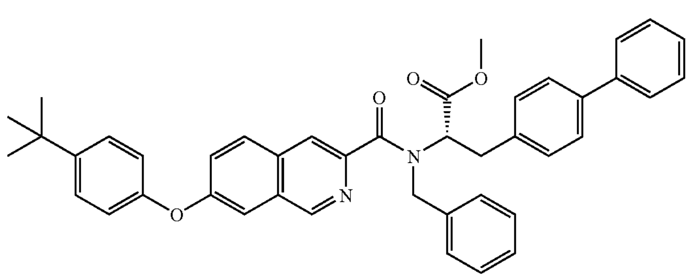 | (2S)-{Benzyl-[7-(4-tert-butyl-phenoxy)-isoquinoline-3-carbonyl]-amino}-3-biphenyl-4-yl-propionic acid methyl ester |

TABLE 1-continued

| Example | Structure | Name |
|---|---|---|
| 398 | 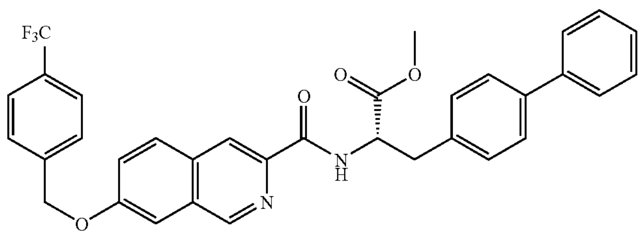 | 3-Biphenyl-4-yl-(2S)-{[7-(4-trifluoromethyl-benzyloxy)-isoquinoline-3-carbonyl]-amino}-propionic acid methyl ester |
| 399 | 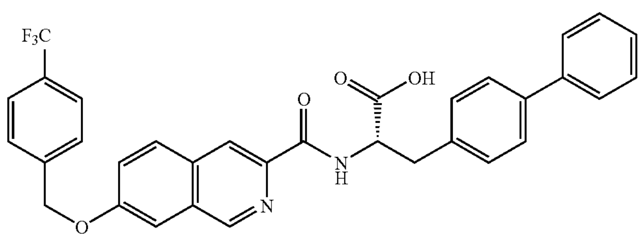 | 3-Biphenyl-4-yl-(2S)-{[7-(4-trifluoromethyl-benzyloxy)-isoquinoline-3-carbonyl]-amino}-propionic acid |
| 400 | 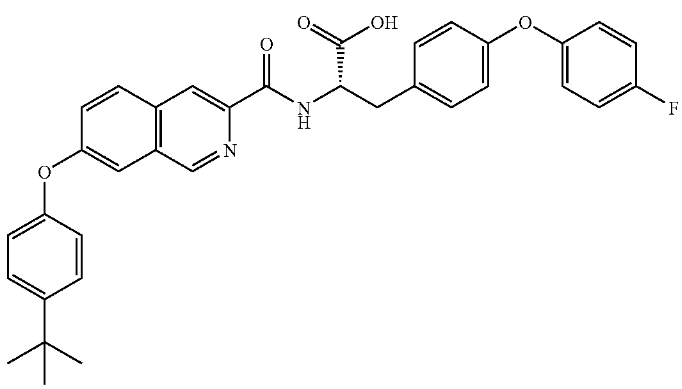 | (2S)-{[7-(4-tert-Butyl-phenoxy)-isoquinoline-3-carbonyl]-amino}-3-[4-(4-fluoro-phenoxy)-phenyl]-propionic acid |
| 401 | 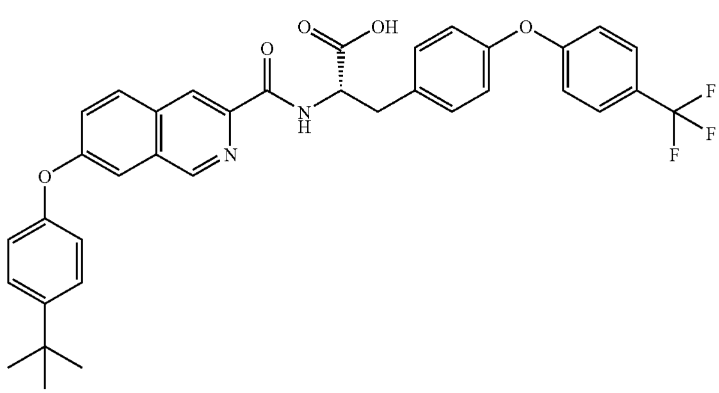 | (2S)-{[7-(4-tert-Butyl-phenoxy)-isoquinoline-3-carbonyl]-amino}-3-[4-(4-trifluoromethyl-phenoxy)-phenyl]-propionic acid |

TABLE 1-continued

| Example | Structure | Name |
|---|---|---|
| 402 | 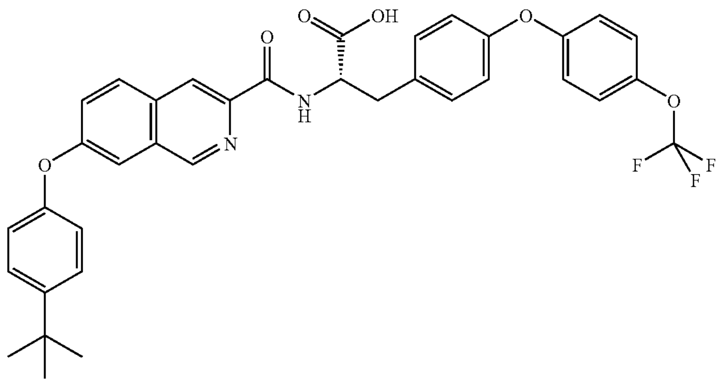 | (2S)-{[7-(4-tert-Butyl-phenoxy)-isoquinoline-3-carbonyl]-amino}-3-[4-(4-trifluoromethoxy-phenoxy)-phenyl]-propionic acid |
| 403 | 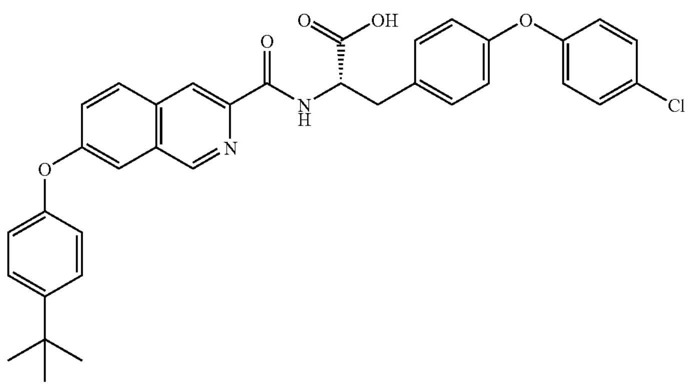 | (2S)-{[7-(4-tert-Butyl-phenoxy)-isoquinoline-3-carbonyl]-amino}-3-[4-(4-chloro-phenoxy)-phenyl]-propionic acid |
| 404 | 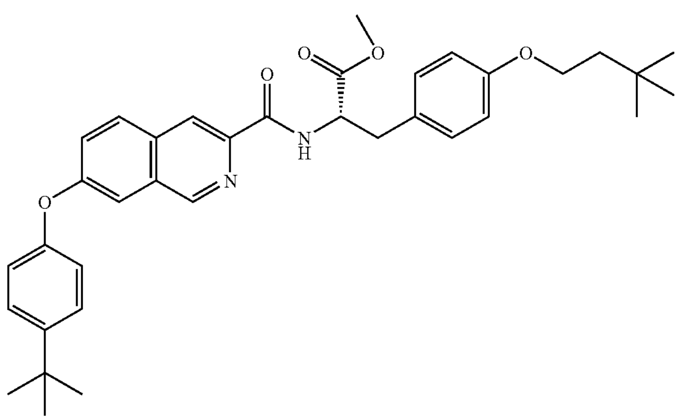 | (2S)-{[7-(4-tert-Butyl-phenoxy)-isoquinoline-3-carbonyl]-amino}-3-[4-(3,3-dimethyl-butoxy)-phenyl]-propionic acid methyl ester |
| 405 | 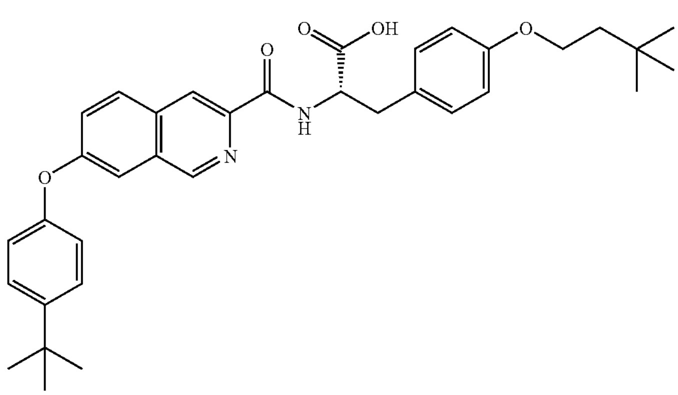 | (2S)-{[7-(4-tert-Butyl-phenoxy)-isoquinoline-3-carbonyl]-amino}-3-[4-(3,3-dimethyl-butoxy)-phenyl]-propionic acid |

TABLE 1-continued

| Example | Structure | Name |
|---|---|---|
| 406 | 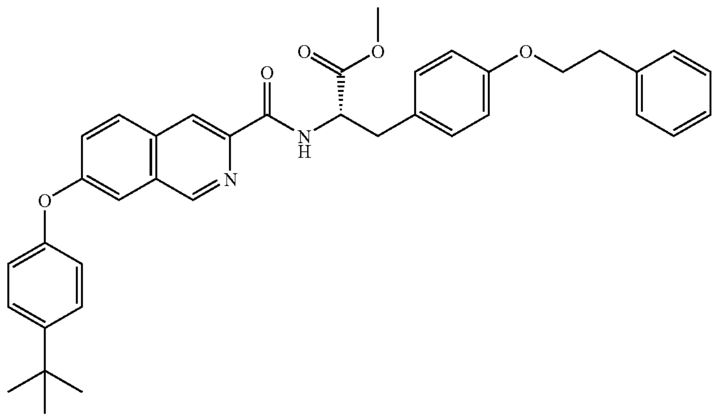 | (2S)-{[7-(4-tert-Butyl-phenoxy)-isoquinoline-3-carbonyl]-amino}-3-(4-phenethyloxy-phenyl)-propionic acid methyl ester |
| 407 | 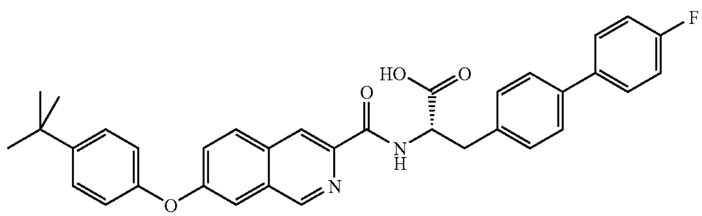 | (2S)-{[7-(4-tert-Butyl-phenoxy)-isoquinoline-3-carbonyl]-amino}-3-(4'-fluoro-biphenyl-4-yl)-propionic acid |
| 408 | 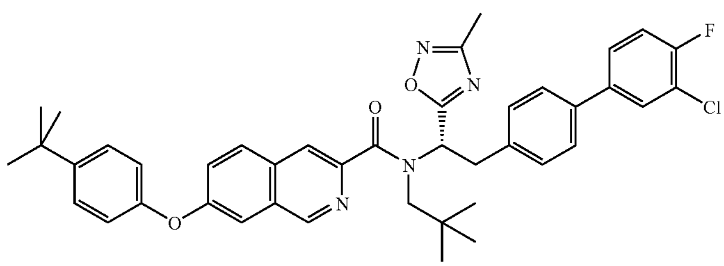 | 7-(4-tert-Butyl-phenoxy)-isoquinoline-3-carboxylic acid [2-(3'-chloro-4'-fluoro-biphenyl-4-yl)-(1S)-(3-methyl-[1,2,4]oxadiazol-5-yl)-ethyl]-(2,2-dimethyl-propyl)-amide |
| 409 | 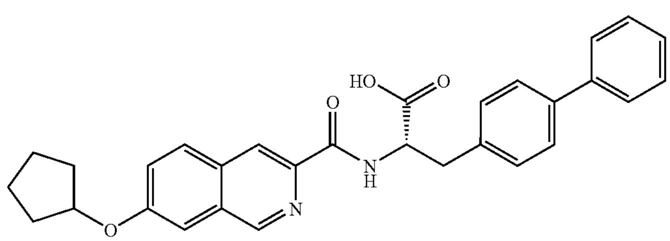 | 3-Biphenyl-4-yl-(2S)-[(7-cyclopentyloxy-isoquinoline-3-carbonyl)-amino]-propionic acid |
| 410 | 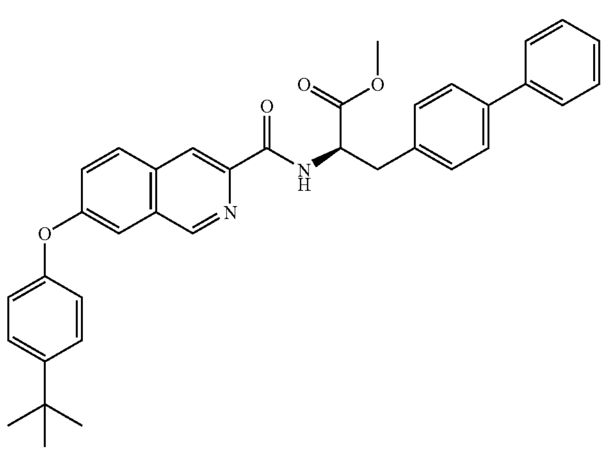 | 3-Biphenyl-4-yl-(2R)-{[7-(4-tert-butyl-phenoxy)-isoquinoline-3-carbonyl]-amino}-propionic acid methyl ester |

TABLE 1-continued

| Example | Structure | Name |
|---|---|---|
| 411 | 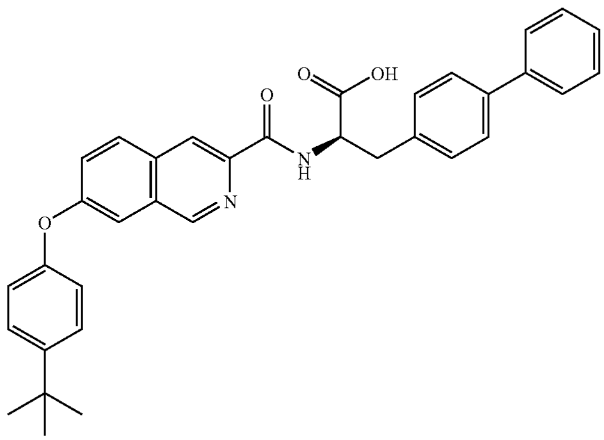 | 3-Biphenyl-4-yl-(2R)-{[7-(4-tert-butyl-phenoxy)-isoquinoline-3-carbonyl]-amino}-propionic acid |
| 412 | 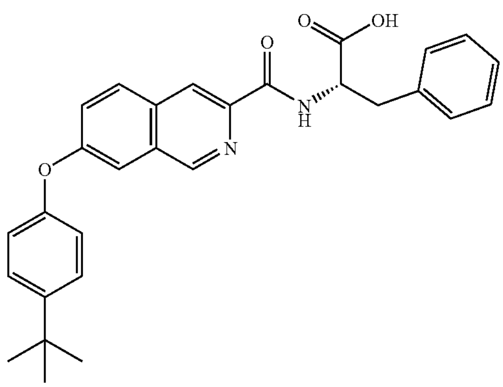 | (2S)-{[7-(4-tert-Butyl-phenoxy)-isoquinoline-3-carbonyl]-amino}-3-phenyl-propionic acid |
| 413 | 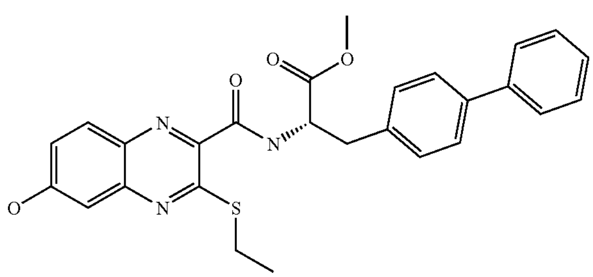 | 3-Biphenyl-4-yl-(2S)-[(3-ethylsulfanyl-6-hydroxy-quinoxaline-2-carbonyl)-amino]-propionic acid methyl ester |
| 414 | 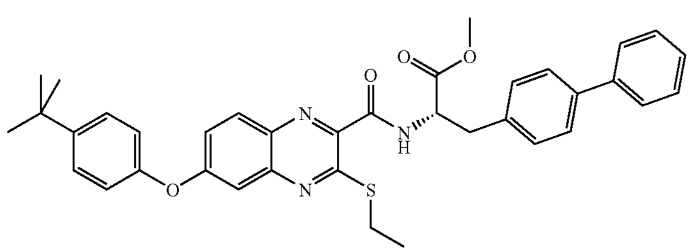 | 3-Biphenyl-4-yl-(2S)-{[6-(4-tert-butyl-phenoxy)-3-ethylsulfanyl-quinoxaline-2-carbonyl]-amino}-propionic acid methyl ester |

TABLE 1-continued

| Example | Structure | Name |
|---|---|---|
| 415 | 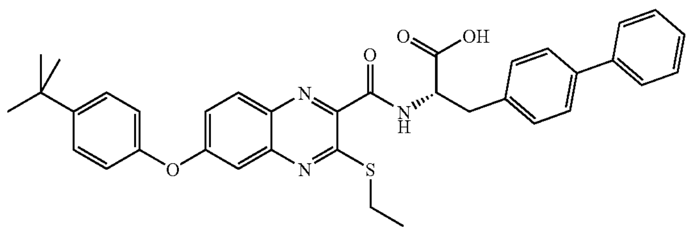 | 3-Biphenyl-4-yl-(2S)-{[6-(4-tert-butyl-phenoxy)-3-ethylsulfanyl-quinoxaline-2-carbonyl]-amino}-propionic acid |
| 416 | 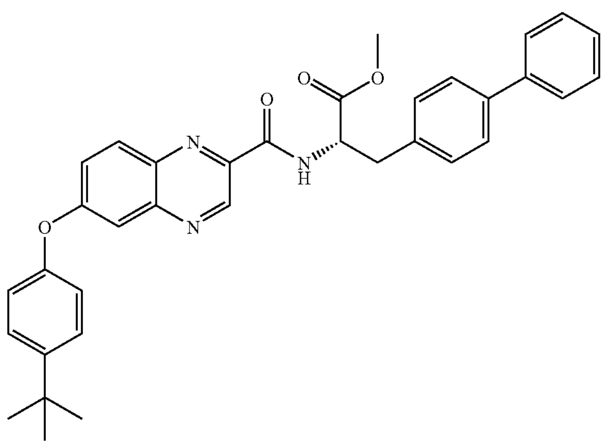 | 3-Biphenyl-4-yl-(2S)-{[6-(4-tert-butyl-phenoxy)-quinoxaline-2-carbonyl]-amino}-propionic acid methyl ester |
| 417 | 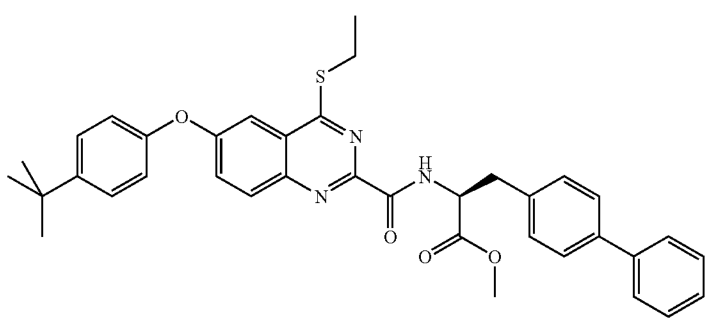 | 3-Biphenyl-4-yl-(2S)-{[6-(4-tert-butyl-phenoxy)-4-ethylsulfanyl-quinazoline-2-carbonyl]-amino}-propionic acid methyl ester |
| 418 | 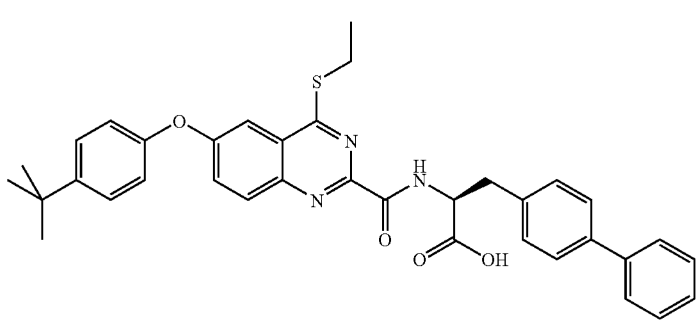 | 3-Biphenyl-4-yl-(2S)-{[6-(4-tert-butyl-phenoxy)-4-ethylsulfanyl-quinazoline-2-carbonyl]-amino}-propionic acid |

TABLE 1-continued

| Example | Structure | Name |
| --- | --- | --- |
| 419 | 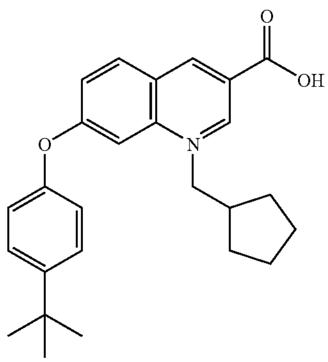 | 7-(4-tert-Butyl-henoxy)-1-cyclopentylmethyl-isoquinoline-3-carboxylic acid |
| 420 | 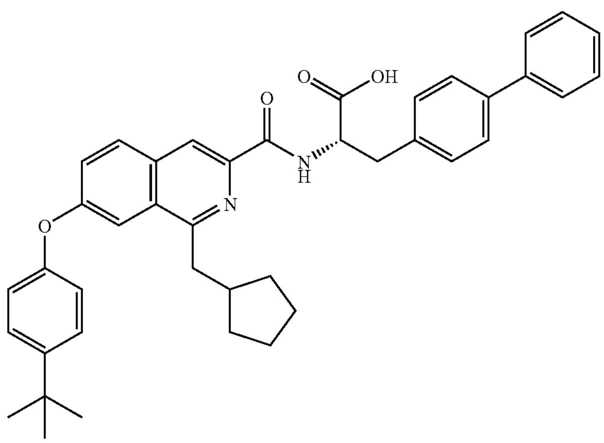 | 3-Biphenyl-4-yl-(2S)-{[7-(4-tert-butyl-phenoxy)-1-yclopentylm-ethyl-isoquinoline-(3S)-carbonyl]-amino}-propionic acid |
| 421 | 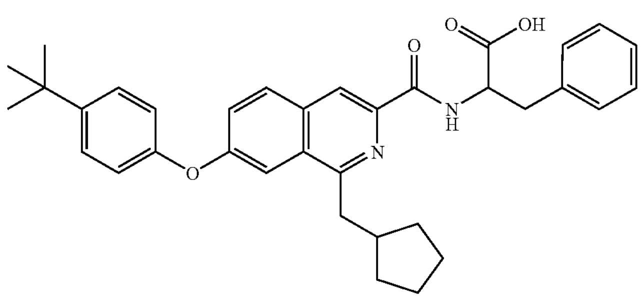 | (2S)-{[7-(4-tert-Butyl-phenoxy)-1-cyclopentylmethyl-isoquinoline-3-carbonyl]-amino}-3-phenyl-propionic acid |
| 422 | 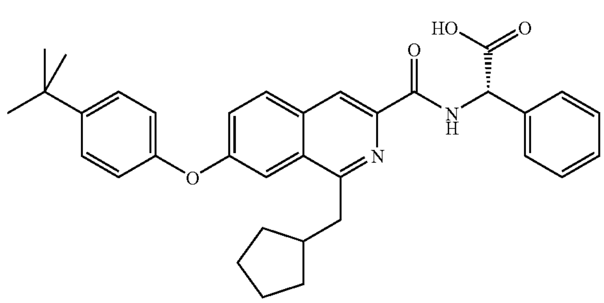 | (2S)-{[7-(4-tert-Butyl-phenoxy)-1-cyclopentylmethyl-isoquinoline-3-carbonyl]-amino}-phenyl-acetic acid |

TABLE 1-continued

| Example | Structure | Name |
|---|---|---|
| 423 | 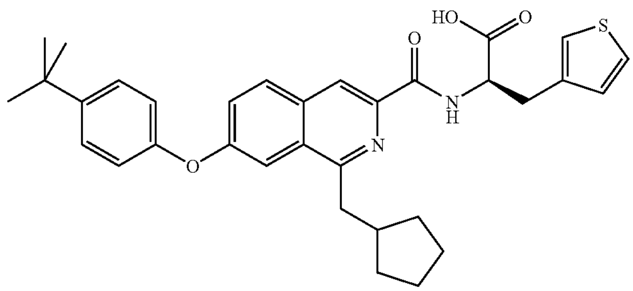 | (2R)-{[7-(4-tert-Butyl-phenoxy)-1-cyclopentylmethyl-isoquinoline-3-carbonyl]-amino}-3-thiophen-3-yl-propionic acid |
| 424 | 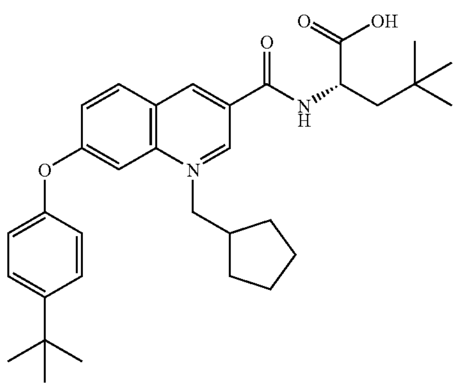 | (2S)-{[7-(4-tert-Butyl-phenoxy)-1-cyclopentylmethyl-isoquinoline-3-carbonyl]-amino}-4,4-dimethyl-pentanoic acid |
| 425 | 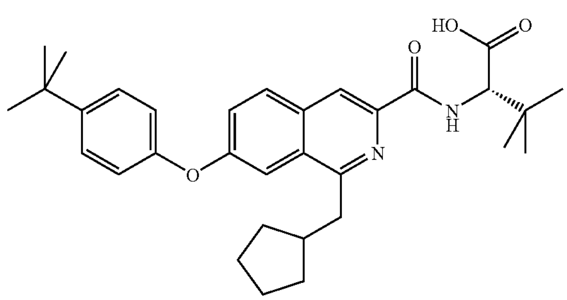 | (2S)-{[7-(4-tert-Butyl-phenoxy)-1-cyclopentylmethyl-isoquinoline-3-carbonyl]-amino}-3,3-dimethyl-butyric acid |
| 426 | 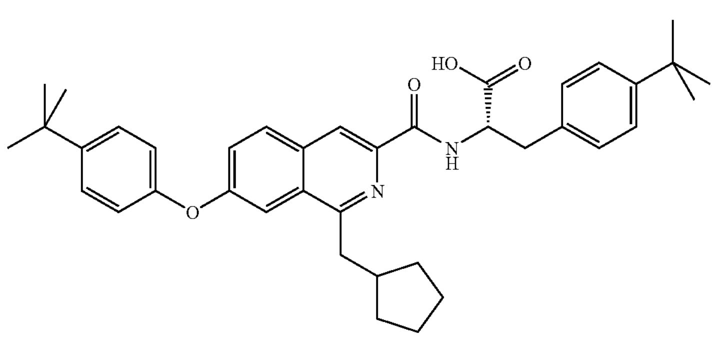 | (2S)-{[7-(4-tert-Butyl-phenoxy)-1-cyclopentylmethyl-isoquinoline-3-carbonyl]-amino}-3-(4-tert-butyl-phenyl)-propionic acid |

TABLE 1-continued

| Example | Structure | Name |
|---|---|---|
| 427 | 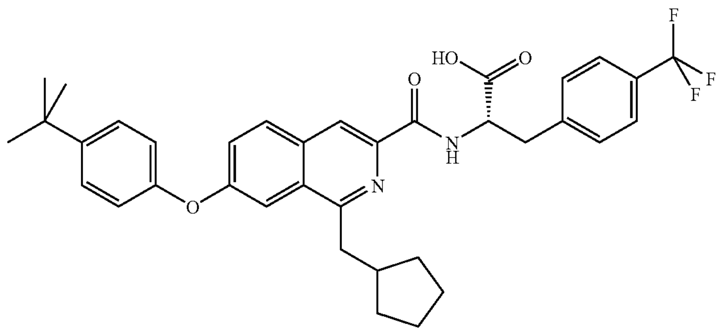 | (2S)-{[7-(4-tert-Butyl-phenoxy)-1-cyclopentylmethyl-isoquinoline-3-carbonyl]-amino}-3-(4-trifluoromethyl-phenyl)-propionic acid |
| 428 | 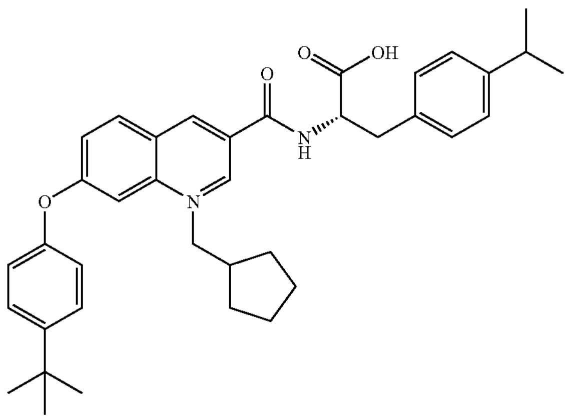 | (2S)-{[7-(4-tert-Butyl-phenoxy)-1-cyclopentylmethyl-isoquinoline-3-carbonyl]-amino}-3-(4-isopropyl-phenyl)-propionic acid |
| 429 | 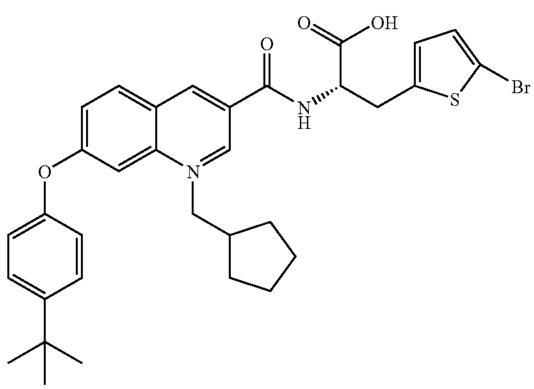 | 3-(5-Bromo-thiophen-2-yl)-(2S)-{[7-(4-tert-butyl-phenoxy)-1-cyclopentylmethyl-isoquinoline-3-carbonyl]-amino}-propionic acid |
| 430 | 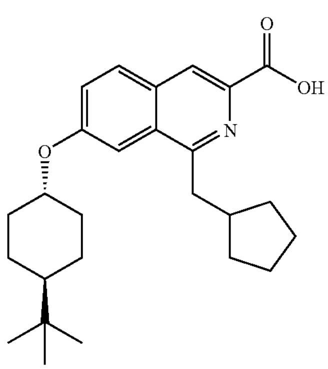 | 7-(trans-4-tert-Butyl-cyclohexyloxy)-1-cyclopentylmethyl-isoquinoline-3-carboxylic acid |

TABLE 1-continued

| Example | Structure | Name |
|---|---|---|
| 431 | 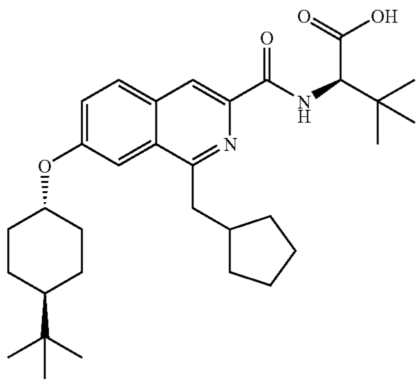 | (2R)-{[7-(trans-4-tert-Butyl-cyclohexyloxy)-1-cyclopentylmethyl-isoquinoline-3-carbonyl]-amino}-3,3-dimethyl-butyric acid |
| 432 | 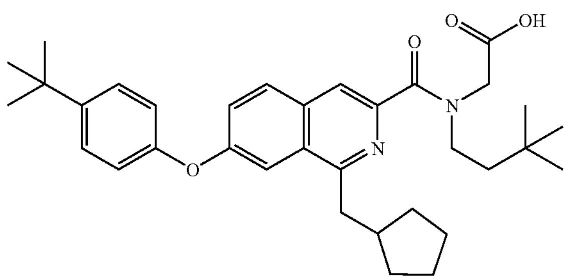 | [[7-(4-tert-Butyl-phenoxy)-1-cyclopentylmethyl-isoquinoline-3-carbonyl]-(3,3-dimethyl-butyl)-amino]-acetic acid |
| 433 | 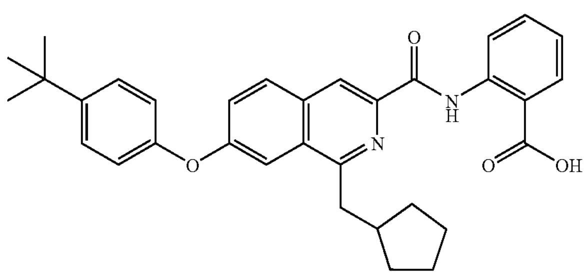 | 2-{[7-(4-tert-Butyl-phenoxy)-1-cyclopentylmethyl-isoquinoline-3-carbonyl]-amino}-benzoic acid |
| 434 | 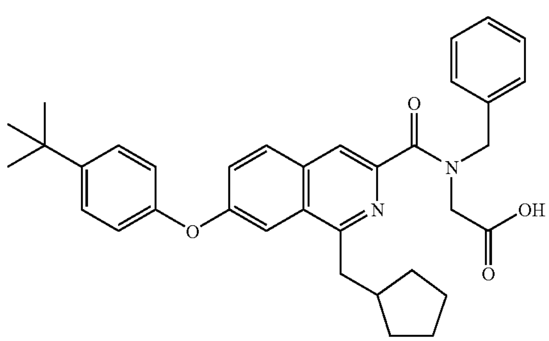 | Benzyl-[7-(4-tert-butyl-phenoxy)-1-cyclopentylmethyl-isoquinoline-3-carbonyl]-amino}-acetic acid |

TABLE 1-continued

| Example | Structure | Name |
|---|---|---|
| 435 | 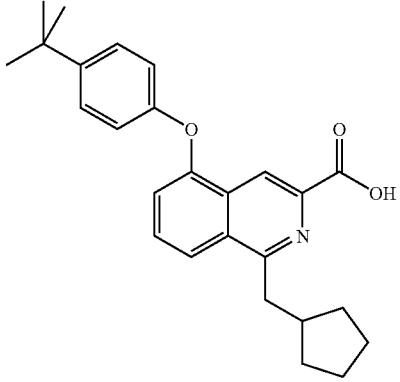 | 5-(4-tert-Butyl-phenoxy)-1-cyclopentylmethyl-isoquinoline-3-carboxylic acid |
| 436 | 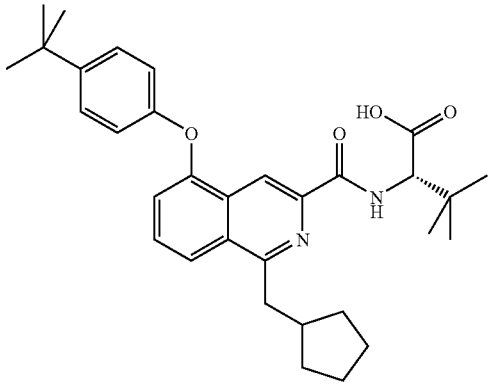 | (2S)-{[5-(4-tert-Butyl-phenoxy)-1-cyclopentylmethyl-isoquinoline-3-carbonyl]-amino}-3,3-dimethyl-butyric acid |
| 437 | 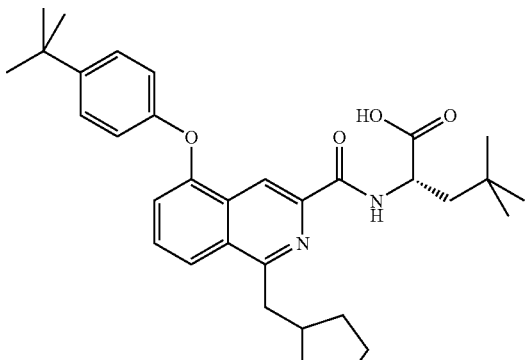 | (2S)-{[5-(4-tert-Butyl-phenoxy)-1-cyclopentylmethyl-isoquinoline-3-carbonyl]-amino}-4,4-dimethyl-pentanoic acid |
| 438 | 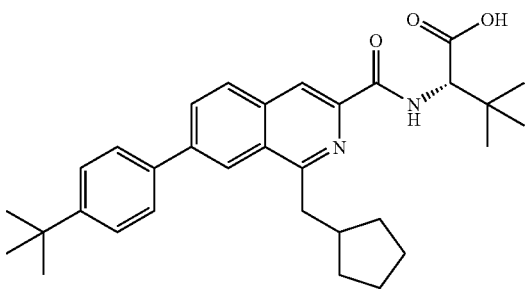 | (2S)-{[7-(4-tert-Butyl-phenyl)-1-cyclopentylmethyl-isoquinoline-3-carbonyl]-amino}-3,3-dimethyl-butyric acid |

TABLE 1-continued

| Example | Structure | Name |
|---|---|---|
| 439 | 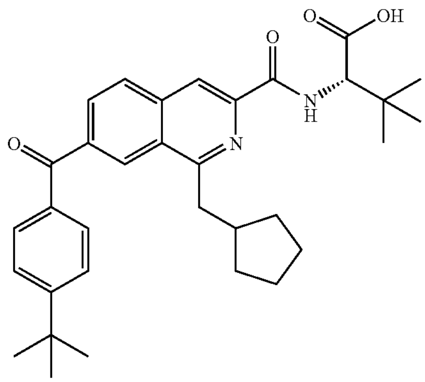 | (2S)-{[7-(4-tert-Butyl-benzoyl)-1-cyclopentylmethyl-isoquinoline-3-carbonyl]-amino}-3,3-dimethyl-butyric acid |
| 440 | 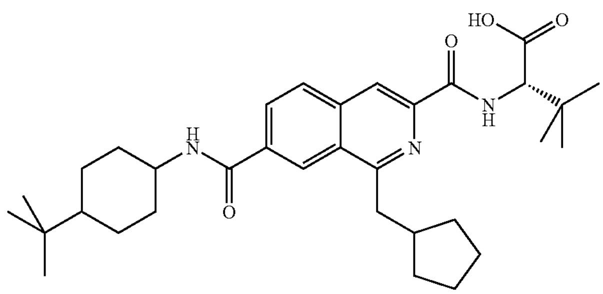 | (2S)-{[7-(4-tert-Butyl-cyclohexylcarbamoyl)-1-cyclopentylmethyl-isoquinoline-3-carbonyl]-amino}-3,3-dimethyl-butyric acid |
| 441 | 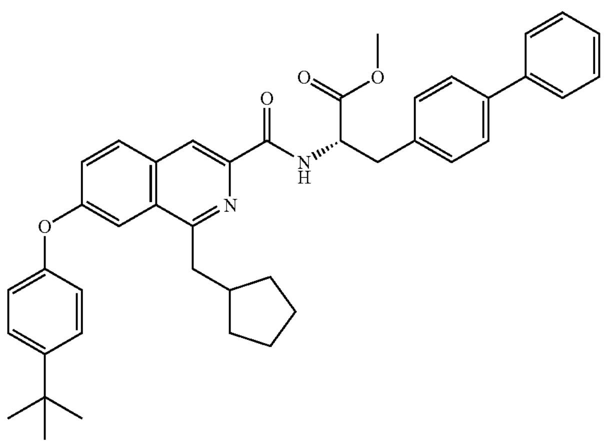 | 3-Biphenyl-4-yl-(2S)-[7-(4-tert-butyl-phenoxy)-1-cyclopentylmethyl-isoquinoline-3-carbonyl]-amino}-propionic acid methyl ester |
| 442 | 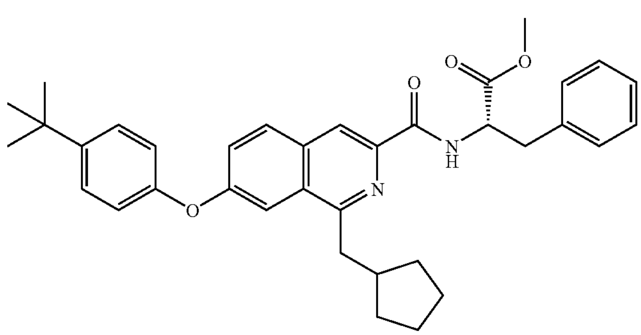 | (2S)-{[7-(4-tert-Butyl-phenoxy)-1-cyclopentylmethyl-isoquinoline-3-carbonyl]-amino}-3-phenyl-propionic acid methyl ester |

TABLE 1-continued

| Example | Structure | Name |
|---|---|---|
| 443 | 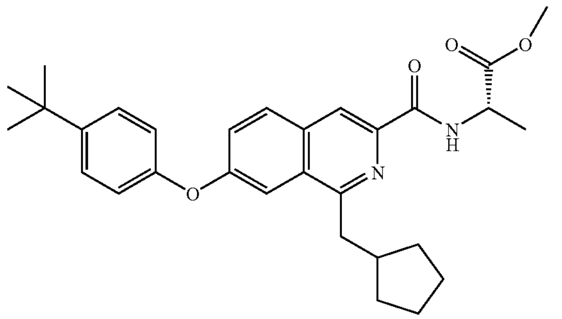 | (2S)-{[7-(4-tert-Butyl-phenoxy)-1-cyclopentylmethyl-isoquinoline-3-carbonyl]-amino}-propionic acid methyl ester |
| 444 | 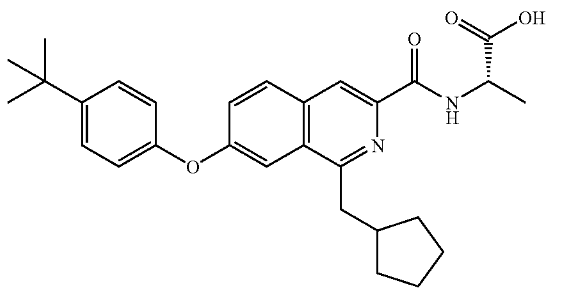 | (2S)-{[7-(4-tert-Butyl-phenoxy)-1-cyclopentylmethyl-isoquinoline-3-carbonyl]-amino}-propionic acid |
| 445 | 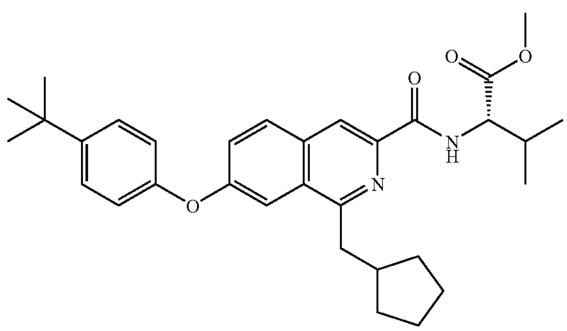 | (2S)-{[7-(4-tert-Butyl-phenoxy)-1-cyclopentylmethyl-isoquinoline-3-carbonyl]-amino)-3-methyl-butyric acid methyl ester |
| 446 | 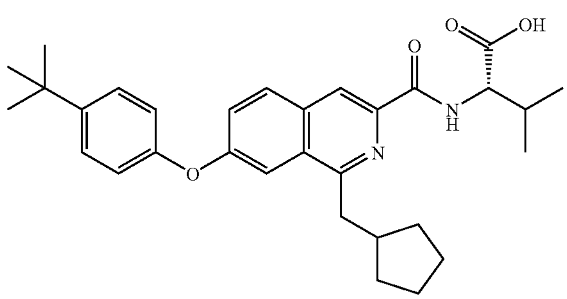 | (2S)-{[7-(4-tert-Butyl-phenoxy)-1-cyclopentylmethyl-isoquinoline-3-carbonyl]-amino)-3-methyl-butyric acid |
| 447 | 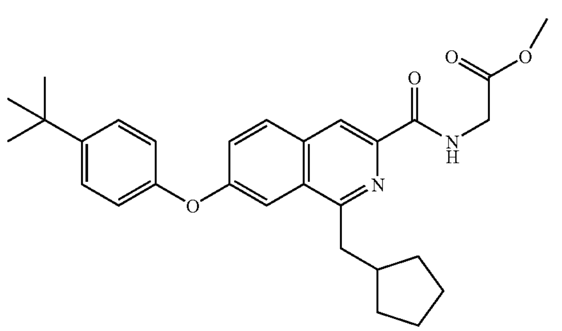 | {[7-(4-tert-Butyl-phenoxy)-1-cyclopentylmethyl-isoquinoline-3-carbonyl]-amino}-acetic acid methyl ester |

TABLE 1-continued

| Example | Structure | Name |
|---|---|---|
| 448 | 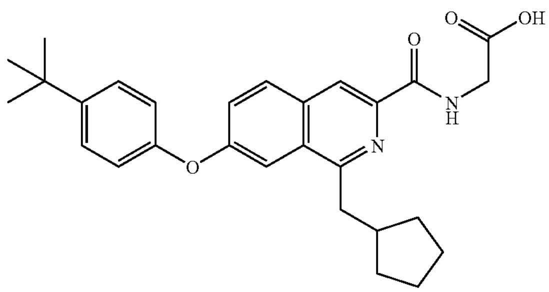 | {[7-(4-tert-Butyl-phenoxy)-1-cyclopentylmethyl-isoquino-line-3-carbonyl]-amino}-acetic acid |
| 449 | 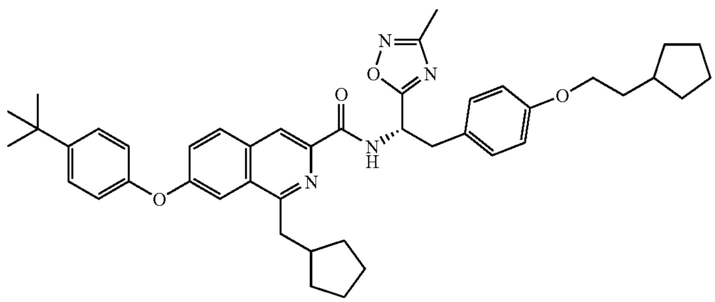 | 7-(4-tert-Butyl-phenoxy)-1-cyclopentylmethyl-isoquino-line-3-carboxylic acid [2-[4-(2-cy-clopentyl-ethoxy)-phenyl]-(1S)-(3-me-thyl-[1,2,4]oxadiazol-5-yl)-ethyl]-amide |
| 450 | 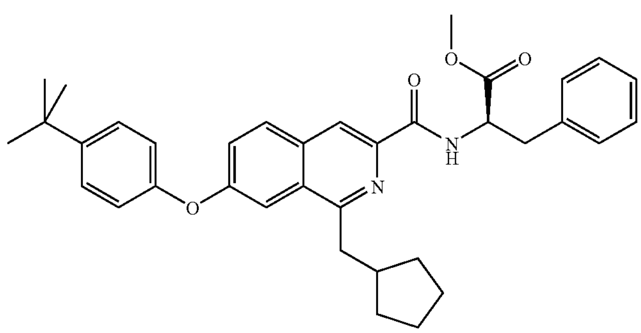 | (2R)-{[7-(4-tert-Butyl-phe-noxy)-1-cyclopentylmethyl-isoquino-line-3-carbonyl]-amino}-3-phenyl-propionic acid methyl ester |
| 451 | 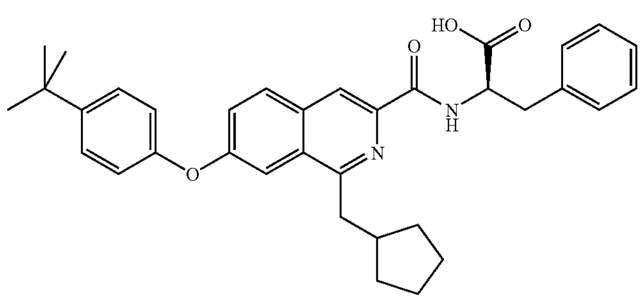 | (2R)-{[7-(4-tert-Butyl-phe-noxy)-1-cyclopentylmethyl-isoquino-line-3-carbonyl]-amino}-3-phenyl-propionic acid |
| 452 | 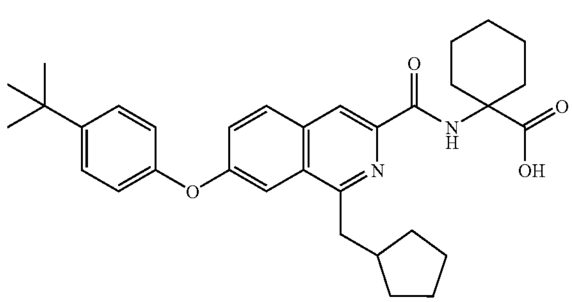 | 1-{[7-(4-tert-Butyl-phenoxy)-1-cyclopentylmethyl-isoquino-line-3-carbonyl]-amino}-cyclohexanecarboxylic acid |

TABLE 1-continued

| Example | Structure | Name |
|---|---|---|
| 453 | 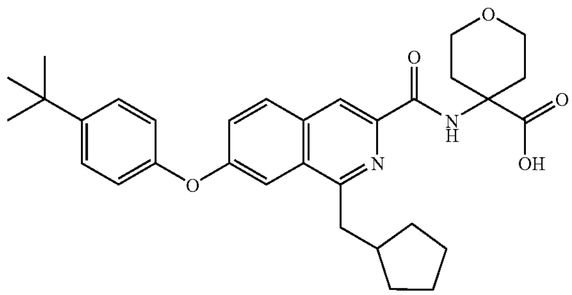 | 4-{[7-(4-tert-Butyl-phenoxy)-1-cyclopentylmethyl-isoquinoline-3-carbonyl]-amino}-tetrahydropyran-4-carboxylic acid |
| 454 | 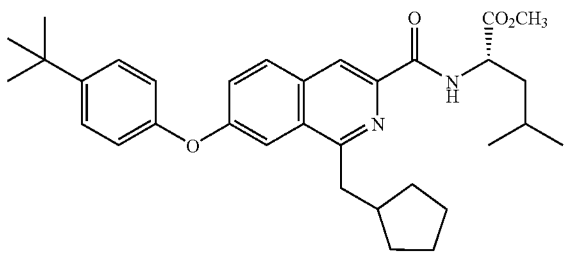 | 2S-{[7-(4-tert-Butyl-phenoxy)-1-cyclopentylmethyl-isoquinoline-3-carbonyl]-amino}-4-methyl-pentanoic acid methyl ester |
| 455 | 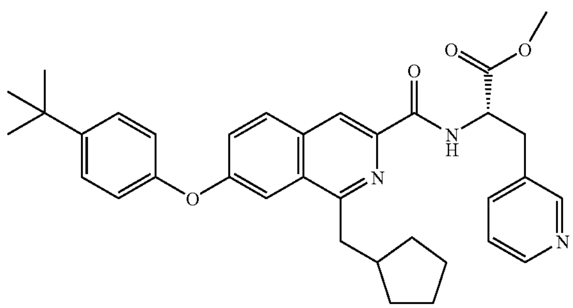 | 2S-{[7-(4-tert-Butyl-phenoxy)-1-cyclopentylmethyl-isoquinoline-3-carbonyl]-amino}-3-pyridin-3-yl-propionic acid methyl ester |
| 456 | 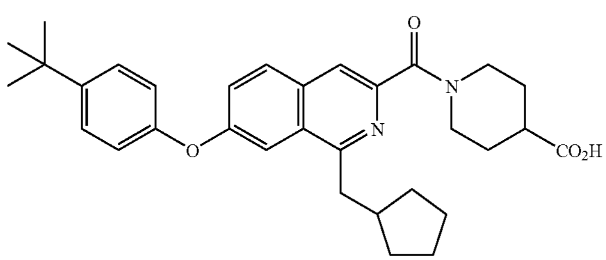 | 1-[7-(4-tert-Butyl-phenoxy)-1-cyclopentylmethyl-isoquinoline-3-carbonyl]piperidine-4-carboxylic acid |
| 457 | 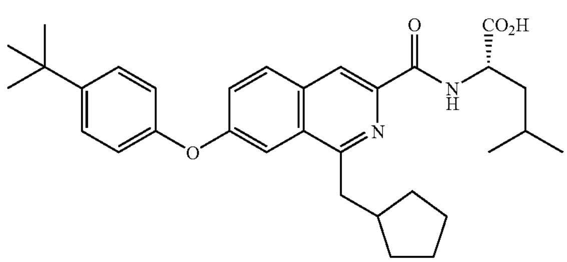 | 2S-{[7-(4-tert-Butyl-phenoxy)-1-cyclopentylmethyl-isoquinoline-3-carbonyl]amino]-4-methyl-pentanoic acid |

TABLE 1-continued

| Example | Structure | Name |
|---|---|---|
| 458 | 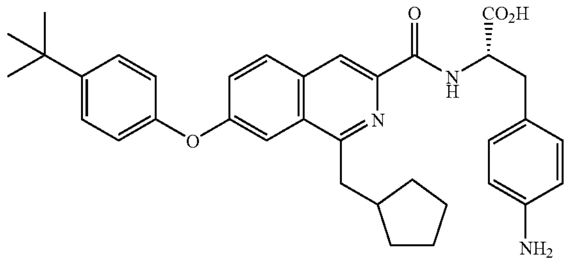 | 3-(4-Amino-phenyl)-(2S)-{[7-(4-tert-butyl-phenoxy)-1-cyclopentylmethyl-isoquinoline-3-carbonyl]-amino}-propionic acid |
| 459 | 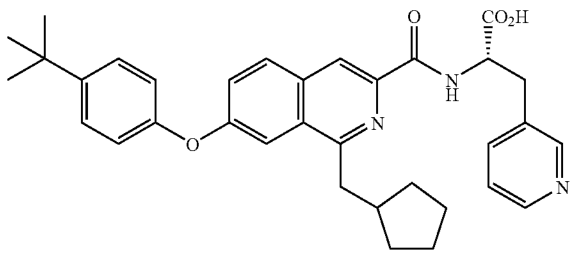 | (2S)-{[7-(4-tert-Butyl-phenoxy)-1-cyclopentylmethyl-isoquinoline-3-carbonyl]-amino}-3-pyridin-3-yl-propionic acid |
| 460 | 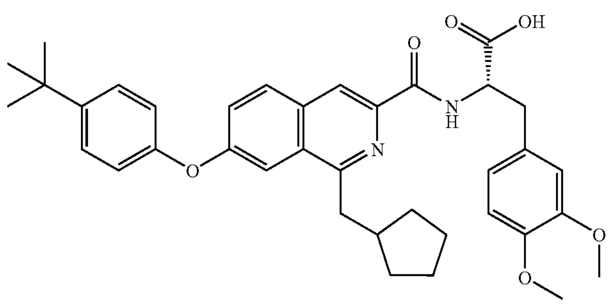 | (2S)-{[7-(4-tert-Butyl-phenoxy)-1-cyclopentylmethyl-isoquinoline-3-carbonyl]-amino}-3-(3,4-dimethoxy-phenyl)-propionic acid |
| 461 | 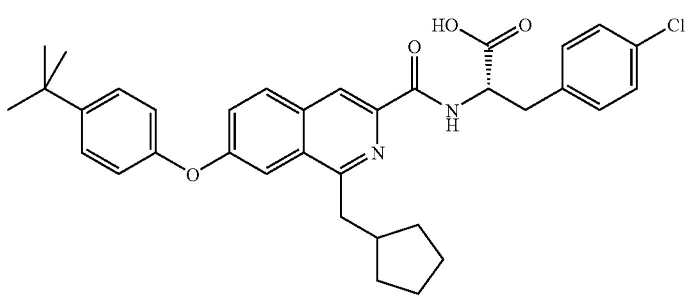 | (2S)-{[7-(4-tert-Butyl-phenoxy)-1-cyclopentylmethyl-isoquinoline-3-carbonyl]-amino}-3-(4-chloro-phenyl)-propionic acid |
| 462 | 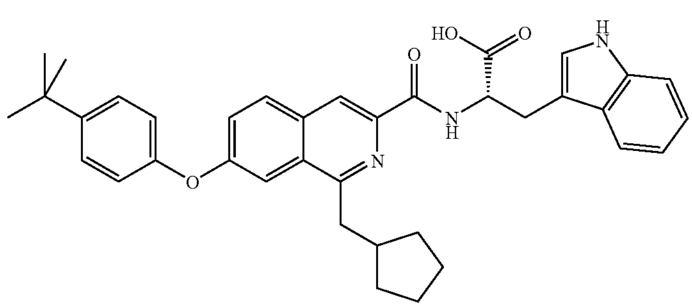 | (2S)-{[7-(4-tert-Butyl-phenoxy)-1-cyclopentylmethyl-isoquinoline-3-carbonyl]-amino}-3-(1H-indol--yl)-propionic acid |

| Example | Structure | Name |
|---|---|---|
| 463 | 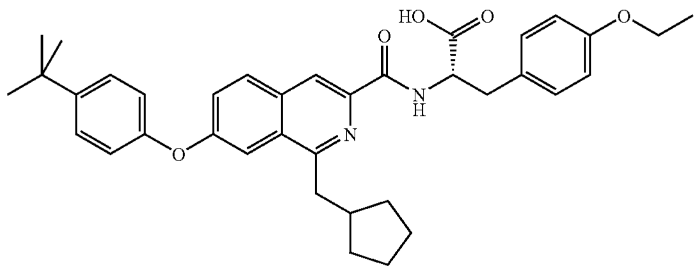 | (2S)-{[7-(4-tert-Butyl-phenoxy)-1-cyclopentylmethyl-isoquinoline-3-carbonyl]-amino}-3-(4-ethoxy-phenyl)-propionic acid |
| 464 | 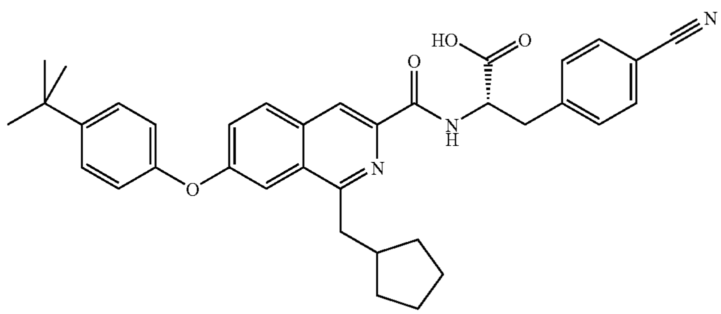 | (2S)-{[7-(4-tert-Butyl-phenoxy)-1-cyclopentylmethyl-isoquinoline-3-carbonyl]-amino}-3-(4-cyano-phenyl)-propionic acid |
| 465 | 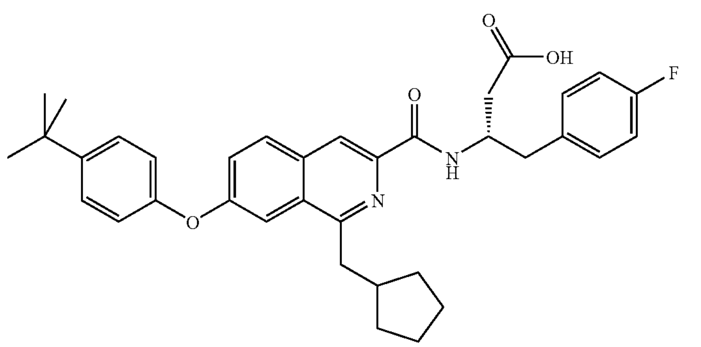 | (3S)-{[7-(4-tert-Butyl-phenoxy)-1-cyclopentylmethyl-isoquinoline-3-carbonyl]-amino}-4-(4-fluoro-phenyl)-butyric acid |
| 466 | 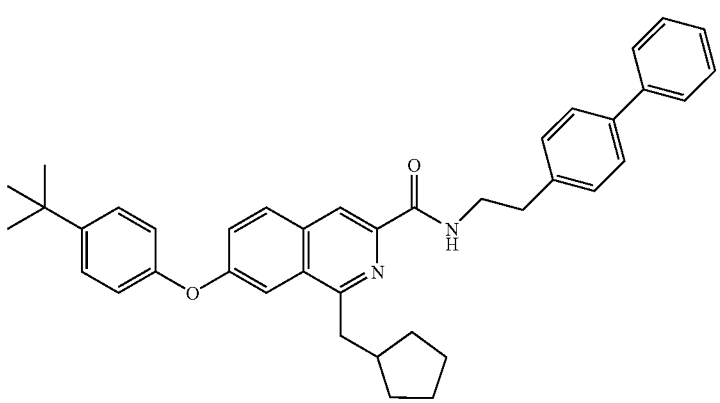 | 7-(4-tert-Butyl-phenoxy)-1-cyclopentylmethyl-isoquinoline-3-carboxylic acid (2-biphenyl-4-yl-ethyl)-amide |

TABLE 1-continued

| Example | Structure | Name |
|---|---|---|
| 467 | 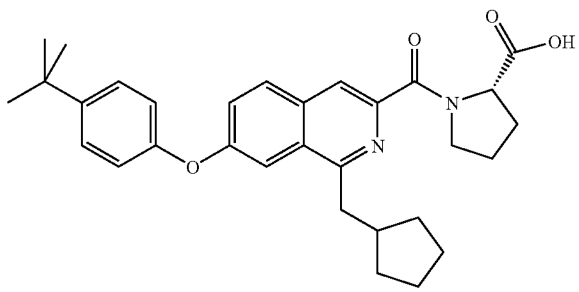 | 1-[7-(4-tert-Butyl-phenoxy)-1-cyclopentylmethyl-isoquinoline-3-carbonyl]-pyrrolidine-(2S)-carboxylic acid |
| 468 | 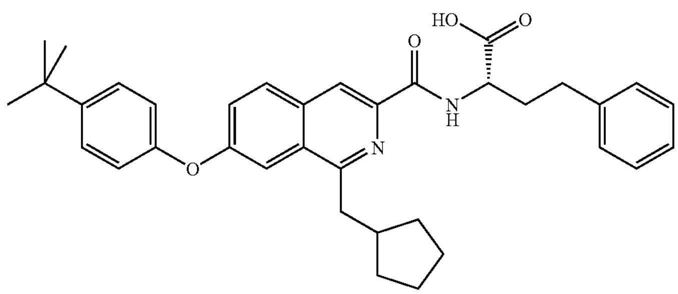 | (2S)-{[7-(4-tert-Butyl-phenoxy)-1-cyclopentylmethyl-isoquinoline-3-carbonyl]-amino}-4-phenyl-butyric acid |
| 469 | 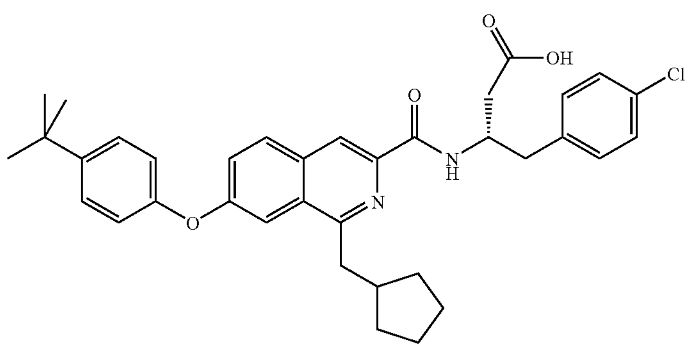 | (3S)-{[7-(4-tert-Butyl-phenoxy)-1-cyclopentylmethyl-isoquinoline-3-carbonyl]-amino}-4-(4-chloro-phenyl)-butyric acid |
| 470 | 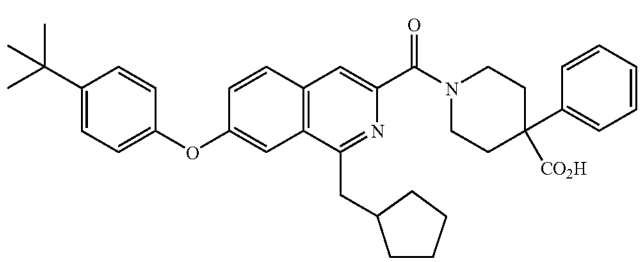 | 1-[7-(4-tert-Butyl-phenoxy)-1-cyclopentylmethyl-isoquinoline-3-carbonyl]-4-phenyl-piperidine-4-carboxylic acid |
| 471 | 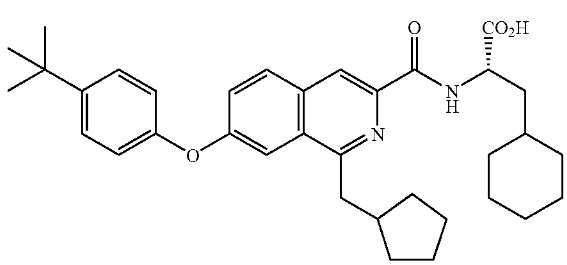 | (2S)-{[7-(4-tert-Butyl-phenoxy)-1-cyclopentylmethyl-isoquinoline-3-carbonyl]-amino}-3-cyclohexyl-propionic acid |

TABLE 1-continued

| Example | Structure | Name |
|---|---|---|
| 472 | 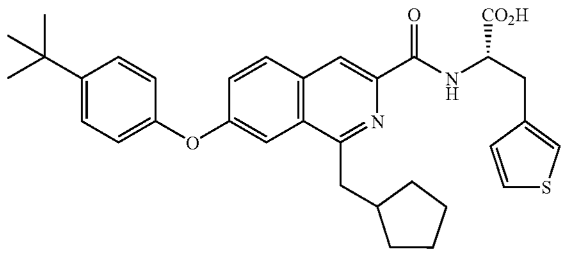 | (2S)-{[7-(4-tert-Butyl-phenoxy)-1-cyclopentylmethyl-isoquinoline-3-carbonyl]-amino}-3-thiophen-3-yl-propionic acid |
| 473 | 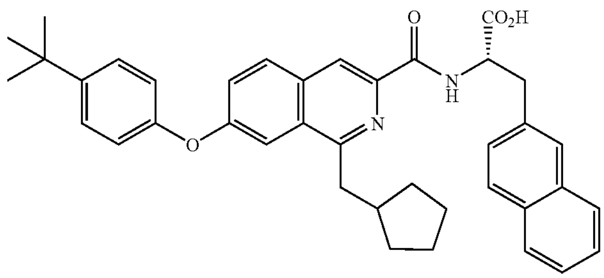 | (2S)-{[7-(4-tert-Butyl-phenoxy)-1-cyclopentylmethyl-isoquinoline-3-carbonyl]-amino}-3-naphthalen-2-yl-propionic acid |
| 474 | 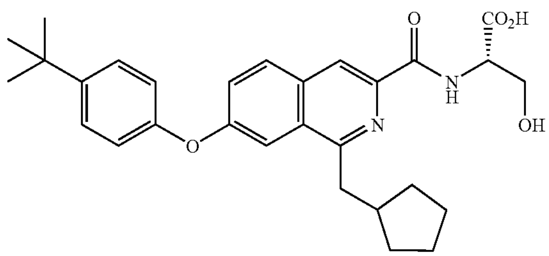 | (2S)-{[7-(4-tert-Butyl-phenoxy)-1-cyclopentylmethyl-isoquinoline-3-carbonyl]-amino}-3-hydroxy-propionic acid |
| 475 | 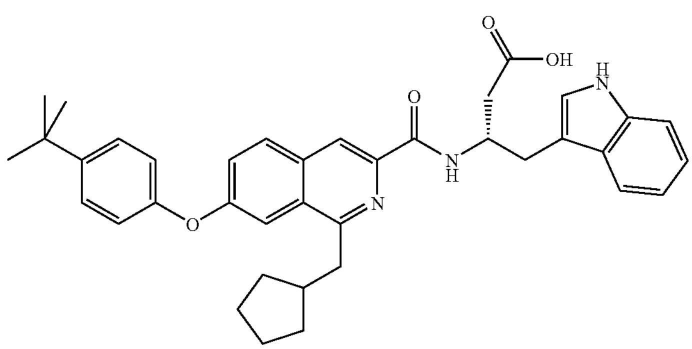 | (3S)-{[7-(4-tert-Butyl-phenoxy)-1-cyclopentylmethyl-isoquinoline-3-carbonyl]-amino}-4-(1H-indol-3-yl)-butyric acid |
| 476 | 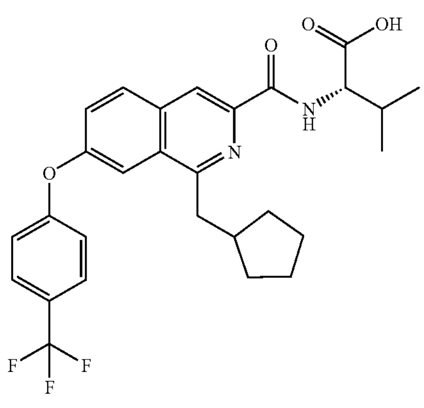 | (2S)-{[1-Cyclopentylmethyl-7-(4-trifluoromethyl-phenoxy)-isoquinoline-3-carbonyl]-amino}-3-methyl-butyric acid |

TABLE 1-continued

| Example | Structure | Name |
|---|---|---|
| 477 | 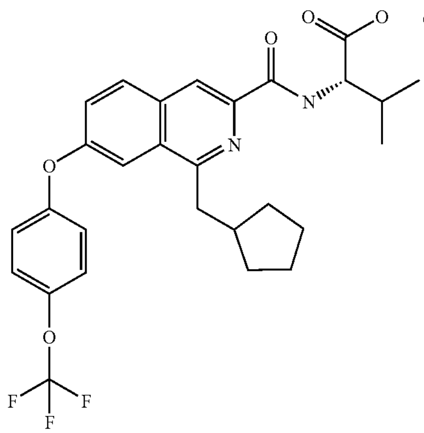 | (2S)-{[1-Cyclopentylmethyl-7-(4-trifluoromethoxy-phenoxy)-isoquinoline-3-carbonyl]-amino}-3-methyl-butyric acid |
| 478 | 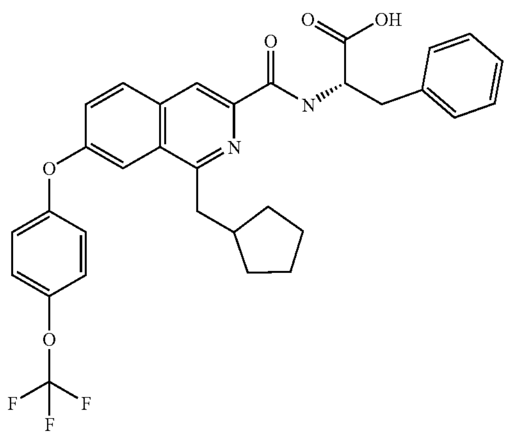 | (2S)-{[1-Cyclopentylmethyl-7-(4-trifluoromethoxy-phenoxy)-isoquinoline-3-carbonyl]-amino}-3-phenyl-propionic acid |
| 479 | 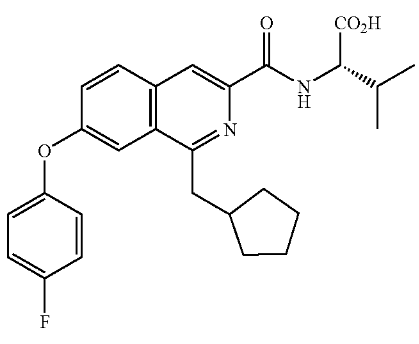 | (2S)-{[1-Cyclopentylmethyl-7-(4-fluoro-phenoxy)-isoquinoline-3-carbonyl]-amino}-3-methyl-butyric acid |
| 480 | 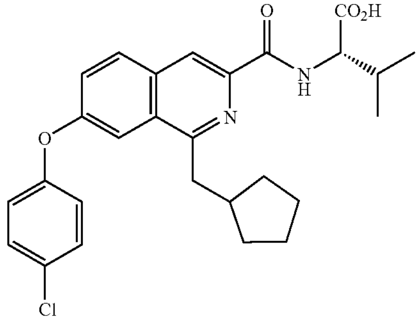 | (2S)-{[7-(4-Chloro-phenoxy)-1-cyclopentylmethyl-isoquinoline-3-carbonyl]-amino}-3-methyl-butyric acid |

TABLE 1-continued

| Example | Structure | Name |
|---|---|---|
| 481 | 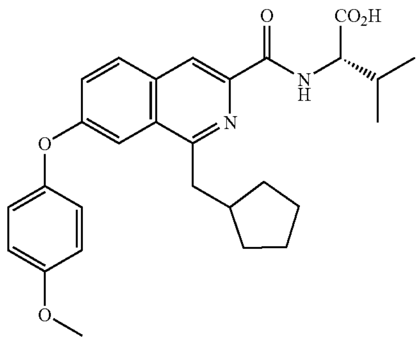 | (2S)-{[1-Cyclopentylmethyl-7-(4-methoxy-phenoxy)-isoquinoline-3-carbonyl]-amino}-3-methyl-butyric acid |
| 482 | 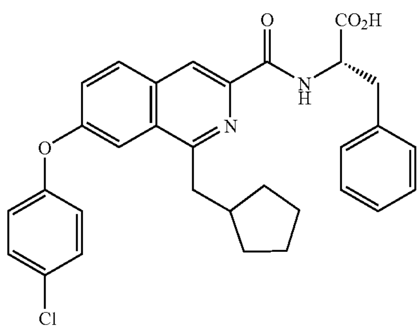 | (2S)-{[7-(4-Chloro-phenoxy)-1-cyclopentylmethyl-isoquinoline-3-carbonyl]-amino}-3-phenyl-propionic acid |
| 483 | 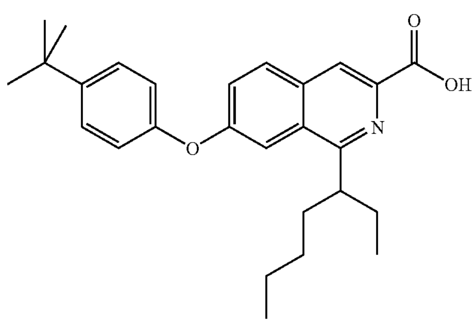 | 7-(4-tert-Butyl-phenoxy)-1-(1-ethyl-pentyl)-isoquinoline-3-carboxylic acid |
| 484 | 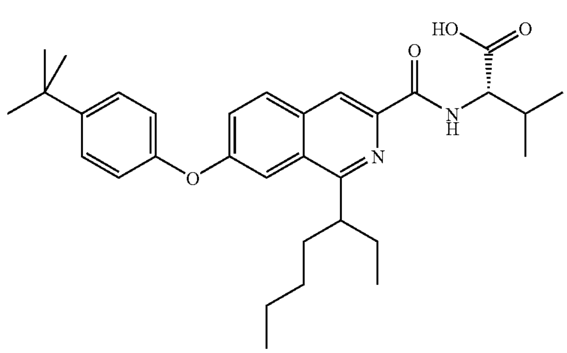 | (2S)-{[7-(4-tert-Butyl-phenoxy)-1-(1-ethyl-pentyl)-isoquinoline-3-carbonyl]-amino}-3-methyl-butyric acid |

TABLE 1-continued

| Example | Structure | Name |
|---|---|---|
| 485 | 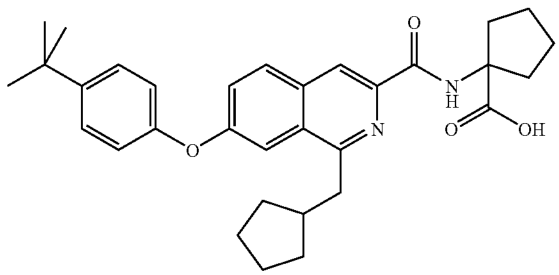 | 1-{[7-(4-tert-Butyl-phenoxy)-1-cyclopentylmethyl-isoquinoline-3-carbonyl]amino}-cyclopentanecarboxylic acid |
| 486 | 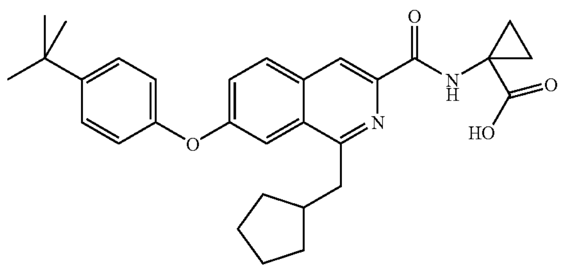 | 1-{[7-(4-tert-Butyl-phenoxy)-1-cyclopentylmethyl-isoquinoline-3-carbonyl]amino}-cyclopropanecarboxylic acid |
| 487 | 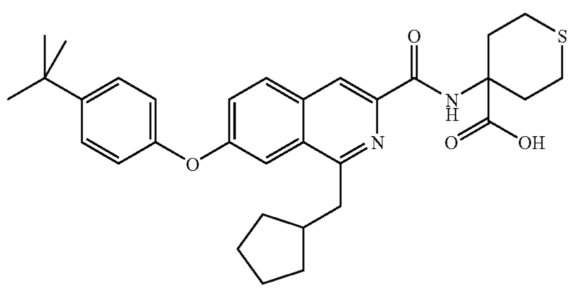 | 4-{[7-(4-tert-Butyl-phenoxy)-1-cyclopentylmethyl-isoquinoline-3-carbonyl]-amino}-tetrahydrothiopyran-4-carboxylic acid |
| 488 | 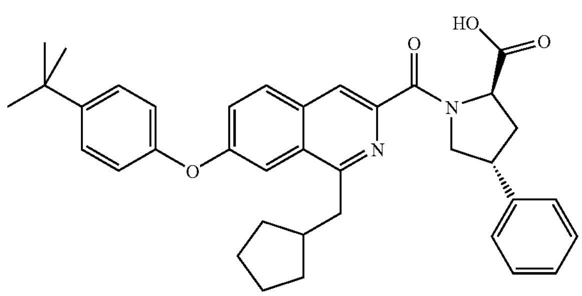 | 1-[7-(4-tert-Butyl-phenoxy)-1-cyclopentylmethyl-isoquinoline-3-carbonyl]-(4S)-phenyl-pyrrolidine-(2S)-carboxylic acid |
| 489 | 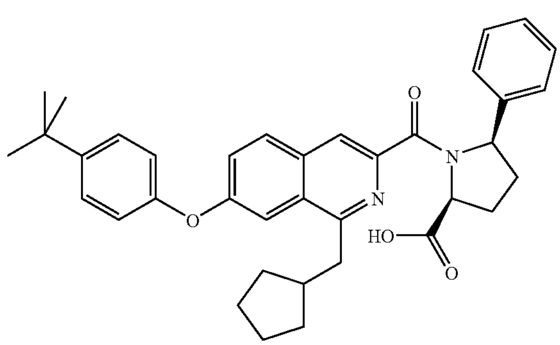 | 1-[7-(4-tert-Butyl-phenoxy)-1-cyclopentylmethyl-isoquinoline-3-carbonyl]-(5R)-phenyl-pyrrolidine-(2S)-carboxylic acid |

TABLE 1-continued

| Example | Structure | Name |
|---|---|---|
| 490 | 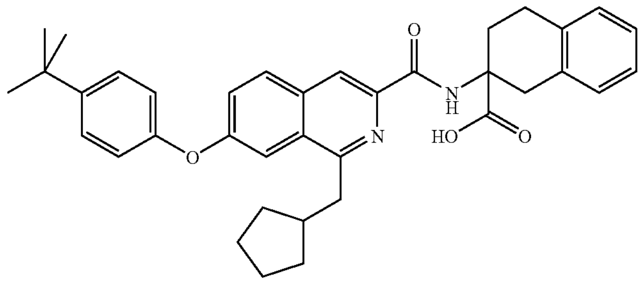 | 2-{[7-(4-tert-Butyl-phenoxy)-1-cyclopentylmethyl-isoquinoline-3-carbonyl]-amino}-1,2,3,4-tetrahydro-naphthalene-2-carboxylic acid |
| 491 | 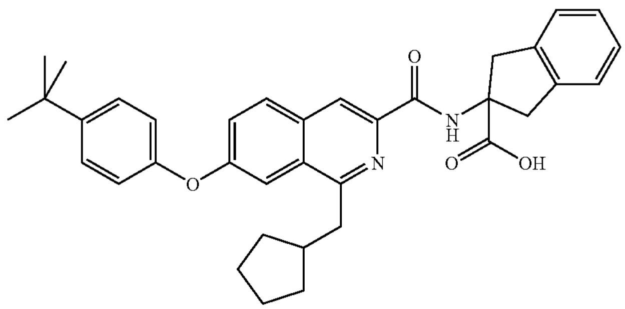 | 2-{[7-(4-tert-Butyl-phenoxy)-1-cyclopentylmethyl-isoquinoline-3-carbonyl]-amino}-indan-2-carboxylic acid |
| 492 | 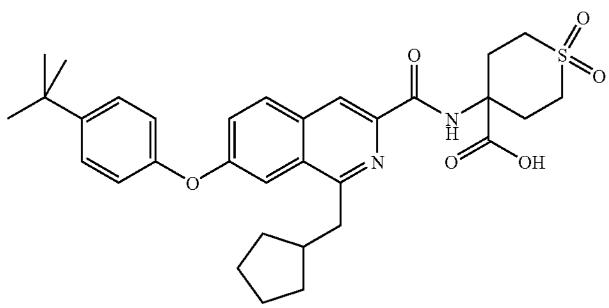 | 4-{[7-(4-tert-Butyl-phenoxy)-1-cyclopentylmethyl-isoquinoline-3-carbonyl]-amino}-1,1-dioxo-tetrahydrothiopyran-4-carboxylic acid |
| 493 | 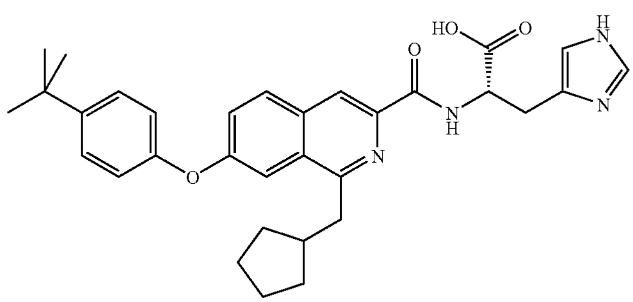 | (2S)-{[7-(4-tert-Butyl-phenoxy)-1-cyclopentylmethyl-isoquinoline-3-carbonyl]-amino}-3-(1H-imidazol-4-yl)-propionic acid |
| 494 | 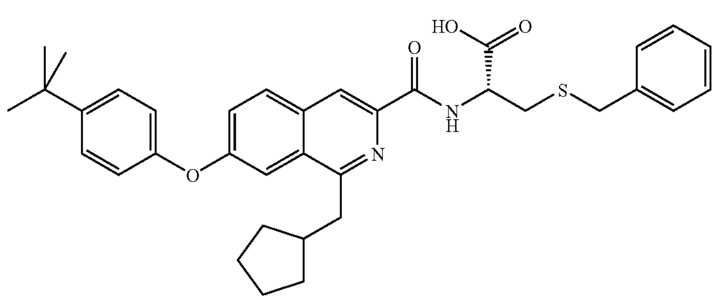 | 3-Benzylsulfanyl-(2S)-{[7-(4-tert-butyl-phenoxy)-1-cyclopentylmethyl-isoquinoline-3-carbonyl]-amino}-propionic acid |

TABLE 1-continued

| Example | Structure | Name |
|---|---|---|
| 495 | 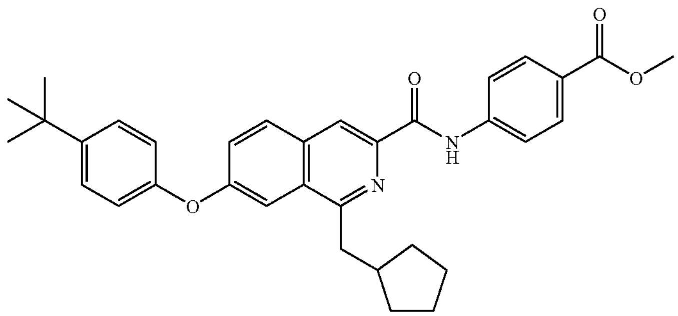 | <4-{[7-(4-tert-Butyl-phenoxy)-1-cyclopentylmethyl-isoquinoline-3-carbonyl]-amino}-benzoic acid methyl ester |
| 496 | 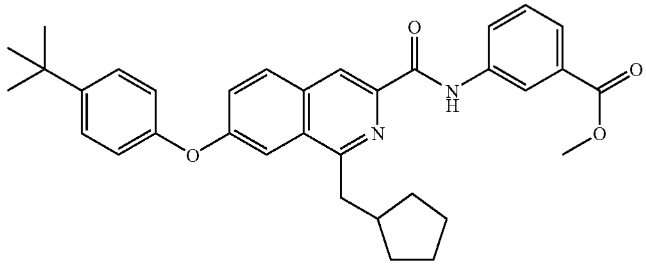 | 3-{[7-(4-tert-Butyl-phenoxy)-1-cyclopentylmethyl-isoquinoline-3-carbonyl]-amino}-benzoic acid methyl ester |
| 497 | 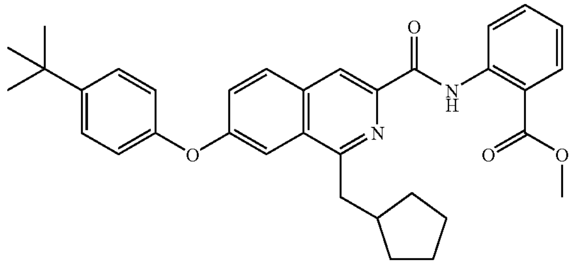 | 2-{[7-(4-tert-Butyl-phenoxy)-1-cyclopentylmethyl-isoquinoline-3-carbonyl]-amino}-benzoic acid methyl ester |
| 498 | 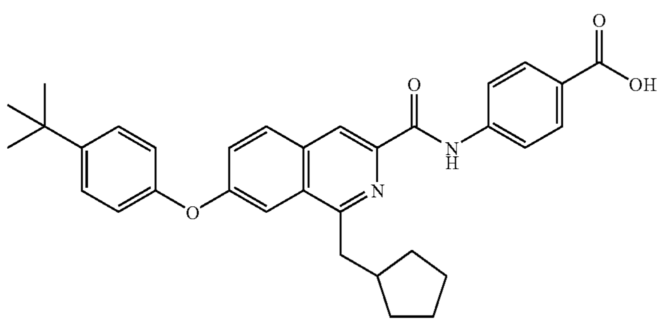 | 4-{[7-(4-tert-Butyl-phenoxy)-1-cyclopentylmethyl-isoquinoline-3-carbonyl]-amino}-benzoic acid |
| 499 | 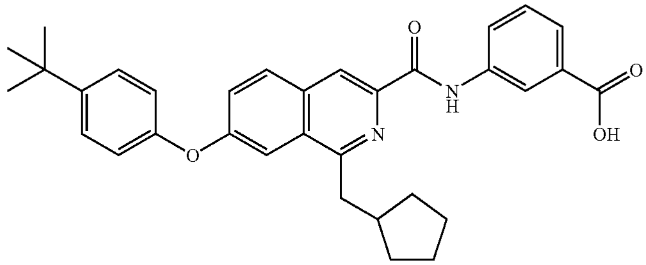 | 3-{[7-(4-tert-Butyl-phenoxy)-1-cyclopentylmethyl-isoquinoline-3-carbonyl]-amino}-benzoic acid |

TABLE 1-continued

| Example | Structure | Name |
|---|---|---|
| 500 | 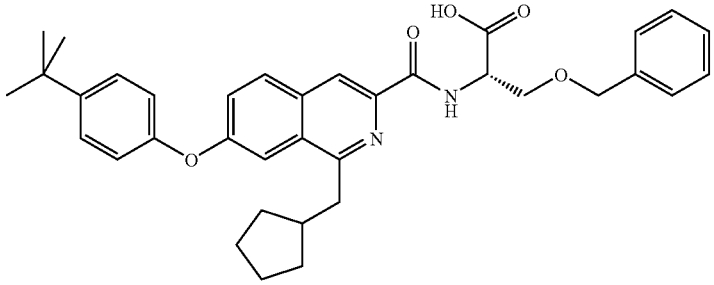 | 3-Benzyloxy-(2S)-{[7-(4-tert-butyl-phenoxy)-1-cyclopentylmethyl-ethyl-isoquinoline-3-carbonyl]-amino}-propionic acid |
| 501 | 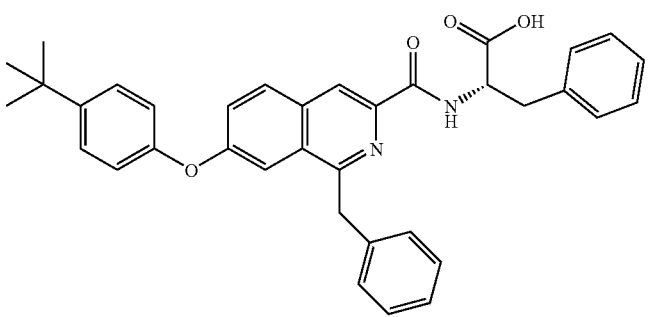 | (2S)-{[1-Benzyl-7-(4-tert-butyl-phenoxy)-isoquinoline-3-carbonyl]-amino}-3-phenyl-propionic acid |
| 502 | 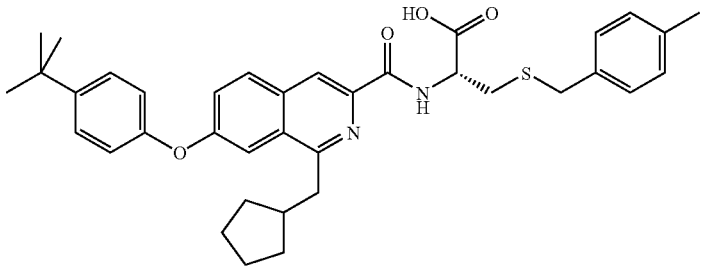 | (2S)-{[7-(4-tert-Butyl-phenoxy)-1-cyclopentylmethyl-isoquinoline-3-carbonyl]amino}-3-(4-methyl-benzylsulfanyl)-propionic acid |
| 503 | 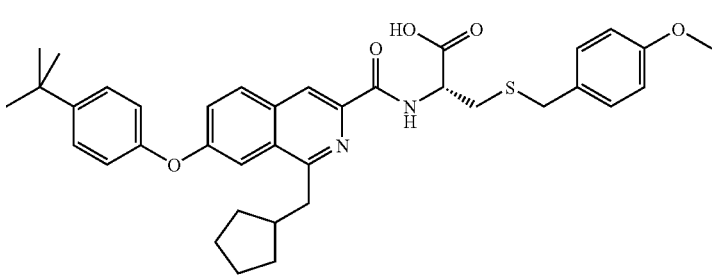 | (2S)-{[7-(4-tert-Butyl-phenoxy)-1-cyclopentylmethyl-isoquinoline-3-carbonyl]amino}-3-(4-methoxy-benzylsulfanyl)-propionic acid |
| 504 | 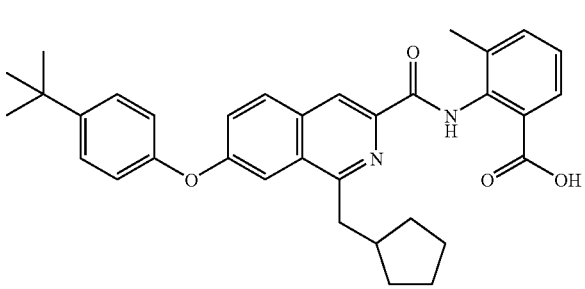 | 2-{[7-(4-tert-Butyl-phenoxy)-1-cyclopentylmethyl-isoquinoline-3-carbonyl]-amino}-3-methyl-benzoic acid |

TABLE 1-continued

| Example | Structure | Name |
|---|---|---|
| 505 | 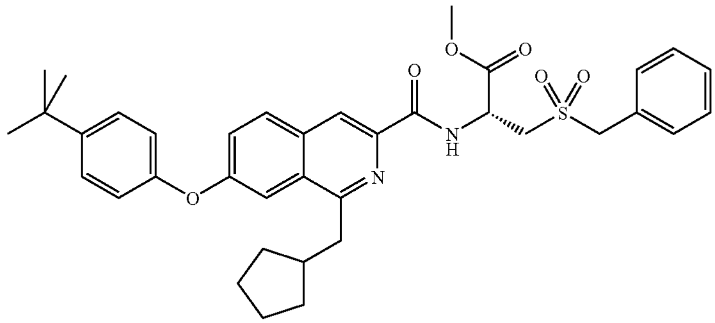 | (2S)-{[7-(4-tert-Butyl-phenoxy)-1-cyclopentylmethyl-isoquinoline-3-carbonyl]-amino}-3-phenylmethanesulfonyl-propionic acid methyl ester |
| 506 | 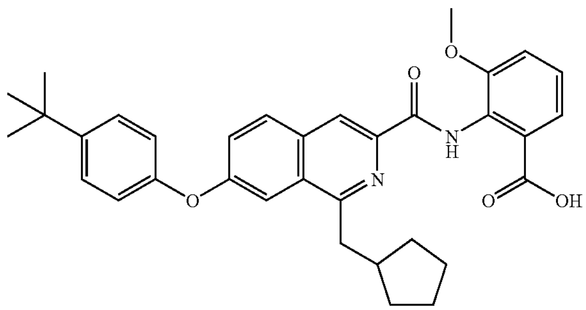 | 2-{[7-(4-tert-Butyl-phenoxy)-1-cyclopentylmethyl-isoquinoline-3-carbonyl]-amino}-3-methoxy-benzoic acid |
| 507 | 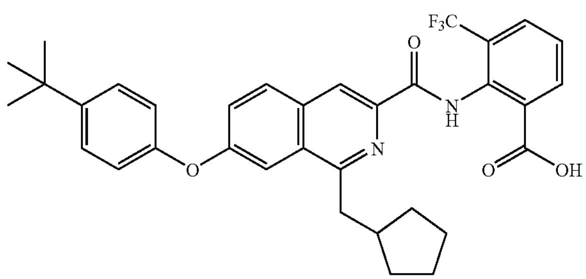 | 2-{[7-(4-tert-Butyl-phenoxy)-1-cyclopentylmethyl-isoquinoline-3-carbonyl]-amino}-3-trifluoromethyl-benzoic acid |
| 508 | 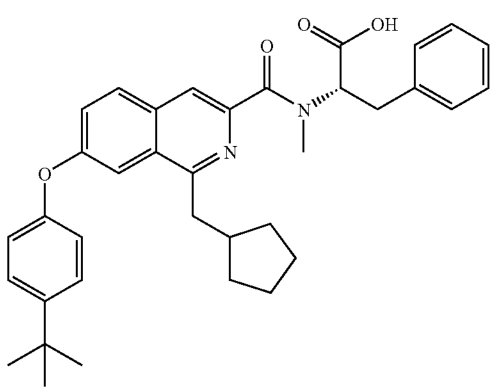 | (2S)-{[7-(4-tert-Butyl-phenoxy)-1-cyclopentylmethyl-isoquinoline-3-carbonyl]-methyl-amino}-3-phenyl-propionic acid |

TABLE 1-continued

| Example | Structure | Name |
|---|---|---|
| 509 | 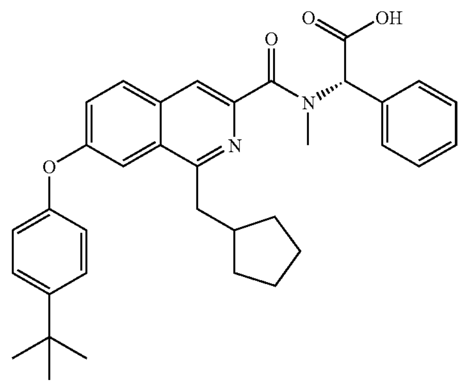 | {[7-(4-tert-Butyl-phenoxy)-(1S)-cyclopentylmethyl-isoquinoline-3-carbonyl]-methyl-amino}-phenyl-acetic acid |
| 510 | 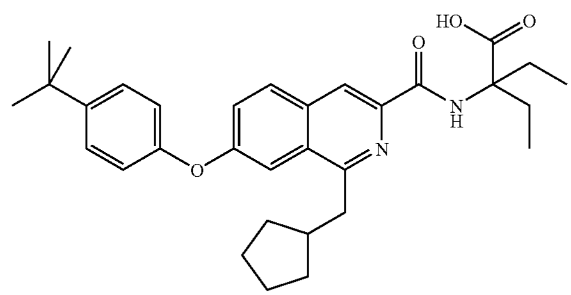 | 2-{[7-(4-tert-Butyl-phenoxy)-1-cyclopentylmethyl-isoquinoline-3-carbonyl]-amino}-2-ethyl-butyric acid |
| 511 | 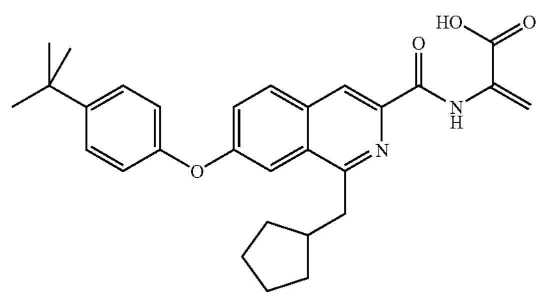 | 2-{[7-(4-tert-Butyl-phenoxy)-1-cyclopentylmethyl-isoquinoline-3-carbonyl]-amino}-acrylic acid |
| 512 | 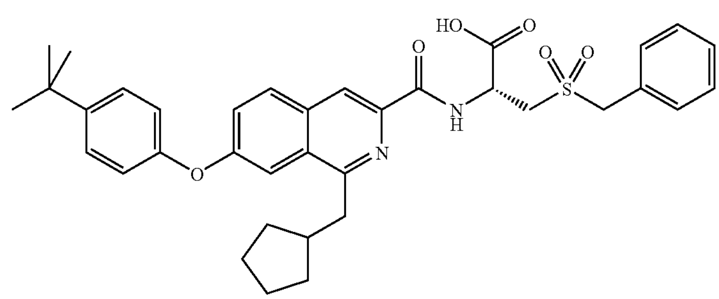 | (2S)-{[7-(4-tert-Butyl-phenoxy)-1-cyclopentylmethyl-isoquinoline-3-carbonyl]amino}-3-phenylmethanesulfonyl-propionic acid |
| 513 | 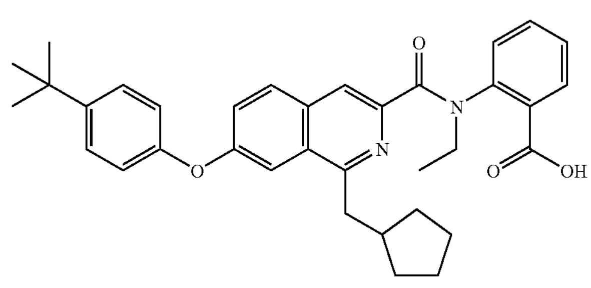 | 2-{[7-(4-tert-Butyl-phenoxy)-1-cyclopentylmethyl-isoquinoline-3-carbonyl]-ethyl-amino}-benzoic acid |

TABLE 1-continued

| Example | Structure | Name |
|---|---|---|
| 514 | 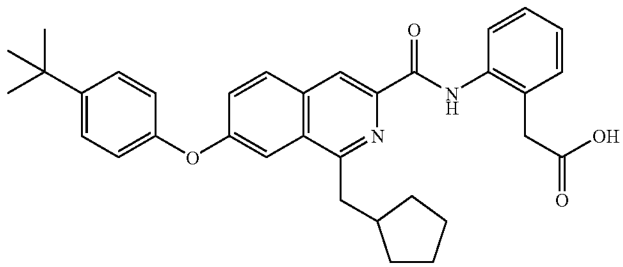 | (2-{[7-(4-tert-Butyl-phenoxy)-1-cyclopentylmethyl-isoquinoline-3-carbonyl]-amino}-phenyl)-acetic acid |
| 515 | 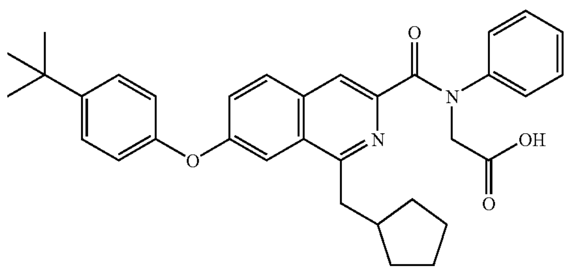 | {[7-(4-tert-Butyl-phenoxy)-1-cyclopentylmethyl-isoquinoline-3-carbonyl]-phenyl-amino}-acetic acid |
| 516 | 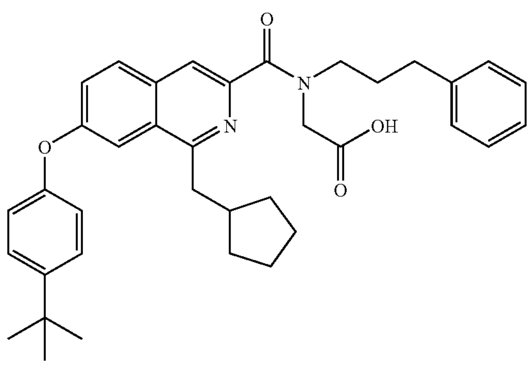 | [[7-(4-tert-Butyl-phenoxy)-1-cyclopentylmethyl-isoquinoline-3-carbonyl]-(3-phenyl-propyl)-amino]-acetic acid |
| 517 | 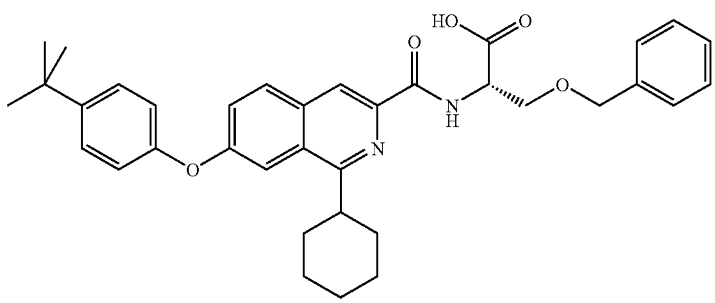 | 3-Benzyloxy-(2S)-{[7-(4-tert-butyl-phenoxy)-1-cyclohexyl-isoquinoline-3-carbonyl]-amino}-propionic acid |
| 518 | 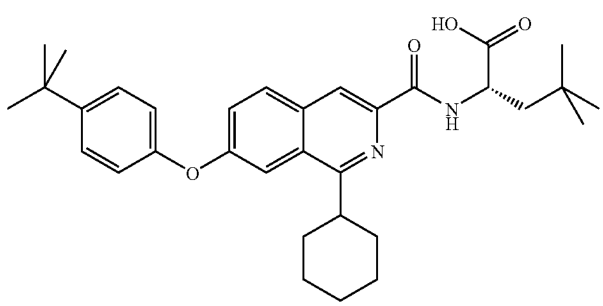 | (2S)-{[7-(4-tert-Butyl-phenoxy)-1-cyclohexyl-isoquinoline-3-carbonyl]-amino]-4,4-dimethyl-pentanoic acid |

TABLE 1-continued

| Example | Structure | Name |
|---|---|---|
| 519 | 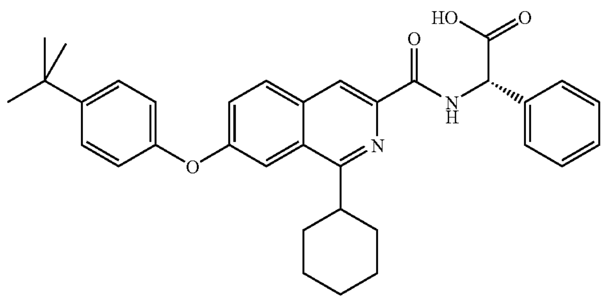 | (2S)-{[7-(4-tert-Butyl-phenoxy)-1-cyclohexyl-isoquinoline-3-carbonyl]-amino}-phenyl-acetic acid |
| 520 | 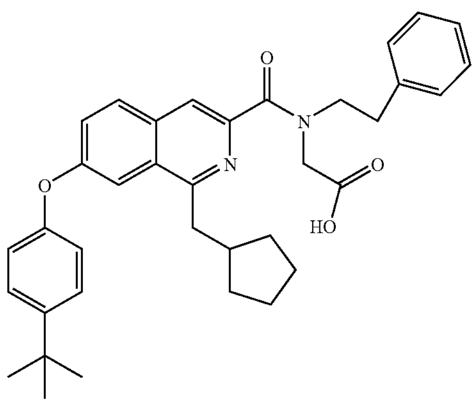 | {[7-(4-tert-Butyl-phenoxy)-1-cyclopentylmethyl-isoquinoline-3-carbonyl]-phenethyl-amino}-acetic acid |
| 521 | 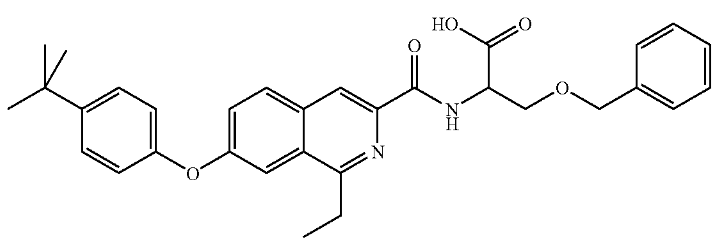 | 3-Benzyloxy-(2S)-{[7-(4-tert-butyl-phenoxy)-1-ethyl-isoquinoline-3-carbonyl]-amino}-propionic acid |
| 522 | 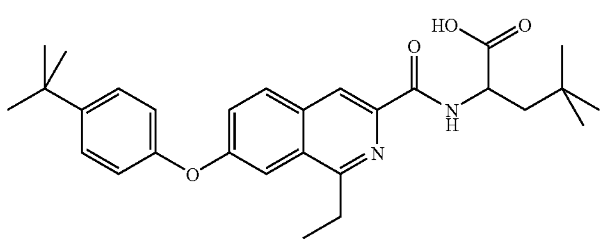 | 2-{[7-(4-tert-Butyl-phenoxy)-1-ethyl-isoquinoline-3-carbonyl]-amino}-4,4-dimethyl-pentanoic acid |
| 523 | 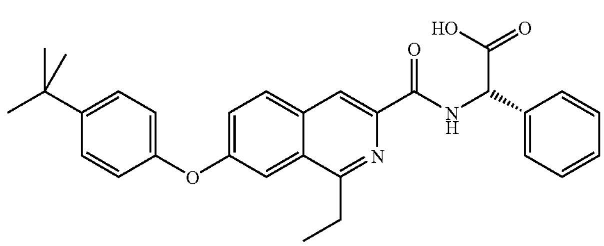 | (2S)-{[7-(4-tert-Butyl-phenoxy)-ethyl-isoquinoline-3-carbonyl]-amino}-phenyl-acetic acid |

TABLE 1-continued

| Example | Structure | Name |
|---|---|---|
| 524 | 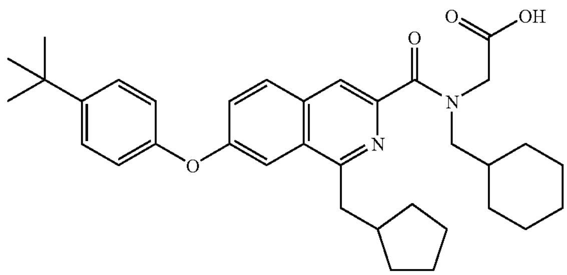 | {[7-(4-tert-Butyl-phenoxy)-1-cyclopentylmethyl-isoquinoline-3-carbonyl]-cyclohexylmethyl-amino}-acetic acid |
| 525 | 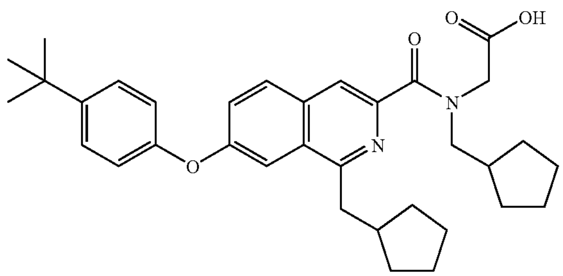 | {[7-(4-tert-Butyl-phenoxy)-1-cyclopentylmethyl-isoquinoline-3-carbonyl]-cyclopentylmethyl-amino}-acetic acid |
| 526 | 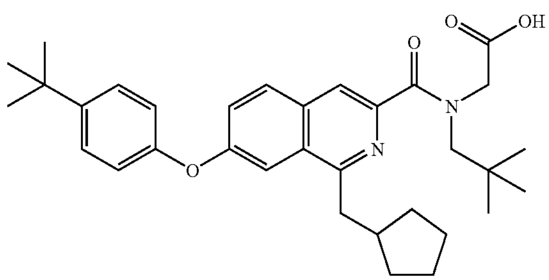 | [[7-(4-tert-Butyl-phenoxy)-1-cyclopentylmethyl-isoquinoline-3-carbonyl]-(2,2-dimethyl-propyl)-amino]-acetic acid |
| 527 | 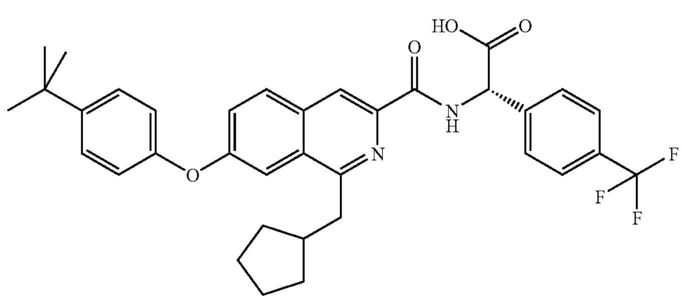 | (2S)-{[7-(4-tert-Butyl-phenoxy)-1-cyclopentylmethyl-isoquinoline-3-carbonyl]-amino}-(4-trifluoromethyl-phenyl)-acetic acid |
| 528 | 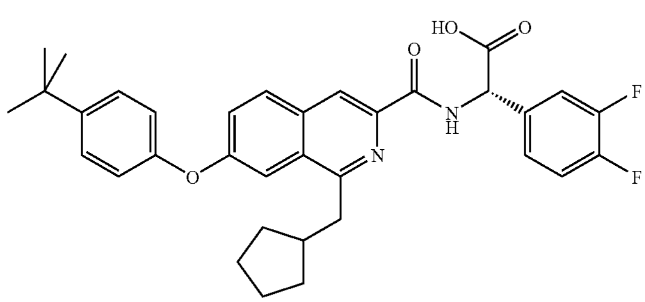 | (2S)-{[7-(4-tert-Butyl-phenoxy)-1-cyclopentylmethyl-isoquinoline-3-carbonyl]-amino}-(3,4-difluoro-phenyl)-acetic acid |

TABLE 1-continued

| Example | Structure | Name |
|---|---|---|
| 529 | 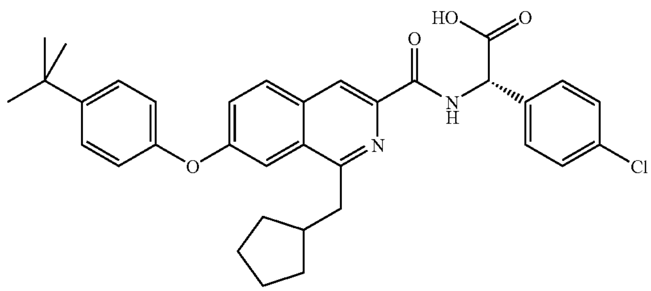 | (2S)-{[7-(4-tert-Butyl-phe-noxy)-1-cyclopentylmethyl-isoquino-line-3-carbonyl]-amino}-(4-chloro-phenyl)-acetic acid |
| 530 | 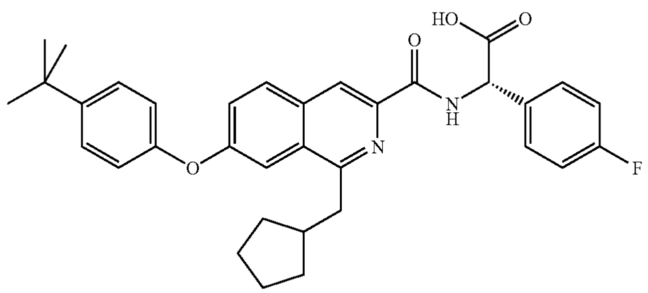 | (2S)-{[7-(4-tert-Butyl-phe-noxy)-1-cyclopentylmethyl-isoquino-line-3-carbonyl]-amino}-(4-fluoro-phenyl)-acetic acid |
| 531 | 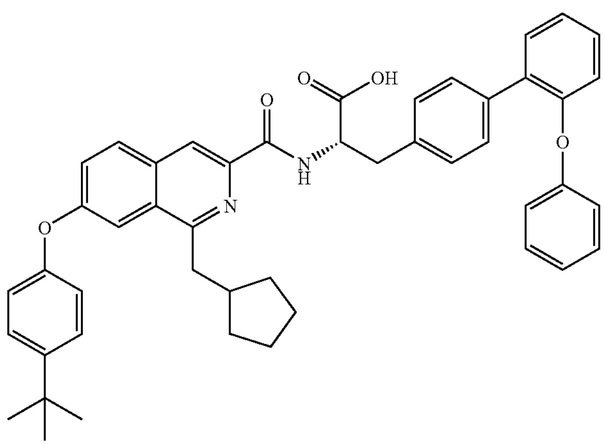 | (2S)-{[7-(4-tert-Butyl-phe-noxy)-1-cyclopentylmethyl-isoquino-line-3-carbonyl]-amino}-3-(2'-phe-noxy-biphenyl-4-yl)-propionic acid |
| 532 | 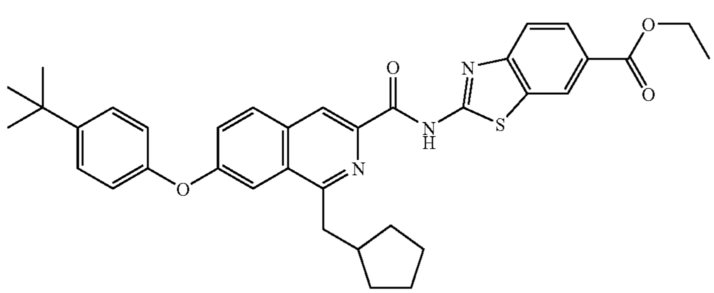 | 2-{[7-(4-tert-Butyl-phenoxy)-1-cyclopentylmethyl-isoquino-line-3-carbonyl]-amino}-benzothia-zole-6-carboxylic acid ethyl ester |

TABLE 1-continued

| Example | Structure | Name |
|---|---|---|
| 533 | 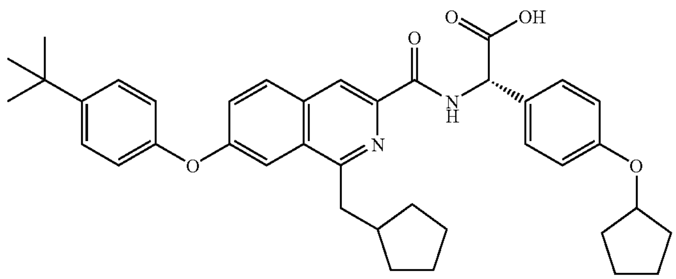 | (2S)-{[7-(4-tert-Butyl-phenoxy)-1-cyclopentylmethyl-isoquinoline-3-carbonyl]-amino}-(4-cyclopentyloxy-phenyl)-acetic acid |
| 534 | 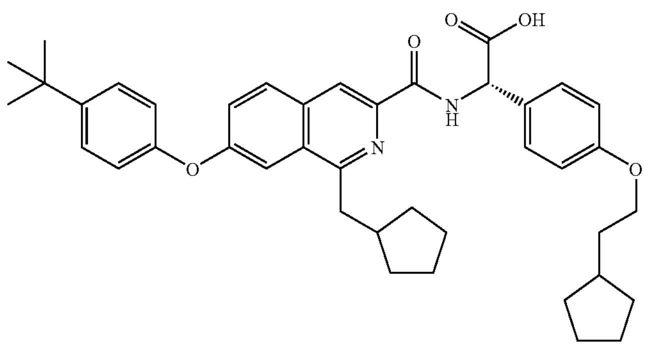 | (2S)-{[7-(4-tert-Butyl-phenoxy)-1-cyclopentylmethyl-isoquinoline-3-carbonyl]-amino}-[4-(2-cyclopentyl-ethoxy)-phenyl]-acetic acid |
| 535 | 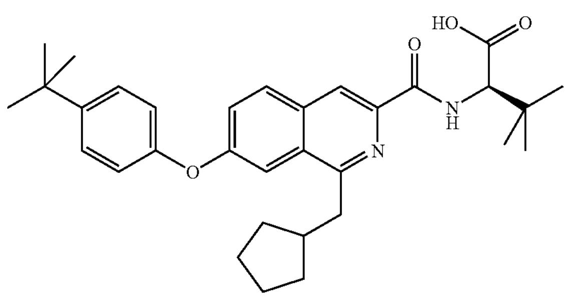 | (2R)-{[7-(4-tert-Butyl-phenoxy)-1-cyclopentylmethyl-isoquinoline-3-carbonyl]-amino}-3,3-dimethyl-butyric acid |
| 536 | 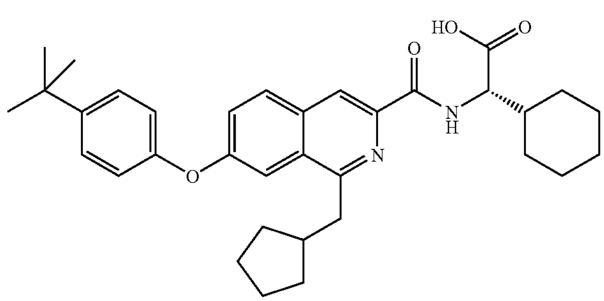 | (2S)-{[7-(4-tert-Butyl-phenoxy)-1-cyclopentylmethyl-isoquinoline-3-carbonyl]-amino}-cyclohexyl-acetic acid |

TABLE 1-continued

| Example | Structure | Name |
|---|---|---|
| 537 | 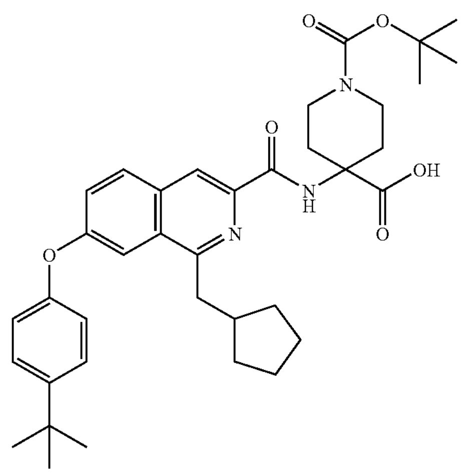 | 4-{[7-(4-tert-Butyl-phenoxy)-1-cyclopentylmethyl-isoquinoline-3-carbonyl]-amino}-piperidine-1,4-dicarboxylic acid mono-tert-butyl ester |
| 538 | 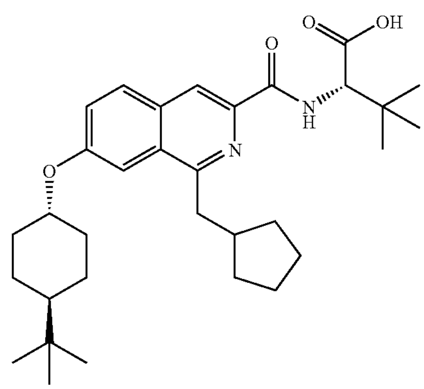 | (2S)-{[7-(4-tert-Butyl-cyclohexyloxy)-1-cyclopentylmethyl-isoquinoline-3-carbonyl]-amino}-3,3-dimethyl-butyric acid |
| 539 | 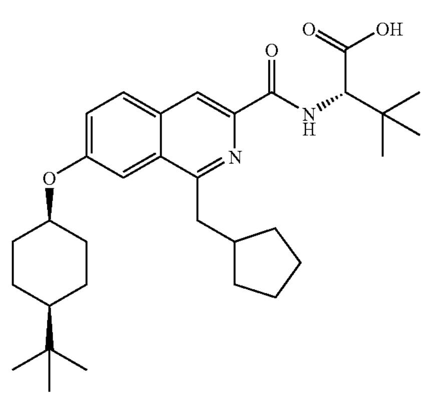 | (2S)-{[7-(4-tert-Butyl-cyclohexyloxy)-1-cyclopentylmethyl-isoquinoline-3-carbonyl]-amino}-3,3-dimethyl-butyric acid |

TABLE 1-continued

| Example | Structure | Name |
|---|---|---|
| 540 | 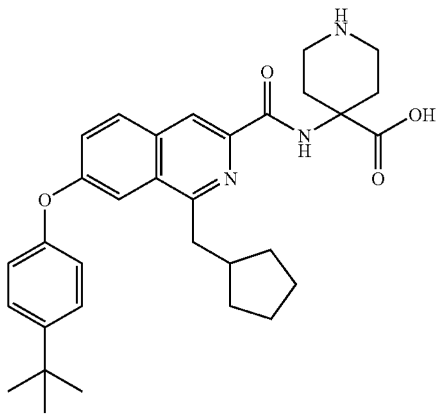 | 4-{[7-(4-tert-Butyl-phenoxy)-1-cyclopentylmethyl-isoquinoline-3-carbonyl]-amino}-piperidine-4-carboxylic acid |
| 541 | 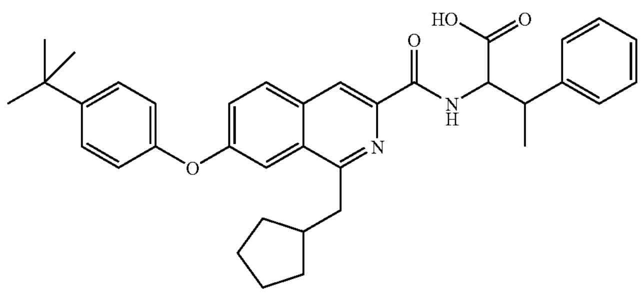 | 2-{[7-(4-tert-Butyl-phenoxy)-1-cyclopentylmethyl-isoquinoline-3-carbonyl]-amino}-3-phenyl-butyric acid |
| 542 | 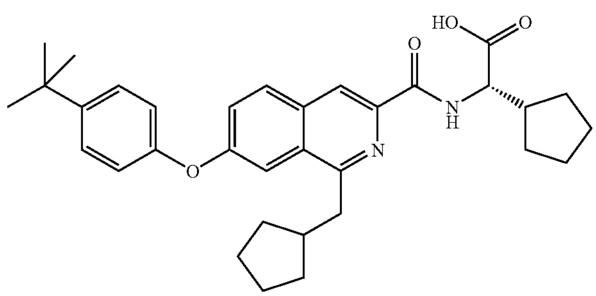 | (2S)-{[7-(4-tert-Butyl-phenoxy)-1-cyclopentylmethyl-isoquinoline-3-carbonyl]-amino}-cyclopentyl-acetic acid |
| 543 | 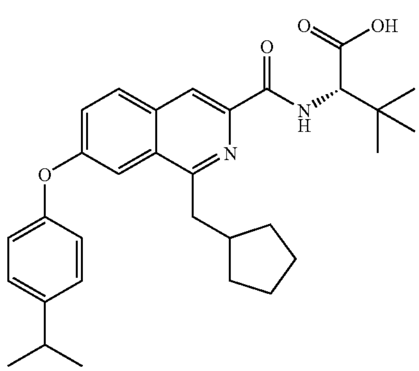 | (2S)-{[1-Cyclopentylmethyl-7-(4-isopropyl-phenoxy)-isoquinoline-3-carbonyl]-amino}-3,3-dimethyl-butyric acetic |

TABLE 1-continued

| Example | Structure | Name |
|---|---|---|
| 544 | 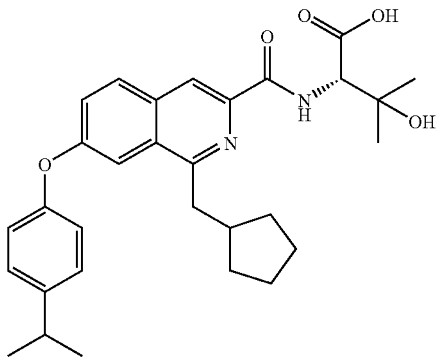 | (2S)-{[7-(4-tert-Butyl-phenoxy)-1-cyclopentylmethyl-isoquinoline-3-carbonyl]-amino}-3-hydroxy-3-methyl-butyric acid |
| 545 | 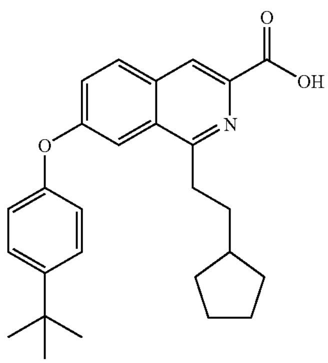 | 7-(4-tert-Butyl-phenoxy)-1-(2-cyclopentyl-ethyl)-isoquinoline-3-carboxylic acid |
| 546 | 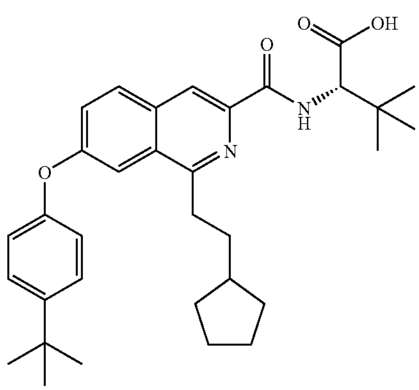 | (2S)-{[7-(4-tert-Butyl-phenoxy)-1-(2-cyclopentyl-ethyl)-isoquinoline-3-carbonyl]amino}-3,3-dimethyl-butyric acid |
| 547 | 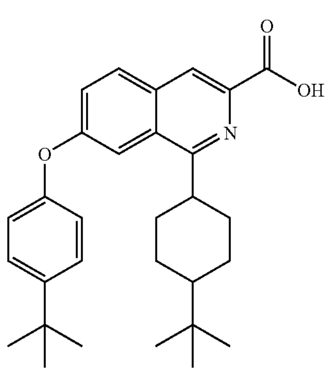 | 1-(4-tert-Butyl-cyclohexyl)-7-(4-tert-butyl-phenoxy)-isoquinoline-3-carboxylic acid |

TABLE 1-continued

| Example | Structure | Name |
|---|---|---|
| 548 | 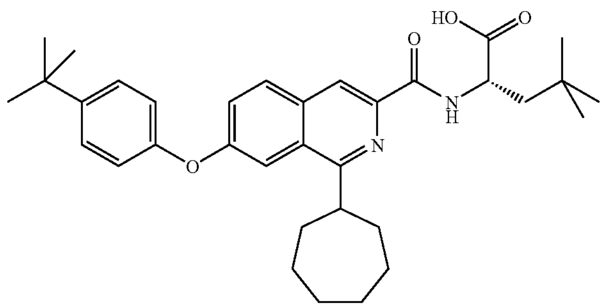 | (2S)-{[7-(4-tert-Butyl-phe-noxy)-1-cycloheptyl-isoquinoline-3-carbonyl]-amino}-4,4-dimethyl-pentanoic acid |
| 549 | 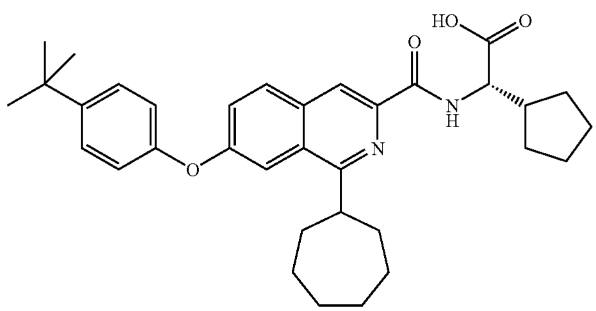 | (2S)-{[7-(4-tert-Butyl-phe-noxy)-1-cycloheptyl-isoquinoline-3-carbonyl]-amino}-cyclopentyl-acetic acid |
| 550 | 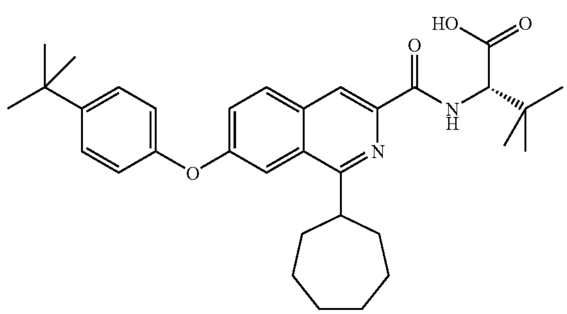 | (2S)-{[7-(4-tert-Butyl-phe-noxy)-1-cycloheptyl-isoquinoline-3-carbonyl]-amino}-3,3-dimethyl-butyric acid |
| 551 | 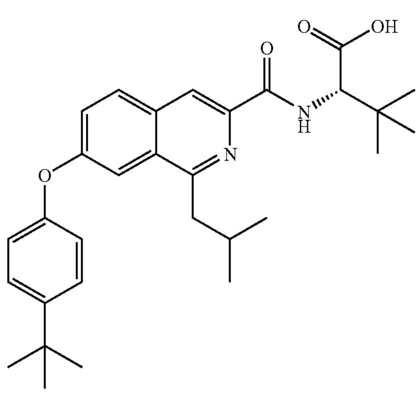 | (2S)-{[7-(4-tert-Butyl-phe-noxy)-1-cycloheptyl-isoquinoline-3-carbonyl]-amino}-3,3-dimethyl-butyric acid |

TABLE 1-continued

| Example | Structure | Name |
|---|---|---|
| 552 | 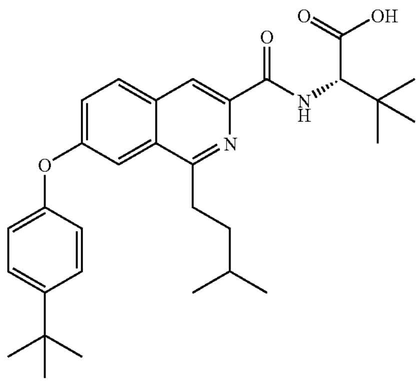 | (2S)-{[7-(4-tert-Butyl-phenoxy)-1-(3-methyl-butyl)-isoquinoline-3-carbonyl]-amino}-3,3-dimethyl-butyric acid |
| 553 | 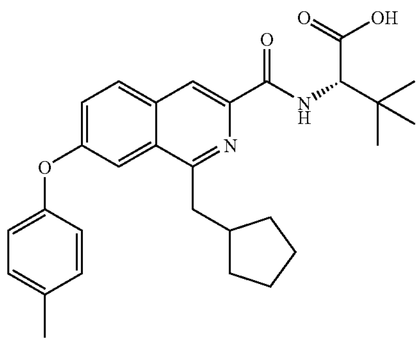 | (2S)-[(1-Cyclopentylmethyl-7-p-tolyloxy-isoquinoline-3-carbonyl)-amino]-3,3-dimethyl-butyric acid |
| 554 | 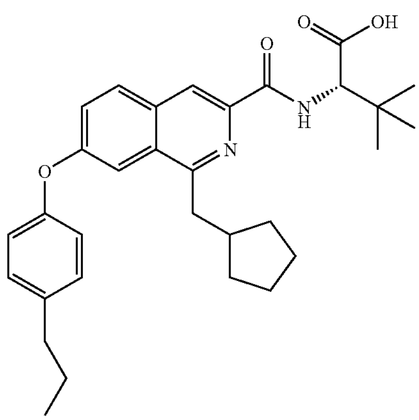 | (2S)-{[1-Cyclopentylmethyl-7-(4-propyl-phenoxy)-isoquinoline-3-carbonyl]amino}-3,3-dimethyl-butyric acid |
| 555 | 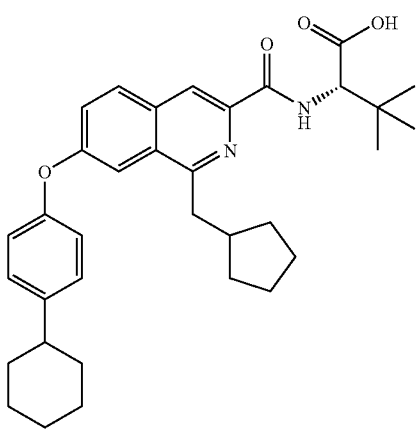 | (2S)-{[7-(4-Cyclohexyl-phenoxy)-1-cyclopentylmethyl-isoquinoline-3-carbonyl]-amino)-3,3-dimethyl-butyric acid |

TABLE 1-continued

| Example | Structure | Name |
|---|---|---|
| 556 | 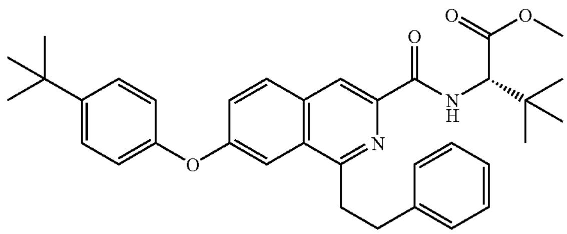 | (2S)-{[7-(4-tert-Butyl-phenoxy)-1-phenethyl-isoquinoline-3-carbonyl]-amino}-3,3-dimethyl-butyric acid methyl ester |
| 557 | 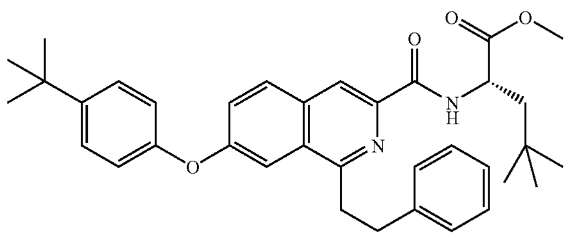 | (2S)-{[7-(4-tert-Butyl-phenoxy)-1-phenethyl-isoquinoline-3-arbonyl]-amino}-4,4-dimethyl-pentanoic acid methyl ester |
| 558 | 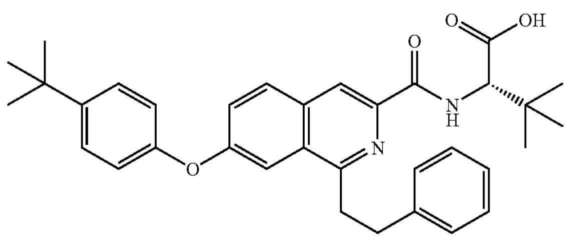 | (2S)-{[7-(4-tert-Butyl-phenoxy)-1-phenethyl-isoquinoline-3-arbonyl]-amino}-3,3-dimethyl-butyric acid |
| 559 | 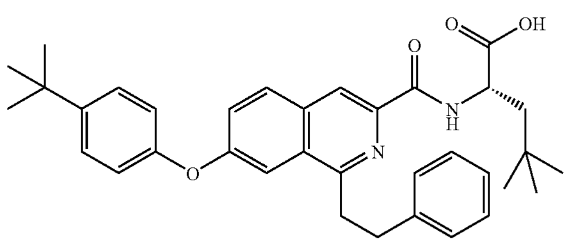 | (2S)-{[7-(4-tert-Butyl-phenoxy)-1-phenethyl-isoquinoline-3-arbonyl]-amino}-4,4-dimethyl-pentanoic acid |
| 560 | 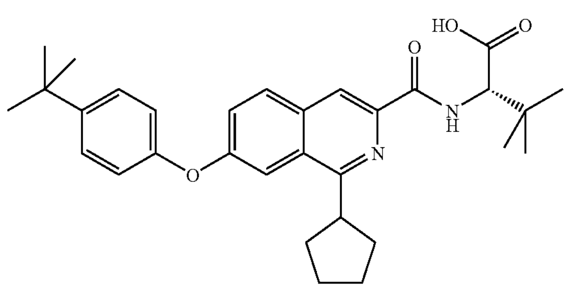 | (2S)-{[7-(4-tert-Butyl-phenoxy)-1-cyclopentyl-isoquinoline-3-carbonyl]-amino}-3,3-dimethyl-butyric acid |
| 561 | 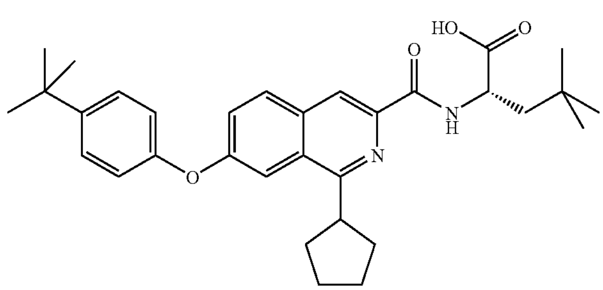 | (2S)-{[7-(4-tert-Butyl-phenoxy)-1-cyclopentyl-isoquinoline-3-carbonyl]-amino}-4,4-dimethyl-pentanoic acid |

TABLE 1-continued

| Example | Structure | Name |
|---|---|---|
| 562 | 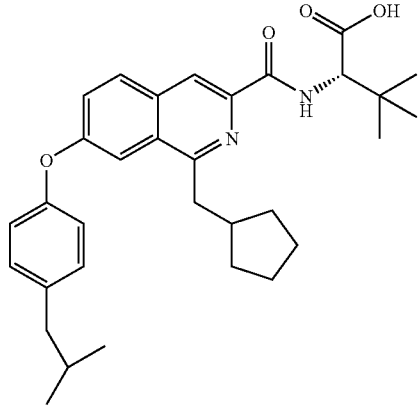 | (2S)-{[1-Cyclopentylmethyl-7-(4-isobutyl-phenoxy)-isoquinoline-3-carbonyl]-amino}-3,3-dimethyl-butyric acid |
| 563 | 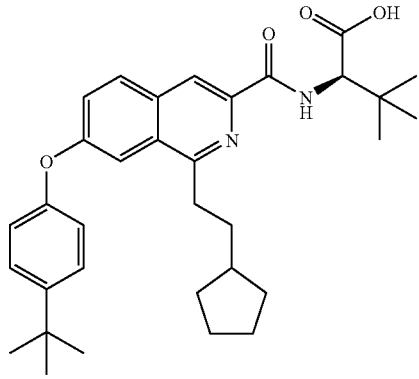 | (2R)-{[7-(4-tert-Butyl-phenoxy)-1-(2-cyclopentyl-ethyl)-isoquinoline-3-carbonyl]-amino}-3,3-dimethyl-butyric acid |
| 564 | 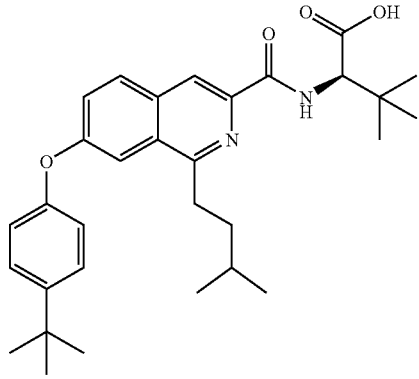 | (2R)-{[7-(4-tert-Butyl-phenoxy)-1-(3-methyl-butyl)-isoquinoline-3-carbonyl]-amino}-3,3-dimethyl-butyric acid |
| 565 | 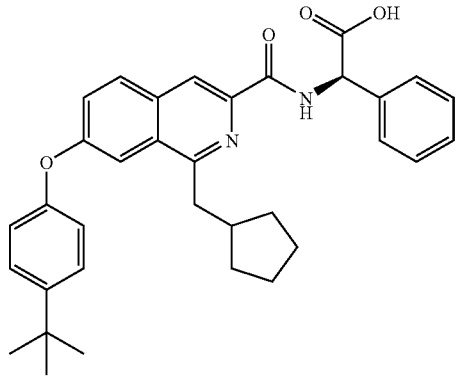 | (2R)-{[7-(4-tert-Butyl-phenoxy)-1-cyclopentylmethyl-isoquinoline-3-carbonyl]-amino}-phenyl-acetic acid |

TABLE 1-continued

| Example | Name |
|---|---|
| 566 | (2R)-{[7-(4-tert-Butyl-phenoxy)-1-cyclopentylmethyl-isoquinoline-3-carbonyl]-amino}-cyclopentyl-acetic acid |
| 567 | (2R)-{[7-(trans-4-tert-Butyl-cyclohexyloxy)-1-cyclopentylmethyl-isoquinoline-3-carbonyl]-amino}-cyclopentyl-acetic acid |
| 568 | (2R)-{[7-(trans-4-tert-Butyl-cyclohexyloxy)-1-cyclopentylmethyl-isoquinoline-3-carbonyl]-amino}-3-thiophen-3-yl-propionic acid |
| 569 | (2R)-{[7-(trans-4-tert-Butyl-cyclohexyloxy)-1-cyclopentylmethyl-isoquinoline-3-carbonyl]-amino}-phenyl-acetic acid |

TABLE 1-continued

| Example | Structure | Name |
|---|---|---|
| 570 | 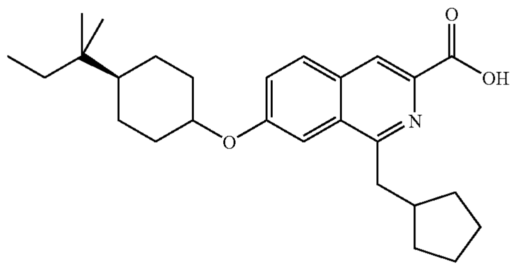 | 1-Cyclopentylmethyl-7-[4-(1,1-dimethyl-propyl)-trans-cyclo-hexyloxy]-isoquinoline-3-carboxylic acid |
| 571 | 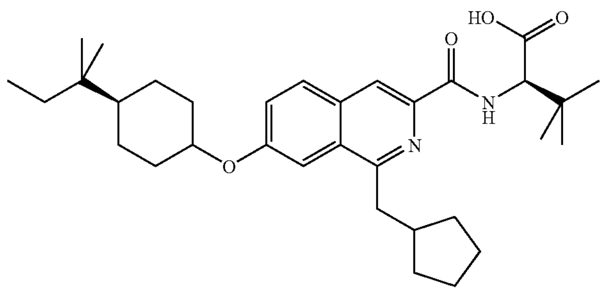 | (2R)-({1-Cyclopentylmethyl-7-[4-(1,1-dimethyl-propyl)-trans-cyclo-hexyloxy]-isoquinoline-3-carbonyl}-amino)-3,3-dimethyl-butyric acid |
| 572 | 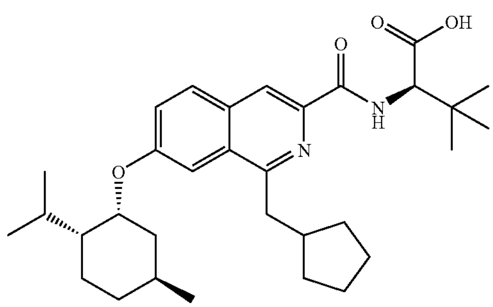 | (2R)-{[1-Cyclopentylmethyl-7-((2S)-isopropyl-(5R)-methyl-(1R)-cyclohexyloxy)-isoquinoline-3-carbonyl]-amino}-3,3-dimethyl-butyric acid |
| 573 | 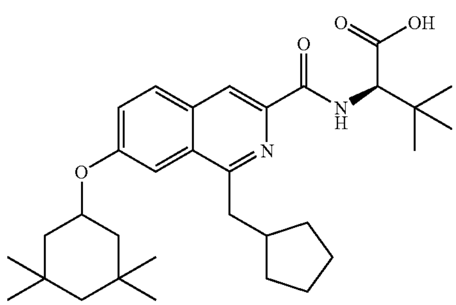 | (2R)-{[1-Cyclopentylmethyl-7-(3,3,5,5-tetramethyl-cyclohexyloxy)-isoquinoline-3-carbonyl]-amino}-3,3-dimethyl-butyric acid |
| 574 | 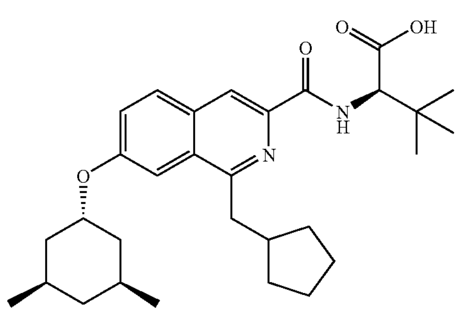 | (2R)-{[1-Cyclopentylmethyl-7-(cis, cis, trans 3,5-dimethyl-cyclohexyloxy)-isoquinoline-3-carbonyl]-amino}-3,3-dimethyl-butyric acid |

TABLE 1-continued

| Example | Structure | Name |
|---|---|---|
| 575 | 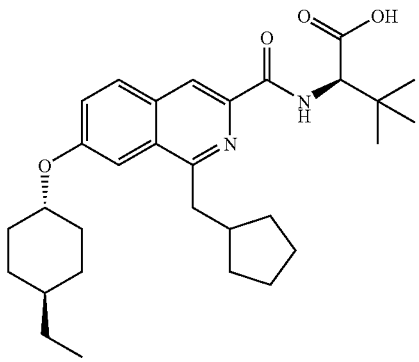 | (2R)-{[1-Cyclopentylmethyl-7-(trans-4-ethyl-cyclohexyloxy)-isoquinoline-3-carbonyl]-amino}-3,3-dimethyl-butyric acid |
| 576 | 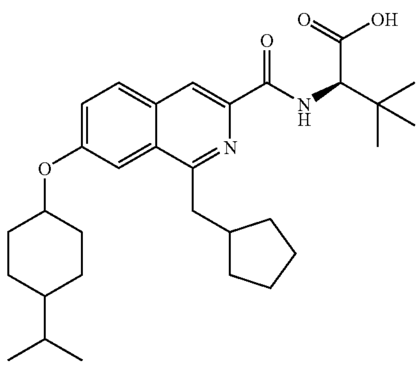 | (2R)-{[1-Cyclopentylmethyl-7-(4-isopropyl-cyclohexyloxy)-isoquinoline-3-carbonyl]-amino}-3,3-dimethyl-butyric acid |
| 577 | 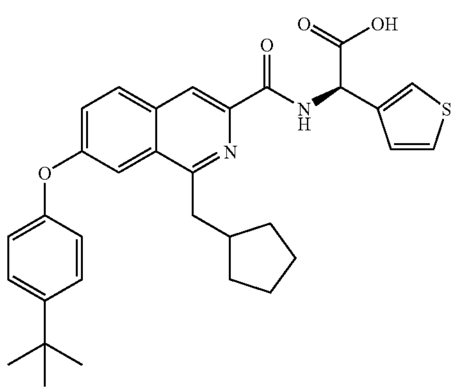 | (2R)-{[7-(4-tert-Butyl-phenoxy)-1-cyclopentylmethyl-isoquinoline-3-carbonyl]-amino}-thiophen-3-yl-acetic acid |
| 578 | 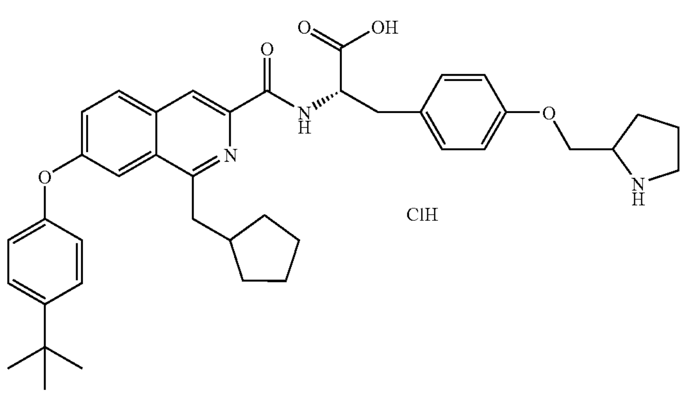 | (2S)-{[7-(4-tert-Butyl-phenoxy)-1-cyclopentylmethyl-isoquinoline-3-carbonyl]-amino}-3-[4-(pyrrolidin-2-ylmethoxy)-phenyl]-propionic acid |

TABLE 1-continued

| Example | Structure | Name |
|---|---|---|
| 579 | 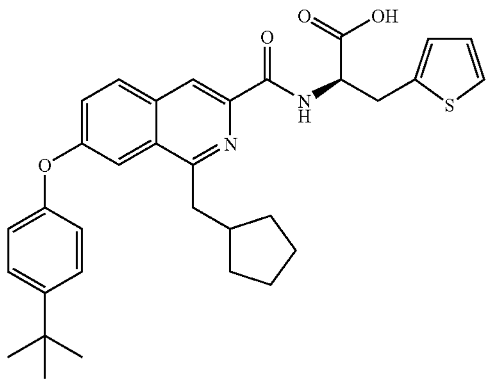 | (2R)-{[7-(4-tert-Butyl-phenoxy)-1-cyclopentylmethyl-isoquinoline-3-carbonyl]-amino}-3-thiophen-2-yl-propionic acid |
| 580 | 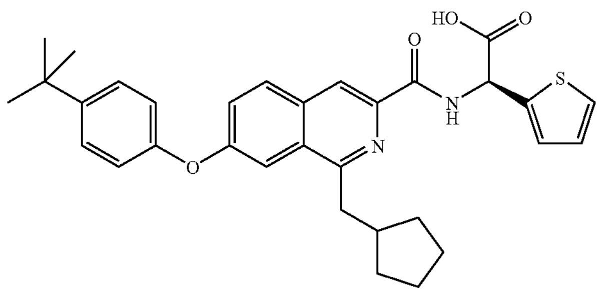 | (2R)-[7-(4-tert-Butyl-phenoxy)-1-cyclopentylmethyl-isoquinoline-3-carbonyl]-amino}-thiophen-2-yl-acetic acid |
| 581 | 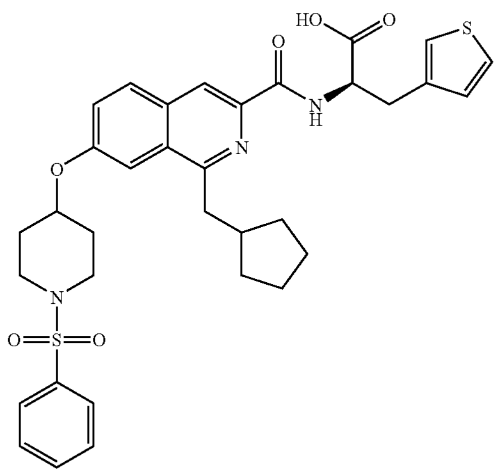 | (2R)-{[7-(1-Benzenesulfonyl-piperidin-4-yloxy)-1-cyclopentylmethyl-isoquinoline-3-carbonyl]-amino}-3-thiophen-3-yl-propionic acid |
| 582 | 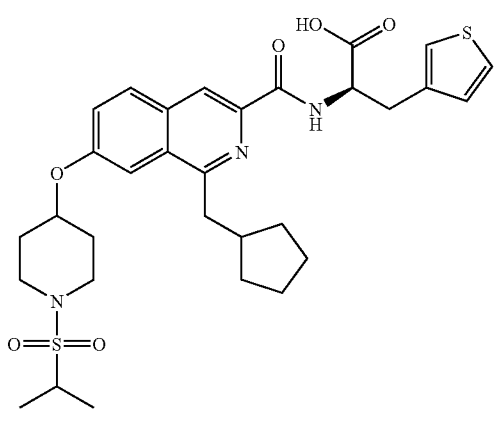 | (2R)-({1-Cyclopentylmethyl-7-[1-(propane-2-sulfonyl)-piperidin-4-yloxy]-isoquinoline-3-carbonyl}-amino)-3-thiophen-3-yl-propionic acid |

TABLE 1-continued

| Example | Structure | Name |
|---|---|---|
| 583 | 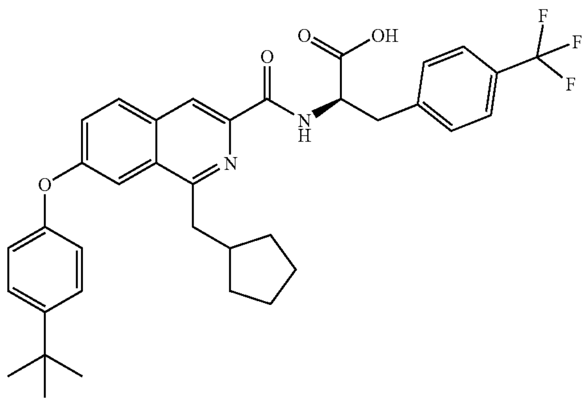 | (2R)-{[7-(4-tert-Butyl-phenoxy)-1-cyclopentylmethyl-isoquinoline-3-carbonyl]-amino}-3-(4-trifluoromethyl-phenyl)-propionic acid |
| 584 | 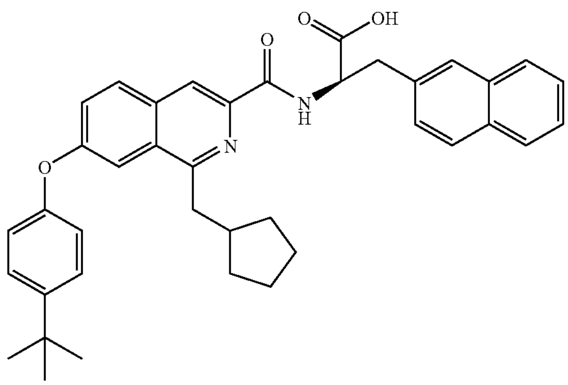 | (2R)-{[7-(4-tert-Butyl-phenoxy)-1-cyclopentylmethyl-isoquinoline-3-carbonyl]-amino}-3-naphthalen-2-yl-propionic acid |
| 585 | 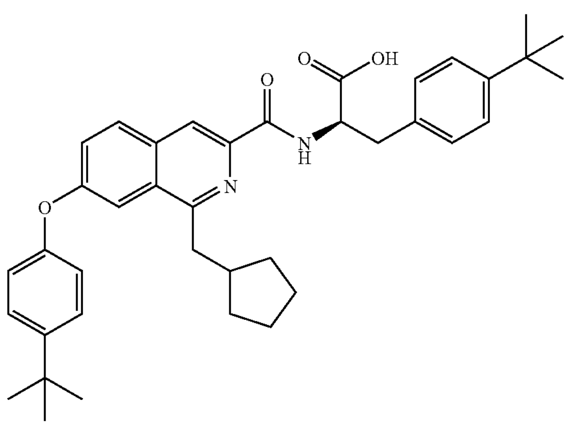 | (2R)-{[7-(4-tert-Butyl-phenoxy)-1-cyclopentylmethyl-isoquinoline-3-carbonyl]-amino}-3-(4-tert-butyl-phenyl)-propionic acid |
| 586 | 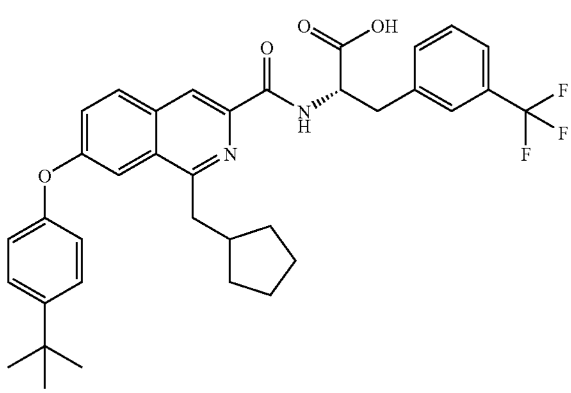 | (2S)-{[7-(4-tert-Butyl-phenoxy)-1-cyclopentylmethyl-isoquinoline-3-carbonyl]-amino}-3-(3-trifluoromethyl-phenyl)-propionic acid |

TABLE 1-continued

| Example | Structure | Name |
|---|---|---|
| 587 | 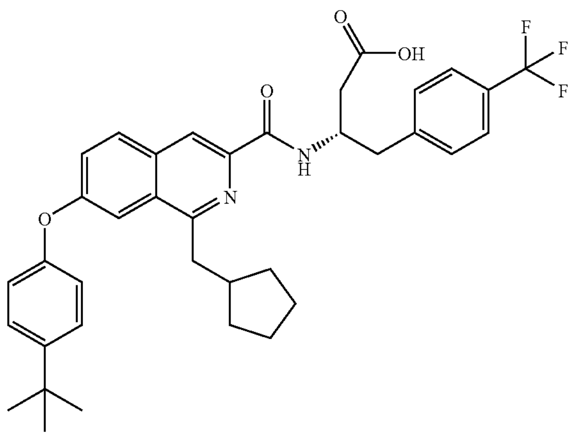 | (3S)-{[7-(4-tert-Butyl-phenoxy)-1-cyclopentylmethyl-isoquinoline-3-carbonyl]-amino}-4-(4-trifluoromethyl-phenyl)-butyric acid |
| 588 | 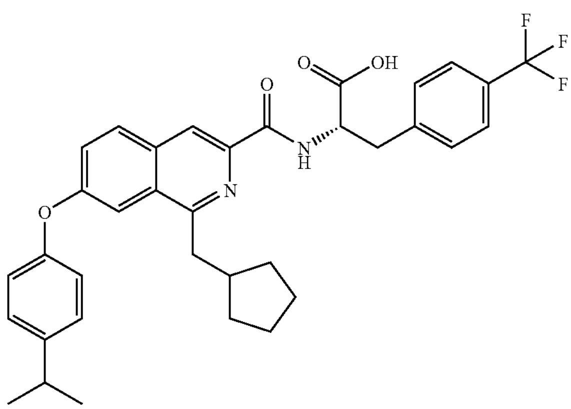 | (2S)-{[1-Cyclopentylmethyl-7-(4-isopropyl-phenoxy)-isoquinoline-3-carbonyl]-amino}-3-(4-trifluoromethyl-phenyl)-propionic acid |
| 589 | 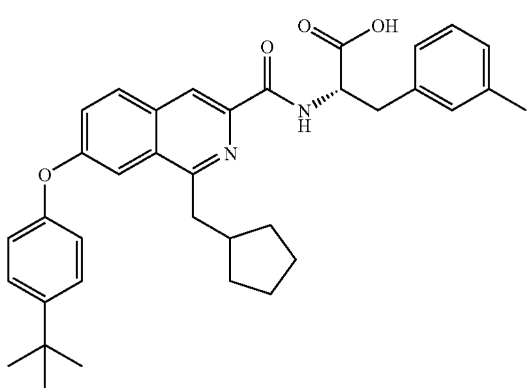 | (2S)-{[7-(4-tert-Butyl-phenoxy)-1-cyclopentylmethyl-isoquinoline-3-carbonyl]-amino}-3-m-tolyl-propionic acid |

TABLE 1-continued

| Example | Structure | Name |
| --- | --- | --- |
| 590 | 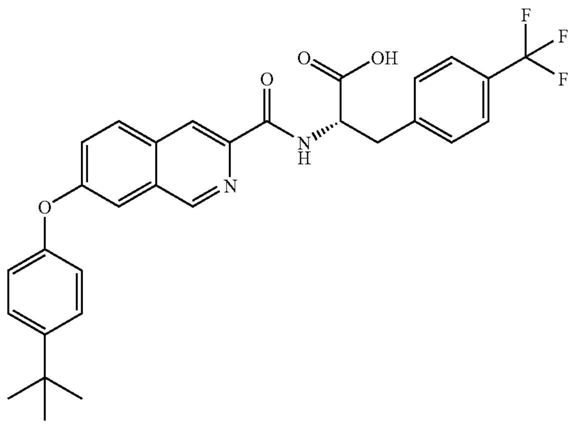 | (2S)-{[7-(4-tert-Butyl-phenoxy)-isoquinoline-3-carbonyl]-amino}-3-(4-trifluoromethyl-phenyl)-propionic acid |
| 591 | 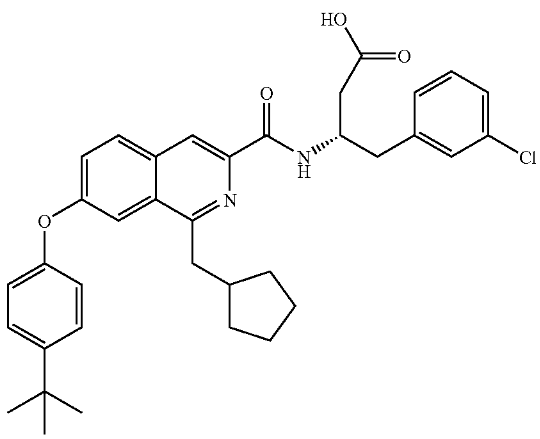 | (3R)-{[7-(4-tert-Butyl-phenoxy)-1-cyclopentylmethyl-isoquinoline-3-carbonyl]-amino}-4-(3-chloro-phenyl)-butyric acid |
| 592 | 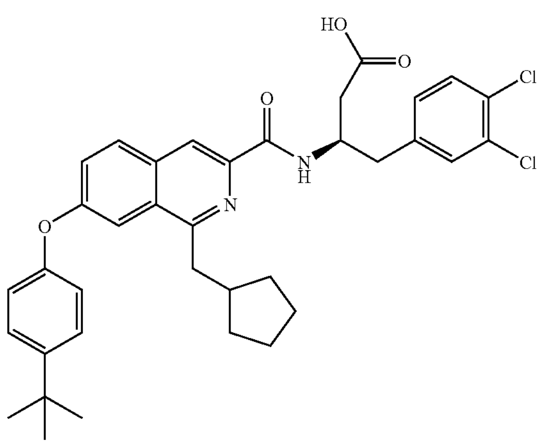 | (3R)-{[7-(4-tert-Butyl-phenoxy)-1-cyclopentylmethyl-isoquinoline-3-carbonyl]-amino}-4-(3,4-dichloro-phenyl)-butyric acid |

TABLE 1-continued

| Example | Structure | Name |
|---------|-----------|------|
| 593 | 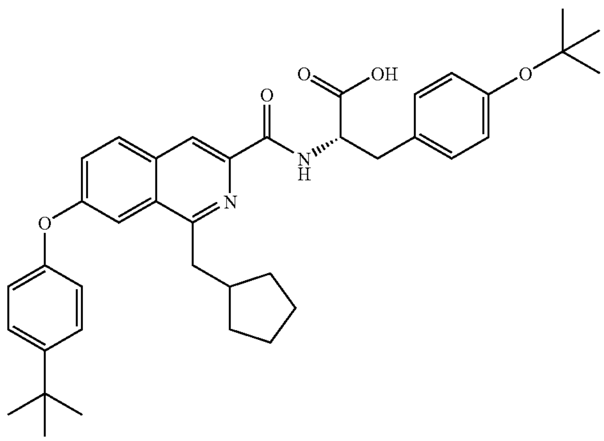 | 3-(4-tert-Butoxy-phenyl)-(2S)-{[7-(4-tert-butyl-phenoxy)-1-cyclopentylmethyl-isoquinoline-3-carbonyl]-amino}-propionic acid |
| 594 | 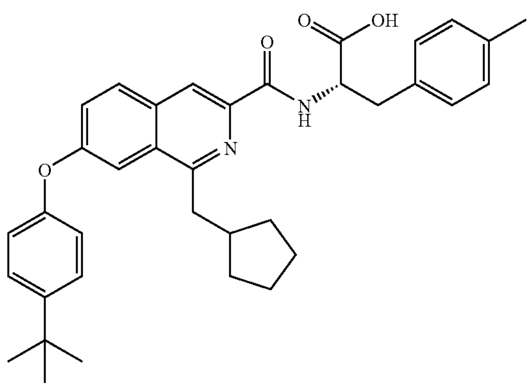 | (2S)-{[7-(4-tert-Butyl-phenoxy)-1-cyclopentylmethyl-isoquinoline-3-carbonyl]-amino)-3-p-tolyl-propionic acid |
| 595 | 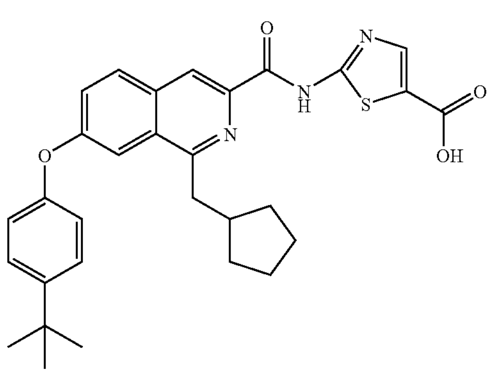 | 2-{[7-(4-tert-Butyl-phenoxy)-1-cyclopentylmethyl-isoquinoline-3-carbonyl]-amino}-thiazole-5-carboxylic acid |

TABLE 1-continued

| Example | Structure | Name |
|---|---|---|
| 596 | 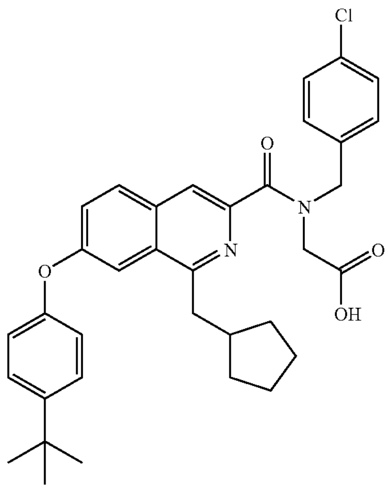 | [[7-(4-tert-Butyl-phenoxy)-1-cyclopentylmethyl-isoquinoline-3-carbonyl]-(4-chloro-benzyl)-amino]-acetic acid |
| 597 | 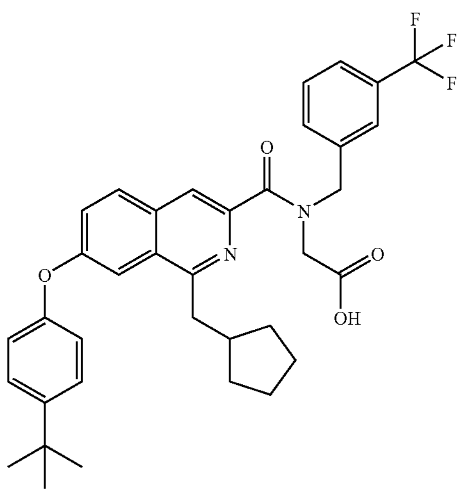 | [[7-(4-tert-Butyl-phenoxy)-1-cyclopentylmethyl-isoquinoline-3-carbony]-(3-trifluoromethyl-benzyl)-amino]-acetic acid |
| 598 | 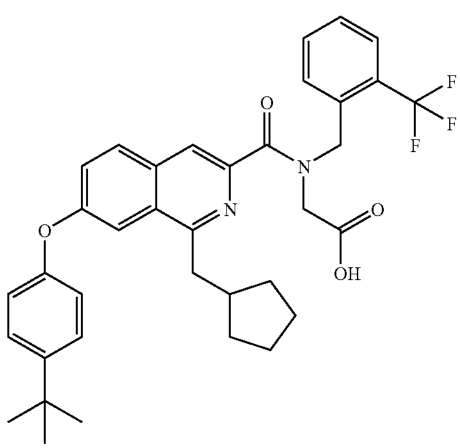 | [[7-(4-tert-Butyl-phenoxy)-1-cyclopentylmethyl-isoquinoline-3-carbonyl]-(2-trifluoromethyl-benzyl)-amino]-acetic acid |

TABLE 1-continued

| Example | Structure | Name |
|---|---|---|
| 599 | 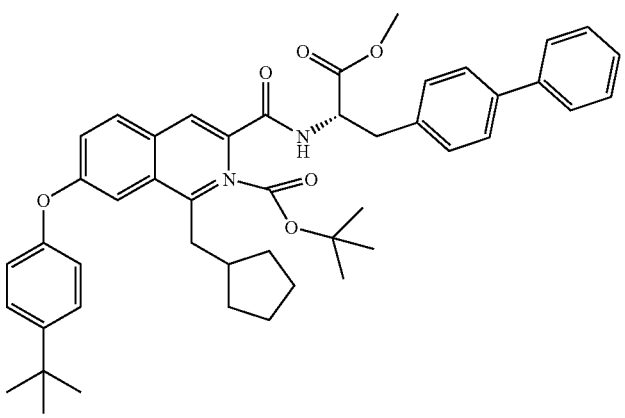 | (3S)-(2-Biphenyl-4-yl-(1S)-methoxycarbonyl-ethylcarbamoyl)-7-(4-tert-butyl-phenoxy)-1-cyclopentylmethyl-3,4-dihydro-1H-isoquinoline-2-carboxylic acid tert-butyl ester |
| 600 | 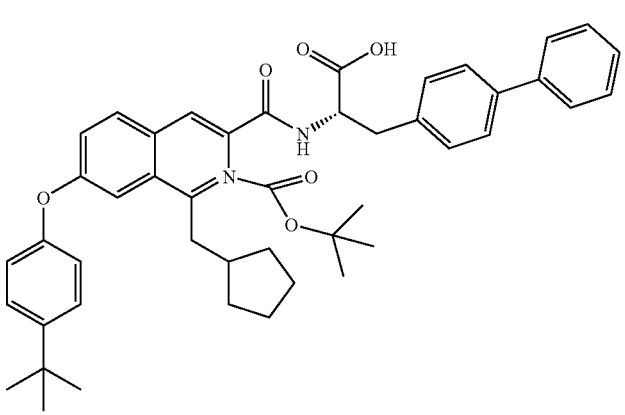 | (3S)-(2-Biphenyl-4-yl-(1S)-carboxy-ethylcarbamoyl)-7-(4-tert-butyl-phenoxy)-1-cyclopentylmethyl-3,4-dihydro-1H-isoquinoline-2-carboxylic acid tert-butyl ester |
| 601 | 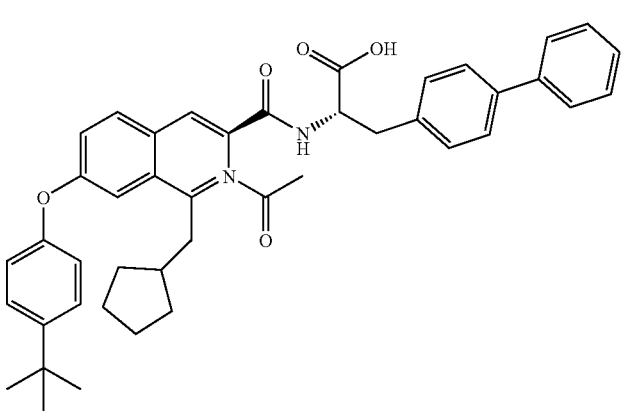 | (2S)-{[2-Acetyl-7-(4-tert-butyl-phenoxy)-1-cyclopentylmethyl-1,2,3,4-tetrahydro-isoquinoline-(3S)-carbonyl]-amino}-3-biphenyl-4-yl-propionic acid |
| 602 | 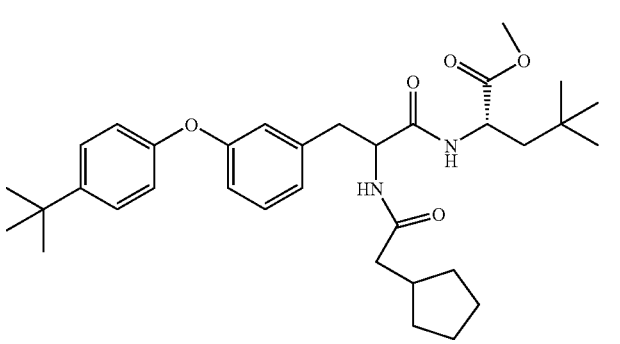 | (2S)-[3-[3-(4-tert-Butyl-phenoxy)-phenyl]-2-(2-cyclopentyl-acetylamino)-propionylamino]-4,4-dimethyl-pentanoic acid methyl ester |

TABLE 1-continued

| Example | Structure | Name |
|---|---|---|
| 603 | 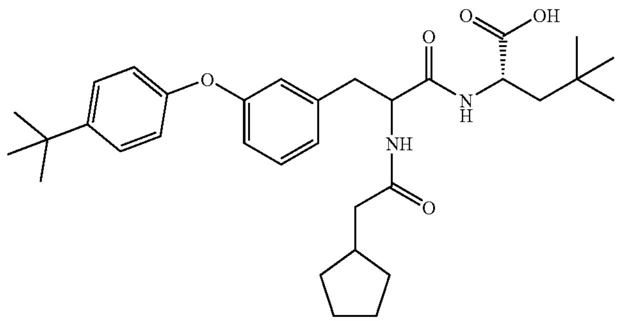 | (2S)-[3-[3-(4-tert-Butyl-phenoxy)-phenyl]-2-(2-cyclopentyl-acetylamino)-propionylamino]-4,4-dimethyl-pentanoic acid |
| 604 | 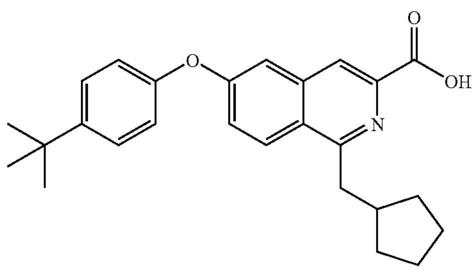 | 6-(4-tert-Butyl-phenoxy)-1-cyclopentylmethyl-isoquinoline-3-carboxylic acid |
| 605 | 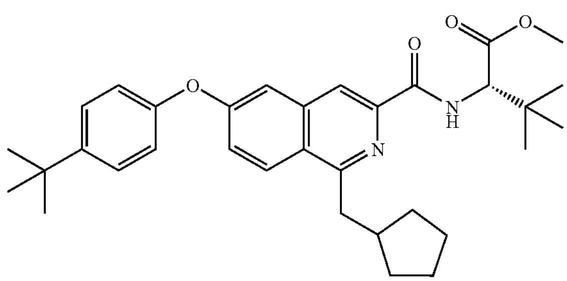 | (2S)-{[6-(4-tert-Butyl-phenoxy)-1-cyclopentylmethyl-isoquinoline-3-carbonyl]-amino}-3,3-dimethyl-butyric acid methyl ester |
| 606 | 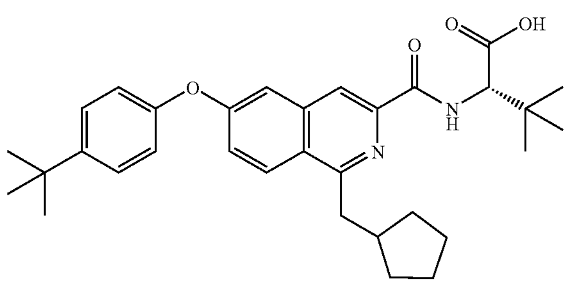 | (2S)-{[6-(4-tert-Butyl-phenoxy)-1-cyclopentylmethyl-isoquinoline-3-carbonyl]-amino}-3,3-di methyl-butyric acid |
| 607 | 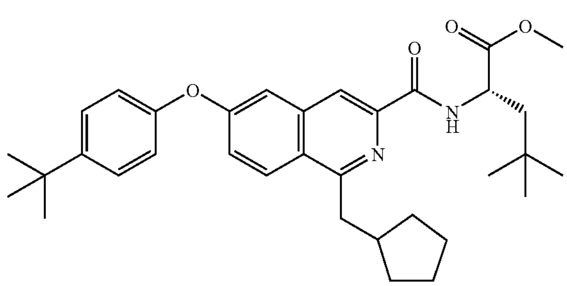 | (2S)-{[6-(4-tert-Butyl-phenoxy)-1-cyclopentylmethyl-isoquinoline-3-carbonyl]-amino}-4,4-dimethyl-pentanoic acid methyl ester |

TABLE 1-continued

| Example | Structure | Name |
|---|---|---|
| 608 | 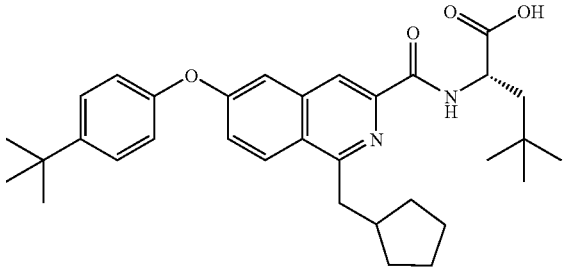 | (2S)-{[6-(4-tert-Butyl-phenoxy)-1-cyclopentylmethyl-isoquinoline-3-carbonyl]-amino}-4,4-dimethyl-pentanoic acid |
| 609 | 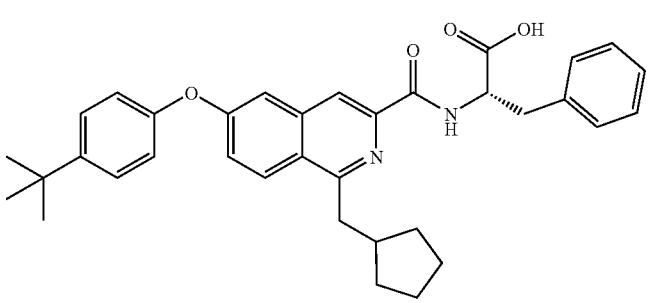 | (2S)-{[6-(4-tert-Butyl-phenoxy)-1-cyclopentylmethyl-isoquinoline-3-carbonyl]-amino}-3-phenyl-propionic acid |
| 610 | 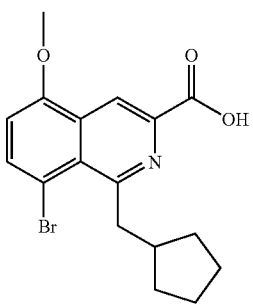 | 8-Bromo-1-cyclopentylmethyl-5-methoxy-isoquinoline-3-carboxylic acid |
| 611 | 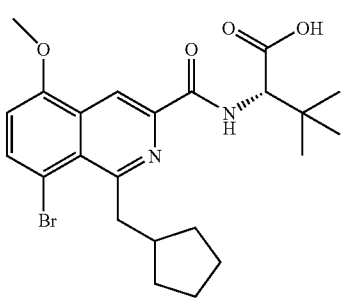 | (2S)-[(8-Bromo-1-cyclopentylmethyl-5-methoxy-isoquinoline-3-carbonyl)-amino]-3,3-dimethyl-butyric acid |
| 612 | 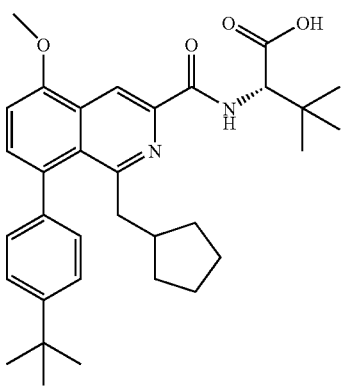 | (2S)-{[8-(4-tert-Butyl-phenyl)-1-cyclopentylmethyl-5-methoxy-isoquinoline-3-carbonyl]-amino}-3,3-dimethyl-butyric acid |

TABLE 1-continued

| Example | Structure | Name |
|---|---|---|
| 613 | 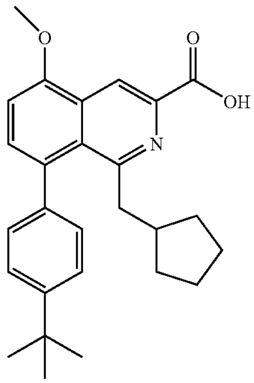 | 8-(4-tert-Butyl-phenyl)-1-cyclopentylmethyl-5-methoxy-isoquinoline-3-carboxylic acid |
| 614 | 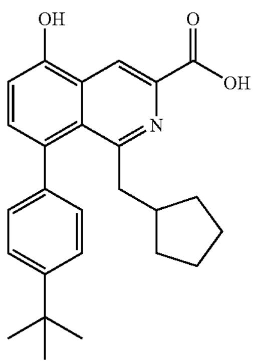 | 8-(4-tert-Butyl-phenyl)-1-cyclopentylmethyl-5-hydroxy-isoquinoline-3-carboxylic acid |
| 615 | 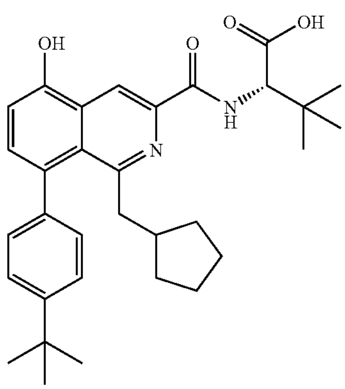 | (2S)-{[8-(4-tert-Butyl-phenyl)-1-cyclopentylmethyl-5-hydroxy-isoquinoline-3-carbonyl]-amino}-3,3-dimethyl-butyric acid |
| 616 | 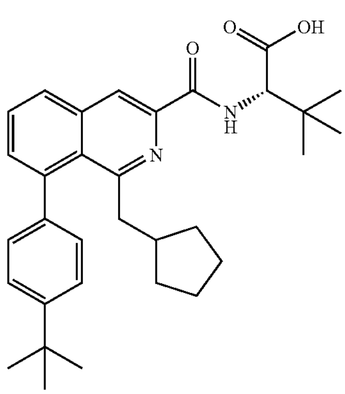 | (2S)-{[8-(4-tert-Butyl-phenyl)-1-cyclopentylmethyl-isoquinoline-3-carbonyl]-amino}-3,3-dimethyl-butyric acid |

TABLE 1-continued

| Example | Structure | Name |
|---------|-----------|------|
| 617 | 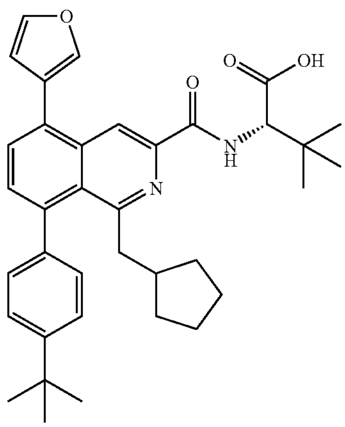 | (2S)-{[8-(4-tert-Butyl-phenyl)-1-cyclopentylmethyl-5-furan-3-yl-isoquinoline-3-carbonyl]-amino}-3,3-dimethyl-butyric acid |
| 618 | 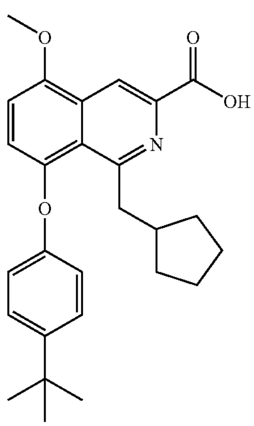 | 8-(4-tert-Butyl-phenoxy)-1-cyclopentylmethyl-5-methoxy-isoquinoline-3-carboxylic acid |
| 619 | 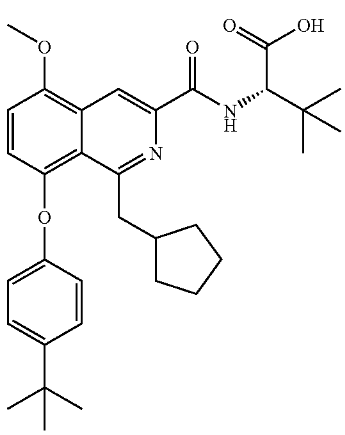 | (2S)-{[8-(4-tert-Butyl-phenoxy)-1-cyclopentylmethyl-5-methoxy-isoquinoline-3-carbonyl]-amino}-3,3-dimethyl-butyric acid |

TABLE 1-continued

| Example | Structure | Name |
|---|---|---|
| 620 | 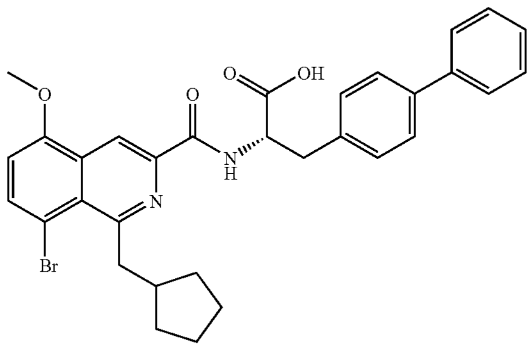 | 3-Biphenyl-4-yl-(2S)-[(8-bromo-1-cyclopentylmethyl-5-methoxy-isoquinoline-3-carbonyl)-amino]-propionic acid |
| 621 | 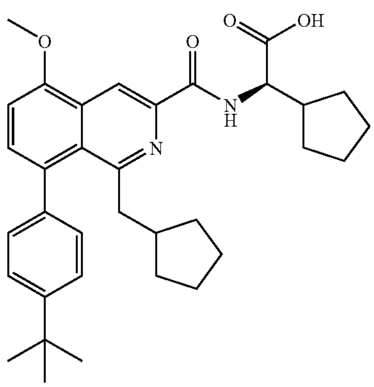 | (2R)-{[8-(4-tert-Butyl-phenyl)-1-cyclopentylmethyl-5-methoxy-isoquinoline-3-carbonyl]-amino}-cyclopentyl-acetic acid |
| 622 | 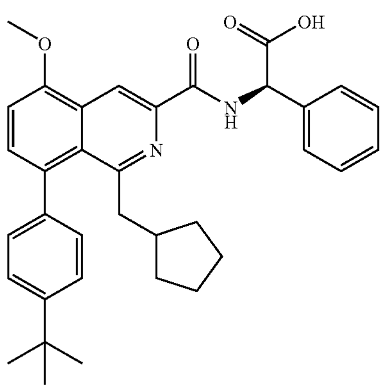 | (2R)-{[8-(4-tert-Butyl-phenyl)-1-cyclopentylmethyl-5-methoxy-isoquinoline-3-carbonyl]-amino}-phenyl-acetic acid |
| 623 | 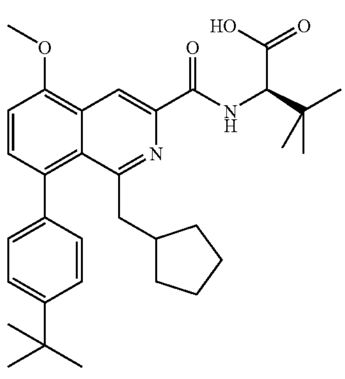 | (2R)-{[8-(4-tert-Butyl-phenyl)-1-cyclopentylmethyl-5-methoxy-isoquinoline-3-carbonyl]-amino}-3,3-dimethyl-butyric acid |

Also included within the scope of the invention are the individual enantiomers of the compounds represented by Formula (I) above as well as any wholly or partially racemic mixtures thereof. The present invention also covers the individual enantiomers of the compounds represented by formula above as mixtures with diastereoisomers thereof in which one or more stereocenters are inverted.

In another aspect, the present invention comprises a pharmaceutical composition comprising the compound of Formula (I) and one or more pharmaceutically acceptable carriers, excipients, or diluents.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may containing one or more O, S, S(O), or S(O)$_2$ atoms. Examples of "alkyl" as used herein include, but are not limited to, methyl, n-butyl, t-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may containing one or more O, S, S(O), or S(O)$_2$ atoms. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may containing one or more O, S, S(O), or S(O)$_2$ atoms.

As used herein, the term "alkenylene" refers to a straight or branched chain divalent hydrocarbon radical having from two to ten carbon atoms and one or more carbon-carbon double bonds, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may containing one or more O, S, S(O), or S(O)$_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or S(O)$_2$ atoms.

As used herein, the term "alkynylene" refers to a straight or branched chain divalent hydrocarbon radical having from two to ten carbon atoms and one or more carbon-carbon triple bonds, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may containing one or more O, S, S(O), or S(O)$_2$ atoms. Examples of "alkynylene" as used herein include, but are not limited to, ethyne-1,2-diyl, propyne-1,3-diyl, and the like.

As used herein, "cycloalkyl" refers to a alicyclic hydrocarbon group optionally possessing one or more degrees of unsaturation, having from three to twelve carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an nonaromatic alicyclic divalent hydrocarbon radical having from three to twelve carbon atoms and optionally possessing one or more degrees of unsaturation, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring optionally possessing one or more degrees of unsaturation, containing one or more heteroatomic substitutions selected from S, SO, SO$_2$, O, or N, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclylene" refers to a three to twelve-membered heterocyclic ring diradical optionally having one or more degrees of unsaturation containing one or more heteroatoms selected from S, SO, $SO_2$, O, or N, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-dyil, and the like.

As used herein, the term "aryl" refers to a benzene ring or to an optionally substituted benzene ring system fused to one or more optionally substituted benzene rings, optionally substituted with substituents selected from the group consisting of halo, lower alkyl, lower alkoxy, lower alkylsulfanyl, lower alkylsulfenyl, lower alkylsulfonyl, di(lower alkyl)aminoalkyl, aminoalkyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acylamino, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of halo, lower alkyl, lower alkoxy, lower alkylsulfanyl, lower alkylsulfenyl, lower alkylsulfonyl, di(lower alkyl)aminoalkyl, aminoalkyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acylamino, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include 5-indanyl, 5,6,7,8-tetrahydro-2-naphthyl,

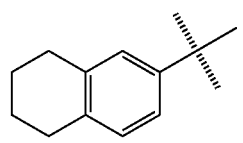

, and the like.

As used herein, the term "fused cycloalkylarylene" refers to a fused cycloalkylaryl, wherein the aryl group is divalent. Examples include

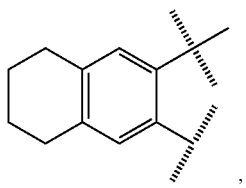

, and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

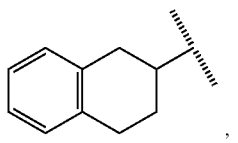

, and the like.

As used herein, the term "fused arylcycloalkylene" refers to a fused arylcycloalkyl, wherein the cycloalkyl group is divalent. Examples include

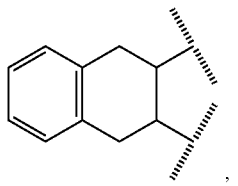

, and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include 3,4-methylenedioxy-1-phenyl,

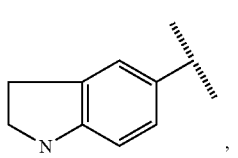

, and the like

As used herein, the term "fused heterocyclylarylene" refers to a fused heterocyclylaryl, wherein the aryl group is divalent. Examples include

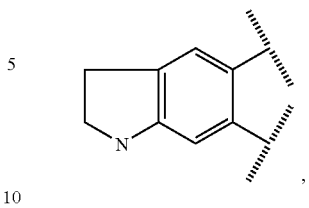

, and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include 2-(1,3-benzodioxolyl),

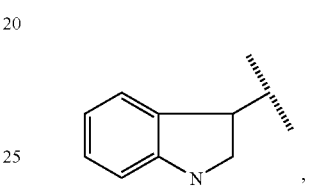

, and the like.

As used herein, the term "fused arylheterocyclylene" refers to a fused arylheterocyclyl, wherein the heterocyclyl group is divalent. Examples include

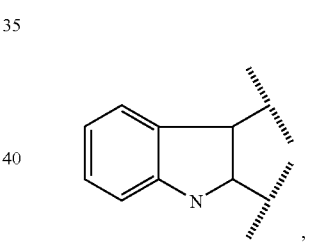

, and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include 5-aza-6-indanyl,

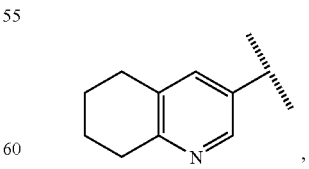

, and the like.

As used herein, the term "fused cycloalkylheteroarylene" refers to a fused cycloalkylheteroaryl, wherein the heteroaryl group is divalent. Examples include

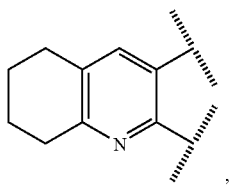

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include 5-aza-1-indanyl,

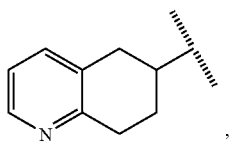

and the like.

As used herein, the term "fused heteroarylcycloalkylene" refers to a fused heteroarylcycloalkyl, wherein the cycloalkyl group is divalent. Examples include

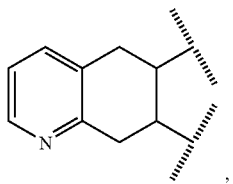

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include 1,2,3,4-tetrahydro-beta-carbolin-8-yl,

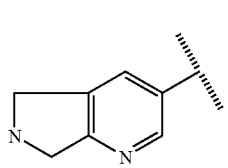

and the like.

As used herein, the term "fused heterocyclylheteroarylene" refers to a fused heterocyclylheteroaryl, wherein the heteroaryl group is divalent. Examples include

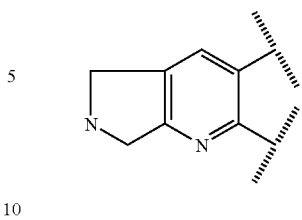

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include -5-aza-2,3-dihydrobenzofuran-2-yl,

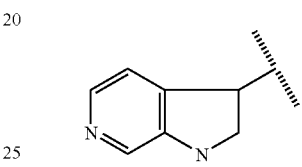

and the like.

As used herein, the term "fused heteroarylheterocyclylene" refers to a fused heteroarylheterocyclyl, wherein the heterocyclyl group is divalent. Examples include

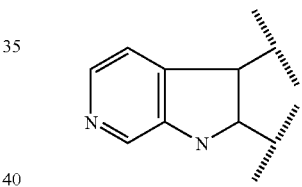

and the like.

As used herein, the term "acid isostere" refers to a substituent group that may ionize at physiological pH to bear a net negative charge. Examples of such "acid isosteres" include but are not limited to heteroaryl groups such as but not limited to isoxazol-3-ol-5-yl, 1H-tetrazole-5-yl, or 2H-tetrazole-5-yl. Such acid isosteres include but are not limited to heterocyclyl groups such as but not limited to imidazolidine-2,4-dione-5-yl, imidazolidine-2,4-dione-1-yl, 1,3-thiazolidine-2,4-dione-5-yl, or 5-hydroxy-4H-pyran-4-on-2-yl, 1,2,5-thiadiazolidin-3-one-1,1-dioxide-4-yl, or 1,2-5-thiadiazolidin-3-one-1,1-dioxide-5-yl.

As used herein, the term "ester isostere" refers to a substituent group that can be metabolically stable and can retain the selectivity and affinity of a corresponding ester toward a target protein. Examples of such "ester isosteres" include, but are not limited to, heteroaryl groups such as, but not limited to, 1,3-oxazole-5-yl, 1,3-oxazole-2-yl, 1,2,3-oxadiazole-5-yl, 1,2,4-oxadiazole-5-yl, 1,3,4-oxadiazole-5-yl, 1,2,3-thiadiazole-5-yl, 1,2,4-thiadiazole-5-yl, 1,3,4-thiadiazole-5-yl, 5-alkyl-1,3-oxazole-2-yl, 2-alkyl-1,3-oxazole-5-yl, 4-alkyl-1,2,3-oxadiazole-5-yl, 3-alkyl-1,2,4-oxadiazole-5-yl, 2-alkyl-1,3,4-oxadiazole-5-yl, 4-alkyl-1,2,3-thiadiazole-5-yl, 3-alkyl-1,2,4-thiadiazole-5-yl, 2-alkyl-1,3,4-thiadiazole-5-yl, 1,2,4-triazole-1-yl, 3-alkyl-1,2,4-triazole-1-yl, tetrazole-1-yl, and 1-alkyl-tetrazole-5-yl; aryl groups such as, but not limited to, 3,5-difluoro-4-alkoxyphenyl; and heterocyclyl groups such as, but not limited to, 1-alkyl-imidazolidine-2,4-dione-5-yl, imidazolidine-2,4-dione-1-yl, 3-alkyl-1,3-thiazolidine-2,4-dione-5-yl, and 5-alkoxy-4H-pyran-4-on-2-yl. The alkyl groups in the heterocyclyl, aryl, and heteroaryl groups of the ester isosteres may be replaced with a phenyl or alkylphenyl group.

As used herein, the term "direct bond", where part of a structural variable specification, refers to the direct joining of the substituents flanking (preceding and succeeding) the variable taken as a "direct bond".

As used herein, the term "alkoxy" refers to the group $R_aO-$, where $R_a$ is alkyl.

As used herein, the term "alkenyloxy" refers to the group $R_aO-$, where $R_a$ is alkenyl.

As used herein, the term "alkynyloxy" refers to the group $R_aO-$, where $R_a$ is alkynyl.

As used herein, the term "alkylsulfanyl" refers to the group $R_aS-$, where $R_a$ is alkyl.

As used herein, the term "alkenylsulfanyl" refers to the group $R_aS-$, where $R_a$ is alkenyl.

As used herein, the term "alkynylsulfanyl" refers to the group $R_aS-$, where $R_a$ is alkynyl.

As used herein, the term "alkylsulfenyl" refers to the group $R_aS(O)-$, where $R_a$ is alkyl.

As used herein, the term "alkenylsulfenyl" refers to the group $R_aS(O)-$, where $R_a$ is alkenyl.

As used herein, the term "alkynylsulfenyl" refers to the group $R_aS(O)-$, where $R_a$ is alkynyl.

As used herein, the term "alkylsulfonyl" refers to the group $R_aSO_2-$, where $R_a$ is alkyl.

As used herein, the term "alkenylsulfonyl" refers to the group $R_aSO_2-$, where $R_a$ is alkenyl.

As used herein, the term "alkynylsulfonyl" refers to the group $R_aSO_2-$, where $R_a$ is alkynyl.

As used herein, the term "acyl" refers to the group $R_aC(O)-$, where $R_a$ is alkyl, alkenyl, alkynyl, cycloalkyl, cycloalkenyl, or heterocyclyl.

As used herein, the term "aroyl" refers to the group $R_aC(O)-$, where $R_a$ is aryl.

As used herein, the term "heteroaroyl" refers to the group $R_aC(O)-$, where $R_a$ is heteroaryl.

As used herein, the term "alkoxycarbonyl" refers to the group $R_aOC(O)-$, where $R_a$ is alkyl.

As used herein, the term "acyloxy" refers to the group $R_aC(O)O-$, where $R_a$ is alkyl, alkenyl, alkynyl, cycloalkyl, cycloalkenyl, or heterocyclyl.

As used herein, the term "aroyloxy" refers to the group $R_aC(O)O-$, where $R_a$ is aryl.

As used herein, the term "heteroaroyloxy" refers to the group $R_aC(O)O-$, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, $-CH_2-O-CH_2-$, $-CH_2-SO_2-CH_2-$, $-CH_2-NH-CH_3$ and so forth.

As used herein, the term "solvate" is a complex of variable stoichiometry formed by a solute (in this invention, a compound of Formula (I)) and a solvent. Such solvents for the purpose of the invention may not sunstantially interfere with the biological activity of the solute. Solvents may be, by way of example, water, ethanol, or acetic acid.

As used herein, the term "biohydrolyzable ester" is an ester of a drug substance (in this invention, a compound of formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to Formula (I) in plasma. Many examples of such are known in the art and include by way of example lower alkyl esters (e.g., $C_1$-$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to Formula (I) in plasma. Many examples of such are known in the art and include by way of example lower alkyl amides, alpha-amino acid amides, alkoxyacyl amides, and alkylaminoalkylcarbonyl amides.

As used herein, the term "prodrug" includes biohydrolyzable amides and biohydrolyzable esters and encompasses a) compounds in which the biohydrolyzable functionality in such a prodrug is encompassed in the compound of formula (I), and b) compounds which may be oxidized or reduced biologically at a given functional group to yield drug substances of formula (I). Examples of these functional groups include, but are not limited to, 1,4-dihydropyridine, N-alkylcarbonyl-1,4-dihydropyridine, 1,4-cyclohexadiene, tert-butyl, and the like.

Whenever the terms "alkyl" or "aryl" or either of their prefix roots appear in a name of a substituent (e.g. arylalkoxyaryloxy) they shall be interpreted as including those limitations given above for "alkyl" and "aryl". Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —$C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —S(O)$_2$—.

The compounds can be prepared according to the following reaction Schemes (in which variables are as defined before or are defined in the Schemes and methods below). In these reactions, it is also possible to make use of variants that are known to those of ordinary skill in this art, but are not mentioned in greater detail.

The present invention also provides a method for the synthesis of compounds useful as intermediates in the preparation of compounds of Formula (I) along with methods for the preparation of compounds of Formula (I).

Scheme I describes the synthesis of an intermediate of structure (4).

Ar$_3$ and Ar$_4$ are, independently, groups such as, but not limited to, a heteroaryl, heteroarylene, arylene, or aryl ring system.

As shown in Scheme I, in one embodiment, bromo- or iodo-substituted aryl alanine methyl ester (or amino acid esterified in linkage to Wang resin) (1) is treated with a carboxylic acid in the presence of a coupling reagent, such as, but not limited to, diisopropyl carbodiimide (DIC) to form the amide (2). The resulting amide is then subjected to coupling with an arylboronic acid in the presence of a catalyst such as but not limited to tetrakis(triphenylphosphine)palladium (0), in the presence of base such as, but not limited to, sodium carbonate to form compound (3). The methyl ester (3) is hydrolyzed using a base such as, but not limited to, LiOH to provide the free carboxylic acid (4), where Ar$_1$ and Ar$_2$ are as defined for Formula (I).

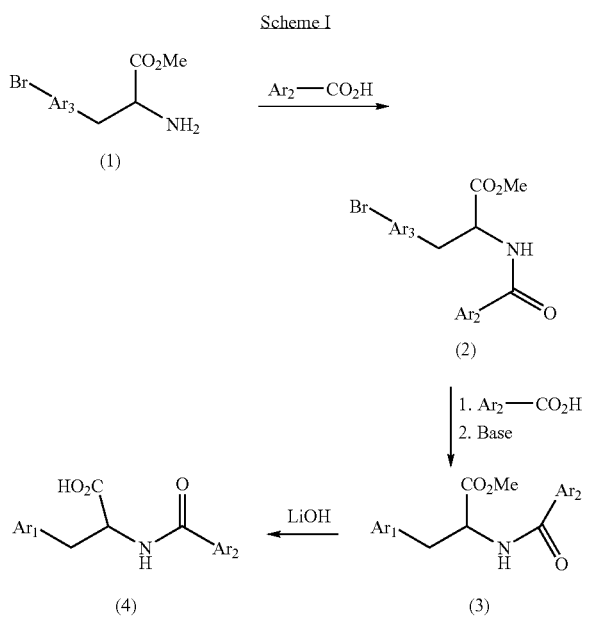

Scheme II describes the preparation of a compound of structure (4).

Ar$_3$ and Ar$_4$ are, independently, groups such as but not limited to a heteroaryl, heteroarylene, arylene, or aryl ring system.

As shown in Scheme II, in another embodiment, an aryl hydroxy amino acid methyl ester (or amino acid esterified in linkage to Wang resin) (5) is treated with a carboxylic acid Ar$_2$—CO$_2$H in the presence of a coupling reagent such as, but not limited to, diisopropyl carbodiimide (DIC) to form the amide (6). The resulting amide is then subjected to: 1) nucleophilic substitutions with an optionally substituted electron-deficient fluoroaromatic or fluoroheteroaromatic in the presence of base such as, but not limited to, potassium carbonate; or 2) coupling with an aryl bromide, or heteroaryl bromide, and copper iodide in the presence of a base including, but not limited to, cesium carbonate to form compound (7). The methyl ester in (7) is hydrolyzed using a base such as LiOH to provide the free carboxylic acid (4), where Ar$_1$ and Ar$_2$ are as defined for Formula (I)

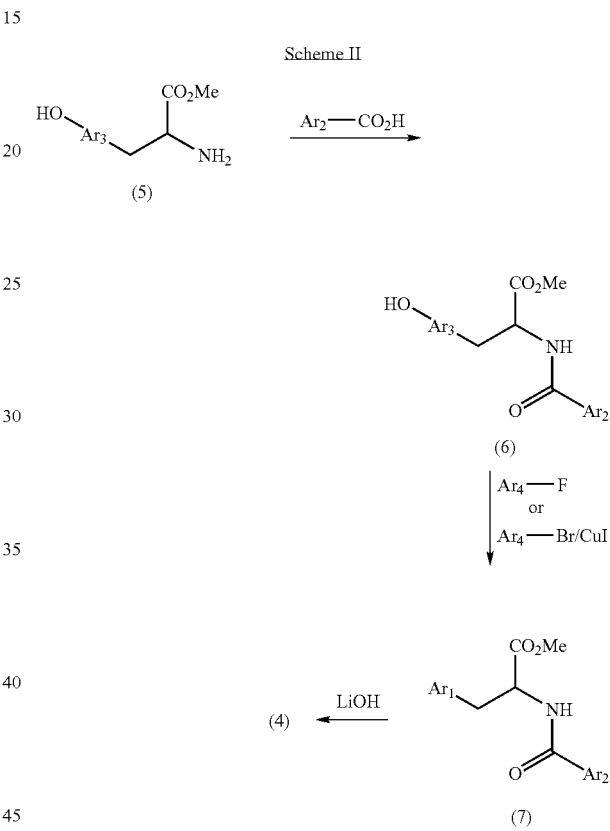

Scheme III describes the preparation of a compouind of formula (4).

Ar$_5$ and Ar$_6$ are, independently, groups such as but not limited to a heteroaryl, heteroarylene, arylene, or aryl ring system.

As shown in Scheme III, in another embodiment, an amino acid methyl ester (or, alternately, an amino acid esterified in linkage to Wang resin) (8) is treated with a bromo-substituted aryl carboxylic acid in the presence of a coupling reagent such as, but not limited to, diisopropyl carbodiimide (DIC) to form the amide (9). The resulting amide then is subjected to coupling with an arylboronic acid or heteroarylboronic acid in the presence of a catalyst such as but not limited to tetrakis (triphenylphosphine)palladium(0), in the presence of base such as, but not limited to, sodium carbonate to form compound (10). The methyl ester (10) is hydrolyzed using a base such as, but not limited to, LiOH to provide the free carboxylic acid (4), where Ar$_1$ and Ar$_2$ are as defined for Formula (I).

Scheme III

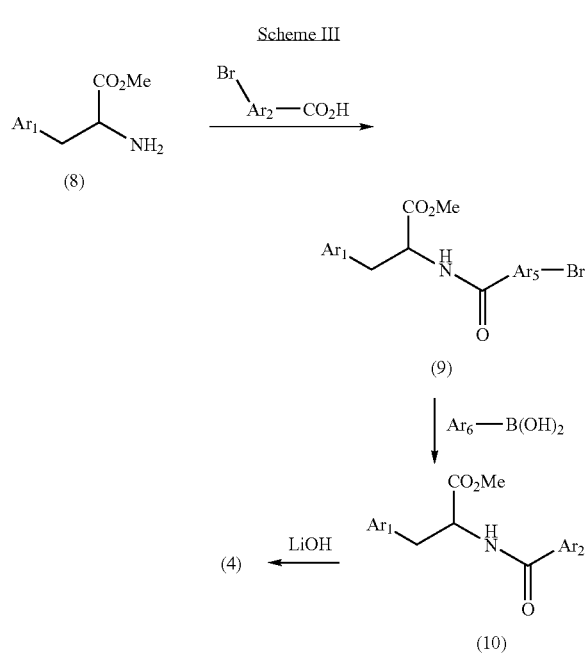

Scheme IV describes the synthesis of a compound of formula (4).

$Ar_3, Ar_7, Ar_5$ and $Ar_6$ are, independently, groups such as but not limited to a heteroaryl, heteroarylene, arylene, or aryl ring system.

As shown in Scheme IV, in another embodiment, a bromo or iodo aryl alanine methyl ester (or amino acid esterified in linkage to Wang resin) (11) is subjected to coupling with an arylboronic acid in the presence of a catalyst such as but not limited to tetrakis(triphenylphosphine)palladium(0), in the presence of base such as but not limited to sodium carbonate to form compound (12). The resulting compound is treated with a bromo- or iodo-substituted aryl carboxylic acid in the presence of a coupling reagent such as, but not limited to, diisopropyl carbodiimide (DIC) to form the amide (13). The resulting amide is then subjected to coupling with a arylboronic acid or heteroarylboronic acid in the presence of a catalyst such as but not limited to tetrakis(triphenylphosphine)plladium(0), in the presence of base such as, but not limited to, sodium carbonate, and the product methyl ester is hydrolyzed using a base such as LiOH to provide the free carboxylic acid (4), where $Ar_1$ and $Ar_2$ are as defined for Formula (I).

Scheme IV

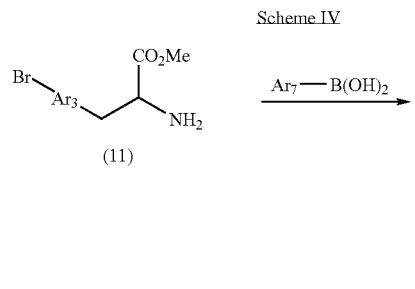

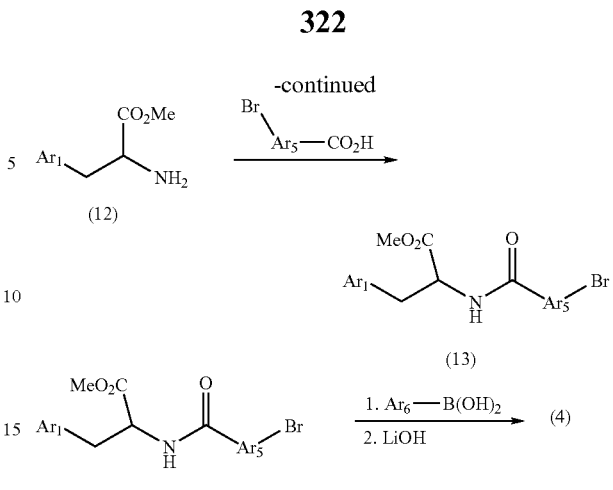

Scheme V describes the preparation of a compound of formula (16).

$Ar_3$ and $Ar_7$ are, independently, groups such as but not limited to a heteroaryl, heteroarylene, arylene, or aryl ring system.

Pol is a functionalized polymeric support, such as but not limited to Wang Resin.

As shown in Scheme V, in another embodiment, a hydroxy aryl ester loaded onto the Wang Bromo resin or Merrifield resin using base such as, but not limited to, sodium methoxide in DMA, and hydrolyzed to give (14), is coupled with a bromo- or iodo-subsituted aryl amino acid methyl ester (11) in the presence of a coupling reagent such as, but not limited to, diisopropyl carbodiimide (DIC) to give the amide (15). The resulting amide (15) is then subjected to a coupling with an arylboronic acid or heteroarylboronic acid in the presence of a catalyst such as but not limited to tetrakis(triphenylphosphine)palladium(O), in the presence of base such as, but not limited to, sodium carbonate followed by cleavage from the resin with TMSBr/TFA/DCM (1:1:1) or a similar suitable cleavage cocktail to yield the desired product (16), where $Ar_1$ and $Ar_2$ are as defined for Formula (I).

Scheme V

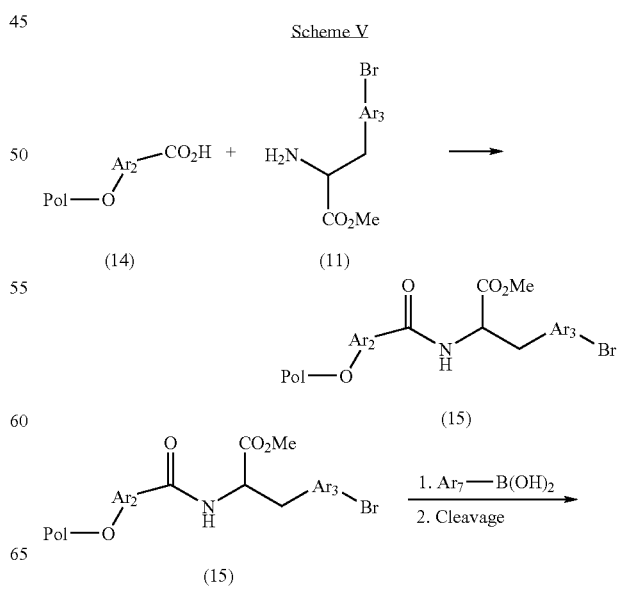

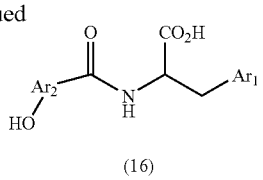

(16)

Scheme VI describes the preparation of a compound of formula (19).

$Ar_6$ and $Ar_8$ are, independently, groups such as but not limited to a heteroaryl, heteroarylene, arylene, or aryl ring system.

Pol is a functionalized polymeric support, such as but not limited to Wang Resin.

As shown in Scheme VI, in another embodiment, a hydroxy aryl ester loaded onto the Wang Bromo resin, Merrifiend resin, or other suitable support using base such as, but not limited to, sodium methoxide in DMA, is hydrolyzed to give (17), and is coupled with an amino acid methyl ester (8) in the presence of a coupling reagent such as, but not limited to, diisopropyl carbodiimide (DIC) to give the amide (18). The resulting amide (18) is then subjected to a coupling with an arylboronic acid or heteroarylboronic acid in the presence of a catalyst such as but not limited to tetrakis(triphenylphosphine)palladium(0), in the presence of base such as, but not limited to, sodium carbonate, and is then cleaved from the resin with TMSBr/TFA/DCM (1:1:1) or a similar suitable cleavage cocktail to yield the desired product (19), where $Ar_1$ and $Ar_2$ are as defined for Formula (I).

Pol is a functionalized polymeric support, such as but not limited to Wang Resin.

As shown in Scheme VII, in another embodiment, a bromo hydroxy aryl ester loaded onto Wang Bromo resin, Merrifield resin, or other suitable support using base such as, but not limited to, sodium methoxide in DMF, is hydrolyzed to give (20) and then subjected to a coupling with an arylboronic acid or heteroarylboronic acid in the presence of a catalyst such as but not limited to tetrakis(triphenylphosphine)plladium(0), in the presence of base such as, but not limited to, sodium carbonate, followed by hydrolysis of the product ester to yield the acid (21). The resulting carboxylic acid (21) is then subjected to coupling with a bromo- or iodo-substituted aryl amino acid methyl ester (11) in the presence of a coupling reagent such as, but not limited to, disopropyl carbodimide (DIC) to give the amide (22). The resulting amide (22) is then subjected to a coupling with an arylboronic acid or heteroaryl boronic acid in the presence of a catalyst such as but not limited to tetrakis(triphenylphosphine)plladium(0), in the presence of base such as, but not limited to, sodium carbonate followed by cleavage from the resin with TMSBr/TFA/DCM (1:1:1) or a similar cleavage cocktail to yield the desired product (23), where $Ar_1$ and $Ar_2$ are as defined for Formula (I).

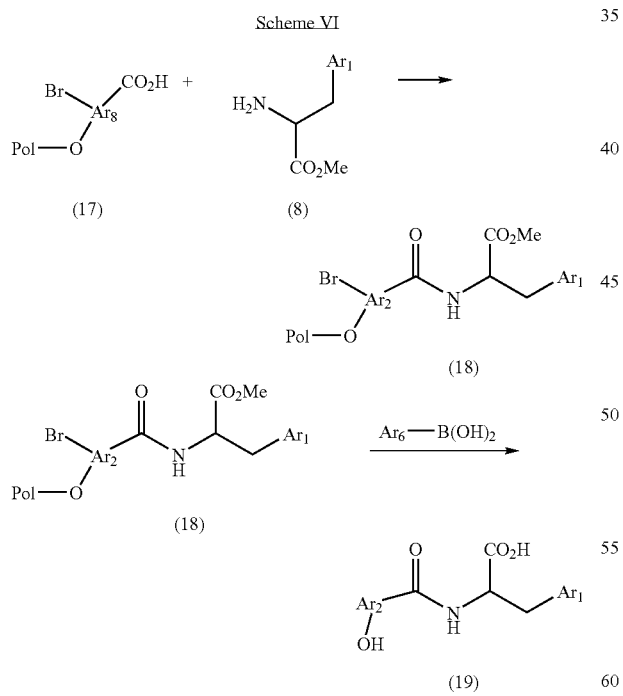

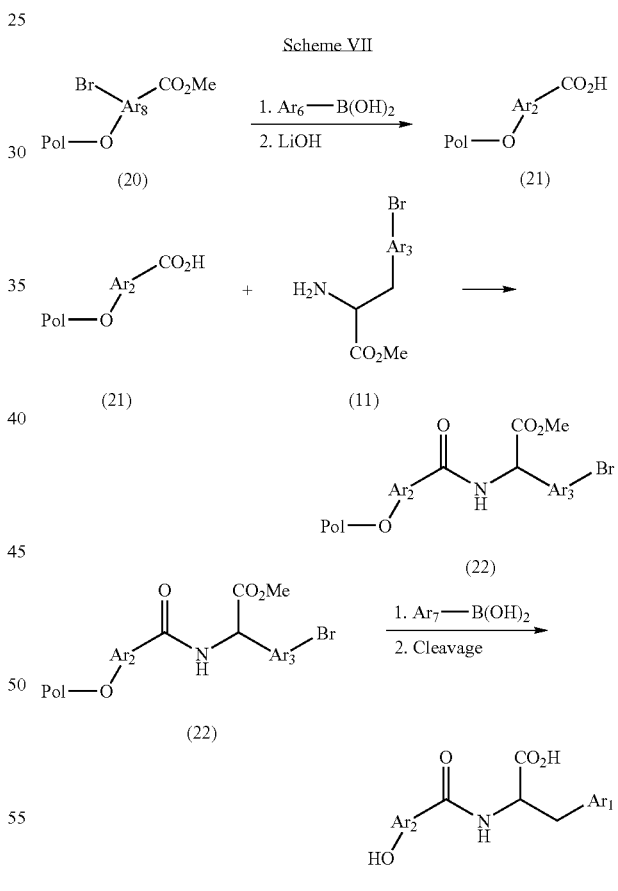

Scheme VII describes the synthesis of a compound of formula (23).

$Ar_6$, $Ar_7$, and $Ar_8$ are, independently, groups such as but not limited to a heteroaryl, heteroarylene, arylene, or aryl ring system.

Scheme VIII describes the preparation of a compound of formula (29).

$Ar_7$, $Ar_9$, $Ar_{10}$, and $Ar_{11}$ are, independently, groups such as but not limited to a heteroaryl, heteroarylene, arylene, or aryl ring system.

As shown in Scheme VIII, in another embodiment, a fluoro nitro phenol (24) loaded onto a polymer such as Wang Bromo resin using base such as, but not limited to, sodium methoxide in DMA, is hydrolyzed to give (24) and then treated with a hydroxy aryl compound (25) in the presence of base, followed by reduction of the nitro group to give the free amine (26). The resulting amine (26) is then subjected to coupling with a bromo- or iodo-substituted aryl acid (27) in the presence of a coupling reagent such as, but not limited to, diisopropyl carbodiimide (DIC) to give the amide (28). The resulting amide (28) is then subjected to a coupling with an arylboronic acid or heteroarylboronic acid in the presence of a catalyst such as but not limited to tetrakis(triphenylphosphine)palladium(0), in the presence of base such as, but not limited to, sodium carbonate followed by cleavage from the resin with TMSBr/TFA/DCM (1:1:1) or a similar suitable cleavage cocktail to yield the desired product (29), where $Ar_1$ and $Ar_2$ are as defined for Formula (I).

by treatment with, in the case of $PG_1$ as tert-butoxycarbonyl, TFA, and is then treated with an aroyl chloride in the presence of a base such as pyridine or TEA to give the iodo amide (31). The amide (31) is subjected to coupling with an arylboronic acid or heteroaryl boronic acid in the presence of a catalyst such as but not limited to tetrakis(triphenylphosphine)palladium(0), in the presence of base such as, but not limited to, sodium carbonate. Hydrolysis of the product methyl ester with an alkaline reagent such as LiOH provides compound (32), where $Ar_1$ and $Ar_2$ are as defined for Formula (I).

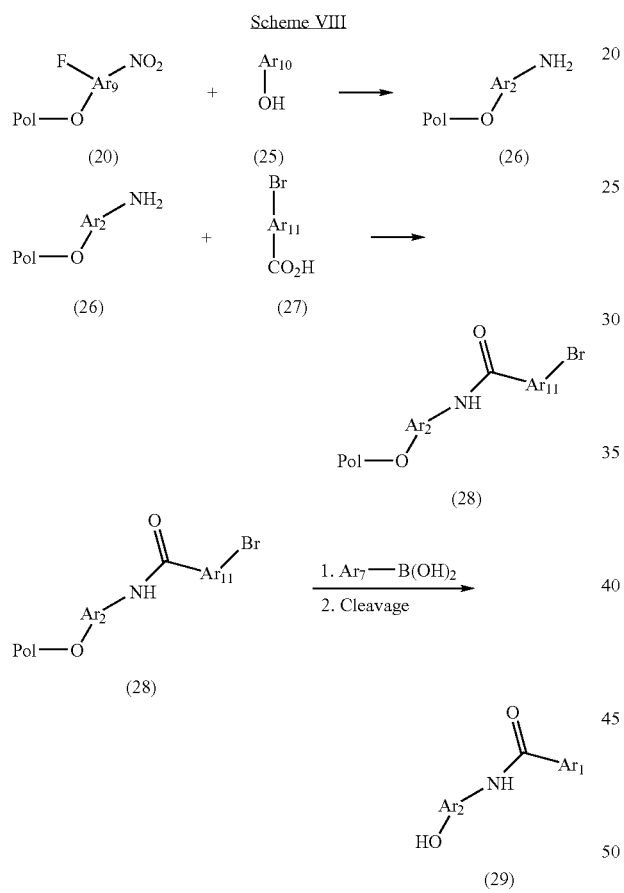

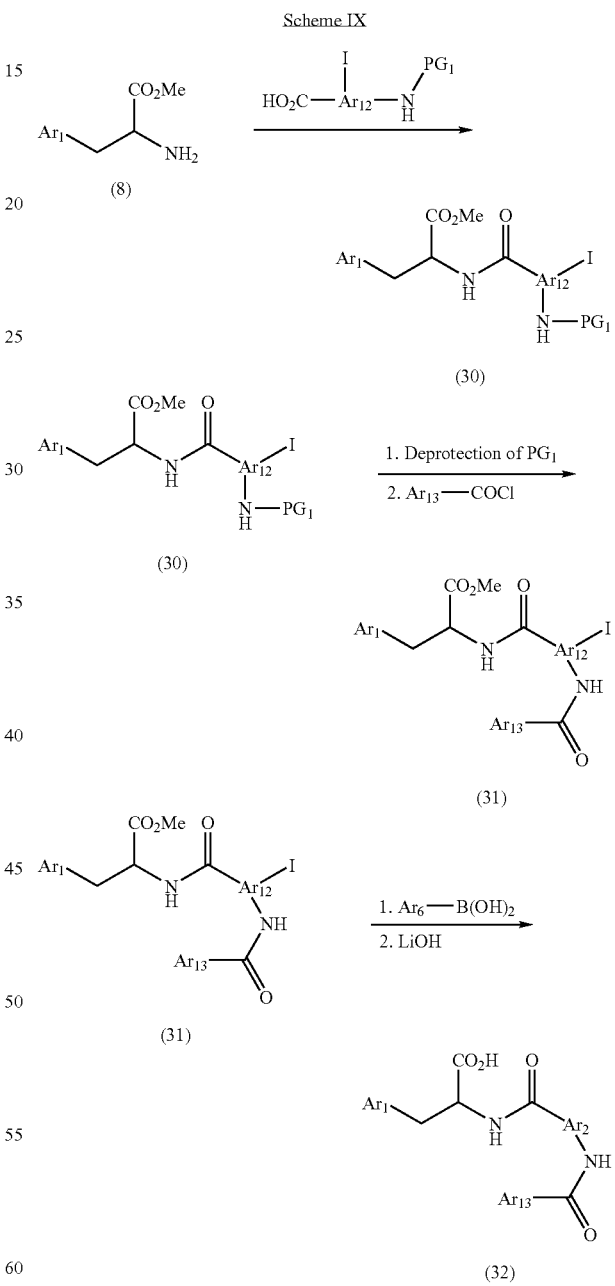

Scheme IX describes the preparation of a compound of formula (32).

$Ar_6$, $Ar_{12}$, and $Ar_{13}$ are, independently, groups such as but not limited to a heteroaryl, heteroarylene, arylene, or aryl ring system.

$PG_1$ is an amino protecting group such as allyloxycarbonyl or tert-butoxycarbonyl.

As shown in Scheme IX, In another embodiment, an aryl amino acid methyl ester (8) is reacted with an iodo-subsituted aryl amino carboxylic acid (the amino group of which may be protected with an amino protecting group $PG_1$) in the presence of a coupling reagent such as, but not limited to, diisopropyl carbodiimide (DIC) giving the amide (30). The amino group of the amide (30) may be then deprotected, if desired, In Scheme X, in another embodiment, a beta ketoester (33) may be treated with a reagent such as triethyl orthoformate or triethyl orthoacetate in the presence of acetic anhydride and heat to afford the ethoxy olefin derivative (34). $R_4$ is a group such as but not limited to aryl, heteroaryl, or alkyl. The derivative (34) may be treated with a hydrazine derivative (35) to afford the pyrazole (36). Hydrolysis of the ester of (36) with aqueous alkali and mild scidification with a weak acid such as aqueous citric acid affords (37).

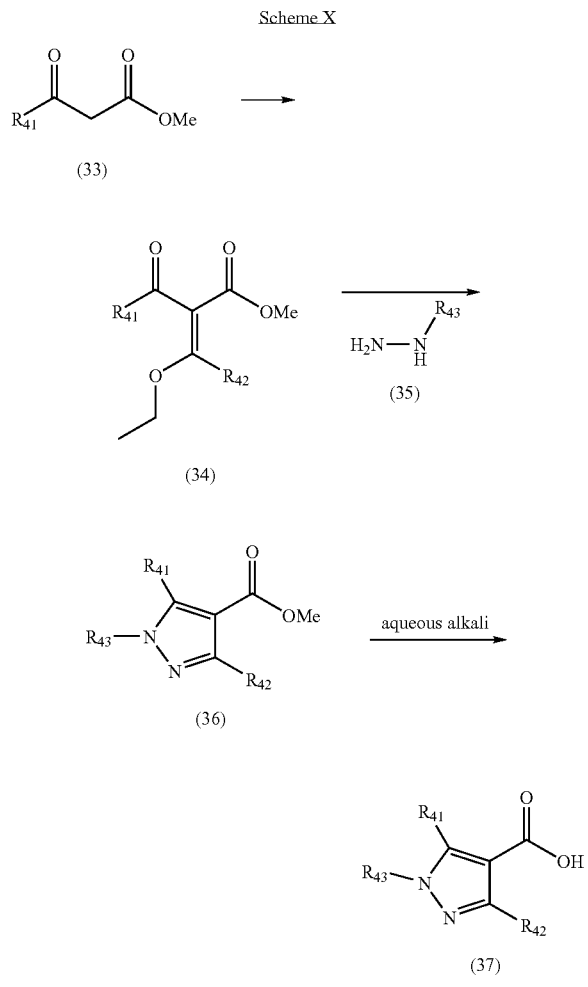

Scheme XI describes another embodiment showing the derivitization of aniline and amine nitrogen atoms. $L_1$ is either a direct bond or a group such as an alkylene group. An amide derivative (38) may be prepared substantially in like manner as (30) and may be deprotected to afford (39). For example, where $PG_1$ is a tert-butoxycarbonyl group, treatment of (38) with TFA followed by neutralization affords (39). (39) may be treated with $R_{44}$—C(O)OH in the presence of a coupling agent such as HBTU or DCC to afford (40), or $R_4$—COCl in the presence of a weak base such as triethylamine, to afford (40). (39) may be treated with an aldehyde or ketone and a reducing agent such as sodium cyanoborohydroide or sodium triacetoxyborohydride to afford (42). (39) may be treated with a sulfonyl chloride $R_{44}SO_2Cl$ in the presence of a weak base such as triethylamine or pyridine to afford (43). (39) may also be treated with an activated aromatic halide such as 4-fluorobenzonitrile in the presence of a weak base such as DIEA, in a solvent such as DMF, at a temperature of from 25° C. to 120° C., to afford the product of ipso halide displacement (41). Other activated or electron-deficient heteroaryl or aryl groups may be employed in this reaction. Alternately, where $L_1$ is a direct bond, the aniline may be arylated by treatment of (39) with cuprous acetate and $Ar_{14}$—$B(OH)_2$, and a weak base such as triethylamine, in a solvent such as DCM or 1,2-dichloroethane, to afford (41).

The derivative (42) may be reductively aminated a second time in the manner described above. (42) may also be acylated or sulfenylated as described above to afford (45) and (46), respectively.

Scheme XI

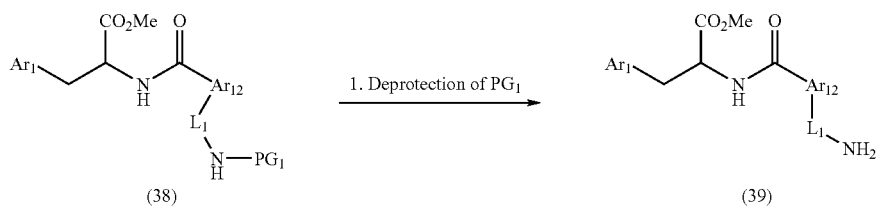

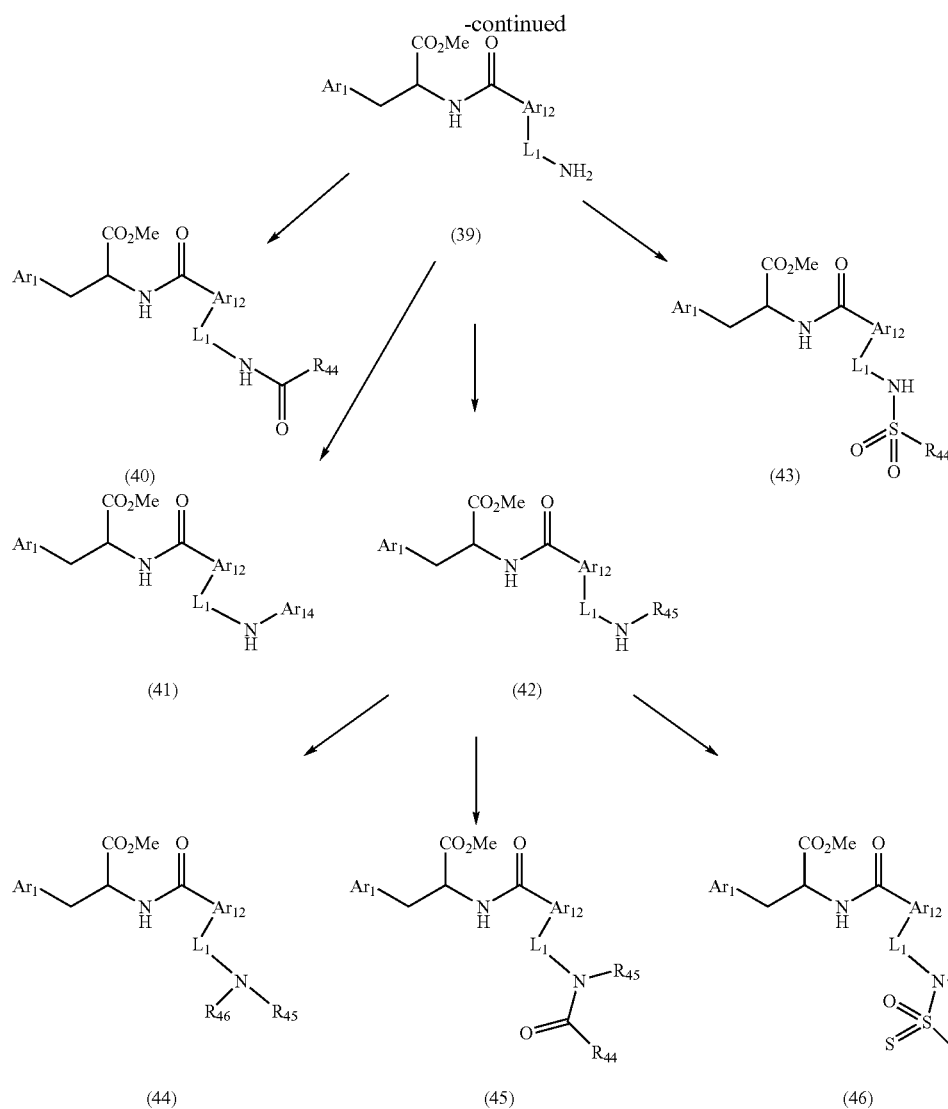

Scheme XII describes an additional embodiment. In Scheme XII, an amino ester and a protected phenolic aryl carboxylic acid or similar species are coupled as in Scheme 1. The protecting group $PG_2$ is removed, where $PG_2$ is a hydroxyl or alcohol protecting group. For example, where $PG_2$ is a tert-butyldimethylsilyl group, treatment of (49) with tetrabutylammonium fluoride in THF affords (50). (50) may be treated with a reagent such as but not limited to potassium carbonate and an alkyl halide $R_{47}$-X, where $R_{47}$ is a group such as alkyl or substituted alkyl and X is a group such as bromo or iodo, to afford (51). Alternately, where $R_{47}$ is an activated or unactivated aromatic or heteroaromatic ring system and X is fluoro, treatment of (50) with $R_{47}$-X in the presence of a base such as but not limited to potassium carbonate in a solvent such as DMF, at a temperature of 25° C. to 120° C., affords (51). Hydrolysis of the ester as described previously affords (52).

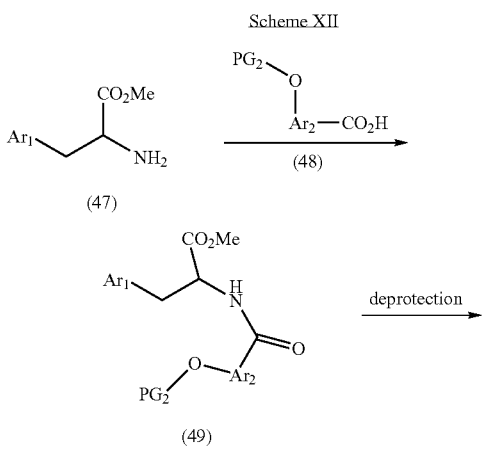

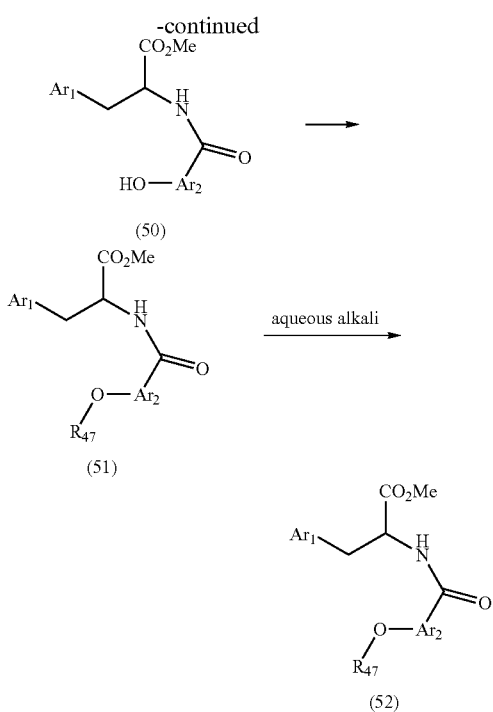

Scheme XIII describes another embodiment. $L_3$ is a group such as -alkylene-. The amino ester (53) may be coupled with a carboxylic acid as described in Scheme I to afford 54. The protecting group $PG_3$ may be removed. Where J is NH and $PG_3$ is, for example, a tert-butoxycarbonylamino group, treatment of (54) with TFA or HCl in dioxane solvent affords the amine salt (55). Where J is O and $PG_3$ is, for example, a benzyl group, treatment of (54) with a reagent such as but not limited to palladium on carbon in a solvent such as methanol or ethanol under a hydrogen atmosphere affords (55). Where J is S and $PG_3$ is, for example, a trityl group, treatment of (54) with catalytic HCl or other acid in a solvent such as methanol under a nitrogen atmosphere affords (55). (55) where J is O or S may be alkylated with a reagent $R_{48}$—X, where $R_{48}$ is (un)substituted alkyl and X is bromo or iodo or chloro, by reacting (55) with a base such as sodium hydride in a solvent such as THF or DMF and treating the reaction mixture with $R_{48}$—X. The resulting compounds (56) and (57) may be processed on to compounds of formula (I). Additionally, (56) may be oxidized to the sulfoxide or sulfone, respectively, by treatment with one or two equivalents of an oxidizing agent such as m-chloroperbenzoic acid in a solvent such as DCM or 1,2-dichloroethane. (55) may be treated with a carboxylic acid $R_{49}$—COOH and a coupling agent such as DCC under conditions described previoulsy to afford (59), where $L_4$ is —C(O)—. Alternately, (55) may be treated with a sulfonyl chloride $R_{49}$—$SO_2$Cl in the presence of a base such as TEA or pyridine to afford (59), where $L_4$ is —$SO_2$—. The amine (55) may be reductively aminated employing a ketone or aldehyde under conditions described previously to afford (58), and (58) may be reductively aminated with a ketone or aldehyde to afford (60). Alternately, the amine (58) may be sulfenylated or acylated as described above to afford (61), where $L_4$ is —$SO_2$— or —C(O)—.

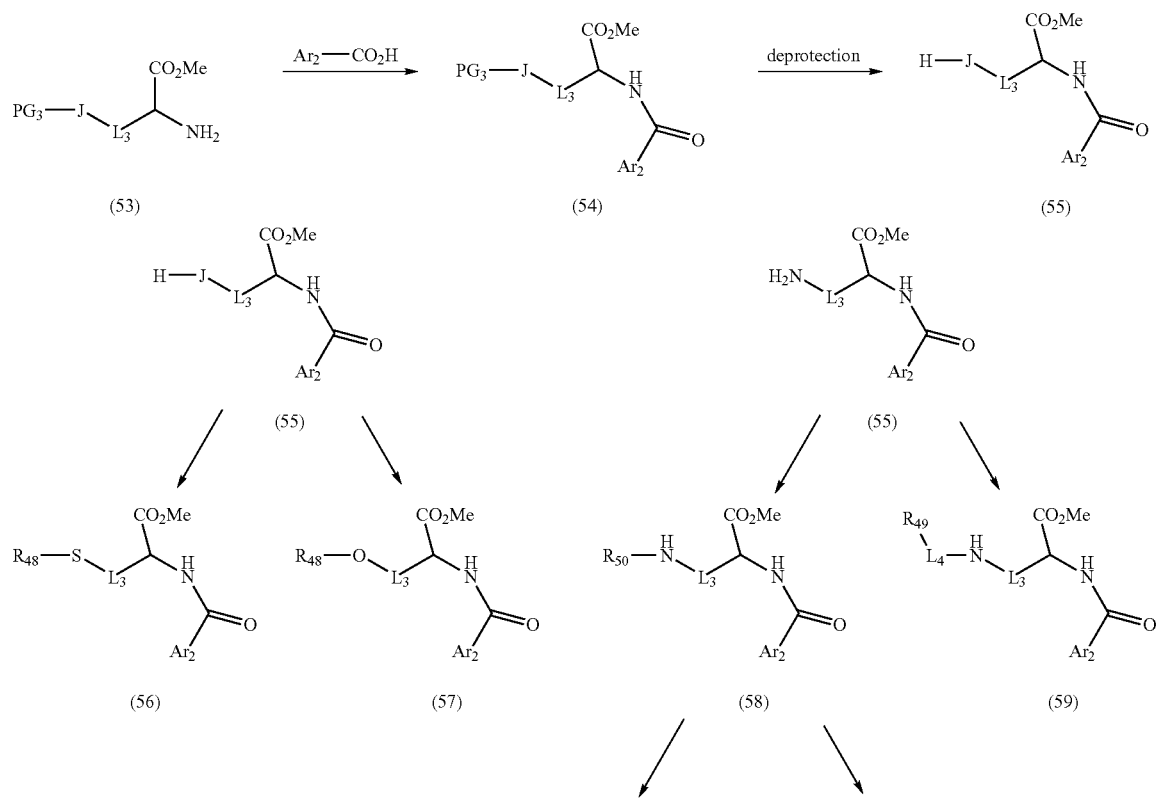

Scheme XIII

-continued

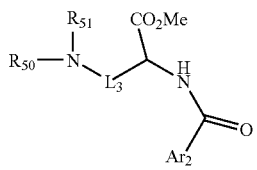

(60)

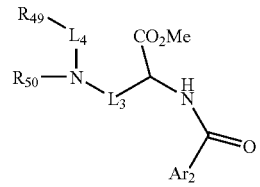

(61)

Scheme XIV describes the synthesis of a compound of formula (66). $R_{85}$ and $R_{86}$ may be groups such as but not limited to hydrogen, alkyl, or -alkylene-aryl. $R_{81}$ may be a group such as the side chain of a natural or unnatural amino acid. $R_{82}$ may be a group such as aryl, heteroaryl, alkyl, or cycloalkyl. $R_{84}$ may be a group such as but not limited to alkyl, aryl, heteroaryl, cycloalkyl, -alkylene-cycloalkyl, or -alkylene-aryl.

Compound (62) represents a nitrogen containing fused heterocyclylaryl ring system which may be synthesized by methods known in the art, such as acid catalyzed condensation of the corresponding amino acid with a carbonyl compound $R_{85}C(O)R_{86}$, followed by protection at nitrogen with a protecting group group such as but not limited to BOC. (62) may be treated with a peptide coupling agent such as DIC or HBTU, in the presence or absence of a base such as DIEA, in a solvent such as DMF of DCM, and an amino ester such as (63), to provide (64). An amine similar in structure to (63) may also be used to provide (64) without a methoxycarbonyl functionality. The phenol functionality of (64) may be functionalized by treatment of (64) with a primary or secondary alcohol in a solvent such as THF, with dialkyl azodicarboxylate and triphenylphosphine at a temperature of from $-20°$ C. to $25°$ C., to give (65) where $R_{82}$ is alkyl, substituted alkyl, or cycloalkyl. (64) may also be treated with a aryl or heteroaryl boronic acid and copper (II) acetate to afford (65) where $R_{82}$ is aryl or heteroaryl. The $PG_1$ group of (65) may be removed as appropriate; the nitrogen thus freed may be functionalized with $R_{83}$, where $R_{83}$ represents groups such as but not limited to a alkylsulfenyl group, a alkoxycarbonyl group, or an acyl or alkanoyl group. The methyl ester of the intermediate may be removed by treatment with, for example, lithium hydroxide in aqueous THF-methanol at a temperature of from $0°$ C. to $25°$ C., to afford (66).

Scheme XIV

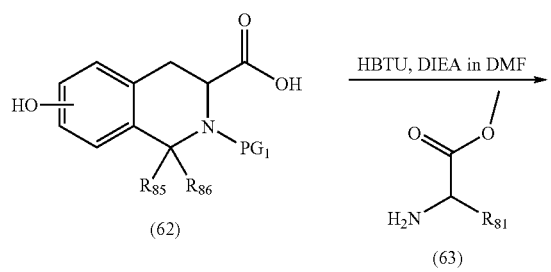

(62)

HBTU, DIEA in DMF (63)

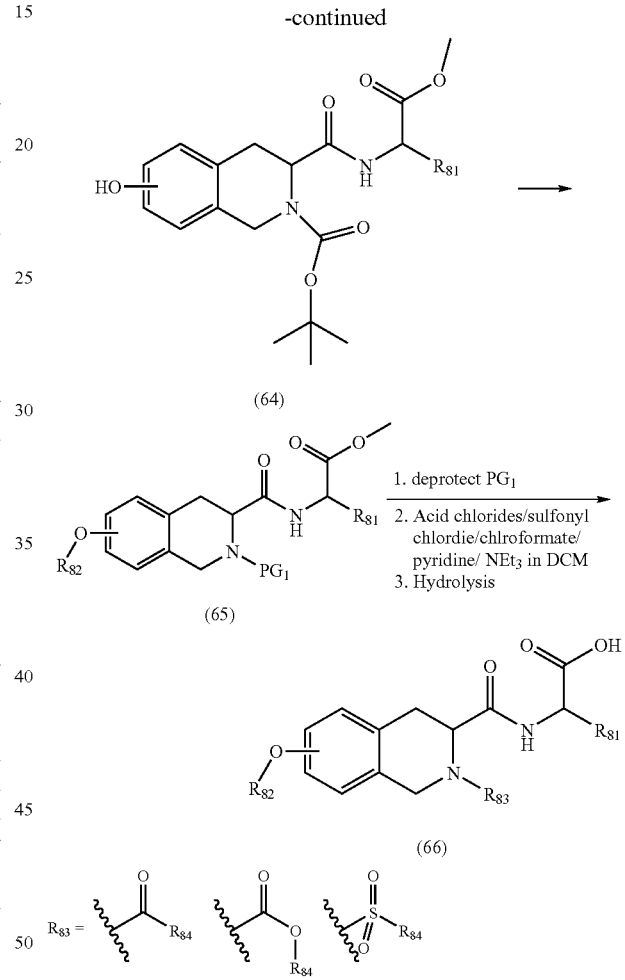

Scheme XV depicts the synthesis of a compound of formula (70). $R_{85}$, $R_{82}$, and $R_{81}$ have the meanings described for Scheme XIV. The phenolic functionality of (67) may be functionalized as in Scheme XIV, and the $PG_1$ protecting group may be removed with a reagent such as TFA, where $PG_1$ is tBOC. (68) may be treated with a reagent such as dichlorodicyanoquinone (DDQ) in a solvent such as toluene, at a temperature of from $25°$ C. to $110°$ C., to afford the acid (69) after hydrolysis of the ester with a reagent such as lithium hydroxide in a solvent such as aqueous THF. In manner similar to that described in Scheme XIV, the acid (69) may be coupled with an amino ester or other amine and the ester, if present, may be hydrolyzed with aqueous alkali to afford (70).

Scheme XV

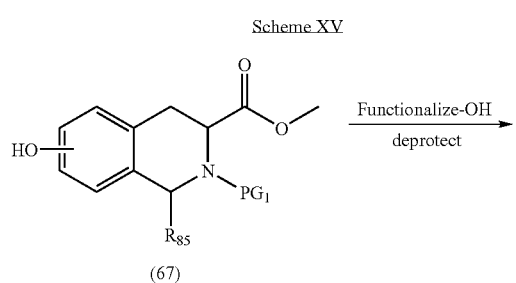

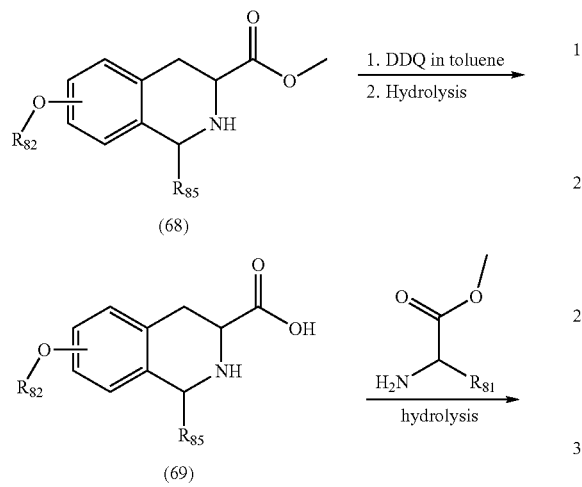

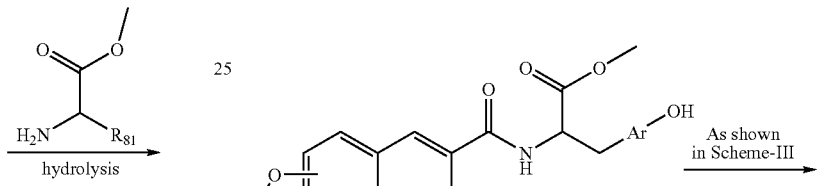

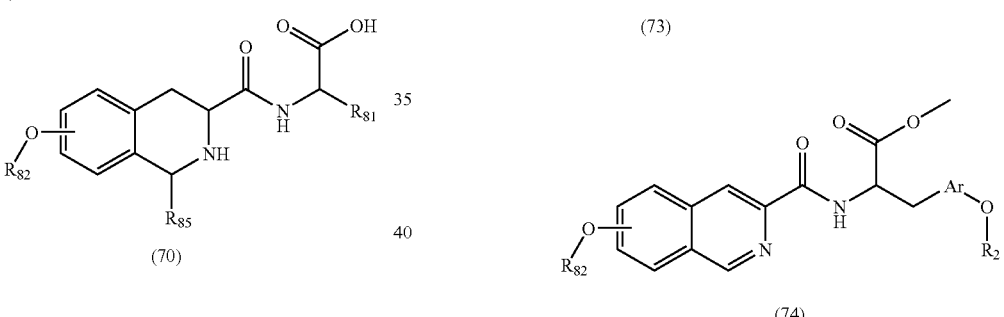

Scheme XVI describes the synthesis of intermediates and further compounds of Formula I. The acid (69) may be coupled with a functionalized bromoaryl alanine ester, or other similar bromoaromatic substituted amine, under conditions described previously to afford (71). (71) may be transformed to (72) employing conditions described in Scheme II. Similarly, (69) may be coupled with a hydroxyaryl alanine ester, or other similar hydroxyaryl or hydroxyheteroaryl substituted amine, to give (73), which may be functionalized as described in Scheme III to provide (74).

Scheme XVI

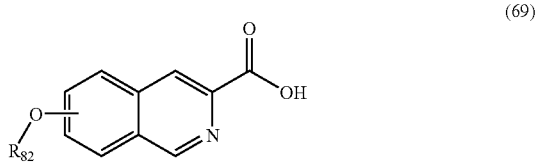

Scheme XVII describes synthesis of compounds of formula (79) $R_{85}$, $R_{82}$, and $R_{81}$ have the meanings as described for Scheme XIV. $PG_2$ represents a hydroxyl protecting group. An N-acylated amino acid ester (75) may be treated with a reagent such as oxalyl chloride in a solvent such as DCM, at a temperature of from 0° C. to 25° C., to afford a imidoyl chloride intermediate, which is treated with a reagent such as but not limited to $FeCl_3$ in DCM, followed by treatment with sulfuric acid in methanol to afford the cyclized product; concomitant removal of $PG_2$ (where $PG_2$ is tert-butyl or benzyl) may occur, to afford (76). Where $PG_2$ is not removed during these above steps, it may be removed, where $PG_2$ is tert-butyl, by treatment with TFA or HCl in dioxane. (76) may be dehydrogenated by treatment with Pd/C in xylene at a temperature of from 25° C. to 130° C., or by treatment with copper (II) acetate in DCM, to afford (77). The phenolic function of (77) may be functionalized as for Scheme XIV; as well, the product (78) after ester hydrolysis may be coupled with an amine or amino acid ester to give, after hydrolysis, the acid (79).

Scheme XVII

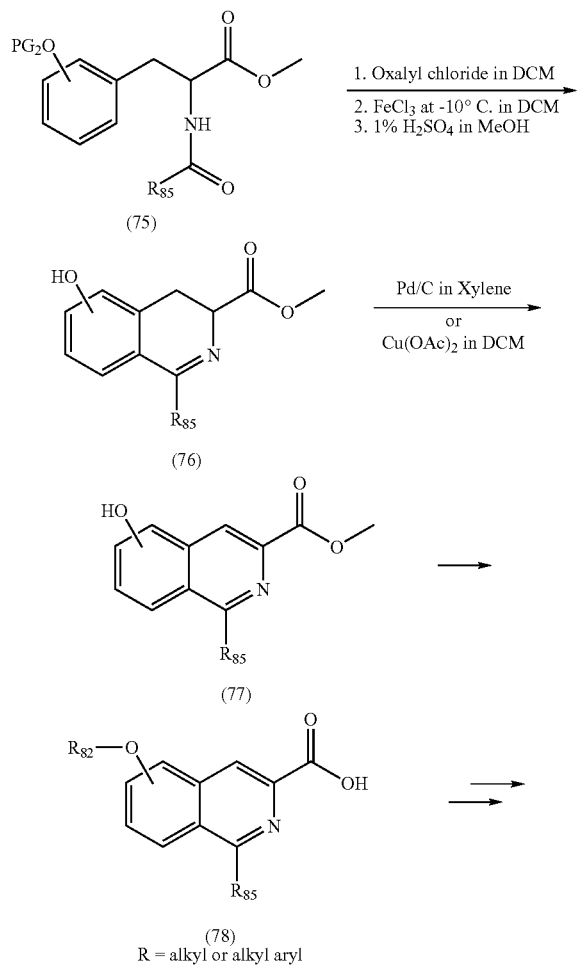

(78)
R = alkyl or alkyl aryl

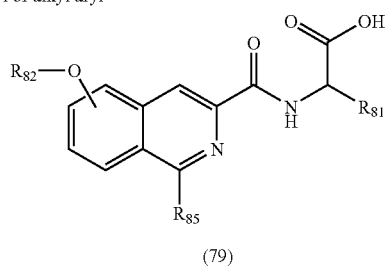

(79)

Scheme XVIII describes the synthesis of a compound of formula (83). $PG_1$ is an amino protecting group, and $R_{87}$ may be a group such as but not limited to alkyl, aryl, or -alkylenearyl. A protected amino acid (80) may be treated with a coupling agent such as DCC and pentafluorophenol in a solvent such as DCM or THF or DMF. The resulting pentafluorophenyl ester is treated with a substituted hydroxyamidine reagent in a solvent such as THF or dioxane, at a temperature of from 25° C. to 100° C., to afford the oxadiazole. The resulting oxadiazole is deprotected at nitrogen to provide the free amine oxadiazole (81). If $PG_1$ is BOC, then treatment with an acidic reagent such as TFA or HCl in doxane serves to remove $PG_1$. The amine may then be utilized; for example, coupling with an acid (82) in the presence of a coupling agent such as HBTU or DCC or DIC in the presence or absence of a base such as NMM or TEA in a solvent such as DMF or THF, affords (83). The method of synthesis of the oxadiazole (81) may thus be applied to carboxylic acid functionalities within a varied context to afford compounds of Formula (I).

Scheme XVIII

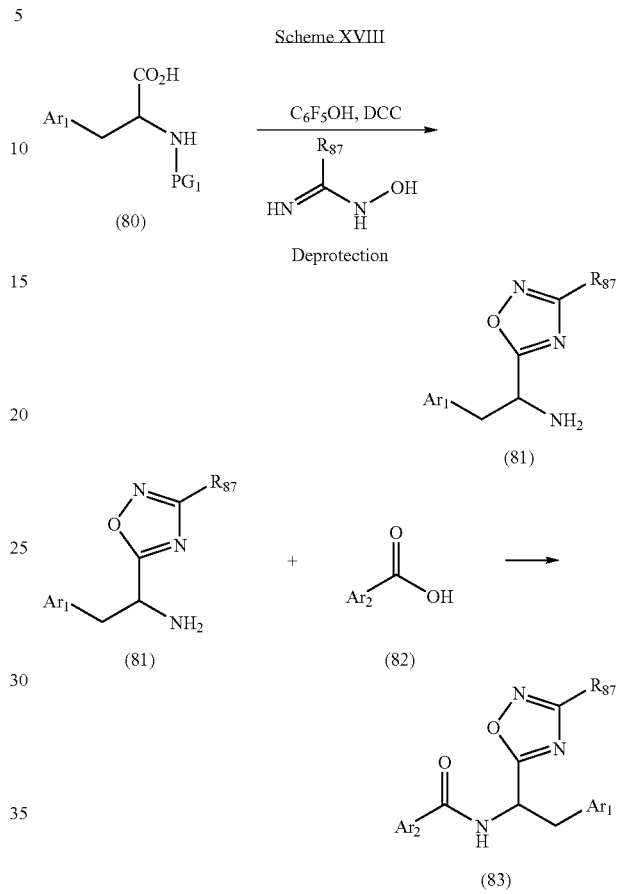

The term "amino protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. Commonly used amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. The related term "protected amino" or "protected amino group" defines an amino group substituted with an amino-protecting group discussed above.

The term "hydroxyl protecting group" as used herein refers to substituents of the alcohol group commonly employed to block or protect the alcohol functionality while reacting other functional groups on the compound. Examples of such alcohol-protecting groups include the 2-tetrahydropyranyl group, 2-ethoxyethyl group, the trityl group, the trichloroacetyl group, urethane-type blocking groups such as benzyloxycarbonyl, and the trialkylsilyl group, examples of such being trimethylsilyl, tert-butyldimethylsilyl, phenyldimethylsilyl, triiospropylsilyl and thexyldimethylsilyl. The choice of alcohol-protecting group employed is not critical so long as the derivatized alcohol group is stable to the condition of subsequent reaction(s) on other positions of the compound of the formulae and can be removed at the desired point without disrupting the remainder of the molecule. The related term "protected hydroxyl" or "protected alcohol" defines a hydroxyl group substituted with a hydroxyl-protecting group as discussed above.

The term "carboxyl protecting group" as used herein refers to substituents of the carboxyl group commonly employed to block or protect the —OH functionality while reacting other functional groups on the compound. Examples of such alcohol-protecting groups include the 2-tetrahydropyranyl group, 2-ethoxyethyl group, the trityl group, the allyl group, the trimethylsilylethoxymethyl group, the 2,2,2-trichloroethyl group, the benzyl group, and the trialkylsilyl group, examples of such being trimethylsilyl, tert-butyldimethylsilyl, phenyldimethylsilyl, triiospropylsilyl and thexyldimethylsilyl. The choice of carboxyl protecting group employed is not critical so long as the derivatized alcohol group is stable to the condition of subsequent reaction(s) on other positions of the compound of the formulae and can be removed at the desired point without disrupting the remainder of the molecule. The related term "protected carboxyl" defines a carboxyl group substituted with a carboxyl-protecting group as discussed above.

Further examples of progroups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981.

The invention further provides pharmaceutical compositions comprising the factor XI or dual Factor IX/XI modulating compounds of the invention. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The term "factor IX" is used herein to refer to blood coagulation factor IX, including both activated and non-activated forms thereof.

The term "therapeutically effective amount" is used herein to denote that amount of a drug or pharmaceutical agent that will elicit the therapeutic response of an animal or human that is being sought.

As used herein, the term "subject" includes mammalian subjects such as, but not limited not, humans, cows, horses, and other agricultural live stock, and birds. In an embodiment, a subject may include one that either suffers from one or more aforesaid diseases or disease states of blood coagulation. Accordingly, in the context of the method of treatment comprising administration of a compound of Formula (I) or a pharmaceutical composition comprising a compound of Formula (I) to a subject prophylactically, or prior to the onset of or diagnosis of such diseases or disease states of blood coagulation.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles. The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines. Also provided by the present invention are prodrugs of the invention.

Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Methanesulfonate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

Other salts which are not pharmaceutically acceptable may be useful in the preparation of compounds of the invention and these form a further aspect of the invention.

In addition, some of the compounds of Formula (I) may form solvates with water or common organic solvents. Such solvates are also encompassed within the scope of the invention.

Thus, in another aspect of the present invention, there is provided a pharmaceutical composition comprising a therapeutically effective amount of a compound of Formula (I), or a pharmaceutically acceptable salt, solvate, or prodrug therof, and one or more pharmaceutically acceptable carriers, excipients, or diluents. In an embodiment of the pharmaceutical composition, the compound of Formula (I) is an antagonist of factor XI or an antagonist of factor IX/XI activity. In another embodiment of the pharmaceutical composition, the compound of Formula (I) is a partial antagonist of factor XI activity or of both factor XI/IX activity, wherein a partial antagonist comprises a compound that inhibits less than complete activity at a physiological dose. In another embodiment of the pharmaceutical composition, the compound of Formula (I) is a partial antagonist of factor XI activity or of factor IX/XI activity, wherein the compound of Formula (I) inhibits up to 95% of factor IX or factor IX/XI activity. In another embodiment of the pharmaceutical composition, the compound of Formula (I) is a partial antagonist of factor XI activity or of factor IX/XI activity, wherein the compound of Formula (I) inhibits up to 80% of factor XI or factor IX/XI activity. In another embodiment of the pharmaceutical composition, the compound of Formula (I) is a partial antagonist of factor XI activity or of factor IX/XI activity, wherein the compound of Formula (I) inhibits up to 50% of factor XI or IX/XI activity. In another embodiment of the pharmaceutical composition, the compound of Formula (I) antagonizes blood clotting mediated by factor XI or IX/XI.

In another aspect of the present invention, there is provided a pharmaceutical composition comprising a therapeutically effective amount of a compound of Formula (I), or a pharmaceutically acceptable salt, solvate, or prodrug therof, and one or more pharmaceutically acceptable carriers, excipients, or diluents, wherein said therapeutically effective amount of Formula (I) preferentially inhibits the intrinsic clotting cascade as compared to the extrinsic clotting cascade. In an embodiment of the pharmaceutical composition, said therapeutically effective amount of Formula (I) inhibits the intrinsic clotting cascade by greater than 80% and inhibits the extrinsic clotting cascade by less than 50%. In another embodiment of the pharmaceutical composition, said therapeutically effective amount of Formula (I) comprises an amount sufficient to achieve and maintain a sustained blood level that at least partially antagonizes factor XI or factor IX/XI biological activity. In another embodiment, said sustained blood level comprises a concentration ranging from about 0.01 µM to 2 mM. In another embodiment, said sustained blood level comprises a concentration ranging from about 1 µM to 300 µM. In another embodiment, said sustained blood level comprises a concentration ranging from about 20 µM to about 100 µM. In another embodiment, said sustained blood level comprises a concentration ranging from about 1 µM to 10 µM.

In another aspect of the present invention, there is provided a pharmaceutical composition comprising a therapeutically effective amount of a compound of Formula (I), or a pharmaceutically acceptable salt, solvate, or prodrug therof, and one or more pharmaceutically acceptable carriers, excipients, or diluents, wherein said therapeutically effective amount comprises a sufficient amount of the compound of Formula (I) to at least partially inhibit the biological activity of factor XI or factor IX/XI in a subject, a sufficient amount of the compound of Formula (I) for at least partial amelioration of at least one factor XI- or factor IX/XI-mediated disease, or a sufficient amount of the compound of Formula (I) to at least partially inhibit the intrinsic clotting cascade in a subject. In an embodiment of the pharmaceutial composition, said factor XI- or factor IX/XI-mediated disease comprises stroke. In another embodiment of the pharmaceutial composition, said factor XI- or factor IX/XI-mediated disease comprises deep vein thrombosis. In another embodiment of the pharmaceutial composition, said factor XI- or factor IX/XI-mediated disease comprises deep vein thrombosis, wherein said thrombosis is associated with surgical procedures, long periods of confinement, acquired or inherited pro-coagulant states including anti-phospholipid antibody syndrome, protein C deficiency and protein S deficiency, or acute and chronic inflammation including recurrent miscarriage or Systemic Lupus Erythmatosis (SLE). In another embodiment, said factor XI- or factor IX/XI-mediated disease comprises excessive clotting associated with the treatment of kidney diseases by hemodialysis and/or venous hemofiltration. In another embodiment, said factor XI- or factor IX/XI-mediated disease comprises cardiovascular disease. In another embodiment, said factor XI- or factor IX/XI-mediated disease comprises cardiovascular disease, wherein said cardiovascular disease comprises myocardial infarction, arrhythmia, or aneurysm.

In another aspect, the present invention provides a pharmaceutical composition comprising a therapeutically effective amount of the compound of Formula (I), and one or more pharmaceutically acceptable carriers, excipients, or diluents, wherein said pharmaceutical composition is used to replace or supplement compounds that reduce clotting.

In another aspect, the present invention provides a pharmaceutical composition comprising a therapeutically effective amount of the compound of Formula (I), and one or more pharmaceutically acceptable carriers, excipients, or diluents, further comprising one or more therapeutic agents.

In another aspect, the present invention provides a method for the inhibition of the normal biological function of factor XI or factor IX/XI comprising administering to a subject in need thereof a compound of Formula (I). In embodiment of the method, said compound of Formula (I) is an antagonist of factor XI or factor IX/XI activity. In another embodiment of the method, said compound of Formula (I) antagonizes blood clotting mediated by factor XI or factor IX/XI. In another embodiment of the method, said compound of Formula (I) is administered in an amount sufficient to partially antagonize the biological activity of factor XI or factor IX/XI in said subject. In another embodiment of the method, said compound of Formula (I) is a partial antagonist of factor XI or factor IX/XI activity. In another embodiment of the method, said compound of Formula (I) antagonizes blood clotting mediated by factor XI or factor IX/XI. In another embodiment of the method, said compound of Formula (I) is administered in an amount sufficient to partially antagonize the biological activity of factor XI or factor IX/XI in said subject. In another embodiment of the method, said pharmaceutical composition is administered in the form of an oral dosage or parenteral dosage unit. In another embodiment of the method, said compound of Formula (I) is administered as a dose in a range from about 0.01 to 1,000 mg/kg of body weight per day. In another embodiment of the method, said compound of Formula (I) is administered as a dose in a range from about 0.1 to 100 mg/kg of body weight per day. In another embodiment of the method, said compound of Formula (I) is administered as a dose in a range from about 0.5 to 10 mg/kg of body weight per day. In another embodiment, said compound of Formula (I) is used to replace or supplement compounds that reduce clotting.

In another aspect, the present invention provides a method for the inhibition of the normal biological function of factor XI or factor IX/XI comprising administering to a subject in need thereof a compound of Formula (I), wherein said compound of Formula (I) is administered to said subject as a pharmaceutical composition comprising a therapeutically effective amount of said compound of Formula (I) and one or more pharmaceutically acceptable carriers, excipients, or diluents. In an embodiment of the method, said therapeutically effective amount of the compound of Formula (I) comprises a sufficient amount of the compound of Formula (I) to at least partially inhibit the intrinsic clotting cascade in said subject. In another embodiment of the method, said therapeutically effective amount of Formula (I) preferentially inhibits the intrinsic clotting cascade as compared to the extrinsic clotting cascade. In another embodiment of the method, said therapeutically effective amount of Formula (I) inhibits the intrinsic clotting cascade by greater than 80% and inhibits the extrinsic clotting cascade by less than 50%. In another embodiment of the method, said therapeutically effective amount of the compound of Formula I comprises an amount sufficient to achieve and maintain a sustained blood level that at least partially antagonizes factor XI or factor IX/XI biological activity. In another embodiment, said sustained blood level comprises a concentration ranging from about 0.01 µM to 2 mM. In another embodiment, said sustained blood level comprises a concentration ranging from about 1 µM to 300 µM In another embodiment, said sustained blood level comprises a concentration ranging from about 1 µM to 10 µM In another embodiment, said sustained blood level comprises a concentration ranging from about 20 µM to about 100 µM. In another embodiment of the method, said pharmaceutical composition further comprises one or more therapeutic agents.

In another aspect, the present invention provides a method for the inhibition of the normal biological function of factor XI or factor IX/XI comprising administering to a subject in need thereof a compound of Formula (I), wherein said compound of Formula (I) is a partial antagonist of factor XI or factor IX/XI, wherein a partial antagonist comprises a compound that inhibits less than complete activity at a physiological dose. In an embodiment of the method, said compound of Formula (I) inhibits up to 95% of factor XI or factor IX/XI activity. In another embodiment of the method, said compound of Formula (I) inhibits up to 80% of factor XI or factor IX/XI activity. In another embodiment of the method, said compound of Formula (I) inhibits up to 50% of factor XI or factor IX/XI activity.

In another aspect, the present invention provides a method for the inhibition of the normal biological function of factor XI or factor IX/XI comprising administering to a subject in need thereof a compound of Formula (I), wherein said compound of Formula (I) is administered to said subject as a pharmaceutical composition comprising a therapeutically effective amount of said compound of Formula (I) and one or more pharmaceutically acceptable carriers, excipients, or diluents, wherein said therapeutically effective amount of the compound of Formula (I) comprises a sufficient amount of the compound of Formula (I) for treatment or prevention of factor XI- or factor IX/XI-mediated diseases. In an embodiment of the method, said factor XI- or factor IX/XI-mediated disease comprises stroke. In another embodiment of the method, said factor XI- ofr factor IX/XI-mediated disease comprises deep vein thrombosis. The thrombosis may be associated with surgical procedures, long periods of confinement, acquired or inherited pro-coagulant states including anti-phospholipid antibody syndrome, protein C deficiency and protein S deficiency, or acute and chronic inflammation including recurrent miscarriage or Systemic Lupus Erythmatosis (SLE). In another embodiment of the method, said factor XI- or factor IX/XI-mediated disease comprises clotting associated with the treatment of kidney disease by hemodialysis and/or venous hemofiltration. In another embodiment of the method, said factor XI- or factor IX/XI-mediated disease comprises cardiovascular disease. The cardiovascular disease may be associated myocardial infarction, arrhythmia, or aneurysm.

In a further aspect of the present invention, the factor XI or dual factor IX/XI modulators of the invention are utilized in adjuvant therapeutic or combination therapeutic treatments with other known therapeutic agents.

The term "treatment" as used herein, refers to the full spectrum of treatments for a given disorder from which the patient is suffering, including alleviation of one, most of all symptoms resulting from that disorder, to an outright cure for the particular disorder or prevention of the onset of the disorder.

The following is a non-exhaustive listing of adjuvants and additional therapeutic agents which may be utilized in combination with the factor IXa antagonists of the present invention:

1. Analgesics: Aspirin

2. NSAIDs (Nonsteroidal anti-inflammatory drugs): Ibuprofen, Naproxen, Diclofenac 3. DMARDs (Disease-Modifying Antirheumatic drugs): Methotrexate, gold preparations, hydroxychloroquine, sulfasalazine 4. Biologic Response Modifiers, DMARDs: Etanercept, Infliximab Glucocorticoids In another embodiment, the present invention provides a method of treating or preventing a factor IXa mediated diseases, the method comprising administering to a subject in need thereof, a therapeutically effective amount of a compound of Formula (I) alone or in combination with therapeutic agents selected from the group consisting of antibiotics, hormones, biologic response modifiers, analgesics, NSAIDs, DMARDs, glucocorticoids, thrombolytic agents, antidepressants, and anticonvulsants.

The compound of Formula (I) of the present invention, may be administered at a dosage level of from about 0.01 to 1000 mg/kg of the body weight of the subject being treated. In another embodiment, The compound of Formula (I) of the present invention, may be administered at a dosage range between 0.01 and 100 mg/kg In another embodiment, the compound of Formula (I) of the present invention, may be administered at a dosage range between 0.5 to 10 mg/kg of body weight per day. The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms will generally contain between from about 5 mg to about 500 mg of active ingredient. This dosage may be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

The general procedures used in the methods of the present invention are described below.

EXAMPLES

General Experimental

LC-MS data was obtained using gradient elution on a Waters 600 controller equipped with a 2487 dual wavelength detector and a Leap Technologies HTS PAL Autosampler using an YMC Combiscreen ODS-A 50×4.6 mm column. A three minute gradient was run from 25% B (97.5%acetonitrile, 2.5% water, 0.05% TFA) and 75% A (97.5% water, 2.5% acetonitrile, 0.05% TFA) to 100% B. The mass spectrometer used was a Micromass ZMD instrument. All data was obtained in the positive mode unless otherwise noted. $^1$H NMR data was obtained on a Varian 400 MHz spectrometer.

Common names and definitions for resin reagents used in the disclosure are;

| | |
|---|---|
| Merrifield | p-Chloromethyl polystyrene |
| Hydroxy-Merrifield | p-Hydroxymethyl polystyrene |
| Wang | (4-Hydroxymethyl)phenoxymethyl polystyrene |
| Wang carbonate | 4-(p-nitrophenyl carbonate) phenoxymethyl polystyrene |
| Rink Resin | 4-(2',4'-Dimethoxyphenyl-Fmco-aminomethyl)-phenoxy polystyrene resin |
| Wang Bromo Resin | (4-Bromomethyl)phenoxymethyl polystyrene |
| THP Resin | 3,4-Dihydro-2H-pyran-2-ylmethoxymethyl polystyrene |

Aldehyde resin can refer to the following:
4-Benzyloxybenzaldehyde polystyrene
3-Benzyloxybenzaldehyde polystyrene
4-(4-Formyl-3-methoxyphenoxy)butyryl-aminomethyl polystyrene
2-(4-Formyl-3-methoxyphenoxy)ethyl polystyrene
2-(3,5-dimethoxy-4-formylphenoxy)ethoxy-methyl polystyrene
2-(3,5-dimethoxy-4-formylphenoxy)ethoxy polystyrene
(3-Formylindolyl)acetamidomethyl polystyrene
(4-Formyl-3-methoxyphenoxy) grafted (polyethyleneglycol)-polystyrene; or
(4-Formyl-3-methoxyphenoxy)methylpolystyrene.

Abbreviations used in the Examples are as follows:
APCI=atmospheric pressure chemical ionization
BOC=tert-butoxycarbonyl
BOP=(1-benzotriazolyloxy)tris(dimethylamino)phosphonium hexafluorophosphate
d=day
DIAD=diisopropyl azodicarboxylate
DCC=dicyclohexylcarbodiimide
DCE=1,2-dichloroethane
DCM=dichloromethane
DIC=diisopropylcarbodiimide
DIEA=diisopropylethylamine
DMA=N,N-dimethylacetamide
DMAP=dimethylaminopyridine
DME=1,2 dimethoxyethane
DMF=N,N-dimethylformamide
DMPU=1,3-dimethypropylene urea
DMSO=dimethylsulfoxide
EDC=1-ethyl-3-(3-dimethylaminopropyl)-carbodiimide hydrochloride
EDTA=ethylenediamine tetraacetic acid
ELISA=enzyme-linked immunosorbent assay
ESI=electrospray ionization
ether=diethyl ether
EtOAc=ethyl acetate
FBS=fetal bovine serum
g=gram
h=hour
HBTU=O-benzotriazol-1-yl-N,N,N',N'-tetramethyluronium hexafluorophosphate
HMPA=hexamethylphosphoric triamide
HOBt=1-hydroxybenzotriazole
Hz=hertz
i.v.=intravenous
kD=kiloDalton
L=liter
LAH=lithium aluminum hydride
LDA=lithium diisopropylamide
LPS=lipopolysaccharide
M=molar
m/z=mass to charge ratio
mbar=millibar
MeOH=methanol
mg=milligram
min=minute
mL=milliliter
mM=millimolar
mmol=millimole
mol=mole
mp=melting point
MS=mass spectrometry
N=normal
NMM=N-methylmorpholine, 4-methylmorpholine
NMR=nuclear magnetic resonance spectroscopy
p.o.=per oral
PBS=phosphate buffered saline solution
PMA=phorbol myristate acetate
ppm=parts per million
psi=pounds per square inch
Rf=relative TLC mobility
rt=room temperature
s.c.=subcutaneous
SPA=scintillation proximity assay
TEA=triethylamine
TFA=trifluoroacetic acid
THF=tetrahydrofuran
THP=tetrahydropyranyl
TLC=thin layer chromatography
TMSBr=bromotrimethylsilane, trimethylsilylbromide
Tr=retention time Thus, in an embodiment, the following compounds were synthesized according to the Schemes described herein.

General procedure A:

To a solution of a carboxylic acid (1.0-1.5 mmol) in DMF (6 mL) was added an amino acid methyl ester (1.0-1.5 mmol), HBTU (1.0-1.5 mmol), and DIEA (2.0-3.0 mmol) and the mixture was stirred overnight. After completion of the reaction, sufficient amount of water was added and the mixture was extracted with ethyl acetate (3×15 ml). The combined organic layer was washed with water and brine, and then dried over sodium sulfate. The solvent was removed in vacuum to afford the amide, which was used for further transformation without further purification or purified by flash chromatography.

General procedure B:

To a mixture of phenol and aryl or heteroaryl fluoride (2 eq) in DMF was added solid potassium carbonate (10 eq), and the mixture was heated at 80° C. for 12 h. After completion of the reaction, sufficient amount of water was added, and the mixture was extracted with ethyl acetate. The combined organic layer was washed with water and brine, dried over sodium sulfate. The solvent was removed in vacuum and the crude material obtained was purified by flash chromatography to afford the desired ether.

General procedure C:

To a solution of ester in THF-CH$_3$OH (4:1), 2 N lithium hydroxide solution (5 eq) was added, and the resulting reaction mixture was stirred at 0° C. for 30 minutes and then warmed to room temperature. After completion of the reaction the mixture was acidified with 2N HCl, extracted with ethyl acetate, the organic layer was washed with brine, dried over sodium sulfate, and the solvent was removed in vacuo to afford the product.

General procedure D:

To a solution of an aryl bromide or heteroaryl bromide in DME or toluene were added a boronic acid (5 eq), Pd(PPh$_3$)$_4$ (ca. 5 mol %), 2N Na$_2$CO$_3$ solution (5 eq). The mixture was heated at 75° C. for 12 h. After completion of the reaction, solvent was evaporated in vacuo. During the reaction, most of the ester was hydrolyzed to the corresponding acid. Therefore, crude product so obtained was re-esterfied by dissolving it in CH$_3$OH containing 1% HCl. The mixture was refluxed for 6 h and after the completion of the reaction, the reaction mixture was concentrated under reduced pressure. The residue was purified by column chromatography (silica, CH$_2$Cl$_2$) to provide the desired ester. The resulting ester was hydrolyzed as described in procedure C yielding the acid.

General procedure E:

To a solution of an aniline or amine (1.0 mmol) in DCE (10 mL) was added an aldehyde (2.0-2.2 mmol), acetic acid (3.0 mmol) and sodium triacetoxyborohydride (2.5 mmol) or sodium cyanoborohydride and the mixture was stirred overnight. After completion of the reaction, 50 mL of DCM was added and the organic layer was washed with saturated sodium bicarbonate solution and brine, and then dried over sodium sulfate. The solvent was removed in vacuum to afford the product, which was purified by flash chromatography.

General procedure F:

To a solution of an aniline or amine (1.0 mmol) in DCM (10 mL) was added a sulfonyl chloride (1.0 mmol), pyridine (10.0 mmol), and the mixture was stirred overnight. After completion of the reaction, 50 mL of DCM was added and the organic layer was washed with 1N HCl, saturated sodium bicarbonate solution, and brine, and then dried over sodium sulfate. The solvent was removed in vacuum to afford the sulfonamide, which was purified by flash chromatography.

General procedure G:

A flask is charged with phenol or aniline (1.0 equiv), Cu(OAc)$_2$ (1.0 equiv), arylboronic acid (1.0-3.0), and powdered 4 A° molecular sieves. The reaction mixture is diluted with CH$_2$Cl$_2$ to yield a solution approximately 0.1M in phenol or aniline, and the Et$_3$N (5.0 equiv) is added. After stirring the colored heterogeneous reaction mixture for 24 h at 25° C. under ambient atmosphere, the resulting slurry is filtered and the diaryl ether or diaryl amine is isolated from the organic filtrate by flash chromatography.

General procedure H:

To a solution of a phenol (1.0 mmol) in DMF (5 mL) was added an alkyl halide (1.2 mmol) (a catalytic amount of NaI is added for alkyl chloriirdes), and potassium carbonate (2.5 mmol) and the mixture heated at 70° C. overnight. After completion of the reaction, 5 mL of ethyl acetate and 5 mL of water was added. The organic layer was washed with water, and then dried over sodium sulfate. The solvent was removed in vacuum to afford the ether, which was purified by flash chromatography.

General Procedure I:

To a solution of ester in THF was added lithium hydroxide (3-4 eq), water, and methanol. The ratio of THF/water/methanol is 4:1:1. The reaction mixture was stirred at rt for 1-1.5 h. A 10% solution of citric acid was added to adjust the pH between 6-7. Ethyl acetate was added and the organic layer is separated. The aqueous layer was extracted with ethyl acetate twice. The combined organic layer was washed with brine, dried (Na$_2$SO$_4$), and concentrated under reduced pressure to give the product.

General Procedure J:

To a stirring solution of an aniline (2 mmol) dissolved in DCM containing pyridine (4 mmol) was added acid chloride (2.5 mmol) at 0° C. The reaction mixture was stirred at rt for 3 h, extracted with DCM, washed with 1M HCl and brine, and evaporation followed by column chromatography purification gave the amide.

General Procedure K:

To a stirring solution of amine or aniline (1 mmol) dissolved in DCM containing triethyl amine (4 mmol), was added a chloroformate (1.5 mmol) at RT. The reaction mixture was stirred for 1-1.5 h. The reaction mixture was concentrated and purified by chromatography to give the carbamate.

General Procedure L:

To a stirring solution of amine or aniline (1 mmol) dissolved in DCM containing DIEA (4 mmol) was added an isocyanate (1.5 mmol) at rt. The reaction mixture was stirred for 1-1.5 h. The reaction mixture was concentrated and purified by chromatography to give the urea.

The above general methods are for illustration only; Alternative conditions that may optionally be used include: Use of alternative solvents, alternative stoichiometries of reagents, alternative reaction temperatures and alternative methods of purification.

Synthesis of
4'-Trifluoromethyl-biphenyl-4-carboxylic acid

The title compound was made as described in general procedure D using 4-bromo benzoic acid (10 g, 49.4 mmol), 4-trifluoromethyl phenylboronic acid (14.17 g, 74.61 mmol), palladium tetrakis-triphenylphosphine (5.7 g, 4.974 mmol) and 2N Na$_2$CO$_3$ aq. solution (150 mL, 149.2 mmol) in 500 ml of toluene. After the reaction is complete, the reaction mixture was acidified with 2N HCl then filtered. The resulting solid was dissolved in ethyl acetate then passed through a short column of silica gel gave giving 9.7 g of the compound as a white solid.

(2S)-Amino-3-(2'-phenoxy-biphenyl-4-yl)-propionic
acid methyl ester

The title compound was prepared following the procedure D using (L)-4-bromophenylalanine (8.55 g, 35.0 mmol), 2-phenoxyphenyl boronic acid (10.00 g, 46.73 mmol), and palladium tetrakis(triphenylphosphine) (4.0 g, 10% mmol) ) and 2N Na$_2$CO$_3$ aq. solution (70 mL, 140 mmol) in 140 ml of DME. After removal of solvents, the solid was washed with ether to afford the title compound as the in HCl salt form (10.0 g, 26.20 mmol).

(2S)-Amino-3-(4'-trifluoromethoxy-biphenyl-4-yl)-
propionic acid methyl es ter

The title compound was prepared following the procedure D using (L)-4-bromophenylalanine (8.0 g, 32.7 mmol), 4-trifluoromethoxybenzene boronic acid (10.1 g, 49.1 mmol), palladium tetrakis(triphenylphosphine) (3.7 g, 3.2 mmol), and Na$_2$CO$_3$ (2.0 N, 80.0 mL, 160 mmol) in DME (300 mL). After removal of solvent, the solid was washed with ether to afford the title compound as the HCl salt (10.8 g, 28.7 mmol).

(2S)-Amino-3-(4'-trifluoro-biphenyl-4-yl)-propionic
acid methyl ester

The title compound was prepared exactly following the procedure D using (L)-4-bromophenylalanine (9.0 g, 36.8 mmol), 4-trifluoromethylbenzene boronic acid (10.48 g, 55.2 mmol), palladium tetrakis-triphenylphosphine (4.25 g, 3.6 mmol), and aqueous Na$_2$CO$_3$ (aq)(2.0 N, 90.0 mL, 185 mmol) in DME (300 mL). After removal of solvent, the solid was washed with ether to afford the title compound in HCl salt formas the HCl salt (10.5 g, 29.2 mmol).

Example 1

(2S)-[5-Bromo-2-(4-trifluoromethylbenzyloxy)-benzoylamine]-3-(2'-phenoxybiphenyl-4-yl)-propionic acid 5-Bromo-salicylic acid (2.16 g, 10 mmol) was first transformed into 2-acetyl-5-bromo-salicylic acid (252 g) with acetyl chloride (2.34 g, 30 mmol) and pyridine (3.95 g, 50 mmol) in DCM. The above acid (1.29 g, 5.0 mmol) was converted into acid chloride by using oxalyl chloride (1.97 g, 15 mmol) and catalytic amount of DMF in DCM, then 2-phenoxy-biphenyl alanine (1.45 g, 5.0 mmol) and DIEA (0.77 g, 6.0 mmol) were added to the acid chloride to form (2S)-[5-bromo-2-hydroxybenzoylamine]-3-(2'-phenoxybiphenyl-4-yl)-propionic acid methyl ester (1.92 g). The above methyl ester (50 mg, 0.092 mmol) was reacted with 4-trifluoromethyl benzyl bromide (44 mg, 0.18 mmol) as described in general procedure H to provide (2S)-[5-bromo-2-(4-trifluoromethylbenzyloxy)-benzoylamine]-3-(2'-phenoxybiphenyl-4-yl)-propionic acid methyl ester (55 mg). The ester was hydrolyzed following general procedure C to give the title compound (52 mg).

$^1$H NMR (400 MHz, CDCl$_3$): δ 3.03, 3.22 (ABX, 2H), 4,92 (m, 3H), 6.64 (d, 1H), 6.76 (m, 2H), 6.85(dd, 1H), 6.93 (m, 2H), 7.00 (d, 2H), 7.07-7.24 (m, 7H), 7.39 (m, 4H), 8.22 (d, 1H), 8.26 (d, 1H); LC/MS: 690 (M+1)$^+$.

Example 2

(2S)-(5-Bromo-2-heptyloxy-benzoylamino)-3-[2'-(4-trifluoromethyl-phenoxy)-biphenyl-4-yl]-propionic acid 5-Bromo-2-heptyloxy-benzoic acid was prepared by reacting 5-bromo-2-hydroxy-benzoic acid methyl ester (1.0 g, 4.32 mmol) with iodoheptane (1.46 g, 6.49 mmol) as per general procedure H with potassium carbonate (1.5 g, 10.8 mmol) added. The ester thus obtained was subjected to hydrolysis as per general procedure C to yield the 5-bromo-2-heptyloxy-benzoic acid (0.950 g).

(2S)-Amino-3-(2'-hydroxy-biphenyl-4-yl)-propionic acid was prepared from 4-bromophenylalanine (5.0 g, 20.48 mmol), 2-hydroxyphenylboronic acid (4.23 g, 30.72 mmol) and Pd (PPh$_3$)$_4$ (2.36 g, 2.038 mmol) as per procedure D to yield the corresponding amino acid which was further esterified with anhydrous MeOH containing 2-3 ml of HCl to yield the corresponding HCl salt of the (2S)-amino-3-(2'-hydroxy-biphenyl-4-yl)-propionic acid methyl ester (5.0 g).

5-Bromo-2-heptyloxy-benzoic acid (0.231 g, 0.738 mmol) and the (2S)-amino-3-(2'-hydroxy-biphenyl-4-yl)-propionic acid methyl ester (0.200 g, 0.738 mmol) were then combined as per general procedure A with HBTU (0.335 g, 0.885 mmol) and diisopropylethylamine (0.285 g, 2.21 mmol) to yield the (2S)-(5-bromo-2-heptyloxy-benzoylamino)-3-(2'-hydroxy-biphenyl-4-yl)-propionic acid methyl ester (0.200 g).

The title compound was the prepared from (2S)-(5-bromo-2-heptyloxy-benzoylamino)-3-(2'-hydroxy-biphenyl-4-yl)-propionic acid methyl ester (0.080 g, 0.140 mmol) and the 4-trifluoromethylphenylboronic acid (0.050 g, 0.281 mmol) as per general procedure G to give (2S)-(5-bromo-2-heptyloxy-benzoylamino)-3-[2'-(4-trifluoromethyl-phenoxy)-biphenyl-4-yl]-propionic acid methyl ester which was further hydrolyzed as per general procedure C to give the title compound (0.020 g).

$^1$H-NMR(400 MHz, CDCl$_3$): δ 1.14(t, 3H), 1.53 (m, 8H), 1.92(m, 2H), 3.6(m, 2H), 4.21(m, 2H), 5.21(m, 1H), 7.12(d, 1H), 7.22(m, 2H), 7.36(d, 1H), 7.5(d, 2H), 7.58(m, 2H), 7.66(m, 1H), 7.78 (m, 6H), 8.62 (S, 1H), 8.9 (bs, 1H). LC/MS: 699 (M+1)$^+$.

Example 3

(2S)-(5-Chloro-2-heptyloxy-benzoylamino)-3-(4'-trifluoromethoxy-biphenyl-4-yl)-propionic acid 5-Chloro-2-hydroxy-benzoic acid (2.5 g, 28.97 mmol) was coupled with 2-amino-3-(4-bromo-phenyl)-propionic acid methyl ester hydrochloride (4.26 g, 28.96 mmol) with HBTU (6.59 g, 34.76 mmol) and diisopropylethylamine (8 ml, 86.9 mmol) as per general procedure A to yield the corresponding 3-(4-bromo-phenyl)-(2S)-(5-chloro-2-hydroxy-benzoylamino)-propionic acid methyl ester.

The above hydroxy compound (0.500 g, 1.21 mmol) was then alkylated with heptyliodide (0.410 g, 1.815 mmol) and potassium carbonate (0.050 g, 3.025 mmol) as per general procedure H to yield the 3-(4-bromo-phenyl)-(2S)-(5-chloro-2-heptyloxy-benzoylamino)-propionic acid methyl ester (0.500 g).

The title compound was then prepared from 3-(4-bromo-phenyl)-(2S)-(5-chloro-2-heptyloxy-benzoylamino)-propionic acid methyl ester (0.090 g, 0.176 mmol) and trifluoromethyl boronic acid (0.067 g, 0.352 mmol) with Pd (PPh$_3$) (0.020 g, 0.0176 mmol) and 2 N Na$_2$CO$_3$ (0.528 ml, 0.528 mmol) as per general procedure D to yield the (2S)-(5-chloro-2-heptyloxy-benzoylamino)-3-(4'-trifluoromethoxy-biphenyl-4-yl)-propionic acid methyl ester which was further hydrolyzed as per general procedure C to give the title compound (0.050 g).

$^1$H-NMR(400 MHz, CDCl$_3$): δ 1.11(t, 3H), 1.44(m, 8H), 1.87(m, 2H), 3.65(dddd, 2H, 4.27(m, 2H), 5.50(m, 1H), 7.18 (m, 2H), 7.4(d, 1H), 7.57(m, 4H), 7.68-7.85(m, 4H), 8.52 (S, 1H), 8.98 (bs, 1H). LC/MS: 577 (M+1)$^+$.

By analogous methods to those described above the following Examples were synthesized.

| Example | Name | LC/MS |
|---|---|---|
| 4 | 3-Biphenyl-4-yl-(2S)-(5-bromo-2-heptyloxy-benzoylamino)-propionic acid | 539 |
| 5 | (2S)-(5-Bromo-2-heptyloxy-benzoylamino)-3-(2'-phenoxy-biphenyl-4-yl)-propionic acid | 631 |
| 6 | (2S)-[5-Bromo-2-(4-tert-butyl-benzyloxy)-benzoylamino]-3-(2'-phenoxy-biphenyl-4-yl)-propionic acid | 679 |
| 7 | (2S)-(5-Bromo-2-isopropoxy-benzoylamino)-3-(2'-phenoxy-biphenyl-4-yl)-propionic acid | 575 |
| 8 | (2S)-[5-Bromo-2-(3-trifluoromethyl-phenoxy)-benzoylamino]-3-(2'-phenoxy-biphenyl-4-yl)-propionic acid | 677 |
| 9 | (2S)-(5-Bromo-2-heptyloxy-benzoylamino)-3-[2'-(4-methoxy-phenoxy)-biphenyl-4-yl]-propionic acid | 661 |
| 10 | (2S)-(5-Bromo-2-heptyloxy-benzoylamino)-3-[2'-(4-trifluoromethoxy-phenoxy)-biphenyl-4-yl]-propionic acid | 715 |
| 11 | (2S)-[5-Bromo-2-(3-phenyl-propoxy)-benzoylamino]-3-(2'-phenoxy-biphenyl-4-yl)-propionic acid | 651 |
| 12 | (2S)-[5-Bromo-2-(2-methyl-butoxy)-benzoylamino]-3-(2'-phenoxy-biphenyl-4-yl)-propionic acid | 603 |

Example 13

3-Biphenyl-4-yl-(2S)-[(4'-trifluoromethyl-biphenyl-4-carbonyl)-amino]-propionic acid (2S)-Amino-3-biphenyl-4-yl-propionic acid methyl ester (1.0 g, 4.1 mmol) was reacted with 4-bromo-benzoic acid (1.07 g, 5.3 mmol) as described in general procedure A yielding 3-biphenyl-4-yl-(2S)-[(5-bromo-benzoyl-amino)-propionic acid (1.48 g).

3-Biphenyl-4-yl-(2S)-[(5-bromo-benzoylamino)-propionic acid (100 mg, 0.23 mmol) was reacted with 4-trifluoromethyl phenyl boronic acid (0.133 mg, 0.69 mmol) by following general procedure D yielding the title compound (98 mg) as a white solid.
$^1$H-NMR(400 MHz, DMSO-d$_6$): 3.07-3.25(m, 2H), 4.63-4.69 (m, 1H), 7.26-7.32 (m, 1H), 7.39-7.42 (m, 4H), 7.56-7.62 (m, 4H), 7.1-7.84 (m, 4H), 7.81-7.84 (m, 4H), 7.92-7.95 (m, 4H), 8.86 (d,1H); LC/MS : 490 (M+1)$^+$.

Example 14

3-Biphenyl-4-yl-(2S)-[(3'-chloro-4'-fluoro-biphenyl-4-carbonyl)-amino]-propionic acid 3-Biphenyl-4-yl-(2S)-[(5-bromo-benzoyl-amino)-propionic acid (100 mg, 0.23 mmol) was reacted with 3-chloro-4-fluoro-phenyl boronic acid (0.123 mg, 0.69 mmol) by following general procedure D to afford title compound (89 mg) as a white solid.
$^1$H NMR (400 MHz, CD$_3$COCD$_3$): δ 4.05 (dd, 2H), 5.00 (m, 1H), 7.32 (m, 1H), 7.44 (m, 4H), 7.62 (m, 4H), 7.71 (m, 1H), 7.74 (m, 2H), 7.84 (m, 1H), 7.96 (m, 3H). LC/MS :474 (M+1)$^+$.

Example 15

3-Biphenyl-4-yl-(2S)-[(4'-trifluoromethoxy-biphenyl-4-carbonyl)-amino]-propionic acid 3-Biphenyl-4-yl-(2S)-[(5-bromo-benzoyl-amino)-propionic acid (100 mg, 0.23 mmol) was reacted with 4-trifluoromethoxy phenyl boronic acid (145 mg, 0.69 mmol) by following general procedure D yielding the title compound (101 mg) as a white solid:
$^1$H-NMR(400 MHz, DMSO-d$_6$): δ 3.08-3.15 (m, 1H), 3.20-3.25 (m, 1H), 4.62-4.68 (m,1H), 7.28-7.32 (m,1H ), 7.39-7.46 (m, 6H), 7.55-7.61 (m, 4H), 7.77 (d, 2H), 7.82 (d, 2H), 7.92 (d, 2H), 8.84 (d,1H); LC/MS : 524 (M+1)$^+$.

Example 16

3-Biphenyl-4-yl-(2S)-[(4'-ethyl-biphenyl-4-carbonyl)-amino]-propionic acid

3-Biphenyl-4-yl-(2S)-[(5-bromo-benzoyl-amino)-propionic acid (100 mg, 0.23 mmol) was reacted with 4-ethyl phenyl boronic acid (145 mg, 0.69 mmol) by following general procedure D yielding the title compound (101 mg) as a white solid. LC/MS: 450 (M+1)$^+$.

Example 17

3-Biphenyl-4-yl-(2S)-[(3'-ethyl-biphenyl-3-carbonyl)-amino]-propionic acid (2S)-Amino-3-biphenyl-4yl-propionic acid methyl ester (1.0 g, 4.1 mmol) was reacted with 3-bromo-benzoic acid (1.07 g, 5.3 mmol) as described in general procedure A yielding 3-biphenyl-4-yl-(2S)-(3-bromo-benzoylamino)-propionic acid (1.48 g).

3-Biphenyl-4-yl-(2S)-[(3-bromo-benzoyl-amino)-propionic acid (100 mg, 0.23 mmol) was reacted with 4-ethyl phenyl boronic acid (145 mg, 0.69 mmol) by following general procedure D yielding the title compound (101 mg) as a white solid.
$^1$H-NMR(400 MHz, DMSO-d$_6$): δ 1.22 (t, 3H), 2.61 (q, 2H), 3.25-3.30 (m, 1H), 3.37-3.39 (m, 1H), 5.06-5.08 (m, 1H), 6.75 (d, 1H, J=6.4 Hz), 7.15 (d, 2H), 7.24-7.26 (m, 2H), 7.30-7.33 (m,1H), 7.36-7.43 (m, 5H), 7.49 (t, 4H), 7.60 (d,1H), 7.64 (d,1H), 7.85 (s,1H); LC/MS: 450 (M+1)$^+$.

Example 18

3-Biphenyl-4-yl-(2S)-[(4'-tert-butyl-biphenyl-3-carbonyl)-amino]-propionic acid 3-Biphenyl-4-yl-(2S)-[(3-bromo-benzoyl-amino)-propionic acid (100 mg, 0.23 mmol) was reacted with 4-tert-butyl phenyl boronic acid (125 mg, 0.69 mmol) by following general procedure D yielding the title compound (95 mg) as a white solid.
$^1$H-NMR(400 MHz, DMSO-d$_6$): δ 1.31 (s, 9H), 3.34-3.42 (m, 1H), 3.42-3.46 (m, 1H), 5.10-5.14 (m, 1H), 6.62 (bs, 1H), 7.25 (s, 1H), 7.28 (d, 1H), 7.31-7.35 (m, 1H), 7.37-7.43 (m, 4H), 7.44-7.49 (m, 3H), 7.52-7.56 (m, 4H), 7.64 (d, 1H), 7.70-7.72 (m,1H,), 7.4 (s,1H); LC/MS: 478 (M+1)$^+$.

By analogous methods to those described above the following Examples were synthesized.

| Example | Name | LC/MS |
|---|---|---|
| 19 | 3-(5'-Chloro-2'-methoxy-biphenyl-4-yl)-(2S)-[(4'-trifluoromethyl-biphenyl-4-carbonyl)-amino]-propionic acid | 554 |
| 20 | 3-(4-Thiophen-3-yl-phenyl)-(2S)-[(4'-trifluoromethyl-biphenyl-4-carbonyl)-amino]-propionic acid | 496 |
| 21 | 3-(4-Thiophen-3-yl-phenyl)-(2S)-[(4'-trifluoromethoxy-biphenyl-4-carbonyl)-amino]-propionic acid | 512 |
| 22 | (2S)-(4-Benzyloxy-benzoylamino)-3-(4'-trifluoromethoxy-biphenyl-4-yl)-propionic acid | 536 |

Example 23

(2S)-[5-Bromo-(2-cyclopentyl-acetylamino)-benzoylamino]-3-(2'-phenoxy-biphenyl-4-yl)-propionic acid (S)-(2-Amino-5-bromo-benzoylamino)-3-(2'-phenoxy-biphenyl-4-yl)-propionic acid methyl ester (1.53 g) was prepared from (2S)-amino-3-(2'-phenoxy-biphenyl-4-yl)-propionic acid methyl ester HCl salt (1.0 g, 2.6 mmol) and 5-bromo-2-amino-benzoic acid (0.5 g, 2.9 mmol) as described in general procedure A.

(S)-(2-Amino-5-bromo-benzoylamino)-3-(2'-phenoxy-biphenyl-4-yl)-propionic acid methyl ester (0.2 g, 0.04 mmlo) in 5 ml of DCM was reacted with cyclopentyl acetyl chloride (82.6 mg, 0.06 mmol) and pyridine (60 mg, 0.08 mmol) as described in general procedure K. The resulting ester was hydrolyzed according to the general procedure C to afford the title compound (0.2 g) as a white solid. LCMS: 642 (M+1)$^+$.
$^1$H NMR (CDCl$_3$): δ1.1-1.26 [m, 3H], 1.5-1.75 [m, 3 H], 1.8-1.90 [m, 2 H], 2.2-2.41 μm, 2H], 2.48 [d, 1H], 3.1-3.4 [m, 2H], 5.0-5.1 [m, 1H], 6.6 [d, 1H], 6.89-6.97 [m, 4H], 7.18-7.26 [m, 6H], 7.43-7.52 [m, 5H], 8.48 (d, 1), 10.73 (s, 1H).

Example 24

(2S)-[5-Bromo-2-(3,3,5-trimethyl-hexanoylamino)-benzoylamino]-3-(2'-phenoxy-biphenyl-4-yl)-propionic acid A solution of (2S)-(2-amino-5-bromo-benzoylamino)-3-(2'-phenoxy-biphenyl-4-yl)-propionic acid methyl ester (54.5 mg, 0.10 mmol) from example 294 in 1 mL dry $CH_2Cl_2$ was treated with 3,5,5-trimethylhexanoyl chloride (1.2 eq., 23 μL, 0.12 mmol) and pyridine (1.5 eq., 12 μL, 0.15 mmol) in succession and stirred under an atmosphere of dry $N_2$ for one hour, then concentrated in vacuo. The crude residue was purified by flash column chromatography (hexanes, EtOAc) to afford the desired amide, (2S)-[5-bromo-2-(3,3,5-trimethyl-hexanoylamino)-benzoylamino]-3-(2'-phenoxy-biphenyl-4-yl)-propionic acid methyl ester (68 mg). The methyl ester (20 mg, 29 μmol) was dissolved in 2.0 mL THF and 0.5 mL MeOH and saponified with 2N aqueous LiOH solution (0.25 mL), as described in general procedure C, to afford the title compound, (2S)-[5-bromo-2-(3,3,5-trimethyl-hexanoylamino)-benzoylamino]-3-(2'-phenoxy-biphenyl-4-yl)-propionic acid (20 mg), as a white solid.

LCMS 673 (M+1)$^+$. $^1$H NMR (400 MHz, $CDCl_3$) δ 10.74 [s, 1H], 8.51 [d, 1H], 7.51 [m, 3H], 7.43 [m, 2H], 7.27-7.30 [m, 2H], 7.16-7.26 [m, 5H], 6.98 [d, 2H], 6.88 [d, 2H], 6.59 [d, 1H], 5.03 [dd, 1H], 3.28 [dq, 2H], 2.36 [m, 1H], 2.14 [m, 1H], 1.11-1.25 [m, 3H], 1.00 [s, 3H], 0.92 [s, 3H], 0.91 [d, 6H].

By analogous methods to those described above the following Examples were synthesized.

| Example | Name | LC/MS |
|---|---|---|
| 25 | (2S)-({4-[(Biphenyl-4-carbonyl)-amino]-3'-chloro-4'-fluoro-biphenyl-3-carbonyl}-amino)-3-biphenyl-4-yl-propionic acid | 669 |
| 26 | 2-[5-Bromo-(2S)-(4-tert-butyl-benzoylamino)-benzoylamino]-3-(4'-phenoxy-biphenyl-4-yl)-propionic acid | 692 |
| 27 | (2S)-(5-Bromo-2-phenylacetylamino-benzoylamino)-3-(2'-phenoxy-biphenyl-4-yl)-propionic acid | 650 |
| 28 | (2S)-[5-Bromo-2-(4-bromo-benzoylamino)-benzoylamino]-3-(2'-phenoxy-biphenyl-4-yl)-propionic acid | 715 |
| 29 | (2S)-{5-Bromo-2-[2-(4-fluoro-phenyl)-acetylamino]-benzoylamino}-3-(2'-phenoxy-biphenyl-4-yl)-propionic acid | 668 |
| 30 | 2-{5-Bromo-(2S)-[(naphthalene-2-carbonyl)-amino]-benzoylamino}-3-(2'-phenoxy-biphenyl-4-yl)-propionic acid | 686 |
| 31 | (2S)-{5-Bromo-2-[(naphthalene-1-carbonyl)-amino]-benzoylamino}-3-(2'-phenoxy-biphenyl-4-yl)-propionic acid | 686 |
| 32 | (2S)-[5-Chloro-2-(3-phenoxy-benzoylamino)-benzoylamino]-3-(2'-phenoxy-biphenyl-4-yl)-propionic acid | 683 |
| 33 | (2S)-[2-(3-Benzyloxy-benzoylamino)-5-chloro-benzoylamino]-3-(2'-phenoxy-biphenyl-4-yl)-propionic acid | 697 |
| 34 | (2S)-[5-Bromo-2-(2-propyl-pentanoylamino)-benzoylamino]-3-(2'-phenoxy-biphenyl-4-yl)-propionic acid | 658 |
| 35 | (2S)-[5-Bromo-2-(2-phenoxy-propionylamino)-benzoylamino]-3-(2'-phenoxy-biphenyl-4-yl)-propionic acid | 680 |

Example 36

(2S)-[5-Bromo-2-(4-tert-butyl-benzenesulfonylamino)-benzoylamino]-3-(2'-phenoxy-biphenyl-4-yl)-propionic acid A solution of 2-(2-amino-5-bromo-benzoylamino)-3-(2'-phenoxy-biphenyl-4-yl)-propionic acid (0.06 g, 0.11 mmol) [prepared by reacting (2S)-amino-3-(2'-phenoxy-biphenyl-4-yl) propionic acid methyl ester hydrochloride salt and 2-amino-5-bromobenzoic acid by general procedure A] in $CH_2Cl_2$ was treated with of 4-tert-butylbenzenesulfonyl chloride (0.025 g, 0.11 mmol) according to the general procedure F. Product was purified by flash column chromatography on silicagel using ethyl acetate hexanes to give product as white solid (0.065 g).

2-[5-Bromo-2-(4-t-butyl-benzenesulfonylamino)-benzoylamino]-3-(2'-phenoxy-biphenyl-4-yl) propionic acid methyl ester (0.04 g, 0.054 mmol ) was treated with LiOH (2 eq, 1 N aqueous solution) according to the general procedure C to give 0.034 g of 2-[5-bromo-2-(4-t-butyl-benzenesulfonylamino)-benzoylamino]-3-(2'-phenoxy-biphenyl-4-yl) propionic acid.

$^1$H NMR (400 MHz, DMSO-$d_6$): δ 1.2 (s, 9H) 3.04 (dd, 1H), 3.21 (dd, 1H), 4.58-4.70 (m, 1H), 6.83-6.87 (m, 2H), 6.94-6.99 (m, 2H), 7.20-7.39 (m, 6H), 7.42-7.49 (m, 4H), 7.51-7.56 (m, 2H), 7.64-7.72 (m, 3H), 7.86 (d, 1H), 9.29 (d, 1H), 11.38 (s, 1H), 13.06 (s, 1H). LC/MS: 727.1 (M+1)$^+$.

Example 37

(2S)-[5-Bromo-2-(4-tert-butyl-benzenesulfonylamino)-benzoylamino]-3-(4'-phenoxy-biphenyl-4-yl)-propionic acid To a mixture of (L)-4-bromophenylalanine (8.55, 35.0 mmol), 2-phenoxyphenyl boronic acid (10.00 g, 46.73 mmol), and palladium tetrakis-triphenylphosphine (4.0 g, 10% mmol) were added DME (140 mL) and 2N $Na_2CO_3$ aq. solution (70 mL, 140 mmol). The resulting mixture was heated at 90° C. under $N_2$ for 20 h. While the reaction solution was hot, the aqueous layer was removed and the top organic layer was concentrated. The residue was neutralized with HCl and washed with diethyl ether, and then was dissolved in methanol and the insoluble solid was removed by filtration. The methanol filtrate was refluxed with HCl/ether for 6 h. After removal of solvents, the solid was washed with ether to afford (2S)-amino-3-(4'-phenoxy-biphenyl-4-yl-propionic acid methyl ester in HCl salt form (11.0 g, 28.65 mmol).

(2S)-Amino-3-(4'-phenoxy-biphenyl-4-yl-propionic acid methyl ester (192 mg, 0.5 mmol) was reacted with 5-bromoanthranilic acid (110 mg, 0.5 mmol) as described in general procedure A. The resulting crude compound was sulfonylated by 4-tert-butylbenzenesulfonyl chloride (175 mg, 0.75 mmol) as described in general procedure F. The resulting compound was hydrolyzed according to general procedure C to afford the title product (219 mg) as white solid.

$^1$H-NMR(400 MHz, $CDCl_3$): δ 1.25 (s, 9H), 3.25 (dd, 1H), 3.35 (dd, 1H), 5.01 (dd, 1H), 6.62 (d, 1H), 7.05-7.03 (m, 4H), 7.12 (t, 1H), 7.21 (d, 2H), 7.45-7.33 (m, 6H), 7.54-7.49 (m, 5H), 7.60 (d, 2H), 10.61(s, 1H). LC/MS; 727(M+1)$^+$.

By analogous methods to those described above the following Examples were synthesized.

| Example | Name | LC/MS |
|---|---|---|
| 38 | 3-Biphenyl-4-yl-(2S)-[5-bromo-2-(4-tert-butyl-benzenesulfonylamno)-benzoylamino]-propionic acid | 636 |
| 39 | (2S)-(2-Benzenesulfonyl-amino-5-chloro-benzoylamino)-3-(2'-phenoxy-biphenyl-4-yl)-propionic acid methyl ester | 641 |
| 40 | (2S)-(2-Benzenesulfonyl-amino-5-chloro-benzoylamino)-3-(2'-phenoxy-biphenyl-4-yl)-propionic acid | 627 |
| 41 | (2S)-[2-(4-tert-Butyl-benzenesulfonylamino)-5-chloro-benzoylamino]-3-(2'-phenoxy-biphenyl-4-yl)-propionic acid | 683 |

Example 42

2-{5-Chloro-2-[(naphthalen-1-ylmethyl)-amino]-benzoylamino}-3-(4'-trifluoromethyl-biphenyl-4-yl)-propionic acid A solution of 2-amino-5-chlorobenzoic acid (0.58 g, 3.37 mmol) in DMF (7.0 mL) was reacted with (L)-4-bromophenylalanine methyl ester hydrochloride (1.00 g, 3.37 mmol), HBTU (1.20 g, 3.37 mmol), and DIEA (1.80 mL, 10.13 mmol) by the general procedure A. The crude product was purified by flash column chromatography on silica gel using 1:1 DCM/hexane followed by DCM to give 0.890 g of 2-(2-amino-5-chloro-benzoylamino)-3-(4-bromo-phenyl)-propionic acid methyl ester as a white solid.

A solution of 2-(2-amino-5-chloro-benzoylamino)-3-(4-bromo-phenyl)-propionic acid methyl ester (0.600 g, 1.45 mmol) in DME (10.0 mL) was reacted with 4-trifluoromethylbenzene boronic acid (0.55 g, 2.91 mmol), Pd(PPh$_3$)$_4$ (0.70 g, 0.14 mmol), and Na$_2$CO$_3$ (2.0N, 3.50 mL, 3.64 mmol) by the general procedure D to give 0.850 g of 2-(2-amino-5-chloro-benzoylamino)-3-(4'-trifluoromethyl-biphenyl-4-yl)-propionic acid methyl ester as a brown oil.

A solution of 2-(2-amino-5-chloro-benzoylamino)-3-(4-bromo-phenyl)-propionic acid methyl ester (0.830 g, 1.74 mol) in DCE (15 mL) was reacted with 1-naphthaldehyde (0.244 g, 3.50 mmol), sodium triacetoxyborohydride (0.553 g, 2.61 mmol), and acetic acid/DCM (1.0M, 2.0 mL) by the general procedure E. The crude product was purified by flash column chromatography on silica gel using DCM/hexane (65:35) to give 0.580 g of 2-{5-chloro-2-[(naphthalen-1-ylmethyl)-amino]-benzoylamino}-3-(4'-trifluoromethyl-biphenyl-4-yl)-propionic acid methyl ester as a colorless oil. This ester was treated with LiOH (0.123 g, 2.92 mmol) by the general procedure J to give 0.405 g of the title compound. 2-{5-chloro-2-[(naphthalen-1-ylmethyl)-amino]-benzoylamino}-3-(4'-trifluoromethyl-biphenyl-4-yl)-propionic acid as a white solid.

LCMS 603 (M+1)$^+$. $^1$H NMR (DMSO-d$_6$) δ 8.62 [d, 1H], 8.10 [m, 1H], 8.03 [m, 1 H], 7.92 (m, 1H], 7.81 [m, 2 H], 7.72 [m, 2 H], 7.59 [m, 3 H], 7.50 [m, 2 H], 7.38 [m, 3 H], 7.23 [dd, 1H], 6.67 [d, 1H], 4.47 [m, 1H], 3.25 [dd, 1H], 3.16 [s, 2 H], 3.07 [m, 1H].

By analogous methods to those described above the following Examples were synthesized.

| Example | Name | LC/MS |
|---|---|---|
| 43 | (2S)-{5-Chloro-2-[(naphthalen-1-ylmethyl)-amino]-benzoylamino}-3-(2'-trifluoromethyl-biphenyl-4-yl)-propionic acid | 603 |
| 44 | (2S)-[5-Bromo-2-(2-methyl-pentylamino)-benzoylamino]-3-(2'-phenoxy-biphenyl-4-yl)-propionic acid | 616 |
| 45 | (2S)-[3,5-Dichloro-2-(2-methyl-butylamino)-benzoylamino]-3-(2'-phenoxy-biphenyl-4-yl)-propionic acid | 591 |
| 46 | (2S)-{2-[3-(4-tert-Butyl-phenoxy)-benzylamino]-5-chloro-benzoylamino}-3-(2'-hydroxy-biphenyl-4-yl)-propionic acid | 649 |

Example 47

(2S)-(5-Chloro-2-diethylamino-benzoylamino)-3-[3'-(4-trifluoromethyl-phenoxy)-biphenyl-4-yl]-propionic acid A solution of (L)-4-bromophenylalanine (7.0 g, 28.6 mmol) in DME(100 mL) was reacted with 3-hydroxyphenyl boronic acid(5.14 g, 37.2 mmol), palladium tetrakis-triphenylphosphine (3.3 g, 2.8 mmol), and aqueous Na$_2$CO$_3$ (2.0N, 43.0 mL, 86 mmol) by the general procedure D. After removal of solvent, the solid was washed with ether and DCM to afford (2S)-amino-3-(3'-hydroxy-biphenyl-4-yl)propionic acid methyl ester in HCl salt form (8.20 g, 31.9 mmol).

A solution of 2-amino-5-chloro-benzoic acid (1.95 g, 11.38 mmol) in DMF (10.0 mL) was reacted with (2S)-amino-3-(3'-hydroxy-biphenyl-4-yl)propionic acid methyl ester (3.50 g, 11.38 mmol), HBTU (3.98 g, 10.50 mmol), and DIEA (6.08 mL, 34.15 mmol) by the general procedure A. The crude product was purified by flash column chromatography on silical gel using DCM/hexane 85:15 and increasing the gradient to DCM and finally DCM containing 0.25% methanol, to give 1.75 g of (2S)-(2-amino-5-chloro-benzoylamino)-3-(3'-hydroxy-biphenyl-4-yl)propionic acid methyl ester as a white solid.

LCMS: 425 (M+1)$^+$.

A solution (2S)-(2-amino-5-chloro-benzoylamino)-3-(3'-hydroxy-biphenyl-4-yl)propionic acid methyl ester (0.850 g, 2.00 mmol) was reacted with acetaldehyde (0.350 g, 6.01 mmol), sodium triacetoxyborohydride (0.850 g, 4.00 mmol), and acetic acid/DCM (1.0M, 3.00 mL) by the general procedure E. The crude product was purified by flash column chromatography on silica gel using DCM containing 15% hexane and increasing the gradient to DCM and finally DCM containing 0.25% methanol) to give 0.540 g of the phenolic ester.

A solution of this phenolic ester (0.240 g, 0.49 mmol) in DCM (5.0 mL) was reacted with copper acetate (0.100 g, 0.54 mmol), and 4-trifluoromethylbenzene boronic acid (0.236 g, 1.24 mmol), and triethylamine (0.350 mL) by the general procedure G. The crude product was purified by the flash column chromatography on silica gel using DCM containing 5% hexane) to give 0.133 g of (2S)-(5-chloro-2-diethylamino-benzoylamino)-3-[3'-(4-trifluoromethyl-phenoxy)-biphenyl-4-yl]-propionic acid methyl ester. This ester (0.110 g, 0.17 mmol) was reacted with LiOH (0.030 g, 0.70 mmol) by the general procedure J to give 0.095 g of (2S)-(5-chloro- 2-diethylamino-benzoylamino)-3-[3'-(4-trifluoromethyl-phenoxy)-biphenyl-4-yl]-propionic acid as a white solid.

LCMS: 612 (M+1)+. $^1$H NMR (CDCl$_3$) δ 11.56 [s, 1H], 8.28 [d, 1H], 7.59 [d, 2 H], 7.42 [dd, 1H], 7.35 [dd, 1H], 7.28 [m, 4 H], 7.19 [t, 1H], 7.15 [d, 1H], 7.09 [d, 1H], 7.02 [dd, 1H], 7.00 [dd, 1H], 5.05 [m, 1H], 3.32 [m, 2 H], 2.79 [q, 4 H], 0.69 [t, 6 H].

By analogous methods to those described above the following Examples were synthesized.

| Example | Name | LC/MS |
|---|---|---|
| 48 | (2S)-(5-Chloro-2-diethylamino-benzoylamino)-3-[3'-(3-chloro-4-fluoro-phenoxy)-biphenyl-4-yl]-propionic acid | 595 |
| 49 | (2S)-(5-Bromo-2-piperidin-1-yl-benzoylamino)-3-(2'-phenoxy-biphenyl-4-yl)-propionic acid | 600 |
| 50 | (2S)-(5-Chloro-2-diethylamino-benzoylamino)-3-[3'-(4-methoxy-phenoxy)-biphenyl-4-yl]-propionic acid | 573 |
| 51 | (2S)-(5-Chloro-2-diethylamino-benzoylamino)-3-[3'-(4-trifluoromethoxy-phenoxy)-biphenyl-4-yl]-propionic acid | 627 |
| 52 | 3-[3'-(4-tert-Butyl-phenoxy)-biphenyl-4-yl]-(2S)-(5-chloro-2-diethylamino-benzoylamino)-propionic acid | 599 |

Example 53

(2S)-[5-Chloro-2-(4-methylsulfanyl-phenylamino)-benzoylamino]-3-(2'-phenoxy-biphenyl-4-yl)-propionic acid A solution of (2S)-(2-amino-5-chloro-benzoylamino)-3-(2'-phenoxy-biphenyl-4-yl)-propionic acid (0.154 g, 0.307 mmol), prepared by reacting (2S)-amino-3-(2'-phenoxy-biphenyl-4-yl)-propionic acid methyl ester and 2-amino-5-chlorobenzoic acid by the general procedure A) was reacted with 4-(methylthio)phenylboronic acid (0.130 g, 0.768 mmol), copper acetate (0.084 g, 0.460 mmol), and triethyl amine (0.215 mL, 1.535 mmol) by the general procedure G. The crude product was purified by flash column chromatography on silica gel using DCM containing 25% hexane to give 0.075 g of 2-[5-chloro-2-(4-methylsulfanyl-phenylamino)-benzoylamino]-3-(2'-phenoxy-biphenyl-4-yl)-propionic acid methyl ester as an oil. This ester was treated with LiOH (0.019 g, 0.441 mmol) by the general procedure I to give 0.049 g of 2-[5-chloro-2-(4-methylsulfanyl-phenylamino)-benzoylamino]-3-(2'-phenoxy-biphenyl-4-yl)-propionic acid.

LCMS: 610 (M+1)+. $^1$H NMR (CDCl$_3$) δ 8.94 [bs, 1H], 7.49 [d, 2 H], 7.47 [d, 1H], 7.22 [m, 10 H], 7.06 [d, 2 H], 6.99 [d, 2 H], 6.88 [d, 2 H], 6.50 [d, 1H], 4.99 [m, 1H], 3.30 [m, 2 H], 2.45 [s, 3 H].

Example 54

2S-[5-Chloro-2-(3-chloro-4-fluoro-phenylamino)-benzoylamino]-3-(2'-phen oxy-biphenyl-4-yl)-propionic acid (2S)-(2-amino-5-chloro-benzoylamino)-3-(2'-phenoxy-biphenyl-4-yl)-propionic acid (0.154 g, 0.307 mmol) prepared above was reacted with 3-chloro-4-fluorophenyl boronic acid (0.13 g, 0.77 mmol), copper acetate (0.084 g, 0.460 mmol), and triethyl amine (0.215 mL, 1.535 mmol) as described in the general procedure G. The crude product was purified by column chromatography using DCM as an eluent then hydrolyzed as described in the general proceudure I to afford the title compound (20 mg) as a light yellow solid.

LCMS: 615(M+1)+. $^1$H NMR (CDCl$_3$) δ 3.12 (m, 1H], 3.39 [m, 1H], 4.84 [m, 1H], 6.61 [m, 1H], 6.79-7.58 [m, 19H], 8.88 [s, 1H].

By analogous methods to those described above the following Examples were synthesized.

| Example | Name | LC/MS |
|---|---|---|
| 55 | (2S)-[5-Bromo-2-(4-trifluoromethyl-phenylamino)-benzoylamino]-3-(2'-phenoxy-biphenyl-4-yl)-propionic acid | 676 |
| 56 | (2S)-[5-Chloro-2-(4-trifluoromethyl-phenylamino)-benzoylamino]-3-(2'-phenoxy-biphenyl-4-yl)-propionic acid | 631 |
| 57 | (2S)-[5-Chloro-2-(3-trifluoromethyl-phenylamino)-benzoylamino]-3-(2'-phenoxy-biphenyl-4-yl)-propionic acid | 631 |
| 58 | (2S)-[5-Chloro-2-(4-methoxy-phenylamino)-benzoylamino]-3-(2'-phenoxy-biphenyl-4-yl)-propionic acid | 593 |
| 59 | (2S)-[2-(4-tert-Butyl-phenylamino)-5-chloro-benzoylamino]-3-(2'-phenoxy-biphenyl-4-yl)-propionic acid | 619 |
| 60 | (2S)-[5-Chloro-2-(3,4-difluoro-phenylamino)-benzoylamino]-3-(2'-phenoxy-biphenyl-4-yl)-propionic acid | 599 |
| 61 | (2S)-[5-Chloro-2-(4-fluoro-3-methyl-phenylamino)-benzoylamino]-3-(2'-phenoxy-biphenyl-4-yl)-propionic acid | 595 |
| 62 | (2S)-[5-Chloro-2-(3,4-dichloro-phenylamino)-benzoylamino]-3-(2'-phenoxy-biphenyl-4-yl)-propionic acid | 631 |
| 63 | (2S)-[5-Chloro-2-(4-trifluoromethoxy-phenylamino)-benzoylamino]-3-(2'-phenoxy-biphenyl-4-yl)-propionic acid | 647 |

Example 64

(2S)-[(1-Acetyl-pyrrolidin-(2R)-ylmethyl)-(4'-trifluoromethyl-biphenyl4-carbonyl)-amino]-3-biphenyl-4-yl-propionic acid To a solution of 2-biphenyl-4-yl-(1S)-(methoxycarbonyl) ethylammonium chloride (1.464 g, 5.02 mmol) and (2R)-formyl-pyrrolidine-1-carboxylic acid tert-butyl ester (1.0 eq., 1.00 g, 5.02 mmol) in a mixture of 25 mL methanol and 25 mL THF was added glacial acetic acid (1.5 eq., 0.43 mL, 7.53 mmol) and the mixture was stirred at ambient temperature for ten minutes. To this was added a 1.0N solution of NaCNBH$_3$ in THF (1.5 eq., 7.53 mL, 7.53 mmol) in small portions and the reaction mixture was stirred at rt overnight The solvent was removed and the residue was dissolved in water and DCM and partitioned. The organic portion was dried over Na$_2$SO$_4$, filtered and concentrated. The crude product was purified by flash column chromatography (2:1 EtOAc-Hexanes, then EtOAc) to provide (2R)-[(2-biphenyl-4-yl-(1S)-1-methoxycarbonyl-ethylamino)-methyl]-pyrrolidine-1-carboxylic acid tert-butyl ester (1.440 g) as a clear viscous oil. A portion of the product (450 mg, 1.03 mmol), dissolved in 10 mL dry CH$_2$Cl$_2$, was subsequently condensed with 4'-trifluoromethyl-biphenyl-4-carbonyl chloride (1.2 eq., 351 mg, 1.23 mmol) (synthesized from 4'-trifluoromethyl-biphenyl-4-carboxylic acid by heating at reflux in a neat solution of thionyl chloride, followed by removal of excess reagent and volatiles in vacuo) in dry CH$_2$Cl$_2$ (10 mL), in the presence of triethylamine (3.0 eq., 0.43 mL, 3.08 mmol) at 0° C. The reaction was stirred at that temperature and gradually allowed to warm to ambient temperature until the reaction was shown to be complete by TLC. The solvent was removed and the crude residue was purified by flash column chromatography (1:1 EtOAc/hexanes) to afford (2R)-{[(2-biphenyl-4-yl-(1S)-methoxycarbonyl-ethyl)-(4'-trifluoromethyl-biphenyl-4-carbonyl)-amino]-methyl}-pyrrolidine-1-carboxylic acid tert-butyl ester (496 mg), as a white solid.

Into a dry flask was placed (2R)-{[(2-biphenyl-4-yl-(1S)-methoxycarbonyl-ethyl)-(4'-trifluoromethyl-biphenyl-4-carbonyl)-amino]-methyl}-pyrrolidine-1-carboxylic acid tert-butyl ester (318 mg, 0.463 mmol) and the flask was capped and purged with dry $N_2$. The flask was then charged with 5 mL of 4N HCl/dioxane and stirred at rt for one hour. The solvent was removed and the crude product was rinsed with ether and dried in vacuo to afford 288 mg of the desired product, (2R)-{[(2-biphenyl-4-yl-(1S)-methoxycarbonyl-ethyl)-(4'-trifluoromethyl-biphenyl-4-carbonyl)-amino]-methyl}-pyrrolidinium chloride, which was used without further purification. The amine hydrochloride (15 mg, 24 µmol) was dissolved in anhydrous $CH_2Cl_2$ (1 mL) and to this was added acetyl chloride (3.0 eq., 5.1 µL, 72 µmol), and triethylamine (5.0 eq., 17 µL, 120 µmol) and the reaction carried out as described in general procedure J. The crude product was purified by flash column chromatography to afford (2S)-[(1-acetyl-pyrrolidin-(2R)-ylmethyl)-(4'-trifluoromethyl-biphenyl-4-carbonyl)-amino]-3-biphenyl-4-yl-propionic acid methyl ester (16 mg). The methyl ester (15 mg, 24 gmol) was saponified according to Gereral procedure C to furnish 15 mg of the title compound, (2S)-[(1-acetyl-pyrrolidin-(2R)-ylmethyl)-(4'-trifluoromethyl-biphenyl-4-carbonyl)-amino]-3-biphenyl-4-yl-propionic acid. L

LCMS; 615 (M+1)$^+$

Example 65

(3S)-(2-Biphenyl-4yl-(1S)-carboxy-ethylcarbamoyl)-7-(4-trifluoromethyl-benzyloxy)-3,4-dihydro-1H-isoquinoline-2-carboxylic acid tert-butyl ester A solution of 7-hydroxy-3,4-dihydro-1H-isoquinoline-2,3-(3S)-dicarboxylic acid 2-tert-butyl ester (17.05 mmol, 5.0 g) in dry THF (80 mL) was reacted with 1-bromomethyl-4-trifluoromethylbenzene (37.5 mmol, 9.0 g), and potassium carbonate (85.0 mmol, 11.8 g) by the general procedure H. The reaction was cooled and poured into water (250 ml) and extracted with ethyl acetate (3×100 ml). The organic extracts were washed with brine and dried over sodium sulfate. Removal of the solvent gave 7-(4-trifluoromethyl-benzyloxy)-3,4-dihydro-1H-isoquinoline-2,3-(3S)-dicarboxylic acid 2-tert-butyl ester 3-(4-trifluoromethyl-benzyl) ester, which was used without further purification.

The resulting ester, 7-(4-trifluoromethyl-benzyloxy)-3,4-dihydro-1H-isoquinoline-2,3-(3S)-dicarboxylic acid 2-tert-butyl ester 3-(4-trifluoromethyl-benzyl) ester, was treated with lithium hydroxide monohydrate (28.6 mmol, 1.2 g) in water (30 ml) and THF (60 ml) by the general procedure I. The crude product was purified on silica gel (20% ethyl acetate in hexanes) to give 3.5 g of 7-(4-trifluoromethyl-benzyloxy)-3,4-dihydro-1H-isoquinoline-2,3-(3S)-dicarboxylic acid 2-tert-butyl ester. LC/MS: 352 (M+1-tert-butyl ester).

A solution of 7-(4-trifluoromethyl-benzyloxy)-3,4-dihydro-1H-isoquinoline-2,3-(3S)-dicarboxylic acid 2-tert-butyl ester (0.700 g, 1.552 mmol, prepared as described above) in DMF (8.0 mL) was reacted with (2S)-amino-3-biphenyl-4-yl)propionic acid methyl ester hydrochloride (0.453 g, 1.552 mmol), HBTU (0.590 g, 1.552 mmol), and DIEA (1.00 mL, 5.432 mmol) as described in general procedure A. The crude compound was purified by flash column chromatography on silica gel using hexanes:ethyl acetate (2:1) as the mobile phase to give 0.810 g of (3S)-(2-biphenyl-4-yl-(1S)-methoxycarbonyl-ethylcarbamoyl)-7-(4-trifluoromethyl-benzyloxy)-3,4-dihydro-1H-isoquinoline-2-carboxylic acid tert-butyl ester. A solution of this ester (0.750 g, 1.089 mmol) in THF (12.0 mL) was treated with LiOH (0.182 g, 4.358 mmol) by general procedure I to afford 0.720 g of the title compound (3S)-(2-biphenyl-4yl-(1S)-carboxy-ethylcarbamoyl)-7-(4-trifluoromethyl-benzyloxy)-3,4-dihydro-1H-isoquinoline-2-carboxylic acid tert-butyl ester as a white solid.

LCMS: 675 (M+1)$^+$. $^1$H NMR (CDCl$_3$) δ 7.78 [m, 10 H], 7.42 [d, 1H], 7.11 [m, 2 H], 7.06 [m, 1H], 6.97 [m, 1H], 6.85 [m, 1H], 5.28 [s, 2 H], 5.10 (m, 2 H], 4.69 [m, 2 H], 3.70 [bs, 1H], 3.53 [m, 1H], 3.32 [m, 3 H], 1.71 [s, 9 H].

Example 66

3-Biphenyl-4-yl-(2S)-{[2-(cyclopentyl-acetyl)-7-(4-trifluoromethyl-benzyloxy)-3,2,3,4-tetrahydro-isoquinoline-(3S)-carbonyl]-amino}-propionic acid:

A solution of 3-biphenyl-4-yl-(2S)-{[7-(4-trifluoromethyl-benzyloxy)-1,2,3,4-tetrahydro-isoquinoline-(3S)-carbonyl]-amino}-propionic acid methyl ester hydrochloride (0.060 g, 0.0.095 mmol, prepared by deprotection of (3S)-(2-biphenyl-4yl-(1S)-methoxycarbonyl-ethylcarbamoyl)-7-(4-trifluoromethyl-benzyloxy)-3,4-dihydro-1H-isoquinoline-2-carboxylic acid tert-butyl ester with HCl/dioxane, 4.0M) in DCM (3.0 mL) was reacted with cyclopentylacetyl chloride (0.028 g, 0.191 mmol), and TEA (0.050 mL, 0.335 mmol) as described in general procedure J. The crude compound was purified by flash column chromatography on silica gel using CHCl$_3$ containing 30% hexanes as the mobile phase to give 0.063 g of 3-biphenyl-4-yl-(2S)-{[2-(cyclopentyl-acetyl)-7-(4-trifluoromethyl-benzyloxy)-1,2,3,4-tetrahydro-isoquinoline-(3S)-carbonyl]-amino}-propionic acid methyl ester. A solution of this ester (0.052 g, 0.074 mmol) in THF (3.0 mL) was treated with LiOH (0.013 g, 0.297 mmol) by general procedure I to afford (0.046 g) of the title compound 3-biphenyl-4-yl-(2S)-{[2-(cyclopentyl-acetyl)-7-(4-trifluoromethyl-benzyloxy)-1,2,3,4-tetrahydro-isoquinoline-(3S)-carbonyl]-amino}-propionic acid as a white solid.

LCMS: 685 (M+1)$^+$. $^1$H NMR (DMSO-d$_6$) δ 8.62 [s, 1H], 8.03 [d, 3 H], 7.89 [m, 4 H], 7.61 [m, 4 H], 7.40 [t, 1H], 7.19 [m, 3 H], 5.42 [d, 2H], 4.96 [m, 1H], 4.57 [m, 2 H], 3.43 [m, 4 H], 2.80 [m, 4 H], 2.51 [m, 2 H], 2.03 [m, 2 H], 1.78 [m, 4 H], 1.38 [m, 2H].

Example 67

3-Biphenyl-4-yl-(2S)-{[2-(3,3-dimethyl-butyryl)-7-(4-trifluoromethyl-benzyloxy)-1,2,3,4-tetrahydro-isoquinoline-(3S)-carbonyl]-amino}-propionic acid A solution of 3-biphenyl-4-yl-(2S)-{[7-(4-trifluoromethyl-benzyloxy)-1,2,3,4-tetrahydro-isoquinoline-(3S)-carbonyl]-amino}-propionic acid methyl ester hydrochloride (0.100 g, 0.159 mmol, prepared by deprotection of (3S)-(2-biphenyl-4yl-(1S)-methoxycarbonyl-ethylcarbamoyl)-7-(4-trifluoromethyl-benzyloxy)-3,4-dihydro-1H-isoquinoline-2-carboxylic acid tert-butyl ester with HCl/dioxane, 4.0 M) in DCM (4.0 mL) was reacted with tert-butylacetyl chloride (0.028 g, 0.202 mmol), and TEA (0.085 mL, 0.479 mmol) as described in general procedure J. The crude compound was purified by flash column chromatography on silica gel using CHCl3 containing 30% hexanes) as the mobile phase to give 0.080 g of 3-biphenyl-4-yl-(2S)-{[2-(3,3-dimethyl-butyryl)-7-(4-trifluoromethyl-benzyloxy)-1,2,3,4-tetrahydro-isoquinoline-(3S)-carbonyl]-amino}-propionic acid methyl ester. A solution of this ester (0.047 g, 0.068 mmol) in THF (3.0 mL) was treated with LiOH (0.012 g, 0.273 mmol) by general procedure I to afford (0.039 g) of the title compound 3-biphenyl-4-yl-(2S)-{[2-(3,3-dimethyl-butyryl)-7-(4-trifluoromethyl-benzyloxy)-1,2,3,4-tetrahydro-isoquinoline-(3S)-carbonyl]-amino}-propionic acid as a white solid.

LCMS: 673 (M+1)$^+$. $^1$H NMR (CDCl$_3$) δ 7.38 [m, 8 H], 7.10 [d, 2 H], 7.00 (d, 2 H], 6.78 [m, 3 H], 6.65 [s, 1H], 5.17 [m, 1H], 4.97 [s, 2 H], 4.68 [m, 2 H], 4.45 [m, 1H], 4.10 [d, 1H], 3.26 [dd, 1H], 3.10 [dd, 1H], 3.01 [m, 1H], 2.85 [dd, 1H], 1.02 [s, 2 H], 0.96 [s, 9 H].

Example 68

3-Biphenyl-4-yl-(2S)-{[2-tert-butylcarbamoyl-7-(4-trifluoromethyl-benzyloxy)-1,2,3,4-tetrahydro-isoquinoline-(3S)-carbonyl]-amino}-propionic acid A solution of 3-biphenyl-4-yl-(2S)-{[7-(4-trifluoromethyl-benzyloxy)-1,2,3,4-tetrahydro-isoquinoline-(3S)-carbonyl]-amino}-propionic acid methyl ester hydrochloride (0.120 g, 0.159 mmol, prepared by deprotection of (3S)-(2-biphenyl-4yl-(1S)-methoxycarbonyl-ethylcarbamoyl)-7-(4-trifluoromethyl-benzyloxy)-3,4-dihydro-1H-isoquinoline-2-carboxylic acid tert-butyl ester with HCl/dioxane, 4.0M) in DCM (4.0 mL) was reacted with tert-butyl isocyanate (0.0285 g, 0.287 mmol), and DIEA (0.100 mL, 0.575 mmol) as described in general procedure L. The crude compound was purified by flash column chromatography on silica gel using CHCl$_3$ as the mobile phase to give 0.095 g of 3-biphenyl-4-yl-(2S)-{[2-tert-butylcarbamoyl-7-(4-trifluoromethyl-benzyloxy)-1,2,3,4-tetrahydro-isoquinoline-(3S)-carbonyl]-amino}-propionic acid methyl ester. A solution of this ester (0.065 g, 0.094 mmol) in THF (3.0 mL) was treated with LiOH (0.016 g, 0.378 mmol) by general procedure I to afford 0.051 g of the title compound 3-biphenyl-4-yl-(2S)-{[2-tert-butylcarbamoyl-7-(4-trifluoromethyl-benzyloxy)-1,2,3,4-tetrahydro-isoquinoline-(3S)-carbonyl]-amino}-propionic acid as a white solid.

LCMS: 674 (M+1)$^+$. $^1$H NMR (CDCl$_3$) δ 7.54 [d, 2 H], 7.44 [d, 2 H], 7.36 [d, 2 H], 7.33-7.25 [m, 3 H], 6.99 [d, 1H], 6.93-6.85 [m, 3 H], 6.69 [d, 2 H], 6.58 [s, 1H], 5.01 [bs, 2 H], 4.83 [s, 2 H], 4.76 [m, 1H], 4.53 [m, 1H], 4.14 [q, 2 H], 3.19 [d, 1H], 3.03 [m, 1H], 2.87 [q, 2 H], 1.27 [s, 9 H].

Example 69

(3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid isobutyl ester A solution of 3-biphenyl-4-yl-(2S)-{[7-(4-trifluoromethyl-benzyloxy)-1,2,3,4-tetrahydro-isoquinoline-(3S)-carbonyl]-amino}-propionic acid methyl ester hydrochloride (0.060 g, 0.095 mmol, prepared by deprotection of (3S)-(2-biphenyl-4yl-(1S)-methoxycarbonyl-ethylcarbamoyl)-7-(4-trifluoromethyl-benzyloxy)-3,4-dihydro-1H-isoquinoline-2-carboxylic acid tert-butyl ester with HCl/dioxane, 4.0M) in DCM (3.0 mL) was reacted with isobutyl chloroformate (0.026 g, 0.198 mmol), and TEA (0.050 mL, 0.575 mmol) as described in general procedure K. The crude compound was purified by flash column chromatography on silica gel using CHCl$_3$/hexanes 1:1 as the mobile phase to give 0.060 g of (3S)-(2-biphenyl-4-yl-(1S)-carboxy-ethylcarbamoyl)-7-(4-trifluoromethyl-benzyloxy)-3,4-dihydro-1H-isoquinoline-2-carboxylic acid isobutyl ester methyl ester. A solution of this ester (0.060 g, 0.087 mmol) in THF (3.0 mL) was treated with LiOH (0.015 g, 0.348 mmol) by general procedure I to afford 0.051 g of the title compound (3S)-(2-biphenyl-4-yl-(1S)-carboxy-ethylcarbamoyl)-7-(4-trifluoromethyl-benzyloxy)-3,4-dihydro-1H-isoquinoline-2-carboxylic acid isobutyl ester as a white solid.

LCMS: 674 (M+1)$^+$.

Example 70

(3S)-(2-Biphenyl-4-yl-(1S)-methoxycarbonyl-ethylcarbamoyl)-7-hydroxy-3,4-dihydro-1H-isoquinoline-2-carboxylic acid tert-butyl ester To a solution of (3S)-7-hydroxy-3,4-dihydro-1H-isoquinoline-2,3-dicarboxylic acid 2-tert-butyl ester (5.00 g, 17.05 mmol), 2-biphenyl-4-yl-(1S)-methoxycarbonyl-ethyl-ammonium chloride (1.0 eq., 4.97 g, 17.05 mmol), and HBTU (1.2 eq., 7.76 g, 20.46 mmol) in anhydrous DMF (170 mL) was added DIEA (2.5 eq., 7.42 mL, 42.62 mmol) according to General Procedure A. Flash column chromatography (40-70% EtOAc in hexanes) tafforded 7.55 g of the title compound as a white solid.

LCMS: 531(M+1)$^+$.

Example 71

(3S)-(2-Biphenyl-4-yl-(1S)-methoxycarbonyl-ethylcarbamoyl)-7-(4-trifluoromethyl-phenoxy)-3,4-dihydro-1H-isoquinoline-2-carboxylic acid To a solution of (3S)-(2-biphenyl-4-yl-(1S)-methoxycarbonyl-ethylcarbamoyl)-7-hydroxy-3,4-dihydro-1H-isoquinoline-2-carboxylic acid tert-butyl ester (0.2 g, 0.38 mmol), 4-(trifluoromethyl)phenylboronic acid (2.8 eq., 0.2 g, 1.05 mmol), cupric acetate (1.02 eq., 70 mg, 0.39 mmol) and 1 g of powdered 4-angstrom molecular sieves in 4 mL anhydrous CH$_2$Cl$_2$ was added along with triethylamine (3.8 eq., 0.2 mL, 1.44 mmol), as described in General Procedure G. The crude product was purified by flash column chromatography on silica gel, with CH$_2$Cl$_2$ as eluent, to afford (3S)-(2-biphenyl-4-yl-(1S)-methoxy-carbonyl-ethylcarbamoyl)-7-(4-trifluoromethyl-phenoxy)-3,4-dihydro-1H-isoquinoline-2-carboxylic acid tert-butyl ester. The ester was subsequently saponified according to General Procedure C to yield the title compound, (3S)-(2-biphenyl-4-yl-(1S)-methoxycarbonyl-ethylcarbamoyl)-7-(4-trifluoromethyl-phenoxy)-3,4-dihydro-1H-isoquinoline-2-carboxylic acid (100 mg).

LCMS: 661.(M+1)$^+$.

Example 72

(3S)-(2-Biphenyl-4-yl-(1S)-carboxy-ethylcarbamoyl)-7-(4-tert-butyl-phenoxy)-3,4-dihydro-1H-isoquinoline-2-carboxylic acid isobutyl ester To a solution of Example 70 (0.2 g, 0.38 mmol), 4 tert-butyl phenylboronic acid (3.0 eq., 0.2 g, 1.15 mmol), cupric acetate (1.02 eq, 70 mg, 0.39 mmol) and 1 g of powdered 4-angstrom molecular sieves in 4 mL anhydrous CH$_2$Cl$_2$ was added triethylamine (3.8 eq., 0.2 mL, 1.44 mmol), as described in General Procedure G. The crude product was purified by flash column chromatography on silica gel, with CH$_2$Cl$_2$ as eluent, to afford the (3S)-(2-biphenyl-4-yl-(1S)-carboxy-ethylcarbamoyl)-7-(4-tert-butyl-phenoxy)-3,4-dihydro-1H-isoquinoline-2-carboxylic acid tert-butyl ester which was deprotected according to the general procedure N to give 3-biphenyl-4-yl-(2S)-{[7-(4-tert-butyl-phenoxy)-1,2,3,4-tetrahydro-isoquinoline-(3S)-carbonyl]-amino}-propionic acid methyl ester hydrochloride (0.1 g).

The above compound (0.1 g, 0.17 mmol) was reacted with isobutyl chloroformate (0.070 g, 0.51 mmol), and TEA (0.086 mL, 0.85 mmol) as described in general procedure K. The crude compound was purified by flash column chromatography on silica gel using 30% ethyl acetate in hexanes as the mobile phase to give 0.060 g of (3S)-(2-biphenyl-4-yl-(1S)-methoxycarbonyl-ethylcarbamoyl)-7-(4-tert-butyl-phenoxy)-3,4-dihydro-1H-isoquinoline-2-carboxylic acid isobutyl ester. A solution of this ester (0.060 g, 0.090 mmol) in THF (3.0 mL) was treated with LiOH (0.011 g, 0.27 mmol) by general procedure I to afford 0.051 g of the title compound as a white solid.

LCMS: 650 (M+1)$^+$. $^1$H NMR (DMSO-d$_6$) δ 12.7 [s, 1H], 7.61 [d, 2 H], 7.53 [d, 2 H], 7.43 [d, 2 H], 7.37-7.34 [m, 3H], 7.20 [d, 2 H], 7.15-7.12 [m, 1H], 6.88 [d, 2 H], 6.78 [d, 2 H], 4.80 [m, 1H], 4.55 [m, 2 H], 4.36 [m, 2 H], 3.82 [m, 1H], 3.65 [m, 1H], 3.34 [s, 3H], 3.06-3.02 [m, 2 H], 1.26 [s, 9 H], 0.88 [d, 2H], 0.70 [d, 3H].

Example 73

7-(4-tert-Butyl-phenoxy)-(3S)-[(1S)-carboxy-2-(4-phenoxy-phenyl)-ethylcarbamoyl]-3,4-dihydro-1H-isoquinoline-2-carboxylic acid isobutyl ester 7-Hydroxy-3,4-dihydro-1H-isoquinoline-2,(3S)-dicarboxylic acid 2-tert-butyl ester 3-methyl ester (2.68 g, 8.7 mmol) in DCM (15 mL) was treated with copper acetate (3.17 g, 17.4 mmol), 4-tert-butylphenylboronic acid (4.65 g, 4.8 mmol), and TEA (7.32 mL, 52.2 mmol) by the general procedure G. The crude product was purified by flash column chromatography on silica gel using hexanes:EtOAc (70:30) to give 1.2 g of 7-(4-tert-butyl-phenoxy)-3,4-dihydro-1H-isoquinoline-2,3-dicarboxylic acid 2-tert-butyl ester 3-methyl ester which was deprotected using general procedure N to give 7-(4-tert-butyl-phenoxy)-1,2,3,4-tetrahydro-isoquinoline-(3S)-carboxylic acid methyl ester hydrochloride salt (0.99 g).

0.99 g (2.9 mmol) of above hydrochloride salt was reacted with 0.4 g (2.9 mmol) of isobutyl chloroformate as described in general procedure K. Evaporation of the solvent followed by column chromatography using 7:3 hexane and ethyl acetate gave 1.1 g of the methyl ester which was hydrolyzed as described in general procedure I to give 1.17 g of 7-(4-tert-butyl-phenoxy)-3,4-dihydro-1H-isoquinoline-2,3S-dicarboxylic acid 2-isobutyl ester.

LCMS 426 (M+1)$^+$

The above acid (0.5 g, 1.1 mmol) was reacted with 0.27 g (1.1 mmol) of 2S-amino-3-(4-hydroxy-phenyl)-propionic acid methyl ester as described in general procedure A. The crude product was purified by flash column chromatography on silica gel using 3:2 hexane/ethyl acetate as an eluents, to afford 1.17 g of 7-(4-tert-butyl-phenoxy)-(3S)-[2-(4-hydroxy-phenyl)-(1S)-methoxycarbonyl-ethylcarbamoyl]-3,4-dihydro-1H-isoquinoline-2-carboxylic acid isobutyl ester as a white solid.

LCMS: 603 (M+1)$^+$ 50 mg (0.083 mmol) of above compound was reacted with 30 mg (0.24 mmol) of phenyl boronic acid as described in procedure G. Column chromatography using DCM as an eluent gave the ester which was hydrolyzed as described in general procedure I to give 20 mg of title compound as a white solid.

LCMS 665 (M+1)$^+$

Example 74

3-Biphenyl-4-yl-(2S)-{[7-(4-tert-butyl-phenoxy)-2-(2-cyclopentyl-acetyl)-1,2,3,4-tetrahydro-isoquinoline-(3S)-carbonyl]-amino}-propionic acid 100 mg (0.17 mmol) of 3-biphenyl-4-yl-(2S)-{[7-(4-tert-butyl-phenoxy)-1,2,3,4-tetrahydro-isoquinoline-(3S)-carbonyl]-amino}-propionic acid methyl ester hydrochloride (prepared as described in example 72) was reacted with 28.5 mg (0.19 mmol) of cyclopentyl acetyl chloride as described in general procedure J. Evaporation of the solvent followed by column chromatography using 7:3 hexane/ethyl acetate gave 110 mg of the methyl ester which was hydrolyzed as described in general procedure I to give 107 mg of the title compound as a white solid.

LCMS 659 (M+1)$^+$

Example 75

(3S)-(2-Biphenyl-4-yl-(1S)-carboxy-ethylcarbamoyl)-7-hydroxy-3,4-dihydro-1H-isoquinoline-2-carboxylic acid tert-butyl ester A solution of 7-hydroxy-3,4-dihydro-1H-isoquinoline-2,3-(3S)-dicarboxylic acid 2-tert-butyl ester (2.00 g, 6.80 mmol) in DMF (8.0 mL) was treated with (2S)-amino-3-(4-bromo-phenyl)-propionic acid methyl ester hydrochloride (2.20 g, 7.50 mmol), HBTU (2.54 g, 6.70 mmol), and DIEA (4.25 mL, 23.80 mmol) via the general procedure A. The crude product was purified by flash column chromatography on silica gel using CHCl$_3$ as the mobile phase to give 2.20 g of (3S)-[(2S)-(4-bromo-phenyl)-1-methoxycarbonyl]-7-hydroxy-3,4-dihydro-1H-isoquinoline-2-carboxylic acid tert-butyl ester.

A solution of (3S)-[(2S)-(4-bromo-phenyl)-1-methoxycarbonyl]-7-hydroxy-3,4-dihydro-1H-isoquinoline-2-carboxylic acid tert-butyl ester (1.60 g, 2.99 mmol) in DCM (25 mL) was treated with copper acetate (0.817 g, 4.499 mmol), 4-tert-butylphenylboronic acid (1.33 g, 7.497 mmol), and TEA (2.09 mL, 14.995 mmol) by the general procedure G. The crude product was purified by flash column chromatography on silica gel using hexanes/EtOAc (70:30) to give 0.250 g of 3(S)-[(2S)-(4-bromo-phenyl)-1-methoxycarbonyl]-7-(4-tert-butyl-phenoxy)-3,4-dihydro-1H-isoquinoline-2-carboxylic acid tert-butyl ester.

To (3S)-[(2S)-(4-bromo-phenyl)-1-methoxycarbonyl]-7-(4-tert-butyl-phenoxy)-3,4-dihydro-1H-isoquinoline-2-carboxylic acid tert-butyl ester (0.250 g, 0.414 mmol) was added HCl/dioxane (4.0M, 10 mL) and the solution was stirred at rt for 1 h. The solution was concentrated under reduced pressure to give the corresponding amine as white solid. To this was added DCM (10 mL) and cyclopentylacetyl chloride (52 mg, 0.354 mmol) and TEA (0.140 mL, 0.993 mmol). The reaction was stirred for 30 min and concentrated under reduced pressure. The crude product was purified by flash column chromatography on silica gel using hexanes:EtOAc(70:30) to give 0.150 g of 3-(4-bromo-phenyl)-(2S)-{[7-(4-tert-butyl-phenoxy)-2-(2-cyclopentyl-acetyl)-1,2,3,4-tetrahydro-isoquinoline-(3S)-carbonyl]-amino}-propionic acid methyl ester.

A solution of 3-(4-bromo-phenyl)-(2S)-{[7-(4-tert-butyl-phenoxy)-2-(2-cyclopentyl-acetyl)-1,2,3,4-tetrahydro-isoquinoline-(3S)-carbonyl]-amino}-propionic acid methyl ester (0.160 g, 0.20 mmol) in toluene (3.0 mL) was treated with 3-chloro-4-fluoro-phenylboronic acid (62 mg, 0.353 mmol), Pd(PPh$_3$)$_4$ (35 mg), and Na$_2$CO$_3$ (0.500 mL) by the general procedure D. The crude product was purified by flash column chromatography on silica gel using Hexanes:EtOAC (80:20) to give 0.120 g of (2S)-{[7-(4-tert-butyl-phenoxy)-2-(2-cyclopentyl-acetyl)-1,2,3,4-tetrahydro-isoquinoline-(3S)-carbonyl]-amino}-3-(3'-chloro-4'-fluoro-biphenyl-4-yl)-propionic acid methyl ester which was hydrolyzed according to the general procedure I to give 0.105 g of the title compound as a white solid.

LCMS 711 (M+1)$^+$. $^1$H NMR (CDCl) δ 7.54 [d, 1H], 7.47 [d, 1H], 7.308 [m, 5 H], 7.16-7.04 [m, 3 H], 6.85 [m, 4 H], 6.67 [s, 1H], 5.22 [m, 1H], 4.82-4.66 [m, 2 H], 4.55-4.42 [m, 2 H], 4.08 [d, 1H], 3.40-3.29 [m, 1H], 3.12-2.87 [m, 2 H], 2.42-2.16 [m, 2 H], 1.77 [m, 2 H], 1.59-1.48 (m, 4 H], 1.26 [s, 9 H], 1.07 [m, 2 H].

Example 76

3-Biphenyl-4-yl-(2S)-{[2-(2,2-dimethyl-propionyl)-7-(4-trifluoromethyl-benzyloxy)-1,2,3,4-tetrahydro-isoquinoline-(3S)-carbonyl]-amino}-propionic acid 0.1 g (0.17 mmol) of 3-biphenyl-4-yl-(2S)-{[7-(4-tert-butyl-phenoxy)-1,2,3,4-tetrahydro-isoquinoline-(3S)-carbonyl]-amino}-propionic acid methyl ester hydrochloride (prepared in example 72) in DCE was reacted with isobutyraldehyde (0.024 g, 0.34 mmol), glacial acetic acid (0.03 g, 0.51 mmol) and sodium triacetoxyborohydride (0.089 g, 0.42 mmol) according to general procedure E. The crude compound was purified by flash column chromatography on silica gel using 75% ethyl acetate in hexanes as the mobile phase to give 0.070 g of 3-biphenyl-4-yl-(2S)-{[7-(4-tert-butyl-phenoxy)-2-isobutyl-1,2,3,4-tetrahydro-isoquinoline-(3S)-carbonylamino}-propionic acid methyl ester.

A solution of this ester was hydrolyzed by general procedure I to afford 0.065 g of the title compound 3-biphenyl-4-yl-(2S)-{[2-(2,2-dimethyl-propionyl)-7-(4-trifluoromethyl-benzyloxy)-1,2,3,4-tetrahydro-isoquinoline-(3S)-carbonyl]-amino}-propionic acid as a white solid.

LCMS: 606 (M+1)$^+$

Example 77

3-Biphenyl-4-yl-(2S)-{[7-(4-tert-butyl-phenoxy)-2-(propane-2-sulfonyl)-1,2,3,4-tetrahydro-isoquinoline-(3S)-carbonyl]-amino}-propionic acid 0.1 g (0.17 mmol) of 3-biphenyl-4-yl-(2S)-{[7-(4-tert-butyl-phenoxy)-1,2,3,4-tetrahydro-isoquinoline-(3S)-carbonyl]-amino}-propionic acid methyl ester hydrochloride (as prepared in example 72) in DCM was reacted with isopropyl-sulfonyl chloride (0.024 g, 0.17 mmol), and pyridine (0.134 g, 1.7 mmol) according to general procedure F. The crude compound was purified by flash column chromatography on silica gel using 40% ethyl acetate in hexanes as the mobile phase to give 0.060 g of 3-biphenyl-4-yl-(2S)-{[7-(4-tert-butyl-phenoxy)-2-(propane-2-sulfonyl)-1,2,3,4-tetrahydro-isoquinoline-(3S)-carbonyl]-amino}-propionic acid methyl ester which was hydrolyzed according to the general procedure I to afford 0.065 g of the title compound.

LCMS: 656 (M+1)$^+$.

Example 78

3-Biphenyl-4-yl-(2S)-{[2-dimethylcarbamoylmethyl-7-(4-trifluoromethyl-benzyloxy)-,2,3,4-tetrahydro-isoquinoline-(3S)-carbonyl]-amino}-propionic acid To a stirring solution of 46 mg (0.074 mmol) of 3-biphenyl-4-yl-(2S)-{[7-(4-trifluoromethyl-benzyloxy)-1,2,3,4-tetrahydro-isoquinoline-(3S)-carbonyl]-amino}-propionic acid hydrochloride (as prepared in example 66) in 2 mL of dry CH$_3$CN was added N-isopropyl-α-bromoacetamide (1.2 eq. 0.088 mmol, 15.9 mg) and anhydrous potassium carbonate (3.0 eq., 0.22 mmol, 31 mg) and the resultant mixture heated at reflux for 4-8 hours, then cooled and concentrated. The crude residue was placed directly atop a silica gel column and eluted with ethyl acetate/hexanes to furnish 25 mg of the 3-biphenyl-4-yl-(2S)-{(isopropylcarbamoyl-methyl)-[7-(4-trifluoromethyl-benzyloxy)-1,2,3,4-tetrahydro-isoquinoline-(3S)-carbonyl]-amino}-propionic acid methyl ester.

LCMS 674 (M+1)$^+$.

This ester was saponified according to general procedure C to afford 24 mg of the title compound as a white solid.

LCMS 660 (M+1)$^+$.

Example 79

3-Biphenyl-4-yl-(2S)-{[6-(4-tert-butyl-phenoxy)-2-(2-cyclopentyl-acetyl)-1,2,3,4-tetrahydro-isoquinoline-(3S)-carbonyl]-amino}-propionic acid 6-Hydroxy-3,4-dihydro-1H-isoquinoline-2,3-dicarboxylic acid 2-tert-butyl ester 3-methyl ester (0.5 g, 1.62 mmol) in DCM (15 mL) was treated with copper acetate (0.59 g, 3.3 mmol), 4-tert-butylphenylboronic acid (0.87 g, 4.8 mmol), and TEA (1.0 mL, 7.9 mmol) by the general procedure G. The crude product was purified by flash column chromatography on silica gel using Hexanes:EtOAc (70:30) to give 0.35 g of 6-(4-tert-butyl-phenoxy)-3,4-dihydro-1H-isoquinoline-2,3-dicarboxylic acid 2-tert-butyl ester 3-methyl ester which was deprotected using general procedure N to give 6-(4-tert-butyl-phenoxy)-1,2,3,4-tetrahydro-isoquinoline-(3S)-carboxylic acid methyl ester hydrochloride salt (0.27 g).

270 mg (0.79 mmol) of above hydrochloride salt was reacted with 128 mg (0.87 mmol) of cyclopentyl acetyl chloride as described in general procedure J. Evaporation of the solvent followed by column chromatography using 7:3 hexane and ethyl acetate gave 296 mg of the methyl ester which was hydrolyzed as described in general procedure I to give 221 mg of the title compound as a white solid. LCMS 450 (M+1)$^+$ 100 mg (0.22 mmol) of above acid was reacted with (2S)-amino-3-biphenyl-4-yl-propionic acid methyl ester (59.7 mg, 0.22 mmol) as described in general procedure A. The crude material was subjected to column chromatography using 10% ethyl acetate in hexane to afford the ester, which was hydrolyzed as described in general procedure C to afford 113 mg of the title compound as a white solid.

LCMS: 659 (M+1)$^+$

Example 80

3-Biphenyl-4-yl-2-{[7-[2-(4-tert-butyl-phenyl)-ethoxy]-2-(2-cyclopentyl-acetyl)-1,2,3,4-tetrahydro-isoquinoline-(3S)-carbonyl]-amino}-propionic acid 0.1 g (0.17 mmol) of (3S)-(2-biphenyl-4-yl-(1S)-methoxycarbonyl-ethylcarbamoyl)-7-hydroxy-3,4-dihydro-1H-isoquinoline-2-carboxylic acid tert-butyl ester (example 70), 4-tert-butylphenethyl alcohol (0.047 g, 0.25 mmol) and triphenylphospine on polystyrene (0.25 g, 0.25 mmol) in DCM at −20° C. was added DIAD (0.05 g, 0.25 mmol) according to general procedure M. The crude compound was purified by flash column chromatography on silica gel using 30% ethyl acetate in hexanes as the mobile phase to give (3S)-(2-biphenyl-4-yl-(1S)-methoxycarbonyl-ethylcarbamoyl)-7-[2-(4-tert-butyl-phenyl)-ethoxy]-3,4-dihydro-1H-isoquinoline-2-carboxylic acid tert-butyl ester (0.044 g) which was deprotected according to the general procedure N to give 3-biphenyl-4-yl-(2S)-({7-[2-(4-tert-butyl-phenyl)-ethoxy]-1,2,3,4-tetrahydro-isoquinoline-(3S)-carbonyl}-amino)-propionic acid methyl ester (37 mg).

The above compound (37 mg, 0.062 mmol), cyclopentylacetyl chloride (10.9 mg, 0.075 mmol) in DCM (2 ml) was added TEA (31.6 mg, 0.31 mmol) according to the general procedure J. The crude product was purified by flash column chromatography on silica gel using hexanes: EtOAc (70:30) to give ester which was hydrolyzed according to general procedure I to afford 0.030 g of the title compound.

LCMS: 688 (M+1)$^+$. $^1$H NMR (DMSO-d$_6$) 7.61 [m, 2 H], 7.51-7.41 [m, 4 H], 7.35-7.29 [m, 3 H], 7.19-7.11 [m, 4H], 7.01 [m, 1H], 6.75-6.66 [m, 2 H], 5.10 [m, 1H], 4.69-4.57 [m, 2 H], 4.36 [Br s,1H], 4.26-4.19 [m, 1H], 4.09-3.97 [m, 2 H], 3.34 [d, 4H], 3.06-2.81 [m, 4 H], 2.44 [d, 1H], 2.18-2.01 [m, 2H], 1.73-0.93[m, 15H].

Example 81

3-Biphenyl-4-yl-(2S)-{[7-(4-tert-butyl-phenoxy)-2-(2-pyrrolidin-1-yl-acetyl-(3S)-carbonyl]-amino}-propionic acid 100 mg (0.17 mmol) of (3S)-biphenyl-4-yl-2-{[7-(4-tert-butyl-phenoxy)-1,2,3,4-tetrahydro-isoquinoline-(3S)-carbonyl]-amino}-propionic acid methyl ester hydrochloride (from example 72) in 2 ml of DCM was added bromoacetic acid anhydride (50 mg, 0.2 mmol) and stirred at rt for 20 min. To this reaction mixture pyrrolidine (0.060 g, 0.85 mmol) was added and allowed to react overnight at room temperature. The crude compound was purified by flash column chromatography on silica gel using 70% ethyl acetate in hexanes as the mobile phase to give 0.040 g of the methyl ester which was hydrolyzed by the general procedure I to afford 0.030 g of the title compound as solid.

LCMS: 661 (M+1)$^+$. $^1$H NMR (DMSO-d$_6$) 7.63-7.61 [m, 2 H], 7.55-7.50 [m, 2 H], 7.38-7.33 [m, 2 H], 7.18-7.10 [m, 6H], 6.91-6.85 [m, 3 H], 6.75 [m, 1H], 5.00 [m, 1H], 4.50-4.44 [m, 4 H], 3.34 [Br s, 6H], 3.12-3.03 [m, 4 H], 2.05-1.91 [m, 4H], 1.26[s, 9H].

Example 82

7-(4-tert-Butyl-phenoxy)-(3S)-{(1S)-carboxy-2-[4-(3,3-dimethyl-butoxy)-phenyl]-ethylcarbamoyl}-3,4-dihydro-1H-isoquinoline-2-carboxylic acid isobutyl ester 51 mg (0.5 mmol) of 7-(4-tert-butyl-phenoxy)-(3S)-[2-(4-hydroxy-phenyl)-1-methoxycarbonyl-etylcarbamoyl]-3,4-dihydro-1H-isoquinoline-(2S)-carboxylic acid isobutyl ester (prepared in example 73, step 3), 3,3-dimethylbutyl alcohol (0.051 g, 0.5 mmol) and triphenylphospine on polystyrene (0.5 g, 0.5 mmol) in DCM at −20° C. was added DIAD (0.1 g, 0.5 mmol) according to general procedure M. The crude compound was purified by flash column chromatography on silica gel using 30% ethyl acetate in hexanes as the mobile phase to give 0.053 g of the methyl ester. A solution of this ester (0.053 g, 0.077 mmol) in THF (3.0 mL) was treated with LiOH (0.009 g, 0.23 mmol) by general procedure I to afford 0.040 g of the title compound.

LCMS: 674 (M+1)$^+$.

Example 83

3-Biphenyl-4-yl-(2S)-{[7-(4-tert-butyl-phenyl)-2-(2-cyclopentyl-acetyl)-1,2,3,4-tetrahydro-isoquinoline-(3S)-carbonyl]-amino}-propionic acid To a stirring solution of 0.5 g (0.94 mmol) of (3S)-(2-biphenyl-4-yl-(1S)-methoxycarbonyl-ethylcarbamoyl)-7-hydroxy-3,4-dihydro-1H-isoquinoline-2-carboxylic acid tert-butyl ester (example 70) was deprotected according to general procedure N to give 438 mg of 3-biphenyl-4-yl-(2S)-[(7-hydroxy-1,2,3,4-tetrahydro-isoquinoline-(3S)-carbonyl)-amino]-propionic acid methyl ester hydrochloride salt.

To a stirring solution of the above compound (438 mg, 0.94 mmol) in a mixture of ethyl acetate and saturated NaHCO$_3$ (1:1) was added 151 mg (1.0 mmol) of cyclopentyl-acetyl chloride at 0° C. The reaction mixture was warmed to rt and stirred for another 2 h. The organic layer was separated and washed with water and brine, followed by evaporation of the solvent, to give 500 mg of 3-biphenyl-4-yl-(2S)-{[2-(2-cyclopentyl-acetyl)-7-hydroxy-1,2,3,4-tetrahydro-isoquinoline-(3S)-carbonyl]-amino}-propionic acid methyl ester.

To a stirring solution of above phenol (500 mg, 0.95 mmol), NEt$_3$ (187 mg, 1.85 mmol) and DMAP (cat) in DCM (5 ml) was added trifluoromethylsulfonic anhydride at 0° C. The stirring was continued for another 30 min then 10 ml of DCM was added. The reaction mixture was washed with saturated citric acid, water and brine then dried over anhydrous Na$_2$SO$_4$. Filtration followed by evaporation of the solvent under vacuum gave 528 mg of the triflate, which was used for the next step without purification.

The above triflate (250 mg, 0.37 mmol), 4-tert-butyl phenyl boronic acid (140 mg, 0.74 mmol), Pd(PPh$_3$)$_4$ (42 mg, 0.037 mmol) and 0.75 ml of 2N Na$_2$CO$_3$ were taken in 10 ml of toluene and degassed with nitrogen for 15 min. The reaction mixture stirred over night at 90° C. then usual work up and purification as described in procedure D gave the ester which was hydrolyzed as described in general procedure C to afford 100 mg of the title compound as a white solid.

LCMS: 643 (M+1)$^+$.

By analogous methods to those described above the following Examples were synthesized.

| Example | Name | LC/MS |
|---|---|---|
| 84 | 3-Biphenyl-4-yl-(2S)-{[7-(4-trifluoromethyl-benzyloxy)-1,2,3,4-tetrahydro-isoquinoline-(3S)-carbonyl]-amino}-propionic acid | 575 |
| 85 | (3S)-[1-Carboxy-(2S)-(2'-phenoxy-biphenyl-4-yl)-ethylcarbamoyl]-7-(4-trifluoromethyl-benzyloxy)-3,4-dihydro-1H-isoquinoline-2-carboxylic acid tert-butyl ester | 767 |

| Example | Name | LC/MS |
|---|---|---|
| 86 | 3-(2'-Phenoxy-biphenyl-4-yl)-(2S)-{[7-(4-trifluoromethyl-benzyloxy)-1,2,3,4-tetrahydro-isoquinoline-(3S)-carbonyl]-amino}-propionic acid | 667 |
| 87 | (3S)-(2-Biphenyl-4-yl-(1S)-carboxy-ethylcarbamoyl)-7-hydroxy-3,4-dihydro-1H-isoquinoline-2-carboxylic acid tert-butyl ester | 517 |
| 88 | 3-Biphenyl-4-yl-(2S)-{[2-(2,2-dimethyl-propionyl)-7-(4-trifluoromethyl-benzyloxy)-1,2,3,4-tetrahydro-isoquinoline-(3S)-carbonyl]-amino}-propionic acid | 659 |
| 89 | (2S)-{[2-Acetyl-7-(4-trifluoromethyl-benzyloxy)-1,2,3,4-tetrahydro-isoquinoline-(3S)-carbonyl]-amino}-3-biphenyl-4-yl-propionic acid | 617 |
| 90 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid isopropyl ester | 661 |
| 91 | 3-Biphenyl-4-yl-(2S)-{[2-phenylacetyl-7-(4-trifluoromethyl-benzyloxy)-1,2,3,4-tetrahydro-isoquinoline-(3S)-carbonyl]-amino}-propionic acid | 693 |
| 92 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid methyl ester | 633 |
| 93 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid ethyl ester | 647 |
| 94 | 7-Benzyloxy-(3R)-(2-biphenyl-4-yl-(1R)-carboxy-ethylcarbamoyl)-3,4-dihydro-1H-isoquinoline-2-carboxylic acid tert-butyl ester | 607 |
| 95 | 7-Benzyloxy-(3R)-(2-biphenyl-4-yl-(1S)-carboxy-ethylcarbamoyl)-3,4-dihydro-1H-isoquinoline-2-carboxylic acid tert-butyl ester | 607 |
| 96 | (3S)-(2-Biphenyl-4-yl-(1S)-carboxy-ethylcarbamoyl)-7-(4-trifluoromethyl-phenoxy)-3,4-dihydro-1H-isoquinoline-2-carboxylic acid tert-butyl ester | 661 |
| 97 | (3S)-(2-Biphenyl-4-yl-(1S)-carboxy-ethylcarbamoyl)-7-ethoxy-3,4-dihydro-1H-isoquinoline-2-carboxylic acid tert-butyl ester | 545 |
| 98 | 3-Biphenyl-4-yl-(2S)-{[2-(4-chloro-benzoyl)-7-(4-trifluoromethyl-benzyloxy)-1,2,3,4-tetrahydro-isoquinoline-(3S)-carbonyl]-amino}-propionic acid | 713 |
| 99 | (3S)-(2-Biphenyl-4-yl-(1S)-carboxy-ethylcarbamoyl)-7-(4-trifluoromethoxy-phenoxy)-3,4-dihydro-1H-isoquinoline-2-carboxylic acid tert-butyl ester | 677 |
| 100 | (3S)-(2-Biphenyl-4-yl-(1S)-carboxy-ethylcarbamoyl)-7-(3-chloro-4-fluoro-phenoxy)-3,4-dihydro-1H-isoquinoline-2-carboxylic acid tert-butyl ester | 645 |
| 101 | (3S)-(2-Biphenyl-4-yl-(1S)-carboxy-ethylcarbamoyl)-7-(4-chloro-phenoxy)-3,4-dihydro-1H-isoquinoline-2-carboxylic acid tert-butyl ester | 627 |
| 102 | (3S)-(2-Biphenyl-4-yl-(1S)-carboxy-ethylcarbamoyl)-7-(4-cyano-phenoxy)-3,4-dihydro-1H-isoquinoline-2-carboxylic acid tert-butyl ester | 618 |
| 103 | (3S)-(2-Biphenyl-4-yl-(1S)-carboxy-ethylcarbamoyl)-7-(4-methoxy-phenoxy)-3,4-dihydro-1H-isoquinoline-2-carboxylic acid tert-butyl ester | 623 |
| 104 | (3R)-(2-Biphenyl-4-yl-(1S)-carboxy-ethylcarbamoyl)-7-(4-trifluoromethyl-phenoxy)-3,4-dihydro-1H-isoquinoline-2-carboxylic acid tert-butyl ester | 661 |
| 105 | 3-Biphenyl-4-yl-(2S)-{[2-cyclopropanecarbo--nyl-7-(4-trifluoromethyl-benzyloxy)-1,2,3,4-tetrahydro-isoquinoline-(3S)-carbonyl]-amino}-propionic acid | 643 |
| 106 | 3-Biphenyl-4-yl-(2S)-{[2-cyclobutanecarbonyl-7-(4-trifluoromethyl-benzyloxy)-1,2,3,4-tetrahydro-isoquinoline-(3S)-carbonyl]-amino}-propionic acid | 657 |
| 107 | 3-Biphenyl-4-yl-(2S)-{[2-cyclopentanecarbonyl-7-(4-trifluoromethyl-benzyloxy)-1,2,3,4-tetrahydro-isoquinoline-(3S)-carbonyl]-amino}-propionic acid | 671 |
| 108 | 3-Biphenyl-4-yl-(2S)-{[2-cyclohexanecarbonyl-7-(4-trifluoromethyl-benzyloxy)-1,2,3,4-tetrahydro-isoquinoline-(3S)-carbonyl]-amino}-propionic acid | 685 |
| 109 | (3S)-(2-Biphenyl-4-yl-(1S)-carboxy-ethylcarbamoyl)-7-isopropoxy-3,4-dihydro-1H-isoquinoline-2-carboxylic acid tert-butyl ester | 559 |
| 110 | (3R)-(2-Biphenyl-4-yl-(1R)-carboxy-ethylcarbamoyl)-7-(4-trifluoromethyl-phenoxy)-3,4-dihydro-1H-isoquinoline-2-carboxylic acid tert-butyl ester | 661 |

-continued

| Example | Name | LC/MS |
|---|---|---|
| 111 | (3S)-(2-Biphenyl-4-yl-(1S)-carboxy-ethylcarbamoyl)-7-(3-methyl-butoxy)-3,4-dihydro-1H-isoquinoline-2-carboxylic acid tert-butyl ester | 587 |
| 112 | 3-Biphenyl-4-yl-(2S)-{[2-dimethylcarbamoyl-7-(4-trifluoromethyl-benzyloxy)-1,2,3,4-tetrahydro-isoquinoline-(3S)-carbonyl]-amino}-propionic acid | 646 |
| 113 | 3-Biphenyl-4-yl-(2S)-{[2-diethylcarbamoyl-7-(4-trifluoromethyl-benzyloxy)-1,2,3,4-tetrahydro-isoquinoline-(3S)-carbonyl]-amino}-propionic acid | 674 |
| 114 | 3-Biphenyl-4-yl-(2S)-{[2-(piperidine-1-carbonyl)-7-(4-trifluoromethyl-benzyloxy)-1,2,3,4-tetrahydro-isoquinoline-(3S)-carbonyl]-amino}-propionic acid | 686 |
| 115 | 3-Biphenyl-4-yl-(2S)-{[2-diisopropylcarbamoyl-7-(4-trifluoromethyl-benzyloxy)-1,2,3,4-tetrahydro-isoquinoline-(3S)-carbonyl]-amino}-propionic acid | 702 |
| 116 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid allyl ester | 659 |
| 117 | 3-Biphenyl-4-yl-(2S)-{[2-cycloheptanecarbonyl-7-(4-trifluoromethyl-benzyloxy)-1,2,3,4-tetrahydro-isoquinoline-(3S)-carbonyl]-amino}-propionic acid | 699 |
| 118 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid butyl ester | 675 |
| 119 | 3-Biphenyl-4-yl-(2S)-{[2-(2-cyclopentyl-acetyl)-7-(4-trifluoromethyl-phenoxy)-1,2,3,4-tetrahydro-isoquinoline-(3S)-carbonyl]-amino}-propionic acid | 671 |
| 120 | (3S)-(2-Biphenyl-4-yl-(1S)-carboxy-ethylcarbamoyl)-7-(2-trifluoromethyl-phenoxy)-3,4-dihydro-1H-isoquinoline-2-carboxylic acid tert-butyl ester | 661 |
| 121 | (3S)-(2-Biphenyl-4-yl-(1S)-carboxy-ethylcarbamoyl)-7-(3,4-difluoro-phenoxy)-3,4-dihydro-1H-isoquinoline-2-carboxylic acid tert-butyl ester | 629 |
| 122 | (3S)-[1-Carboxy-(2S)-(4-hydroxy-phenyl)-ethylcarbamoyl]-7-(4-trifluoromethyl-phenoxy)-3,4-dihydro-1H-isoquinoline-2-carboxylic acid tert-butyl ester | 601 |
| 123 | (3S)-[2-(4-Benzyloxy-phenyl)-(1S)-carboxy-ethylcarbamoyl]-7-(4-trifluoromethyl-phenoxy)-3,4-dihydro-1H-isoquinoline-2-carboxylic acid tert-butyl ester | 691 |
| 124 | (3S)-{(1S)-Carboxy-2-[4-(4-trifluoromethyl-phenoxy)-phenyl]-ethylcarbamoyl}-7-(4-trifluoromethyl-henoxy)-3,4-dihydro-1H-isoquinoline-2-carboxylic acid tert-butyl ester | 745 |
| 125 | (3S)-{(1S)-Carboxy-2-[4-(3-chloro-4-fluoro-phenoxy)-phenyl]-ethylcarbamoyl}-7-(4-trifluoromethyl-henoxy)-3,4-dihydro-1H-isoquinoline-2-carboxylic acid tert-butyl ester | 729 |
| 126 | 3-Biphenyl-4-yl-(2S)-{[2-(2-cyclopentyl-acetyl)-7-(2-fluoro-benzyloxy)-1,2,3,4-tetrahydro-isoquinoline-(3S)-carbonyl]-amino}-propionic acid | 635 |
| 127 | 3-Biphenyl-4-yl-(2S)-{[7-(4-chloro-benzyloxy)-2-(2-cyclopentyl-acetyl)-1,2,3,4-tetrahydro-soquinoline-(3S)-carbonyl]-amino}-propionic acid | 651 |
| 128 | 3-Biphenyl-4-yl-(2S)-{[2-(2-cyclopentyl-acetyl)-7-(4-isopropyl-benzyloxy)-1,2,3,4-tetrahydro-isoquinoline-(3S)-carbonyl]-amino}-propionic acid | 659 |
| 129 | 3-Biphenyl-4-yl-(2S)-{[2-(2-cyclopentyl-acetyl)-7-phenethyloxy-1,2,3,4-tetrahydro-isoquinoline-(3S)-carbonyl]-amino}-propionic acid | 631 |
| 130 | 3-Biphenyl-4-yl-(2S)-({2-(2-cyclopentyl-acetyl)-7-[2-(4-methoxy-phenyl)-ethoxy]-1,2,3,4-tetrahydro-isoquinoline-(3S)-carbonyl}-amino)-propionic acid | 661 |
| 131 | 3-Biphenyl-4-yl-(2S)-{[2-(2-cyclopentyl-acetyl)-7-(3-phenyl-propoxy)-1,2,3,4-tetrahydro-isoquinoline-(3S)-carbonyl]-amino}-propionic acid | 645 |
| 132 | 3-Biphenyl-4-yl-(2S)-{[2-(2-cyclopentyl-acetyl)-7-(4-methoxy-benzyloxy)-1,2,3,4-tetrahydro-isoquinoline-(3S)-carbonyl]-amino}-propionic acid | 647 |
| 133 | 3-Biphenyl-4-yl-(2S)-{[2-(2-cyclopentyl-acetyl)-7-(2,4-difluoro-benzyloxy)-1,2,3,4-tetrahydro-isoquinoline-(3S)-carbonyl]-amino}-propionic acid | 653 |
| 134 | (3S)-(2-Biphenyl-4-yl-(1S)-carboxy-ethylcarbamoyl)-7-(3,5-bis-trifluoromethyl-phenoxy)-3,4-dihydro-1H-isoquinoline-2-carboxylic acid tert-butyl ester | 729 |
| 135 | (3S)-(2-Biphenyl-4-yl-(1S)-carboxy-ethylcarbamoyl)-7-(4-butyl-benzyloxy)-3,4-dihydro-1H-isoquinoline-2-carboxylic acid tert-butyl ester | 663 |

-continued

| Example | Name | LC/MS |
|---|---|---|
| 136 | (3S)-(2-Biphenyl-4-yl-(1S)-carboxy-ethylcarbamoyl)-7-[2-(2-methoxy-phenyl)-1-methyl-ethoxy]-3,4-dihydro-1H-isoquinoline-2-carboxylic acid tert-butyl ester | 665 |
| 137 | (3S)-(2-Biphenyl-4-yl-(1S)-carboxy-ethylcarbamoyl)-7-[(4-chloro-phenyl)-phenyl-methoxy]-3,4-dihydro-1H-isoquinoline-2-carboxylic acid tert-butyl ester | 717 |
| 138 | 7-[2-(4-Benzyloxy-phenyl)-ethoxy]-(3S)-(2-biphenyl-4-yl-(1S)-carboxy-ethylcarbamoyl)-3,4-dihydro-1H-isoquinoline-2-carboxylic acid tert-butyl ester | 727 |
| 139 | 3-Biphenyl-4-yl-(2S)-{[2-(2-cyclopentyl-acetyl)-7-(naphthalen-2-ylmethoxy)-1,2,3,4-tetrahydro-isoquinoline-(3S)-carbonyl]-amino}-propionic acid | 667 |
| 140 | 3-Biphenyl-4-yl-(2S)-{[7-(2-chloro-6-fluoro-benzyloxy)-2-(2-cyclopentyl-acetyl)-1,2,3,4-tetrahydro-isoquinoline-(3S)-carbonyl]-amino}-propionic acid | 669 |
| 141 | 3-Biphenyl-4-yl-(2S)-{[7-(4-tert-butyl-benzyloxy)-2-(2-cyclopentyl-acetyl)-1,2,3,4-tetrahydro-isoquinoline-(3S)-carbonyl]-amino}-propionic acid | 673 |
| 142 | 3-Biphenyl-4-yl-(2S)-{[7-[2-(2-bromo-phenyl)-ethoxy]-2-(2-cyclopentyl-acetyl)-1,2,3,4-tetrahydro-soquinoline-(3S)-carbonyl]-amino}-propionic acid | 710 |
| 143 | (3S)-[(1S)-Carboxy-2-(3'-chloro-4'-fluoro-biphenyl-4-yl)-ethylcarbamoyl]-7-(4-trifluoromethyl-phenoxy)-3,4-dihydro-1H-isoquinoline-2-carboxylic acid tert-butyl ester | 713 |
| 144 | 3-Biphenyl-4-yl-(2S)-{[7-(3-cyano-benzyloxy)-2-(2-cyclopentyl-acetyl)-1,2,3,4-tetrahydro-isoquinoline-(3S)-carbonyl]-amino}-propionic acid | 642 |
| 145 | 3-Biphenyl-4-yl-(2S)-({2-(2-cyclopentyl-acetyl)-7-[2-(4-fluoro-phenyl)-ethoxy]-1,2,3,4-tetrahydro-isoquinoline-(3S)-carbonyl}-amino)-propionic acid | 649 |
| 146 | (3S)-[(1S)-Carboxy-2-(4'-trifluoromethyl-biphenyl-4-yl)-ethylcarbamoyl]-7-(4-trifluoromethyl-benzyloxy)-3,4-dihydro-1H-isoquinoline-2-carboxylic acid tert-butyl ester | 743 |
| 147 | (3S)-[(1S)-Carboxy-2-(4'-trifluoromethoxy-biphenyl-4-yl)-ethylcarbamoyl]-7-(4-trifluoromethyl-benzyloxy)-3,4-dihydro-1H-isoquinoline-2-carboxylic acid tert-butyl ester | 759 |
| 148 | (3S)-[(1S)-Carboxy-2-(3'-chloro-4'-fluoro-biphenyl-4-yl)-ethylcarbamoyl]-7-(4-trifluoromethyl-benzyloxy)-3,4-dihydro-1H-isoquinoline-2-carboxylic acid tert-butyl ester | 727 |
| 149 | (3S)-[2-(4'-tert-Butyl-biphenyl-4-yl)-(1S)-carboxy-ethylcarbamoyl]-7-(4-trifluoromethyl-benzyloxy)-3,4-dihydro-1H-isoquinoline-2-carboxylic acid tert-butyl ester | 731 |
| 150 | (3S)-[2-(3',5'-Bis-trifluoromethyl-biphenyl-4-yl)-(1S)-carboxy-ethylcarbamoyl]-7-(4-trifluoromethyl-benzyloxy)-3,4-dihydro-1H-isoquinoline-2-carboxylic acid tert-butyl ester | 811 |
| 151 | (3S)-[(1S)-Carboxy-2-(3'-fluoro-biphenyl-4-yl)-ethylcarbamoyl]-7-(4-trifluoromethyl-benzyloxy)-3,4-dihydro-1H-isoquinoline-2-carboxylic acid tert-butyl ester | 693 |
| 152 | (3S)-(2-Biphenyl-4-yl-(1S)-carboxy-ethylcarbamoyl)-7-[4-(3,4-dichloro-benzyloxy)-benzyloxy]-3,4-dihydro-1H-isoquinoline-2-carboxylic acid tert-butyl ester | 781 |
| 153 | 7-Benzyloxy-(3S)-(2-biphenyl-4-yl-(1S)-carboxy-ethylcarbamoyl)-3,4-dihydro-1H-isoquinoline-2-carboxylic acid tert-butyl ester | 607 |
| 154 | (3S)-(2-Biphenyl-4-yl-(1S)-carboxy-ethylcarbamoyl)-7-(4-methyl-benzyloxy)-3,4-dihydro-1H-isoquinoline-2-carboxylic acid tert-butyl ester | 621 |
| 155 | (3S)-(2-Biphenyl-4-yl-(1S)-carboxy-ethylcarbamoyl)-7-[1-(4-fluoro-phenyl)-ethoxy]-3,4-dihydro-1H-isoquinoline-2-carboxylic acid tert-butyl ester | 639 |
| 156 | (3S)-(2-Biphenyl-4-yl-(1S)-carboxy-ethylcarbamoyl)-7-isopropoxy-3,4-dihydro-1H-isoquinoline-2-carboxylic acid tert-butyl ester | 559 |
| 157 | 3-Biphenyl-4-yl-(2S)-{[2-(2-cyclopentyl-acetyl)-7-(4-methylsulfanyl-benzyloxy)-1,2,3,4-tetrahydro-isoquinoline-(3S)-carbonyl]-amino}-propionic acid | 663 |
| 158 | -Biphenyl-4-yl-(2S)-{[2-(tert-butylcarbamoyl-methyl)-7-(4-trifluoromethyl-benzyloxy)-1,2,3,4-tetrahydro-isoquinoline-(3S)-carbonyl]-amino}-propionic acid | 688 |
| 159 | 3-Biphenyl-4-yl-(2S)-{[2-cyclopentylcarbamoylmethyl-7-(4-trifluoromethyl-benzyloxy)-1,2,3,4-tetrahydro-isoquinoline-(3S)-carbonyl]-amino}-propionic acid | 700 |
| 160 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid tert-butyl ester | 649 |

-continued

| Example | Name | LC/MS |
|---|---|---|
| 161 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid hexyl ester | 703 |
| 162 | (3S)-(2-Biphenyl-4-yl-(1S)-carboxy-ethylcarbamoyl)-7-(4-rifluoromethyl-benzyloxy)-3,4-dihydro-1H-isoquinoline-2-carboxylic acid 2-ethyl-hexyl ester | 731 |
| 163 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid 4-methoxy-phenyl ester | 725 |
| 164 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid benzyl ester | 709 |
| 165 | 3-Biphenyl-4-yl-(2S)-{[2-(2-cyclopentyl-acetyl)-7-(3-fluoro-2-trifluoromethyl-benzyloxy)-1,2,3,4-tetrahydro-isoquinoline-(3S)-carbonyl]-amino}-propionic acid | 703 |
| 166 | 3-Biphenyl-4-yl-(2S)-{[2-(2-cyclopentyl-acetyl)-7-(4-methoxy-3-trifluoromethyl-benzyloxy)-1,2,3,4-tetrahydro-isoquinoline-(3S)-carbonyl]-amino}-propionic acid | 715 |
| 167 | 3-Biphenyl-4-yl-(2S)-{[7-(2-chloro-5-trifluoromethyl-benzyloxy)-2-(2-cyclopentyl-acetyl)-1,2,3,4-tetrahydro-isoquinoline-(3S)-carbonyl]-amino}-propionic acid | 719 |
| 168 | 3-Biphenyl-4-yl-(2S)-{[7-(2-chloro-3-trifluoromethyl-benzyloxy)-2-(2-cyclopentyl-acetyl)-1,2,3,4-tetrahydro-isoquinoline-(3S)-carbonyl]-amino}-propionic acid | 719 |
| 169 | 3-Biphenyl-4-yl-(2S)-{[7-(3-chloro-2-fluoro-5-trifluoromethyl-benzyloxy)-2-(2-cyclopentyl-acetyl)-1,2,3,4-tetrahydro-isoquinoline-(3S)-carbonyl]-amino}-propionic acid | 737 |
| 170 | (2S)-{[7-(4-tert-Butyl-benzyloxy)-2-(2-cyclopentyl-acetyl)-1,2,3,4-tetrahydro-isoquinoline-(3S)-carbonyl]-amino}-3-(3'-chloro-4'-fluoro-biphenyl-4-yl)-propionic acid | 725 |
| 171 | 3-Biphenyl-4-yl-(2S)-{[7-(3,5-bis-trifluoromethyl-benzyloxy)-2-(2-cyclopentyl-acetyl)-1,2,3,4-tetrahydro-isoquinoline-(3S)-carbonyl]-amino}-propionic acid | 753 |
| 172 | 3-Biphenyl-4-yl-(2S)-{[7-(2,5-bis-trifluoromethyl-benzyloxy)-2-(2-cyclopentyl-acetyl)-1,2,3,4-tetrahydro-isoquinoline-(3S)-carbonyl]-amino}-propionic acid | 753 |
| 173 | 3-Biphenyl-4-yl-(2S)-({2-(2-cyclopentyl-acetyl)-7-[2-(4-trifluoromethyl-phenyl)-ethoxy]-1,2,3,4-tetrahydro-isoquinoline-(3S)-carbonyl}-amino)-propionic acid | 699 |
| 174 | 3-Biphenyl-4-yl-(2S)-({2-(2-cyclopentyl-acetyl)-7-[3-(4-trifluoromethyl-phenyl)-propoxy]-1,2,3,4-tetrahydro-isoquinoline-(3S)-carbonyl}-amino)-propionic acid | 713 |
| 175 | (3S)-(2-Biphenyl-4-yl-(1S)-carboxy-ethylcarbamoyl)-7-(4-trifluoromethyl-benzyloxy)-3,4-dihydro-1H-isoquinoline-2-carboxylic acid 2,2-dimethyl-propyl ester | 689 |
| 176 | 3-Biphenyl-4-yl-(2S)-{[2-(2-cyclopentyl-acetyl)-7-(3-trifluoromethyl-benzyloxy)-1,2,3,4-tetrahydro-isoquinoline-(3S)-carbonyl]-amino}-propionic acid | 685 |
| 177 | 3-Biphenyl-4-yl-(2S)-{[2-(2-cyclopentyl-acetyl)-7-(4-fluoro-3-trifluoromethyl-benzyloxy)-1,2,3,4-tetrahydro-isoquinoline-(3S)-carbonyl]-amino}-propionic acid | 703 |
| 178 | 3-Biphenyl-4-yl-(2S)-{[2-(2-cyclopentyl-acetyl)-7-(3-fluoro-4-trifluoromethyl-benzyloxy)-1,2,3,4-tetrahydro-isoquinoline-(3S)-carbonyl]-amino}-propionic acid | 703 |
| 179 | 3-Biphenyl-4-yl-(2S)-{[2-(2-cyclopentyl-acetyl)-7-(5-fluoro-2-trifluoromethyl-benzyloxy)-1,2,3,4-tetrahydro-isoquinoline-(3S)-carbonyl]-amino}-propionic acid | 703 |
| 180 | (2S)-{[2-(2-Cyclopentyl-acetyl)-7-(4-trifluoromethyl-phenoxy)-1,2,3,4-tetrahydro-isoquinoline-(3S)-carbonyl]-amino}-3-[4-(4-trifluoromethyl-phenoxy)-phenyl]-propionic acid | 755 |
| 181 | 3-[4-(3-Chloro-4-fluoro-phenoxy)-phenyl]-(2S)-{[2-(2-cyclopentyl-acetyl)-7-(4-trifluoromethyl-henoxy)-1,2,3,4-tetrahydro-isoquinoline-(3S)-carbonyl]-amino}-propionic acid | 739 |
| 182 | 3-Biphenyl-4-yl-(2S)-{[2-(2-cyclopentyl-acetyl)-7-(2-trifluoromethyl-benzyloxy)-1,2,3,4-tetrahydro-isoquinoline-(3S)-carbonyl]-amino}-propionic acid | 685 |
| 183 | 3-Biphenyl-4-yl-(2S)-{[2-(2-cyclopentyl-acetyl)-7-(2-fluoro-3-trifluoromethyl-benzyloxy)-1,2,3,4-tetrahydro-isoquinoline-(3S)-carbonyl]-amino}-propionic acid | 703 |
| 184 | 3-Biphenyl-4-yl-(2S)-{[2-(2-cyclopentyl-acetyl)-7-(3-fluoro-5-trifluoromethyl-benzyloxy)-1,2,3,4-tetrahydro-isoquinoline-(3S)-carbonyl]-amino}-propionic acid | 703 |
| 185 | 3-Biphenyl-4-yl-(2S)-{[2-(2-cyclopentyl-acetyl)-7-(4-fluoro-2-trifluoromethyl-benzyloxy)-1,2,3,4-tetrahydro-isoquinoline-(3S)-carbonyl]-amino}-propionic acid | 703 |

-continued

| Example | Name | LC/MS |
|---|---|---|
| 186 | 3-Biphenyl-4-yl-(2S)-{[2-(2-cyclopentyl-acetyl)-7-(2-fluoro-6-trifluoromethyl-benzyloxy)-1,2,3,4-tetrahydro-isoquinoline-(3S)-carbonyl]-amino}-propionic acid | 703 |
| 187 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4-hydroxy-henyl)-propionic acid | 599 |
| 188 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4-phenoxy-phenyl)-propionic acid | 675 |
| 189 | (2S)-{[7-(4-tert-Butyl-phenoxy)-2-(2-cyclopentyl-acetyl)-1,2,3,4-tetrahydro-isoquinoline-(3S)-carbonyl]-amino}-3-[4-(3-chloro-4-fluoro-phenoxy)-phenyl]-propionic acid | 727 |
| 190 | (2S)-{[7-(4-tert-Butyl-phenoxy)-2-(2-cyclopentyl-acetyl)-1,2,3,4-tetrahydro-isoquinoline-(3S)-carbonyl]-amino}-3-[4-(4-trifluoromethyl-phenoxy)-phenyl]-propionic acid | 743 |
| 191 | (2S)-{[7-(4-tert-Butyl-phenoxy)-2-(2-cyclopentyl-acetyl)-1,2,3,4-tetrahydro-isoquinoline-(3S)-carbonyl]-amino}-3-[4-(3-trifluoromethyl-phenoxy)-phenyl]-propionic acid | 743 |
| 192 | (2S)-{[7-(4-tert-Butyl-phenoxy)-2-(2-cyclopentyl-acetyl)-1,2,3,4-tetrahydro-isoquinoline-(3S)-carbonyl]-amino}-3-[4-(4-trifluoromethoxy-phenoxy)-phenyl]-propionic acid | 759 |
| 193 | 3-Biphenyl-4-yl-(2S)-{[2-(2-cyclopentyl-acetyl)-7-(pyridin-2-ylmethoxy)-1,2,3,4-tetrahydro-isoquinoline-(3S)-carbonyl]-amino}-propionic acid | 618 |
| 194 | 3-Biphenyl-4-yl-(2S)-{[7-(3-chloro-benzyloxy)-2-(2-cyclopentyl-acetyl)-1,2,3,4-tetrahydro-soquinoline-(3S)-carbonyl]-amino}-propionic acid | 651 |
| 195 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid 2,2-dimethyl-propyl ester | 663 |
| 196 | 3-Biphenyl-4-yl-(2S)-{[7-(4-tert-butyl-phenoxy)-2-cyclopentanecarbonyl-1,2,3,4-tetrahydro-soquinoline-(3S)-carbonyl]-amino}-propionic acid | 645 |
| 197 | 3-Biphenyl-4-yl-(2S)-{[7-(4-tert-butyl-phenoxy)-2-(3,3-dimethyl-butyryl)-1,2,3,4-tetrahydro-isoquinoline-(3S)-carbonyl]-amino}-propionic acid | 647 |
| 198 | 3-Biphenyl-4-yl-(2S)-({2-(2-cyclopentyl-acetyl)-7-[2-(3,4-dimethoxy-phenyl)-ethoxy]-1,2,3,4-tetrahydro-isoquinoline-(3S)-carbonyl}-amino)-propionic acid | 691 |
| 199 | 3-Biphenyl-4-yl-(2S)-{[2-(butane-1-sulfonyl)-7-(4-tert-butyl-phenoxy)-1,2,3,4-tetrahydro-isoquinoline-(3S)-carbonyl]-amino}-propionic acid | 669 |
| 200 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid butyl ester | 649 |
| 201 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid isopropyl ester | 635 |
| 202 | 3-Biphenyl-4-yl-(2S)-{[2-(3,4-difluoro-benzoyl)-7-(4-trifluoromethyl-benzyloxy)-1,2,3,4-tetrahydro-isoquinoline-(3S)-carbonyl]-amino}-propionic acid | 715 |
| 203 | 3-Biphenyl-4-yl-(2S)-{[2-(2-cyclopentyl-acetyl)-7-(4-trifluoromethyl-phenyl)-1,2,3,4-tetrahydro-isoquinoline-3-carbonyl]-amino}-propionic acid | 655 |
| 204 | 3-Biphenyl-4-yl-(2S)-{[7-(4-cyclohexyl-phenoxy)-2-(2-cyclopentyl-acetyl)-1,2,3,4-tetrahydro-isoquinoline-(3S)-carbonyl]-amino}-propionic acid | 685 |
| 205 | 3-Biphenyl-4-yl-(2S)-{[2-(4-tert-butyl-benzoyl)-7-(4-tert-butyl-phenoxy)-1,2,3,4-tetrahydro-isoquinoline-(3S)-carbonyl]-amino}-propionic acid | 709 |
| 206 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4'-trifluoromethyl-biphenyl-4-yl)-propionic acid | 727 |
| 207 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4'-trifluoromethoxy-biphenyl-4-yl)-propionic acid | 743 |
| 208 | (2S)-{[7-(4-tert-Butyl-phenoxy)-2-(2-cyclopentyl-acetyl)-1,2,3,4-tetrahydro-isoquinoline-(3S)-carbonyl]-amino}-3-(3'-chloro-4'-fluoro-biphenyl-4-yl)-propionic acid | 711 |
| 209 | (2S)-{[7-(4-tert-Butyl-phenoxy)-2-(2-cyclopentyl-acetyl)-1,2,3,4-tetrahydro-isoquinoline-(3S)-carbonyl]-amino}-3-[4-(4-methoxy-phenoxy)-phenyl]-propionic acid | 705 |
| 210 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4-phenethyloxy-phenyl)-propionic acid | 703 |

-continued

| Example | Name | LC/MS |
|---|---|---|
| 211 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4-cyclopentyloxy-phenyl)-propionic acid | 667 |
| 212 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4-isopropoxy-phenyl)-propionic acid | 641 |
| 213 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid but-2-ynyl ester | 645 |
| 214 | (3S)-(2-Biphenyl-4-yl-(1S)-carboxy-ethylcarbamoyl)-7-(4-tert-butyl-phenoxy)-3,4-dihydro-1H-isoquinoline-2-carboxylic acid 2-methoxy-ethyl ester | 651 |
| 215 | (2S)-{[7-(4-tert-Butyl-phenoxy)-2-(2-cyclopentyl-acetyl)-1,2,3,4-tetrahydro-isoquinoline-(3S)-carbonyl]-amino}-3-(4'-methoxy-biphenyl-4-yl)-propionic acid | 689 |
| 216 | 3-(4-Benzyloxy-phenyl)-(2S)-{[6-(4-tert-butyl-phenoxy)-2-(2-cyclopentyl-acetyl)-1,2,3,4-tetrahydro-isoquinoline-(3S)-carbonyl]-amino}-propionic acid | 689 |
| 217 | (2S)-{[6-(4-tert-Butyl-phenoxy)-2-(2-cyclopentyl-acetyl)-1,2,3,4-tetrahydro-isoquinoline-(3S)-carbonyl]-amino}-3-[4-(4-methoxy-phenoxy)-phenyl]-propionic acid | 705 |
| 218 | (2S)-{[6-(4-tert-Butyl-phenoxy)-2-(2-cyclopentyl-acetyl)-1,2,3,4-tetrahydro-isoquinoline-(3S)-carbonyl]-amino}-3-[4-(4-fluoro-phenoxy)-phenyl]-propionic acid | 693 |
| 219 | (2S)-{[6-(4-tert-Butyl-phenoxy)-2-(2-cyclopentyl-acetyl)-1,2,3,4-tetrahydro-isoquinoline-(3S)-carbonyl]-amino}-3-[4-(4-trifluoromethyl-phenoxy)-phenyl]-propionic acid | 743 |
| 220 | (2S)-{[6-(4-tert-Butyl-phenoxy)-2-(2-cyclopentyl-acetyl)-1,2,3,4-tetrahydro-isoquinoline-(3S)-carbonyl]-amino}-3-[4-(4-trifluoromethoxy-phenoxy)-phenyl]-propionic acid | 759 |
| 221 | (2S)-{[6-(4-tert-Butyl-phenoxy)-2-(2-cyclopentyl-acetyl)-1,2,3,4-tetrahydro-isoquinoline-(3S)-carbonyl]-amino}-3-[4-(3-chloro-4-fluoro-phenoxy)-phenyl]-propionic acid | 727 |
| 222 | (2S)-{[6-(4-tert-Butyl-phenoxy)-2-(2-cyclopentyl-acetyl)-1,2,3,4-tetrahydro-isoquinoline-(3S)-carbonyl]-amino}-3-(4-phenoxy-phenyl)-propionic acid | 675 |
| 223 | 7-(4-tert-Butyl-phenoxy)-(3S)-{(1S)-carboxy-2-[4-(4-chloro-phenoxy)-phenyl]-ethylcarbamoyl}-3,4-dihydro-1H-isoquinoline-2-carboxylic acid isobutyl ester | 699 |
| 224 | 7-(4-tert-Butyl-phenoxy)-(3S)-{(1S)-carboxy-2-[4-(4-trifluoromethoxy-phenoxy)-phenyl]-ethylcarbamoyl}-3,4-dihydro-1H-isoquinoline-2-carboxylic acid isobutyl ester | 749 |
| 225 | 7-(4-tert-Butyl-phenoxy)-(3S)-{(1S)-carboxy-2-[4-(4-trifluoromethyl-phenoxy)-phenyl]-ethylcarbamoyl}-3,4-dihydro-1H-isoquinoline-2-carboxylic acid isobutyl ester | 733 |
| 226 | 7-(4-tert-Butyl-phenoxy)-(3S)-{(1S)-carboxy-2-[4-(4-fluoro-phenoxy)-phenyl]-ethylcarbamoyl}-3,4-dihydro-1H-isoquinoline-2-carboxylic acid isobutyl ester | 683 |
| 227 | -(4-tert-Butyl-phenoxy)-(3S)-((1S)-carboxy-2-{4-[2-(4-fluoro-phenyl)-ethoxy]-phenyl}-ethylcarbamoyl)-3,4-dihydro-1H-isoquinoline-2-carboxylic acid isobutyl ester | 711 |
| 228 | 7-(4-tert-Butyl-phenoxy)-(3S)-[(1S)-carboxy-2-(4-isobutoxy-phenyl)-ethylcarbamoyl]-3,4-dihydro-1H-isoquinoline-2-carboxylic acid isobutyl ester | 645 |
| 229 | 7-(4-tert-Butyl-phenoxy)-(3S)-{(1S)-carboxy-2-[4-(2-methyl-butoxy)-phenyl]-ethylcarbamoyl}-3,4-dihydro-1H-isoquinoline-2-carboxylic acid isobutyl ester | 659 |
| 230 | 7-(4-tert-Butyl-phenoxy)-(3S)-[(1S)-carboxy-2-(4-cyclopentylmethoxy-phenyl)-ethylcarbamoyl]-3,4-dihydro-1H-isoquinoline-2-carboxylic acid isobutyl ester | 671 |
| 231 | 7-(4-tert-Butyl-phenoxy)-(3S)-{(1S)-carboxy-2-[4-(2-cyclopentyl-ethoxy)-phenyl]-ethylcarbamoyl}-3,4-dihydro-1H-isoquinoline-2-carboxylic acid isobutyl ester | 685 |
| 232 | 7-(4-tert-Butyl-phenoxy)-(3S)-((1S)-carboxy-2-{4-[2-(4-trifluoromethoxy-phenyl)-ethoxy]-phenyl}-ethylcarbamoyl)-3,4-dihydro-1H-isoquinoline-2-carboxylic acid isobutyl ester | 777 |
| 233 | 7-(4-tert-Butyl-phenoxy)-(3S)-[(1S)-carboxy-2-(4'-chloro-biphenyl-4-yl)-ethylcarbamoyl]-3,4-dihydro-1H-isoquinoline-2-carboxylic acid isobutyl ester | 683 |
| 234 | 7-(4-tert-Butyl-phenoxy)-(3S)-[(1S)-carboxy-2-(4'-fluoro-biphenyl-4-yl)-ethylcarbamoyl]-3,4-dihydro-1H-isoquinoline-2-carboxylic acid isobutyl ester | 667 |
| 235 | 7-(4-tert-Butyl-phenoxy)-(3S)-[(1S)-carboxy-2-(4'-trifluoromethyl-biphenyl-4-yl)-ethylcarbamoyl]-3,4-dihydro-1H-isoquinoline-2-carboxylic acid isobutyl ester | 717 |

Example 236

3-(3'-Chloro-4'-fluoro-biphenyl-4-yl)-(2S)-[(4-hydroxy-4'-trifluoromethyl-biphenyl-3-carbonyl)-amino]-propionic acid 5-Bromo-2-hydroxy-benzoic acid (5 g, 23.04 mmol) was reacted with 4-trifluoromethyl phenyl boronic acid (6.56 g, 34.5 mmol) as desribed in general procedure D. The crude product was then was then purified by silica gel column chromatography (ethyl acetate:hexanes from 20:80 to 60:40) to afford 4.5 g of the 4-hydroxy-4'-trifluoromethyl-biphenyl-3-carboxylic acid as a white solid.

To a stirring solution of above phenol (4.5 g, 16.1 mmol), pyridine (2.4 g, 32.2 mmol) in DCM (25 ml) was added acetyl chloride (2.4 g, 32.2 mmol) at −10° C. and the reaction mixture was allowed to warm to room temperature and stirred for another 2 h. Then the reaction mixture was poured in to ice cold water and extracted with DCM (2×25 ml). The organic extracts were combined, dried over $Na_2SO_4$ and concentrated in vacuo to furnish 5.1 g of 4-acetoxy-4'-trifluoromethyl-biphenyl-3-carboxylic acid To a solution of above 4-acetoxy-4'-trifluoromethyl-biphenyl-3-carboxylic acid (5.1 g, 16.1 mmol) in DCM (50 ml) was added oxalyl chloride (25.0 mmol) at −10° C. and the reaction mixture was allowed to warm up to rt. and stirred for 2 hours. Then the reaction mixture concentrated in vacuo to furnish the desired acid chloride (5.3 g).

150 mg (0.43 mmol) of above acid chloride was coupled with (2S)-amino-3-phenyl propionic acid methyl ester (148 mg, 0.48 mmol) as described in general procedure J. The resulting ester was hydrolyzed as described in general procedure C to afford 180 mg of the title compound as a white solid.

LC-MS: 572 (M+1)$^+$; $^1$H NMR (400 MHz, CDCl$_3$): δ 3.34 (q, 2H), 3.84 (s, 3H), 5.10 (q, 1H), 6.85 (d, 1H), 7.10 (d, 1H), 7.21 (d, 3H), 7.38 (m, 1H), 7.45 (m, 3H), 7.58 (d, 3H), 7.64 (d, 3H), and 12.05 (br, 1H).

Example 237

4-Hydroxy-4'-trifluoromethyl-biphenyl-3-carboxylic acid [1-(3'-chloro-4'-fluoro-biphenyl-4-ylmethyl)-(2S)-oxo-2-piperidin-1-yl-ethyl]-amide 55 mg (0.1 mmol) of 3-(3'-chloro-4'-fluoro-biphenyl-4-yl)-(2S)-[(4-hydroxy-4'-trifluoromethyl-biphenyl-3-carbonyl)-amino]-propionic acid (Example 236) was reacted with piperidine (16.7 mg, 0.2 mmol) as described in General Procedure A. The title compound (46 mg) was isolated after column chromatography using 30% ethyl acetate in hexane as an eluent.

LC-MS: 625 (M+1)$^+$; $^1$H NMR (400 MHz, CDCl$_3$): δ 1.24 (m, 2H), 1.54 (m, 2H), 1.75 (m, 2H), 3.20 (m, 2H), 3.40-3.58 (m, 2H), 5.44 (q, 1H), 7.04 (t, 1H), 7.18 (t, 2H), 7.30 (m, 2H), 7.40 (m, 1H), 7.44 (d, 3H), 7.54-7.74 (m, 6H), 7.94 (br, 1H), 8.12 (d, 1H), and 12.36 (br, 1H).

Example 238

4-Methoxy-4'-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide 2.5 g of (2-(3'-chloro-4'-fluoro-biphenyl-4-yl)-(1R)-(3-methyl-[1,2,4]oxadiazol-5-yl)-ethylamine was synthesized as described in general procedure 0 from (2R)-tert-butoxycarbonylamino-3-(3'-chloro-4'-fluoro-biphenyl-4-yl)-propionic acid methyl ester. 31 mg (0.1 mmol) of 4-methoxy-4'-trifluoromethyl-biphenyl-3-carbonyl chloride (prepared from 5-bromo-2-methoxy-benzoic acid as described in example 236) was coupled with 40 mg (0.12 mmol) of 2-(3'-chloro-4'-fluoro-biphenyl-4-yl)-(1R)-(3-methyl-[1,2,4]oxadiazol-5-yl)-ethylamine as described in general procedure J to afford 55 mg of the title compound after column chromatography using 20% ethyl acetate in hexane as eluent.

LC-MS: 610 (M+1)$^+$; $^1$H NMR (400 MHz, CDCl$_3$): δ 2.41 (s, 3H), 3.59 (t, 2H), 3.91 (s, 3H), 5.87 (q, 1H), 7.08 (d, 1H), 7.20 (dd, 2H), 7.38 (m, 1H), 7.46 (d, 3H), 7.58 (dd, 1H), 7.64-7.72 (m, 4H), 7.74 (d, 1H), 7.82 (dd, 1H), and 12.16 (br, 1H).

Example 239

4-Hydroxy-4'-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide To a stirring solution of 122 mg (0.20 mmol) of example 238 in anhydrous DCM (10 mL) was added boron tribromide (0.5 mmol, 1.0 M solution ) at −78° C. and the reaction mixture stirred at −78° C. for 3 hours and allowed to warm up to the ambient temperature. After the reaction was completed, the reaction mixture was slowly quenched with saturated aqueous sodium bicarbonate solution (5 mL) and extracted with DCM (3×20 mL). The reaction mixture was concentrated in vacuo to give the crude product. This crude product was then purified by silica gel chromatography with hexanes: ethyl acetate (from 95:5 to 80-20) as an eluent system to obtain 94 mg of the title compound as a white solid.

Example 240

4-Methoxy-4'-trifluoromethyl-biphenyl-3-carboxylic acid [2-(3'-chloro-4'-fluoro-biphenyl4-yl)-(1R)-methoxymethyl-ethyl]-amide (2R)-tert-Butoxycarbonylamino-3-(3'-chloro-4'-fluoro-biphenyl-4-yl)-propionic acid (2.0 g, 5.07 mmol) was dissolved in 15 mL anhydrous THF and BH$_3$:THF (11 mL, 11.0 mmol, 1M solution in THF) was added dropwise at 0° C. and stirred for 10 h at room temperature. Excess BH$_3$:THF was quenched by adding methanol (~1 mL) at 0° C. Solvent was removed under vacuum and residue was dissolved in EtOAc (20 mL) and washed with water, brine and dried over Na$_2$SO$_4$. Solvent was removed under vacuum and silica gel column chromatography (CH$_2$Cl$_2$:MeOH) gave (R)-[2-(3'-chloro-4'-fluoro-biphenyl-4-yl)-1-hydroxymethyl-ethyl]-carbamic acid tert-butyl ester as white solid (1.6 g).

NaH (55 mg, 1.31 mmol, 60% by wt suspension in mineral oil) was added at 0° C. to a solution of [2-(3'-Chloro-4'-fluoro-biphenyl-4-yl)-1-hydroxymethyl-ethyl]-carbamic acid tert-butyl ester (0.5 g, 1.31 mmol) in 5 mL anhydrous THF and stirred for 20 min at 0° C. MeI (0.37 g, 2.63 mmol) was added to the reaction mixture and stirred for 6 h at room temperature. The reaction mixture was diluted with 5 mL EtOAc, and washed with water, brine and dried over Na$_2$SO$_4$. Solvent was removed under vacuum and silica gel chromatography (EtOAc: Hexanes) gave (R)-[[2-(3'-chloro-4'-fluoro-biphenyl-4-yl)-1-methoxymethyl-ethyl]-carbamic acid tert-butyl ester (0.38 g). The Boc protecting group was removed by stirring the compound in 4M HCl in dioxane (5 ml) for 30 min. Evaporation of the solvent under vacuo gave (R)-2-(3'-chloro4'-fluoro-biphenyl-4-yl)-1-methoxymethyl-ethylamine hydrochloride.

32 mg (0.1 mmol) of 4-methoxy-4'-trifluoromethyl-biphenyl-3-carbonyl chloride (prepared from 5-romo-2-methoxy-benzoic acid as described in example 236) was coupled with 35 mg (0.1 mmol) of (R)-2-(3'-chloro-4'-fluoro-biphenyl-4-yl)-1-methoxymethyl-ethylamine hydrochloride as described in general procedure J to afford 45 mg of the title compound after column chromatography using 30% ethyl acetate in hexane as an eluents.

$^1$HNMR (400 MHz, CDCl$_3$): 3.00 (dd, 1H), 3.10 (dd, 1H), 3.37-3.50 (m, 5H), 3.99 (s, 3H), 4.50-4.61 (m, 1H), 7.07(d, 1H), 7.19 (t, 1H), 7.34-7.51 (m, 5H), 7.60 (dd, 1H), 7.64-7.76 (m, 5H), 8.25 (d, 1H), 8.50 (d,1H); LC/MS : 572 (M+1)$^+$.

Example 241

4-Hydroxy-4'-trifluoromethyl-biphenyl-3-carboxylic acid [2-(3'-chloro-4'-fluoro-biphenyl-4-yl)-(1R)-hydroxymethyl-ethyl]-amide Example 240 (24 mg, 0.04 mmol) was dealkylated as desribed in example 239 to afford the title compounds as a white solid.

$^1$HNMR (400 MHz, CDCl$_3$): δ 3.07 (m, 2H), 3.72-3.89 (m, 2H), 4.45 (m, 1H), 6.75 (d,1H), 7.08 (d,1H), 7.19 (t,1H), 7.32-7.52 (m, 5H ) 7.54-7.68 (m, 8H), 12.2 (br s, 1H); LC/MS : 544 (M+1)$^+$.

Example 242

4-Methoxy-4'-trifluoromethyl-biphenyl-3-carboxylic acid [2-(3'-chloro-4'-fluoro-biphenyl-4-yl)-(1R)-[1,2,4]triazol-1-ylmethyl-ethyl]-amide

[2-(3'-Chloro-4'-fluoro-biphenyl-4-yl)-1-hydroxymethyl-ethyl]-carbamic acid tert-butyl ester (0.78 g, 2.05 mmol) was treated with methanesulfonyl chloride (0.235 g, 2.05 mmol) and pyridine (0.49 g, 6.15 mmol) in 5 mL of anhydrous dichloromethane at 0° C. The reaction mixture was allowed to come to room temperature and stirred for 4 h. The reaction mixture was diluted with 10 mL of dichloromethane and washed with water, brine and dried over Na$_2$SO$_4$. Solvent was removed under reduced pressure and silica gel column chromatography (CH2Cl2:MeOH) gave methanesulfonic acid 2-tert-butoxycarbonylamino-3-(3'-chloro-4'-fluoro-biphenyl-4-yl)-propyl ester (0.71 g).

To a solution of methanesulfonic acid 2-tert-butoxycarbonylamino-3-(3'-chloro-4'-fluoro-biphenyl-4-yl)-propyl ester (0.2 g, 0.43 mmol) in DMF (2 mL) was added sodium(1,2,4) triazole (0.12 g, 1.31 mmol) and heated at 90° C. for 8 h. The reaction mixture was poured into water (2 mL) and extracted with EtOAc (7 mL) and washed with water, brine and dried over Na$_2$SO$_4$. Solvent was removed under reduced pressure and the product [2-(3'-chloro-4'-fluoro-biphenyl-4-yl)-1-[1,2,4]triazol-1-ylmethyl-ethyl]-carbamic acid tert-butyl ester (0.18 g) was used further without any purification. A portion (80 mg, 0.18 mmol) of this compound was deprotected using 4N HCl in dioxane (1.0 ml) and used for the next step without purification.

60 mg (0.16 mmol) of above 2-(3'-chloro-4'-fluoro-biphenyl-4-yl)-(1S) 1,2,4]triazol-1-ylmethyl-ethylamine hydrochloride was coupled with 51 mg (0.16 mmol) of 4-trifluoromethyl-biphenyl-3-carbonyl chloride (prepared from 5-bromo-2-methoxy-benzoic acid as described in example 236) according to the general procedure J to give 66 mg of the title compound as white solid.

LC/MS: 609 (M+1)$^+$

Example 243

4-Hydroxy-4'-trifluoromethyl-biphenyl-3-carboxylic acid [2-(3'-chloro-4'-fluoro-biphenyl-4-yl)-(1R)-[1,2,4]triazol-1-ylmethyl-ethyl]-amide 20 mg (0.032 mmol) of example 242 was demethylated as described in example 239 to give 12 mg of the title compound as a white solid.

$^1$HNMR (400 MHz, CDCl$_3$): δ 2.57 (dd,1H), 3.15 (dd, 1H), 4.38 (d,2H), 4.84 (m,1H), 7.11(d,1H), 7.20 (t,1H), 7.29 (d, 1H), 7.42 (m, 1H), 7.52 (d, 2H), 7.59-7.74 (m, 7H), 8.08 (m, 3H), 12.2 (brs, 1H); LC/MS: 595 (M+1)$^+$.

By analogous methods to those described above the following Examples were synthesized.

| Example | Name | LC/MS |
|---|---|---|
| 244 | 4-{3-(3'-Chloro-4'-fluoro-biphenyl-4-yl)-(2S)-[(4-hydroxy-4'-trifluoromethyl-biphenyl-3-carbonyl)-amino]-propionyl}-piperazine-1-carboxylic acid tert-butyl ester | 726 |
| 245 | 4-Hydroxy-4'-trifluoromethyl-biphenyl-3-carboxylic acid [2-(3'-chloro-4'-fluoro-biphenyl-4-yl)-(1S)-(4-methyl-piperazin-1-ylcarbamoyl)-ethyl]-amide | 655 |
| 246 | 4-Hydroxy-4'-trifluoromethyl-biphenyl-3-carboxylic acid [2-(3'-chloro-4'-fluoro-biphenyl-4-yl)-ethyl]-amide | 514 |
| 247 | 3-(3'-Chloro-4'-fluoro-biphenyl-4-yl)-(2R)-{[5-(4-trifluoromethyl-phenyl)-pyridine-3-carbonyl]-amino}-propionic acid methyl ester | 557 |
| 248 | 3-(3'-Chloro-4'-fluoro-biphenyl-4-yl)-(2R)-(2-hydroxy-benzoylamino)-propionic acid methyl ester | 428 |
| 249 | 4-Hydroxy-4'-trifluoromethyl-biphenyl-3-carboxylic acid [2-(3'-chloro-4'-fluoro-biphenyl-4-yl)-(1R)-(methoxy-methyl-carbamoyl)-ethyl]-amide | 601 |
| 250 | 4-Hydroxy-4'-trifluoromethyl-biphenyl-3-carboxylic acid [(1S)-(2-acetylamino-ethylcarbamoyl)-2-(3'-chloro-4'-fluoro-biphenyl-4-yl)-ethyl]-amide | 642 |
| 251 | 3-(3'-Chloro-4'-fluoro-biphenyl-4-yl)-(2R)-[(4-hydroxy-4'-trifluoromethyl-biphenyl-3-carbonyl)-amino]-propionic acid | 558 |
| 252 | 4-Hydroxy-4'-trifluoromethyl-biphenyl-3-carboxylic acid {2-(3'-chloro-4'-fluoro-biphenyl-4-yl)-(1R)-[(2-dimethylamino-ethyl)-methyl-carbamoyl]-ethyl}-amide | 642 |

-continued

| Example | Name | LC/MS |
|---|---|---|
| 253 | 3'-Fluoro-4,4'-dihydroxy-biphenyl-3-carboxylic acid [2-(3'-chloro-4'-fluoro-biphenyl-4-yl)-(1R)-(3-methyl-[1,2,4]oxadiazol-5-yl)-ethyl]-amide | 562 |
| 254 | 4-Hydroxy-4'-trifluoromethyl-biphenyl-3-carboxylic acid [2-(4'-benzyloxy-3'-fluoro-biphenyl-4-yl)-(1R)-(3-methyl-[1,2,4]oxadiazol-5-yl)-ethyl]-amide | 668 |
| 255 | 4-Hydroxy-4'-trifluoromethyl-biphenyl-3-carboxylic acid [2-(3'-chloro-4'-fluoro-biphenyl-4-yl)-(1R)-(2-hydroxy-propylcarbamoyl)-ethyl]-amide | 615 |
| 256 | 4-Methoxy-4'-trifluoromethyl-biphenyl-3-carboxylic acid [2-(3'-chloro-4'-fluoro-biphenyl-4-yl)-(1R)-hydrazinocarbonyl-ethyl]-amide | 586 |
| 257 | 4-Ethoxy-3',5'-bis-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide | 692 |
| 258 | 4-Hydroxy-3',5'-bis-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide | 664 |
| 259 | 4-Hydroxy-4'-trifluoromethyl-biphenyl-3-carboxylic acid [2-(4'-methanesulfonyl-biphenyl-4-yl)-(1R)-(3-methyl-[1,2,4]oxadiazol-5-yl)-ethyl]-amide | 622 |
| 260 | Acetic acid 3-[2-(3'-chloro-4'-fluoro-biphenyl-4-yl)-(1R)-(3-methyl-[1,2,4]oxadiazol-5-yl)-ethylcarbamoyl]-4'-trifluoromethyl-biphenyl-4-yl ester | 638 |
| 261 | 6-Benzyloxy-4-hydroxy-4'-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide | 702 |
| 262 | 4'-Cyano-4-hydroxy-biphenyl-3-carboxylic acid [2-(3'-chloro-4'-fluoro-biphenyl-4-yl)-(1R)-(3-methyl-[1,2,4]oxadiazol-5-yl)-ethyl]-amide | 553 |
| 263 | 4-Hydroxy-4'-methanesulfonyl-biphenyl-3-carboxylic acid [2-(3'-chloro-4'-fluoro-biphenyl-4-yl)-(1R)-(3-methyl-[1,2,4]oxadiazol-5-yl)-ethyl]-amide | 606 |
| 264 | 5-Bromo-N-[2-(3'-chloro-4'-fluoro-biphenyl-4-yl)-(1R)-(3-methyl-[1,2,4]oxadiazol-5-yl)-ethyl]-2-methoxy-benzamide | 545 |
| 265 | 5-Bromo-N-[2-(3'-chloro-4'-fluoro-biphenyl-4-yl)-(1R)-(3-methyl-[1,2,4]oxadiazol-5-yl)-ethyl]-2-hydroxy-benzamide | 531 |
| 266 | 5-Bromo-N-[2-(4-bromo-phenyl)-(1R)-(3-methyl-[1,2,4]oxadiazol-5-yl)-ethyl]-2-hydroxy-benzamide | 482 |
| 267 | 2,2-Dimethyl-propionic acid 3-[2-(3'-chloro-4'-fluoro-biphenyl-4-yl)-(1R)-(3-methyl-[1,2,4]oxadiazol-5-yl)-ethylcarbamoyl]-4'-trifluoromethyl-biphenyl-4-yl ester | 680 |
| 268 | 3-Methyl-butyric acid 3-[2-(3'-chloro-4'-fluoro-biphenyl-4-yl)-(1R)-(3-methyl-[1,2,4]oxadiazol-5-yl)-ethylcarbamoyl]-4'-trifluoromethyl-biphenyl-4-yl ester | 680 |
| 269 | 4-Hydroxy-6-(3-methyl-butoxy)-4'-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide | 682 |
| 270 | 5-Bromo-4-hydroxy-4'-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide | 675 |
| 271 | 4-Hydroxy-6-isopropoxy-4'-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide | 654 |
| 272 | 4-Hydroxy-3',5'-bis-trifluoromethyl-biphenyl-3-carboxylic acid [2-biphenyl-4-yl-(1R)-(3-methyl-[1,2,4]oxadiazol-5-yl)-ethyl]-amide | 612 |
| 273 | 4-Methoxy-3',5'-bis-trifluoromethyl-biphenyl-3-carboxylic acid [2-biphenyl-4-yl-(1R)-(3-methyl-1,2,4]oxadiazol-5-yl)-ethyl]-amide | 626 |
| 274 | 4-Benzyloxy-3',5'-bis-trifluoromethyl-biphenyl-3-carboxylic acid [2-(4'-methanesulfonyl-biphenyl-4-yl)-(1R)-(3-methyl-[1,2,4]oxadiazol-5-yl)-ethyl]-amide | 780 |
| 275 | 4-Hydroxy-3',5'-bis-trifluoromethyl-biphenyl-3-carboxylic acid [2-(4'-methanesulfonyl-biphenyl-4-yl)-(1R)-(3-methyl-[1,2,4]oxadiazol-5-yl)-ethyl]-amide | 690 |
| 276 | 4-Amino-4'-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide | 595 |
| 277 | 4'-Trifluoromethyl-4-(5-trifluoromethyl-furan-2-ylmethoxy)-biphenyl-3-carboxylic acid [2-(3'-chloro-4'-fluoro-biphenyl-4-yl)-(1R)-(3-methyl-[1,2,4]oxadiazol-5-yl)-ethyl]-amide | 744 |
| 278 | 4'-Hydroxy-4-trifluoromethyl-[1,1';3',1'']terphenyl-5'-carboxylic acid [2-(3'-chloro-4'-fluoro-biphenyl-4-yl)-(1R)-(3-methyl-[1,2,4]oxadiazol-5-yl)-ethyl]-amide | 672 |

-continued

| Example | Name | LC/MS |
|---|---|---|
| 279 | Acetic acid 5'-[2-(3'-chloro-4'-fluoro-biphenyl-4-yl)-(1R)-(3-methyl-[1,2,4]oxadiazol-5-yl)-ethylcarbamoyl]-4-trifluoromethyl-[1,1';3',1"]terphenyl-4'-yl ester | 714 |
| 280 | 5-Chloro-4-hydroxy-4'-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide | 630 |
| 281 | 4-Acetylamino-4'-trifluoromethyl-biphenyl-3-carboxylic acid [2-(3'-chloro-4'-fluoro-biphenyl-4-yl)-(1R)-(3-methyl-[1,2,4]oxadiazol-5-yl)-ethyl]-amide | 637 |
| 282 | 4-Benzyloxy-3',5'-bis-trifluoromethyl-biphenyl-3-carboxylicacid [2-(3',5'-bis-trifluoromethyl-biphenyl-4-yl)-(1R)-(3-methyl-[1,2,4]oxadiazol-5-yl)-ethyl]-amide | 838 |
| 283 | 4-Benzyloxy-3',4'-difluoro-biphenyl-3-carboxylic acid [2-(3',4'-difluoro-biphenyl-4-yl)-(1R)-(3-methyl-[1,2,4]oxadiazol-5-yl)-ethyl]-amide | 638 |
| 284 | 4-Benzyloxy-4'-trifluoromethyl-biphenyl-3-carboxylic acid [(1R)-(3-methyl-[1,2,4]oxadiazol-5-yl)-2-(4'-trifluoromethyl-biphenyl-4-yl)-ethyl]-amide | 702 |
| 285 | 4-Hydroxy-3',5'-bis-trifluoromethyl-biphenyl-3-carboxylic acid [2-(3',5'-bis-trifluoromethyl-biphenyl-4-yl)-(1R)-(3-methyl-[1,2,4]oxadiazol-5-yl)-ethyl]-amide | 748 |
| 286 | 4-Hydroxy-4'-trifluoromethyl-biphenyl-3-carboxylic acid [(1R)-(3-methyl-[1,2,4]oxadiazol-5-yl)-2-(4'-trifluoromethyl-biphenyl-4-yl)-ethyl]-amide | 612 |
| 287 | 3-(3'-Chloro-4'-fluoro-biphenyl-4-yl)-(2S)-{[4-(2,2,2-trifluoro-acetylamino)-4'-trifluoromethyl-biphenyl-3-carbonyl]-amino}-propionic acid methyl ester | 667 |

Example 288

3-(3'-Chloro-4'-fluoro-biphenyl-4-yl)-(2R)-[(4-trifluoromethanesulfonylamino-4'-trifluoromethyl-biphenyl-3-carbonyl)-amino]-propionic acid methyl ester.

4-Amino-4'-trifluoromethyl-biphenyl-3-carboxylic acid methyl ester (3.0 g) was prepared from 2-amino-5-bromobenzoic acid methyl ester (4.58 g, 20 mmol) and 4-trifluoromethylphenyl boronic acid (4.75 g, 25 mmol) following general procedure D, then hydrolyzed following general procedure C. The acid (281 mg, 1.0 mmol) was reacted with (2R)-amino-3-(3'chloro-4'-fluoro-biphneyl-4-yl)-propionic acid methyl ester (343 mg, 1.0 mmol) as described in general procedure A to give (2R)-[(4-amino-4'trifluoromethyl-biphenyl-3-carbonyl)-amino]-3-(3'-chloro-4'-fluoro-biphenyl-4-yl)-propionic acid methyl ester (300 mg).

The 2-[(4-amino-4'trifluoromethyl-biphenyl-3-carbonyl)-amino]-3(R)-(3'-chloro-4'-fluoro-biphenyl-4-yl)-propionic acid methyl ester (50 mg, 0.088 mmol) was reacted with trifluoromethylsulfonyl chloride (17 mg, 0.10 mmol) at −78° C. following general procedure F to give the title compound (35 mg).

$^1$H-NMR (400 MHz, CDCl$_3$): 3.34 (m, 2H), 3.86 (s, 3H), 5.08 (m, 1H), 6.88 (d, 1H), 7.21 (m, 3H), 7.37 (m, 1H), 7.47 (d, 2H), 7.60 (m, 6H), 7.72 (m, 1H), 7.85 (d, 1H); LC/MS: 703 (M+1)$^+$.

Example 289

(2R)-[(4-Benzenesulfonylamino-4'-trifluoromethyl-biphenyl-3-carbonyl)-amino]-(3R)-(3'-chloro-4'-fluoro-biphenyl-4-yl)-propionic acid methyl ester 2-[(4-Benzenesulfonylamino-4'-trifluoromethyl-biphenyl-3-carbonyl)-amino]-(3R)-(3'-chloro-4'-fluoro-biphenyl-4-yl)-propionic acid methyl ester (20 mg, 0.035 mmol) was reacted with phenylsulfonyl chloride (12 mg, 0.070 mmol) following general procedure F to give the title compound (15 mg).

$^1$H-NMR (400 MHz, CDCl$_3$): 3.27 (m, 2H), 3.84 (s, 3H), 4.98 (dd, 1H), 6.55 (d, 1H), 7.18 (m, 3H), 7.39 (d, 1H), 7.43 (m, 4H), 7.53 (m, 3H), 7.57 (m, 3H), 7.62 (dd, 1H), 7.77 (d, 1H), 7.87 (m, 2H); LC/MS: 711 (M+1)$^+$.

Example 290

(2R)-[(4-Benzoylamino-4'-trifluoromethyl-biphenyl-3-carbonyl)-amino]-(3R)-(3'-chloro-4'-fluoro-biphenyl-4-yl)-propionic acid methyl ester To 20 mg (0.035 mmol) of 2-[(4-amino-4'-trifluoromethyl-biphenyl-3-carbonyl)-amino]-(3R)-(3'-chloro-4'-fluoro-biphenyl-4-yl)-propionic acid methyl ester in 1 mL of DCM was added 15 mg (0.11 mmol) of benzoyl chloride following general procedure M to give the title compound (18 mg).

$^1$H-NMR (400 MHz, CDCl$_3$): 3.34 (m, 2H), 3.85 (s, 3H), 5.17 (m, 1H), 6.92 (d, 1H), 7.16 (t, 1H), 7.23 (m, 1H), 7.25 (m, 1H), 7.34 (m, 1H), 7.40 (m, 1H), 7.47 (m, 6H), 7.60 (m, 3H), 7.75 (m, 1H), 7.99 (d, 1H), 8.10 (dd, 2H), 8.89 (dd, 1H); LC/MS: 675 (M+1)$^+$.

Example 291

3-(3'-Chloro-4'-fluoro-biphenyl-4-yl)-(2R)-[(4-isobutyrylamino-4'-trifluoromethyl-biphenyl-3-carbonyl)-amino]-propionic acid methyl ester To 20 mg (0.035 mmol) of 2(R)-[(4-amino-4'-trifluoromethyl-biphenyl-3-carbonyl)-amino]-3-(3'-chloro-4'-fluoro-biphenyl-4-yl)-propionic acid methyl ester in 1 mL of DCM was added 12 mg (0.11 mmol) of isobutyryl chloride following general procedure M to give the title compound (19 mg).

$^1$H-NMR (400 MHz, CDCl$_3$): 1.26 (s, 3H), 1.27 (s, 3H), 2.59 (m, 1H), 3.35 (m, 2H), 3.85 (s, 3H), 5.10 (dd, 1H), 6.67

(d, 1H), 7.22 (m, 3H), 7.37 (m, 1H), 7.48 (m, 3H), 7.58 (m, 5H), 7.71 (dd, 1H), 8.74 (d, 1H); LC/MS: 641 (M+1)+.

Example 292

2-(3'-Chloro-4'-fluoro-biphenyl-4-yl)-ethyl[(4-Hydroxymethyl-4'-trifluoromethyl-biphenyl-3-carboxamide 6-(4-Trifluoromethyl-phenyl)3H-isobenzofuran-2-one was prepared from 6-bromo-3H-isobenzofuran-1-one (1.06 g, 5.0 mmol) and 4-trifluoromethylphenyl boronic acid (1.14 g, 6.0 mmol) following general procedure D. To 6-(4-trifluoromethyl-phenyl)-3H-isobenzofuran-1-one (60 mg, 0.22 mmol) in 1 mL of toluene was added 2-(3'-chloro-4'-fluoro-biphenyl-4-yl)-ethylamine (TFA salt, 50 mg, 0.14 mmol) and the mixture was heated at 80° C. for 4 h. The crude material was purified by flash chromatography (hexane:ethyl acetate 2:1) to give tht title compound (21 mg).
¹H-NMR(400 MHz, CDCl₃): 3.02 (t, 2H), 3.80 (dd, 2H), 4.63 (s, 2H), 7.20 (m, 3H), 7.34 (m, 2H), 7.42 (m, 1H), 7.52 (m, 3H), 7.61 (m, 2H), 7.68 (m, 3H); LC/MS: 528 (M+1)+.

Example 293

3-(3'-Chloro-4'-fluoro-biphenyl-4-yl )-(2R)-[4-oxo-2-trifluoromethyl-6-(4-trifluoromethyl-phenyl)-4H-quinazolin-3-yl]-propionic acid methyl ester To 57 mg (0.10 mmol) of 2-[(4-amino-4'trifluoromethyl-biphenyl-3-carbonyl)-amino]-(3R)-(3'-chloro-4'-fluoro-biphenyl-4-yl)-propionic acid methyl ester in 2 mL of DCM was added 21 mg (0.10 mmol) of trifluoromethylacetic anhydride and 30 mg (0.30 mmol) of DIEA following general procedure M to give the title compound (31 mg).
¹ H-NMR (400 MHz, CDCl₃): 3.19 (m, 1H), 3.36 (m, 1H), 3.76 (s, 3H), 4.86 (dd, 1H), 7.17 (m, 3H), 7.37 (m, 5H), 7.54 (dd, 1H), 7.62 (d, 1H), 7.77 (m, 3H), 7.88 (dd, 1H), 8.44 (d, 1H); LC/MS : 649 (M+1)+.

Example 294

3-(3'-Chloro-4'-fluoro-biphenyl-4-yl )-(2R)-[4-oxo-2-trifluoromethyl-6-(4-trifluoromethyl-phenyl)-4H-quinazolin-3-yl]-propionic acid methyl ester 20 mg (0.03 mmol) of example 293 was hydrolyzed as described in general procedure C to afford 19.5 mg of the title compound as a white solid.
LCMS 635 (M+1)+.

Example 295

6-(4-tert-Butyl-phenoxy)-isoquinoline-3-carboxylic acid

To a suspension of m-tyrosine (20.0 g, 110.38 mmol) in HCl (0.05 N, 85.0 mL) was added formaldehyde (37%, 15.8 mL). The reaction was heated at 90° C. for 1 h. The precipitated product was filtered, washed with cold water and ether and dried under vacuum to give 6-hydroxy-1,2,3,4-tetrahydro-isoquinoline-3-carboxylic acid hydrochloride as a light yellow solid (18.0 g). LCMS: 194 (M+1)+.
The above acid (14 g, 62 mmol) in methanol (200.0 mL) was added HCl/dioxane (50 mL) and conc. HCl (1.0 mL). The reaction was refluxed for 4 h. Upon cooling to rt, reaction mixture was concentrated under reduced pressure to give 6-hydroxy-1,2,3,4-tetrahydro-isoquinoline-3-carboxylic acid methyl ester hydrochloride as an off-white solid (16.0 g).
LCMS: 208 (M+1)+

The above compound (10.0 g, 41.07 mmol) in DCM (180 mL) was added BOC-anhydride (10.75 g, 49.29 mmol) and Na₂CO₃ (125 mL). The reaction was stirred for 2.5 h. The organic layer was separated and the aq. layer was extracted twice with DCM. The combined organic layer was washed with satd. Na₂CO₃, brine, dried (Na₂SO₄), and concentrated under reduced pressure to give 6-hydroxy-3,4-dihydro-1H-isoquinoline-2,3-dicarboxylic acid 2 tert-butyl ester 3-methyl ester as a light yellow oil (13.5 g).
LCMS: 308 (M+1)+.
To a solution of the phenol above (13.5 g, 43.93 mmol) in anhydrous DCM was added 4-tert-butylphenylboronic acid (15.6 g, 87.86 mmol), copper acetate (11.96 g, 65.89 mmol), and 4Å molecular sieves. To this was added triethyl amine (30 mL) and the reaction was stirred at rt under air overnight. The reaction mixture was filtered via a celite pad and washed with copious amounts of DCM. The filtrate was concentrated under reduced pressure and purified by flash column chromatography on silica using hexanes:EtOAc(7%) to elute the 6-(4-tert-Butyl-phenoxy)-3,4-dihydro-1H-isoquinolihne-2, 3-dicarboxylic acid 2-tert-butyl ester 3-methyl ester as a colorless oil (4.22 g). LCMS: 440 (M+1)+.
To 3.30 g of above compound was added HCl/dioxane (4.0 M, 60 mL) and the solution was stirred at rt for 2 h. The solution was concentrated under reduced pressure and dried under vacuum for 1 h to give a white solid. To this was added 25 mL anhydrous toluene and DDQ (4.51 g, 19.88 mmol) and the reaction was heated at 100° C. for 1.5 h. Upon cooling to RT, the reaction mixture was filtered and washed with DCM several times. The filtrate was concentrated under reduced pressure to give a dark brown residue. The residue was dissolved in DCM and the washed with satd. solution of sodium bisulfite. The aq. layer was discarded and the organic layer was washed with brine, dried (Na2SO4) and concentrated under reduced pressure to give 6-(4-tert-butyl-phenoxy)-isoquinoline-3-carboxylic acid methyl ester as brown solid (1.85 g).
The above ester (1.85 g, 5.72 mmol) was hydrolyzed as described in general procedure C to give 6-(4-tert-butyl-phenoxy)-isoquinoline-3-carboxylic acid as an light brown solid (1.80 g).
¹H-NMR (400 MHZ, CDCl₃): 8.47 (s,1H), 7.98 (d,1H), 7.59 (s,1H), 7.53 (dd, 1H), 7.46 (d, 2H), 7.05 (d, 2H), 3.15 (d, 2H), 2.35 (m, 1H), 1.67 (m, 4H), 1.53 (m, 2H), 1.36 (s, 9H), 1.30 (m, 2H). LCMS: 322 (M+1)+.

Example 296

3-Biphenyl-4-yl-(2S)-([6-(4-tert-butyl-phenoxy)-isoquinoline-3-carbonyl]-amino)-propionic acid methyl ester 320 mg (1.0 mmol) of 6-(4-tert-butylphenoxy)-isoquinoline-3-carboxylic acid (example 295) was reacted with 225 mg (1.0 mmol) of (L)-biphenylalanine methyl ester as described in general procedure A. The crude product was purified by flash column chromatography on silica using 20-30% ethyl acetate in hexanes as eluent, to afford 420 mg of the title compound as a white solid. LCMS 560 (M+1)+.

Example 297

3-Biphenyl-4-yl-2S-{[6-(4-tert-butyl-phenoxy)-isoquinoline-3-carbonyl]-amino)-propionic acid 420 mg (0.75 mmol) of above ester (example) was hydrolyzed as described in general procedure C to afford the title compound (408 mg). ¹H NMR: (400 MHz, CDCl₃) δ 9.02 [s, 1H], 8.69 [d, 1H], 8.38 [s, 1H], 7.96 [d, 1H], 7.53-7.47 [m, 4H], 7.45-7.43 [m, 3H], 7.40-7.36 [m, 2H], 7.32-7.30 [m, 3H], 7.22 [dd,1H], 7.03 [m, 2H], 5.14 (X of ABX pattern, 1H], 3.47-3.27 [AB of ABX pattern, 2H], 1.37 [s, 9H]. LCMS 546 (M+1)$^+$.

Example 298

2S-{[6-(4-tert-Butyl-phenoxy)-isoquinoline-3-carbonyl]-amino}-3-(4-hydroxy-phenyl)-propionic acid methyl ester 870 mg (2.71 mmol) of 6-(4-tert-butylphenoxy)-isoquinoline-3-carboxylic acid (example 295) was reacted with 871 mg (2.71 mmol) of (2S)-amino-3-(4-benzyloxy-phenyl)-propionic acid methyl ester as described in general procedure A. The crude product was purified by flash column chromatography on silica using 3:2 hexane/ethyl acetate as eluent to afford 1.205 g of 3-(4-benzyloxy-phenyl)-2-{[6-(4-tert-butyl-phenoxy)-isoquinoline-3-carbonyl]-amino}-propionic acid methyl-ester as a white solid. LCMS 590 (M+1)$^+$.

To a portion of the material described above (1.190 g, 2.02 mmol) in a mixture of 10 mL each of methanol and ethyl acetate was added 120 mg of Pd/C and the resultant suspension was hydrogenated under 4-5 atm of H$_2$ for 16 hours. The reaction mixture was filtered through a plug of diatomaceous earth and concentrated in vacuo to afford 889 mg of the title compound.

$^1$H NMR: (400 MHz, CDCl$_3$) δ 9.04 [s,1H, 8.67 [d, 1H], 8.37 [s, 1H], 7.98 [d, 1H], 7.45 [m, 3H], 7.23 [d, 1H], 7.04 [m, 4H], 6.72 [m, 2H], 5.32 [br s, 1H], 5.08 [X of ABX pattern, 1H], 3.74, [s, 3H], 3.25-3.12 [AB of ABX pattern, 2H], 1.36 [s, 9H].LCMS 500 (M+1)$^+$.

Example 299

2S-{[6-(4-tert-Butyl-phenoxy)-isoquinoline-3-carbonyl]-amino}-3-[4-(4-fluoro-phenoxy)-phenyl]-propionic acid methyl ester 50 mg (0.1 mmol) of 2S-{[6-(4-tert-butyl-phenoxy)-isoquinoline-3-carbonyl]-amino}-3-(4-hydroxy-phenyl)-propionic acid methyl ester (Example 298) was reacted with 42 mg (0.3 mmol) of 4-fluorophenylboronic acid as described in procedure G. Column chromatography using 20-30% ethyl acetate in hexanes as an eluent gave 20 mg of the title compound as a white solid.

LCMS 594 (M+1)$^+$.

Example 300

(2S)-{[6-(4-tert-Butyl-phenoxy)-isoquinoline-3-carbonyl]-amino}-3-[4-(4-fluoro-phenoxy)-phenyl]-propionic acid 20 mg (0.034 mmol) of above ester (example 299) was hydrolyzed as described in general procedure C to afford the title compound (19 mg).

$^1$H NMR: (400 MHz, CDCl$_3$) δ 9.00 [s,1H], 8.64 [d, 1H], 8.35 [s, 1H], 7.95 [d, 2H], 7.44 [app d, 2H], 7.19 [m 3H], 7.06-7.02 [m, 2H], 6.99-6.85 [m, 4H], 6.84 [d, 2H], 4.99 [X of ABX pattern, 1H], 3.36-3.23 [AB of ABX pattern, 2H], 1.36 [s, 9H]. LCMS 580 (M+1)$^+$.

Example 301

(2S)-{[6-(4-tert-Butyl-phenoxy)-isoquinoline-3-carbonyl]-amino}-3-(4-cyclopentylmethoxy-phenyl)-propionic acid methyl ester To a solution of 50 mg (0.1 mmol) of (2S)-{[6-(4-tert-butyl-phenoxy)-isoquinoline-3-carbonyl]-amino}-3-(4-hydroxy-phenyl)-propionic acid methyl ester (Example 298) in dry THF (1 mL) was added cyclopentanemethanol (1.5 eq., 0.15 mmol, 0.016 mL), triphenylphosphine (1.5 eq., 0.15 mmol, 39 mg) and DIAD (1.5 eq., 0.15 mmol, 0.030 mL) according to the procedure M. Chromatography on silica using 20-30% ethyl acetate in hexanes afforded 27 mg of the title compound.

$^1$H NMR: (400 MHz, CDCl$_3$) δ 9.05 [s,1H], 8.65 [d, 1H], 8.38 [s, 1H], 7.98 [d, 1H], 7.44 [m, 3H], 7.24 [d,1H], 7.09-7.04 [m, 4H], 6.80 [m, 2H], 5.07 [X of ABX pattern,1H], 3.78 [d, 2H], 3.73 (s, 3H], 3.20 [AB of ABX pattern, 2H], 2.33 [septet,1H], 1.86-1.78 [m, 2H], 1.66-1.52 [m, 6H], 1.37 [s, 9H]. LCMS 582 (M+1)$^+$.

Example 302

(2S)-{[6-(4-tert-Butyl-phenoxy)-isoquinoline-3-carbonyl]-aminol-3-(4-cyclopentylmethoxy-phenyl)-propionic acid 20 mg (0.034 mmol) of above ester (example 301) was hydrolyzed as described in general procedure C to afford the title compound (19.5 mg).

LCMS 580 (M+1)$^+$.

Example 303

6-(4-tert-Butyl-phenoxy)-isoquinoline-3-carboxylic acid [2-(4-cyclopentylmethoxy-phenyl)-1S-(3-methyl-[1,2,4]oxadiazol-5-yl)-ethyl]-amide To a solution of 2-tert-butoxycarbonylamino-3-(4-hydroxy-phenyl)-propionic acid methyl ester (7.9 g, 26.7 mmol) and triphenylphosphine (1.5 eq., 40.1 mmol, 10.52 g) in 250 mL dry THF was added cyclopentyl methanol (1.5 eq., 40.1 mmol, 5.00 mL) and then diisopropylazodicarboxylate (DIAD) (1.5 eq., 40.1 mmol, 7.90 mL) via a syringe according to the general procedure M. The crude product was purified by chromatography on silica eluting with 15% ethyl acetate in hexanes, to afford 8.8 g of the desired ester which was hydrolyzed according to the general procedure C to yield (2S)-tert-butoxycarbonylamino-3-(4-cyclopentylmethoxy-phenyl)-propionic acid (8.48 g).

LCMS 365 (M+1)$^+$

To a solution of the carboxylic acid above (8.48 g, 22.5 mmol), in 100 mL anhydrous DCM was added DIC (1.05 eq., 24.5 mmol, 3.83 mL) and pentafluorophenol (1.1 eq., 25.6 mmol, 4.72 g) according to the general procedure O. Purification via silica gel chromatography, eluting with 30% ethyl acetate in hexanes, furnished 6.02 g of [2-(4-cyclopentyl-methoxy-phenyl)-(1S)-(3-methyl-[1,2,4]oxadiazol-5-yl)-ethyl]-carbamic acid tert-butyl ester.

LCMS 403 (M+1)$^+$.

The product of the previous reaction (6.02 g, 14.5 mmol) was deprotected according to the general procedure N to afford 2-(4-cyclopentylmethoxy-phenyl)-(1S)-(3-methyl-[1,2,4]oxadiazol-5-yl)-ethylamine (5.1 g).

LCMS 303 (M+1)$^+$.

The title compound was synthesized according to general procedure A, using 44 mg (0.13 mmol) of the amine described above and 44 mg (0.13 mmol) of 6-(4-tert-butylphenoxy)-isoquinoline-3-carboxylic acid (Example 295). Silica gel chromatography (20-30% EtOAc in hexanes) to afforded 63 mg of the title compound. LCMS 605 (M+1); $^1$H NMR: (CDCl$_3$) δ 9.06 [s,1H], 8.78 [d, 1H], 8.38 [s, 1H], 7.99[d, 1H], 7.46 [m,1H], 7.45 [d, 2H], 7.23 [d, 1H], 7.05, [app t, 4H], 6.77 [d, 2H], 5.78 [dt, 1H], 3.91 [t, 2H], 3.33 [d, 2H], 2.38 [s, 3H], 1.93 [m, 1H], 1.86-1.73, [m, 4H], 1.68-1.46 [m, 4H], 1.37 [s, 9H], 1.20-1.08 [m, 2H]

Example 304

6-(4-tert-Butyl-phenoxy)-isoquinoline-3-carboxylic acid [2-(4-benzyloxy-phenyl)-(1S)-(3-methyl-[1,2,4] oxadiazol-5-yl)-ethyl]-propyl-amide (2S)-(4-Benzyloxy-phenyl)-1-(3-methyl-[1,2,4]oxadiazol-5-yl)-ethylamine hydrochloride (1.27 g) was synthesized from N-boc-O-benzyl tyrosine according to the general procedure O and N.

LCMS 311 (M+1)$^+$.

A portion of the above material (150 mg, 0.43 mmol) was treated with propanal (1.1 eq., 0.48 mmol, 0.035 mL) and sodium triacetoxyborohydride (1.5 eq, 0.65 mmol, 138 mg) in 2 mL dry DCM according to general procedure E to afford 116 mg of [2-(4-benzyloxy-phenyl)-1-(3-methyl-[1,2,4]oxadiazol-5-yl)-ethyl]-propyl-amine.

LCMS 353 (M+1)$^+$.

The above material (116 mg, 0.33 mmol) was dissolved in 5 mL anhydrous DCM and 6-(4-tert-butylphenoxy)-isoquinoline-3-carbonyl chloride (125 mg, 0.33 mmol) (prepared reacting example 295 with oxalyl chloride) dissolved in 8 mL of dry DCM was added, followed by triethylamine 3.0 eq. 1.0 mmol, 0.138 mL) and the reaction was carried out according to general procedure J. Chromatography on silica, eluting with ethyl acetate/hexanes, furnished 165 mg of the title compound.

LCMS 656 (M+1)$^+$.

Example 305

3-(3'-Chloro-4'-fluoro-biphenyl-4-yl)-(2S)-{[6-(4-trifluoromethyl-phenoxy)-isoquinoline-3-carbonyl]-amino}-propionic acid methyl ester A solution of 6-hydroxy-3,4-dihydro-1H-isoquinoline-2, 3-dicarboxylic acid 2 tert-butyl ester 3-methyl ester (from example 295) (0.700 g, 2.20 mmol) in anhydrous DCM was treated with 4-trifluorophenylboronic acid (0.860 g, 4.52 mmol), copper acetate (0.619 g, 3.40 mmol), and 4A molecular sieves and triethylamine (1.58 mL, 11.32 mmol) by the general procedure G. The crude product was purified by flash column chromatography on silica using hexanes:EtOAc(7%) to elute 6-(4-trifluoromethyl-phenoxy)-3,4-dihydro-1H-isoquinolihne-2,3-dicarboxylic acid 2-tert-butyl ester 3-methyl ester as a colorless oil (0.427 g).

LCMS: 452 (M+1)$^+$.

To 0.420 g (1.03 mmol) of above compound was added HCl/dioxane (4.0M, 60 mL) and the solution was stirred at rt for 2 h. The solution was concentrated under reduced pressure and dried under vacuum for 1 h to give a white solid. To this was added 25 mL anhydrous toluene and DDQ (0.493 g, 2.175 mmol) and the reaction was heated at 100° C. for 1.5 h. Upon cooling to rt, the reaction mixture was filtered and washed with DCM several times. The filtrate was concentrated under reduced pressure to give a dark brown residue. The residue was dissolved in DCM and the washed with satd. solution of sodium bisulfite. The aq. layer was discarded and the organic layer was washed with brine, dried (Na$_2$SO$_4$) and concentrated under reduced pressure to give 6-(4-trifluoromethyl-phenoxy)-isoquinoline-3-carboxylic acid methyl ester as brown solid (0.368 g).

LCMS: 348 (M+1)$^+$

The above ester (0.368 g, 1.058 mmol) was hydrolyzed as described in general procedure I to give 6-(4-trifluoromethyl-phenoxy)-isoquinoline-3-carboxylic acid as a light brown solid (0.320 g).

A solution of 6-(4-trifluoromethyl-phenoxy)-isoquinoline-3-carboxylic acid (0.050 g, 0.149 mmol) in DMF (2.0 mL) was treated with 2(S)-amino-3-(3'-chloro-4'-fluoro-biphenyl-4-yl)-propionic acid methyl ester hydrochloride (0.051 g, 0.164 mmol), HBTU (0.062 g, 0.164 mmol), and DIEA (0.112 mL) by the general procedure A. The crude product was purified by flash column chromatography on silica gel using Hexanes:EtOAc 88:12 to give 0.025 g of 3-(3'-Chloro-4'-fluoro-biphenyl-4-yl)-(2S)-{[6-(4-trifluoromethyl-phenoxy)-isoquinoline-3-carbonyl]-amino}-propionic acid methyl ester.

$^1$H NMR (CDCl$_3$) δ 9.11 [s, 1H], 8.70 [d, 1H], 8.45 [s, 1H], 8.06 [d, 1H], 7.69 [d, 2 H], 7.58 [dd, 1H], 7.42 [m, 4 H], 7.27-7.15 [m, 6 H], 5.17 [m, 1H], 3.77 [s, 3 H], 3.28 [m, 2 H]. LCMS 623 (M+1)$^+$

Example 306

3-(3'-Chloro-4'-fluoro-biphenyl-4-yu)-(2S)-([6-(4-trifluoromethyl-phenoxy)-isoquinoline-3-carbonyl]-amino}-propionic acid A solution of 3-(3'-chloro-4'-fluoro-biphenyl-4-yl)-(2S)-{[6-(4-trifluoromethyl-phenoxy)-isoquinoline-3-carbonyl]-amino}-propionic acid methyl ester (20 mg, 0.0321 mmol) was treated with LiOH (5 mg, 0.128 mmol) by the General Procedure to give 15 mg of 3-(3'-Chloro-4'-fluoro-biphenyl-4-yl)-(2S)-{[6-(4-trifluoromethyl-phenoxy)-isoquinoline-3-carbonyl]-amino}-propionic acid as a white solid.

$^1$H NMR (CDCl$_3$) δ 9.09 [s, 1H], 8.70 [d, 1H], 8.45 [s, 1H], 8.06 [d, 1H], 7.69 [d, 2 H], 7.55-7.12 [m, 11 H], 5.13 [X, 1H], 3.35 [ABX, 2 H]. LCMS 609 (M+1)$^+$

By analogous methods to those described above the following Examples were synthesized.

| Example | Name | LC/MS |
|---|---|---|
| 307 | (2S)-{[6-(4-tert-Butyl-phenoxy)-isoquinoline-3-carbonyl]-amino}-3-(4'-trifluoromethoxy-biphenyl-4-yl)-propionic acid methyl ester | 643 |
| 308 | (2S)-{[6-(4-tert-Butyl-phenoxy)-isoquinoline-3-carbonyl]-amino}-3-(4'-trifluoromethoxy-biphenyl-4-yl)-propionic acid | 629 |

-continued

| Example | Name | LC/MS |
|---|---|---|
| 309 | (2S)-{[6-(4-tert-Butyl-phenoxy)-isoquinoline-3-carbonyl]-amino}-3-(4'-trifluoromethyl-biphenyl-4-yl)-propionic acid methyl ester | 627 |
| 310 | (2S)-{[6-(4-tert-Butyl-phenoxy)-isoquinoline-3-carbonyl]-amino}-3-(4'-trifluoromethyl-biphenyl-4-yl)-propionic acid | 613 |
| 311 | (2S)-{[6-(4-tert-Butyl-phenoxy)-isoquinoline-3-carbonyl]-amino}-3-(3'-chloro-4'-fluoro-biphenyl-4-yl)-propionic acid methyl ester | 611 |
| 312 | (2S)-{[6-(4-tert-Butyl-phenoxy)-isoquinoline-3-carbonyl]-amino}-3-(3'-chloro-4'-fluoro-biphenyl-4-yl)-propionic acid | 597 |
| 313 | (2S)-{[7-(4-tert-Butyl-phenoxy)-isoquinoline-3-carbonyl]-amino}-3-(4'-tri-fluoromethoxy-biphenyl-4-yl)-propionic acid methyl ester | 643 |
| 314 | (2S)-{[7-(4-tert-Butyl-phenoxy)-isoquinoline-3-carbonyl]-amino}-3-(4'-trifluoromethoxy-biphenyl-4-yl)-propionic acid | 629 |
| 315 | (2S)-{[7-(4-tert-Butyl-phenoxy)-isoquinoline-3-carbonyl]-amino}-3-(4'-trifluoromethyl-biphenyl-4-yl)-propionic acid methyl ester | 627 |
| 316 | (2S)-{[7-(4-tert-Butyl-phenoxy)-isoquinoline-3-carbonyl]-amino}-3-(4'-trifluoromethyl-biphenyl-4-yl)-propionic acid | 613 |
| 317 | (2S)-{[7-(4-tert-Butyl-phenoxy)-isoquinoline-3-carbonyl]-amino}-3-(3'-chloro-4'-fluoro-biphenyl-4-yl)-propionic acid methyl ester | 611 |
| 318 | (2S)-{[7-(4-tert-Butyl-phenoxy)-isoquinoline-3-carbonyl]-amino}-3-(3'-chloro-4'-fluoro-biphenyl-4-yl)-propionic acid | 597 |
| 319 | (2S)-{[7-(4-tert-Butyl-phenoxy)-isoquinoline-3-carbonyl]-amino}-3-(4'-fluoro-biphenyl-4-yl)-propionic acid methyl ester | 577 |
| 320 | (2S)-{[6-(4-tert-Butyl-phenoxy)-isoquinoline-3-carbonyl]-amino}-3-(4-phenoxy-phenyl)-propionic acid methyl ester | 575 |
| 321 | (2S)-{[6-(4-tert-Butyl-phenoxy)-isoquinoline-3-carbonyl]-amino}-3-[4-(4-trifluoromethyl-phenoxy)-phenyl]-propionic acid methyl ester | 643 |
| 322 | (2S)-{[6-(4-tert-Butyl-phenoxy)-isoquinoline-3-carbonyl]-amino}-3-[4-(4-trifluoromethyl-phenoxy)-phenyl]-propionic acid | 629 |
| 323 | (2S)-{[6-(4-tert-Butyl-phenoxy)-isoquinoline-3-carbonyl]-amino}-3-[4-(3,3-dimethyl-butoxy)-phenyl]-propionic acid methyl ester | 583 |
| 324 | (2S)-{[6-(4-tert-Butyl-phenoxy)-isoquinoline-3-carbonyl]-amino}-3-[4-(2-cyclopentyl-ethoxy)-phenyl]-propionic acid methyl ester | 595 |
| 325 | (2S)-{[6-(4-tert-Butyl-phenoxy)-isoquinoline-3-carbonyl]-amino}-3-{4-[2-(4-fluoro-phenyl)-ethoxy]-phenyl}-propionic acid methyl ester | 621 |
| 326 | (2S)-{[6-(4-tert-Butyl-phenoxy)-isoquinoline-3-carbonyl]-amino}-3-{4-[2-(4-chloro-phenyl)-ethoxy]-phenyl}-propionic acid methyl ester | 637 |
| 327 | (2S)-{[6-(4-tert-Butyl-phenoxy)-isoquinoline-3-carbonyl]-amino}-3-[4-(3,3-dimethyl-butoxy)-phenyl]-propionic acid | 569 |
| 328 | (2S)-{[6-(4-tert-Butyl-phenoxy)-isoquinoline-3-carbonyl]-amino}-3-[4-(2-cyclopentyl-ethoxy)-phenyl]-propionic acid | 581 |
| 329 | (2S)-{[6-(4-tert-Butyl-phenoxy)-isoquinoline-3-carbonyl]-amino}-3-{4-[2-(4-fluoro-phenyl)-ethoxy]-phenyl}-propionic acid | 607 |
| 330 | (2S)-{[6-(4-tert-Butyl-phenoxy)-isoquinoline-3-carbonyl]-amino}-3-{4-[2-(4-chloro-phenyl)-ethoxy]-phenyl}-propionic acid | 623 |
| 331 | 6-(4-tert-Butyl-phenoxy)-isoquinoline-3-carboxylic acid [2-(4-cyclopentylmethoxy-phenyl)-(1S)-dimethylcarbamoyl-ethyl]-amide | 594 |
| 332 | 6-(4-tert-Butyl-phenoxy)-isoquinoline-3-carboxylic acid {2-[4-(2-cyclopentyl-ethoxy)-phenyl]-(1S)-dimethylcarbamoyl-ethyl}-amide | 608 |
| 333 | 6-(4-tert-Butyl-phenoxy)-isoquinoline-3-carboxylic acid [2-[4-(3,3-dimethyl-butoxy)-phenyl]-(1S)-(3-methyl-[1,2,4]oxadiazol-5-yl)-ethyl]-amide | 607 |
| 334 | 6-(4-tert-Butyl-phenoxy)-isoquinoline-3-carboxylic acid [2-[4-(2-cyclopentyl-ethoxy)-phenyl]-(1S)-(3-methyl-[1,2,4]oxadiazol-5-yl)-ethyl]-amide | 619 |
| 335 | 6-(4-tert-Butyl-phenoxy)-isoquinoline-3-carboxylic acid [2-{4-[2-(4-fluoro-phenyl)-ethoxy]-phenyl}-(1S)-(3-methyl-[1,2,4]oxadiazol-5-yl)-ethyl]-amide | 645 |
| 336 | 6-(4-tert-Butyl-phenoxy)-isoquinoline-3-carboxylic acid [2-(4-cyclopentyloxy-phenyl)-(1S)-(3-methyl-[1,2,4]oxadiazol-5-yl)-ethyl]-amide | 591 |
| 337 | 6-(4-tert-Butyl-phenoxy)-isoquinoline-3-carboxylic acid [2-(4-benzyloxy-phenyl)-(1S)-(3-methyl-[1,2,4]oxadiazol-5-yl)-ethyl]-propyl-amide | 655 |

-continued

| Example | Name | LC/MS |
|---|---|---|
| 338 | (2S)-{[6-(4-tert-Butyl-phenoxy)-isoquinoline-3-carbonyl]-amino}-3-(2'-phenoxy-biphenyl-4-yl)-propionic acid methyl ester | 651 |
| 339 | 3-Biphenyl-4-yl-(2S)-{[6-(4-trifluoromethyl-phenoxy)-isoquinoline-3-carbonyl]-amino}-propionic acid methyl ester | 571 |
| 340 | 3-Biphenyl-4-yl-(2S)-{[6-(4-trifluoromethyl-phenoxy)-isoquinoline-3-carbonyl]-amino}-propionic acid | 557 |
| 341 | 3-Biphenyl-4-yl-(2R)-{[6-(4-tert-butyl-phenoxy)-isoquinoline-3-carbonyl]-amino}-propionic acid methyl ester | 559 |
| 342 | 6-(4-Trifluoromethyl-phenoxy)-isoquinoline-3-carboxylic acid [2-[4-(2-cyclopentyl-ethoxy)-phenyl]-(1S)-(3-methyl-[1,2,4]oxadiazol-5-yl)-ethyl]-amide | 631 |
| 343 | 3-Biphenyl-4-yl-(2R)-{[6-(4-tert-butyl-phenoxy)-isoquinoline-3-carbonyl]-amino}-propionic acid | 545 |
| 344 | 6-(4-Trifluoromethyl-phenoxy)-isoquinoline-3-carboxylic acid [2-(4-benzyloxy-phenyl)-(1S)-(3-methyl-[1,2,4]oxadiazol-5-yl)-ethyl]-amide | 625 |
| 345 | 6-(4-Trifluoromethoxy-phenoxy)-isoquinoline-3-carboxylic acid [2-[4-(2-cyclopentyl-ethoxy)-phenyl]-(1S)-(3-methyl-[1,2,4]oxadiazol-5-yl)-ethyl]-amide | 647 |
| 346 | 6-(4-tert-Butyl-phenoxy)-isoquinoline-3-carboxylic acid[2-(4-hydroxy-phenyl)-(1S)-(3-methyl-[1,2,4]oxadiazol-5-yl)-ethyl]-amide | 523 |
| 347 | 6-(4-tert-Butyl-phenoxy)-isoquinoline-3-carboxylic acid[2-(4-but-3-ynyloxy-phenyl)-(1S)-(3-methyl-[1,2,4]oxadiazol-5-yl)-ethyl]-amide | 575 |
| 348 | 6-(4-tert-Butyl-phenoxy)-isoquinoline-3-carboxylic acid[2-(4-cyclopropylmethoxy-phenyl)-(1S)-(3-methyl-[1,2,4]oxadiazol-5-yl)-ethyl]-amide | 577 |
| 349 | 6-(4-tert-Butyl-phenoxy)-isoquinoline-3-carboxylic acid[2-[4-(2-methyl-butoxy)-phenyl]-(1S)-(3-methyl-[1,2,4]oxadiazol-5-yl)-ethyl]-amide | 593 |
| 350 | 6-(4-tert-Butyl-phenoxy)-isoquinoline-3-carboxylic acid[2-(4-cyclohexylmethoxy-phenyl)-(1S)-(3-methyl-[1,2,4]oxadiazol-5-yl)-ethyl]-amide | 619 |
| 351 | 6-(4-tert-Butyl-phenoxy)-isoquinoline-3-carboxylic acid[2-[4-(3-cyclohexyl-propoxy)-phenyl]-(1S)-(3-methyl-[1,2,4]oxadiazol-5-yl)-ethyl]-amide | 647 |
| 352 | 6-(4-tert-Butyl-phenoxy)-isoquinoline-3-carboxylic acid[2-[4-(2-aziridin-1-yl-ethoxy)-phenyl]-(1S)-(3-methyl-[1,2,4]oxadiazol-5-yl)-ethyl]-amide | 592 |
| 353 | 6-(4-tert-Butyl-phenoxy)-isoquinoline-3-carboxylic acid{(1S)-(3-methyl-[1,2,4]oxadiazol-5-yl)-2-[4-(2-pyrrolidin-1-yl-ethoxy)-phenyl]-ethyl}-amide | 620 |
| 354 | 6-(4-tert-Butyl-phenoxy)-isoquinoline-3-carboxylic acid{(1S)-(3-methyl-[1,2,4]oxadiazol-5-yl)-2-[4-(1-methyl-piperidin-4-yloxy)-phenyl]-ethyl}-amide | 620 |
| 355 | (2S)-{[6-(4-tert-Butyl-phenoxy)-isoquinoline-3-carbonyl]-amino}-3-(2'-phenoxy-biphenyl-4-yl)-propionic acid | 637 |
| 356 | (2S)-{[6-(4-tert-Butyl-phenoxy)-isoquinoline-3-carbonyl]-amino}-3-[4-(4-nitro-phenoxy)-phenyl]-propionic acid | 606 |
| 357 | (2S)-{[6-(4-tert-Butyl-phenoxy)-isoquinoline-3-carbonyl]-amino}-3-[4-(3-trifluoromethyl-phenoxy)-phenyl]-propionic acid | 629 |
| 358 | 3-(3'-Chloro-4'-fluoro-biphenyl-4-yl)-(2S)-{[6-(4-trifluoromethoxy-phenoxy)-isoquinoline-3-carbonyl]-amino}-propionic acid | 625 |
| 359 | 3-Biphenyl-4-yl-(2S)-{[6-(4-trifluoromethoxy-phenoxy)-isoquinoline-3-carbonyl]-amino}-propionic acid methyl ester | 587 |
| 360 | 3-Biphenyl-4-yl-(2S)-{[6-(4-trifluoromethoxy-phenoxy)-isoquinoline-3-carbonyl]-amino}-propionic acid | 573 |
| 361 | 3-[4-(4-Amino-phenoxy)-phenyl]-(2S)-{[6-(4-tert-butyl-phenoxy)-isoquinoline-3-carbonyl]-amino}-propionic acid | 576 |
| 362 | (2S)-{[6-(4-tert-Butyl-phenoxy)-isoquinoline-3-carbonyl]-amino}-3-{4-[4-(2-carboxy-acetylamino)-phenoxy]-phenyl}-propionic acid | 662 |
| 363 | 4-{4-[4-((2S)-{[6-(4-tert-Butyl-phenoxy)-isoquinoline-3-carbonyl]-amino}-2-carboxy-ethyl)-phenoxy]-phenylcarbamoyl}-butyric acid | 690 |
| 364 | N-{4-[4-((2S)-{[6-(4-tert-Butyl-phenoxy)-isoquinoline-3-carbonyl]-amino}-2-methoxycarbonyl-ethyl)-phenoxy]-phenyl}-succinamic acid methyl ester | 704 |
| 365 | N-{4-[4-((2S)-{[6-(4-tert-Butyl-phenoxy)-isoquinoline-3-carbonyl]-amino}-2-carboxy-ethyl)-phenoxy]-phenyl}-succinamic acid | 676 |

Example 366

2-(2-Biphenyl-4-yl-(1S)-methoxycarbonyl-ethylcarbamoyl)-5-hydroxy-indole-1-carboxylic acid tert-butyl ester 450 mg (1.5 mmol) of 5-hydroxy-indole-1,2-dicarboxylic acid 1-tert-butyl ester (made from 5-hydroxy-1H-indole-2-carboxylic acid by protecting with BOC) was reacted with 470 mg (1.9 mmol) of (2S)-amino-3-biphenyl-4-yl-propionic acid methyl ester as described in general procedure A. The crude product was purified by flash column chromatography on silica using 7:3 hexane/ethyl acetate as an eluents to afford 400 mg of the title compound as a white solid.
LCMS: 514 (M+1)$^+$

Example 367

2-(2-Biphenyl-4-yl-(1S)-methoxycarbonyl-ethylcarbamoyl)-5-(4-tert-butyl-phenoxy)-indole-1-carboxylic acid tert-butyl ester 400 mg (0.78 mmol) of above Example 366 was reacted with 280 mg (1.55 mmol) of 4-tert-butyl phenylboronic acid, as described in general procedure G. The crude product was purified by flash column chromatography on silica using 9:1 hexane/ethyl acetate as an eluents to afford 50 mg of the title compound as a white solid.
LCMS: 647 (M+1)$^+$

Example 368

3-Biphenyl-4-yl-(2S)-{[5-(4-tert-butyl-phenoxy)-1H-indole-2-carbonyl]-amino}-propionic acid methyl ester 20 mg (0.039 mmol) of example 367 was treated with 4.0M HCl in dioxane as described in general procedure N to afford 19.5 mg of the title compound. LCMS: 547 (M+1)$^+$

Example 369

2-(2-Biphenyl-4-yl-(1S)-carboxy-ethylcarbamoyl)-5-(4-tert-butyl-phenoxy)-indole-1-carboxylic acid tert-butyl ester 20 mg (0.039 mmol) of the above Example 367 was hydrolyzed as described in general procedure C to afford the title compound (19.5 mg).
LCMS: 633 (M+1)$^+$

Example 370

(2S)-(2-Biphenyl-4-yl-1-carboxy-ethylcarbamoyl)-5-(4-tert-butyl-phenoxy)-indole-1-carboxylic acid tert-butyl ester 15 mg (0.023 mmol) of above Example 369 was dissolved in 1.0 ml of 4.0M HCl in dioxane and stirred at room temperature for 45 min. Evaporation of the solvent under vacuo gave the title compound (12.6 mg).
LCMS: 533 (M+1)$^+$

Example 371

7-(4-tert-Butylphenoxy)-isoquinoline-3-carboxylic acid

To a solution of (3S)-7-hydroxy-3,4-dihydro-1H-isoquinoline-2,3-dicarboxylic acid 2-tert-butyl ester (1.47 g, 5.0 mmol) in dry DMF (25 mL) at ambient temperature, was added iodomethane (1.2 eq., 6.0 mmol, 0.37 mL) and diisopropylethylamine (1.5 eq. 7.5 mmol, 1.31 mL) in succession, and the reaction mixture was stirred at rt for 3-4 hours, at which point LC/MS analysis showed the presence of product The reaction mixture was poured into 50 mL of water and extracted with DCM (3×50 mL) and the combined DCM extracts were washed with water (3×50 mL) and brine (50 mL), dried over Na$_2$SO$_4$, filtered and concentrated in vacuo. The crude product was purified by flash column chromatography on silica (20-30% ethyl acetate in hexanes) to afford (3S)-7-hydroxy-3,4-dihydro-1H-isoquinoline-2,3-dicarboxylic acid 2-tert-butyl ester 3-methyl ester (1.13 g).
LCMS: 308 (M+1)$^+$.

The above phenol (1.20 g, 3.91 mmol) was reacted with 4-(tert-butyl)phenylboronic acid (1.6 eq., 6.26 mmol, 1.11 g), copper(II) acetate (1.0 eq. 3.91 mmol, 710 mg) as desribed in general procedure G. Flash column chromatography on silica (ethyl acetate/hexanes) provided 750 mg of the desired product, (3S)-7-(4-tert-butylphenoxy)-3,4-dihydro-1H-isoquinoline-2,3-dicarboxylic acid 2-tert-butyl ester 3-methyl ester.
LCMS: 440 (M+1)$^+$ A portion of the material described above (400 mg, 0.91 mmol) was placed in a dry 4 dram vial containing a magnetic stir bar, and was treated with a 4N solution of anhydrous HCl in 1,4-dioxane (1.0 mL, 4.0 mmol, 4.4 eq) The reaction was stirred at ambient temperature for 1 hour, at which point the reaction appeared to be complete by TLC. The solvent and residual HCl was removed under vacuum and the crude product, (3S)-7-(4-tert-butylphenoxy)-1,2,3,4-tetrahydroisoquinoline-3-carboxylic acid methyl ester hydrochloride, was used without further purification.
LCMS: 340 (M+1)$^+$ The above crude product was dissolved in 18 mL of dry toluene and DDQ (3.0 eq., 2.73 mmol, 620 mg) was added in a single portion. The mixture was heated at reflux for 2 hours then cooled and concentrated on a rotary evaporator. The crude residue was placed directly atop a silica gel column and eluted with a 1:1 mixture of ethyl acetate and hexanes to furnish 229 mg of the product, 7-(4-tert-butylphenoxy)-isoquinoline-3-carboxylic acid methyl ester. A portion of the ester (208 mg, 0.62 mmol) was hydrolyzed as described in general procedure C to afford 199 mg of the title compound as a white solid.
$^1$H-NMR (400 MHZ, CDCl$_3$): δ 8.47 (s, 1H), 7.98 (d, 1H), 7.59 (s, 1H), 7.53 (dd, 1H), 7.46 (d, 2H), 7.05 (d, 2H), 3.15 (d, 2H), 2.35 (m, 1H), 1.67 (m, 4H), 1.53 (m, 2H), 1.36 (s, 9H), 1.30 (m, 2H). LCMS: 322 (M+1)$^+$.

Example 372

3-Biphenyl-4-yl-2S-{[7-(4-tert-butylphenoxy)-isoquinoline-3-carbonyl]amino}-propionic acid methyl ester 321 mg (1.0 mmol) of 7-(4-tert-Butylphenoxy)-isoquinoline-3-carboxylic acid (example 371) was reacted with 225 mg (1.0 mmol) of (L)-biphenylalanine methyl ester as described in general procedure A. The crude product was purified by flash column chromatography on silica using 20-30% ethyl acetate in hexanes as eluent, to afford 420 mg of the title compound as a white solid.
LCMS 560 (M+1)$^+$

Example 373

3-Biphenyl-4-yl-(2S)-{[7-(4-tert-butylphenoxy)-isoquinoline-3-carbonyl]amino}-propionic acid 420 mg (0.75 mmol) of above ester (example 372) was hydrolyzed as described in general procedure C to afford the title compound (408 mg).

$^1$H NMR: (400 MHz, CDCl$_3$) δ 8.93 [s,1H], 8.66 [d, 1H], 8.54 [s, 1H], 7.92 [d, 1H], 7.53-7.43 [m, 7H], 7.37 [app t, 2H], 7.30 [m, 4H], 7.03 [dd, 2H], 5.15 [X of ABX pattern, 1H], 3.37 [AB of ABX pattern, 2H], 1.36 [s, 9H]. LCMS 546 (M+1)$^+$

Example 374

(2S)-{[7-(4-tert-Butyl-phenoxy)-isoquinoline-3-carbonyl]-amino}-3-(4-hydroxy-phenyl)-propionic acid methyl ester 500 mg (1.6 mmol) of 7-(4-tert-Butylphenoxy)-isoquinoline-3-carboxylic acid was reacted with 430 mg (1.8 mmol) of (2S)-amino-3-(4-hydroxy-phenyl)-propionic acid methyl ester as described in general procedure A. The crude product was purified by flash column chromatography on silica gel using 3:2 hexane/ethyl acetate as eluent, to afford 600 mg of the title compound as a white solid.

LCMS 499 (M+1)$^+$

Example 375

(2S)-{[7-(4-tert-Butyl-phenoxy)-isoquinoline-3-carbonyl]-amino}-3-(4-phenoxy-phenyl)-propionic acid methyl ester

Example 376

(2S)-{[7-(4-tert-Butyl-phenoxy)-isoquinoline-3-carbonyl]-aminophenyl}-3-(4-phenoxy-phenyl)-propionic acid methyl ester 50 mg (0.1 mmol) of (2S)-{[7-(4-tert-butyl-phenoxy)-isoquinoline-3-carbonyl]-amino}-3-(4-hydroxy-phenyl)-propionic acid methyl ester (Example 374) was reacted with 24 mg (0.2 mmol) of phenyl boronic acid as described in procedure G. Column chromatography using DCM as an eluent gave 10 mg of example 375 [LCMS 575 (M+1)$^+$] and 15.0 mg of example 376 [LCMS: 651 (M+1)$^+$] as a white solids.

Example 377

(2S)-{[7-(4-tert-Butyl-phenoxy)-isoq uinoline-3-carbonyl]-amino}-3-(4-phenoxy-phenyl)-propionic acid 8.0 mg (0.013 mmol) of above ester (Example 375) was hydrolyzed as described in general procedure C to afford the 7.0 mg of the title compound as a white solid.

$^1$H-NMR (400 MHZ, CDCl$_3$): δ 8.95 (s, 1H), 8.60 (d, 1H), 8.54 (s, 1H), 7.96 (d, 1H), 7.56 (dd, 2H), 7.45 (dd, 2H), 7.33 (m, 7H), 7.05 (m, 2H), 6.94 (m, 3H), 5.04 (m,1H), 3.91 (m, 1H), 3.25 (m, 1H), 1.36 (s, 9H). LCMS 561 (M+1)$^+$

Example 378

(2S)-{[7-(4-tert-Butyl-phenoxy)-isoquinoline-3-carbonyl]-phenyl-amino}-3-(4-phenoxy-phenyl)-propionic acid 6.0 mg (0.009 mmol) of above ester (Example 376) was hydrolyzed as desribed in general procedure C to afford the 5.0 mg of the title compound as a white solid.

LCMS 637 (M+1)$^+$

Example 379

3-(4-Bromo-phenyl)-(2S)-{[7-(4-tert-butyl-phenoxy)-isoquinoline-3-carbonyl]-amino)-propionic acid methyl ester 500 mg (1.55 mmol) of 7-(4-tert-butylphenoxy)-isoquinoline-3-carboxylic acid (Example 371) was reacted with 441 mg (1.7 mmol) of (2S)-amino-3-(4-bromo-phenyl)-propionic acid methyl ester as described in general procedure A. The crude product was purified by flash column chromatography on silica using 8:2 hexane/ethyl acetate as eluent, to afford 830 mg of the title compound as a white solid.

LCMS: 562 (M+1)$^+$

Example 380

(2S)-{[7-(4-tert-Butyl-phenoxy)-isoquinoline-3-carbonyl]-amino}-3-(3'-chloro-4'-fluoro-biphenyl-4-yl)-propionic acid methyl ester 50 mg (0.089 mmol) of 3-(4-bromo-phenyl)-(2S)-{[7-(4-tert-butyl-phenoxy)-isoquinoline-3-carbonyl]-amino}-propionic acid was reacted with 31 mg (0.17 mmol) of 3-chloro-4-fluorophenylboronic acid in toluene as described in procedure D. Column chromatography using 8:2 hexane and ethyl acetate as an eluent gave 46 mg of title compound as a white solid.

LCMS: 611 (M+1)$^+$

Example 381

(2S)-{[7-(4-tert-Butyl-phenoxy)-isoquinoline-3-Garbonyl]-amino}-3-(3'-chloro-4'-fluoro-biphenyl-4-yl)-propionic acid 40 mg (0.065 mmol) of above ester Example 380 was hydrolyzed as described in general procedure C to afford the 38.5 mg of the title compound as a white solid.

LCMS: 597 (M+1)$^+$

Example 382

(2S)-[(7-Benzyloxy-isoquinoline-3-carbonyl)-amino]-3-biphenyl-4-yl-propionic acid methyl ester 2.0 g, (6.8 mmol) of (3S)-7-hydroxy-3,4-dihydro-1H-isoquinoline-2,3-dicarboxylic acid 2-tert-butyl ester was reacted with 2.56 g (15.0 mmol) of benzyl bromide as described in general procedure H. The resulting crude product was subjected to hydrolysis as described in general procedure C. The crude product was purified by column chromatography using 1:1 ethyl acetate and hexane as eluent to afford 0.5 g of 7-benzyloxy-3,4-dihydro-1H-isoq uinoline-2,3-dicarboxylic acid 2-tert-butyl ester.

LCMS: 384 (M+1)$^+$ 0.5 g (13.0 mmol) of above compound was deprotected according to the general procedure N and oxidation with DDQ as described for the synthesis of example 371 gave 0.25 g of 7-benzyloxy-isoquinoline-3-carboxylic acid as a light yellow solid.

LCMS: 280 (M+1)$^+$ 250 mg (0.9 mmol) of above 7-benzyloxy-isoquinoline-3-carboxylic acid was reacted with 228 mg (0.9 mmol) of (L)-biphenylalanine methyl ester as described in general procedure A. The crude product was purified by flash column chromatography on silica using 15% ethyl acetate in hexanes as eluent, to afford 416 mg of the title compound as a white solid.

LCMS: 517 (M+1)$^+$

Example 383 (201344)

(2S)-[(7-Benzyloxy-isoquinoline-3-carbonyl)-amino]-3-biphenyl-4-yl-propionic acid 16 mg (0.031 mmol) of example 382 was hydrolyzed as described in general procedure C to afford 15.5 mg of the title compound as a white solid.

LCMS: 503 (M+1)$^+$

Example 384

3-Biphenyl-4-yl-(2S)-[(7-hydroxy-isoquinoline-3-carbonyl)-amino]-propionic acid methyl ester 400 mg (0.77 mmol) of example 382 was dissolved in 4:1 MeOH/ethyl acetate (25 ml) and 50 mg of Pd(OH)$_2$ was added to the reaction mixture at rt and hydrogenated at 60 psi overnight. Then the reaction mixture was filtered and evaporated in vacuo to give 300 mg of the title compound.

LCMS: 427 (M+1)$^+$

Example 385

3-Biphenyl-4-yl-(2S)-[(7-cyclopentyloxy-isoquinoline-3-carbonyl)-amino]-propionic acid methyl ester Example 384 (50 mg, 0.012 mmol) was reacted with 2-cyclopentyl-ethanol (26.9 mg, 0.023 mmol) as described in general procedure N. The resulting crude product was subjected to column chromatography using 15% ethyl acetate in hexane to give 57 mg of the title compound.

LCMS: 523 (M+1)$^+$

Example 386

3-Biphenyl-4-yl-(2S)-[(7-cyclopentyloxy-isoquinoline-3-carbonyl)-amino]-propionic acid 20 mg (0.038 mmol) of example 385 was hydrolyzed as described in general procedure C to afford 19.4 mg of the title compound as a white solid. $^1$H-NMR (400 MHZ, CDCl$_3$): δ 9.01 (s, 1H), 8.66 (d, 1H), 8.51 (s, 1H), 7.87 (d, 1H), 7.51 (m, 4H), 7.40 (m, 3H), 7.33 (m, 2H), 7.25 (d, 2H), 5.13 (m, 1H), 4.13 (t, 2H), 3.43 (m, 1H), 3.33 (m, 1H), 2.00 (m, 1H), 1.90 (m, 4H), 1.67 (m, 2H), 1.56 (m, 2H), 1.22 (m, 2H). LCMS: 508 (M+1)$^+$ Example 387 (200735)

3-Biphenyl-4-yl-2-{[7-(4-tert-butylphenoxy)-isoquinoline-3-carbonyl]propylamino}-propionic acid methyl ester To a solution of N-propyl-(L)-biphenylalanine methyl ester (1.0 eq, 0.1 mmol, 30 mg) in 1 mL of dry DCM was added 7-(4-tert-butoxyphenoxy)-isoquinoline-3-carbonyl chloride (made from example 371 by reaction with oxalyl chloride) (1.4 eq., 0.14 mmol, 48 mg) in dry DCM (1.4 mL), followed by the addition of triethylamine (5.0 eq., 0.5 mmol, 70 μL). The reaction was stirred at rt for 1 hour. The solvent was removed and the crude residue was purified by flash column chromatography on silica using 20% ethyl acetate in hexanes as eluent, to afford 60 mg of the title compound.

LCMS: 601 (M+1)$^+$

Example 388

3-Biphenyl-4-yl-(2S)-{[7-(4-tert-butylphenoxy)-isoquinoline-3-carbonyl]propylamino}-propionic acid The title compound was prepared (19.5 mg) by saponification of Example 387 (20 mg, 0.033 mmol) according to the general procedure C.

$^1$H NMR: (400 MHz, CDCl$_3$) δ 8.95 [s,1H], 8.11 [s, 1H], 7.91 [d, 1H], 7.63 [dd, 1H], 7.53 [m, 2H], 7.47-7.40 [m, 6H], 7.36-7.32 [m, 2H], 7.07-7.02 [m, 4H], 4.78 [X of ABX pattern, 1H], 3.82 [m, 1H], 3.34-3.12 [AB of ABX pattern, 2H], 3.24 [m, 1H], 1.78 [dt,2H], 1.36 [s, 9H], 0.98 [t, 3H]. LCMS: 587 (M+1)$^+$ Example 389 (200733)

3-Biphenyl-4-yl-(2S)-{[7-(4-tert-butylphenoxy)-isoquinoline-3-carbonyl]-(2,2-imethylpropyl)-amino}-propionic acid methyl ester The preparation of the title compound (34 mg) is carried out as for the preparation of compound 387, except for the use of N-neopentyl-(L)-biphenylalanine methyl ester as the amine.

Example 390

3-Biphenyl-4-yl-(2S)-{[7-(4-tert-butylphenoxy)-isoquinoline-3-carbonyl]-(2,2-dimethylpropyl)-amino}-propionic acid The title compound was prepared (19.5 mg) by saponification of the example 387 (20 mg, 0.033 mmol) according to the general procedure C.

$^1$H NMR: (400 MHz, CDCl$_3$) δ 8.23 [s, 1H], 7.95 [d, 1H], 7.51 [d, 1H], 7.46 [app d, 2H], 7.05 [app d, 2H], 4.04 [br s, 2H], 3.63 [m, 2H], 3.15 [d, 2H], 2.13 [septet, 1H], 1.64 [m, 2H], 1.60-1.51 [m, 2H], 1.50-1.44 [m, 2H], 1.37 [s, 9H], 1.31-1.18 [m, 4H], 0.99 [s, 9H]. LCMS: 587 (M+1)$^+$

Example 391

7-(4-tert-Butyl-phenoxy)-isoquinoline-3-carboxylic acid [2-[4-(2-cyclopentyl-ethoxy)-phenyl]-(1S)-(3-methyl-[1,2,4]oxadiazol-5-yl)-ethyl]-amide The title compound was synthesized according to general procedure A, using 44 mg (0.13 mmol) of 2-[4-(2-yclopentyl-ethoxy)-phenyl]-(1S)-(3-methyl-[1,2,4]oxadiazol-5-yl)-ethylamine (synthesized as described for 2-(4-cyclopentyl-methoxy-phenyl)-1-(3-methyl-[1,2,4]oxadiazol-5-yl)-ethylamine in example 303), 7-(4-tert-Butylphenoxy)-isoquinoline-3-carboxylic acid (example 371) (1.0 eq., 44 mg, 0.13 mmol), HBTU (1.2 eq., 0.15 mmol, 57 mg), DIEA, (4.0 eq., 0.50 mmol, 0.088 mL) in dry DMF (1.3 mL). Silica chromatography (20-30% EtOAc in hexanes) afforded 63 mg of the title compound.

$^1$H NMR: (400 MHz, CDCl$_3$) δ 8.98 [s,1H], 8.73 [d, 1H], 8.54 [s, 1H], 7.95 [d, 1H], 7.55 [dd, 1H], 7.45 [m, 2H], 7.34 [d, 1H], 7.08-7.02 [m, 4H], 6.77 [m, 2H], 5.80 [dt, 1H], 3.90 [t, 2H], 3.35 [d, 2H], 2.39 [s, 3H], 1.93 [septet, 1H], 1.85-1.75 [m, 1H], 1.76 [q, 2H], 1.64-1.57 [m, 2H], 1.56 [m, 1H], 1.55-1.50 [m, 2H], 1.37 [s, 9H], 1.13 [m, 2H]. LCMS 620 (M+1).

By analogous methods to those described above the following Examples were synthesized:

| Example | Name | LC/MS |
|---|---|---|
| 392 | (2S)-[[7-(4-tert-Butyl-phenoxy)-isoquinoline-3-carbonyl]-(4-fluoro-phenyl)-amino]-3-[4-(4-fluoro-phenoxy)-phenyl]-propionic acid methyl ester | 687 |
| 393 | (2S)-[[7-(4-tert-Butyl-phenoxy)-isoquinoline-3-carbonyl]-(4-trifluoromethyl-phenyl)-amino]-3-[4-(4-trifluoromethyl-phenoxy)-phenyl]-propionic acid methyl ester | 787 |
| 394 | (2S)-[[7-(4-tert-Butyl-phenoxy)-isoquinoline-3-carbonyl]-(4-trifluoromethoxy-phenyl)-amino]-3-[4-(4-trifluoromethoxy-phenoxy)-phenyl]-propionic acidmethyl ester | 819 |
| 395 | (2S)-[[7-(4-tert-Butyl-phenoxy)-isoquinoline-3-carbonyl]-(4-chloro-phenyl)-amino]-3-[4-(4-chloro-phenoxy)-phenyl]-propionic acid methyl ester | 719 |
| 396 | 3-Biphenyl-4-yl-(2S)-{[7-(4-tert-butyl-phenoxy)-isoquinoline-3-carbonyl]-cyclopentylmethyl-amino}-propionic acid methyl ester | 641 |
| 397 | (2S)-{Benzyl-[7-(4-tert-butyl-phenoxy)-isoquinoline-3-carbonyl]-amino}-3-biphenyl-4-yl-propionic acidmethyl ester | 649 |
| 398 | 3-Biphenyl-4-yl-(2S)-{[7-(4-trifluoromethyl-benzyloxy)-isoquinoline-3-carbonyl]-amino}-propionic acid methyl ester | 585 |
| 399 | 3-Biphenyl-4-yl-(2S)-{[7-(4-trifluoromethyl-benzyloxy)-isoquinoline-3-carbonyl]-amino}-propionic acid | 571 |
| 400 | (2S)-{[7-(4-tert-Butyl-phenoxy)-isoquinoline-3-carbonyl]-amino}-3-[4-(4-fluoro-phenoxy)-phenyl]-propionic acid | 579 |
| 401 | (2S)-{[7-(4-tert-Butyl-phenoxy)-isoquinoline-3-carbonyl]-amino}-3-[4-(4-trifluoromethyl-phenoxy)-phenyl]-propionic acid | 629 |
| 402 | (2S)-{[7-(4-tert-Butyl-phenoxy)-isoquinoline-3-carbonyl]-amino}-3-[4-(4-trifluoromethoxy-phenoxy)-phenyl]-propionic acid | 645 |
| 403 | (2S)-{[7-(4-tert-Butyl-phenoxy)-isoquinoline-3-carbonyl]-amino}-3-[4-(4-chloro-phenoxy)-phenyl]-propionic acid | 595 |
| 404 | (2S)-{[7-(4-tert-Butyl-phenoxy)-isoquinoline-3-carbonyl]-amino}-3-[4-(3,3-dimethyl-butoxy)-phenyl]-propionic acid methyl ester | 583 |
| 405 | (2S)-{[7-(4-tert-Butyl-phenoxy)-isoquinoline-3-carbonyl]-amino}-3-[4-(3,3-dimethyl-butoxy)-phenyl]-propionic acid | 569 |
| 406 | (2S)-{[7-(4-tert-Butyl-phenoxy)-isoquinoline-3-carbonyl]-amino}-3-(4-phenethyloxy-phenyl)-propionic acid methyl ester | 603 |
| 407 | (2S)-{[7-(4-tert-Butyl-phenoxy)-isoquinoline-3-carbonyl]-amino}-3-(4'-fluoro-biphenyl-4-yl)-propionic acid | 563 |
| 408 | 7-(4-tert-Butyl-phenoxy)-isoquinoline-3-carboxylic acid [2-(3'-chloro-4'-fluoro-biphenyl-4-yl)-(1S)-(3-methyl-[1,2,4]oxadiazol-5-yl)-ethyl]-(2,2-dimethyl-propyl)-amide | 705 |
| 409 | 3-Biphenyl-4-yl-(2S)-[(7-cyclopentyloxy-isoquinoline-3-carbonyl)-amino]-propionic acid | 481 |
| 410 | 3-Biphenyl-4-yl-(2R)-{[7-(4-tert-butyl-phenoxy)-isoquinoline-3-carbonyl]-amino}-propionic acid methyl ester | 559 |
| 411 | 3-Biphenyl-4-yl-(2R)-{[7-(4-tert-butyl-phenoxy)-isoquinoline-3-carbonyl]-amino}-propionic acid | 545 |
| 412 | (2S)-{[7-(4-tert-Butyl-phenoxy)-isoquinoline-3-carbonyl]-amino}-3-phenylpropionic acid | 469 |

Example 413

3-Biphenyl-4-yl-2S-[(3-ethylsulfanyl-6-hydroxy-quinoxaline-2-carbonyl)-amino]-propionic acid methyl ester 2-Amino-4-methoxy aniline (5.0 g, 36.2 mmol) was dissolved in 50 mL of ethanol and triethylamine (5.08 mL, 69.1 mmol) added. The mixture was cooled to 0° C. and diethylbromomalonate (8.02 mL, 47.0 mmol) in 8 mL of ethanol was added dropwise over 30 minutes. Mixture is stirred at 0° C. for 30 minutes and 16 h at room temperature. The resulting solid was isolated and stirred in 200 mL water and 50 mL 1N HCl for 1 h. The solid was filtered, suspended in toluene and evaporated to dryness to give the 6-methoxy-3-oxo-3,4-dihydro-quinoxaline-2-carboxylic acid ethyl ester as a solid (5.2 g).

LCMS 249 (M+1)$^+$.

6-Methoxy-3-oxo-3,4-dihydro-quinoxaline-2-carboxylic acid ethyl ester (5.2 g, 20.9 mmol) was suspended in 75 mL of POCl$_3$ and resulting mixture heated to 100° C. for 1 h. The reaction mixture was poured onto 500 mL of ice-water and the pH of the solution adjusted to 3 with conc. NH$_4$OH. Mixture was extracted twice with 300 mL of EtOAc. The combined organic layers were dried over Na$_2$SO$_4$ and evaporated to give the 3-chloro-6-methoxy-quinoxaline-2-carboxylic acid ethyl ester (4.6 g).

LCMS 267 (M+1)$^+$.

To a solution of 3-chloro-6-methoxy-quinoxaline-2-carboxylic acid ethyl ester (2.0 g, 7.5 mmol) in 80 mL of DMF was added sodium ethanethiolate (5.0 g, 60 mmol) and the resulting mixture was heated at 115° C. for 3 h. The mixture was poured onto 100 mL EtOAc and 300 mL 1N HCl. The organic layer was washed twice with 1N, dried over Na$_2$SO$_4$ and evaporated to give the sulfide(1.6 g).

LCMS 251 (M+1)$^+$.

3-Ethylsulfanyl-6-hydroxy-quinoxaline-2-carboxylic acid (1.0 g, 4.0 mmol) was coupled with (2S)-amino-3-biphenyl-4-yl-propionic acid methyl ester hydrochloride (1.16 g, 4.0 mmol) as described in general procedure A. Column chromatography over silica using 8:2 and 7:3 hexanes-ethyl acetate as eluants gave the title compound (1.2 g).

LCMS 488 (M+1)$^+$.

Example 414

3-Biphenyl-4-yl-(2S)-{[6-(4-tert-butyl-phenoxy)-3-ethylsulfanyl-quinoxaline-2-carbonyl]-amino}-propionic acid methyl ester 600 mg (1.22 mmol) of Example 413 was reacted with 4-t-butylphenylboronic acid (329 mg, 1.9 mmol), Cu(OAc)$_2$ (223 mg, 1.2 mmol), and triethylamine (0.86 mL, 6.2 mmol) as described in general procedure G. Column chromatography over silica using 8:2 and 6:4 DCM-hexanes as eluants gave the title compound (62 mg). LCMS 620 (M+1)$^+$.

Example 415

3-Biphenyl-4-yl-(2S)-{[6-(4-tert-butyl-phenoxy)-3-ethylsulfanyl-quinoxaline-2-carbonyl]-amino}-propionic acid 3-Biphenyl-4-yl-(2S)-{[6-(4-tert-butyl-phenoxy)-3-ethylsulfanyl-quinoxaline-2-carbonyl]-amino}-propionic acid methyl ester (30 mg, 0.048 mmol) was hydrolyzed as described in general procedure C. Column chromatography over silica using DCM and 95:5 DCM-methanol as eluants gave the title compound (22 mg).
LCMS 606 (M+1)$^+$.

Example 416

3-Biphenyl-4-yl-(2S)-{[6-(4-tert-butyl-phenoxy)-quinoxaline-2-carbonyl]-amino}-propionic acid methyl ester To a stirring solution of 50 mg (0.089 mmol) of Example 372 in MeOH, 0.2 ml of Raney nickel in water (suspension) was added at rt and stirring continued for another 30 min. Then the reaction mixture was filtered and evaporated solvent to afford 30 mg of the title compound as a white solid.
LCMS 560 (M+1)

Example 417

3-Biphenyl-4-yl-(2S)-{[6-(4-tert-butyl-phenoxy)-4-ethylsulfanyl-quinazoline-2-carbonyl]-amino}-propionic acid methyl ester To a suspension of 2-amino-5-methoxy-benzoic acid (8.0 g, 47.8 mmol) in toluene (100 mL) was added a solution of phosgene (20%, 50.0 mL) in toluene and triethyl amine (13.40 mL). The reaction mixture was heated at 80 C. for 1.5 h. The precipitated product was filtered and washed with hexanes and toluene and dried to give 9.00 g of 6-methoxy-1H-benzo[d][1.3]oxazine-2,4-dione as a light brown solid. This was used directly for the next step.

To a solution of 6-methoxy-1H-benzo[d][1.3]oxazine-2,4-dione (7.0 g, 36.2 mmol) in THF (50 mL) was added NH$_4$OH (20 mL) and the reaction was stirred at rt for 1 h. The solution was concentrated under reduced pressure and dried to give 5.0 g of 2-amino-5-methoxy-benzamide as a dark brown solid.
LCMS: 169 (M+1)$^+$ To a solution of 2-amino-5-methoxy-benzamide (4.42 g, 26.597 mmol) in pyridine (20 mL) was added ethyloxalyl chloride (4.02 g, 29.46 mmol) and the reation was stirred at RT for 4 h. The reaction was concentrated under reduced pressure to remove pyridine. The residue was dissolved in acetic acid (70 mL) and acetic anhydride (12 mL) and the solution was refluxed overnight. The reaction mixture was concentrated and dissolved in EtOAc and washed with water, dried (Na$_2$SO$_4$), and concentrated under reduced pressure to give 1.74 g of 6-methoxy-4-oxo-3,4-dihydro-quinazoline-2-carboxylic acid ethyl ester.
LCMS: 249 (M+1)$^+$ To 6-methoxy-4-oxo-3,4-dihydro-quinazoline-2-carboxylic acid ethyl ester (1.38 g, 5.438 mmol) was added POCl$_3$ (25 mL) and the solution was heated at 100° C. for 1.5 h. The solution was concentrated under reduced pressure and the residue was dissolved in EtOAc and washed with water, brine, dried (Na$_2$SO$_4$) and concentrated under reduced pressure to give 1.22 g of 4-chloro-6-methoxy-quinazoline-2-carboxylic acid ethyl ester.
LCMS: 268 (M+1)$^+$ To a solution of 4-chloro-6-methoxy-quinazoline-2-carboxylic acid ethyl ester (1.22 g, 4.574 mmol) in anhydrous DMF (4.0 mL) was added sodium ethanethiolate (3.07 g, 36.59 mmol) and the reaction mixture was heated at 140° C. for 3 h. Water and EtOAc was added. The pH of the aq. layer was adjusted to 6 with citric acid. The organic layer was separated and the aq. layer was extracted with EtOAc. The combined organic layer was washed with water, brine, dried (Na$_2$SO$_4$) and concentrated under reduced pressure to give 0.770 g of 4-ethylsulfanyl-6-hydroxy-quinazoline-2-carboxylic acid.
LCMS: 252 (M+1)$^+$ A solution of 4-ethylsulfanyl-6-hydroxy-quinazoline-2-carboxylic acid (0.770 g, 3.07 mmol) in anhydrous DMF (6.0 mL) was treated with (2S)-amino-3-biphenyl-4-yl-propionic acid methyl ester hydrochloride (0.900 g, 3.07 mmol), HBTU (1.16 g, 3.07 mmol), and DIEA (1.20 mL, 10.7 mmol) by the general procedure A. The crude product was purified by flash column chromatography on silica gel using EtOAc containing 0.25% methanol to give 0.725 g of 3-biphenyl-4-yl-2-[(4-ethylsulfanyl-6-hydroxy-quinazoline-2(S)-carbonyl)-amino]-propionic acid methyl ester.
LCMS: 489 (M+1)$^+$ A solution of 3-biphenyl-4-yl-2-[(4-ethylsulfanyl-6-hydroxy-quinazoline-2(S)-carbonyl)-amino]-propionic acid methyl ester (0.350 g, 0.717 mmol) in anhydrous DCM (12.0 mL) was treated with 4-tert-butylphenylboronic acid (0.320 g, 1.794 mmol), copper acetate (0.195 g, 1.076 mmol), and TEA (0.500 mL, 3.589 mmol) by the general procedure G. The crude product was purified by flash column chromatography on silica gel using hexanes/EtOAc 3:2 to give 34 mg of 3-biphenyl-4-yl-(2S)-{[6-(4-tert-butyl-phenoxy)-4-ethylsulfanyl-quinazoline-2-carbonyl]-amino}-propionic acid methyl ester.
LCMS: 620 (M+1)$^+$

Example 418

3-Biphenyl-4-yl-(2S)-{[6-(4-tert-butyl-phenoxy)-4-ethylsulfanyl-quinazoline-2-carbonyl]-amino}-propionic acid A solution of 3-biphenyl-4-yl-2-{[6-(4-tert-butyl-phenoxy)-4-ethylsulfanyl-quinazoline-(2S)-carbonyl]-amino}-propionic acid methyl ester (29 mg, 0.047 mmol) in THF:MeOH (4:1,1.0 mL) was treated with LiOH solution (8 mg, 0.188 mmol) in water by the general procedure I to give 23 mg of 3-biphenyl-4-yl-(2S)-{[6-(4-tert-butyl-phenoxy)-4-ethylsulfanyl-quinazoline-2-carbonyl]-amino}-propionic acid as a white solid.

¹H NMR: (400 MHz, CDCl₃): δ 8.65 [d, 1H], 8.13 [d, 1H}, 7.58-7.25 [m, 12 H], 7.02 [d, 2 H], 5.23 [m, 2 H], 4.09 [s, 1H], 3.42 [bs, 2 H], 3.16 [m, 2 H], 3.03 [bs, 1H], 1.34 [s, 9 H], 1.22 [t, 3 H]. LCMS: 606 (M+1)⁺

Example 419

7-(4-tert-Butyl-phenoxy)-1-cyclopentylmethyl-isoquinoline-3-carboxylic acid

To a stirring of solution of H-Tyr(O-tBu)-OMe HCl (15 g, 52.1 mmol), NEt₃ (13.1 g, 129.7 mmol) in 400 ml of DCM at 0° C. was added cyclopentyl acetyl chloride (8.4 g, 57.3 mmol). Reaction mixture was warmed to rt and stirring was continued for 45 min. Then the organic layer was washed with water, 1.0 N HCl and brine then dried over Na₂SO₄. Evaporation of the solvent gave 19 g of amide, which was used for further step without purification.

LCMS: 438 (M+1)⁺

To a stirring solution of above amide (19 g, 52.1 mmol) in 400 ml of anhydrous DCM at 0° C. was added oxalyl chloride (7.9 g, 63.1 mmol). The reaction mixture was brought to rt and stirring continued for another one hour. Then the reaction mixture was cooled to −10° C. and to it anhydrous FeCl₃ (10.1 g, 62.3 mmol) was added portionwise. The stirring was continued for 12 h at r.t and the reaction mixture was treated with 200 ml of 2.0M HCl for 2 h. The Organic layer was separated washed with water and brine, dried over Na₂SO₄ and concentrated in vacuo. Methanol (400 ml) and conc. H₂SO₄ (10 ml) was added to the foamy residue and reaction was heated to reflux for 12 h, methanol was evaporated and the crude product was extracted with ethyl acetate (2×100 ml). The aqueous layer was basified with NH₄OH (pH>9) and extracted with DCM (2×100 ml). The organic layer was washed with water and brine and dried over Na₂SO₄ evaporation of the solvent gave 7.0 g of 1-cyclopentylmethyl-7-hydroxy-3, 4-dihydro-isoquinoline-3-carboxylic acid methyl ester.

LCMS: 288 (M+1)⁺

The above compound (7 g, 24.3 mmol) was dissolved in 200 ml of DCM, then 8.8 g (48.6 mmol) of copper acetate and 12.3 g (121 mmol) of NEt₃ was added. The resulting mixture was stirred at rt for 2.0 h, filtered, and the filtrate was concentrated followed by column chromatography using 1:1 ethyl acetate and hexane to give 6.6 g of 1-cyclopentylmethyl-7-hydroxy-isoquinoline-3-carboxylic acid methyl ester.

LCMS: 286 (M+1)⁺

3.0 g (10.5 mmol) of above phenol, 2.7 g (15.7 mmol) of 4-tert-butyl phenylboronic acid, 1.9 g (10.5 mmol) of copper acetate and 1 g of crushed 4 A molecular sieves were taken up in 115 ml of DCM. To this stirring solution 5.3 g (115 mmol) of NEt₃ was added and stirring was continued for 12 h. Filtration and evaporation of the solvent followed by column chromatography using 4:1 hexane and ethyl acetate as eluant gave 1.5 g of 7-(4-tert-butyl-phenoxy)-1-cyclopentylmethyl-isoquinoline-3-carboxylic acid methyl ester. 1.0 g of starting phenol was isolated by eluting with 1:1 ethyl acetate and hexane.

LCMS: 418 (M+1)⁺

To a stirring solution of 1.5 g (3.6 mmol) of ester in 9.0 ml of THF and 2.16 ml of MeOH was added 2.16 ml of 2N LiOH (4:1:1) at rt. Stirring was continued for 30 min and the mixture was acidified with 1.0N HCl (pH=3) and extracted with 2×25 ml of ethyl acetate. The organic layer was dried over anhydrous sodium sulfate and oncentrated to give 1.37 g of title compound as a light yellow solid.

¹H-NMR (400 MHZ, CDCl₃): δ 8.47 (s,1H), 7.98 (d,1H), 7.59 (s,1H), 7.53 (dd, 1H), 7.46 (d, 2H), 7.05 (d, 2H), 3.15 (d, 2H), 2.35 (m, 1H), 1.67 (m, 4H), 1.53 (m, 2H), 1.36 (s, 9H), 1.30 (m, 2H). LCMS: 404 (M+1)⁺

Example 420

3-Biphenyl-4-yl-(2S)-{[7-(4-tert-butyl-phenoxy)-1-cyclopentylmethyl-isoquinoline-3-carbonyl]-amino}-propionic acid 50 mg (0.12 mmol) of 7-(4-tert-butyl-phenoxy)-1-cyclopentylmethyl-isoquinoline-3-carboxylic acid was reacted with (2S)-amino-3-biphenyl-4-yl-propionic acid methyl ester (34.8 mg, 0.13 mmol) as described in general procedure A. The resulting ester was hydrolyzed as described in general procedure C to afford 70 mg of the title compound as a white solid.

LCMS: 627 (M+1)⁺

Example 421

(2S)-{[7-(4-tert-Butyl-phenoxy)-1-cyclopentylmethyl-isoquinoline-3-carbonyl]-amino}-3-phenyl-propionic acid 50 mg (0.12 mmol) of 7-(4-tert-butyl-phenoxy)-1-cyclopentylmethyl-isoquinoline-3-carboxylic acid (Example 419) was reacted with (2S)-amino-3-phenyl propionic acid methyl ester (24.4 mg, 0.13 mmol) as described in general procedure A. The resulting ester was hydrolyzed as described in general procedure C to afford 59.2 mg of the title compound as a white solid.

LCMS: 551 (M+1)⁺

Example 422

(2S)-{[7-(4-tert-Butyl-phenoxy)-1-cyclopentylmethyl-isoquinoline-3-carbonyl]-amino}-phenyl-acetic acid 50 mg (0.12 mmol) of 7-(4-tert-butyl-phenoxy)-1-cyclopentylmethyl-isoquinoline-3-carboxylic acid (Example 419) was reacted with L-phenylglycine methyl ester hydrochloride (23.1 mg, 0.13 mmol) as described in general procedure A. The resulting ester was hydrolyzed as described in general procedure C to afford 59.1 mg of the title compound as a white solid.

LCMS: 537 (M+1)⁺

Example 423

(2R)-{[7-(4-tert-Butyl-phenoxy)-1-cyclopentylmethyl-isoquinoline-3-carbonyl]-amino}-3-thiophen-3-yl-propionic acid 50 mg (0.12 mmol) of 7-(4-tert-butyl-phenoxy)-1-cyclopentylmethyl-isoquinoline-3-carboxylic acid (Example 419) was reacted with (2R)-amino-3-thiophen-3-yl-propionic acid methyl ester HCl (28.1 mg, 0.14 mmol) as described in general procedure A. The resulting ester was hydrolyzed as described in general procedure C to afford 63.4 mg of the title compound as a white solid.

¹H-NMR (400 MHZ, CDCl₃): δ 8.8 (d, 1H), 8.38 (s, 1H), 7.90 (d, 1H), 7.50 (s, 1H), 7.43 (m, 3H), 7.26 (m, 1H), 7.17 (m, 1H), 7.01 (m, 3H), 5.06 (m, 1H), 3.39 (m, 2H), 3.10 (m, 1H), 3.03 (m,1H), 2.45 (m,1H), 1.65 (m, 4H), 1.51 (m, 2H), 1.35 (s, 9H), 1.29 (m, 2H). LCMS: 557 (M+1)⁺

Example 424

(2S)-{[7-(4-tert-Butyl-phenoxy)-1-cyclopentylmethyl-isoquinoline-3-carbonyl]-amino}-4,4-dimethyl-pentanoic acid 50 mg (0.12 mmol) of 7-(4-tert-butyl-phenoxy)-1-cyclopentylmethyl-isoquinoline-3-carboxylic acid (Example 419) was reacted with (2S)-amino-4, 4-dimethyl-pentanoic acid methyl ester HCL (26.4 mg, 0.14 mmol) as described in general procedure A. The resulting ester was hydrolyzed as described in general procedure C to afford 56.5 mg of the title compound as a white solid.
LCMS: 531 (M+1)$^+$

Example 425

(2S)-{[7-(4-tert-Butyl-phenoxy)-1-cyclopentylmethyl-isoquinoline-3-carbonyl]-amino}-3,3-dimethyl-butyric acid 50 mg (0.12 mmol) of 7-(4-tert-butyl-phenoxy)-1-cyclopentylmethyl-isoquinoline-3-carboxylic acid (Example 419) was reacted with (2S)-amino-3,3-dimethyl-butyric acid methyl ester HCl (24.5 mg, 0.14 mmol) as described in general procedure A. The resulting ester was hydrolyzed by sonication at rt for 3 h and then usual work up as described in general procedure C afforded 54.3 mg of the title compound as a white solid.
$^1$H-NMR (400 MHZ, CDCl$_3$): δ 9.0 (d, 1H), 8.39 (s, 1H), 7.93 (d, 1H), 7.60 (s, 1H), 7.43 (m, 3H), 7.02 (m, 2H), 4.68 (d, 1H), 3.15 (m, 2H), 2.45 (m, 1H), 1.79 (m, 2H), 1.64 (m, 2H), 1.54 (m, 2H), 1.35 (s, 9H), 1.29 (m, 2H), 1.15 (s, 9H). LCMS: 517 (M+1)$^+$

Example 426

(2S)-{[7-(4-tert-Butyl-phenoxy)-1-cyclopentylmethyl-isoquinoline-3-carbonyl]-amino}-3-(4-tert-butyl-phenyl)-propionic acid 50 mg (0.12 mmol) of 7-(4-tert-butyl-phenoxy)-1-cyclopentylmethyl-isoquinoline-3-carboxylic acid (Example 419) was reacted with (2S)-amino-3-(4-tert-butyl-phenyl)-propionic acid methyl ester HCl (36.8 mg, 0.14 mmol) as described in general procedure A. The resulting ester was hydrolyzed as described in general procedure C to afford 71.4 mg of the title compound as a white solid.
$^1$H-NMR (400 MHZ, CDCl$_3$): δ 8.76 (d, 1H), 8.35 (s, 1H), 7.88 (d, 1H), 7.53 (d, 1H), 7.43 (m, 3H), 7.27 (m, 2H), 7.22 (d, 2H), 7.02 (d, 2H), 4.99 (m,1H), 3.33 (m, 2H), 3.13 (m, 1H), 3.01 (m, 1H), 2.30 (m, 1H), 1.64 (m, 4H), 1.49 (m, 2H), 1.35 (s, 9H), 1.25 (s, 9H), 1.23 (m, 2H). LCMS: 607 (M+1)$^+$

Example 427

(2S)-{[7-(4-tert-Butyl-phenoxy)-1-cyclopentylmethyl-isoquinoline-3-carbonyl]-amino}-3-(4-trifluoromethyl-phenyl)-propionic acid 50 mg (0.12 mmol) of 7-(4-tert-butyl-phenoxy)-1-cyclopentylmethyl-isoquinoline-3-carboxylic acid (Example 419) was reacted with (2S)-amino-3-(4-trifluoromethyl-phenyl)-propionic acid methyl ester HCl (38.4 mg, 0.14 mmol) as described in general procedure A. The resulting ester was hydrolyzed as described in general procedure C to afford 70.4 mg of the title compound as a white solid.
$^1$H-NMR (400 MHZ, CDCl$_3$): δ 8.76 (d, 1H), 8.35 (s, 1H), 7.88 (d, 1H), 7.53 (m, 8H), 7.02 (d, 2H), 4.99 (m, 1H), 3.33 (m, 2H), 3.13 (m, 1H), 3.01 (m, 1H), 2.30 (m, 1H), 1.64 (m, 4H), 1.49 (m, 2H), 1.35 (s, 9H),1.23 (m, 2H). LCMS: 619 (M+1)$^+$

Example 428

(2S)-{[7-(4-tert-Butyl-phenoxy)-1-cyclopentylmethyl-isoquinoline-3-carbonyl]-amino}-3-(4-isopropyl-phenyl)-propionic acid 50 mg (0.12 mmol) of 7-(4-tert-butyl-phenoxy)-1-cyclopentylmethyl-isoquinoline-3-carboxylic acid (Example 419) was reacted with (2S)-amino-3-(4-trifluoromethyl-phenyl)-propionic acid methyl ester HCl (34.9 mg, 0.14 mmol) as described in general procedure A. The resulting ester was hydrolyzed as described in general procedure C to afford 66.2 mg of the title compound as a white solid.
$^1$H-NMR (400 MHZ, CDCl$_3$): δ 8.78 (d, 1H), 8.38 (s, 1H), 7.92 (d, 1H), 7.56 (s, 1H), 7.43 (m, 3H), 7.22 (d, 2H), 7.13 (d, 2H), 7.03 (d, 2H), 5.06 (m, 1H), 3.34 (m, 2H), 3.16 (m, 1H), 3.04 (m, 1H), 2.86 (m, 1H), 2.34 (m, 1H), 1.65 (m, 4H), 1.50 (m, 2H), 1.35 (s, 9H), 1.25 (m, 2H). LCMS: 593 (M+1)$^+$

Example 429

3-(5-Bromo-thiophen-2-yl)-(2S)-{[7-(4-tert-butyl-phenoxy)-1-cyclopentylmethyl-isoquinoline-3-carbonyl]-amino}-propionic acid 50 mg (0.12 mmol) of 7-(4-tert-butyl-phenoxy)-1-cyclopentylmethyl-isoquinoline-3-carboxylic acid (Example 419) was reacted with (2S)-amino-3-(5-bromo-thiophen-2-yl)-propionic acid methyl ester HCl (40.1 mg, 0.14 mmol) as described in general procedure A. The resulting ester was hydrolyzed as described in general procedure C to afford 66.9 mg of the title compound as a white solid.
$^1$H-NMR (400 MHZ, CDCl$_3$): δ 8.96 (d,1H), 8.40 (s,1H), 7.94 (d,1H), 7.59 (d, 1H), 7.43 (m, 3H), 7.03 (m, 2H), 6.87 (d, 1H), 6.70 (d, 1H), 5.1 (m, 1H), 3.5 (m, 2H), 3.16 (m, 1H), 3.08 (m, 1H), 2.45 (m, 1H), 1.68 (m, 4H), 1.52 (m, 2H), 1.35 (s, 9H), 1.25 (m, 2H). LCMS: 636 (M+1)$^+$

Example 430

7-(trans-4-tert-Butyl-cyclohexyloxy)-1-cyclopentylmethyl-isoquinoline-3-carboxylic acid 0.7 g (2.5 mmol) of 1-cyclopentylmethyl-7-hydroxy-isoquinoline-3-carboxylic acid methyl ester (Example 419, Step 3), 3.0 g (5.0 mmol) of triphenyl phosphine resin and 0.42 g (2.7 mmol) of alcohol were taken in 25 ml of DCM. To this solution 0.6 g (3.0 mmol) of DIAD was added at rt. The reaction mixture was shaken for 2 h. Filtration and evaporation of the solvent followed by column chromatography using using 4:1 hexane/ethyl acetate gave 0.75 g (70%) of product which was hydrolyzed as described in general procedure C to afford 669 mg of the title compound as a light yellow solid.
LCMS: 410 (M+1)$^+$

Example 431

(2R)-{[7-(trans-4-tert-Butyl-cyclohexyloxy)-1-cyclopentylmethyl-isoquinoline-3-carbonyl]-amino}-3,3-dimethyl-butyric acid 50 mg (0.12) of 7-(4-tert-Butyl-cyclohexyloxy)-1-cyclopentylmethyl-isoquinoline-3-carboxylic acid (Example 430) was reacted with (2S)-amino-3,3-dimethyl-butyric acid methyl ester HCL (24.7 mg, 0.14 mmol) as described in general procedure A. The resulting ester was hydrolyzed by sonication at rt for 3 h and then usual work up as described in general procedure C afforded 54.3 mg of the title compound as a white solid.
LCMS: 523 (M+1)$^+$

Example 432

[[7-(4-tert-Butyl-phenoxy)-1-cyclopentylmethyl-isoquinoline-3-carbonyl]-(3,3-dimethyl-butyl)-amino]-acetic acid A solution of glycine methyl ester hydrochloride (3.0 mmol, 377 mg) in 10 mL of dry DCM was combined with 3,3-dimethylbutyraldehyde (1.1 eq., 3.3 mmol, 0.414 mL) and to this was added sodium triacetoxyborohydride (1.5 eq., 4.5 mmol, 954 mg) according to general procedure E. A portion of the resulting crude amine (17.3 mg, 0.1 mmol) was dissolved in 1 mL of dry DCM and to this was added 46 mg (0.1 mmol) of 7-(4-tert-butyl-phenoxy)-1-cyclopentylmethyl-isoquinoline-3-carbonyl chloride (prepared from example 418 by reacting with oxalyl chloride) and triethylamine (3.0 eq., 0.3 mmol, 0.042 mL) according to general procedure J, and purified by silica gel chromatography to afford 40 mg of the ester [LCMS 560 (M+1)$^+$]. The above material (40 mg, 0.072 mmol) was saponified according to general procedure C to furnish the title compound (39 mg).
$^1$H NMR: (400 MHz, CDCl$_3$) δ 8.23 [s, 1H], 7.95 [d, 1H], 7.51 [d, 1H], 7.46 [app d, 2H], 7.05 [app d, 2H], 4.04 [br s, 2H], 3.63 [m, 2H], 3.15 [d, 2H], 2.13 [septet, 1H], 1.64 [m, 2H], 1.60-1.51 [m, 2H], 1.50-1.44 [m, 2H], 1.37 [s, 9H], 1.31-1.18 [m, 4H], 0.99 [s, 9H]. LCMS 546 (M+1)$^+$.

Example 433

2-{[7-(4-tert-Butyl-phenoxy)-1-cyclopentylmethyl-isoquinoline-3-carbonyl]-amino}-benzoic acid The title compound (30 mg) was prepared following the same procedures that was described for example 432 from methyl-2-aminobenzoate (0.1 mmol, 15.1 mg) and 7-(4-tert-butyl-phenoxy)-1-cyclopentylmethyl-isoquinoline-3-carbonyl chloride (46 mg, 0.1 mmol).
LCMS: 523 (M+1)$^+$

Example 434

{Benzyl-[7-(4-tert-butyl-phenoxy)-1-cyclopentylmethyl-isoquinoline-3-carbonyl]-amino}-acetic acid The title compound (39 mg) was prepared following the same procedures that was described for example 432 from benzyl glycine methyl ester (17.9 mg, 0.1 mmol) and 7-(4-tert-butyl-phenoxy)-1-cyclopentylmethyl-isoquinoline-3-carbonyl chloride (46 mg, 0.1 mmol).
$^1$H NMR: (400 MHz, CDCl$_3$) δ 8.31 [s,1H], 7.96 [d, 1H], 7.60 [dd, 1H], 7.51 [d, 1H], 7.49-7.45 [m, 4H], 7.40-7.35 [m, 2H], 7.34-7.29 [m, 1H], 7.06 [d, 2H], 4.81 [br, 2H], 3.98 [br s, 2H], 3.16 [d, 2H], 2.12 [septet, 1H], 1.69-1.60 [m, 2H], 1.59-1.51 [m, 2H], 1.50-1.41 [m, 2H], 1.36 [s, 9H], 1.28-1.18 [m, 2H]. LCMS: 551 (M+1)$^+$

Example 435

5-(4-tert-Butyl-phenoxy)-1-cyclopentylmethyl-isoquinoline-3-carboxylic acid

The title compound was prepared (350 mg) by following the same procedure as described for Example 419 starting with 2-amino-3-(2-hydroxy-phenyl)-propionic acid methyl ester hydrochloride (2.00 g, 8.632 mmol) and cyclopentylacetic acid (1.217 g, 9.496 mmol) in 6 steps.
LCMS: 404 (M+1)$^+$

Example 436

(2S)-{[5-(4-tert-Butyl-phenoxy)-1-cyclopentylmethyl-isoquinoline-3-carbonyl]-amino}-3,3-dimethyl-butyric acid A solution of 5-(4-tert-butyl-phenoxy)-1-cyclopentylmethyl-isoquinoline-3-carboxylic acid (27 mg, 0.0663 mmol) in DMF (1.0 mL) was treated with (2S)-mino-3,3-dimethyl-butyric acid methyl ester HCl (18 mg, 0.100 mmol), HBTU (38 mg, 0.100 mmol), and DIEA (0.050 mL, 0.267 mmol) by the general procedure A. The crude product was purified by flash column chromatography on silica gel using 4:1 hexanes/EtOAc to give 28 mg of (2S)-{[5-(4-tert-Butyl-phenoxy)-1-cyclopentylmethyl-isoquinoline-3-carbonyl]-amino}-3,3-dimethyl-butyric acid methyl ester as colorless oil.
LCMS: 531 (M+1)$^+$ A solution of (2S)-{[5-(4-tert-Butyl-phenoxy)-1-cyclopentylmethyl-isoquinoline-3-carbonyl]-amino}-3,3-dimethyl-butyric acid methyl ester (28 mg, 0.052 mmol) in THF-MeOH (2.0 mL) was treated with LiOH solution (2.0M, 0.400 mL) by the general procedure I to give 24 mg of (2S)-{[5-(4-tert-Butyl-phenoxy)-1-cyclopentylmethyl-isoquinoline-3-carbonyl]-amino}-3,3-dimethyl-butyric acid as a white solid.
$^1$H NMR: (400 MHz, CDCl$_3$) δ 9.93 [s, 1H], 8.69 [d, 1H], 7.89 [d, 1H], 7.53 [t, 1 H], 7.40 [m, 2 H], 7.01 [m, 2 H], 4.74 [m, 1H], 3.39-3.23 [m, 2 H], 2.49 [m, 2 H], 2.15 [dd, 1H], 1.84-1.54 [m, 6 H], 1.30 [m, 12 H], 1.03 [s, 9 H]. LCMS: 517 (M+1)$^+$

Example 437

(2S)-{[5-(4-tert-Butyl-phenoxy)-1-cyclopentylmethyl-isoquinoline-3-carbonyl]-amino}-4,4-dimethyl-pentanoic acid A solution of 5-(4-tert-butyl-phenoxy)-1-cyclopentylmethyl-isoquinoline-3-carboxylic acid (27 mg, 0.0663 mmol) in DMF (1.0 mL) was treated with (2S)-amino-4,4-dimethyl-pentanoic acid methyl ester HCL (18 mg, 0.100 mmol), HBTU (38 mg, 0.100 mmol), and DIEA (0.050 mL, 0.267 mmol) by the general procedure A. The crude product was purified by flash column chromatography on silica gel using 4:1 hexanes/EtOAc to give 28 mg of the ester which was hydrolyzed according to the general procedure I to give 24 mg of the title compound as a white solid.
LCMS: 517 (M+1)$^+$

Example 438

(2S)-{[7-(4-tert-Butyl-phenyl)-1-cyclopentylmethyl-isoquinoline-3-carbonyl]-amino}-3,3-dimethyl-butyric acid 1-Cyclopentylmethyl-7-hydroxy-isoquinoline-3-carboxylic acid methyl ester (1.2 g, 4.2 mmol) (Example 419, Step 3) was hydrolyzed as described in general procedure C to afford 1.08 g of the acid. The resulting acid (1.08 g, 3.52 mmol) was reacted with (2S)-amino-3,3-dimethyl-butyric acid methyl ester HCl (0.76 g, 4.22 mmol) as described in general procedure A. 0.9 g of ester was isolated after flash chromatography using 7:3 hexane and ethyl acetate.

LCMS: 399 (M+1)$^+$

To a stirring solution of above phenol (150 mg, 0.37 mmol), NEt$_3$ (70 mg, 0.7 mmol) and DMAP (cat) in DCM (5 ml) was added, followed by excess trifluoromethanesulfonic anhydride at 0° C. The stirring was continued for another 30 min then 10 ml of DCM was added. The reaction mixture was washed with saturated citric acid, water and brine then dried over anhydrous Na$_2$SO$_4$. Filtration followed by evaporation of the solvent under vacuum gave 168 mg of triflate, which was used for the next step without purification.

LCMS: 531 (M+1)$^+$

The above triflate (168 mg, 0.31 mmol), 4-tert-butyl phenyl boronic acid (112 mg, 0.62 mmol), Pd (PPh$_3$)$_4$ (18.2 mg, 0.015 mmol) and 0.75 ml of 2N Na$_2$CO$_3$ were taken in 10 ml of toluene and degassed with nitrogen for 15 min. The reaction mixture stirred overnight at 90° C. then usual work up and purification as described in procedure D gave ester which was hydrolyzed by sonication at rt for 3 h and then usual work up as described in general procedure C afforded 121 mg of the title compound as a white solid.

$^1$H-NMR (400 MHZ, CDCl$_3$): δ 9.07 (d, 1H), 8.44 (s, 1H), 8.34 (s, 1H), 8.02 (d, 1H), 7.96 (dd,1H), 7.65 (m, 2H), 7.56 (m, 2H), 4.70 (dd,1H), 3.38 (m, 2H), 2.60 (m,1H), 1.89 (m, 2H), 1.71 (m, 2H), 1.58 (m, 2H), 1.35 (s, 9H), 1.25 (m, 2H), 1.12 (s, 9H). LCMS: 501 (M+1)$^+$

Example 439

(2S)-{[7-(4-tert-Butyl-benzoyl)-1-cyclopentylmethyl-isoquinoline-3-carbonyl]-amino}-3,3-dimethyl-butyric acid 130 mg (0.25 mmol) of triflate (example 438, step 2), 65 mg (0.36 mmol) of 4-tert-butyl phenyl boronic acid, 20 mg (0.02 mmol) of PdCl$_2$(dppf), 100 mg (0.75 mmol) of powdered K$_2$CO$_3$, and 100 mg (0.75 mmol) of crushed NaI were added to a flask filted with a reflux condenser, a septum inlet and a magnetic stir bar. The flask was flushed with CO and then charged with anisole (6 ml). The mixture was stirred at 80° C. for 48 h under an atmospheric pressure of CO. The reaction mixture was cooled to rt and extracted with ethyl acetate, the organic layer was washed with water and brine, and dried over Na$_2$SO$_4$. Evaporation of the solvent followed by column chromatography using 9:1 hexane/ethyl acetate gave 40 mg of ester which was hydrolyzed by sonication at rt for 3 h. Usual work up as described in general procedure C afforded 35 mg of the title compound as a white solid.

$^1$H-NMR (400 MHZ, CDCl$_3$): δ 9.04 (d, 1H), 8.64 (s, 1H), 8.49 (s, 1H), 8.11 (dd, 1H), 8.04 (d,1H), 7.83 (m, 2H), 7.56 (m, 2H), 4.70 (dd,1H), 3.33 (m, 2H), 2.54 (m,1H), 1.84 (m, 2H), 1.68 (m, 2H), 1.57 (m, 2H), 1.39 (s, 9H), 1.25 (m, 2H), 1.16 (s, 9H). LCMS: 529 (M+1)$^+$

Example 440

(2S)-{[7-(4-tert-Butyl-cyclohexylcarbamoyl)-1-cyclopentylmethyl-isoquinoline-(3S)-carbonyl]-amino}3,3-dimethylbutyric acid To a solution of 1-cyclopentylmethyl-7-hydroxy-isoquinoline-3-carboxylic acid methyl ester (0.500 g, 1.647 mmol) in anhydrous DCM (10 mL) at 0 C. was added triflic anhydride (0.557 g, 1.976 mmol) and triethylamine (0.460 mL, 3.294 mmol). The reaction was stirred at 0° C. for 10 min and warmed to rt and stirred for 1 h. The reaction mixture was diluted with DCM and the organic layer was washed with satd. Na$_2$CO$_3$, brine, dried (Na$_2$SO$_4$), and concentrated under reduced pressure to give 0.510 g of 1-cyclopentylmethyl-7-trifluoromethanesulfonyloxy-isoquinoline-3-carboxylic acid methyl ester. This was used without further purification for the next step.

LCMS: 418 (M+1)$^+$

To a solution of 1-cyclopentylmethyl-7-trifluoromethanesulfonyloxy-isoquinoline-3-carboxylic acid methyl ester (0.150 g, 0.359 mmol) in DMSO (7.0 mL) was added potassium acetate (0.317 g, 3.23 mmol), dppf(0.140 mmol), dppp (50 mg), and Pd(OAc)$_2$ (20 mg). The reaction mixture was degassed under vacuum for 5 min and then CO gas was purged through the reaction mixture for 10 min. The reaction mixture was then heated at 75° C. overnight under an atmosphere of CO gas. The reaction mixture was diluted with DCM and extracted with 10% citric acid solution. The organic phase was dried (Na$_2$SO$_4$), and concentrated in vacuo. The crude product was purified by flash column chromatography on silica gel using EtOAc to give 38 mg of 1-cyclopentylmethyl-isoquinoline-3,7-dicarboxylic acid 3-methyl ester as a white solid.

LCMS: 314 (M+1)$^+$

A solution of 1-cyclopentylmethyl-isoquinoline-3,7-dicarboxylic acid 3-methyl ester (38 mg, 0.121 mmol) in DMF(1.5 mL) was treated with 4-tert-butylcyclohexylamine (0.028 g, 0.181 mmol), HBTU (69 mg, 0.181 mmol), and DIEA (0.075 mL, 0.424 mmol) by the General Procedure A to give 57 mg of the desired 7-(4-tert-butyl-cyclohexylcarbamoyl)-1-cyclopentylmethyl-isoquinoline-3-carboxylic acid methyl ester as a colorless oil. This was used directly for the next step without purification.

LCMS: 451 (M+1)$^+$

A solution of 7-(4-tert-butyl-cyclohexylcarbamoyl)-1-cyclopentylmethyl-isoquinoline-3-carboxylic acid methyl ester (57 mg, 0.126 mmol) in THF:MeOH was treated with an aq. solution of LiOH (26 mg, 0.632 mmol) via the general procedure I to give 65 mg of 7-(4-tert-butyl-cyclohexylcarbamoyl)-1-cyclopentylmethyl-isoquinoline-3-carboxylic acid. This was used directly for the next step.

LCMS: 437 (M+1)$^+$

A solution of 7-(4-tert-butyl-cyclohexylcarbamoyl)-1-cyclopentylmethyl-isoquinoline-3-carboxylic acid (65 mg, 0.148 mmol) in DMF(1.5 mL) was treated with (2S)-amino-3,3-dimethyl-butyric acid methyl ester HCL (35 mg, 0.193 mmol), HBTU (73 mg), and DIEA (0.106 mL) by the General Procedure A. The crude product was purified by flash column chromatography on silica gel using 88:12 Hexanes/EtOAc to give 18 mg of 2(S)-{[7-(4-tert-butyl-cyclohexylcarbamoyl)-1-cyclopentylmethyl-isoquinoline-3-carbonyl]-amino}3,3-dimethylbutyric acid methyl ester as a colorless oil. This was used for the next step.

LCMS: 565 (M+1)$^+$

A solution of (2S)-{[7-(4-tert-butyl-cyclohexylcarbamoyl)-1-cyclopentylmethyl-isoquinoline-3-carbonyl]- amino}3,3-dimethylbutyric acid methyl ester (18 mg, 0.032 mmol) in THF:MeOH(4:1, 2.0 mL) was treated with a solution of LiOH (2.0 M, 0.240 mL) by the general procedure I to give 15 mg of 2(S)-{[7-(4-tert-butyl-cyclohexylcarbamoyl)-1-cyclopentylmethyl-isoquinoline-3-carbonyl]amino}3,3-dimethylbutyric acid as a white solid.

¹H-NMR (400 MHZ, CDCl₃): δ 9.01 [d, 1H], 8.68 [s, 1H], 8.41 [s,1H], 7.95 [m, 1 H], 6.15 [m, 1H], 3.92 [m, 1H], 3.37 [m, 2 H], 2.93 [s,1H], 2.61 [m, 1H], 2.21 [m, 3 H], 1.88 [m, 4 H], 1.70 [m, 4 H], 1.58 [m, 3 H], 1.43-0.83 [m, 18 H]. LCMS: 550 (M+1)⁺

By analogous methods to those described above the following Examples were synthesized.

| Example | Name | LC/MS |
|---|---|---|
| 441 | 3-Biphenyl-4-yl-(2S)-[7-(4-tert-butyl-phenoxy)-1-cyclopentylmethyl-isoquinoline-3-carbonyl]-amino}-propionic acid methyl ester | 641 |
| 442 | (2S)-{[7-(4-tert-Butyl-phenoxy)-1-cyclopentylmethyl-isoquinoline-3-carbonyl]-amino}-3-phenyl-propionic acid methyl ester | 565 |
| 443 | (2S)-{[7-(4-tert-Butyl-phenoxy)-1-cyclopentylmethyl-isoquinoline-3-carbonyl]-amino}-propionic acid methyl ester | 489 |
| 444 | (2S)-{[7-(4-tert-Butyl-phenoxy)-1-cyclopentylmethyl-isoquinoline-3-carbonyl]-amino}-propionic acid | 475 |
| 445 | (2S)-{[7-(4-tert-Butyl-phenoxy)-1-cyclopentylmethyl-isoquinoline-3-carbonyl]-amino}-3-methyl-butyric acid methyl ester | 517 |
| 446 | (2S)-{[7-(4-tert-Butyl-phenoxy)-1-cyclopentylmethyl-isoquinoline-3-carbonyl]-amino}-3-methyl-butyric acid | 503 |
| 447 | {[7-(4-tert-Butyl-phenoxy)-1-cyclopentylmethyl-isoquinoline-3-carbonyl]-amino}-acetic acid methyl ester | 475 |
| 448 | {[7-(4-tert-Butyl-phenoxy)-1-cyclopentylmethyl-isoquinoline-3-carbonyl]-amino}-acetic acid | 461 |
| 449 | 7-(4-tert-Butyl-phenoxy)-1-cyclopentylmethyl-isoquinoline-3-carboxylic acid [2-[4-(2-cyclopentyl-ethoxy)-phenyl]-(1S)-(3-methyl-[1,2,4]oxadiazol-5-yl)-ethyl]-amide | 701 |
| 450 | (2R)-{[7-(4-tert-Butyl-phenoxy)-1-cyclopentylmethyl-isoquinoline-3-carbonyl]-amino}-3-phenyl-propionic acid methyl ester | 565 |
| 451 | (2R)-{[7-(4-tert-Butyl-phenoxy)-1-cyclopentylmethyl-isoquinoline-3-carbonyl]-amino}-3-phenyl-propionic acid | 551 |
| 452 | 1-{[7-(4-tert-Butyl-phenoxy)-1-cyclopentylmethyl-isoquinoline-3-carbonyl]-amino}-cyclohexanecarboxylic acid | 529 |
| 453 | 4-{[7-(4-tert-Butyl-phenoxy)-1-cyclopentylmethyl-isoquinoline-3-carbonyl]-amino}-tetrahydro-pyran-4-carboxylic acid | 531 |
| 454 | (2S)-{[7-(4-tert-Butyl-phenoxy)-1-cyclopentylmethyl-isoquinoline-3-carbonyl]-amino}-4-methyl-pentanoic acid methyl ester | 531 |
| 455 | (2S)-{[7-(4-tert-Butyl-phenoxy)-1-cyclopentylmethyl-isoquinoline-3-carbonyl]-amino}-3-pyridin-3-yl-propionic acid methyl ester | 566 |
| 456 | 1-[7-(4-tert-Butyl-phenoxy)-1-cyclopentylmethyl-isoquinoline-3-carbonyl]-piperidine-4-carboxylic acid | 515 |
| 457 | (2S)-{[7-(4-tert-Butyl-phenoxy)-1-cyclopentylmethyl-isoquinoline-3-carbonyl]-amino}-4-methyl-pentanoic acid | 517 |
| 458 | 3-(4-Amino-phenyl)-(2S)-{[7-(4-tert-butyl-phenoxy)-1-cyclopentylmethyl-isoquinoline-3-carbonyl]-amino}-propionic acid | 566 |
| 459 | (2S)-{[7-(4-tert-Butyl-phenoxy)-1-cyclopentylmethyl-isoquinoline-3-carbonyl]-amino}-3-pyridin-3-yl-propionic acid | 552 |
| 460 | (2S)-{[7-(4-tert-Butyl-phenoxy)-1-cyclopentylmethyl-isoquinoline-3-carbonyl]-amino}-3-(3,4-dimethoxy-phenyl)-propionic acid | 611 |
| 461 | (2S)-{[7-(4-tert-Butyl-phenoxy)-1-cyclopentylmethyl-isoquinoline-3-carbonyl]-amino}-3-(4-chloro-phenyl)-propionic acid | 585 |
| 462 | (2S)-{[7-(4-tert-Butyl-phenoxy)-1-cyclopentylmethyl-isoquinoline-3-carbonyl]-amino}-3-(1H-indol--yl)-propionic acid | 590 |
| 463 | (2S)-{[7-(4-tert-Butyl-phenoxy)-1-cyclopentylmethyl-isoquinoline-3-carbonyl]-amino}-3-(4-ethoxy-phenyl)-propionic acid | 595 |
| 464 | (2S)-{[7-(4-tert-Butyl-phenoxy)-1-cyclopentylmethyl-isoquinoline-3-carbonyl]-amino}-3-(4-cyano-phenyl)-propionic acid | 576 |
| 465 | (3S)-{[7-(4-tert-Butyl-phenoxy)-1-cyclopentylmethyl-isoquinoline-3-carbonyl]-amino}-4-(4-fluoro-phenyl)-butyric acid | 583 |
| 466 | 7-(4-tert-Butyl-phenoxy)-1-cyclopentylmethyl-isoquinoline-3-carboxylic acid (2-biphenyl-4-yl-ethyl)-amide | 583 |
| 467 | 1-[7-(4-tert-Butyl-phenoxy)-1-cyclopentylmethyl-isoquinoline-3-carbonyl]-pyrrolidine-(2S)-carboxylic acid | 501 |
| 468 | (2S)-{[7-(4-tert-Butyl-phenoxy)-1-cyclopentylmethyl-isoquinoline-3-carbonyl]-amino}-4-phenyl-butyric acid | 565 |
| 469 | (3S)-{[7-(4-tert-Butyl-phenoxy)-1-cyclopentylmethyl-isoquinoline-3-carbonyl]-amino}-4-(4-chloro-phenyl)-butyric acid | 599 |
| 470 | 1-[7-(4-tert-Butyl-phenoxy)-1-cyclopentylmethyl-isoquinoline-3-carbonyl]-4-phenyl-piperidine-4-carboxylic acid | 591 |
| 471 | (2S)-{[7-(4-tert-Butyl-phenoxy)-1-cyclopentylmethyl-isoquinoline-3-carbonyl]-amino}-3-cyclohexyl-propionic acid | 557 |
| 472 | (2S)-{[7-(4-tert-Butyl-phenoxy)-1-cyclopentylmethyl-isoquinoline-3-carbonyl]-amino}-3-thiophen-3-yl-propionic acid | 557 |

-continued

| Example | Name | LC/MS |
|---|---|---|
| 473 | (2S)-{[7-(4-tert-Butyl-phenoxy)-1-cyclopentylmethyl-isoquinoline-3-carbonyl]-amino}-3-naphthalen-2-yl-propionic acid | 601 |
| 474 | (2S)-{[7-(4-tert-Butyl-phenoxy)-1-cyclopentylmethyl-isoquinoline-3-carbonyl]-amino}-3-hydroxy-propionic acid | 491 |
| 475 | (3S)-{[7-(4-tert-Butyl-phenoxy)-1-cyclopentylmethyl-isoquinoline-3-carbonyl]-amino}-4-(1H-indol-3-yl)-butyric acid | 604 |
| 476 | (2S)-{[1-Cyclopentylmethyl-7-(4-trifluoromethyl-phenoxy)-isoquinoline-3-carbonyl]-amino}-3-methyl-butyric acid | 515 |
| 477 | (2S)-{[1-Cyclopentylmethyl-7-(4-trifluoromethoxy-phenoxy)-isoquinoline-3-carbonyl]-amino}-3-methyl-butyric acid | 531 |
| 478 | (2S)-{[1-Cyclopentylmethyl-7-(4-trifluoromethoxy-phenoxy)-isoquinoline-3-carbonyl]-amino}-3-phenyl-propionic acid | 579 |
| 479 | (2S)-{[1-Cyclopentylmethyl-7-(4-fluoro-phenoxy)-isoquinoline-3-carbonyl]-amino}-3-methyl-butyric acid | 465 |
| 480 | (2S)-{[7-(4-Chloro-phenoxy)-1-cyclopentylmethyl-isoquinoline-3-carbonyl]-amino}-3-methyl-butyric acid | 481 |
| 481 | (2S)-{[1-Cyclopentylmethyl-7-(4-methoxy-phenoxy)-isoquinoline-3-carbonyl]-amino}-3-methyl-butyric acid | 477 |
| 482 | (2S)-{[7-(4-Chloro-phenoxy)-1-cyclopentylmethyl-isoquinoline-3-carbonyl]-amino}-3-phenyl-propionic acid | 529 |
| 483 | 7-(4-tert-Butyl-phenoxy)-1-(1-ethyl-pentyl)-isoquinoline-3-carboxylic acid | 420 |
| 484 | (2S)-{[7-(4-tert-Butyl-phenoxy)-1-(1-ethyl-pentyl)-isoquinoline-3-carbonyl]-amino}-3-methyl-butyric acid | 519 |
| 485 | 1-{[7-(4-tert-Butyl-phenoxy)-1-cyclopentylmethyl-isoquinoline-3-carbonyl]-amino}-cyclopentanecarboxylic acid | 515 |
| 486 | 1-{[7-(4-tert-Butyl-phenoxy)-1-cyclopentylmethyl-isoquinoline-3-carbonyl]-amino}-cyclopropanecarboxylic acid | 487 |
| 487 | 4-{[7-(4-tert-Butyl-phenoxy)-1-cyclopentylmethyl-isoquinoline-3-carbonyl]-amino}-tetrahydro-thiopyran-4-carboxylic acid | 547 |
| 488 | 1-[7-(4-tert-Butyl-phenoxy)-1-cyclopentylmethyl-isoquinoline-3-carbonyl]-(4S)-phenyl-pyrrolidine-(2S)-carboxylic acid | 577 |
| 489 | 1-[7-(4-tert-Butyl-phenoxy)-1-cyclopentylmethyl-isoquinoline-3-carbonyl]-(5R)-phenyl-pyrrolidine-(2S)-carboxylic acid | 577 |
| 490 | 2-{[7-(4-tert-Butyl-phenoxy)-1-cyclopentylmethyl-isoquinoline-3-carbonyl]-amino}-1,2,3,4-tetrahydro-naphthalene-2-carboxylic acid | 577 |
| 491 | 2-{[7-(4-tert-Butyl-phenoxy)-1-cyclopentylmethyl-isoquinoline-3-carbonyl]-amino}-indan-2-carboxylic acid | 563 |
| 492 | 4-{[7-(4-tert-Butyl-phenoxy)-1-cyclopentylmethyl-isoquinoline-3-carbonyl]-amino}-1,1-dioxo-tetrahydrothiopyran-4-carboxylic acid | 579 |
| 493 | (2S)-{[7-(4-tert-Butyl-phenoxy)-1-cyclopentylmethyl-isoquinoline-3-carbonyl]-amino}-3-(1H-imidazol-4-yl)-propionic acid | 541 |
| 494 | 3-Benzylsulfanyl-(2S)-{[7-(4-tert-butyl-phenoxy)-1-cyclopentylmethyl-isoquinoline-3-carbonyl]-amino}-propionic acid | 597 |
| 495 | 4-{[7-(4-tert-Butyl-phenoxy)-1-cyclopentylmethyl-isoquinoline-3-carbonyl]-amino}-benzoic acid methyl ester | 537 |
| 496 | 3-{[7-(4-tert-Butyl-phenoxy)-1-cyclopentylmethyl-isoquinoline-3-carbonyl]-amino}-benzoic acid methyl ester | 537 |
| 497 | 2-{[7-(4-tert-Butyl-phenoxy)-1-cyclopentylmethyl-isoquinoline-3-carbonyl]-amino}-benzoic acid methyl ester | 537 |
| 498 | 4-{[7-(4-tert-Butyl-phenoxy)-1-cyclopentylmethyl-isoquinoline-3-carbonyl]-amino}-benzoic acid | 523 |
| 499 | 3-{[7-(4-tert-Butyl-phenoxy)-1-cyclopentylmethyl-isoquinoline-3-carbonyl]-amino}-benzoic acid | 523 |
| 500 | 3-Benzyloxy-(2S)-{[7-(4-tert-butyl-phenoxy)-1-cyclopentylmethyl-isoquinoline-3-carbonyl]-amino}-propionic acid | 581 |
| 501 | (2S)-{[1-Benzyl-7-(4-tert-butyl-phenoxy)-isoquinoline-3-carbonyl]-amino}-3-phenyl-propionic acid | 559 |
| 502 | (2S)-{[7-(4-tert-Butyl-phenoxy)-1-cyclopentylmethyl-isoquinoline-3-carbonyl]-amino}-3-(4-methyl-benzylsulfanyl)-propionic acid | 611 |
| 503 | (2S)-{[7-(4-tert-Butyl-phenoxy)-1-cyclopentylmethyl-isoquinoline-3-carbonyl]-amino}-3-(4-methoxy-benzylsulfanyl)-propionic acid | 627 |
| 504 | 2-{[7-(4-tert-Butyl-phenoxy)-1-cyclopentylmethyl-isoquinoline-3-carbonyl]-amino}-3-methyl-benzoic acid | 537 |
| 505 | (2S)-{[7-(4-tert-Butyl-phenoxy)-1-cyclopentylmethyl-isoquinoline-3-carbonyl]-amino}-3-phenylmethanesulfonyl-propionic acid methyl ester | 643 |
| 506 | 2-{[7-(4-tert-Butyl-phenoxy)-1-cyclopentylmethyl-isoquinoline-3-carbonyl]-amino}-3-methoxy-benzoic acid | 553 |
| 507 | 2-{[7-(4-tert-Butyl-phenoxy)-1-cyclopentylmethyl-isoquinoline-3-carbonyl]-amino}-3-trifluoromethyl-benzoic acid | 591 |
| 508 | (2S)-{[7-(4-tert-Butyl-phenoxy)-1-cyclopentylmethyl-isoquinoline-3-carbonyl]-methyl-amino}-3-phenyl-propionic acid | 565 |
| 509 | {[7-(4-tert-Butyl-phenoxy)-(1S)-cyclopentylmethyl-isoquinoline-3-carbonyl]-methyl-amino}-phenyl-acetic acid | 551 |

-continued

| Example | Name | LC/MS |
|---|---|---|
| 510 | 2-{[7-(4-tert-Butyl-phenoxy)-1-cyclopentylmethyl-isoquinoline-3-carbonyl]-amino}-2-ethyl-butyric acid | 517 |
| 511 | 2-{[7-(4-tert-Butyl-phenoxy)-1-cyclopentylmethyl-isoquinoline-3-carbonyl]-amino}-acrylic acid | 473 |
| 512 | (2S)-{[7-(4-tert-Butyl-phenoxy)-1-cyclopentylmethyl-isoquinoline-3-carbonyl]-amino}-3-phenylmethanesulfonyl-propionic acid | 629 |
| 513 | 2-{[7-(4-tert-Butyl-phenoxy)-1-cyclopentylmethyl-isoquinoline-3-carbonyl]-ethyl-amino}-benzoic acid | 551 |
| 514 | (2-{[7-(4-tert-Butyl-phenoxy)-1-cyclopentylmethyl-isoquinoline-3-carbonyl]-amino}-phenyl)-acetic acid | 537 |
| 515 | {[7-(4-tert-Butyl-phenoxy)-1-cyclopentylmethyl-isoquinoline-3-carbonyl]-phenyl-amino}-acetic acid | 537 |
| 516 | [[7-(4-tert-Butyl-phenoxy)-1-cyclopentylmethyl-isoquinoline-3-carbonyl]-(3-phenyl-propyl)-amino]-acetic acid | 579 |
| 517 | 3-Benzyloxy-(2S)-{[7-(4-tert-butyl-phenoxy)-1-cyclohexyl-isoquinoline-3-carbonyl]-amino}-propionic acid | 581 |
| 518 | (2S)-{[7-(4-tert-Butyl-phenoxy)-1-cyclohexyl-isoquinoline-3-carbonyl]-amino}-4,4-dimethyl-pentanoic acid | 531 |
| 519 | (2S)-{[7-(4-tert-Butyl-phenoxy)-1-cyclohexyl-isoquinoline-3-carbonyl]-amino}-phenyl-acetic acid | 537 |
| 520 | {[7-(4-tert-Butyl-phenoxy)-1-cyclopentylmethyl-isoquinoline-3-carbonyl]-phenethyl-amino}-acetic acid | 565 |
| 521 | 3-Benzyloxy-(2S-{[7-(4-tert-butyl-phenoxy)-1-ethyl-isoquinoline-3-carbonyl]-amino}-propionic acid | 527 |
| 522 | 2-{[7-(4-tert-Butyl-phenoxy)-1-ethyl-isoquinoline-3-carbonyl]-amino}-4,4-dimethyl-pentanoic acid | 477 |
| 523 | (2S)-{[7-(4-tert-Butyl-phenoxy)-ethyl-isoquinoline-3-carbonyl]-amino}-phenyl-acetic acid | 483 |
| 524 | {[7-(4-tert-Butyl-phenoxy)-1-cyclopentylmethyl-isoquinoline-3-carbonyl]-cyclohexylmethyl-amino}-acetic acid | 557 |
| 525 | {[7-(4-tert-Butyl-phenoxy)-1-cyclopentylmethyl-isoquinoline-3-carbonyl]-cyclopentylmethyl-amino}-acetic acid | 543 |
| 526 | [[7-(4-tert-Butyl-phenoxy)-1-cyclopentylmethyl-isoquinoline-3-carbonyl]-(2,2-dimethyl-propyl)-amino]-acetic acid | 531 |
| 527 | (2S)-{[7-(4-tert-Butyl-phenoxy)-1-cyclopentylmethyl-isoquinoline-3-carbonyl]-amino}-(4-trifluoromethyl-phenyl)-acetic acid | 605 |
| 528 | (2S)-{[7-(4-tert-Butyl-phenoxy)-1-cyclopentylmethyl-isoquinoline-3-carbonyl]-amino}-(3,4-difluoro-phenyl)-acetic acid | 573 |
| 529 | (2S)-{[7-(4-tert-Butyl-phenoxy)-1-cyclopentylmethyl-isoquinoline-3-carbonyl]-amino}-(4-chloro-phenyl)-acetic acid | 571 |
| 530 | (2S)-{[7-(4-tert-Butyl-phenoxy)-1-cyclopentylmethyl-isoquinoline-3-carbonyl]-amino}-(4-fluoro-phenyl)-acetic acid | 555 |
| 531 | (2S)-{[7-(4-tert-Butyl-phenoxy)-1-cyclopentylmethyl-isoquinoline-3-carbonyl]-amino}-3-(2'-phenoxy-biphenyl-4-yl)-propionic acid | 719 |
| 532 | 2-{[7-(4-tert-Butyl-phenoxy)-1-cyclopentylmethyl-isoquinoline-3-carbonyl]-amino}-benzothiazole-6-carboxylic acid ethyl ester | 608 |
| 533 | (2S)-{[7-(4-tert-Butyl-phenoxy)-1-cyclopentylmethyl-isoquinoline-3-carbonyl]-amino}-(4-cyclopentyloxy-phenyl)-acetic acid | 621 |
| 534 | (2S)-{[7-(4-tert-Butyl-phenoxy)-1-cyclopentylmethyl-isoquinoline-3-carbonyl]-amino}-[4-(2-cyclopentyl-ethoxy)-phenyl]-acetic acid | 649 |
| 535 | (2R)-{[7-(4-tert-Butyl-phenoxy)-1-cyclopentylmethyl-isoquinoline-3-carbonyl]-amino}-3,3-dimethyl-butyric acid | 517 |
| 536 | (2S)-{[7-(4-tert-Butyl-phenoxy)-1-cyclopentylmethyl-isoquinoline-3-carbonyl]-amino}-cyclohexyl-acetic acid | 543 |
| 537 | 4-{[7-(4-tert-Butyl-phenoxy)-1-cyclopentylmethyl-isoquinoline-3-carbonyl]-amino}-piperidine-1,4-dicarboxylic acid mono-tert-butyl ester | 630 |
| 538 | 2S)-{[7-(4-tert-Butyl-cyclohexyloxy)-1-cyclopentylmethyl-isoquinoline-3-carbonyl]-amino}-3,3-dimethyl-butyric acid | 523 |
| 539 | (2S)-{[7-(4-tert-Butyl-cyclohexyloxy)-1-cyclopentylmethyl-isoquinoline-3-carbonyl]-amino}-3,3-dimethyl-butyric acid | 523 |
| 540 | 4-{[7-(4-tert-Butyl-phenoxy)-1-cyclopentylmethyl-isoquinoline-3-carbonyl]-amino}-piperidine-4-carboxylic acid | 530 |
| 541 | 2-{[7-(4-tert-Butyl-phenoxy)-1-cyclopentylmethyl-isoquinoline-3-carbonyl]-amino}-3-phenyl-butyric acid | 565 |
| 542 | {(2S)-{[7-(4-tert-Butyl-phenoxy)-1-cyclopentylmethyl-isoquinoline-3-carbonyl]-amino}-cyclopentyl-acetic acid | 529 |
| 543 | (2S)-{[1-Cyclopentylmethyl-7-(4-isopropyl-phenoxy)-isoquinoline-3-carbonyl]-amino}-3,3-dimethyl-butyric acid | 503 |
| 544 | (2S)-{[7-(4-tert-Butyl-phenoxy)-1-cyclopentylmethyl-isoquinoline-3-carbonyl]-amino}-3-hydroxy-3-methyl-butyric acid | 519 |
| 545 | 7-(4-tert-Butyl-phenoxy)-1-(2-cyclopentyl-ethyl)-isoquinoline-3-carboxylic acid | 418 |
| 546 | (2S)-{[7-(4-tert-Butyl-phenoxy)-1-(2-cyclopentyl-ethyl)-isoquinoline-3-carbonyl]-amino}-3,3-dimethyl-butyric acid | 531 |

-continued

| Example | Name | LC/MS |
|---|---|---|
| 547 | 1-(4-tert-Butyl-cyclohexyl)-7-(4-tert-butyl-phenoxy)-isoquinoline-3-carboxylic acid | 460 |
| 548 | (2S)-{[7-(4-tert-Butyl-phenoxy)-1-cycloheptyl-isoquinoline-3-carbonyl]-amino}-4,4-dimethyl-pentanoic acid | 545 |
| 549 | (2S)-{[7-(4-tert-Butyl-phenoxy)-1-cycloheptyl-isoquinoline-3-carbonyl]-amino}-cyclopentyl-acetic acid | 543 |
| 550 | (2S)-{[7-(4-tert-Butyl-phenoxy)-1-cycloheptyl-isoquinoline-3-carbonyl]-amino}-3,3-dimethyl-butyric acid | 531 |
| 551 | (2S)-{[7-(4-tert-Butyl-phenoxy)-1-cycloheptyl-isoquinoline-3-carbonyl]-amino}-3,3-dimethyl-butyric acid | 491 |
| 552 | (2S)-{[7-(4-tert-Butyl-phenoxy)-1-(3-methyl-butyl)-isoquinoline-3-carbonyl]-amino}-3,3-dimethyl-butyric acid | 505 |
| 553 | (2S)-[(1-Cyclopentylmethyl-7-p-tolyloxy-isoquinoline-3-carbonyl)-amino]-3,3-dimethyl-butyric acid | 475 |
| 554 | (2S)-{[1-Cyclopentylmethyl-7-(4-propyl-phenoxy)-isoquinoline-3-carbonyl]-amino}-3,3-dimethyl-butyric acid | 503 |
| 555 | (2S)-{[7-(4-Cyclohexyl-phenoxy)-1-cyclopentylmethyl-isoquinoline-3-carbonyl]-amino}-3,3-dimethyl-butyric acid | 543 |
| 556 | (2S)-{[7-(4-tert-Butyl-phenoxy)-1-phenethyl-isoquinoline-3-carbonyl]-amino}-3,3-dimethyl-butyric acid methyl ester | 553 |
| 557 | (2S)-{[7-(4-tert-Butyl-phenoxy)-1-phenethyl-isoquinoline-3-carbonyl]-amino}-4,4-dimethyl-pentanoic acid methyl ester | 567 |
| 558 | (2S)-{[7-(4-tert-Butyl-phenoxy)-1-phenethyl-isoquinoline-3-arbonyl]-amino}-3,3-dimethyl-butyric acid | 539 |
| 559 | (2S)-{[7-(4-tert-Butyl-phenoxy)-1-phenethyl-isoquinoline-3-arbonyl]-amino}-4,4-dimethyl-pentanoic acid | 553 |
| 560 | (2S)-{[7-(4-tert-Butyl-phenoxy)-1-cyclopentyl-isoquinoline-3-carbonyl]-amino}-3,3-dimethyl-butyric acid | 503 |
| 561 | (2S)-{[7-(4-tert-Butyl-phenoxy)-1-cyclopentyl-isoquinoline-3-carbonyl]-amino}-4,4-dimethyl-pentanoic acid | 517 |
| 562 | (2S)-{[1-Cyclopentylmethyl-7-(4-isobutyl-phenoxy)-isoquinoline-3-carbonyl]-amino}-3,3-dimethyl-butyric acid | 517 |
| 563 | (2R)-{[7-(4-tert-Butyl-phenoxy)-1-(2-cyclopentyl-ethyl)-isoquinoline-3-carbonyl]-amino}-3,3-dimethyl-butyric acid | 531 |
| 564 | (2R)-{[7-(4-tert-Butyl-phenoxy)-1-(3-methyl-butyl)-isoquinoline-3-carbonyl]-amino}-3,3-dimethyl-butyric acid | 505 |
| 565 | (2R)-{[7-(4-tert-Butyl-phenoxy)-1-cyclopentylmethyl-isoquinoline-3-carbonyl]-amino}-phenyl-acetic acid | 537 |
| 566 | (2R)-{[7-(4-tert-Butyl-phenoxy)-1-cyclopentylmethyl-isoquinoline-3-carbonyl]-amino}-cyclopentyl-acetic acid | 529 |
| 567 | (2R)-{[7-(trans-4-tert-Butyl-cyclohexyloxy)-1-cyclopentylmethyl-isoquinoline-3-carbonyl]-amino}-cyclopentyl-acetic acid | 535 |
| 568 | (2R)-{[7-(trans-4-tert-Butyl-cyclohexyloxy)-1-cyclopentylmethyl-isoquinoline-3-carbonyl]-amino}-3-thiophen-3-yl-propionic acid | 563 |
| 569 | (2R)-{[7-(trans-4-tert-Butyl-cyclohexyloxy)-1-cyclopentylmethyl-isoquinoline-3-carbonyl]-amino}-phenyl-acetic acid | 543 |
| 570 | 1-Cyclopentylmethyl-7-[4-(1,1-dimethyl-propyl)-trans-cyclohexyloxy]-isoquinoline-3-carboxylic acid | 424 |
| 571 | (2R)-({1-Cyclopentylmethyl-7-[4-(1,1-dimethyl-propyl)-trans-cyclohexyloxy]-isoquinoline-3-carbonyl}-amino)-3,3-dimethyl-butyric acid | 537 |
| 572 | (2R)-{[1-Cyclopentylmethyl-7-((2S)-isopropyl-(5R)-methyl-(1R)-cyclohexyloxy)-isoquinoline-3-carbonyl]-amino}-3,3-dimethyl-butyric acid | 523 |
| 573 | (2R)-{[1-Cyclopentylmethyl-7-(3,3,5,5-tetramethyl-cyclohexyloxy)-isoquinoline-3-carbonyl]-amino}-3,3-dimethyl-butyric acid | 523 |
| 574 | (2R)-{[1-Cyclopentylmethyl-7-(cis, cis, trans 3,5-dimethyl-cyclohexyloxy)-isoquinoline-3-carbonyl]-amino}-3,3-dimethyl-butyric acid | 495 |
| 575 | (2R)-{[1-Cyclopentylmethyl-7-(trans-4-ethyl-cyclohexyloxy)-isoquinoline-3-carbonyl]-amino}-3,3-dimethyl-butyric acid | 495 |
| 576 | (2R)-{[1-Cyclopentylmethyl-7-(4-isopropyl-cyclohexyloxy)-isoquinoline-3-carbonyl]-amino}-3,3-dimethyl-butyric acid | 509* |
| 577 | (2R)-{[7-(4-tert-Butyl-phenoxy)-1-cyclopentylmethyl-isoquinoline-3-carbonyl]-amino}-thiophen-3-yl-acetic acid | 543 |
| 578 | (2S)-{[7-(4-tert-Butyl-phenoxy)-1-cyclopentylmethyl-isoquinoline-3-carbonyl]-amino}-3-[4-(pyrrolidin-2-ylmethoxy)-phenyl]-propionic acid | 650 |
| 579 | (2R)-{[7-(4-tert-Butyl-phenoxy)-1-cyclopentylmethyl-isoquinoline-3-carbonyl]-amino}-3-thiophen-2-yl-propionic acid | 557 |
| 580 | (2R)-[7-(4-tert-Butyl-phenoxy)-1-cyclopentylmethyl-isoquinoline-3-carbonyl]-amino}-thiophen-2-yl-acetic acid | 543 |
| 581 | (2R)-{[7-(1-Benzenesulfonyl-piperidin-4-yloxy)-1-cyclopentyl-methyl-isoquinoline-3-carbonyl]-amino}-3-thiophen-3-yl-propionic acid | 648 |

-continued

| Example | Name | LC/MS |
|---|---|---|
| 582 | (2R)-({1-Cyclopentylmethyl-7-[1-(propane-2-sulfonyl)-piperidin-4-yloxy]-isoquinoline-3-carbonyl}-amino)-3-thiophen-3-yl-propionic acid | 614 |
| 583 | (2R)-{[7-(4-tert-Butyl-phenoxy)-1-cyclopentylmethyl-isoquinoline-3-carbonyl]-amino}-3-(4-trifluoromethyl-phenyl)-propionic acid | 619 |
| 584 | (2R)-{[7-(4-tert-Butyl-phenoxy)-1-cyclopentylmethyl-isoquinoline-3-carbonyl]-amino}-3-naphthalen-2-yl-propionic acid | 601 |
| 585 | (2R)-{[7-(4-tert-Butyl-phenoxy)-1-cyclopentylmethyl-isoquinoline-3-carbonyl]-amino}-3-(4-tert-butyl-phenyl)-propionic acid | 607 |
| 586 | (2S)-{[7-(4-tert-Butyl-phenoxy)-1-cyclopentylmethyl-isoquinoline-3-carbonyl]-amino}-3-(3-trifluoromethyl-phenyl)-propionic acid | 619 |
| 587 | (3S)-{[7-(4-tert-Butyl-phenoxy)-1-cyclopentylmethyl-isoquinoline-3-carbonyl]-amino}-4-(4-trifluoromethyl-phenyl)-butyric acid | 633 |
| 588 | (2S)-{[1-Cyclopentylmethyl-7-(4-isopropyl-phenoxy)-isoquinoline-3-carbonyl]-amino}-3-(4-trifluoromethyl-phenyl)-propionic acid | 605 |
| 589 | (2S)-{[7-(4-tert-Butyl-phenoxy)-1-cyclopentylmethyl-isoquinoline-3-carbonyl]-amino}-3-m-tolyl-propionic acid | 565 |
| 590 | (2S)-{[7-(4-tert-Butyl-phenoxy)-isoquinoline-3-carbonyl]-amino}-3-(4-trifluoromethyl-phenyl)-propionic acid | 537 |
| 591 | (3R)-{[7-(4-tert-Butyl-phenoxy)-1-cyclopentylmethyl-isoquinoline-3-carbonyl]-amino}-4-(3-chloro-phenyl)-butyric acid | 599 |
| 592 | (3R)-{[7-(4-tert-Butyl-phenoxy)-1-cyclopentylmethyl-isoquinoline-3-carbonyl]-amino}-4-(3,4-dichloro-phenyl)-butyric acid | 633 |
| 593 | 3-(4-tert-Butoxy-phenyl)-(2S)-{[7-(4-tert-butyl-phenoxy)-1-cyclopentylmethyl-isoquinoline-3-carbonyl]-amino}-propionic acid | 623 |
| 594 | (2S)-{[7-(4-tert-Butyl-phenoxy)-1-cyclopentylmethyl-isoquinoline-3-carbonyl]-amino}-3-p-tolyl-propionic acid | 565 |
| 595 | 2-{[7-(4-tert-Butyl-phenoxy)-1-cyclopentylmethyl-isoquinoline-3-carbonyl]-amino}-thiazole-5-carboxylic acid | 530 |
| 596 | [[7-(4-tert-Butyl-phenoxy)-1-cyclopentylmethyl-isoquinoline-3-carbonyl]-(4-chloro-benzyl)-amino]-acetic acid | 585 |
| 597 | [[7-(4-tert-Butyl-phenoxy)-1-cyclopentylmethyl-isoquinoline-3-carbony]-(3-trifluoromethyl-benzyl)-amino]-acetic acid | 619 |
| 598 | [[7-(4-tert-Butyl-phenoxy)-1-cyclopentylmethyl-isoquinoline-3-carbonyl]-(2-trifluoromethyl-benzyl)-amino]-acetic acid | 619 |

Example 599

3-Biphenyl-4-yl-(2S)-{[7-(4-tert-butyl-phenoxy)-1-cyclopentylmethyl-2-(2,2-dimethyl-propionyl)-1,2,3,4-tetrahydro-isoquinoline-(3S)-carbonyl]-amino}-propionic acid methyl ester 400 mg (0.1 mmol) of 1-cyclopentylmethyl-7-hydroxy-3,4-dihydro-isoquinoline-3-carboxylic acid methyl ester (Example 419, Step 2) was dissolved in 20 ml of methanol with a catalytic amount of Pd/C and stirred overnight under $H_2$ atmosphere (60 psi). Filtaration followed by evaporation of the solvent under vacuo gave 0.4 g of 1-cyclopentylmethyl-7-hydroxy-1,2,3,4-tetrahydro-isoquinoline-3-carboxylic acid methyl ester as a thick liquid.

To a stirring solution of 400 mg (1.4 mmol) of the above compound, 790 mg (6.9 mmol) of $NEt_3$ in DCM (10 ml) and 300 mg (1.6 mmol) of BOC anhydride was added at room temperature and stirring continued for another 2 h. Evaporation of the solvent followed by column chromatography using 3:2 hexane and ethyl acetate gave 410 mg of 1-cyclopentylmethyl-2-(2,2-dimethyl-propionyl)-7-hydroxy-1,2,3,4-tetrahydro-isoquinoline-(3S)-carboxylic acid methyl ester as a thick liquid.

LCMS; 374 (M+1)$^+$ 400 mg (1.02 mmol) of above phenol was reacted with 370 mg (2.04 mmol) of 4-tert-butyl phenylboronic acid, as described in general procedure G. The ester was purified by column chromatography using 9:1 hexane and ethyl acetate as an eluant and hydrolyzed as described in general procedure C to give 180 mg of the 7-(4-tert-butyl-phenoxy)-1-cyclopentylmethyl-2-(2,2-dimethyl-propionyl)-1,2,3,4-tetrahydro-isoquinoline-(3S)-carboxylic acid as a white solid.

LCMS: 492 (M+1)$^+$.

240 mg (0.47 mmol) of above acid was reacted with (2S)-amino-3-biphenyl-4-yl-propionic acid methyl ester (152 mg, 0.52 mmol) as described in general procedure A. The ester (290 mg) was isolated after column chromatography using 9:1 hexane/ethyl acetate as an eluents.

LCMS: 729 (M+1)$^+$.

Example 600

3-Biphenyl-4-yl-(2S)-{[7-(4-tert-butyl-phenoxy)-1-cyclopentylmethyl-2-(2,2-dimethyl-propionyl)-1,2,3,4-tetrahydro-isoquinoline-3-carbonyl]-amino}-propionic acid 20 mg (0.028 mmol) of the ester (example 599) was hydrolyzed as shown in general procedure C to afford 19.6 mg of the title compound as a white solid.

LCMS: 715 (M+1)$^+$.

Example 601

(2S)-{[2-Acetyl-7-(4-tert-butyl-phenoxy)-1-cyclopentylmethyl-1,2,3,4-tetrahydro-isoquinoline-(3S)-carbonyl]-amino}-3-biphenyl-4-yl-propionic acid 20 mg (0.028 mmol) of the example 599 was dissolved in 4.0 M HCl in dioxane (2 ml) and stirred for 45 min at rt. Evaporation of the solvent under vacuo gave 18.2 mg of 3-biphenyl-4-yl-(2S)-{[7-(4-tert-butyl-phenoxy)-1-cyclopentylmethyl-1,2,3,4-tetrahydro-isoquinoline-3-carbonyl]-amino}-propionic acid methyl ester HCl.

To a stirring of solution of above compound (18.2 mg, 0.026 mmol) and NEt₃ (81 mg, 0.08 mmol) in 4 ml of DCM at 0° C. was added acetyl chloride (10.6 mg, 0.13 mmol). Reaction mixture was warmed to r.t and stirring was continued for 45 min. Then the organic layer was washed with water, 1.0 N HCl and brine then dried over Na₂SO₄. Evaporation of the solvent gave an amide, which was hydrolyzed as described in general procedure C to give 15 mg of the title compound as a white solid.

LCMS: 673 (M+1)⁺.

Example 602

(2S)-[3-[3-(4-tert-Butyl-phenoxy)-phenyl]-2-(2-cyclopentyl-acetylamino)-propionylamino]-4,4-dimethyl-pentanoic acid methyl ester 12.5 g (54.3 mmol) of 2-amino-3-(3-hydroxy-phenyl)-propionic acid methyl ester was reacted with cyclopentyl acetic acid (6.97 g, 54.3 mmol) as described in general procedure A. The compound was purified using gradient elution with 10% to 100% ethyl acetate in hexanes to yield 9.1 g of 2-(2-cyclopentyl-acetylamino)-3-(3-hydroxy-phenyl)-propionic acid methyl ester.

LCMS 307 (M+1)⁺.

A portion of the material from the previous step (4.0 g, 13.1 mmol) was dissolved in 120 mL anhydrous DCM, and to this was added 4-tert-butylphenyl boronic acid (2.0 eq., 26.2 mmol, 4.66 g), copper(II) acetate (1.1 eq., 14.4 mmol, 2.62 g), and 20 9 of powdered 4A molecular sieves. To the stirring mixture was added triethylamine (3.0 eq., 39.3 mmol, 5.5 mL) and the reaction carried out according to general procedure G. Chromatographic purification on silica eluting with ethyl acetate in hexanes afforded 2.50 g of 3-[3-(4-tert-butyl-phenoxy)-phenyl]-2-(2-cyclopentyl-acetylamino)-propionic acid methyl ester.

LCMS: 439 (M+1)⁺.

A portion of the product obtained in the previous step (107 mg, 0.24 mmol) was saponified according to general procedure C to afford 102 mg of of 2-(2-cyclopentyl-acetylamino)-3-(3-hydroxy-phenyl)-propionic acid.

LCMS: 425 (M+1)⁺.

A portion of the carboxylic acid described in the previous step (33 mg, 0.078 mmol) was coupled with neopentyl glycine methyl ester (2.0 eq., 0.16 mmol, 30 mg) using HBTU (3.0 eq., 0.23 mmol, 89 mg), and DIEA (5.0 eq., 0.39 mmol, 0.068 mL) in 1.0 mL of dry DMF according to general procedure A, to afford 41 mg of the title compound.

LCMS: 565 (M+1)⁺.

Example 603

2-[3-[3-(4-tert-Butyl-phenoxy)-phenyl]-2-(2-cyclopentyl-acetylamino)-propionylamino]-4,4-dimethyl-pentanoic acid.

A portion of the material from example 602 (15 mg, 0.026 mmol) was saponified according to general procedure C to afford the title compound in quantitative yield (14.6 mg).

¹H NMR: (400 MHz, CDCl₃) δ 7.32 [m, 2H], 7.18 [t, 1H], 7.16 [brd, 1H], 6.93 [d, 1H], 6.89 [m, 1H], 6.88 [m, 2H], 6.80 [ddd,1H], 6.66 [br d, 1H], 4.92 [X of ABX pattern, 1H], 4.48 [dt, 1H], 3.12-2.88 [AB of ABX pattern, 2H], 2.18-2.03 [m, 3H], 1.79 [dd,1H], 1.73-1.59 [m, 2H], 1.59-1.36 [m, 5H], 1.32 [s, 9H], 1.08-0.96 [m, 2H], 0.91 [s, 9H].

LCMS: 551 (M+1)⁺.

Example 604

6-(4-tert-Butyl-phenoxy)-1-cyclopentylmethyl-isoquinoline-3-carboxylic acid 1.77 g (4.07 mmol) of 3-[3-(4-tert-butyl-phenoxy)-phenyl]-2-(2-cyclopentyl-acetylamino)-propionic acid methyl ester (synthesized in example 602, step 2) was dissolved in 40 mL anhydrous toluene and phosphoryl chloride was added and the mixture heated at 90° C. for several hours and then cooled. The solvent and excess reagent was removed and the residue was purified via column chromatography on silica eluting with 20-30% ethyl acetate in hexanes to afford 380 mg of the cyclized product, 6-(4-tert-butyl-phenoxy)-1-cyclopentylmethyl-3,4-dihydro-isoquinoline-3-carboxylic acid methyl ester.

LCMS 421 (M+1)⁺.

The product of the previous reaction (380 mg, 0.91 mmol) was dissolved in 9 mL dry DCM and triethylamine (5.0 eq., 4.53 mmol, 0.63 mL) and copper(II)acetate (2.2 eq., 1.99 mmol, 362 mg) was added and the mixture stirred at rt for several hours. The mixture was cooled and concentrated and purified via column chromatography on silica eluting with 20-30% ethyl acetate in hexanes to afford 378 mg of 6-(4-tert-butyl-phenoxy)-1-cyclopentylmethyl-isoquinoline-3-carboxylic acid methyl ester. LCMS 419 (M+1)⁺.

The above material was taken in its entirety (378 mg, 0.905 mmol) and saponified according to general procedure C to afford the title compound as a white solid (365 mg).

LCMS 405 (M+1)⁺.

Example 605

(2S)-{[6-(4-tert-Butyl-phenoxy)-1-cyclopentylmethyl-isoquinoline-3-carbonyl]-amino}-3,3-dimethyl-butyric acid methyl ester To a solution of 6-(4-tert-butyl-phenoxy)-1-cyclopentylmethyl-isoquinoline-3-carboxylic acid (50 mg, 0.124 mmol) in dry DMF (1.25 mL) was added HBTU (1.5 eq., 0.19 mmol, 71 mg), tert-butylglycine methyl ester (1.1 eq., 0.14 mmol, 25 mg) and DIEA (3.0 eq., 0.37 mmol, 0.065 mL) according to general procedure A. Purification by chromatography on silica afforded 23 mg of the title compound.

LCMS 532 (M+1)⁺.

Example 606

(2S)-{[6-(4-tert-Butyl-phenoxy)-1-cyclopentylmethyl-isoquinoline-3-carbonyl]-amino}-3,3-dimethyl-butyric acid The product of the previous example was saponified according to the general procedure C to furnish the title compound (22 mg).

¹H NMR: (400 MHz, CDCl₃) δ 9.04 [d, 1H], 8.23 [s, 1H], 8.17 [d, 1H], 7.43 [m, 2H], 7.41 [dd,1H], 7.23 [d, 1H], 7.04 [m, 2H], 4.66 [d, 1H], 3.34-3.22 [d of ABq, 2H], 2.53 [septet, 1H], 1.91, 1.78 [m, 2H], 1.75-1.64 [m, 2H], 1.63-1.51 [m, 2H], 1.36 [s, 9H], 1.39-1.28 [m, 2H], 1.14 [s, 9H]. LCMS 518 (M+1)⁺.

By analogous methods to those described above the following Examples were synthesized.

| Example | Name | LC/MS |
|---|---|---|
| 607 | (2S)-{[6-(4-tert-Butyl-phenoxy)-1-cyclopentylmethyl-isoquinoline-3-carbonyl]-amino}-4,4-dimethyl-pentanoic acid methyl ester | 545 |
| 608 | (2S)-{[6-(4-tert-Butyl-phenoxy)-1-cyclopentylmethyl-isoquinoline-3-carbonyl]-amino}-4,4-dimethyl-pentanoic acid | 531 |
| 609 | (2S)-{[6-(4-tert-Butyl-phenoxy)-1-cyclopentylmethyl-isoquinoline-3-carbonyl]-amino}-3-phenyl-propionic acid | 551 |

Example 610

8-Bromo-1-cyclopentylmethyl-5-methoxy-isoquinoline-3-carboxylic acid

To a stirring of solution of 2-amino-3-(5-bromo-2-methoxy-phenyl)-propionic acid methyl ester HCl (1.0 g, 3.08 mmol), $NEt_3$ (0.78 g, 7.7 mmol) in 30 ml of DCM at 0° C. was added cyclopentyl acetyl chloride (8.4 g, 57.3 mmol). Work up gave 1.2 g of amide, which was used for further step without purification.

To a stirring solution of above amide (1.14, 2.86 mmol) in 28 ml of anhydrous DCM at 0° C. was added oxalyl chloride (0.5 g, 4.2 mmol). The reaction mixture was brought to rt and stirring continued for another one hour. Then the reaction mixture was cooled to −10° C. and to it anhydrous $FeCl_3$ (0.7 g, 4.2 mmol) was added portion wise. The stirring was continued for 12 h at rt and the reaction mixture was treated with 5.0 ml of 2.0 M HCl for 2 h. The organic layer was separated washed with water and brine, dried over $Na_2SO_4$ and concentrated in vacuo. Methanol (20 ml) and conc $H_2SO_4$ (0.2 ml) was added to the foamy residue and reaction was heated to reflux for 12 h; usual work up as desribed in example 418 gave 0.5 g of 8-bromo-1-cyclopentylmethyl-5-methoxy-3,4-dihydro-isoquinoline-3-carboxylic acid methyl ester.

The above compound (0.5 g, 1.3 mmol) was dissolved in 15 ml of DCM then 0.6 g (3.3 mmol) of copper acetate and 0.66 g (0.6 mmol) of $NEt_3$ was added. Usual work up gave 0.4 g of 8-bromo-1-cyclopentylmethyl-5-methoxy-isoquinoline-3-carboxylic acid methyl ester.

To a stirring solution of 0.4 g (1.05 mmol) of the above ester in 2.5 ml of THF, 0.6 ml of MeOH was added along with 0.6 ml of 2N LiOH at rt. Usual work up as described in general procedure C gave 0.38 g of title compound as a light yellow solid.

$^1$H-NMR (400 MHZ, $CDCl_3$): δ 8.96 (s, 1H), 7.98 (d, 1H), 6.90 (d, 1H), 4.02 (s, 3H), 3.81 (d, 2H), 2.46 (m,1H), 1.71 (m, 4H), 1.54 (m, 2H), 1.30 (m, 2H). LCMS: 365 (M+1).

Example 611

(2S)-[(8-Bromo-1-cyclopentylmethyl-5-methoxy-isoquinoline-3-carbonyl)-amino]-3,3-dimethyl-butyric acid 0.3 g (0.96 mmol) of 8-Bromo-1-cyclopentylmethyl-5-methoxy-isoquinoline-3-carboxylic acid (example 610) was reacted with (2S)-amino-3,3-dimethyl-butyric acid methyl ester HCL (0.26 g, 1.4 mmol) as described in general procedure A. 0.35 g of ester was isolated after column chromatography using 4:1 hexane ethyl acetate as an eluents. 20 mg ester was hydrolyzed by sonication at rt for 3 h and then usual work up as described in general procedure C to afford 19.0 mg of the title compound as a white solid.
LCMS: 478 (M+1).

Example 612

(2S)-{[8-(4-tert-Butyl-phenyl)-1-cyclopentylmethyl-5-methoxy-isoquinoline -3-carbonyl]-amino}-3,3-dimethyl-butyric acid (2S)-[(8-Bromo-1-cyclopentylmethyl-5-methoxy-isoquinoline-3-carbonyl)-amino]-3,3-dimethyl-butyric acid methyl ester (62 mg, 0.012 mmol) from above example, 4-tert-butyl phenyl boronic acid (44 mg, 0.024 mmol), Pd $(PPh_3)_4$ (14.6 mg, 0.0012 mmol) and 0.6 ml of 2N $Na_2CO_3$ were taken up in 10 ml of toluene and degassed with nitrogen for 15 min. The reaction mixture stirred over night at 90° C. then usual work up and purification as described in General Procedure D gave the ester which was hydrolyzed by sonication at rt for 3 h and then usual work up as described in general procedure C to afford 38 mg of the title compound as a white solid.

$^1$H-NMR (400 MHZ, $CDCl_3$): δ 8.97 (d, 1H), 8.90 (s, 1H), 7.45 (m, 4H), 7.22 (m, 1H), 7.00 (d, 1H), 4.68 (d, 1H), 4.03 (s, 3H), 2.49 (d, 2H), 2.2 (m, 1H), 1.36 (m, 6H), 1.35 (s, 9H), 1.25 (m, 2H), 1.12 (s, 9H). LCMS: 531 (M+1).

Example 613

8-(4-tert-Butyl-phenyl)-1-cyclopentylmethyl-5-methoxy-isoquinoline-3-carboxylic acid 0.2 g (0.52 mmol) of 8-bromo-1-cyclopentylmethyl-5-methoxy-isoquinoline-3-carboxylic acid methyl ester (from Example 610, step 3), 4-tert-butyl phenyl boronic acid (139 mg, 0.78 mmol), Pd $(PPh_3)_4$ (60 mg, 0.05 mmol) and 0.26 ml of 2N $Na_2CO_3$ were taken in 10 ml of toluene and degassed with nitrogen for 15 min. The reaction mixture stirred over night at 90° C. then usual work up and purification as described in procedure D gave ester which was hydrolyzed as described in general procedure C to afford 0.19 g of the title compound as a white solid.
LCMS: 418 (M+1).

Example 614

8-(4-tert-Butyl-phenyl)-1-cyclopentylmethyl-5-hydroxy-isoquinoline-3-carboxylic acid To a stirring solution of 8-(4-tert-butyl-phenyl)-1-cyclopentylmethyl-5-methoxy-isoquinoline-3-carboxylic acid (190 mg, 0.45 mmol) in 3 ml of DMF was added sodium ethane thiolate (383 mg, 4.5 mmol) and resulting mixture was heated at 120° C. for 4 h. Ethyl acetate was added (10 ml) to mixture and washed with 1 N HCl, water and brine and dried over $Na_2SO_4$. Evaporation of the solvent under vacuo gave 160 mg of the title compound as a thick liquid.
LCMS: 404 (M+1).

Example 615

(2S)-{[8-(4-tert-Butyl-phenyl)-1-cyclopentylmethyl-5-hydroxy-isoquinoline-3-carbonyl]-amino}-3,3-dimethyl-butyric acid 0.15 g (0.37 mmol) of above acid (Example 614) was reacted with (2S)-amino-3,3-dimethyl-butyric acid methyl ester HCl (0.13 g, 0.74 mmol) as described in general procedure A. 0.17 g of ester was isolated after column chromatography using 7:1 hexane and ethyl acetate as an eluents. 20 mg ester was hydrolyzed by sonicating at rt for 3 h and then usual work up as described in general procedure C afforded 19.0 mg of the title compound as a white solid.
LCMS: 517 (M+1).

Example 616 (204373)

(2S)-{[8-(4-tert-Butyl-phenyl)-1-cyclopentylmethyl-isoquinoline-3-carbonyl]-amino}-3,3-dimethyl-butyric acid To a stirring solution of (from example 615) (2S)-{[8-(4-tert-Butyl-phenyl)-1-cyclopentylmethyl-5-hydroxy-isoquinoline-3-carbonyl]-amino}-3,3-dimethyl-butyric acid methyl ester (150 mg, 0.22 mmol), $NEt_3$ (420 mg, 4.2 mmol) and DMAP (cat) in DCM (5 ml) was added trifluoromethane sulfonic anhydride (95.8 mg, 0.33 mmol) at 0° C. The stirring was continued for another 30 min then 10 ml of DCM was added. The reaction mixture was washed with saturated citric acid, water and brine then dried over anhydrous $Na_2SO_4$. Filtration followed by evaporation of the solvent under vacuum gave 168 mg of triflate, which was used for the next step without purification.

The above triflate (25 mg, 0.037 mmol), $PdCl_2$ (dppf) (3.0 mg, 0.0037 mmol), $NEt_3$ (18.9 mg, 0.18 mmol) and 8.6 pL of formic acid were taken in 2 ml of DMF heated at 90° C. for 2 h. Evaporation of the DMF under vacuo followed by column chromatography using 9:1 hexane and ethyl acetate as an eluents gave ester which was hydrolyzed by sonication at r.t for 3 h and then usual work up as described in general procedure C to afford 10 mg of the title compound as a white solid.
LCMS: 501 (M+1).

Example 617

(2S)-{[8-(4-tert-Butyl-phenyl)-1-cyclopentylmethyl-5-furan-3-yl-isoquinoline-3-carbonyl]-amino}-3,3-dimethyl-butyric acid 30 mg (0.05 mmol) of triflate (from example 616, step 1), thiophene-3-boronic acid (10.1 mg, 0.09 mmol), Pd $(PPh_3)_4$ (5.3 mg, 0.005 mmol) and 0.15 ml of 2N $Na_2CO_3$ were taken in 3 ml of toluene and degassed with nitrogen for 15 min. The reaction mixture stirred over night at 90° C. then usual work up and purification as described in procedure D gave ester which was hydrolyzed as described in general procedure C to afford 18 mg of the title compound as a white solid.
LCMS: 567 (M+1).

Example 618

8-(4-tert-Butyl-phenoxy)-1-cyclopentylmethyl-5-methoxy-isoquinoline-3-carboxylic acid The stirring solution of 100 mg (0.26 mmol) of 8-bromo-1-cyclopentylmethyl-5-methoxy-isoquinoline-3-carboxylic acid methyl ester (example 610, step 3), 59 mg (0.4 mmol) of 4-tert-butyl phenol, 170 mg (0.52 mmol) of $Cs_2CO_3$, 4.9 mg (0.026 mmol) of CuI and 8.1 mg (0.078 mmol) of N,N-dimethylglycine HCl in 3 ml of dioxane was degassed for 10 min then heated at 90° C. for 48 h. Evaporation of the dioxane followed by column chromatography using 9:1 hexane and ethyl acetate as eluent gave ester, which was hydrolyzed as described in general procedure C to afford 35 mg of the title compound as a white solid.
LCMS: 434 (M+1)+

Example 619

(2S)-{[8-(4-tert-Butyl-phenoxy)-1-cyclopentylmethyl-5-methoxy-isoquinoline-3-carbonyl]-amino}-3,3-dimethyl-butyric acid 25 mg (0.057 mmol) of above acid (Example 618) was reacted with (2S)-amino-3,3-dimethyl-butyric acid methyl ester HCl (20 mg, 0.11 mmol) as described in general procedure A. The ester was isolated after column chromatography using 7:1 hexane and ethyl acetate as eluent and was hydrolyzed by sonicating at rt for 3 h and then usual work up as described in general procedure C to afford 15.0 mg of the title compound as a white solid.
LCMS: 547 (M+1)+.

By analogous methods to those described above the following Examples were synthesized.

| Example | Name | LC/MS |
|---|---|---|
| 620 | 3-Biphenyl-4-yl-(2S)-[(8-bromo-1-cyclopentylmethyl-5-methoxy-isoquinoline-3-carbonyl)-amino]-propionic acid | 588 |
| 621 | (2R)-{[8-(4-tert-Butyl-phenyl)-1-cyclopentylmethyl-5-methoxy-isoquinoline-3-carbonyl]-amino}-cyclopentyl-acetic acid | 543 |
| 622 | (2R)-{[8-(4-tert-Butyl-phenyl)-1-cyclopentylmethyl-5-methoxy-isoquinoline-3-carbonyl]-amino}-phenyl-acetic acid | 551 |
| 623 | (2R)-{[8-(4-tert-Butyl-phenyl)-1-cyclopentylmethyl-5-methoxy-isoquinoline-3-carbonyl]-amino}-3,3-dimethyl-butyric acid | 531 |

Biological Assay

The following assay methods may be used to identify compounds of Formula (I) that are effective in antagonizing the function of factor IX. Compounds of Formula (I) are effective in antagonizing the function of factor IX may be as inhibitors of the intrinsic clotting pathway.

General Assay Procedure

Factor IXa Florescence Based Molecular Assay:

To determine the $IC_{50}$ of compounds of Formula (I) relative to factor IXa, 12 μL solutions of compounds of Formula (I) at various concentrations (2% DMSO final concentration) were incubated for 10 min at room temp. with a 24 gL solution of FIXa (HCIXA-0050 Haemotologic Technologies Inc. Essex Junction, VT; 3.9 units/mL) in buffer containing 80% Ethylene glycol, 10 mM $CaCl_2$, 200 mM NaCl, and 100 mM Tris (pH 7.4) where the 24 μL solution of FIXa had an activity of 3.9 units/mL. The reaction was started by the addition of 12 μL of 0.5 mM FIXa substrate (Pefa-10148 from Pentapharm Basel, Switzerland; methyl sulfonyl-D-cyclohexylglycyl-glycyl-arginine-7-amino-4-methylcoumarid monoacetate, available from Centerchem, Inc.). After incubating the reaction for 10 min at room temp, the plate was read in a Spectromax Gemini fluorescence plate reader with and exitation wavelenth of 340 nm and an emmision wavelength of 440 nm. From the varying concentrations of test compound, $IC_{50}$'s are then calculated.

Factor XIa Chromogenic Based Molecular Assay:

To determine the $IC_{50}$ of compounds of Formula (I) relative to factor XIa, 20 μL solutions of compounds of Formula (I) at various concentrations (2% DMSO final concentration) were incubated for 10 min at room temp. with a 10 μL solution of FXIa (HCXIA-0160 from Haemotologic Technologies Inc.

Essex Junction, VT) in buffer containing 50 mM Tris (pH 7.4) and 150 mM NaCl where the 10 μL solution of FXIa had an activity of 2 units/mL, and 150 μL of buffer. The reaction was started by the addition of 20 μL of 10 mM FXIa substrate (Pefa-3371 from Pentapharm Basel, Switzerland; Pyr-Phg-Arg-pNA monoacetate, available from Centerchem, Inc.). After incubating the reaction for 10 min at room temp, the plate was read in a Spectromax UV/vis plate reader at 405 nm.

The Examples in Table 1 inhibit Factor IX in the Factor IXa Florescence assay and Factor XI in the Factor XIa Chromogenic assay with an $IC_{50}$ of less than 30 micromolar, or the Examples in Table 1 inhibit Factor XI in the Factor XIa Chromogenic assay with $IC_{50}$ of less than 30 micromolar.

FIXa In Vitro Clotting Assay

Compounds of Formula (I) of the present invention were evaluated for their inhibition of clotting in plasma to which exogenous Factor IXa was added. 20 μL solutions of compounds of Formula (I) at various concentrations having 2% DMSO were incubated with 30 μL FIXa (HCXIA-0160 from Haemotologic Technologies Inc. Essex Junction, Vt.) 3.2 units/mL in assay buffer containing 20 mM HEPES (pH 7.4) and 150 mM NaCl, 50 μL of 1:64 dilution of ALEXIN (trinity biosciences) in assay buffer, and 50 μL reconstituted human citrated plasma (Sigma) for 10 min at 37° C. The reaction was started by the addition of 50 μL of 40 mM $CaCl_2$ in assay buffer. The plate was read in kinetic mode at 405 nm and 37° C. immediately after addition of calcium. The plate was read for 5-10 min (depending on clot time) in 10 sec intervals on a Spectromax UV/vis plate reader.

FXIa In Vitro Clotting Assay:

Compounds of Formula (I) of the present invention were evaluated for their inhibition of clotting in plasma to which exogenous Factor XI was added. 20 μL solutions of compounds of Formula (I) at various concentrations having 2% DMSO were incubated with 30 μL FXIa (HCXIA-0160 from Haemotologic Technologies Inc. Essex Junction, Vt.) 0.4 units/mL in assay buffer containing 20 mM HEPES (pH 7.4) and 150 mM NaCl, 50 μL of 1:64 dilution of ALEXIN (trinity biosciences) in assay buffer, and 50 μL reconstituted human citrated plasma (Sigma) for 10 min at 37° C. The reaction was started by the addition of 50 μL of 40 mM $CaCl_2$ in assay buffer. The plate was read in kinetic mode at 405 nm and 37° C. immediately after addition of calcium. The plate was read for 5-10 min (depending on clot time) in 10 sec intervals on a Spectromax UV/vis plate reader.

The Examples in Table 1 either inhibit Factor IX in the Factor IXa in vitro clotting assay and Factor XI in the in vitro clotting assay with an $IC_{50}$ of less than 30 micromolar, or the Examples in Table 1 inhibit Factor XI in the Factor XIa in vitro clotting assay with $IC_{50}$ of less than 30 micromolar.

While the invention has been described and illustrated with reference to certain preferred embodiments therof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for factor IXa-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:
1. The compound of Formula (I):

$$Ar_2—K \qquad (I)$$

wherein $Ar_2$ is 3-isoquinolinyl or a 3-tetrahydroisoquinolyl group substituted with a 7-(alkyl-phenoxy) or a 6-(alkyl-phenoxy) group and further optionally substituted 1 to 6 times, wherein the substituents are independently selected from the group consisting of:

a) -fluoro;
b) -chloro;
c) -bromo;
d) -iodo;
e) -cyano;
f) -nitro;
g) -perfluoroalkyl;
h) -$T_1$-$R_{20}$;
i) -alkyl;
j) -aryl;
k) -heteroaryl;
l) -heterocyclyl;
m) -cycloalkyl;
n) -alkylene-aryl;
o) -alkylene-arylene-aryl;
p) -alkylene-arylene-alkyl;
q) -arylene-alkyl;
r) -arylene-aryl;
s) -arylene-heteroaryl;
t) -heteroarylene-aryl;
u) -heteroarylene-heteroaryl;
v) -heteroarylene-heterocyclyl;
w) -arylene-heterocyclyl;
x) -arylene-arylene-alkyl;
y) -$T_1$-alkyl;
z) -$T_1$-aryl;
aa) -$T_1$-alkylene-aryl;
bb) -$T_1$-alkenylene-aryl;
cc) -$T_1$-alkylene-heteroaryl;
dd) -$T_1$-alkenylene-heteroaryl;
ee) -$T_1$-cycloalkylene-aryl;
ff) -$T_1$-cycloalkylene-heteroaryl;
gg) -$T_1$-heterocyclylene-aryl;
hh) -$T_1$-heterocyclylene-heteroaryl;
ii) -$T_1$-arylene-alkyl;
jj) -$T_1$-arylene-alkenyl;
kk) -$T_1$-alkylene-arylene-aryl;
ll) -$T_1$-arylene-$T_2$-aryl;
mm) -$T_1$-arylene-arylene-aryl;
nn) -$T_1$-alkylene-arylene-alkyl;
oo) -alkylene-$T_1$-alkylene-aryl;
pp) -arylene-$T_1$-alkyl;
qq) -arylene-$T_1$-alkylene-aryl;
rr) -$T_1$-alkylene-$T_2$-aryl;
ss) -$T_1$-alkylene-aryl;
tt) -alkylene-$T_1$-heteroaryl;
uu) -alkylene-$T_1$-cycloalkyl;
vv) -alkylene-$T_1$-heterocyclyl;
ww) -alkylene-T-arylene-alkyl;
xx) -alkylene-$T_1$-alkylene-arylene-alkyl;
yy) -alkylene-$T_1$-alkyl;
zz) -alkylene-$T_1$-$R_{20}$;
aaa) -arylene-$T_1$-$R_{20}$;
bbb) -alkylene-cycloalkyl;
ccc) -$T_1$-arylene-$T_2$-alkylene-aryl;
ddd) -$T_1$-arylene-aryl;
eee) -$T_1$-alkylene-cycloalkyl;

fff) -$T_1$-cycloalkyl;
ggg) -$T_1$-heterocyclyl-$T_2$-aryl;
hhh) -$T_1$-alkynyl;
iii) -$T_1$-alkylene-$T_2$-alkyl; and
jjj) -hydrogen;
wherein
$R_{20}$ is selected from the group consisting of -hydrogen, -alkyl, -alkenyl, -alkylene-cycloalkyl, -alkynene-heterocyclyl, -aryl, -heteroaryl, -arylene-alkyl, -alkylene-aryl, -alkylene-arylene-alkyl, -alkylene-arylene-aryl, -alkylene-arylene-alkyl-aryl, -alkylene-arylene-O-arylene, and alkylene-arylene-O-alkylene-aryl;
$T_1$ is selected from the group consisting of —$CH_2$—, —O—, —$N(R_{21})$—, —$C(O)$—, —$CON(R_{21})$—, —$N(R_{21})C(O)$—, —$N(R_{21})CON(R_{22})$—, —$N(R_{21})C(O)O$—, —$OC(O)N(R_{21})$—, —$N(R_{21})SO_2$—, —$SO_2N(R_{21})$—, —$C(O)$—, —S—, —$S(O)$—, —$S(O_2)$—, —$N(R_{21})SO_2N(R_{22})$—,

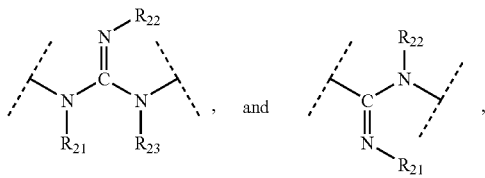

wherein
$R_{21}$, $R_{22}$ and $R_{23}$, are independently selected from the group consisting of: -hydrogen, -alkyl, -alkenyl, -alkylene-cycloalkyl, -alkynene-heterocyclyl, -aryl, -heteroaryl, -arylene-alkyl, -alkylene-aryl, -alkylene-arylene-alkyl, -alkylene-arylene-aryl, -alkylene-arylene-alkylene-aryl, -alkylene-arylene-O-arylene, and alkylene-arylene-O-alkylene-aryl; and
$T_2$ is selected from the group consisting of a direct bond, —$CH_2$—, —O—, —$N(R_{24})$—, —$C(O)$—, —$CON(R_{24})$—, —$N(R_{24})C(O)$—, —$N(R_{24})CON(R_{25})$—, —$N(R_{24})C(O)O$—, —$OC(O)N(R_{24})$—, —$N(R_{24})SO_2$—, —$SO_2N(R_{24})$—, —$C(O)$—O—, —O—$C(O)$—, —S—, —$S(O)$—, —$S(O_2)$—, and —$N(R_{24})SO_2N(R_{25})$—,
wherein $R_{24}$ and $R_{25}$ are independently selected from the group consisting of: -hydrogen, -alkyl, -alkenyl, -alkylene-cycloalkyl, alkynene-heterocyclyl, -aryl, -heteroaryl, -arylene-alkyl, -alkylene-aryl, and -alkylene-arylene-alkyl; and
K is selected from the group consisting of a group of the formula

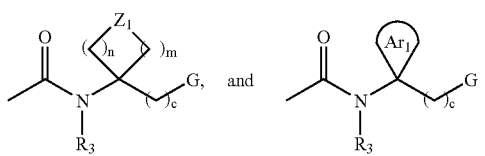

wherein
c is equal to 0, 1, or 2; wherein the values of 0, 1, and 2 are a direct bond, —$CH_2$—, and —$CH_2$—$CH_2$—, optionally substituted 1 to 4 times with a substituent selected from the group consisting of: -alkyl, -aryl, -alkylene-aryl, -arylene -alkyl, -alkylene-arylene-alkyl, —O-alkyl, —O-aryl, and -hydroxyl;
G is —$CO_2R_1$,
wherein
$R_1$ is selected from the group consisting of: -hydrogen, -alkyl, alkoxy, alkylhydroxy, alkyl-N,N'-dialkyl-amino, alkyl-amino-acyl, -aryl, -arylene-alkyl, -alkylene-aryl, -alkylene-arylene-alkyl, and
$R_3$ is selected from the group consisting of: hydrogen, -alkyl, alkylene-aryl, -aryl, and -alkylene-cycloalkyl;
$Z_1$ is selected from the group consisting of —$CH_2$—, —$C(O)$—, —O—, —$N(H)$—, —S—, —$S(O)$—, —$S(O_2)$—, —$CON(H)$—, —$NHC(O)$—, —$NHC(O)N(H)$—, —$NH(SO_2)$—, —$S(O_2)N(H)$—, —(O)CO—, —$NHS(O_2)NH$—, —$OC(O)$—, —$N(R_6)$—, —$N(C(O)R_6)$—, —$N(C(O)NHR_6)$—, —$N(S(O_2)NHR_6)$—, —$N(SO_2R_6)$—, and —$N(C(O)OR_6)$—;
wherein
$R_6$ is selected from the group consisting of: -hydrogen, alkyl, aryl, and alkylene-aryl;
m and n are, independently, 1, 2, 3, or 4;
$Ar_1$ is selected from the group consisting of an fused cycloalkylaryl, fused cycloalkylheteroaryl, fused heterocyclylaryl, and fused heterocyclylheteroaryl group optionally substituted 1 to 7 times, wherein the substituents are independently selected from the group consisting of:
a) -fluoro;
b) -chloro;
c) -bromo;
d) -iodo;
e) -cyano;
f) -nitro;
g) -perfluoroalkyl;
h) -$D_1$-$R_{14}$;
i) -alkyl;
j) -aryl;
k) -heteroaryl;
l) -heterocyclyl;
m) -cycloalkyl;
n) -alkylene-aryl;
o) -alkylene-heteroaryl;
p) -alkylene-arylene-$D_1$-$R_{14}$;
q) -alkylene-heteroarylene-$D_1$-$R_{14}$;
r) -alkylene-arylene-aryl;
s) -alkylene-heteroarylene-aryl;
t) -alkylene-arylene-heteroaryl;
u) -alkylene-arylene-arylene-$D_1$-$R_{14}$;
v) -alkylene-arylene-alkyl;
w) -alkylene-heteroarylene-alkyl;
x) -$D_1$-cycloalkyl;
y) -arylene-cycloalkyl;
z) -heteroarylene-alkyl;
aa) -arylene-arylene-alkyl;
bb) -$D_1$-alkyl;
cc) -$D_1$-aryl;
dd) -$D_1$-heteroaryl;
ee) -$D_1$-arylene-$D_2R_{14}$;
ff) -$D_1$-heteroarylene-$D_2$-$R_{14}$;
gg) -$D_1$-alkylene-heteroaryl;
hh) -$D_1$-alkylene-aryl;
ii) -$D_1$-alkylene-arylene-$D_2$-$R_{14}$
jj) -$D_1$-alkylene-heteroarylene-$D_2$-$R_{14}$
kk) -$D_1$-arylene-alkyl;
ll) -$D_1$-heteroarylene-alkyl;
mm) -$D_1$-alkylene-arylene-aryl;
nn) -$D_1$-alkylene-heteroarylene-aryl;

oo) -D$_1$-arylene-arylene-aryl;
pp) -D$_1$-alkylene-arylene-alkyl;
qq) -D$_1$-alkylene-heteroarylene-alky
ss) -alkylene-D$_1$-alkylene-aryl;
tt) -alkylene-D$_1$-alkylene-arylene-D$_2$-R$_{14}$
uu) -arylene-D$_1$-alkyl;
vv) -arylene-D$_1$-cycloalkyl;
ww) -arylene-D$_1$-heterocyclyl;
xx) -alkylene-D$_1$-aryl;
yy) -alkylene-D$_1$-heteroaryl;
zz) -alkylene-D$_1$-arylene-D$_2$-R$_{14}$
aaa) -alkylene-D$_1$-heteroarylene-D$_2$-R$_{14}$
bbb) -alkylene-D$_1$-heteroaryl;
ccc) -alkylene-D$_1$-cycloalkyl;
ddd) -alkylene-D$_1$-heterocyclyl;
eee) -alkylene-D$_1$-arylene-alkyl;
fff) -alkylene-D$_1$-heteroarylene-alkyl;
ggg) -alkylene-D$_1$-alkylene-arylene-alkyl;
hh) -alkylene-D$_1$-alkylene-heteroarylene-alkyl;
iii) -alkylene-D$_1$-alkyl;
jjj) -alkylene-D$_1$-R$_{14}$;
kkk) -arylene-D$_1$-R$_{14}$;
lll) -heteroarylene-D$_1$-R$_{14}$;
mmm) -D$_1$-alkynyl;
nnn) -D$_1$-alkylene-cycloalkyl;
ooo) -arylene-D$_1$-arylene-D$_2$-R$_{14}$ and
ppp) -hydrogen;
    wherein
    R$_{14}$, is selected from the group consisting of: -hydrogen, -alkyl, -aryl, -heteroaryl, -arylene-alkyl, -heteroarylene-alkyl, -alkylene-aryl, -alkylene-heteroaryl, -alkylene-arylene-alkyl, and -alkylene-heteroaryle-alkyl;
    D$_1$ is selected from the group consisting of —CH$_2$—, -alkylene-, -alkenylene-, -alkylene-S—, —S-alkylene-, -alkylene-O—, —O-alkylene-, -alkylene-S(O)$_2$—, —S(O)$_2$-alkylene, —O—, —N(R$_{15}$)—, —C(O)—, —CON(R$_{15}$)—, —N(R$_{15}$)C(O)—, —N(R$_{15}$)CON(R$_{16}$)—, —N(R$_{15}$)C(O)O—, —OC(O)N(R$_{15}$)—, —N(R$_{15}$)SO$_2$—, —SO$_2$N(R$_{15}$)—, —C(O)—O—, —O—C(O)—, —S—, —S(O)—, —S(O$_2$)—, —N(R$_{15}$)SO$_2$N(R$_{16}$)—,

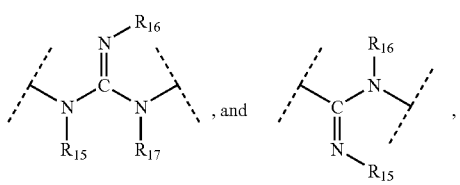

wherein
    R$_{15}$, R$_{16}$, and R$_{17}$ are independently selected from the group consisting of: -hydrogen, -alkyl, -aryl, -heteroaryl, -arylene-alkyl, -heteroarylene-alkyl, -alkylene-aryl, -alkylene-heteroaryl, -alkylene-arylene-alkyl, and -alkylene-heteroarylene-alkyl; and
    D$_2$ is selected from the group consisting of —CH$_2$—, -alkylene-, -alkenylene-, -alkylene-S—, —S-alkylene-, -alkylene-O—, —O-alkylene-, -alkylene-S(O)$_2$—, —S(O)$_2$-alkylene, —O—, —N(R$_{18}$)—, —C(O)—, —CON(R$_{18}$)—, —N(R$_{18}$)C(O)—, —N(R$_{18}$)CON(R$_{19}$)—, —N(R$_{18}$)C(O)O—, —OC(O)N(R$_{18}$)—, —N(R$_{18}$)S$_2$—, —SO$_2$N(R$_{18}$)—, —C(O)—C—, —O—C(O)—, —S—, —S(O)—, —S(O$_2$)—, and —N(R$_{18}$)SO$_2$N(R$_{19}$)—,
    wherein
    R$_{18}$ and R$_{19}$ are independently selected from the group consisting of: -hydrogen, -alkyl, -aryl, -arylene-alkyl, -alkylene-aryl, and -alkylene-arylene-alkyl;
and wherein
    the alkyl, aryl, heteroaryl, alkylene, and arylene groups in Ar$_1$, Ar$_2$, R$_1$-R$_{26}$ may be optionally substituted 1 to 4 times with a substituent group selected from the group consisting of:
    a) -hydrogen;
    b) -fluoro;
    c) -chloro;
    d) -bromo;
    e) -iodo;
    f) -cyano;
    g) -nitro;
    h) -perfluoroalkyl;
    i) -Q-perfluoroalkyl
    j) -Q-R$_{27}$;
    k) -Q-alkyl;
    l) -Q-aryl;
    m) -Q-alkylene-aryl;
    n) -Q-alkylene-NR$_{27}$R$_{28}$; and
    o) -Q-alkyl-W—R$_{28}$;
    wherein
    Q and W are independently selected from the group consisting of: —CH$_2$—, —O—, —N(R$_{29}$)—, —C(O)—, —CON(R$_{29}$)—, —N(R$_{29}$)C(O)—, —N(R$_{29}$)CON(R$_{30}$)—, —N(R$_{29}$)C(O)O—, —OC(O)N(R$_{29}$)—, —N(R$_{29}$)SO$_2$—, —SO$_2$N(R$_{29}$)—, —C(O)—O—, —O—C(O)—, and —N(R$_{29}$)SO$_2$N(R$_{30}$)—, wherein R$_{27}$, R$_{28}$, R$_{29}$, and R$_{30}$ are independently selected from the group consisting of: -hydrogen, -alkyl, -aryl, -arylene-alkyl, -alkylene-aryl, and -alkylene-arylene-alkyl;
or a pharmaceutically acceptable salt, or solvate thereof.

2. The compound of Formula (I) in claim 1 or a pharmaceutically acceptable salt, or solvate thereof, wherein Ar$_2$ is a 3-isoquinolinyl group substituted with a 7-(alkyl-phenoxy) or a 6-(alkyl-phenoxy) group and further substituted 1 to 6 times.

3. The compound of Formula (I) in claim 1 or a pharmaceutically acceptable salt, or solvate thereof, wherein Ar$_2$ is a 3-isoquinolyl or a 3-tetrahydroisoquinolyl group with a 7-(alkyl-phenoxy) or a 6-(alkyl-phenoxy) group-further having 1 to 5 substituents, wherein the substituents are independently selected from the group consisting of:
    a) -fluoro;
    b) -chloro;
    c) -bromo;
    d) -iodo;
    e) -cyano;
    f) -nitro;
    g) -perfluoroalkyl;
    h) -T$_1$-R$_{20}$;
    i) -alkyl;
    j) -aryl;
    k) -heteroaryl;
    l) -heterocyclyl;
    m) -cycloalkyl;
    n) -alkylene-aryl;
    o) -alkylene-arylene-aryl;
    p) -alkylene-arylene-alkyl;
    q) -arylene-alkyl;

r) -arylene-aryl;
s) -arylene-heteroaryl;
t) -heteroarylene-aryl;
u) -heteroarylene-heteroaryl;
v) -heteroarylene-heterocyclyl;
w) -arylene-heterocyclyl;
x) -arylene-arylene-alkyl;
y) -$T_1$-alkyl;
z) -$T_1$-aryl;
aa) -$T_1$-alkylene-aryl;
bb) -$T_1$-alkenylene-aryl;
cc) -$T_1$-alkylene-heteroaryl;
dd) -$T_1$-alkenylene-heteroaryl;
ee) -$T_1$-cycloalkylene-aryl;
ff) -$T_1$-cycloalkylene-heteroaryl;
gg) -$T_1$-heterocyclylene-aryl;
hh) -$T_1$-heterocyclylene-heteroaryl;
ii) -$T_1$-arylene-alkyl;
jj) -$T_1$-arylene-alkenyl;
kk) -$T_1$-alkylene-arylene-aryl;
ll) -$T_1$-arylene-$T_2$-aryl;
mm) -$T_1$-arylene-arylene-aryl;
nn) -$T_1$-alkylene-arylene-alkyl;
oo) -alkylene-$T_1$-alkylene-aryl;
pp) -arylene-$T_1$-alkyl;
qq) -arylene-$T_1$-alkylene-aryl;
rr) -$T_1$-alkylene-$T_2$-aryl;
ss) -$T_1$-alkylene-aryl;
tt) -alkylene-$T_1$-heteroaryl;
uu) -alkylene-$T_1$-cycloalkyl;
vv) -alkylene-$T_1$-heterocyclyl;
ww) -alkylene-T-arylene-alkyl;
xx) -alkylene-$T_1$-alkylene-arylene-alkyl;
yy) -alkylene-$T_1$-alkyl;
zz) -alkylene-$T_1$-$R_{20}$;
aaa) -arylene-$T_1$-$R_{20}$;
bbb) -alkylene-cycloalkyl;
ccc) -$T_1$-arylene-$T_2$-alkylene-aryl;
ddd) -$T_1$-arylene-aryl;
eee) -$T_1$-alkylene-cycloalkyl;
fff) -$T_1$-cycloalkyl;
ggg) -$T_1$-heterocyclyl-$T_2$-aryl;
hhh) -$T_1$-alkynyl;
iii) -$T_1$-alkylene-$T_2$-alkyl; and
jjj) -hydrogen;
wherein
$R_{20}$ is selected from the group consisting of: -hydrogen, -alkyl, -alkenyl, -alkylene-cycloalkyl, -alkynene-heterocyclyl, -aryl, -heteroaryl, -arylene-alkyl, -alkylene-aryl, -alkylene-arylene-alkyl, -alkylene-arylene-aryl, -alkylene-arylene-alkylene-aryl, -alkylene-arylene-O-arylene, and alkylene-arylene-O-alkylene-aryl;
$T_1$ is selected from the group consisting of —$CH_2$—, —O—, —N($R_{21}$)—, —C(O)—, —CON($R_{21}$)—, —N($R_{21}$)CON($R_{22}$)—, —N($R_{21}$)C(O)O—, —OC(O)N($R_{21}$)—, —N($R_{21}$)SO_2—, —SO_2N($R_{21}$)—, —C(O)—O—, —O—C(O)—, —S—, —S(O)—, —S(O_2)—, —N($R_{21}$)SO_2N($R_{22}$)—,

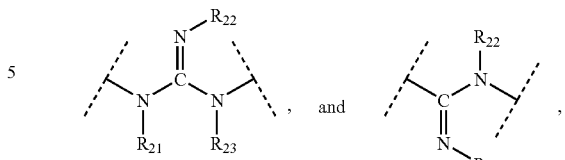

wherein
$R_{21}$, $R_{22}$ and $R_{23}$, are independently selected from the group consisting of: -hydrogen, -alkyl, -alkenyl, -alkylene-cycloalkyl, -alkynene-heterocyclyl, -aryl, -heteroaryl, -arylene-alkyl, -alkylene-aryl, -alkylene-arylene-alkyl, -alkylene-arylene-aryl, -alkylene-arylene-alkylene-aryl, -alkylene-arylene-O-arylene, and alkylene-arylene-O-alkylene-aryl; and
$T_2$ is selected from the group consisting of a direct bond, —$CH_2$—, —O—, —N($R_{24}$)—, —C(O)—, —CON($R_{24}$)—, —N($R_{24}$C(O)—, —N($R_{24}$)CON ($R_{25}$)—, —N($R_{24}$)C(O)O—, —OC(O)N($R_{24}$)—, —N($R_{24}$)SO_2—, —SO_2N($R_{24}$)—, —C(O)—O—, —O—C(O)—, —S—, —S(O)—, —S(O_2)—, and
wherein
$R_{24}$ and $R_{25}$ are independently selected from the group consisting of: -hydrogen, -alkyl, -alkenyl, -alkylene-cycloalkyl, alkynene-heterocyclyl, -aryl, -heteroaryl, -arylene-alkyl, -alkylene-aryl, and -alkylene-arylene-alkyl.

4. The compound of Formula (I) in claim 1 or a pharmaceutically acceptable salt, or solvate thereof, wherein $Ar_2$ is selected from the group consisting of: a substituted 3-isoquinolyl, and a substituted 3-tetrahydroisoquinolyl group with a 7-(alkyl-phenoxy) or a 6-(alkyl-phenoxy) group - further having 1 to 5 substituents independently selected from the group consisting of:
a) -fluoro;
b) -chloro;
c) -bromo;
d) -iodo;
e) -cyano;
f) -nitro;
g) -perfluoroalkyl;
h) -$T_1$-$R_{20}$;
i) -alkyl;
j) -aryl;
k) -arylene-alkyl;
l) -$T_1$-alkyl;
m) -$T_1$-alkylene-aryl;
n) -$T_1$-alkylene-arylene-aryl;
o) -$T_1$-alkylene-arylene-alkyl;
p) -arylene-$T_1$-alkyl;
q) -alkylene-cycloalkyl; and
r) -$T_1$-arylene-alkyl;
wherein
$T_1$ is selected from the group consisting of —$CH_2$—, —O—, —N($R_{21}$)—, —CON($R_{21}$)—, —C(O)O— $R_{21}$, and —N($R_{21}$)C(O)—; wherein $R_{20}$ and $R_{21}$ are independently selected from the group consisting of: -hydrogen, -alkyl- and -aryl.

5. The compound of Formula (I) in claim 1 or a pharmaceutically acceptable salt, or solvate thereof, wherein $Ar_2$ is a 1-(alkylene-cycloalkyl)-7-(alkyl-phenoxy)-isoquinolyl-3-yl group.

6. The compound of Formula (I) in claim 1 or a pharmaceutically acceptable salt, or solvate thereof, wherein $Ar_2$ is selected from the group consisting of: 7-(4-tert-butyl-phenoxy)-2-(2-cyclopentyl-acetyl)-1,2,3,4-tetrahydro-isoquinoline, 6-(4-tert-butyl-phenoxy)-2-(2-cyclopentyl-acetyl)-1,2,3,4-tetrahydro-isoquinoline, 7-(4-tert-butyl-phenoxy)-3,4-dihydro-1H-isoquinoline-2-carboxylic acid isobutyl ester, 6-(4-tert-butyl-phenoxy)-isoquinoline, 7-(4-tert-butyl-phenoxy)-isoquinoline, and 6-(4-tert-butyl-phenoxy)-isoquinoline.

7. The compound of Formula (I) in claim 1 or a pharmaceutically acceptable salt, or solvate thereof, wherein $Ar_2$ is selected from the group consisting of: 7-(4-tert-butyl-phenoxy)-1-cyclopentylmethyl-isoquinoline, 7-(4-tert-butyl-phenoxy)-1-cyclohexyl-isoquinoline, 7-(4-tert-Butyl-phenoxy)-1-cycloheptyl-isoquinoline, 7-(4-tert-Butyl-phenoxy)-1-phenethyl-isoquinoline, and 6-(4-tert-butyl-phenoxy)-1-cyclopentylmethyl-isoquinoline.

8. The compound of Formula (I) in claim 1 or a pharmaceutically acceptable salt, or solvate thereof, wherein c is equal to 0 or 1.

9. The compound of Formula (I) in claim 1 or a pharmaceutically acceptable salt, or solvate thereof, wherein c is equal to 0.

10. The compound of Formula (I) in claim 1 or a pharmaceutically acceptable salt, or solvate thereof, wherein G is $CO_2R_1$, wherein $R_1$ is independently selected from the group consisting of: -hydrogen, -alkyl, -aryl, -arylene-alkyl, -alkylene-aryl, and -alkylene-arylene-alkyl.

11. The compound of Formula (I) in claim 1 or a pharmaceutically acceptable salt, or solvate thereof, wherein G is $-CO_2R_1$; wherein $R_1$ is selected from the group consisting of: -hydrogen, -alkyl and aryl.

12. The compound of Formula (I) in claim 1 or a pharmaceutically acceptable salt, or solvate thereof, wherein G is $-CO_2H$.

13. The compound of Formula (I) in claim 1 or a pharmaceutically acceptable salt, or solvate thereof, wherein G $-CO_2R_1$ wherein $R_1$ is selected from the group consisting of -alkyl, -alkylene-aryl, and -aryl.

14. The compound of Formula (I) in claim 1 or a pharmaceutically acceptable salt, or solvate thereof, wherein K is a group of the formula:

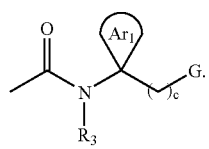

15. The compound of Formula (I) in claim 14 or a pharmaceutically acceptable salt, or solvate thereof, wherein $Ar_1$ is selected from the group consisting of a fused cycloalkylaryl optionally substituted 1 to 7 times.

16. A pharmaceutical composition comprising a compound of Formula (I) as in claim 1 or a pharmaceutically acceptable salt, or solvate thereof.

17. The pharmaceutical composition of claim 16, wherein the compound of Formula (I) or a pharmaceutically acceptable salt, or solvate thereof is an antagonist of factor XI or factor IX/XI activity.

18. The pharmaceutical composition of claim 17, wherein the compound of Formula (I) or a pharmaceutically acceptable salt, or solvate thereof is a partial antagonist of both factor XI and factor XI/IX activity, wherein a partial antagonist comprises a compound that inhibits less than complete activity at a physiological dose.

19. The pharmaceutical composition of claim 18, wherein the compound of Formula (I) or a pharmaceutically acceptable salt, or solvate thereof inhibits up to 95% of factor XI or factor IX/XI activity.

20. The pharmaceutical composition of claim 18, wherein the compound of Formula (I) or a pharmaceutically acceptable salt, or solvate thereof inhibits up to 80% of factor XI or factor IX/XI activity.

21. The pharmaceutical composition of claim 17, wherein the compound of Formula (I) or a pharmaceutically acceptable salt, or solvate thereof antagonizes blood clotting mediated by factor XI or factor IX/XI.

22. The pharmaceutical composition of claim 17, comprising a therapeutically effective amount of the compound of Formula (I) or a pharmaceutically acceptable salt, or solvate thereof, wherein said therapeutically effective amount of Formula (I) or a pharmaceutically acceptable salt, or solvate thereof preferentially inhibits the intrinsic clotting cascade as compared to the extrinsic clotting cascade.

23. The pharmaceutical composition of claim 22, wherein said therapeutically effective amount of Formula (I) or a pharmaceutically acceptable salt, or solvate thereof inhibits the intrinsic clotting cascade by greater than 80% and inhibits the extrinsic clotting cascade by less than 50%.

24. The pharmaceutical composition of claim 23, wherein said therapeutically effective amount of Formula (I) or a pharmaceutically acceptable salt, or solvate thereof comprises an amount sufficient to achieve and maintain a sustained blood level that at least partially antagonizes factor XI or factor IX/XI biological activity.

25. The pharmaceutical composition of claim 24, wherein said sustained blood level comprises a concentration ranging from about 0.01 μM to 2 mM.

26. The pharmaceutical composition of claim 24, wherein said sustained blood level comprises a concentration ranging from about 1 μM to 300 μM.

27. The pharmaceutical composition of claim 24, wherein said sustained blood level comprises a concentration ranging from about 20 μM to about 100 μM.

28. The pharmaceutical composition of claim 16, wherein the compound of Formula (I) or a pharmaceutically acceptable salt, or solvate thereof is an antagonist of factor IX activity.

29. The pharmaceutical composition of claim 28, wherein the compound of Formula (I) or a pharmaceutically acceptable salt, or solvate thereof is a partial antagonist of factor IX activity, wherein a partial antagonist comprises a compound that inhibits less than complete activity at a physiological dose.

30. The pharmaceutical composition of claim 29, wherein the compound of Formula (I) or a pharmaceutically acceptable salt, or solvate thereof inhibits up to 95% of factor IX activity.

31. The pharmaceutical composition of claim 29, wherein the compound of Formula (I) or a pharmaceutically acceptable salt, or solvate thereof inhibits up to 80% of factor IX activity.

32. The pharmaceutical composition of claim 29, wherein the compound of Formula (I) or a pharmaceutically acceptable salt, or solvate thereof inhibits up to 50% of factor IX activity.

33. The pharmaceutical composition of claim 28, wherein the compound of Formula (I) or a pharmaceutically acceptable salt, or solvate thereof antagonizes blood clotting mediated by factor IX.

34. The pharmaceutical composition of claim 16, comprising a therapeutically effective amount of the compound of Formula (I) or a pharmaceutically acceptable salt, or solvate thereof, wherein said therapeutically effective amount comprises a sufficient amount of the compound of Formula (I) or a pharmaceutically acceptable salt, or solvate thereof to at least partially inhibit the biological activity of factor IX in a subject.

35. The pharmaceutical composition of claim 16, comprising a therapeutically effective amount of the compound of Formula (I) or a pharmaceutically acceptable salt, or solvate thereof, wherein said therapeutically effective amount of Formula (I) or a pharmaceutically acceptable salt, or solvate thereof comprises a sufficient amount of the compound of Formula (I) or a pharmaceutically acceptable salt, or solvate thereof to at least partially inhibit the intrinsic clotting cascade in a subject.

36. The pharmaceutical composition of claim 35, wherein said therapeutically effective amount of Formula (I) or a pharmaceutically acceptable salt, or solvate thereof preferentially inhibits the intrinsic clotting cascade as compared to the extrinsic clotting cascade.

37. The pharmaceutical composition of claim 35, wherein said therapeutically effective amount of Formula (I) or a pharmaceutically acceptable salt, or solvate thereof inhibits the intrinsic clotting cascade by greater than 80% and inhibits the extrinsic clotting cascade by less than 50%.

38. The pharmaceutical composition of claim 35, wherein said therapeutically effective amount of Formula (I) or a pharmaceutically acceptable salt, or solvate thereof comprises a sufficient amount of the compound of Formula (I) for at least partial amelioration of at least one factor IX-mediated disease.

39. The pharmaceutical composition of claim 16 in the form of an oral dosage or parenteral dosage unit.

40. The pharmaceutical composition of claim 16, wherein said compound of Formula (I) or a pharmaceutically acceptable salt, or solvate thereof comprises a dose in a range from about 0.01 to 1,000 mg/kg of body weight per day.

41. The pharmaceutical composition of claim 16, wherein said compound of Formula (I) or a pharmaceutically acceptable salt, or solvate thereof comprises a dose in a range from about 0.1 to 100 mg/kg of body weight per day.

42. The pharmaceutical composition of claim 16, wherein said compound of Formula (I) or a pharmaceutically acceptable salt, or solvate thereof comprises a dose in a range from about 0.5 to 10 mg/kg of body weight per day.

43. The pharmaceutical composition of claim 38, wherein said factor IX-mediated disease comprises stroke.

44. The pharmaceutical composition of claim 38, wherein said factor IX-mediated disease comprises deep vein thrombosis.

45. The pharmaceutical composition of claim 44, wherein said thrombosis is associated with surgical procedures, long periods of confinement, acquired or inherited pro-coagulant states including anti-phospholipid antibody syndrome, protein C deficiency and protein S deficiency, or acute and chronic inflammation including recurrent miscarriage or Systemic Lupus Erythmatosis (SLE).

46. The pharmaceutical composition of claim 38, wherein said factor IX-mediated disease comprises excessive clotting associated with the treatment of kidney diseases by hemodialysis and/or venous hemofiltration.

47. The pharmaceutical composition of claim 38, wherein said factor IX-mediated disease comprises cardiovascular disease.

48. The pharmaceutical composition of claim 47, wherein said cardiovascular disease comprises myocardial infarction, arrhythmia, or aneurysm.

49. The pharmaceutical composition of claim 16 further comprising one or more therapeutic agents.

50. The pharmaceutical composition of claim 16, comprising a therapeutically effective amount of the compound of Formula (I) or a pharmaceutically acceptable salt, or solvate thereof, wherein said therapeutically effective amount comprises a sufficient amount of the compound of Formula (I) or a pharmaceutically acceptable salt, or solvate thereof to at least partially inhibit the biological activity of factor XI or factor IX/XI in a subject.

51. The pharmaceuticai composition of claim 16, wherein the compound of Formula (I) or a pharmaceutically acceptable salt, or solvate thereof antagonizes blood clotting.

52. The pharmaceutical composition of claim 16, comprising a therapeutically effective amount of the compound of Formula (I) or a pharmaceutically acceptable salt, or solvate thereof, wherein said therapeutically effective amount of Formula (I) or a pharmaceutically acceptable salt, or solvate thereof comprises a sufficient amount of the compound of Formula (I) or a pharmaceutically acceptable salt, or solvate thereof to at least partially inhibit blood clotting in a subject.

53. A pharmaceutical composition comprising a compound of Formula (I) as in claim 2 or a pharmaceutically acceptable salt, or solvate thereof.

54. A pharmaceutical composition comprising a compound of Formula (I) as in claim 3 or a pharmaceutically acceptable salt, or solvate thereof.

55. A pharmaceutical composition comprising a compound of Formula (I) as in claim 4 or a pharmaceutically acceptable salt, or solvate thereof.

56. A pharmaceutical composition comprising a compound of Formula (I) as in claim 5 or a pharmaceutically acceptable salt, or solvate thereof.

57. A pharmaceutical composition comprising a compound of Formula (I) as in claim 6 or a pharmaceutically acceptable salt, or solvate thereof.

58. A pharmaceutical composition comprising a compound of Formula (I) as in claim 7 or a pharmaceutically acceptable salt, or solvate thereof.

59. A pharmaceutical composition comprising a compound of Formula (I) as in claim 8 or a pharmaceutically acceptable salt, or solvate thereof.

60. A pharmaceutical composition comprising a compound of Formula (I) as in claim 9 or a pharmaceutically acceptable salt, or solvate thereof.

61. A pharmaceutical composition comprising a compound of Formula (I) as in claim 10 or a pharmaceutically acceptable salt, or solvate thereof.

62. A pharmaceutical composition comprising a compound of Formula (I) as in claim 11 or a pharmaceutically acceptable salt, or solvate thereof.

63. A pharmaceutical composition comprising a compound of Formula (I) as in claim 12 or a pharmaceutically acceptable salt, or solvate thereof.

64. A pharmaceutical composition comprising a compound of Formula (I) as in claim 13 or a pharmaceutically acceptable salt, or solvate thereof.

65. A pharmaceutical composition comprising a compound of Formula (I) as in claim 14 or a pharmaceutically acceptable salt, or solvate thereof.

66. A pharmaceutical composition comprising a compound of Formula (I) as in claim 15 or a pharmaceutically acceptable salt, or solvate thereof.

* * * * *

UNITED STATES PATENT AND TRADEMARK OFFICE
CERTIFICATE OF CORRECTION

PATENT NO. : 7,544,699 B2
APPLICATION NO. : 10/913168
DATED : June 9, 2009
INVENTOR(S) : Adnan M. M. Mjalli et al.

It is certified that error appears in the above-identified patent and that said Letters Patent is hereby corrected as shown below:

Title Page, Item (56) References Cited:
Page 2, Column 2, under Other Publications, line 3, please delete "Intergrin", please insert -- Integrin --.

Page 2, Column 2, under Other Publications, line 34, after "of", please insert -- Copy of --.

Page 2, Column 2, under Other Publications, line 38, after "of", please insert -- Copy of --.

Page 2, Column 2, under Other Publications, line 42, after "of", please insert -- Copy of --.

Page 2, Column 2, under Other Publications, line 46, after "of", please insert -- Copy of --.

Column 1, line 9, please delete "Antviral", please insert -- Antiviral --.

Column 1, line 10, please delete "Componds", please insert -- Compounds --.

Column 1, line 29, after "collective", please delete "activity".

Column 2, line 31, please delete "intrinisic", please insert -- intrinsic --.

Column 3, line 36, please delete "Tthe", please insert -- The --.

Column 4, line 35, please delete "The", please insert -- There --.

Column 5, line 6, please delete "throbosis", please insert -- thrombosis --.

Column 5, line 7, please delete "etal.", please insert -- et al. --.

UNITED STATES PATENT AND TRADEMARK OFFICE
CERTIFICATE OF CORRECTION

PATENT NO. : 7,544,699 B2
APPLICATION NO. : 10/913168
DATED : June 9, 2009
INVENTOR(S) : Adnan M. M. Mjalli et al.

It is certified that error appears in the above-identified patent and that said Letters Patent is hereby corrected as shown below:

Column 5, lines 8-16, please delete "Thus, embodiments of the present invention, provide compounds of Formula (1), pharmaceutical compositions, and methods to inhibit the clotting activities of factor XI and/or both factor IX and factor XI. Inhibition of hemostasis with agents that may selectively inhibit the intrinsic pathway intact and allow the formation of small, but hemostatically important amounts of factor Xa and thrombin.", after "(1999)]", please insert new paragraph -- Thus, embodiments of the present invention, provide compounds of Formula (1), pharmaceutical compositions, and methods to inhibit the clotting activities of factor XI and/or both factor IX and factor XI. Inhibition of hemostasis with agents that may selectively inhibit the intrinsic pathway intact and allow the formation of small, but hemostatically important amounts of factor Xa and thrombin. --.

Column 5, line 30, please delete "Forumula", please insert -- Formula --.

Column 5, lines 33-34, please delete "inveniton", please insert -- invention --.

Column 5, line 38, please delete "inveniton", please insert -- invention --.

Column 6, line 59, please delete "-$T_1$-alkylene-$T_2$-alkyl;or", please insert -- -$T_1$-alkylene-$T_2$-alkyl; or --.

Column 6, line 64, please delete "-alkynene", please insert -- alkylene --.

Column 7, line 17, please delete "alkynene", please insert -- alkylene --.

Column 7, line 28 (approx.), please delete "alkynene", please insert -- alkylene --.

Column 8, line 22, please delete "isotere,", please insert -- isostere, --.

Column 8, lines 25-30, please delete " 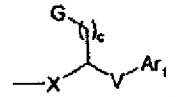 ", please insert --       --.

Column 10, line 30, please delete "—N(SO$_2$R1$_2$)—", please insert -- —N(SO$_2$R$_{12}$)— --.

Column 12, line 6, please delete "D$_1$comprises", please insert -- D$_1$ comprises --.

UNITED STATES PATENT AND TRADEMARK OFFICE
CERTIFICATE OF CORRECTION

PATENT NO. : 7,544,699 B2
APPLICATION NO. : 10/913168
DATED : June 9, 2009
INVENTOR(S) : Adnan M. M. Mjalli et al.

It is certified that error appears in the above-identified patent and that said Letters Patent is hereby corrected as shown below:

Column 12, line 46, please delete "sustituents:", please insert -- substituents: --.

Column 13, lines 10-15 (approx.), please delete "  ", please insert

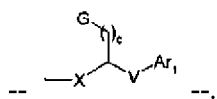 --.

Column 13, line 21, please delete "comprises", please insert -- comprises: --.

Columns 17-18, (Example 6) (Table 1), line 3, please delete "benzoyl-amino]", please insert -- benzoylamino] --.

Columns 17-18, (Example 8) (Table 1), line 3, please delete "benzoyl-amino]", please insert -- benzoylamino] --.

Columns 25-26, (Example 24) (Structure) (Table 1), line 1, should read

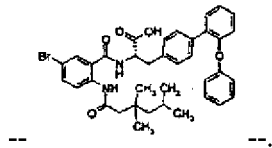 --.

Columns 39-40 (Example 49) (Structure) (Table 1), line 1, should read

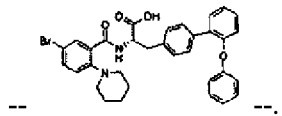 --.

Columns 43-44 (Example 54) (Structure) (Table 1), line 1, should read

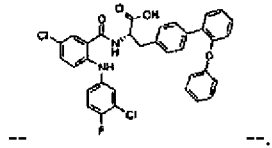 --.

UNITED STATES PATENT AND TRADEMARK OFFICE
CERTIFICATE OF CORRECTION

PATENT NO. : 7,544,699 B2  
APPLICATION NO. : 10/913168  
DATED : June 9, 2009  
INVENTOR(S) : Adnan M. M. Mjalli et al.

It is certified that error appears in the above-identified patent and that said Letters Patent is hereby corrected as shown below:

Columns 43-44 (Example 55) (Structure) (Table 1), line 1, should read

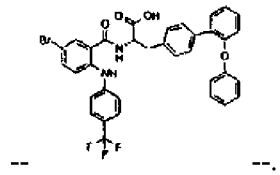

-- --.

Columns 45-46 (Example 58) (Structure) (Table 1), line 1, should read

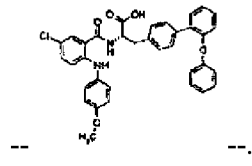

-- --.

Columns 47-48 (Example 64) (Table 1), line 3, please delete "(4-", please insert -- (4'- --.

Columns 49-50 (Example 65) (Table 1), line 1, please delete "4yl", please insert -- 4-yl --.

Columns 49-50 (Example 66) (Table 1), line 9, please delete "acid:", please insert -- acid --.

Columns 49-50 (Example 67) (Table 1), line 1, please delete "(2", please insert -- [2 --.

Columns 55-56 (Example 78) (Table 1), lines 4-5, please delete ",2,3,4-", please insert -- 1,2,3,4 --.

Columns 55-56 (Example 80) (Table 1), lines 3-4, please delete "cyctopentyl-", please insert -- cyclopentyl- --.

Columns 55-56 (Example 81) (Table 1), line 1, please delete "3-Biphenyt", please insert -- 3-Biphenyl --.

Columns 57-58 (Example 83) (Structure) (Table 1), line 1, should read

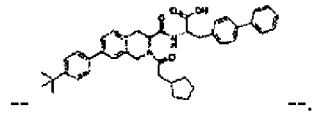

-- --.

UNITED STATES PATENT AND TRADEMARK OFFICE
CERTIFICATE OF CORRECTION

PATENT NO.       : 7,544,699 B2
APPLICATION NO.  : 10/913168
DATED            : June 9, 2009
INVENTOR(S)      : Adnan M. M. Mjalli et al.

It is certified that error appears in the above-identified patent and that said Letters Patent is hereby corrected as shown below:

Columns 65-66 (Example 99) (Structure) (Table 1), line 1, should read

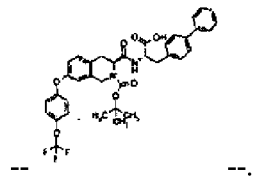
-- --.

Columns 67-68 (Example 100) (Structure) (Table 1), line 1, should read

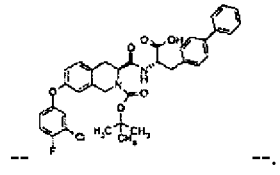
-- --.

Columns 73-74 (Example 112) (Table 1), line 1, please delete "(2", please insert
-- [2 --.

Columns 73-74 (Example 114) (Table 1), line 8, please delete "amino)-", please insert
-- amino}- --.

Columns 79-80 (Example 124) (Table 1), line 6, please delete "henoxy)-", please insert
-- phenoxy)- --.

Columns 79-80 (Example 125) (Table 1), line 6, please delete "henoxy)-", please insert
-- phenoxy)- --.

Columns 79-80 (Example 126) (Table 1), line 1, please delete "{(2-", please insert
-- {[2- --.

Columns 83-84 (Example 133) (Table 1), line 6, please delete "isoquinoiine-",
please insert -- isoquinoline- --.

Columns 93-94 (Example 150) (Table 1), line 1, please delete "(3,", please insert
-- (3', --.

Columns 97-98 (Example 158) (Structure) (Table 1), line 1, should read

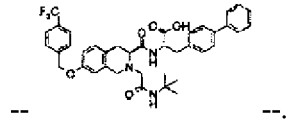
-- --.

UNITED STATES PATENT AND TRADEMARK OFFICE
CERTIFICATE OF CORRECTION

PATENT NO.       : 7,544,699 B2
APPLICATION NO.  : 10/913168
DATED            : June 9, 2009
INVENTOR(S)      : Adnan M. M. Mjalli et al.

It is certified that error appears in the above-identified patent and that said Letters Patent is hereby corrected as shown below:

Columns 99-100 (Example 162) (Table 1), lines 3-4, please delete "(4-rifluoromethyl-", please insert -- (4-trifluoromethyl- --.

Columns 111-112 (Example 187) (Table 1), line 7, please delete "-henyl", please insert -- phenyl --.

Columns 111-112 (Example 190) (Table 1), line 7, please delete "(4-trifl uoromethyl-", please insert -- (4-trifluoromethyl- --.

Columns 117-118 (Example 202) (Table 1), line 1, please delete "{(2-", please insert -- {[2- --.

Columns 119-120 (Example 205) (Table 1), line 7, please delete "carbonyl]amino]", please insert -- carbonyl]-amino} --.

Columns 123-124 (Example 211) (Structure) (Table 1), line 1, should read

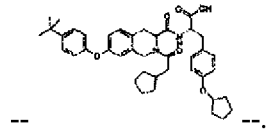

--                            --.

Columns 123-124 (Example 212) (Structure) (Table 1), line 1, should read

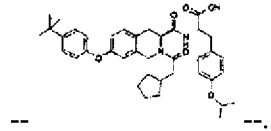

--                            --.

Columns 125-126 (Example 215) (Structure) (Table 1), line 1, should read

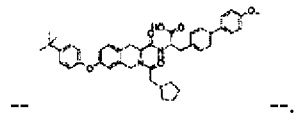

--                            --.

Columns 127-128 (Example 220) (Table 1), line 9, please delete "phenyl]propionic", please insert -- phenyl]-propionic --.

Columns 131-132 (Example 227) (Table 1), line 1, please delete "-(4-tert-", please insert -- 7-(4-tert- --.

UNITED STATES PATENT AND TRADEMARK OFFICE
CERTIFICATE OF CORRECTION

PATENT NO.       : 7,544,699 B2
APPLICATION NO.  : 10/913168
DATED            : June 9, 2009
INVENTOR(S)      : Adnan M. M. Mjalli et al.

It is certified that error appears in the above-identified patent and that said Letters Patent is hereby corrected as shown below:

Columns 131-132 (Example 227) (Table 1), line 7, please delete "isoquinoiine", please insert -- isoquinoline --.

Columns 133-134 (Example 232) (Structure) (Table 1), line 1, should read

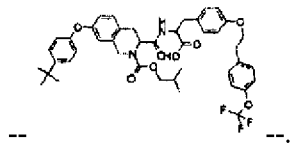

-- --.

Columns 135-136 (Example 238) (Table 1), line 7, please delete "oxadiazo]", please insert -- oxadiazol --.

Columns 135-136 (Example 239) (Table 1), line 7, please delete "oxadiazo]", please insert -- oxadiazol --.

Columns 141-142 (Example 253) (Table 1), line 7, please delete "oxadiazo]", please insert -- oxadiazol --.

Columns 141-142 (Example 254) (Table 1), line 7, please delete "oxadiazo]", please insert -- oxadiazol --.

Columns 143-144 (Example 257) (Table 1), line 7, please delete "oxadiazo]", please insert -- oxadiazol --.

Columns 143-144 (Example 258) (Table 1), line 1, please delete "5-", please insert -- 5'- --.

Columns 143-144 (Example 258) (Table 1), line 7, please delete "oxadiazo]", please insert -- oxadiazol --.

Columns 143-144 (Example 259) (Table 1), line 6, please delete "oxadiazo]", please insert -- oxadiazol --.

Columns 145-146 (Example 260) (Table 1), line 5, please delete "oxadiazo]", please insert -- oxadiazol --.

Columns 145-146 (Example 261) (Table 1), line 4, please delete "(3-", please insert -- (3'- --.

UNITED STATES PATENT AND TRADEMARK OFFICE
CERTIFICATE OF CORRECTION

PATENT NO.         : 7,544,699 B2
APPLICATION NO. : 10/913168
DATED                  : June 9, 2009
INVENTOR(S)       : Adnan M. M. Mjalli et al.

It is certified that error appears in the above-identified patent and that said Letters Patent is hereby corrected as shown below:

Columns 145-146 (Example 261) (Table 1), line 7, please delete "oxadiazo]", please insert -- oxadiazol --.

Columns 145-146 (Example 262) (Table 1), line 7, please delete "oxadiazo]", please insert -- oxadiazol --.

Columns 145-146 (Example 263) (Table 1), line 7, please delete "oxadiazo]", please insert -- oxadiazol --.

Columns 147-148 (Example 264) (Table 1), line 5, please delete "oxadiazo]", please insert -- oxadiazol --.

Columns 147-148 (Example 265) (Table 1), line 5, please delete "oxadiazo]", please insert -- oxadiazol --.

Columns 147-148 (Example 266) (Table 1), line 3, please delete "oxadiazo]", please insert -- oxadiazol --.

Columns 147-148 (Example 267) (Table 1), line 5, please delete "oxadiazo]", please insert -- oxadiazol --.

Columns 147-148 (Example 268) (Table 1), line 5, please delete "oxadiazo]", please insert -- oxadiazol --.

Columns 149-150 (Example 270) (Table 1), line 7, please delete "oxadiazo]", please insert -- oxadiazol --.

Columns 149-150 (Example 272) (Table 1), line 6, please delete "oxadiazo]", please insert -- oxadiazol --.

Columns 151-152 (Example 273) (Table 1), line 6, please delete "oxadiazo]", please insert -- oxadiazol --.

Columns 151-152 (Example 274) (Table 1), line 7, please delete "oxadiazo]", please insert -- oxadiazol --.

Columns 151-152 (Example 275) (Table 1), line 7, please delete "oxadiazo]", please insert -- oxadiazol --.

UNITED STATES PATENT AND TRADEMARK OFFICE
CERTIFICATE OF CORRECTION

PATENT NO.      : 7,544,699 B2
APPLICATION NO. : 10/913168
DATED           : June 9, 2009
INVENTOR(S)     : Adnan M. M. Mjalli et al.

It is certified that error appears in the above-identified patent and that said Letters Patent is hereby corrected as shown below:

Columns 151-152 (Example 276) (Table 1), line 7, please delete "oxadiazo]", please insert -- oxadiazol --.

Columns 153-154 (Example 277) (Table 1), lines 1-2, please delete "triftuoromethyl-", please insert -- trifluoromethyl- --.

Columns 153-154 (Example 277) (Table 1), line 9, please delete "oxadiazo]", please insert -- oxadiazol --.

Columns 153-154 (Example 278) (Table 1), line 3, please delete "1';3'", please insert -- 1',3' --.

Columns 153-154 (Example 279) (Table 1), line 5, please delete "oxadiazo]", please insert -- oxadiazol --.

Columns 153-154 (Example 279) (Table 1), line 7, please delete "1';3'", please insert -- 1',3' --.

Columns 153-154 (Example 280) (Table 1), line 3, please delete "carboxylicacid", please insert -- carboxylic acid --.

Columns 153-154 (Example 280) (Table 1), line 7, please delete "oxadiazo]", please insert -- oxadiazol --.

Columns 155-156 (Example 281) (Table 1), line 7, please delete "oxadiazo]", please insert -- oxadiazol --.

Columns 155-156 (Example 282) (Table 1), line 3, please delete "carboxylicacid", please insert -- carboxylic acid --.

Columns 155-156 (Example 282) (Table 1), line 7, please delete "oxadiazo]", please insert -- oxadiazol --.

Columns 155-156 (Example 283) (Table 1), line 7, please delete "oxadiazo]", please insert -- oxadiazol --.

Columns 157-158 (Example 284) (Table 1), line 5, please delete "oxadiazo]", please insert -- oxadiazol --.

UNITED STATES PATENT AND TRADEMARK OFFICE
CERTIFICATE OF CORRECTION

PATENT NO.       : 7,544,699 B2
APPLICATION NO.  : 10/913168
DATED            : June 9, 2009
INVENTOR(S)      : Adnan M. M. Mjalli et al.

It is certified that error appears in the above-identified patent and that said Letters Patent is hereby corrected as shown below:

Columns 157-158 (Example 285) (Table 1), line 7, please delete "oxadiazo]", please insert -- oxadiazol --.

Columns 157-158 (Example 286) (Table 1), line 5, please delete "oxadiazo]", please insert -- oxadiazol --.

Columns 163-164 (Example 300) (Table 1), line 3, please delete "isoquinoiine-", please insert -- isoquinoline- --.

Columns 163-164 (Example 303) (Table 1), line 6, please delete "oxadiazo]", please insert -- oxadiazol --.

Columns 165-166 (Example 304) (Table 1), line 5, please delete "penyl", please insert -- phenyl --.

Columns 165-166 (Example 304) (Table 1), line 6, please delete "oxadiazo]", please insert -- oxadiazol --.

Columns 169-170 (Example 315) (Table 1), line 3, please delete "isoquinoiine-", please insert -- isoquinoline- --.

Columns 171-172 (Example 321) (Table 1), line 3, please delete "isoquinoiine-", please insert -- isoquinoline- --.

Columns 171-172 (Example 323) (Table 1), line 3, please delete "isoquinoiine-", please insert -- isoquinoline- --.

Columns 173-174 (Example 334) (Table 1), line 7, please delete "oxadiazo]", please insert -- oxadiazol --.

Columns 175-176 (Example 337) (Table 1), line 6, please delete "oxad iazo]", please insert -- oxadiazol --.

Columns 175-176 (Example 338) (Table 1), line 3, please delete "isoqunoline-", please insert -- isoquinoline- --.

Columns 177-178 (Example 343) (Table 1), line 5, please delete "amino]-", please insert -- amino}- --.

UNITED STATES PATENT AND TRADEMARK OFFICE
CERTIFICATE OF CORRECTION

PATENT NO. : 7,544,699 B2
APPLICATION NO. : 10/913168
DATED : June 9, 2009
INVENTOR(S) : Adnan M. M. Mjalli et al.

It is certified that error appears in the above-identified patent and that said Letters Patent is hereby corrected as shown below:

Columns 179-180 (Example 349) (Table 1), line 7, please delete "oxadiazo]", please insert -- oxadiazol --.

Columns 187-188 (Example 365) (Table 1), line 7, please delete "phenyl]succinamic", please insert -- phenyl}-succinamic --.

Columns 189-190 (Example 371) (Table 1), lines 1-2, please delete "isoquinoiine-", please insert -- isoquinoline- --.

Columns 189-190 (Example 372) (Table 1), line 5, please delete "amino}-", please insert -- -amino}- --.

Columns 189-190 (Example 373) (Table 1), line 4, please delete "amino}-", please insert -- -amino}- --.

Columns 209-210 (Example 414) (Table 1), line 3, please delete "ethylsuifanyl-", please insert -- ethylsulfanyl- --.

Columns 213-214 (Example 419) (Table 1), line 1, please delete "henoxy)-", please insert -- phenoxy)- --.

Columns 213-214 (Example 420) (Table 1), lines 3-4, please delete "yclopentylmethyl", please insert -- cyclopentylmethyl --.

Columns 213-214 (Example 421) (Structure) (Table 1), line 1, should read

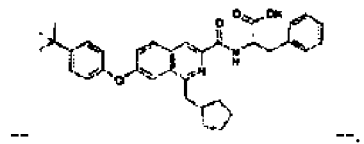
-- --.

Columns 217-218 (Example 428) (Structure) (Table 1), line 1, should read

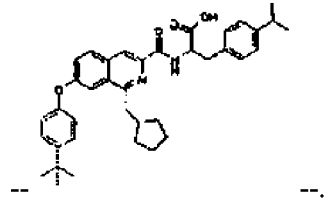
-- --.

UNITED STATES PATENT AND TRADEMARK OFFICE
CERTIFICATE OF CORRECTION

PATENT NO.        : 7,544,699 B2                                        Page 12 of 23
APPLICATION NO.  : 10/913168
DATED              : June 9, 2009
INVENTOR(S)       : Adnan M. M. Mjalli et al.

It is certified that error appears in the above-identified patent and that said Letters Patent is hereby corrected as shown below:

Columns 217-218 (Example 429) (Structure) (Table 1), line 1, should read

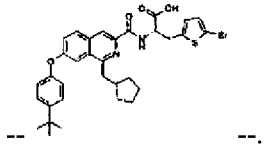
-- --.

Columns 229-230 (Example 455) (Table 1), lines 4-5, please delete "isoquinoiine-3-", please insert -- isoquinoline-3- --.

Columns 229-230 (Example 457) (Table 1), line 5, please delete "carbonyl]amino]", please insert -- carbonyl]-amino} --.

Columns 231-232 (Example 462) (Table 1), line 6, please delete "indol- -yl", please insert -- indol-yl --.

Columns 239-240 (Example 478) (Structure) (Table 1), line 1, should read

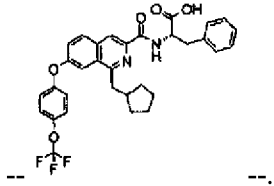
-- --.

Columns 243-244 (Example 485) (Table 1), line 5, please delete "carbonyl]amino}", please insert -- carbonyl]-amino} --.

Columns 243-244 (Example 486) (Table 1), line 5, please delete "carbonyl]amino}", please insert -- carbonyl]-amino} --.

Columns 247-248 (Example 495) (Table 1), line 1, please delete
"<4-{[7-(4-tert-Butyl-phe-", please insert -- 4-{[7-(4-tert-Butyl-phe- --.

Columns 249-250 (Example 502) (Table 1), line 5, please delete
"carbonyl]amino}-3-(4-me-", please insert -- carbonyl]-amino}-3-(4-me- --.

Columns 249-250 (Example 503) (Table 1), line 5, please delete "carbonyl]amino}-3-", please insert -- carbonyl]-amino}-3- --.

Column 255-256 (Example 518) (Table 1), line 5, please delete
"amino]-4,4-dimethyl-pen-", please insert -- amino}-4,4-dimethyl-pen- --.

UNITED STATES PATENT AND TRADEMARK OFFICE
CERTIFICATE OF CORRECTION

PATENT NO.        : 7,544,699 B2
APPLICATION NO.   : 10/913168
DATED             : June 9, 2009
INVENTOR(S)       : Adnan M. M. Mjalli et al.

It is certified that error appears in the above-identified patent and that said Letters Patent is hereby corrected as shown below:

Columns 267-268 (Example 543) (Table 1), line 7, please delete "acetic", please insert -- acid --.

Columns 273-274 (Example 554) (Table 1), line 5, please delete "carbonyl]amino]-3,3-dim-", please insert -- carbonyl]-amino}-3,3-dim- --.

Columns 273-274 (Example 555) (Table 1), line 5, please delete "carbonyl]amino]-3,3-dim-", please insert -- carbonyl]-amino}-3,3-dim- --.

Columns 275-276 (Example 557) (Table 1), line 4, please delete "arbonyl]-", please insert -- carbonyl]- --.

Columns 275-276 (Example 558) (Table 1), line 4, please delete "arbonyl]-", please insert -- carbonyl]- --.

Columns 275-276 (Example 559) (Table 1), line 4, please delete "arbonyl]-", please insert -- carbonyl]- --.

Columns 285-286 (Example 580) (Table 1), line 1, please delete "(2R)-[7-(4-tert-Butyl-phe-", please insert -- (2R)-{[7-(4-tert-Butyl-phe --.

Columns 291-292 (Example 591) (Structure) (Table 1), line 1, should read

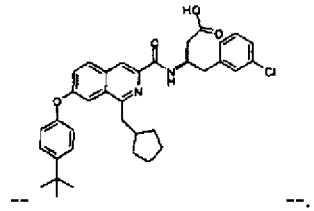

Columns 293-294 (Example 594) (Table 1), line 5, please delete "carbonyl]-amino)-3-p-tolyl-", please insert -- carbonyl]-amino}-3-p-tolyl- --.

Columns 295-296 (Example 597) (Table 1), line 4, please delete "carbony]-", please insert -- carbonyl]- --.

UNITED STATES PATENT AND TRADEMARK OFFICE
CERTIFICATE OF CORRECTION

PATENT NO. : 7,544,699 B2
APPLICATION NO. : 10/913168
DATED : June 9, 2009
INVENTOR(S) : Adnan M. M. Mjalli et al.

It is certified that error appears in the above-identified patent and that said Letters Patent is hereby corrected as shown below:

Columns 297-298 (Example 600) (Structure) (Table 1), line 1, should read

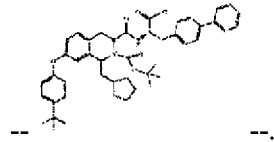
-- --.

Columns 301-302 (Example 609) (Table 1), line 1, should read

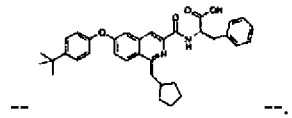
-- --.

Column 311, line 31, please delete "dyil,", please insert -- diyl, --.

Column 313, line 64 (approx.), after "like", please insert -- . --.

Column 318, line 2, please delete "sunstantially", please insert -- substantially --.

Column 319, line 49, please delete "CO$_2$H", please insert -- B(OH)$_2$ --.

Column 320, line 48, please delete "compouind", please insert -- compound --.

Column 321, line 6 (approx.), should read -- 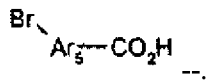 --.

Column 321, line 49, please delete "plladium", please insert -- palladium --.

Column 322, line 32 (approx.), please delete "subsituted", please insert -- substituted --.

Column 323, lines 19-20, please delete "Merrifiend", please insert -- Merrifield --.

Column 323, line 37, should read

-- 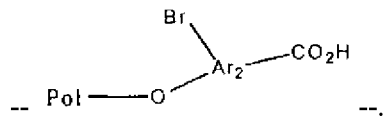 --.

UNITED STATES PATENT AND TRADEMARK OFFICE
CERTIFICATE OF CORRECTION

PATENT NO. : 7,544,699 B2  
APPLICATION NO. : 10/913168  
DATED : June 9, 2009  
INVENTOR(S) : Adnan M. M. Mjalli et al.

It is certified that error appears in the above-identified patent and that said Letters Patent is hereby corrected as shown below:

Column 324, line 9, please delete "plladium", please insert -- palladium --.

Column 324, line 15, please delete "disopropyl carbodimide",
please insert -- diisopropyl carbodiimide --.

Column 324, line 19, please delete "plladium", please insert -- palladium --.

Column 325, line 40 (approx.), should read

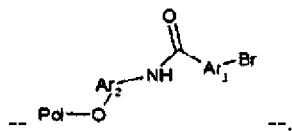

--.

Column 325, line 62, please delete "subsituted", please insert -- substituted --.

Column 327, line 3, please delete "scidification", please insert -- acidification --.

Column 328, line 2, please delete "derivitization", please insert -- derivatization --.

Column 328, line 16, please delete "cyanoborohydroide", please insert
-- cyanoborohydride --.

Column 332, line 23, please delete "previoulsy", please insert -- previously --.

Column 333, line 29, before "such", please delete "group".

Column 341, line 13, please delete "alchol", please insert -- alcohol --.

Column 341, line 41, please delete "injectible", please insert -- injectable --.

Column 342, line 51, please delete "therof,", please insert -- thereof, --.

Column 343, line 12, please delete "therof,", please insert -- thereof, --.

Column 343, line 37, please delete "therof,", please insert -- thereof, --.

Column 343, line 47, please delete "pharmaceutial", please insert -- pharmaceutical --.

Column 343, line 49, please delete "pharmaceutial", please insert -- pharmaceutical --.

UNITED STATES PATENT AND TRADEMARK OFFICE
CERTIFICATE OF CORRECTION

| | | |
|---|---|---|
| PATENT NO. | : 7,544,699 B2 | |
| APPLICATION NO. | : 10/913168 | |
| DATED | : June 9, 2009 | |
| INVENTOR(S) | : Adnan M. M. Mjalli et al. | |

It is certified that error appears in the above-identified patent and that said Letters Patent is hereby corrected as shown below:

Column 343, line 51, please delete "pharmaceutial", please insert -- pharmaceutical --.

Column 345, line 39, please delete "ofr factor", please insert -- or factor --.

Column 346, lines 60-61 (approx.), please delete "97.5%acetonitrile", please insert -- 97.5% acetonitrile --.

Column 347, line 43 (approx.), please delete "dimethypropylene", please insert -- dimethylpropylene --.

Column 349, line 5, please delete "esterfied", please insert -- esterified --.

Column 349, line 45, please delete "NaI", please insert -- NaI --.

Column 349, line 46, please delete "chloriirdes", please insert -- chlorides --.

Column 350, line 51, please delete "es ter", please insert -- ester --.

Column 351, lines 3-4, please delete "in HCl salt formas the HCl salt", please insert -- as the HCl salt --.

Column 351, line 18, please delete "biphenyl alanine", please insert -- biphenylalanine --.

Column 352, line 3, after "(0.020g)", please insert -- . --.

Column 352, line 66, please delete "4yl", please insert -- 4-yl --.

Column 354, line 60, please delete "mmlo", please insert -- mmol --.

Column 356, line 16, please delete "silicagel", please insert -- silica gel --.

Column 357, line 2, (Below Name) (Table), please delete "benzenesulfonylamno", please insert -- benzenesulfonylamino --.

Column 358, line 41, please delete "silical", please insert -- silica --.

Column 360, line 1, please delete "proceudure", please insert -- procedure --.

Column 360, line 40, please delete "biphenyl4", please insert -- biphenyl-4 --.

UNITED STATES PATENT AND TRADEMARK OFFICE
CERTIFICATE OF CORRECTION

| | | |
|---|---|---|
| PATENT NO. | : 7,544,699 B2 | |
| APPLICATION NO. | : 10/913168 | |
| DATED | : June 9, 2009 | |
| INVENTOR(S) | : Adnan M. M. Mjalli et al. | |

It is certified that error appears in the above-identified patent and that said Letters Patent is hereby corrected as shown below:

Column 360, line 51, after "overnight", please insert -- . --.

Column 361, line 28, please delete "Gereral", please insert -- General --.

Column 361, line 31, after "acid.", please delete "L".

Column 361, line 36, please delete "4yl", please insert -- 4-yl --.

Column 362, line 10, please delete "4yl", please insert -- 4-yl --.

Column 362, line 28, please delete "4yl", please insert -- 4-yl --.

Column 362, line 61, please delete "4yl", please insert -- 4-yl --.

Column 363, line 1, please delete "CHCl3", please insert -- $CHCl_3$ --.

Column 363, line 27, please delete "4yl", please insert -- 4-yl --.

Column 363, line 40, please delete "0.051 gof", please insert -- 0.051 g of --.

Column 363, line 60, please delete "4yl", please insert -- 4-yl --.

Column 364, line 25, please delete "tafforded", please insert -- afforded --.

Column 367, line 14, please delete "$(M+1)^{+\cdot}$", please insert -- $(M+1)^{+}$. --.

Column 368, lines 66-67, please delete "triphenylphospine", please insert -- triphenylphosphine --.

Column 369, line 15, please delete "hexanes: EtOAc", please insert -- hexanes:EtOAc --.

Column 369, line 54, please delete "etylcarbamoyl", please insert -- ethylcarbamoyl --.

Column 370, line 3, please delete "triphenylphospine", please insert -- triphenylphosphine --.

Column 373 (Example 124) (Table), line 2, please delete "henoxy", please insert -- phenoxy --.

UNITED STATES PATENT AND TRADEMARK OFFICE
CERTIFICATE OF CORRECTION

PATENT NO. : 7,544,699 B2
APPLICATION NO. : 10/913168
DATED : June 9, 2009
INVENTOR(S) : Adnan M. M. Mjalli et al.

It is certified that error appears in the above-identified patent and that said Letters Patent is hereby corrected as shown below:

Column 373 (Example 125) (Table), line 2, please delete "henoxy", please insert -- phenoxy --.

Column 377 (Example 162) (Table), line 2, please delete "rifluoromethyl", please insert -- trifluoromethyl --.

Column 377 (Example 181) (Table), line 2, please delete "henoxy", please insert -- phenoxy --.

Column 379 (Example 187) (Table), line 3, please delete "henoxy", please insert -- phenoxy --.

Column 383, line 9, please delete "desribed", please insert -- described --.

Column 383, line 22, after "acid", please insert -- . --.

Column 384, line 37, please delete "biphenyl4", please insert -- biphenyl-4 --.

Column 384, line 66, please delete "chloro4'", please insert -- chloro-4' --.

Column 385, line 2, please delete "romo", please insert -- bromo --.

Column 385, lines 20-21, please delete "desribed", please insert -- described --.

Column 386, line 2, please delete "CH2Cl2", please insert -- $CH_2Cl_2$ --.

Column 389 (Example 282) (Table), line 2, please delete "carboxylicacid", please insert -- carboxylic acid --.

Column 389, line 42 (approx.), please delete "3'chloro", please insert -- 3'-chloro --.

Column 389, line 42 (approx.), please delete "biphneyl", please insert -- biphenyl --.

Column 389, line 44 (approx.), please delete "4'trifluoromethyl", please insert -- 4'-trifluoromethyl --.

Column 389, line 47 (approx.), please delete "4'trifluoromethyl", please insert -- 4'-trifluoromethyl --.

UNITED STATES PATENT AND TRADEMARK OFFICE
CERTIFICATE OF CORRECTION

PATENT NO. : 7,544,699 B2
APPLICATION NO. : 10/913168
DATED : June 9, 2009
INVENTOR(S) : Adnan M. M. Mjalli et al.

It is certified that error appears in the above-identified patent and that said Letters Patent is hereby corrected as shown below:

Column 391, line 17 (approx.), please delete "tht", please insert -- the --.

Column 391, line 28, please delete "4'trifluoromethyl", please insert -- 4'-trifluoromethyl --.

Column 391, line 34, please delete "$^1$ H-NMR", please insert -- $^1$H-NMR --.

Column 392, line 19, please delete "isoquinolihne", please insert -- isoquinoline --.

Column 392, line 32, please delete "Na2SO4", please insert -- $Na_2SO_4$ --.

Column 394, line 18, please delete "ABX pattern,1H", please insert -- ABX pattern, 1H --.

Column 394, line 20, please delete "[septet,1H]", please insert -- [septet, 1H] --.

Column 394, line 26, please delete "aminol", please insert -- amino} --.

Column 395, line 11, after "2H]", please insert -- . --.

Column 396, line 1, please delete "quinolihne", please insert -- quinoline --.

Column 396, line 41 (approx.), please delete "yu", please insert -- yl --.

Column 402, line 18, please delete "desribed", please insert -- described --.

Column 403, line 56, please delete "isoq uinoline", please insert -- isoquinoline --.

Column 404, line 8, please delete "desribed", please insert -- described --.

Column 404, lines 44-45, please delete "Garbonyl", please insert -- carbonyl --.

Column 404, line 65, please delete "isoq uinoline", please insert -- isoquinoline --.

Column 405, line 13, please delete "eluent,to", please insert -- eluent, to --.

UNITED STATES PATENT AND TRADEMARK OFFICE
CERTIFICATE OF CORRECTION

PATENT NO. : 7,544,699 B2
APPLICATION NO. : 10/913168
DATED : June 9, 2009
INVENTOR(S) : Adnan M. M. Mjalli et al.

It is certified that error appears in the above-identified patent and that said Letters Patent is hereby corrected as shown below:

Column 405, lines 62-67, please delete "$^1$H-NMR (400 MHZ, CDCl$_3$): δ 9.01 (s, 1H), 8.66 (d,1H), 8.51 (s, 1H), 7.87 (d, 1H), 7.51 (m, 4H), 7.40 (m, 3H), 7.33 (m, 2H), 7.25 (d, 2H0, 5.13 (m, 1H), 4.13 (t, 2H), 3.43 (m, 1H), 3.33 (m, 1H), 2.00 (m, 1H), 1.90 (m, 4H), 1.67 (m, 2H), 1.56 (m, 2H), 1.22 (m, 2H). LCMS: 508 (M+1)$^+$", please insert below "solid." -- $^1$H-NMR (400 MHZ, CDCl$_3$): δ 9.01 (s, 1H), 8.66 (d,1H), 8.51 (s, 1H), 7.87 (d, 1H), 7.51 (m, 4H), 7.40 (m, 3H), 7.33 (m, 2H), 7.25 (d, 2H0, 5.13 (m, 1H), 4.13 (t, 2H), 3.43 (m, 1H), 3.33 (m, 1H), 2.00 (m, 1H), 1.90 (m, 4H), 1.67 (m, 2H), 1.56 (m, 2H), 1.22 (m, 2H). LCMS: 508 (M+1)$^+$ --.

Column 406, lines 3-4, please delete "isoq uinoline", please insert -- isoquinoline --.

Column 406, line 36, please delete "[dt,2H]", please insert -- [dt, 2H] --.

Column 406, line 42 (approx.), please delete "imethylpropyl)-", please insert -- dimethylpropyl)- --.

Column 407, line 9 (approx.), please delete "yclopentyl", please insert -- cyclopentyl --.

Column 407, line 17, before "chromatography", please insert -- gel --.

Column 407 (Example 394) (Table), line 4, please delete "acidmethyl", please insert -- acid methyl --.

Column 407 (Example 397) (Table), line 3, please delete "acidmethyl", please insert -- acid methyl --.

Column 409, line 63, please delete "reation", please insert -- reaction --.

Column 410, line 21, please delete "added .", please insert -- added. --.

Column 410, line 63, please delete "(4:1,1.0 mL)", please insert -- (4:1, 1.0 mL) --.

Column 411, line 64, please delete "oncentrated", please insert -- concentrated --.

Column 414, line 62, after "chromatography", please delete "using".

Column 416, line 28, please delete "mino", please insert -- amino --.

UNITED STATES PATENT AND TRADEMARK OFFICE
CERTIFICATE OF CORRECTION

PATENT NO. : 7,544,699 B2
APPLICATION NO. : 10/913168
DATED : June 9, 2009
INVENTOR(S) : Adnan M. M. Mjalli et al.

It is certified that error appears in the above-identified patent and that said Letters Patent is hereby corrected as shown below:

Column 417, line 51, please delete "NaI", please insert -- NaI --.

Column 417, line 52, please delete "filted", please insert -- fitted --.

Column 425 (Example 558) (Table), line 2, please delete "arbonyl", please insert -- carbonyl --.

Column 425 (Example 559) (Table), line 2, please delete "arbonyl", please insert -- carbonyl --.

Column 427 (Example 597) (Table), line 2, please delete "carbony]", please insert -- carbonyl --.

Column 427, line 47, please delete "Filtaration", please insert -- Filtration --.

Column 429, line 33 (approx.), please delete "20 9", please insert -- 20 g --.

Column 429, line 43, after "102 mg", please delete "of".

Column 431, line 38 (approx.), please delete "desribed", please insert -- described --.

Column 431, line 40, after "ester", please insert -- . --.

Column 433, line 26, please delete "8.6 pL", please insert -- 8.6 µL --.

Column 434, line 47 (approx.), please delete "24 gL", please insert -- 24 µL- -

Column 434, lines 57-58 (approx.), please delete "exitation wavelenth", please insert -- excitation wavelength --.

Column 434, line 58 (approx.), please delete "emmision", please insert -- emission --.

Column 435, line 53, please delete "therof,", please insert -- thereof, --.

Column 437, line 9 (approx.), In Claim 1, please delete "alkynene", please insert -- alkylene --.

Column 437, line 33 (approx.), In Claim 1, please delete "alkynene", please insert -- alkylene --.

UNITED STATES PATENT AND TRADEMARK OFFICE
CERTIFICATE OF CORRECTION

PATENT NO.       : 7,544,699 B2
APPLICATION NO.  : 10/913168
DATED            : June 9, 2009
INVENTOR(S)      : Adnan M. M. Mjalli et al.

It is certified that error appears in the above-identified patent and that said Letters Patent is hereby corrected as shown below:

Column 437, line 49 (approx.), In Claim 1, please delete "alkynene", please insert -- alkylene --.

Column 438, line 58, In Claim 1, please delete "$D_2R_{14}$;", please insert -- $D_2$-$R_{14}$; --.

Column 439, line 34, In Claim 1, please delete "heteroaryle-", please insert -- heteroarylene --.

Column 439, line 67, In Claim 1, please delete "-$N(R_{18})S_2$-,", please insert -- -$N(R_{18})SO_2$-, --.

Column 440, line 1, In Claim 1, please delete "-C(O)-C-,", please insert -- -C(O)-O-, --.

Column 441, line 56, In Claim 3, please delete "alkynene", please insert -- alkylene --.

Column 442, line 14, In Claim 3, please delete "alkynene", please insert -- alkylene --.

Column 442, line 22, In Claim 3, please delete "-$N(R_{24}C(O)$-,", please insert -- -$N(R_{24})C(O)$-, --.

Column 442, line 25, In Claim 3, after "and", please insert -- $N(R_{24})SO_2N(R_{24})$-, --.

Column 442, line 29, In Claim 3, please delete "alkynene", please insert -- alkylene --.

Column 442, line 35, In Claim 4, please delete "quinolyl,", please insert -- quinolyl --.

Column 442, line 63, In Claim 4, please delete "alkyl-", please insert -- alkyl, --.

Column 443, line 27, In Claim 10, please delete "$CO_2R_1$,", please insert -- -$CO_2R_1$, --.

Column 443, line 33, In Claim 11, please delete "alkyl and aryl.", please insert -- alkyl, and –aryl. --.

Column 443, line 38, In Claim 13, please delete "G", please insert -- G is: --.

Column 443, line 55, In Claim 15, please delete "cycloalkylaryl", please insert -- cycloalkylaryl- --.

UNITED STATES PATENT AND TRADEMARK OFFICE
CERTIFICATE OF CORRECTION

PATENT NO. : 7,544,699 B2
APPLICATION NO. : 10/913168
DATED : June 9, 2009
INVENTOR(S) : Adnan M. M. Mjalli et al.

It is certified that error appears in the above-identified patent and that said Letters Patent is hereby corrected as shown below:

Column 445, line 57, In Claim 45, please delete "Erythmatosis", please insert
-- Erythematosus --.

Column 446, line 13, In Claim 51, please delete "pharmaceuticai", please insert
-- pharmaceutical --.

Signed and Sealed this

First Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,544,699 B2 | Page 1 of 1 |
| APPLICATION NO. | : 10/913168 | |
| DATED | : June 9, 2009 | |
| INVENTOR(S) | : Mjalli et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 754 days.

Signed and Sealed this
Sixteenth Day of August, 2011

David J. Kappos
*Director of the United States Patent and Trademark Office*